US006696473B2

(12) United States Patent
Martin et al.

(10) Patent No.: US 6,696,473 B2
(45) Date of Patent: Feb. 24, 2004

(54) HETEROCYCLIC MODULATORS OF NUCLEAR RECEPTORS

(75) Inventors: Richard Martin, San Diego, CA (US); Brenton Todd Flatt, Poway, CA (US); Jeffrey Dean Kahl, San Diego, CA (US); Tie-Lin Wang, San Diego, CA (US)

(73) Assignee: X-Ceptor Therapeutics, Inc., San Diego, CA (US)

( * ) Notice: Subject to any disclaimer, the term of this patent is extended or adjusted under 35 U.S.C. 154(b) by 0 days.

(21) Appl. No.: 10/329,668

(22) Filed: Dec. 20, 2002

(65) Prior Publication Data

US 2003/0212111 A1 Nov. 13, 2003

Related U.S. Application Data

(60) Provisional application No. 60/342,720, filed on Dec. 21, 2001.

(51) Int. Cl.$^7$ .................... A61K 31/425; C07D 277/62; C07D 277/04

(52) U.S. Cl. ....................... 514/367; 514/369; 514/370; 548/180; 548/190

(58) Field of Search ................................ 548/190, 180; 514/367, 369, 370

(56) References Cited

U.S. PATENT DOCUMENTS

| | | | | | |
|---|---|---|---|---|---|
| 5,476,945 | A | * | 12/1995 | Ikegawa et al. | 548/152 |
| 5,618,831 | A | * | 4/1997 | Shishido et al. | 514/366 |
| 5,670,530 | A | * | 9/1997 | Chen et al. | 514/366 |
| 6,548,505 | B1 | * | 4/2003 | Martin et al. | 514/252.13 |
| 6,559,168 | B2 | * | 5/2003 | Marfat et al. | 514/338 |
| 6,569,874 | B1 | * | 5/2003 | Pruitt et al. | 514/342 |

OTHER PUBLICATIONS

Abdel–Megid, M. et al; "A Faale Synthesis of P–Bis(4–Thiazolidinon–3–yl) Phenylenes . . . ", CA 137: 370017, 2002.*

* cited by examiner

*Primary Examiner*—Deborah C. Lambkin
(74) *Attorney, Agent, or Firm*—Stephanie L. Seidman; Dale L. Rieger; Heller Ehrman White & McAuliffe, LLP

(57) ABSTRACT

Compounds, compositions and methods for modulating the activity of nuclear receptors are provided. In particular, heterocyclic compounds are provided for modulating the activity of farnesoid X receptor (FXR), liver X receptor (LXR) and/or orphan nuclear receptors. In certain embodiments, the compounds are thiazolidinone derivatives.

62 Claims, 11 Drawing Sheets

| EXAMPLE | EC50_AVG | EFF_AVG | IC50_AVG | INHIB_AVG |
|---|---|---|---|---|
| 1 | D | C | | |
| 2 | D | C | | |
| 3 | D | C | | |
| 4 | D | B | | |
| 5 | C | B | | |
| 6 | D | C | | |
| 7 | D | D | | |
| 8 | C | B | | |
| 9 | C | B | | |
| 10 | C | C | | |
| 11 | B | B | | |
| 12 | C | C | | |
| 13 | C | B | | |
| 14 | D | C | | |
| 15 | C | C | | |
| 16 | C | A | | |
| 17 | C | C | | |
| 18 | C | C | | |
| 19 | C | D | | |
| 20 | D | C | | |
| 21 | C | B | | |
| 22 | B | B | | |
| 23 | C | C | | |
| 24 | D | C | | |
| 25 | D | C | | |
| 26 | C | B | | |
| 27 | C | B | | |

FIG. 1A

| | | | | |
|---|---|---|---|---|
| 28 | D | C | | |
| 29 | C | B | | |
| 30 | C | A | | |
| 31 | B | B | | |
| 32 | B | B | | NEG |
| 32 | B | B | | |
| 32 | A | B | | |
| 33 | B | B | | |
| 34 | C | C | | |
| 35 | C | B | | |
| 36 | B | A | | |
| 37 | D | B | | |
| 38 | A | A | | |
| 39 | NC | NC | | |
| 40 | NC | NC | | |
| 41 | NC | NC | | |
| 42 | NC | NC | | |
| 43 | D | D | | |
| 44 | D | D | | |
| 45 | D | D | | |
| 46 | NC | NC | | |
| 47 | C | C | C | F |
| 48 | C | C | B | F |
| 49 | C | C | C | F |
| 50 | D | C | | G |
| 51 | NC | D | | |
| 52 | B | D | B | F |
| 55 | A | A | | |

FIG. 1B

| | | | | |
|---|---|---|---|---|
| 56 | A | A | | |
| 57 | B | B | | |
| 58 | B | D | A | F |
| 59 | B | C | | |
| 60 | NC | NC | B | E |
| 61 | D | C | | NEG |
| 62 | C | D | | |
| 63 | C | C | | |
| 64 | C | B | | |
| 65 | C | C | | |
| 66 | B | C | | |
| 67 | C | A | | |
| 68 | D | C | | |
| 69 | C | C | | |
| 70 | NC | NC | | |
| 71 | C | B | | |
| 72 | C | C | | |
| 73 | C | B | | |
| 74 | C | C | | |
| 75 | D | C | | |
| 76 | NC | NC | | |
| 77 | NC | NC | | |
| 78 | C | A | | |
| 79 | C | B | | |
| 80 | C | B | | |
| 81 | B | B | | |
| 82 | B | B | | |
| 82 | B | B | | |

FIG. 1C

| | | | | |
|---|---|---|---|---|
| 83 | B | A | | |
| 84 | B | B | | |
| 85 | B | B | | |
| 86 | C | B | | |
| 87 | A | A | | |
| 88 | NC | NC | | |
| 89 | D | D | | |
| 90 | B | B | | |
| 91 | B | B | | NEG |
| 91 | B | B | | NEG |
| 92 | B | B | | H |
| 93 | C | B | | NEG |
| 94 | B | C | | NEG |
| 95 | D | B | | NEG |
| 96 | B | C | C | G |
| 97 | B | B | | NEG |
| 98 | C | B | | H |
| 99 | B | B | | NEG |
| 100 | B | C | | H |
| 101 | B | B | | NEG |
| 102 | C | B | | H |
| 103 | B | B | D | H |
| 104 | NC | NC | | |
| 105 | C | C | | |
| 106 | C | D | | |
| 107 | NC | NC | | |
| 108 | B | C | | |
| 109 | C | C | | |

FIG. 1D

| | | | |
|---|---|---|---|
| 110 | C | C | |
| 112 | NC | NC | |
| 113 | C | C | |
| 114 | C | B | |
| 115 | C | C | |
| 116 | D | B | |
| 117 | C | C | H |
| 118 | C | B | NEG |
| 119 | C | C | H |
| 120 | C | C | H |
| 121 | C | B | NEG |
| 122 | C | C | H |
| 123 | C | C | H |
| 124 | C | D | H |
| 125 | C | D | G |
| 126 | C | C | NEG |
| 127 | NC | NC | H |
| 128 | C | B | NEG |
| 129 | B | B | NEG |
| 130 | B | B | NEG |
| 131 | B | C | NEG |
| 132 | C | C | NEG |
| 133 | D | D | NEG |
| 134 | B | B | NEG |
| 135 | A | C | H |
| 136 | B | B | NEG |
| 137 | B | B | NEG |
| 138 | B | B | NEG |

FIG. 1E

| | | | | |
|---|---|---|---|---|
| 139 | B | B | | NEG |
| 140 | C | B | | H |
| 141 | C | B | | NEG |
| 142 | B | A | | NEG |
| 143 | B | C | | G |
| 144 | C | C | D | E |
| 145 | A | C | D | F |
| 146 | B | D | B | E |
| 147 | A | A | | H |
| 148 | NC | D | | G |
| 149 | B | D | C | E |
| 150 | A | B | | |
| 151 | B | B | | |
| 152 | A | B | | G |
| 153 | B | B | | |
| 154 | NC | NC | C | F |
| 155 | NC | NC | | |
| 156 | NC | D | | |
| 157 | B | B | | |
| 158 | B | C | | |
| 159 | B | D | A | F |
| 160 | C | D | B | F |
| 161 | B | D | B | F |
| 162 | B | C | B | F |
| 163 | B | D | A | F |
| 164 | B | D | B | F |
| 165 | C | D | | G |
| 166 | NC | D | | |

FIG. 1F

| | | | | |
|---|---|---|---|---|
| 167 | C | C | | |
| 168 | B | B | | |
| 169 | C | B | | |
| 170 | C | B | | |
| 171 | C | A | | |
| 172 | C | A | | |
| 173 | C | A | | |
| 174 | C | C | | |
| 175 | C | B | | |
| 176 | B | B | | |
| 177 | NC | NC | B | E |
| 178 | D | C | C | G |
| 179 | B | A | | |
| 180 | C | D | | |
| 181 | D | C | | |
| 182 | C | B | | |
| 183 | C | D | D | G |
| 184 | C | B | | NEG |
| 185 | C | C | | H |
| 186 | B | B | | NEG |
| 187 | NC | D | | H |
| 188 | D | D | A | G |
| 189 | C | D | C | F |
| 190 | C | B | | NEG |
| 191 | C | B | | H |
| 192 | C | D | C | E |
| 193 | C | C | D | G |
| 194 | C | C | | H |

FIG. 1G

| | | | | |
|---|---|---|---|---|
| 195 | C | C | | H |
| 196 | D | D | C | G |
| 197 | B | D | B | F |
| 198 | C | D | C | E |
| 199 | C | D | B | F |
| 200 | C | D | B | F |
| 201 | C | C | | H |
| 202 | D | C | | H |
| 203 | C | C | | H |
| 204 | C | D | B | F |
| 205 | NC | D | | NEG |
| 206 | B | A | | NEG |
| 207 | C | C | | NEG |
| 208 | C | B | | NEG |
| 209 | C | B | | NEG |
| 210 | C | B | | NEG |
| 211 | B | B | | NEG |
| 212 | C | C | | H |
| 213 | D | D | | H |
| 214 | C | D | C | G |
| 215 | C | D | C | F |
| 216 | C | D | B | E |
| 217 | B | D | B | F |
| 218 | B | D | B | E |
| 219 | B | C | B | G |
| 220 | C | D | B | E |
| 221 | B | D | B | F |
| 222 | D | D | D | E |

FIG. 1H

| | | | | |
|---|---|---|---|---|
| 223 | B | D | B | G |
| 224 | C | D | C | F |
| 225 | C | C | | G |
| 227 | B | C | | |
| 228 | C | B | | |
| 229 | B | C | B | G |
| 230 | D | B | | |
| 231 | NC | NC | C | E |
| 232 | B | C | | G |
| 233 | C | D | | G |
| 234 | B | D | B | F |
| 235 | NC | NC | | |
| 236 | D | C | | |
| 237 | D | D | | |
| 238 | D | D | | |
| 239 | NC | NC | | |
| 240 | NC | NC | | |
| 241 | NC | D | | |
| 241 | NC | NC | | |
| 242 | C | D | | |
| 242 | NC | NC | | |
| 243 | B | B | | |
| 244 | C | A | | |
| 244 | A | A | | |
| 245 | B | C | | |
| 246 | NC | D | | |
| 247 | C | C | | |
| 248 | B | D | C | E |

FIG. 1I

| | | | | |
|---|---|---|---|---|
| 248 | B | D | C | E |
| 249 | C | C | A | G |
| 250 | B | C | | |
| 251 | C | C | | |
| 252 | NC | D | | |
| 253 | D | D | | |
| 254 | C | D | | |
| 255 | B | D | A | E |
| 256 | D | D | | |
| 257 | NC | NC | C | F |
| 258 | C | D | C | F |
| 259 | NC | NC | C | F |
| 259 | NC | NC | C | F |
| 259 | C | D | B | E |
| 260 | NC | NC | B | G |
| 261 | B | D | B | G |
| 262 | B | C | A | H |
| 263 | C | D | B | F |
| 264 | B | D | A | F |
| 265 | B | B | | |
| 266 | C | B | | |
| 267 | B | B | | |
| 268 | B | D | A | G |
| 269 | B | C | | |
| 270 | B | B | | H |
| 271 | B | D | B | F |
| 272 | B | B | | NEG |
| 273 | D | C | | H |

FIG. 1J

| | | | | |
|---|---|---|---|---|
| 274 | B | D | B | E |
| 275 | A | D | | NEG |
| 276 | B | C | | NEG |
| 277 | C | D | | G |
| 278 | NC | NC | | G |
| 279 | C | D | C | F |
| 280 | C | D | C | G |
| 281 | C | D | | NEG |
| 282 | C | D | C | E |
| 283 | NC | NC | C | E |
| 284 | NC | NC | | H |
| 285 | NC | C | A | G |
| 286 | B | C | A | G |
| 287 | C | D | B | G |
| 288 | C | D | C | G |
| 289 | C | D | | H |
| 290 | B | C | | NEG |

FIG. 1K

HETEROCYCLIC MODULATORS OF NUCLEAR RECEPTORS

RELATED APPLICATION

Benefit of priority under 35 U.S.C. 119(e) is claimed herein to U.S. provisional patent application No. 60/342,720, filed Dec. 21, 2001, to Martin et al., entitled "HETEROCYCLIC MODULATORS OF NUCLEAR RECEPTORS." The disclosure of the above-referenced application is incorporated by reference herein in its entirety.

FIELD

Compounds, compositions and methods for modulating the activity of nuclear receptors are provided. In particular, heterocyclic compounds are provided for modulating the activity of orphan nuclear receptors.

BACKGROUND

Nuclear Receptors

Nuclear receptors are a superfamily of regulatory proteins that are structurally and functionally related and are receptors for, e.g., steroids, retinoids, vitamin D and thyroid hormones (see, e.g., Evans (1988) *Science* 240:889–895). These proteins bind to cis-acting elements in the promoters of their target genes and modulate gene expression in response to ligands for the receptors.

Nuclear receptors can be classified based on their DNA binding properties (see, e.g., Evans, supra and Glass (1994) *Endocr. Rev.* 15:391–407). For example, one class of nuclear receptors includes the glucocorticoid, estrogen, androgen, progestin and mineralocorticoid receptors which bind as homodimers to hormone response elements (HREs) organized as inverted repeats (see, e.g., Glass, supra). A second class of receptors, including those activated by retinoic acid, thyroid hormone, vitamin $D_3$, fatty acids/peroxisome proliferators (i.e., peroxisome proliferator activated receptor (PPAR)) and ecdysone, bind to HREs as heterodimers with a common partner, the retinoid X receptors (i.e., RXRs, also known as the 9-cis retinoic acid receptors; see, e.g., Levin et al. (1992) *Nature* 355:359–361 and Heyman et al. (1992) *Cell* 68:397–406).

RXRs are unique among the nuclear receptors in that they bind DNA as a homodimer and are required as a heterodimeric partner for a number of additional nuclear receptors to bind DNA (see, e.g., Mangelsdorf et al. (1995) *Cell* 83:841–850). The latter receptors, termed the class II nuclear receptor subfamily, include many which are established or implicated as important regulators of gene expression. There are three RXR genes (see, e.g., Mangelsdorf et al. (1992) *Genes Dev.* 6:329–344), coding for RXRα, -β, and -γ, all of which are able to heterodimerize with any of the class II receptors, although there appear to be preferences for distinct RXR subtypes by partner receptors in vivo (see, e.g., Chiba et al. (1997) *Mol. Cell. Biol.* 17:3013–3020). In the adult liver, RXRα is the most abundant of the three RXRs (see, e.g., Mangelsdorf et al. (1992) *Genes Dev.* 6:329–344), suggesting that it might have a prominent role in hepatic functions that involve regulation by class II nuclear receptors. See also, Wan et al. (2000) *Mol. Cell. Biol.* 20:4436–4444.

Orphan Nuclear Receptors

Included in the nuclear receptor superfamily of regulatory proteins are nuclear receptors for whom the ligand is known and those which lack known ligands. Nuclear receptors falling in the latter category are referred to as orphan nuclear receptors. The search for activators for orphan receptors has led to the discovery of previously unknown signaling pathways (see, e.g., Levin et al., (1992), supra and Heyman et al., (1992), supra). For example, it has been reported that bile acids, which are involved in physiological processes such as cholesterol catabolism, are ligands for FXR (infra).

Since it is known that products of intermediary metabolism act as transcriptional regulators in bacteria and yeast, such molecules may serve similar functions in higher organisms (see, e.g., Tomkins (1975) *Science* 189:760–763 and O'Malley (1989) *Endocrinology* 125:1119–1120). For example, one biosynthetic pathway in higher eukaryotes is the mevalonate pathway, which leads to the synthesis of cholesterol, bile acids, porphyrin, dolichol, ubiquinone, carotenoids, retinoids, vitamin D, steroid hormones and farnesylated proteins.

FXR

FXR (originally isolated as RIP14 (retinoid X receptor-interacting protein-14), see, e.g., Seol et al. (1995) *Mol. Endocrinol.* 9:72–85) is a member of the nuclear hormone receptor superfamily and is primarily expressed in the liver, kidney and intestine (see, e.g., Seol et al., supra and Forman et al. (1995) *Cell* 81:687–693). It functions as a heterodimer with the retinoid X receptor (RXR) and binds to response elements in the promoters of target genes to regulate gene transcription. The FXR-RXR heterodimer binds with highest affinity to an inverted repeat-1 (IR-1) response element, in which consensus receptor-binding hexamers are separated by one nucleotide. FXR is part of an interrelated process, in that FXR is activated by bile acids (the end product of cholesterol metabolism) (see, e.g., Makishima et al. (1999) *Science* 284:1362–1365, Parks et al. (1999) *Science* 284:1365–1368, Wang et al. (1999) *Mol. Cell.* 3:543–553), which serve to inhibit cholesterol catabolism. See also, Urizar et al. (2000) *J. Biol. Chem.* 275:39313–39317.

LXRα and LXRβ

LXRα is found predominantly in the liver, with lower levels found in kidney, intestine, spleen and adrenal tissue (see, e.g., Willy, et al. (1995) *Gene Dev.* 9(9):1033–1045). LXRβ, also known as UR (ubiquitous receptor), is ubiquitous in mammals and was found in nearly all tissues examined. LXRs are activated by certain naturally occurring, oxidized derivatives of cholesterol (see, e.g., Lehmann, et al. (1997) *J. Biol. Chem.* 272(6):3137–3140). LXRα is activated by oxycholesterol and promotes cholesterol metabolism (Peet et al. (1998) *Cell* 93:693–704). Thus, LXRs appear to play a role in, e.g., cholesterol metabolism (see, e.g., Janowski, et al. (1996) *Nature* 383:728–731).

Nuclear Receptors and Disease

Nuclear receptor activity has been implicated in a variety of diseases and disorders, including, but not limited to, hypercholesterolemia (see, e.g., International Patent Application Publication No. WO 00/57915), osteoporosis and vitamin deficiency (see, e.g., U.S. Pat. No. 6,316,5103), hyperlipoproteinemia (see, e.g., International Patent Application Publication No. WO 01/60818), hypertriglyceridemia, lipodystrophy, peripheral occlusive disease, ischemic stroke, hyperglycemia and diabetes mellitus (see, e.g., International Patent Application Publication No. WO 01/82917), atherosclerosis and gallstones (see, e.g., International Patent Application Publication No. WO 00/37077), disorders of the skin and mucous membranes (see, e.g., U.S. Pat. Nos. 6,184,215 and 6,187,814, and International Patent Application Publication No. WO 98/32444), acne (see, e.g., International Patent Application Publication No. WO 00/49992), and cancer, Parkinson's disease and Alzheimer's disease (see, e.g., International Patent Application Publication No. WO 00/17334). Activity of nuclear receptors, including FXR, LXRs and/or orphan nuclear receptors, has been implicated in physiological processes including, but not limited to, bile acid biosynthesis, cholesterol metabolism or catabolism, and modulation of cholesterol 7α-hydroxylase gene (CYP7A1) transcription (see, e.g., Chiang et al. (2000) *J. Biol. Chem.* 275:10918–10924), HDL metabolism (see, e.g., Urizar et al. (2000) *J. Biol. Chem.* 275:39313–39317), hyperlipidemia, cholestasis, and increased cholesterol efflux and increased expression of ATP binding cassette transporter protein (ABC1) (see, e.g., International Patent Application Publication No. WO 00/78972).

Thus, there is a need for compounds, compositions and methods of modulating the activity of nuclear receptors, including FXR, LXRs and/or orphan nuclear receptors. Such compounds are useful in the treatment, prevention, or amelioration of one or more symptoms of diseases or disorders in which nuclear receptor activity is implicated.

SUMMARY

Compounds for use in compositions and methods for modulating the activity of nuclear receptors are provided. In particular, compounds for use in compositions and methods for modulating farnesoid X receptor (FXR), liver X receptors (LXRα and LXRβ) and/or orphan nuclear receptors, are provided. In certain embodiments, the compounds are heterocyclic compounds that are substituted with a heterocyclylene group and an imine moiety. In one embodiment, the compounds provided herein are agonists of FXR and/or LXR. In another embodiment, the compounds provided herein are antagonists of FXR and/or LXR. Agonists that exhibit low efficacy are, in certain embodiments, antagonists.

In one embodiment, the compounds for use in the compositions and methods provided herein have formulae I:

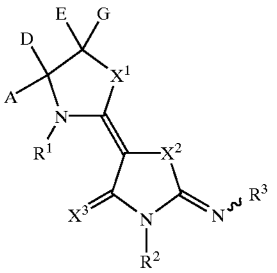

or

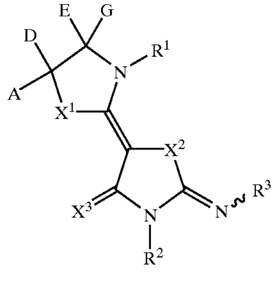

or a pharmaceutically acceptable derivative thereof, where A, D, E and G are selected from (i) or (ii) as follows:

(i) A and G are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted heteroarylium, substituted or unsubstituted heteroaryliumalkyl, halo, pseudohalo, $OR^{10}$, $SR^{10}$, $S(=O)R^{13}$, $S(=O)_2R^{13}$, $NR^{11}R^{12}$ and $C(=J)R^{13}$, or A and G together form substituted or unsubstituted alkylene, substituted or unsubstituted azaalkylene, substituted or unsubstituted oxaalkylene, substituted or unsubstituted thiaalkylene, substituted or unsubstituted alkenylene, substituted or unsubstituted alkynylene, substituted or unsubstituted 1,3-butadienylene, substituted or unsubstituted 1-aza-1,3-butadienylene, or substituted or unsubstituted 2-aza-1,3-butadienylene;

D and E are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo and pseudohalo or D and E together form a bond; or (ii) A and D; or E and G; together form substituted or unsubstituted alkylene, substituted or unsubstituted azaalkylene, substituted or unsubstituted oxaalkylene, or substituted or unsubstituted thiaalkylene; and the others of A, D, E and G are selected as in (i);

$X^1$ and $X^2$ are each independently selected from O, S, $S(=O)$, $S(=O)_2$, Se, $NR^5$, $CR^6R^7$ and $CR^8=CR^9$; $X^3$ is O, S, Se, $NR^5$ or $CR^6R^7$; $R^1$ and $R^2$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted heteroarylium, substituted or unsubstituted heteroaryliumalkyl, $OR^{10}$, $SR^{10}$, $S(=O)R^{13}$, $S(=O)_2$ $R^{13}$, $NR^{11}R^{12}$ and $C(=J)R^{13}$; $R^3$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted heteroarylium, substituted or unsubstituted aralkyl, substituted or unsubstituted heteroaralkyl, substituted or unsubstituted heteroaryliumalkyl, $OR^{10}$, $SR^{10}$, $S(=O)R^{13}$, $S(=O)_2R^{13}$, $NR^{11}R^{12}$ and $C(=J)R^{13}$; where $R^5$, $R^6$, $R^7$, $R^8$ and $R^9$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo, pseudohalo, $OR^{10}$, $NR^{14}R^{15}$ and $C(=J)R^{13}$;

$R^{10}$, $R^{11}$ and $R^{12}$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl or $C(=J)R^{13}$;

J is O, S or $NR^{14}$;

$R^{13}$ is selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, pseudohalo, $OR^{16}$ and $NR^{14}R^{15}$;

$R^{14}$, $R^{15}$ and $R^{16}$ are each independently selected from hydrogen, alkyl, alkenyl, alkynyl, cycloalkyl, heterocyclyl, cycloalkylalkyl, heterocyclylalkyl, aryl, heteroaryl, aralkyl and heteroaralkyl;

where the alkyl, alkenyl, alkynyl, cycloalkyl, heterocyclyl, cycloalkylalkyl, heterocyclylalkyl, aryl, heteroaryl, heteroarylium, aralkyl, heteroaralkyl and heteroaryliumalkyl moieties of A, D, E, G, $R^1$, $R^2$, $R^3$, $R^5$, $R^6$, $R^7$, $R^8$, $R^9$, $R^{10}$, $R^{11}$, $R^{12}$ and $R^{13}$ are unsubstituted or substituted with one or more substituents, in one embodiment one to three or four substituents, each independently selected from $Q^1$, where $Q^1$ is halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, imino, hydroxyimino, alkoxyimino, aryloxyimino, aralkoxyimino, alkylazo, arylazo, aralkylazo, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $-N^+R^{51}R^{52}R^{53}$, $P(R^{50})_2$, $P(=O)(R^{50})_2$, $OP(=O)(R^{50})_2$, $-NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy (i.e., $-O-(CH_2)_y-O-$), thioalkylenoxy (i.e., $-S-(CH_2)-O-$)or alkylenedithioxy (i.e., $-S-(CH_2)_y-S-$) where y is 1 or 2; or two $Q^1$ groups, which substitute the same atom, together form alkylene; and each $Q^1$ is independently unsubstituted or substituted with one or more substituents, in one embodiment one, two or three substituents, each independently selected from $Q^2$;

each $Q^2$ is independently halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{51}R^{52}R^{53}$, $P(R^{50})_2$, $P(=O)(R^{50})_2$, $OP(=O)(R^{50})_2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^2$ groups, which substitute atoms in a 1,2 or 1,3 arrangement, together form alkylenedioxy (i.e., $—O—(CH_2)_y—O—$), thioalkylenoxy (i.e., $—S—(CH_2)_y—O—$)or alkylenedithioxy (i.e., $—S—(CH_2)_y—S—$) where y is 1 or 2; or two $Q^2$ groups, which substitute the same atom, together form alkylene;

each $Q^2$ is independently unsubstituted or substituted with one or more, in one embodiment one, two or three, substituents each independently selected from alkyl, halo and pseudohalo;

$R^{50}$ is hydroxy, alkoxy, aralkoxy, alkyl, heteroaryl, heterocyclyl, aryl or $—NR^{70}R^{71}$, where $R^{70}$ and $R^{71}$ are each independently hydrogen, alkyl, aralkyl, aryl, heteroaryl, heteroaralkyl or heterocyclyl, or $R^{70}$ and $R^{71}$ together form alkylene, azaalkylene, oxaalkylene or thiaalkylene;

$R^{51}$, $R^{52}$ and $R^{53}$ are each independently hydrogen, alkyl, aryl, aralkyl, heteroaryl, heteroaralkyl, heterocyclyl or heterocyclylalkyl;

$R^{60}$ is hydrogen, alkyl, aryl, aralkyl, heteroaryl, heteroaralkyl, heterocyclyl or heterocyclylalkyl; and $R^{63}$ is alkoxy, aralkoxy, alkyl, heteroaryl, heterocyclyl, aryl or $—NR^{70}R^{71}$.

In another embodiment, the compounds for use in the compositions and methods provided herein have formulae I:

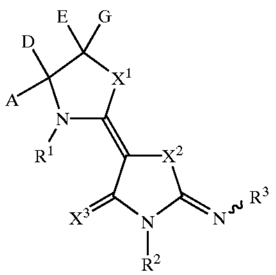

or

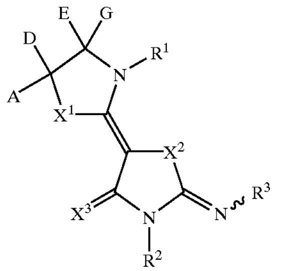

or a pharmaceutically acceptable derivative thereof, where A, D, E and G are selected from (i) or (ii) as follows:

(i) A and G are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted heteroarylium, substituted or unsubstituted heteroaryliumalkyl, halo, pseudohalo, $OR^{10}$, $SR^{10}$, $S(=O)R^{13}$, $S(=O)_2R^{13}$, $NR^{11}R^{12}$ and $C(=J)R^{13}$, or A and G together form substituted or unsubstituted alkylene, substituted or unsubstituted azaalkylene, substituted or unsubstituted oxaalkylene, substituted or unsubstituted thiaalkylene, substituted or unsubstituted alkenylene, substituted or unsubstituted alkynylene, substituted or unsubstituted 1,3-butadienylene, substituted or unsubstituted 1-aza-1,3-butadienylene, or substituted or unsubstituted 2-aza-1,3-butadienylene;

D and E are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo and pseudohalo or D and E together form a bond; or (ii) A and D; or E and G; together form substituted or unsubstituted alkylene, substituted or unsubstituted azaalkylene, substituted or unsubstituted oxaalkylene, or substituted or unsubstituted thiaalkylene; and the others of A, D, E and G are selected as in (i);

$X^1$ and $X^2$ are each independently selected from O, S, S(=O), $S(=O)_2$, Se, $NR^5$, $CR^6R^7$ and $CR^8$=$CR^9$; $X^3$ is O, S, Se, $NR^5$ or $CR^6R^7$; $R^1$ and $R^2$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted heteroarylium, substituted or unsubstituted heteroaryliumalkyl, $OR^{10}$, $SR^{10}$, $S(=O)R^{13}$, $S(=O)_2R^{13}$, $NR^{11}R^{12}$ and $C(=J)R^{13}$; $R^3$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted heteroarylium, substituted or unsubstituted aralkyl, substituted or unsubstituted heteroaralkyl, substituted or unsubstituted heteroaryliumalkyl, $OR^{10}$, $SR^{10}$, $S(=O)R^{13}$, $S(=O)_2R^{13}$, $NR^{11}R^{12}$ and $C(=J)R^{13}$; where $R^5$, $R^6$, $R^7$, $R^8$ and $R^9$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo, pseudohalo, $OR^{10}$, $NR^{14}R^{15}$ and $C(=J)R^{13}$;

$R^{10}$, $R^{11}$ and $R^{12}$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl or $C(=J)R^{13}$;

J is O, S or $NR^{14}$;

$R^{13}$ is selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, pseudohalo, $OR^{16}$ and $NR^{14}R^{15}$;

$R^{14}$, $R^{15}$ and $R^{16}$ are each independently selected from hydrogen, alkyl, alkenyl, alkynyl, cycloalkyl, heterocyclyl, cycloalkylalkyl, heterocyclylalkyl, aryl, heteroaryl, aralkyl and heteroaralkyl;

where the alkyl, alkenyl, alkynyl, cycloalkyl, heterocyclyl, cycloalkylalkyl, heterocyclylalkyl, aryl, heteroaryl, heteroarylium, aralkyl, heteroaralkyl and heteroaryliumalkyl moieties of A, D, E, G, $R^1$, $R^2$, $R^3$, $R^5$, $R^6$, $R^7$, $R^8$, $R^9$, $R^{10}$, $R^{11}$, $R^{12}$ and $R^{13}$ are unsubstituted or substituted with one or more substituents, in one embodiment one to three or four substituents, each independently selected from $Q^1$, where $Q^1$ is halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{51}R^{52}R^{53}$, $P(R^{50})_2$, $P(=O)(R^{50})_2$, $OP(=O)(R^{50})_2$, $—NR^{60}C(=O)R^{63}$, dialkyl phosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy (i.e., $—O—(CH_2)_y—O—$), thioalkylenoxy (i.e., $—S—(CH_2)_y—O—$)or alkylenedithioxy (i.e., $—S—(CH_2)_y—S—$) where y is 1 or 2; or two $Q^1$ groups, which substitute the same atom, together form alkylene; and each $Q^1$ is independently unsubstituted or substituted with one or more substituents, in one embodiment one, two or three substituents, each independently selected from $Q^2$;

each $Q^2$ is independently halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{51}R^{52}R^{53}$, $P(R^{50})_2$, $P(=O)(R^{15})_2$, $OP(=O)(R^{50})_2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^2$ groups, which substitute atoms in a 1,2 or 1,3 arrangement, together form alkylenedioxy (i.e., $—O—(CH_2)_y—O—$), thioalkylenoxy (i.e., $—S—(CH_2)_y—O—$)or alkylenedithioxy (i.e., $—S—(CH_2)_y—S—$) where y is 1 or 2; or two $Q^2$ groups, which substitute the same atom, together form alkylene;

$R^{50}$ is hydroxy, alkoxy, aralkoxy, alkyl, heteroaryl, heterocyclyl, aryl or $—NR^{70}R^{71}$, where $R^{70}$ and $R^{71}$ are each independently hydrogen, alkyl, aralkyl, aryl, heteroaryl, heteroaralkyl or heterocyclyl, or $R^{70}$ and $R^{71}$ together form alkylene, azaalkylene, oxaalkylene or thiaalkylene;

$R^{51}$, $R^{52}$ and $R^{53}$ are each independently hydrogen, alkyl, aryl, aralkyl, heteroaryl, heteroaralkyl, heterocyclyl or heterocyclylalkyl;

$R^{60}$ is hydrogen, alkyl, aryl, aralkyl, heteroaryl, heteroaralkyl, heterocyclyl or heterocyclylalkyl; and $R^{63}$ is alkoxy, aralkoxy, alkyl, heteroaryl, heterocyclyl, aryl or $—NR^{70}R^{71}$.

In certain embodiments herein, the compounds are selected with the proviso that when $R^3$ is substituted or unsubstituted heteroarylium then the heteroatom substituent is not alkyl or aryl. In another embodiment, the compounds are selected with the proviso that $R^3$ is not substituted or unsubstituted heteroarylium or substituted or unsubstituted heteroaryliumalkyl. In other embodiments, the compounds are selected with the proviso that $R^3$ is not heteroaryl. In further embodiments, the compounds are selected with the proviso that $R^3$ is not alkyl. In another embodiment, the compounds are selected with the proviso that $R^3$ is not heterocycloaryl (i.e., an aryl group possessing a fused heterocyclic moiety).

The groups A, D, E, G, $X^1$, $X^2$, $X^3$, $R^1$, $R^2$ and $R^3$ are selected such that the resulting compound has nuclear receptor modulation activity, such as in at least one assay described herein, such as FXR antagonist or agonist activity, and, in certain embodiments, at an $IC_{50}$ or $EC_{50}$ of less than about 100 $\mu$M. The FXR $IC_{50}$ or $EC_{50}$ values for the compounds provided herein are, in certain embodiments, less than about 50 $\mu$M, 25 $\mu$M, 10 $\mu$M, 1 $\mu$M, 100 nM, 10 nM or 1 nM.

Also of interest are any pharmaceutically-acceptable derivatives, including salts, esters, enol ethers, enol esters, solvates, hydrates and prodrugs of the compounds described herein. Pharmaceutically-acceptable salts, include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl) aminomethane; alkali metal salts, such as but not limited to lithium, potassium and sodium; alkali earth metal salts, such as but not limited to barium, calcium and magnesium; transition metal salts, such as but not limited to zinc, aluminum, and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates.

Pharmaceutical compositions formulated for administration by an appropriate route and means containing effective concentrations of one or more of the compounds provided herein, or pharmaceutically acceptable derivatives thereof, that deliver amounts effective for the treatment, prevention, or amelioration of one or more symptoms of diseases or disorders that are modulated or otherwise affected by nuclear receptor activity, including FXR, LXR and/or orphan nuclear receptor activity, or in which nuclear receptor activity, including FXR, LXR and/or orphan nuclear receptor activity, is implicated, are also provided. The effective amounts and concentrations are effective for ameliorating any of the symptoms of any of the diseases or disorders.

Methods for treatment, prevention, or amelioration of one or more symptoms of diseases or disorders mediated by or in which nuclear receptor activity, including FXR, LXR and/or orphan nuclear receptor activity, is implicated, are provided. Such methods include methods of treatment, prevention and amelioration of one or more symptoms of hypercholesterolemia, hyperlipoproteinemia, hypertriglyceridemia, lipodystrophy, hyperglycemia, diabetes mellitus, dyslipidemia, atherosclerosis, gallstone disease, acne vulgaris, acneiform skin conditions, diabetes, Parkinson's disease, cancer, Alzheimer's disease, inflammation, immunological disorders, lipid disorders, obesity, conditions characterized by a perturbed epidermal barrier function, hyperlipidemia, cholestasis, peripheral occlusive disease, ischemic stroke, conditions of disturbed differentiation or excess proliferation of the epidermis or mucous membrane, or cardiovascular disorders, using one or more of the compounds provided herein, or pharmaceutically acceptable derivatives thereof.

Methods of modulating the activity of nuclear receptors, including FXR, LXR and/or-orphan nuclear receptors, using the compounds and compositions provided herein are also provided. The compounds and compositions provided herein are active in assays that measure the activity of nuclear receptors, including FXR, LXR and/or orphan nuclear receptors, including the assays provided herein. These methods include inhibiting and up-regulating the activity of nuclear receptors, including FXR, LXR and/or orphan nuclear receptors.

Methods of reducing cholesterol levels in a subject in need thereof by administration of one or more compounds or compositions provided herein are also provided.

Methods of modulating cholesterol metabolism using the compounds and compositions provided herein are provided.

Methods of treating, preventing, or ameliorating one or more symptoms of diseases or disorders which are affected by cholesterol, triglyceride, or bile acid levels by administration of one or more of the compounds and compositions provided herein are also provided.

In practicing the methods, effective amounts of the compounds or compositions containing therapeutically effective concentrations of the compounds, which are formulated for systemic delivery, including parenteral, oral, or intravenous delivery, or for local or topical application, for the treatment of nuclear receptor, including FXR, LXR and/or orphan nuclear receptor, mediated diseases or disorders, or diseases or disorders in which nuclear receptor activity, including FXR, LXR and/or orphan nuclear receptor activity, is implicated, including, but not limited to, hypercholesterolemia, hyperlipoproteinemia, hypertriglyceridemia, lipodystrophy, hyperglycemia, diabetes mellitus, dyslipidemia, atherosclerosis, gallstone disease, acne vulgaris, acneiform skin conditions, diabetes, Parkinson's disease, cancer, Alzheimer's disease, inflammation, immunological disorders, lipid disorders, obesity, conditions characterized by a perturbed epidermal barrier function, hyperlipidemia, cholestasis, peripheral occlusive disease, ischemic stroke, conditions of disturbed differentiation or excess proliferation of the epidermis or mucous membrane, or cardiovascular disorders, are administered to an individual exhibiting the symptoms of these diseases or disorders. The amounts are effective to ameliorate or eliminate one or more symptoms of the diseases or disorders.

Articles of manufacture containing packaging material, a compound or composition, or pharmaceutically acceptable derivative thereof, provided herein, which is effective for modulating the activity of nuclear receptors, including FXR, LXR and/or orphan nuclear receptors, or for treatment, prevention or amelioration of one or more symptoms of nuclear receptor, including FXR, LXR and/or orphan nuclear receptor, mediated diseases or disorders, or diseases or disorders in which nuclear receptor activity, including FXR, LXR and/or orphan nuclear receptor activity, is implicated, within the packaging material, and a label that indicates that the compound or composition, or pharmaceutically acceptable derivative thereof, is used for modulating the activity of nuclear receptors, including FXR, LXR and/or orphan nuclear receptors, or for treatment, prevention or amelioration of one or more symptoms of nuclear receptor, including FXR, LXR and/or orphan nuclear receptor, mediated diseases or disorders, or diseases or disorders in which nuclear receptor activity, including FXR, LXR and/or orphan nuclear receptor activity, is implicated, are provided.

BRIEF DESCRIPTION OF DRAWINGS

FIG. 1 provides in vitro data for the compounds whose synthesis is described in the Examples. Average $EC_{50}$ ("EC50__AVG") for FXR agonism is provided as follows: A=0.0001–0.01 μM, B=0.01–0.1 μM, C=0.1–1.0 μM, D=1.0–10.0 μM and NC=not calculated or inactive. Average percent efficacy ("EFF__AVG") for FXR agonism relative to control (chenodeoxycholic acid, CDCA) is provided as follows: A=>150%, B=100–150%, C=50–100%, D=0–50% and NC=not calculated or inactive. Average $IC_{50}$ ("IC50__AVG") for FXR antagonism is provided as follows: A=0.0001–0.01 μM, B=0.01–0.1 μM, C=0.1–1.0 μM and D=1.0–10.0 μM. Average percent inhibition ("INHIB__AVG") for FXR antagonism relative to control (chenodeoxycholic acid, CDCA) is provided as follows: E=>75%, F=50–75%, G=25–50%, H=0–25% and NEG=negative.

DETAILED DESCRIPTION OF EMBODIMENTS

A. Definitions

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

As used herein, a nuclear receptor is a member of a superfamily of regulatory proteins that are receptors for, e.g., steroids, retinoids, vitamin D and thyroid hormones. These proteins bind to cis-acting elements in the promoters of their target genes and modulate gene expression in response to a ligand therefor. Nuclear receptors may be classified based on their DNA binding properties. For example, the glucocorticoid, estrogen, androgen, progestin and mineralocorticoid receptors bind as homodimers to hormone response elements (HRES) organized as inverted repeats. Another example are receptors, including those activated by retinoic acid, thyroid hormone, vitamin $D_3$, fatty acids/peroxisome proliferators and ecdysone, that bind to HREs as heterodimers with a common partner, the retinoid X receptor (RXR). Among the latter receptors are FXR and LXR.

As used herein, an orphan nuclear receptor is a nuclear receptor for which the natural ligand is unknown.

As used herein, the term farnesoid X receptor or FXR refers to all mammalian forms of such receptor including, for example, alternative splice isoforms and naturally occurring isoforms. Representative FXR species include, without limitation rat FXR (SEQ ID NO. 5), mouse FXR, and human FXR (SEQ ID NO. 7).

As used herein, liver X receptor or LXR or UR refers to a nuclear receptor implicated in cholesterol homeostasis. As used herein, the term LXR refers to both LXRα and LXRβ, two forms of the protein found in mammals. Liver X receptor-α or LXRα refers to the receptor described in U.S. Pat. No. 5,757,661 and Willy et al. (1995) *Gene Dev.* 9(9):1033–1045. Liver X receptor-β or LXRβ refers to the receptor described in Peet et al. (1998) *Curr. Opin. Genet. Dev.* 8(5):571–575; Song et al. (1995) *Ann. N. Y. Acad. Sci.* 761:38–49; Alberti et al., (2000) *Gene* 243(1–2):93–103; and references cited therein.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl) aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C═C(OR) where R is hydrogen, alkyl, alkenyl, alkynyl, aryl, heteroaryl, aralkyl, heteroaralkyl, cycloalkyl ar heterocyclyl. Pharmaceutically acceptable enol esters include, but are not limited to, derivatives of formula C═C(OC(O)R) where R is hydrogen, alkyl, alkenyl, alkynyl, aryl, heteroaryl, aralkyl, heteroaralkyl, cycloalkyl ar heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment also encompasses any pharmaceutical use of the compositions herein, such as use for treating a nuclear receptor, including FXR, LXR and/or orphan nuclear receptor, mediated diseases or disorders, or diseases or disorders in which nuclear receptor activity, including FXR, LXR and/or orphan nuclear receptor activity, is implicated.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, the $IC_{50}$ refers to an amount, concentration or dosage of a particular test compound that achieves a 50% inhibition of a maximal response, such as modulation of FXR activity, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388–392).

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound. The instant disclosure is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, the nomenclature alkyl, alkoxy, carbonyl, etc. is used as is generally understood by those of skill in this art.

As used herein, alkyl, alkenyl and alkynyl carbon chains, if not specified, contain from 1 to 20 carbons, or 1 to 16 carbons, and are straight or branched. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-penytyl and isohexyl. As used herein, lower alkyl, lower alkenyl, and lower alkynyl refer to carbon chains having from about 1 or about 2 carbons up to about 6 carbons. As used herein, "alk(en)(yn)yl" refers to an alkyl group containing at least one double bond and at least one triple bond.

As used herein, "cycloalkyl" refers to a saturated mono- or multicyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond.

As used herein, "substituted alkyl," "substituted alkenyl," "substituted alkynyl," "substituted cycloalkyl," "substituted cycloalkenyl," and "substituted cycloalkynyl" refer to alkyl, alkenyl, alkynyl, cycloalkyl, cycloalkenyl and cycloalkynyl groups, respectively, that are substituted with one or more substituents, in certain embodiments one to three or four substituents, where the substituents are as defined herein, generally selected from $Q^1$.

As used herein, "aryl" refers to aromatic monocyclic or multicyclic groups containing from 6 to 19 carbon atoms. Aryl groups include, but are not limited to groups such as fluorenyl, substituted fluorenyl, phenyl, substituted phenyl, naphthyl and substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrrolidinyl, pyrimidinyl, tetrazolyl, thienyl, pyridyl, pyrrolyl, N-methylpyrrolyl, quinolinyl and isoquinolinyl.

As used herein, a "heteroarylium" group is a heteroaryl group that is positively charged on one or more of the heteroatoms.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "substituted aryl," "substituted heteroaryl" and "substituted heterocyclyl" refer to aryl, heteroaryl and heterocyclyl groups, respectively, that are substituted with one or more substituents, in certain embodiments one to three or four substituents, where the substituents are as defined herein, generally selected from $Q^1$.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyanide, cyanate, thiocyanate, selenocyanate, trifluoromethoxy, and azide.

As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "haloalkoxy" refers to RO— in which R is a haloalkyl group.

As used herein, "sulfinyl" or "thionyl" refers to —S(O)—. As used herein, "sulfonyl" or "sulfuryl" refers to $—S(O)_2—$. As used herein, "sulfo" refers to $—S(O)_2O—$.

As used herein, "carboxy" refers to a divalent radical, —C(O)O—.

As used herein, "aminocarbonyl" refers to $—C(O)NH_2$.

As used herein, "alkylaminocarbonyl" refers to —C(O) NHR in which R is alkyl, including lower alkyl. As used herein, "dialkylaminocarbonyl" refers to —C(O)NR'R in which R' and R are independently alkyl, including lower alkyl; "carboxamide" refers to groups of formula —NRCOR in which R' and R are independently alkyl, including lower alkyl.

As used herein, "diarylaminocarbonyl" refers to —C(O) NRR' in which R and R' are independently selected from aryl, including lower aryl, such as phenyl.

As used herein, "arylalkylaminocarbonyl" refers to —C(O)NRR' in which one of R and R' is aryl, including lower aryl, such as phenyl, and the other of R and R' is alkyl, including lower alkyl.

As used herein, "arylaminocarbonyl" refers to —C(O) NHR in which R is aryl, including lower aryl, such as phenyl.

As used herein, "hydroxycarbonyl" refers to —COOH.

As used herein, "alkoxycarbonyl" refers to —C(O)OR in which R is alkyl, including lower alkyl.

As used herein, "aryloxycarbonyl" refers to —C(O)OR in which R is aryl, including lower aryl, such as phenyl.

As used herein, "alkoxy" and "alkylthio" refer to RO— and RS—, in which R is alkyl, including lower alkyl.

As used herein, "aryloxy" and "arylthio" refer to RO— and RS—, in which R is aryl, including lower aryl, such as phenyl.

As used herein, "alkylene" refers to a straight, branched or cyclic, in certain embodiments straight or branched, divalent aliphatic hydrocarbon group, in one embodiment having from 1 to about 20 carbon atoms, in another embodiment having from 1 to 12 carbons. In a further embodiment alkylene includes lower alkylene. There may be optionally inserted along the alkylene group one or more oxygen, sulfur, including S(=O) and $S(=O)_2$ groups, or substituted or unsubstituted nitrogen atoms, including —NR— and $—N^+RR—$ groups, where the nitrogen substituent(s) is(are) alkyl, aryl, aralkyl, heteroaryl, heteroaralkyl or COR', where R' is alkyl, aryl, aralkyl, heteroaryl, heteroaralkyl, —OY or —NYY, where Y is hydrogen, alkyl, aryl, heteroaryl, cycloalkyl or heterocyclyl. Alkylene groups include, but are not limited to, methylene ($—CH_2—$), ethylene ($—CH_2CH_2—$), propylene ($—(CH_2)_3—$), methylenedioxy ($—O—CH_2—O—$) and ethylenedioxy ($—O—(CH_2)_2—O—$). The term "lower alkylene" refers to alkylene groups having 1 to 6 carbons. In certain embodiments, alkylene groups are lower alkylene, including alkylene of 1 to 3 carbon atoms.

As used herein, "azaalkylene" refers to $—(CRR)_n—NR—(CRR)_m—$, where n and m are each independently an integer from 0 to 4. As used herein, "oxaalkylene" refers to $—(CRR)_n—O—(CRR)_m—$, where n and m are each independently an integer from 0 to 4. As used herein, "thiaalkylene" refers to $—(CRR)_n—S—(CRR)_m—$, $—(CRR)_n—S(=O)—(CRR)_m—$, and $—(CRR)_n—S(=O)_2—(CRR)_m—$, where n and m are each independently an integer from 0 to 4. In certain embodiments herein, the "R" groups in the definitions of azaalkylene, oxaalkylene and thiaalkylene are each independently selected from hydrogen and $Q^1$, as defined herein.

As used herein, "alkenylene" refers to a straight, branched or cyclic, in one embodiment straight or branched, divalent aliphatic hydrocarbon group, in certain embodiments having from 2 to about 20 carbon atoms and at least one double bond, in other embodiments 1 to 12 carbons. In further embodiments, alkenylene groups include lower alkenylene. There may be optionally inserted along the alkenylene group one or more oxygen, sulfur or substituted or unsubstituted nitrogen atoms, where the nitrogen substituent is alkyl. Alkenylene groups include, but are not limited to, —CH=CH—CH=CH— and $—CH=CH—CH_2—$. The term "lower alkenylene" refers to alkenylene groups having 2 to 6 carbons. In certain embodiments, alkenylene groups are lower alkenylene, including alkenylene of 3 to 4 carbon atoms.

As used herein, "alkynylene" refers to a straight, branched or cyclic, in certain embodiments straight or branched, divalent aliphatic hydrocarbon group, in one embodiment having from 2 to about 20 carbon atoms and at least one triple bond, in another embodiment 1 to 12 carbons. In a further embodiment, alkynylene includes lower alkynylene. There may be optionally inserted along the alkynylene group one or more oxygen, sulfur or substituted or unsubstituted nitrogen atoms, where the nitrogen substituent is alkyl. Alkynylene groups include, but are not limited to, —C≡C—C≡C—, —C≡C— and $—C≡C—CH_2—$. The term "lower alkynylene" refers to alkynylene groups having 2 to 6 carbons. In certain embodiments, alkynylene groups are lower alkynylene, including alkynylene of 3 to 4 carbon atoms.

As used herein, "alk(en)(yn)ylene" refers to a straight, branched or cyclic, in certain embodiments straight or branched, divalent aliphatic hydrocarbon group, in one embodiment having from 2 to about 20 carbon atoms and at least one triple bond, and at least one double bond; in another embodiment 1 to 12 carbons. In further embodiments, alk(en)(yn)ylene includes lower alk(en)(yn) ylene. There may be optionally inserted along the alkynylene group one or more oxygen, sulfur or substituted or unsubstituted nitrogen atoms, where the nitrogen substituent is alkyl. Alk(en)(yn)ylene groups include, but are not limited to, —C═C—$(CH_2)_n$—C≡C—, where n is 1 or 2. The term "lower alk(en)(yn)ylene" refers to alk(en)(yn)ylene groups having up to 6 carbons. In certain embodiments, alk(en)(yn) ylene groups have about 4 carbon atoms.

As used herein, "cycloalkylene" refers to a divalent saturated mono- or multicyclic ring system, in certain embodiments of 3 to 10 carbon atoms, in other embodiments 3 to 6 carbon atoms; cycloalkenylene and cycloalkynylene refer to divalent mono- or multicyclic ring systems that respectively include at least one double bond and at least one triple bond. Cycloalkenylene and cycloalkynylene groups may, in certain embodiments, contain 3 to 10 carbon atoms, with cycloalkenylene groups in certain embodiments containing 4 to 7 carbon atoms and cycloalkynylene groups in certain embodiments containing 8 to 10 carbon atoms. The ring systems of the cycloalkylene, cycloalkenylene and cycloalkynylene groups may be composed of one ring or two or more rings which may be joined together in a fused, bridged or spiro-connected fashion. "Cycloalk(en)(yn) ylene" refers to a cycloalkylene group containing at least one double bond and at least one triple bond.

As used herein, "substituted alkylene," "substituted alkenylene," "substituted alkynylene," "substituted cycloalkylene," "substituted cycloalkenylene," and "substituted cycloalkynylene" refer to alkylene, alkenylene, alkynylene, cycloalkylene, cycloalkenylene and cycloalkynylene groups, respectively, that are substituted with one or more substituents, in certain embodiments one to three or four substituents, where the substituents are as defined herein, generally selected from $Q^1$.

As used herein, "arylene" refers to a monocyclic or polycyclic, in certain embodiments monocyclic, divalent aromatic group, in one embodiment having from 5 to about 20 carbon atoms and at least one aromatic ring, in another embodiment 5 to 12 carbons. In further embodiments, arylene includes lower arylene. Arylene groups include, but are not limited to, 1,2-, 1,3- and 1,4-phenylene. The term "lower arylene" refers to arylene groups having 5 or 6 carbons.

As used herein, "heteroarylene" refers to a divalent monocyclic or multicyclic aromatic ring system, in one embodiment of about 5 to about 15 members where one or more, in certain embodiments 1 to 3, of the atoms in the ring system is a heteroatom, that is, an element other than carbon, including but not limited to, nitrogen, oxygen or sulfur.

As used herein, "heterocyclylene" refers to a divalent monocyclic or multicyclic non-aromatic ring system, in certain embodiments of 3 to 10 members, in one embodiment 4 to 7 members, in another embodiment 5 to 6 members, where one or more, including 1 to 3, of the atoms in the ring system is a heteroatom, that is, an element other than carbon, including but not limited to, nitrogen, oxygen or sulfur.

As used herein, "substituted arylene," "substituted heteroarylene" and "substituted heterocyclylene" refer to arylene, heteroarylene and heterocyclylene groups, respectively, that are substituted with one or more substituents, in certain embodiments one to three of four substituents, where the substituents are as defined herein, generally selected from $Q^1$.

As used herein, "alkylidene" refers to a divalent group, such as ═CR'R", which is attached to one atom of another group, forming a double bond. Alkylidene groups include, but are not limited to, methylidene (═$CH_2$) and ethylidene (═$CHCH_3$). As used herein, "arylalkylidene" refers to an alkylidene group in which either R' or R" is an aryl group. "Cycloalkylidene" groups are those where R' and R" are linked to form a carbocyclic ring. "Heterocyclylidene" groups are those where at least one of R' and R" contain a heteroatom in the chain, and R' and R" are linked to form a heterocyclic ring.

As used herein, "amido" refers to the divalent group —C(O)NH—. "Thioamido" refers to the divalent group —C(S)NH—. "Oxyamido" refers to the divalent group —OC(O)NH—. "Thiaamido" refers to the divalent group —SC(O)NH—. "Dithiaamido" refers to the divalent group —SC(S)NH—. "Ureido" refers to the divalent group —HNC(O)NH—. "Thioureido" refers to the divalent group —HNC(S)NH—.

As used herein, "semicarbazide" refers to —NHC(O) NHNH—. "Carbazate" refers to the divalent group —OC (O)NHNH—. "Isothiocarbazate" refers to the divalent group —SC(O)NHNH—. "Thiocarbazate" refers to the divalent group —OC(S)NHNH—. "Sulfonylhydrazide" refers to the group —$SO_2$NHNH—. "Hydrazide" refers to the divalent group —C(O)NHNH—. "Azo" refers to the divalent group —N═N—. "Hydrazinyl" refers to the divalent group —NH—NH—.

Where the number of any given substituent is not specified (e.g., "haloalkyl"), there may be one or more substituents present. For example, "haloalkyl" may include one or more of the same or different halogens. As another example, "$C_{1-3}$alkoxyphenyl" may include one or more of the same or different alkoxy groups containing one, two or three carbons.

As used herein, the following terms have their accepted meaning in the chemical literature:

| | |
|---|---|
| AcOH | acetic acid |
| $CHCl_3$ | chloroform |
| conc | concentrated |
| DBU | 1,8-diazabicyclo[5.4.0]undec-7-ene |
| DCM | dichloromethane |
| DME | 1,2-dimethoxyethane |
| DMF | N,N-dimethylformamide |
| DMSO | dimethylsulfoxide |
| EtOAc | ethyl acetate |
| EtOH | ethanol (100%) |
| $Et_2O$ | diethyl ether |
| Hex | hexanes |
| $H_2SO_4$ | sulfuric acid |
| MeCN | acetonitrile |
| MeOH | methanol |
| Pd/C | palladium on activated carbon |
| TEA | triethylamine |
| THF | tetrahydrofuran |
| TFA | trifluoroacetic acid |

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942–944).

B. Heterocyclic Modulators of Nuclear Receptors

Compounds for use in compositions and methods for modulating the activity of nuclear receptors are provided. In particular, compounds for use in compositions and methods for modulating farnesoid X receptor (FXR), liver X receptors (LXRα and LXRβ) and/or orphan nuclear receptors, are provided.

In certain embodiments, the compounds are thiazolidinones, i.e., compounds of formulae I where $X^2$ is S and $X^3$ is O, that are substituted with a heterocyclylene group and an imine moiety. Thus, in these embodiments, the compounds have formulae II:

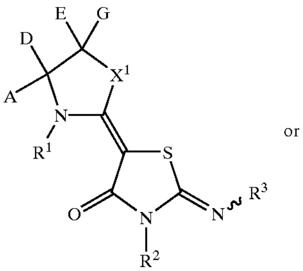

or

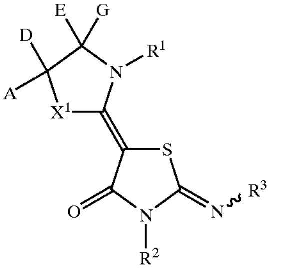

or a pharmaceutically acceptable derivative thereof, where A, D, E and G are selected from (i) or (ii) as follows:

(i) A and G are each independently selected from hydrogen, substituted or unsubstituted alkyl, substituted or unsubstituted alkenyl, substituted or unsubstituted alkynl, substituted or unsubstituted cycloalkyl, substituted or unsubstituted heterocyclyl, substituted or unsubstituted cycloalkylalkyl, substituted or unsubstituted heterocyclyalkyl, substituted or unsubstituted aryl, substituted or unsubstituted heteroaryl, substituted or unsubstituted aralkyl, substituted or unsubstituted heteroaralkyl, substituted or unsubstituted heteroarylium, substituted or unsubstituted heteroaryliumalkyl, halo, pseudohalo, $OR^{10}$, $SR^{10}$, $S(=O)R^{13}$, $NR^{11}R^{12}$ and $C(=J)R^{13}$, or A and G together form substituted or unsubstituted alkylene, substituted or unsubstituted azaalkylene, substituted or unsubstituted oxaalkylene, substituted or unsubstituted thiaalkylene, substituted or unsubstituted alkenylene, substituted or unsubstituted alkynylene, substituted or unsubstituted 1,3-butadienylene, substituted or unsubstituted 1-aza-1,3-butadienylene, or substituted or unsubstituted 2-aza-1,3-butadienylene.

D and E are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocylyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo and pseudohalo or D and E together form a bond; or (ii) A and D; or E and G; together form substituted or unsubstituted alkylene, substituted or unsubstituted azaalkylene, substituted or unsubstituted oxaalkylene, or substituted or unsubstituted thiaalkylene; and the others of A, D, E and G are selected as in (i);

$X^1$ is selected from O, S, S(=O), $S(=O)_2$, Se, $NR^5$, $CR^6R^7$ and $CR^8=CR^9$; $R^1$ and $R^2$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted heteroarylium, substituted or unsubstituted heteroaryliumalkyl, $OR^{10}$, $SR^{10}$, $S(=O)R^{13}$, $S(=O)_2R^{13}$, $NR^{11}R^{12}$ and $C(=J)R^{13}$; $R^3$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted heteroarylium, substituted or unsubstituted aralkyl, substituted or unsubstituted heteroaralkyl, substituted or unsubstituted heteroaryliumalkyl, $OR^{10}$, $SR^{10}$, $S(=O)R^{13}$, $S(=O)_2R^{13}$, $NR^{11}R^{12}$ and $C(=J)R^{13}$; where:

$R^5$, $R^6$, $R^7$, $R^8$ and $R^9$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo, pseudohalo, $OR^{10}$, $NR^{14}R^{15}$ and $C(=J)R^{13}$;

$R^{10}$, $R^{11}$ and $R^{12}$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl or $C(=J)R^{13}$;

J is O, S or $NR^{14}$;

$R^{13}$ is selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, pseudohalo, $OR^{16}$ and $NR^{14}R^{15}$;

$R^{14}$, $R^{15}$ and $R^{16}$ are each independently selected from hydrogen, alkyl, alkenyl, alkynyl, cycloalkyl, heterocyclyl, cycloalkylalkyl, heterocyclylalkyl, aryl, heteroaryl, aralkyl and heteroaralkyl;

where the alkyl, alkenyl, alkynyl, cycloalkyl, heterocyclyl, cycloalkylalkyl, heterocyclylalkyl, aryl, heteroaryl, heteroarylium, aralkyl, heteroaralkyl and heteroaryliumalkyl moieties of $R^1$, $R^2$, $R^3$, $R^5$, $R^6$, $R^7$, $R^8$, $R^9$, $R^{10}$, $R^{11}$, $R^{12}$ and $R^{13}$ are unsubstituted or substituted with one or more substituents each independently selected from $Q^1$, where $Q^1$ is halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, imino, hydroxyimino, alkoxyimino, aryloxyimino, aralkoxyimino, alkylazo, arylazo, aralkylazo, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{51}R^{52}R^{53}$, $P(R^{50})_2$, $P(=O)(R^{50})_2$, $OP(=O)(R^{50})_2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy (i.e., $—O—(CH_2)_y—O—$), thioalkylenoxy (i.e., $—S—(CH_2)_y—O—$)or alkylenedithioxy (i.e., $—S—(CH_2)_y—S—$) where y is 1 or 2; or two $Q^1$ groups, which substitute the same atom, together form alkylene;

each $Q^1$ is independently unsubstituted or substituted with one or more substituents each independently selected from $Q^2$;

each $Q^2$ is independently halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{51}R^{52}R^{53}$, $P(R^{50})_2$, $P(=O)(R^{50})_2$, $OP(=O)(R^{50})_2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^2$ groups, which substitute atoms in a 1,2 or 1,3 arrangement, together form alkylenedioxy (i.e., $—O—(CH_2)_y—O—$), thioalkylenoxy (i.e., $—S—(CH_2)_y—O—$)or alkylenedithioxy (i.e., $—S—(CH_2)_y—S—$) where y is 1 or 2; or two $Q^2$ groups, which substitute the same atom, together form alkylene;

each Q2 group is independently unsubstituted or substituted with one or more, in one embodiment one, two or three, substituents each independently selected from alkyl, halo and pseudohalo;

$R^{50}$ is hydroxy, alkoxy, aralkoxy, alkyl, heteroaryl, heterocyclyl, aryl or $—NR^{70}R^{71}$, where $R^{70}$ and $R^{71}$ are each independently hydrogen, alkyl, aralkyl, aryl, heteroaryl, heteroaralkyl or heterocyclyl, or $R^{70}$ and $R^{71}$ together form alkylene, azaalkylene, oxaalkylene or thiaalkylene;

$R^{51}$, $R^{52}$ and $R^{53}$ are each independently hydrogen, alkyl, aryl, aralkyl, heteroaryl, heteroaralkyl, heterocyclyl or heterocyclylalkyl;

$R^{60}$ is hydrogen, alkyl, aryl, aralkyl, heteroaryl, heteroaralkyl, heterocyclyl or heterocyclylalkyl;

$R^{63}$ is alkoxy, aralkoxy, alkyl, heteroaryl, heterocyclyl, aryl or $—NR^{70}R^{71}$.

In another embodiment, the compounds have formulae II:

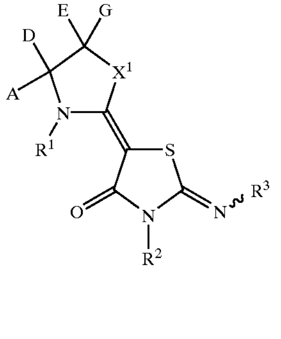

or

-continued

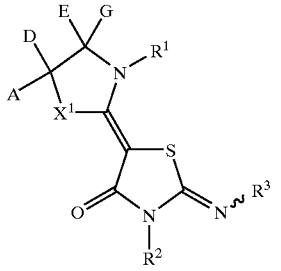

or a pharmaceutically acceptable derivative thereof, where A, D, E and G are selected from (i) or (ii) as follows:

(i) A and G are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted heteroarylium, substituted or unsubstituted heteroaryliumalkyl, halo, pseudohalo, $OR^{10}$, $SR^{10}$, $S(=O)R^{13}$, $S(=O)_2R^{13}$, $NR^{11}R^{12}$ and $C(=J)R^{13}$, or A and G together form substituted or unsubstituted alkylene, substituted or unsubstituted azaalkylene, substituted or unsubstituted oxaalkylene, substituted or unsubstituted thiaalkylene, substituted or unsubstituted alkenylene, substituted or unsubstituted alkynylene, substituted or unsubstituted 1,3-butadienylene, substituted or unsubstituted 1-aza-1,3-butadienylene, or substituted or unsubstituted 2-aza-1,3-butadienylene;

D and E are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo and pseudohalo or D and E together form a bond; or (ii) A and D; or E and G; together form substituted or unsubstituted alkylene, substituted or unsubstituted azaalkylene, substituted or unsubstituted oxaalkylene, or substituted or unsubstituted thiaalkylene; and the others of A, D, E and G are selected as in (i);

$X^1$ is selected from O, S, S(=O), $S(=O)_2$, Se, $NR^5$, $CR^5R^7$ and $CR^8=CR^9$; $R^1$ and $R^2$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted heteroarylium, substituted or unsubstituted heteroaryliumalkyl, $OR^{10}$, $SR^{10}$, $S(=O)R^{13}$, $S(=O)_2R^{13}$, $NR^{11}R^{12}$ and $C(=J)R^{13}$; $R^3$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted heteroarylium, substituted or unsubstituted aralkyl, substituted or unsubstituted heteroaralkyl, substituted or unsubstituted heteroaryliumalkyl, $OR^{10}$, $SR^{10}$, $S(=O)R^{13}$, $S(=O)_2R^{13}$, $NR^{11}R^{12}$ and $C(=J)R^{13}$; where:

$R^5$, $R^6$, $R^7$, $R^8$ and $R^9$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo, pseudohalo, $OR^{10}$, $NR^{14}R^{15}$ and $C(=J)R^{13}$;

$R^{10}$, $R^{11}$ and $R^{12}$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl or $C(=J)R^{13}$;

J is O, S or $NR^{14}$;

$R^{13}$ is selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, pseudohalo, $OR^{16}$ and $NR^{14}R^{15}$;

$R^{14}$, $R^{15}$ and $R^{16}$ are each independently selected from hydrogen, alkyl, alkenyl, alkynyl, cycloalkyl, heterocyclyl, cycloalkylalkyl, heterocyclylalkyl, aryl, heteroaryl, aralkyl and heteroaralkyl;

where the alkyl, alkenyl, alkynyl, cycloalkyl, heterocyclyl, cycloalkylalkyl, heterocyclylalkyl, aryl, heteroaryl, heteroarylium, aralkyl, heteroaralkyl and heteroaryliumalkyl moieties of $R^1$, $R^2$, $R^3$, $R^5$, $R^6$, $R^7$, $R^8$, $R^9$, $R^{10}$, $R^{11}$, $R^{12}$ and $R^{13}$ are unsubstituted or substituted with one or more substituents each independently selected from $Q^1$, where $Q^1$ is halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $-N^+R^{51}R^{52}R^{53}$, $P(R^{50})_2$, $P(=O)(R^{50})_2$, $OP(=O)(R^{50})_2$, $-NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy (i.e., $-O-(CH_2)_y-O-$), thioalkylenoxy (i.e., $-S-(CH_2)_y-O-$)or alkylenedithioxy (i.e., $-S-(CH_2)_y-S-$) where y is 1 or 2; or two $Q^1$ groups, which substitute the same atom, together form alkylene;

each $Q^1$ is independently unsubstituted or substituted with one or more substituents each independently selected from $Q^2$;

each $Q^2$ is independently halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{51}R^{52}R^{53}$, $P(R^{50})_2$, $P(=O)(R^{50})_2$, $OP(=O)(R^{50})2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^2$ groups, which substitute atoms in a 1,2 or 1,3 arrangement, together form alkylenedioxy (i.e., $—O—(CH_2)_y—O—$), thioalkylenoxy (i.e., $—S—(CH2)_y—O—$)or alkylenedithioxy (i.e., $—S—(CH_2)_y—S—$) where y is 1 or 2; or two $Q^2$ groups, which substitute the same atom, together form alkylene;

$R^{50}$ is hydroxy, alkoxy, aralkoxy, alkyl, heteroaryl, heterocyclyl, aryl or $—NR^{70}R^{71}$, where $R^{70}$ and $R^{71}$ are each independently hydrogen, alkyl, aralkyl, aryl, heteroaryl, heteroaralkyl or heterocyclyl, or $R^{70}$ and $R^{71}$ together form alkylene, azaalkylene, oxaalkylene or thiaalkylene;

$R^{51}$, $R^{52}$ and $R^{53}$ are each independently hydrogen, alkyl, aryl, aralkyl, heteroaryl, heteroaralkyl, heterocyclyl or heterocyclylalkyl;

$R^{60}$ is hydrogen, alkyl, aryl, aralkyl, heteroaryl, heteroaralkyl, heterocyclyl or heterocyclylalkyl;

$R^{63}$ is alkoxy, aralkoxy, alkyl, heteroaryl, heterocyclyl, aryl or $—NR^{70}R^{71}$.

In another embodiment, A and G are each independently selected from hydrogen, substituted or unsubstituted alkyl, or substituted or unsubstituted aryl, or together form substituted or unsubstituted 1,3-butadienyl. In a further embodiment, A and G are each independently hydrogen, substituted or unsubstituted methyl, substituted or unsubstituted naphthyl, or substituted or unsubstituted phenyl, or together form 1,3-butadienyl. In another embodiment, A and G are both hydrogen.

In another embodiment, D and E are each hydrogen, or together form a bond.

In another embodiment, the compounds for use in the compositions and methods provided herein have formulae I where D and E together form a bond, and A and G together form 1,3-butadienyl. Thus, in this embodiment, the compounds have formulae III:

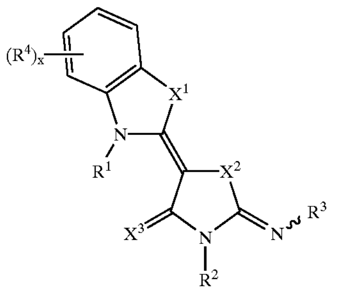

or

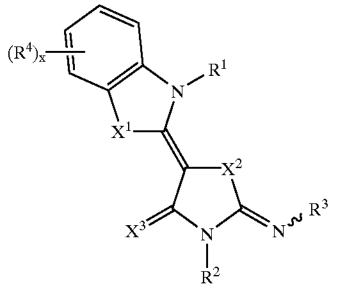

or a pharmaceutically acceptable derivative thereof, where $R^1$, $R^2$, $R^3$, $X^1$, $X^2$ and $X^3$ are selected as above; each $R^4$ is independently substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted guanidino, substituted or unsubstituted isothioureido, halo, pseudohalo, $OR^{10}$, $SR^{10}$, $S(=O)R^{13}$, $S(=O)_2R^{13}$, $NR^{11}R^{12}$ or $C(=J)R^{13}$; x is an integer from 0 to 4; and the amino, alkyl, alkenyl, alkynyl, cycloalkyl, heterocyclyl, cycloalkylalkyl, heterocyclylalkyl, aryl, heteroaryl, heteroarylium, aralkyl, heteroaralkyl and heteroaryliumalkyl moieties of $R^4$ are unsubstituted or substituted with one or more substituents each independently selected from $Q^2$, as defined above.

In another embodiment, the compounds for use in the compositions and methods provided herein have formulae IV:

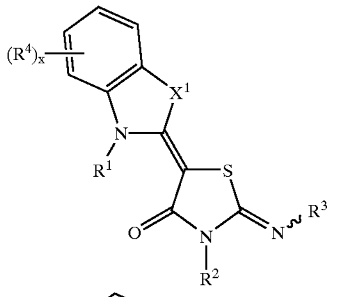

or

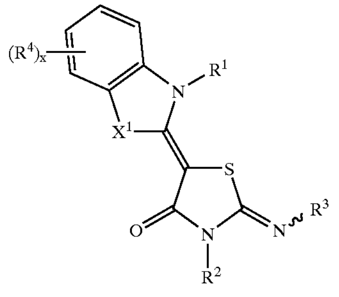

or a pharmaceutically acceptable derivative thereof, where $R^1$, $R^2$, $R^3$, $X^1$, $X^2$ and $X^3$ are selected as above; each $R^4$ is independently substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted guanidino, substituted or unsubstituted isothioureido, halo, pseudohalo, $OR^{10}$, $SR^{10}$, $S(=O)R^{13}$, $S(=O)_2R^{13}$, $NR^{11}R^{12}$ or $C(=J)R^{13}$; x is an integer from 0 to 4; and the amino, alkyl, alkenyl, alkynyl, cycloalkyl, heterocyclyl, cycloalkylalkyl, heterocyclylalkyl, aryl, heteroaryl, heteroarylium, aralkyl, heteroaralkyl and heteroaryliumalkyl moieties of $R^4$ are unsubstituted or-substituted with one or more, in certain embodiments one to three or four, substituents each independently selected from $Q^2$, as defined above.

In certain embodiments herein, the compounds are of formulae III or IV, and are selected with the proviso that when $R^3$ is substituted or unsubstituted heteroarylium then the heteroatom substituent is not alkyl or aryl. In another embodiment, the compounds are of formulae III or IV, and are selected with the proviso that $R^3$ is not substituted or unsubstituted heteroarylium or substituted or unsubstituted heteroaryliumalkyl. In other embodiments, the compounds are of formula III or IV and are selected with the proviso that $R^3$ is not heteroaryl. In further embodiments, the compounds are of formula III or IV and are selected with the proviso that $R^3$ is not alkyl. In another embodiment, the compounds are of formula III or IV and are selected with the proviso that $R^3$ is not heterocycloaryl (i.e., an aryl groups possessing a fused heterocyclic moiety).

In certain embodiments herein, $X^1$ is O, S or $NR^5$. In other embodiments, $X^1$ is O or S. In another embodiment, $X^1$ is S.

In other embodiments, $R^1$ is substituted or unsubstituted alkyl. In further embodiments, $R^1$ is methyl.

In another embodiment, $R^2$ is substituted or unsubstituted alkyl or substituted or unsubstituted aralkyl. In further embodiments, $R^2$ is ethyl, n-butyl or benzyl. In another embodiment, $R^2$ is benzyl. In another embodiment, $R^2$ is substituted or unsubstituted heteroaralkyl. In another embodiment, $R^2$ is pyridylmethyl. In another embodiment, $R^2$ is picolyl (i.e., 2-, 3-, or 4-pyridylmethyl). In another embodiment, $R^2$ is 2-furylmethyl. In another embodiment, $R^2$ is 3-pyridylmethyl.

In another embodiment, $R^3$ is substituted or unsubstituted aryl or substituted or unsubstituted heteroaryl. In further embodiments, $R^3$ is substituted or unsubstituted phenyl, substituted or unsubstituted naphthyl, substituted or unsubstituted pyridyl, substituted or unsubstituted indazolyl, or substituted or unsubstituted quinolinyl. In another embodiment, $R^3$ is substituted or unsubstituted quinolyl, substituted or unsubstituted phenyl, substituted or unsubstituted naphthyl, substituted or unsubstituted isoquinolyl, substituted or unsubstituted pyridyl, or substituted or unsubstituted indazolyl. In certain embodiments, $R^3$ is substituted or unsubstituted phenyl or substituted or unsubstituted naphthyl. In another embodiment, $R^3$ is substituted or unsubstituted phenyl.

In another embodiment, $Q^1$ is selected from halo, hydroxy, nitrile, nitro, hydroxycarbonyl, alkyl, haloalkyl, polyhaloalkyl, heteroaryl, alkylcarbonyl, alkoxycarbonyl, aminocarbonyl, alkoxy, perfluoroalkoxy, aralkoxy, hydroxyimino, alkoxyimino, aralkoxyimino, arylazo, haloalkylcarbonylamino, amino, alkylamino, dialkylamino, haloalkylamino, alkylcarbonylamino, dialkylcarbonyloxy or heterocyclyl; or two $Q^1$ groups, which substitute atoms in a 1,2 arrangement, form alkylenedioxy. In another embodiment, $Q^1$ is selected from halo, hydroxy, nitrile, nitro, hydroxycarbonyl, alkyl, haloalkyl, polyhaloalkyl, heteroaryl, alkylcarbonyl, alkoxycarbonyl, aminocarbonyl, alkoxy, perfluoroalkoxy, aralkoxy, amino, alkylamino, dialkylamino, haloalkylamino, alkylcarbonylamino, dialkylcarbonyloxy or heterocyclyl; or two $Q^1$ groups, which substitute atoms in a 1,2 arrangement, form alkylenedioxy. In further embodiments, $Q^1$ is methoxy, dimethylamino, $NH_2$, benzyloxy, hydroxy, CN, isopropyl, methyl, nitro, ethylamino, trifluoromethyl, acetyl, chloro, n-propyl, ethoxy, methylcarbonylamino, $CONH_2$, methoxycarbonyl, methylamino, trifluoromethoxy, imidazolyl, hydroxycarbonyl, isopropylamino, tert-butylamino, 2,2,2-trifluoroethylamino, piperidinyl, dimethylaminocarbonyloxy, 2-hydroxyethoxy, 2-(N-morpholinyl)ethoxy or morpholinyl, or two $Q^1$ groups, which substitute atoms in a 1,2 arrangement, form methylenedioxy. In another embodiment, $Q^1$ is hydroxycarbonyl or ethylamino.

In further embodiments, the compounds for use in the compositions and methods provided herein are of formulae IV where x is 0, $R^1$ is methyl, $R^2$ is benzyl, $X^1$ is S and $R^3$ is a substituted or unsubstituted phenyl group. Thus, in these embodiments, the compounds have formulae V:

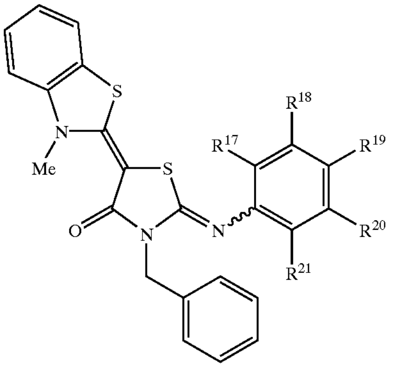

or

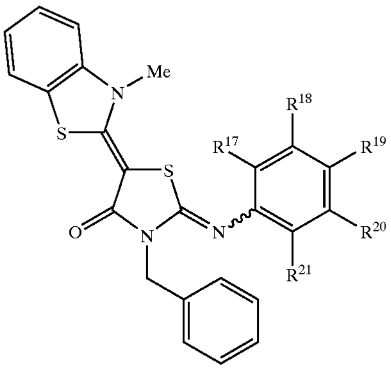

or a pharmaceutically acceptable derivative thereof, where $R^{17}$, $R^{18}$, $R^{19}$, $R^{20}$ and $R^{21}$ are each independently selected from hydrogen, halo, pseudohalo, hydroxyl, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^{+}R^{51}R^{52}R^{53}$, $P(R^{50})_2$, $P(=O)(R^{50})_2$, $OP(=O)(R^{50})_2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl, or any two of $R^{17}$, $R^{18}$, $R^{19}$, $R^{20}$ and $R^{21}$, which substitute adjacent carbons on the ring, together form alkylenedioxy; and the aryl and heteroaryl groups of $R^{17}$, $R^{18}$, $R^{19}$, $R^{20}$ and $R^{21}$ are unsubstituted or substituted with one or more substituents, in one embodiment one to three or four substituents, each independently selected from $R^{30}$, where $R^{30}$ is alkyl, halo, pseudohalo, alkoxy, aryloxy or alkylenedioxy.

In another embodiment, $R^{17}$, $R^{18}$, $R^{19}$, $R^{20}$ and $R^{21}$ are each independently selected from hydrogen, halo, hydroxy, nitrile, nitro, hydroxycarbonyl, alkyl, haloalkyl, polyhaloalkyl, heteroaryl, alkylcarbonyl, alkoxycarbonyl, aminocarbonyl, alkoxy, perfluoroalkoxy, aralkoxy, amino, alkylamino, dialkylamino, haloalkylamino, alkylcarbonylamino or heterocyclyl; or any two of $R^{17}$, $R^{18}$, $R^{19}$, $R^{20}$ and $R^{21}$, which substitute adjacent carbons on the ring, form alkylenedioxy. In further embodiments, $R^{17}$, $R^{18}$, $R^{19}$, $R^{20}$ and $R^{21}$ are each independently hydrogen, methoxy, dimethylamino, $NH_2$, benzyloxy, hydroxy, CN, isopropyl, methyl, nitro, ethylamino, trifluoromethyl, acetyl, chloro, n-propyl, ethoxy, methylcarbonylamino, $CONH_2$, methoxycarbonyl, methylamino, trifluoromethoxy, imidazolyl, hydroxycarbonyl, isopropylamino, tert-butylamino, 2,2,2-trifluoroethylamino, piperidinyl or morpholinyl, or any two of $R^{17}$, $R^{18}$, $R^{19}$, $R^{20}$ and $R^{21}$, which substitute adjacent carbons on the ring, form methylenedioxy.

In another embodiment, A is phenyl which is unsubstituted or is substituted with one or more, in one embodiment, one, two or three, groups each independently selected from $Q^1$.

In another embodiment, the compounds for use in the compositions and methods provided herein have formulae II where $X^1$ is S; $R^1$ is methyl; $R^2$ is benzyl; A is phenyl; G is hydrogen; and D and E together form a bond. Thus, in this embodiment, the compounds have formulae VI:

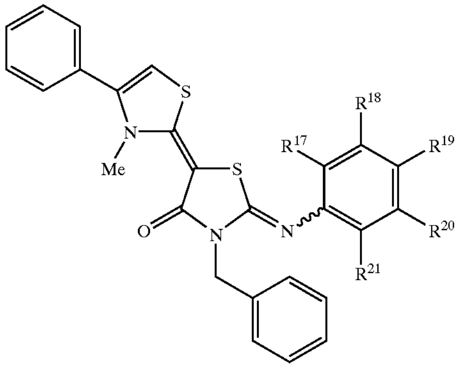

or

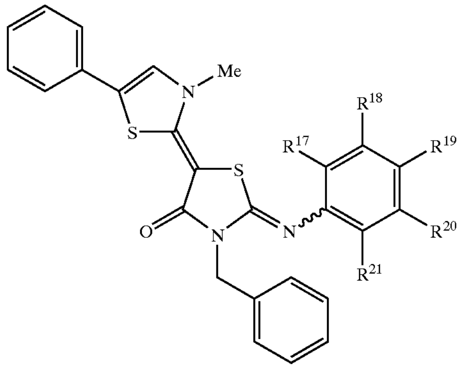

or a pharmaceutically acceptable derivative thereof, where $R^{17}$, $R^{18}$, $R^{19}$, $R^{20}$ and $R^{21}$ are selected as above.

In another embodiment, the compounds for use in the compositions and methods provided herein have formulae II where $X^1$ is S; $R^1$ is methyl; $R^2$ is benzyl; A and G are hydrogen; and D and E together form a bond. Thus, in this embodiment, the compounds have formulae VII:

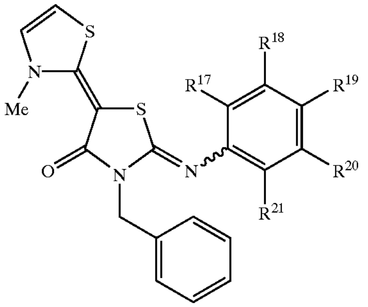

or

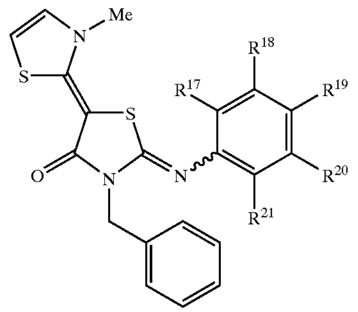

or a pharmaceutically acceptable derivative thereof, where $R^{17}$, $R^{18}$, $R^{19}$, $R^{20}$ and $R^{21}$ are selected as above.

In another embodiment, the compounds for use in the compositions and methods provided herein have formulae II where $X^1$ is S; $R^1$ is methyl; $R^2$ is benzyl; and A, G, D and E are hydrogen. Thus, in this embodiment, the compounds have formulae VIII:

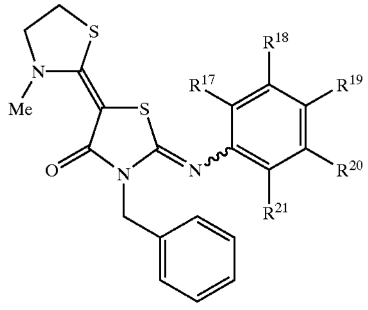

or

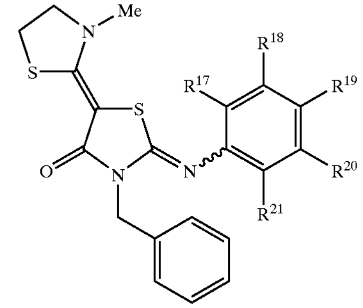

or a pharmaceutically acceptable derivative thereof, where $R^{17}$, $R^{18}$, $R^{19}$, $R^{20}$ and $R^{21}$ are selected as above.

In another embodiment, the compounds for use in the compositions and methods provided herein have formulae II where $X^1$ is S; $R^1$ is methyl; $R^2$ is benzyl; A is phenyl; G is methyl; and D and E together form a bond. Thus, in this embodiment, the compounds have formulae IX:

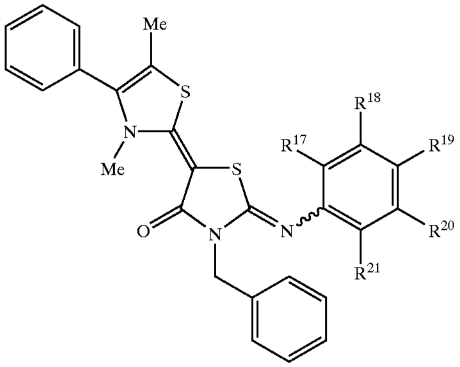

or

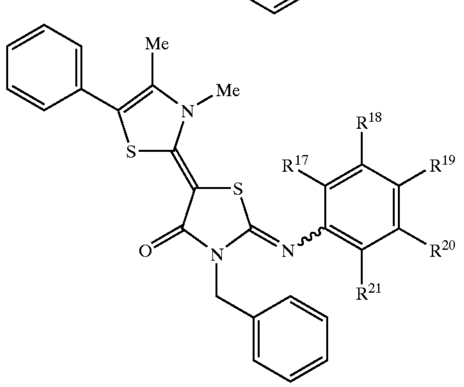

or a pharmaceutically acceptable derivative thereof, where $R^{17}$, $R^{18}$, $R^{19}$, $R^{20}$ and $R^{21}$ are selected as above.

In another embodiment, the compounds provided herein have formulae V–XI, where $R^{17}$, $R^{18}$, $R^{19}$, $R^{20}$ and $R^{21}$ are each independently selected from (i) or (ii) as follows:

(i) $R^{21}$ is ethylamino; $R^{18}$ is cyano; and $R^{17}$, $R^{19}$ and $R^{20}$ are each hydrogen; or (ii) $R^{17}$ is ethylamino; $R^{20}$ is cyano; and $R^{18}$, $R^{19}$ and $R^{21}$ are each hydrogen.

In certain embodiments, the compounds have formulae I, where $X^1$, $X^2$ and $X^3$ are selected from (i) or (ii) as follows: (i) $X^1$, $X^2$ and $X^3$ are each independently S, O or $NR^5$; or (ii) $X^1$ is —$CR^8$═$CR^9$—, where $R^8$ and $R^9$ are as defined herein, and $X^2$ and $X^3$ are each independently S, O or $NR^5$; $R^1$ is substituted or unsubstituted alkyl, where there are 0 to 6 substituents selected from alkoxy, alkoxyalkyl, hydroxycarbonyl, alkylcarbonyloxy, hydroxy, halo, pseudohalo, aryl and heteroaryl; $R^2$ is substituted or unsubstituted aralkyl, substituted or unsubstituted aryl, substituted or unsubstituted alkenyl, substituted or unsubstituted alkyl, substituted or unsubstituted cycloalkyl, substituted or unsubstituted heteroaralkyl, or substituted or unsubstituted heterocyclylalkyl; where there are 0 or 1 substituents selected from alkoxycarbonyl and hydroxycarbonyl; $R^3$ is substituted or unsubstituted heteroaryl, substituted or unsubstituted aryl, or substituted or unsubstituted aralkyl; where there are 0 to 5 substituents selected from alkylamino, cyano, cycloalkyl, hydroxy, alkoxy, dialkylamino, amino, heterocyclyl, aralkoxy, alkyl, nitro, haloalkyl, alkylcarbonyl, halo, alkylcarbonylamino, alkoxyalkylcarbonylamino, dialkylaminoalkylcarbonylamino, aminocarbonyl, alkoxycarbonyl, aralkylamino, cycloalkylamino, heterocyclylamino, haloalkylamino, haloalkoxy, hydroxycarbonyl, aminosulfonyl, alkylcarbonylaminosulfonyl, or haloalkylcarbonylamino, or any two substituents, which substitute atoms in a 1,2 or 1,3 arrangement, together form alkylenedioxy; A and G are each independently selected from hydrogen, substituted or unsubstituted aryl, substituted or unsubstituted alkyl, substituted or unsubstituted alkoxycarbonyl, hydroxycarbonyl, and substituted or unsubstituted alkylcarbonyl, where there are 0 to 5 substituents selected from aryl, haloalkyl, haloalkoxy, nitro, halo, pseudohalo, hydroxy, alkyl and alkoxy, or A and G together form substituted or unsubstituted alkylene, substituted or unsubstituted azaalkylene or substituted or unsubstituted 1,3-butadienylene, in one embodiment substituted or unsubstituted alkylene, where there are 0 to 4 substituents selected from halo, pseudohalo, alkoxy, nitro, haloalkyl, alkylcarbonylamino, hydroxy, alkylaminocarbonyloxy, alkoxycarbonylalkoxy, aminocarbonylalkoxy, hydroxyalkoxy, alkyl, haloalkylaminocarbonyloxy and alkylaminoalkoxy; D and E are each hydrogen, or together form a bond; and $R^5$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo, pseudohalo, $OR^{10}$, $SR^{10}$, $S(═O)R^{13}$, $S(═O)_2R^{13}$, $NR^{14}R^{15}$ or $C(═J)R^{13}$; $R^{10}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl or $C(═J)R^{13}$; J is O, S or $NR^{14}$; $R^{13}$ is selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, pseudohalo, $OR^{16}$ and $NR^{14}R^{15}$; $R^{14}$, $R^{15}$ and $R^{16}$ are each independently selected from hydrogen, alkyl, alkenyl, alkynyl, cycloalkyl, heterocyclyl, cycloalkylalkyl, heterocyclylalkyl, aryl, heteroaryl, aralkyl and heteroaralkyl; where the alkyl, alkenyl, alkynyl, cycloalkyl, heterocyclyl, cycloalkylalkyl, heterocyclylalkyl, aryl, heteroaryl, aralkyl and heteroaralkyl moieties of $R^5$, $R^{10}$ and $R^{13}$ are unsubstituted or substituted with one or more substituents each independently selected from $Q^1$, where $Q^1$ is halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, imino, hydroxyimino, alkoxyimino, aralkoxyimino, arylazo, haloalkylcarbonylamino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{51}R^{52}R^{53}$, $P(R^{50})_2$, $P(═O)(R^{50})_2$, $OP(═O)(R^{50})_2$, $—NR^{60}C(═O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy, thioalkylenoxy or alkylenedithioxy; or two $Q^1$ groups, which substitute the same atom, together form alkylene; each $Q^1$ is independently unsubstituted or substituted with one or more substituents each independently selected from $Q^2$; each $Q^2$ is independently halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{51}R^{52}R^{53}$, $P(R^{50})_2$, $P(=O)(R^{50})_2$, $OP(=O)(R^{50})_2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^2$ groups, which substitute atoms in a 1,2 or 1,3 arrangement, together form alkylenedioxy (i.e., $—O—(CH_2)_y—O—$), thioalkylenoxy (i.e., $—S—(CH_2)_y—O—$)or alkylenedithioxy (i.e., $—S—(CH_2)_y—S—$) where y is 1 or 2; or two $Q^2$ groups, which substitute the same atom, together form alkylene;

$R^{50}$ is hydroxy, alkoxy, aralkoxy, alkyl, heteroaryl, heterocyclyl, aryl or $—NR^{70}R^{71}$, where $R^{70}$ and $R^{71}$ are each independently hydrogen, alkyl, aralkyl, aryl, heteroaryl, heteroaralkyl or heterocyclyl, or $R^{70}$ and $R^{71}$ together form alkylene, azaalkylene, oxaalkylene or thiaalkylene;

$R^{51}$, $R^{52}$ and $R^{53}$ are each independently hydrogen, alkyl, aryl, aralkyl, heteroaryl, heteroaralkyl, heterocyclyl or heterocyclylalkyl;

$R^{60}$ is hydrogen, alkyl, aryl, aralkyl, heteroaryl, heteroaralkyl, heterocyclyl or heterocyclylalkyl;

$R^{63}$ is alkoxy, aralkoxy, alkyl, heteroaryl, heterocyclyl, aryl or $—NR^{70}R^{71}$.

In certain embodiments, the compounds have formulae I, where $X^1$, $X^2$ and $X^3$ are each independently S, O or $NR^5$; $R^1$ is substituted or unsubstituted alkyl, where there are 0 to 6 substituents selected from halo, pseudohalo, aryl and heteroaryl; $R^2$ is substituted or unsubstituted aralkyl, substituted or unsubstituted aryl, substituted or unsubstituted alkenyl, substituted or unsubstituted alkyl, substituted or unsubstituted cycloalkyl, substituted or unsubstituted heteroaralkyl, or substituted or unsubstituted heterocyclylalkyl; where there are 0 or 1 substituents selected from alkoxycarbonyl and hydroxycarbonyl; $R^3$ is substituted or unsubstituted heteroaryl, substituted or unsubstituted aryl, or substituted or unsubstituted aralkyl; where there are 0 to 5 substituents selected from alkylamino, cyano, cycloalkyl, hydroxy, alkoxy, dialkylamino, amino, heterocyclyl, aralkoxy, alkyl, nitro, haloalkyl, alkylcarbonyl, halo, alkylcarbonylamino, aminocarbonyl, alkoxycarbonyl, aralkylamino, cycloalkylamino, heterocyclylamino, haloalkylamino, haloalkoxy, hydroxycarbonyl, aminosulfonyl, alkylcarbonylaminosulfonyl, or haloalkylcarbonylamino, or any two substituents, which substitute atoms in a 1,2 or 1,3 arrangement, together form alkylenedioxy; A and G are each independently selected from hydrogen, substituted or unsubstituted aryl, substituted or unsubstituted alkyl and substituted or unsubstituted alkylcarbonyl, where there are 0 to 5 substituents selected from nitro, halo, pseudohalo, alkyl and alkoxy, or A and G together form substituted or unsubstituted alkylene or substituted or unsubstituted 1,3-butadienylene, in one embodiment substituted or unsubstituted alkylene, where there are 0 to 4 substituents selected from halo, pseudohalo, alkoxy, nitro, haloalkyl, alkylcarbonylamino, hydroxy, alkylaminocarbonyloxy, alkoxycarbonylalkoxy, aminocarbonylalkoxy, hydroxyalkoxy, alkyl, haloalkylaminocarbonyloxy and alkylaminoalkoxy; D and E are each hydrogen, or together form a bond; and $R^5$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo, pseudohalo, $OR^{10}$, $SR^{10}$, $S(=O)R^{13}$, $S(=O)_2R^{13}$, $NR^{14}R^{15}$ or $C(=J)R^{13}$; $R^{10}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl or C(=J)$R^{13}$; J is O, S or $NR^{14}$; $R^{13}$ is selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, pseudohalo, $OR^{16}$ and $NR^{14}R^{15}$; $R^{14}$, $R^{15}$ and $R^{16}$ are each independently selected from hydrogen, alkyl, alkenyl, alkynyl, cycloalkyl, heterocyclyl, cycloalkylalkyl, heterocyclylalkyl, aryl, heteroaryl, aralkyl and heteroaralkyl; where the alkyl, alkenyl, alkynyl, cycloalkyl, heterocyclyl, cycloalkylalkyl, heterocyclylalkyl, aryl, heteroaryl, aralkyl and heteroaralkyl moieties of $R^5$, $R^{10}$ and $R^{13}$ are unsubstituted or substituted with one or more substituents each independently selected from $Q^1$, where $Q^1$ is halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy,, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —$N^+R^{51}R^{52}R^{53}$, $P(R^{50})_2$, P(=O)$(R^{50})_2$, OP(=O)$(R^{50})_2$, —$NR^{60}$C(=O)$R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy, thioalkylenoxy or alkylenedithioxy; or two $Q^1$ groups, which substitute the same atom, together form alkylene; each $Q^1$ is independently unsubstituted or substituted with one or more substituents each independently selected from $Q^2$; each $Q^2$ is independently halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —$N^+R^{51}R^{52}R^{53}$, $P(R^{50})_2$, P(=O)$(R^5)_2$, OP(=O)$(R^{50})_2$, —$NR^{60}$C(=O)$R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^2$ groups, which substitute atoms in a 1,2 or 1,3 arrangement, together form alkylenedioxy (i.e., —O—$(CH_2)_y$—O—), thioalkylenoxy (i.e., —S—$(CH_2)_y$—O—)or alkylenedithioxy (i.e., —S—$(CH_2)_y$—S—) where y is 1 or 2; or two $Q^2$ groups, which substitute the same atom, together form alkylene;

$R^{50}$ is hydroxy, alkoxy, aralkoxy, alkyl, heteroaryl, heterocyclyl, aryl or —$NR^{70}R^{71}$, where $R^{70}$ and $R^{71}$ are each independently hydrogen, alkyl, aralkyl, aryl, heteroaryl, heteroaralkyl or heterocyclyl, or $R^{70}$ and $R^{71}$ together form alkylene, azaalkylene, oxaalkylene or thiaalkylene;

$R^{51}$, $R^{52}$ and $R^{53}$ are each independently hydrogen, alkyl, aryl, aralkyl, heteroaryl, heteroaralkyl, heterocyclyl or heterocyclylalkyl;

$R^{60}$ is hydrogen, alkyl, aryl, aralkyl, heteroaryl, heteroaralkyl, heterocyclyl or heterocyclylalkyl;

$R^{63}$ is alkoxy, aralkoxy, alkyl, heteroaryl, heterocyclyl, aryl or —$NR^{70}R^{71}$.

In certain embodiments, the compounds claimed herein exhibit improved in vitro activity, efficacy, potency and/or pharmacokinetic properties, such as solubility, oral half-life, bioavailability, oral absorption, and/or in vivo activity, over related commercially available compounds or related compounds disclosed previously.

In certain embodiments, A and G are selected with the proviso that A and G are not both methyl. In another embodiment, A and G together form butadienyl with the proviso that the resulting benzo-fused group is not substituted at the 5-position with methoxy or chloro and is not substituted at the 6-position with methoxy or methyl. In another embodiment, A and G together form butadienyl with the proviso that the resulting benzo-fused group is not substituted at the 5-position with alkoxy or halo and is not substituted at the 6-position with alkoxy or alkyl. In another embodiment, A and G together form butadienyl with the proviso that the resulting benzo-fused group is not substituted with methoxy, methyl or chloro. In another embodiment, A and G together form butadienyl with the proviso that the resulting benzo-fused group is not substituted with alkoxy, alkyl or halo.

In another embodiment, $X^1$ is S. In another embodiment, $X^1$ is —$CR^8$═$CR^9$—. In another embodiment, $X^2$ is S. In another embodiment, $X^3$ is O.

In another embodiment, $R^1$ is substituted alkyl. In another embodiment, $R^1$ is 2-methoxy-1-ethyl, 3-methoxy-1-propyl, methoxycarbonylmethyl, hydroxycarbonylmethyl, 2-acetoxy-1-ethyl or 2-hydroxy-1-ethyl. In another embodiment, $R^1$ is unsubstituted alkyl. In other embodiments, $R^1$ is methyl.

In another embodiment, $R^2$ is benzyl, phenyl, allyl, ethyl, butyl, cyclohexyl, propyl, 3-pyridylmethyl, 2-furylmethyl, 4-methoxycarbonylbenzyl, 4-hydroxycarbonylbenzyl, 2-phenethyl or 2-(4-morpholinyl)ethyl. In another embodiment, $R^2$ is benzyl. In another embodiment, $R^2$ is pyridylmethyl. In another embodiment, $R^2$ is picolyl (i.e., 2-, 3-, or 4-pyridylmethyl). In another embodiment, $R^2$ is 2-furylmethyl. In another embodiment, $R^2$ is 3-pyridylmethyl.

In another embodiment, $R^3$ is substituted or unsubstituted quinolyl, substituted or unsubstituted phenyl, substituted or unsubstituted naphthyl, substituted or unsubstituted isoquinolyl, substituted or unsubstituted pyridyl, or substituted or unsubstituted indazolyl. In another embodiment, $R^3$ is substituted or unsubstituted phenyl. In other embodiments, $R^3$ is substituted with 0 to 5 substituents selected from ethylamino, cyano, cyclohexyl, hydroxy, methoxy, dimethylamino, amino, 4-morpholinyl, methylamino, isopropylamino, benzyloxy, methyl, isopropyl, nitro, trifluoromethyl, methylcarbonyl, chloro, propyl, ethoxy, methylcarbonylamino, aminocarbonyl, methoxycarbonyl, methoxymethylcarbonylamino, dimethylaminomethylcarbonylamino, butylamino, benzylamino, cyclopentylamino, 1-pyrrolidinylamino, pyrrolidinyl, t-butylamino, 2,2,2-trifluoroethylamino, piperidinyl, trifluoromethoxy, hydroxycarbonyl, aminosulfonyl, methylcarbonylaminosulfonyl, trifluoromethylcarbonylamino and t-butoxycarbonyl, or any two substituents, which substitute atoms in a 1,2 arrangement, together form methylenedioxy. In further embodiments, $R^3$ is 5-quinolyl, 2-ethylamino-5-cyanophenyl, 4-cyclohexylphenyl, 2-hydroxy-1-naphthyl, 6-quinolyl, 3-methoxyphenyl, 4-dimethylaminophenyl, 4-aminophenyl, 4-(4-morpholinyl)phenyl, 2-methylamino-5-cyanophenyl, 2-dimethylamino-5-cyanophenyl, 2-ethylaminophenyl, 3-cyanophenyl, 2-aminophenyl, 2-isopropylamino-5-cyanophenyl, 4-benzyloxyphenyl, 2-methyl4-hydroxy-5-isopropylphenyl, 2-ethylamino-5-nitrophenyl, 3-trifluoromethylphenyl, 3-methylcarbonylphenyl, 3-chlorophenyl, 2-propylphenyl, 2-ethoxyphenyl, 3-methylcarbonylaminophenyl, 3-aminocarbonylphenyl, 3-methoxycarbonylphenyl, 8-quinolyl, 8-hydroxy-5-quinolyl, 2-butylamino-5-cyanophenyl, 2-benzylamino-5-cyanophenyl, 2-cyclopentylamino-5-cyanophenyl, 2-(1-pyrrolidinyl)amino-5-cyanophenyl, 5-isoquinolyl, 1-isoquinolyl, 4-methylcarbonylaminophenyl, 2-t-butylamino-5-cyanophenyl, 2-(2,2,2-trifluoroethyl)amino-5-cyanophenyl, 2-piperidinyl-5-cyanophenyl, 4-methylcarbonylphenyl, 4-aminocarbonylphenyl, 2-ethylamino-5-methoxymethylcarbonylaminophenyl, 2-ethylamino-5-dimethylaminomethyl-carbonylaminophenyl, 1-naphthyl, 2-naphthyl, 2-pyridyl, 3-pyridyl, 2-ethoxy-5-methylcarbonylaminophenyl, 4-pyridyl, 4-methoxycarbonylphenyl, 4-trifluoromethoxyphenyl, 5-indazolyl, 4-(imidazol-1-yl) phenyl, 3,4-methylenedioxyphenyl, 3-hydroxycarbonylphenyl, 2-ethylamino-5-methylcarbonylphenyl, 4-aminosulfonylphenyl, 4-methylcarbonylaminosulfonylphenyl, 3-methylcarbonylphenyl, 2-methylcarbonylamino-5-pyridyl, 4-cyano-3-methylcarbonylaminophenyl, 2-methylamino-5-methylcarbonylphenyl, 4-trifluoromethylcarbonylaminophenyl, 2-ethylamino-5-methoxycarbonylphenyl, 2-hydroxycarbonylphenyl or 2-ethylamino-5-t-butoxycarbonylphenyl.

In another embodiment, A and G are each independently selected from hydrogen, substituted or unsubstituted phenyl, substituted or unsubstituted methyl, substituted or unsubstituted naphthyl, hydroxycarbonyl, substituted and unsubstituted ethoxycarbonyl, and substituted or unsubstituted methylcarbonyl, or A and G together from substituted or unsubstituted butylene, substituted or unsubstituted propylene, substituted or unsubstituted methyleneazaethylene, or substituted or unsubstituted 1,3-butadienylene. In other embodiments, A and G are each independently selected from hydrogen, substituted or unsubstituted phenyl, substituted or unsubstituted methyl, substituted or unsubstituted naphthyl, and substituted or unsubstituted methylcarbonyl, and are substituted with 0 to 4 substituents selected from chloro, bromo, methoxy, fluoro, ethoxy, nitro, trifluoromethylcarbonylamino, dimethylaminocarbonyloxy, 2-(1-piperidinyl)ethoxy, 2-(1-methyl-4-piperazinyl)ethoxy, 2-(N-morpholinyl)ethoxy, 2-dimethylaminoethoxy, hydroxycarbonylmethoxy, methylcarbonylamino, phenyl, trifluoromethyl, trifluoromethoxy, hydroxy, ethylaminocarbonyloxy, methoxycarbonyl methoxy, aminocarbonylmethoxy, 2-hydroxyethoxy, 2-hydroxypropoxy, methyl, 2-chloroethylaminocarbonyloxy and 2-methylaminoethoxy. In further embodiments, A and G together form substituted or unsubstituted 1,3-butadienylene and are substituted with 0 to 5 substituents selected from nitro, fluoro, chloro, methyl and methoxy. In another embodiment, A and G are each independently selected from hydrogen, 4-phenylphenyl, 4-trifluoromethylphenyl, 2-trifluoromethylphenyl, 4-trifluoromethoxyphenyl, 4-nitrophenyl, 4-fluorophenyl, 4-chlorophenyl, 4-methylphenyl, 4-methoxyphenyl, methyl, 2-naphthyl, 4-bromophenyl, 2-methoxyphenyl, 3-fluorophenyl, 2,4-dimethoxyphenyl, ethoxycarbonyl, benzyl, hydroxycarbonyl, 2-hydroxyphenyl, 3-hydroxyphenyl, 4-hydroxyphenyl, phenyl and methylcarbonyl, or A and G together form 1,3-butadienylene, 2-chloro-1,3-butadienylene, 2-methoxy-1,3-butadienylene, 2-fluoro-1,3-butadienylene, 2-ethoxy-1,3-butadienylene, 2-nitro-1,3-butadienylene, 2-trifluoromethyl-1,3-butadienylene, 2-trifluoromethoxy-1,3-butadienylene, 2-methylcarbonylamino-1,3-butadienylene, 2-trifluoromethylcarbonylamino- 1,3-butadienylene, 2-aminocarbonylmethoxy-1,3-butadienylene, 2-(2-hydroxyethoxy)-1,3-butadienylene, 2-(3-hydroxypropoxy)-1,3-butadienylene, 2-dimethylaminocarbonyloxy-1,3-butadienylene, 2-(1-piperidinyl)ethoxy-1,3-butadienylene, 2-(4-(1-methylpiperazin)yl)ethoxy-1,3-butadienylene, 2-(4-morpholinyl)ethoxy-1,3-butadienylene, 2-dimethylaminoethoxy-1,3-butadienylene, 2-hydroxycarbonylmethoxy-1,3-butadienylene, 2-hydroxy-1,3-butadienylene, 2-ethylaminocarbonyloxy-1,3-butadienylene, 2-methoxycarbonylmethoxy-1,3-butadienylene, 2-aminocarbonylmethoxy-1,3-butadienylene, 2-(2-hydroxyethoxy)-1,3-butadienylene, 1-methoxy-1,3-butadienylene, 1-methyl-1,3-butadienylene, 1-chloro-1,3-butadienylene, 2-(2-chloroethylaminocarbonyloxy)-1,3-butadienylene or 2-(2-methylaminoethoxy)-1,3-butadienylene.

In another embodiment, D and E are each hydrogen or together form a bond.

In certain embodiments herein, the compounds are selected from the following compounds. In other embodiments, the compounds are selected from those disclosed in the Examples. All isomers of these compounds are within the scope of the disclosure herein:

3-benzyl-5-(3-methyl-3H-benzothiazol-2-ylidene)-2-phenylimino-thiazolidine-4-one;

3-benzyl-2-(4-methoxyphenylimino)-5-(3-methyl-3H-benzothiazol-2-ylidene)thiazolidine-4-one;

3-benzyl-2-(4-dimethylaminophenylimino)-5-(3-methyl-3H-benzothiazol-2-ylidene)thiazolidine-4-one;

2-(4-aminophenylimino)-3-benzyl-5-(3-methyl-3H-benzothiazol-2-ylidene)thiazolidine-4-one;

3-benzyl-5-(3-methyl-3H-benzothiazol-2-ylidene)-2-(quinolin-6-ylimino)-thiazolidine-4-one;

2-(2-aminophenylimino)-3-benzyl-5-(3-methyl-3H-benzothiazol-2-ylidene)thiazolidine-4-one;

3-benzyl-2-(4-benzyloxyphenylimino)-5-(3-methyl-3H-benzothiazol-2-ylidene)thiazolidine-4-one;

3-benzyl-2-(2-hydroxy- 1-naphthylimino)-5-(3-methyl-3H-benzothiazol-2-ylidene)thiazolidine-4-one;

3-[3-benzyl-5-(3-methyl-3H-benzothiazol-2-ylidene)-4-oxothiazolidin-2-ylideneamino]benzonitrile;

3-benzyl-2-(4-hydroxy-5-isopropyl-2-methylphenylimino)-5-(3-methyl-3H-benzothiazol-2-ylidene)thiazolidine-4-one;

3-benzyl-2-(2-ethylamino-5-nitrophenylimino)-5-(3-methyl-3H-benzothiazol-2-ylidene)thiazolidine-4-one;

3-benzyl-5-(3-methyl-3H-benzothiazol-2-ylidene)-2-[3-(trifluoromethyl)-phenylimino]thiazolidine-4-one;

2-(3-acetylphenylimino)-3-benzyl-5-(3-methyl-3H-benzothiazol-2-ylidene)thiazolidine-4-one;

3-benzyl-2-(3-chlorophenylimino)-5-(3-methyl-3H-benzothiazol-2-ylidene)thiazolidine-4-one;

3-benzyl-5-(3-methyl-3H-benzothiazol-2-ylidene)-2-(2-propyl-phenylimino)thiazolidine-4-one;

3-benzyl-5-(3-methyl-3H-benzothiazol-2-ylidene)-2-(quinolin-5-ylimino)thiazolidine-4-one;

3-benzyl-2-(2-ethoxyphenylimino)-5-(3-methyl-3H-benzothiazol-2-ylidene)thiazolidine-4-one;

N-{3-[3-benzyl-5-(3-methyl-3H-benzothiazol-2-ylidene)-4-oxothiazolidin-2-ylideneamino]phenyl}acetamide;

3-[3-benzyl-5-(3-methyl-3H-benzothiazol-2-ylidene)-4-oxothiazolidin-2-ylideneamino]benzamide;

3-[3-benzyl-5-(3-methyl-3H-benzothiazol-2-ylidene)-4-oxothiazolidin-2-ylideneamino]benzoic acid, methyl ester;

3-benzyl-5-(3-methyl-3H-benzothiazol-2-ylidene)-2-(pyridin-3-ylimino)-thiazolidine-4-one;

N-{3-[3-benzyl-5-(3-methyl-3H-benzothiazol-2-ylidene)-4-oxothiazolidin-2-ylideneamino]-4-ethoxyphenyl}acetamide;

3-benzyl-5-(3-methyl-3H-benzothiazol-2-ylidene)-2-(pyridin-4-ylimino)thiazolidine-4-one;

4-[3-benzyl-5-(3-methyl-3H-benzothiazol-2-ylidene)-4-oxothiazolidin-2-ylideneamino]benzoic acid, methyl ester;

3-benzyl-5-(3-methyl-3H-benzothiazol-2-ylidene)-2-[4-(trifluoromethoxy)phenylimino]thiazolidine-4-one;

3-benzyl-2-(1H-indazol-5-ylimino)-5-(3-methyl-3H-benzothiazol-2-ylidene)thiazolidin-4-one;

3-benzyl-2-(4-imidazol-1-ylphenylimino)-5-(3-methyl-3H-benzothiazol-2-ylidene)thiazolidine-4-one;

2-(benzo[1,3]dioxol-5-ylimino)-3-benzyl-5-(3-methyl-3H-benzothiazol-2-ylidene)thiazolidin-4-one;

3-[3-benzyl-5-(3-methyl-3H-benzothiazol-2-ylidene)-4-oxothiazolidin-2-ylideneamino]benzoic acid;

3-benzyl-2-[2-(ethylamino)phenylimino]-5-(3-methyl-3H-benzothiazol-2-ylidene)thiazolidine-4-one;

3-[3-benzyl-5-(3-methyl-3H-benzothiazol-2-ylidene)-4-oxothiazolidin-2-ylideneamino]-4-(methylamino)benzonitrile;

3-[3-benzyl-5-(3-methyl-3H-benzothiazol-2-ylidene)-4-oxothiazolidin-2-ylideneamino]-4-(ethylamino)benzonitrile;

3-[3-benzyl-5-(3-methyl-3H-benzothiazol-2-ylidene)-4-oxothiazolidin-2-ylideneamino]-4-(isopropylamino)benzonitrile;

3-[3-benzyl-5-(3-methyl-3H-benzothiazol-2-ylidene)-4-oxothiazolidin-2-ylideneamino]-4-(dimethylamino)benzonitrile;

3-[3-benzyl-5-(3-methyl-3H-benzothiazol-2-ylidene)-4-oxothiazolidin-2-ylideneamino]-4-(tert-butylamino)benzonitrile;

3-[3-benzyl-5-(3-methyl-3H-benzothiazol-2-ylidene)-4-oxothiazolidin-2-ylideneamino]-4-(2,2,2-trifluoroethylamino)benzonitrile;

3-[3-benzyl-5-(3-methyl-3H-benzothiazol-2-ylidene)-4-oxothiazolidin-2-ylideneamino]-4-piperidin-1-ylbenzonitrile;

2-[5-acetyl-2-(ethylamino)phenylimino]-3-benzyl-5-(3-methyl-3H-benzothiazol-2-ylidene)thiazolidin-4-one;

3-ethyl-5-(3-methyl-3H-benzothiazol-2-ylidene)-2-(quinolin-6-ylimino)thiazolidin-4-one;

3-ethyl-5-(3-methyl-3H-benzothiazol-2-ylidene)-2-(4-morpholin4-ylphenylimino)thiazolidin-4-one;

3-[3-ethyl-5-(3-methyl-3H-benzothiazol-2-ylidene)-4-oxothiazolidin-2-ylideneamino]-4-(methylamino)benzonitrile;

4-dimethylamino-3-[3-ethyl-5-(3-methyl-3H-benzothiazol-2-ylidene)-4-oxothiazolidin-2-ylideneamino]benzonitrile;

4-ethylamino-3-[3-ethyl-5-(3-methyl-3H-benzothiazol-2-ylidene)-4-oxothiazolidin-2-ylideneamino]benzonitrile;

3-[3-ethyl-5-(3-methyl-3H-benzothiazol-2-ylidene)-4-oxothiazolidin-2-ylideneamino]-4-(isopropylamino)benzonitrile;

3-[3-butyl-5-(3-methyl-3H-benzothiazol-2-ylidene)-4-oxothiazolidin-2-ylideneamino]benzonitrile;

3-benzyl-5-(3-methyl-3H-benzoxazol-2-ylidene)-2-(quinolin-5-ylimino)thiazolidin-4-one;

N-[4-(3'-benzyl-3-methyl-4'-oxo-4-phenyl-3',4'-dihydro-3H-[2,5']-bithiazolyliden-2'-ylideneamino)phenyl]acetamide;

2'-[5-acetyl-2-(ethylamino)phenylimino]-3'-benzyl-3-methyl-4-phenyl-2',3'-dihydro-3H-[2,5']bithiazolyliden-4'-one;

3-(3'-benzyl-3-methyl-4'-oxo-4-phenyl-3',4'-dihydro-3H-[2,5']bithiazol-yliden-2'-ylideneamino)-4-(ethylamino)benzonitrile;

N-[4-(3'-benzyl-3-methyl-4'-oxo-3',4'-dihydro-3H-[2,5']bithiazolyliden-2'-ylideneamino)phenyl]acetamide;

N-[4-(3'-benzyl-3-methyl-4'-oxo-[2,5']bithiazolidinyliden-2'-ylideneamino)phenyl]acetamide;

3-(3'-benzyl-3,5-dimethyl-4'-oxo-4-phenyl-3',4'-dihydro-3H-[2,5']bithiazolyliden-2'-ylideneamino)-4-(ethylamino)benzonitrile;

4-ethylamino-3-[3-benzyl-5-(3-methyl-5-chloro-3H-benzothiazol-2-ylidene)-4-oxo-thiazolidin-2-ylideneamino]benzonitrile;

3-phenyl-5-(3-methyl-3H-benzothiazol-2-ylidene)-2-(4-cyclohexylphenyl)imino-thiazolidine-4-one;

3-allyl-5-(3-methyl-3H-benzothiazol-2-ylidene)-2-(2-hydroxy-1-naphthyl)imino-thiazolidine-4-one;

4-ethylamino-3-[3-phenyl-5-(3-methyl-3H-benzothiazol-2-ylidene)-4-oxo-thiazolidin-2-ylideneamino]benzonitrile;

4-ethylamino-3-[3-benzyl-5-(3-methyl-5-methoxy-3H-benzothiazol-2-ylidene)-4-oxo-thiazolidin-2-ylideneamino]benzonitrile;

3-allyl-5-(3-methyl-3H-benzothiazol-2-ylidene)-2-(5-quinolyl)imino-thiazolidine-4-one;

4-ethylamino-3-[3-allyl-5-(3-methyl-3H-benzothiazol-2-ylidene)-4-oxo-thiazolidin-2-ylideneamino]benzonitrile;

3-phenyl-5-(3-methyl-3H-benzothiazol-2-ylidene)-2-benzylimino-thiazolidine-4-one;

3-benzyl-5-(3-methyl-3H-benzothiazol-2-ylidene)-2-(8-quinolyl)imino-thiazolidine-4-one;

3-benzyl-5-(3-methyl-3H-benzothiazol-2-ylidene)-2-(8-hydroxy-5-quinolyl)imino-thiazolidine-4-one;

3-benzyl-5-(3-methyl-3H-benzothiazol-2-ylidene)-2-(5-isoquinolyl)imino-thiazolidine-4-one;

3-benzyl-5-(3-methyl-3H-benzothiazol-2-ylidene)-2-(1-isoquinolyl)imino-thiazolidine-4-one;

3-benzyl-5-(3-methyl-3H-benzothiazol-2-ylidene)-2-(4-methylcarbonylamino)phenylimino-thiazolidine-4-one;

3-benzyl-5-(3-methyl-3H-benzothiazol-2-ylidene)-2-(4-methylcarbonyl)phenylimino-thiazolidine-4-one;

3-benzyl-5-(3-methyl-3H-benzothiazol-2-ylidene)-2-(4-aminocarbonyl)phenylimino-thiazolidine-4-one;

3-benzyl-5-(3-methyl-3H-benzothiazol-2-ylidene)-2-(1-naphthyl)imino-thiazolidine-4-one;

3-benzyl-5-(3-methyl-3H-benzothiazol-2-ylidene)-2-(2-naphthyl)imino-thiazolidine-4-one;

3-benzyl-5-(3-methyl-3H-benzothiazol-2-ylidene)-2-(2-pyridyl)imino-thiazolidine-4-one;

3-benzyl-5-(3-methyl-3H-benzothiazol-2-ylidene)-2-(4-aminosulfonyl)phenylimino-thiazolidine-4-one;

3-benzyl-5-(3-methyl-3H-benzothiazol-2-ylidene)-2-(4-methylcarbonylaminosulfonyl)phenylimino-thiazolidine-4-one;

3-benzyl-5-(3-methyl-3H-benzothiazol-2-ylidene)-2-(3-methylcarbonyl)phenylimino-thiazolidine-4-one;

3-benzyl-5-(3-methyl-3H-benzothiazol-2-ylidene)-2-(2-methylcarbonylamino-5-pyridyl)imino-thiazolidine-4-one;

3-benzyl-5-(3-methyl-3H-benzothiazol-2-ylidene)-2-(4-cyano-5-methylcarbonylaminophenyl)imino-thiazolidine-4-one;

3-benzyl-5-(3-methyl-3H-benzothiazol-2-ylidene)-2-(2-ethylamino-5-methylcarbonylphenyl)imino-thiazolidine-4-one;

3-benzyl-5-(3-methyl-3H-benzothiazol-2-ylidene)-2-(2-methylamino-5-methylcarbonylphenyl)imino-thiazolidine-4-one;

3-benzyl-5-(3-methyl-3H-benzothiazol-2-ylidene)-2-(4-trifluoromethylcarbonylaminophenyl)imino-thiazolidine-4-one;

3-benzyl-5-(3-methyl-3H-benzothiazol-2-ylidene)-2-(2-ethylamino-5-methoxycarbonylphenyl)imino-thiazolidine-4-one;

3-benzyl-5-(3-methyl-3H-benzothiazol-2-ylidene)-2-(2-hydroxycarbonylphenyl)imino-thiazolidine-4-one;

3-benzyl-5-(3-methyl-3H-benzothiazol-2-ylidene)-2-(2-ethylamino-5-tert-butoxycarbonylphenyl)imino-thiazolidine-4-one;

4-butylamino-3-[3-benzyl-5-(3-methyl-3H-benzothiazol-2-ylidene)-4-oxo-thiazolidin-2-ylideneamino]benzonitrile;

4-benzylamino-3-[3-benzyl-5-(3-methyl-3H-benzothiazol-2-ylidene)-4-oxo-thiazolidin-2-ylideneamino]benzonitrile;

4-cyclopentylamino-3-[3-benzyl-5-(3-methyl-3H-benzothiazol-2-ylidene)-4-oxo-thiazolidin-2-ylideneamino]benzonitrile;

4-pyrrolidinylamino-3-[3-benzyl-5-(3-methyl-3H-benzothiazol-2-ylidene)-4-oxo-thiazolidin-2-ylideneamino]benzonitrile;

4-pyrrolidinyl-3-[3-benzyl-5-(3-methyl-3H-benzothiazol-2-ylidene)-4-oxo-thiazolidin-2-ylideneamino]benzonitrile;

4-ethylamino-3-[3-cyclohexyl-5-(3-methyl-3H-benzothiazol-2-ylidene)-4-oxo-thiazolidin-2-ylideneamino]benzonitrile;

3-allyl-5-(3-methyl-3H-benzothiazol-2-ylidene)-2-(4-hydroxy-2-methyl-5-isopropylphenyl)imino-thiazolidine-4-one;

3-cyclohexyl-5-(3-methyl-3H-benzothiazol-2-ylidene)-2-(2-hydroxy-1-naphthyl)imino-thiazolidine-4-one;

4-ethylamino-3-[3-benzyl-5-(6-fluoro-3-methyl-3H-benzothiazol-2-ylidene)-4-oxo-thiazolidin-2-ylideneamino]benzonitrile;

4-ethylamino-3-[3-benzyl-5-(6-ethoxy-3-methyl-3H-benzothiazol-2-ylidene)-4-oxo-thiazolidin-2-ylideneamino]benzonitrile;

4-ethylamino-3-[3-benzyl-5-(6-nitro-3-methyl-3H-benzothiazol-2-ylidene)-4-oxo-thiazolidin-2-ylideneamino]benzonitrile;

4-ethylamino-3-[3-benzyl-5-(5-trifluoromethyl-3-methyl-3H-benzothiazol-2-ylidene)-4-oxo-thiazolidin-2-ylideneamino]benzonitrile;

4-ethylamino-3-[3-benzyl-5-(6-methylcarbonylamino-3-methyl-3H-benzothiazol-2-ylidene)-4-oxo-thiazolidin-2-ylideneamino]benzonitrile;

4-ethylamino-3-[3-benzyl-5-(5-hydroxy-3-methyl-3H-benzothiazol-2-ylidene)-4-oxo-thiazolidin-2-ylideneamino]benzonitrile;

4-ethylamino-3-[3-benzyl-5-(6-hydroxy-3-methyl-3H-benzothiazol-2-ylidene)-4-oxo-thiazolidin-2-ylideneamino]benzonitrile;

4-ethylamino-3-[3-benzyl-5-(5-ethylaminocarbonyloxy-3-methyl-3H-benzothiazol-2-ylidene)-4-oxo-thiazolidin-2-ylideneamino]benzonitrile;

4-ethylamino-3-[3-benzyl-5-(5-methoxycarbonylmethoxy-3-methyl-3H-benzothiazol-2-ylidene)-4-oxo-thiazolidin-2-ylideneamino]benzonitrile;

4-ethylamino-3-[3-benzyl-5-(5-aminocarbonylmethoxy-3-methyl-3H-benzothiazol-2-ylidene)-4-oxo-thiazolidin-2-ylideneamino]benzonitrile;

4-ethylamino-3-[3-benzyl-5-(5-(2-hydroxyethoxy)-3-methyl-3H-benzothiazol-2-ylidene)-4-oxo-thiazolidin-2-ylideneamino]benzonitrile;

4-ethylamino-3-[3-benzyl-5-(4-methoxy-3-methyl-3H-benzothiazol-2-ylidene)-4-oxo-thiazolidin-2-ylideneamino]benzonitrile;

4-ethylamino-3-[3-benzyl-5-(4-methyl-3-methyl-3H-benzothiazol-2-ylidene)-4-oxo-thiazolidin-2-ylideneamino]benzonitrile;

4-ethylamino-3-[3-benzyl-5-(4-chloro-3-methyl-3H-benzothiazol-2-ylidene)-4-oxo-thiazolidin-2-ylideneamino]benzonitrile;

4-ethylamino-3-[3-benzyl-5-(5-(2-chloroethylaminocarbonyloxy)-3-methyl-3H-benzothiazol-2-ylidene)-4-oxo-thiazolidin-2-ylideneamino]benzonitrile;

4-ethylamino-3-[3-benzyl-5-(5-(2-methylaminoethoxy)-3-methyl-3H-benzothiazol-2-ylidene)-4-oxo-thiazolidin-2-ylideneamino]benzonitrile;

4-ethylamino-3-[3-propyl-5-(3-methyl-3H-benzothiazol-2-ylidene)-4-oxo-thiazolidin-2-ylideneamino]benzonitrile;

3-(3-pyridylmethyl)-5-(3-methyl-3H-benzothiazol-2-ylidene)-2-(3-acetylphenyl)imino-thiazolidine-4-one;

3-(3-pyridylmethyl)-5-(3-methyl-3H-benzothiazol-2-ylidene)-2-(2-ethylamino-5-acetylphenyl)imino-thiazolidine-4-one;

4-ethylamino-3-[3-(3-pyridylmethyl)-5-(3-methyl-3H-benzothiazol-2-ylidene)-4-oxo-thiazolidin-2-ylideneamino]benzonitrile;

4-ethylamino-3-[3-(2-furylmethyl)-5-(3-methyl-3H-benzothiazol-2-ylidene)-4-oxo-thiazolidin-2-ylideneamino]benzonitrile;

3-(4-methoxycarbonylbenzyl)-5-(3-methyl-3H-benzothiazol-2-ylidene)-2-(2-ethylamino-5-acetylphenyl)imino-thiazolidine-4-one;

3-(4-hydroxycarbonylbenzyl)-5-(3-methyl-3H-benzothiazol-2-ylidene)-2-(2-ethylamino-5-acetylphenyl)imino-thiazolidine-4-one;

4-ethylamino-3-[3-(2-phenylethyl)-5-(3-methyl-3H-benzothiazol-2-ylidene)-4-oxo-thiazolidin-2-ylideneamino]benzonitrile;

4-ethylamino-3-[3-(2-(4-morpholinyl)-1-ethyl)-5-(3-methyl-3H-benzothiazol-2-ylidene)-4-oxo-thiazolidin-2-ylideneamino]benzonitrile;

3-benzyl-5-(3-methylthiazolin-2-ylidene)-2-(4-methylcarbonylaminophenyl)imino-thiazolidine-4-one;

3-benzyl-5-(3-methyl-4-phenylthiazol-2-ylidene)-2-(4-methylcarbonylaminophenyl)imino-thiazolidine-4-one;

3-benzyl-5-(3-methyl-4-phenylthiazol-2-ylidene)-2-(2-ethylamino-5-acetylphenyl)imino-thiazolidine-4-one;

3-benzyl-5-(3-methylthiazol-2-ylidene)-2-(4-methylcarbonylaminophenyl)imino-thiazolidine-4-one;

4-ethylamino-3-[3-benzyl-5-(3-methyl-4-phenylthiazol-2-ylidene)-4-oxo-thiazolidin-2-ylideneamino]benzonitrile;

4-ethylamino-3-[3-benzyl-5-(3-methyl-4,5-dimethylthiazol-2-ylidene)-4-oxo-thiazolidin-2-ylideneamino]benzonitrile;

4-ethylamino-3-[3-benzyl-5-(3-methyl-4-phenyl-5-methylthiazol-2-ylidene)-4-oxo-thiazolidin-2-ylideneamino]benzonitrile;

4-ethylamino-3-[3-benzyl-5-(3-methyl-4,5-butylenylthiazol-2-ylidene)-4-oxo-thiazolidin-2-ylideneamino]benzonitrile;

4-ethylamino-3-[3-benzyl-5-(3-methyl-4-ethylthiazol-2-ylidene)-4-oxo-thiazolidin-2-ylideneamino]benzonitrile;

4-ethylamino-3-[3-benzyl-5-(3-methyl-4-(4-nitrophenyl)thiazol-2-ylidene)-4-oxo-thiazolidin-2-ylideneamino]benzonitrile;

4-ethylamino-3-[3-benzyl-5-(3-methyl-4-(4-fluorophenyl)thiazol-2-ylidene)-4-oxo-thiazolidin-2-ylideneamino]benzonitrile;

4-ethylamino-3-[3-benzyl-5-(3-methyl-4-(4-chlorophenyl)thiazol-2-ylidene)-4-oxo-thiazolidin-2-ylideneamino]benzonitrile;

4-ethylamino-3-[3-benzyl-5-(3-methyl-4-(4-methylphenyl)thiazol-2-ylidene)-4-oxo-thiazolidin-2-ylideneamino]benzonitrile;

4-ethylamino-3-[3-benzyl-5-(3-methyl-4-(4-methoxyphenyl)thiazol-2-ylidene)-4-oxo-thiazolidin-2-ylideneamino]benzonitrile;

4-ethylamino-3-[3-benzyl-5-(3-methyl-4-methyl-5-acetylthiazol-2-ylidene)-4-oxo-thiazolidin-2-ylideneamino]benzonitrile;

4-ethylamino-3-[3-benzyl-5-(3-methyl-4,5-propylenylthiazol-2-ylidene)-4-oxo-thiazolidin-2-ylideneamino]benzonitrile;

4-ethylamino-3-[3-benzyl-5-(3-methyl-4,5-diphenylthiazol-2-ylidene)-4-oxo-thiazolidin-2-ylideneamino]benzonitrile;

4-ethylamino-3-[3-benzyl-5-(3-methyl-4-methylthiazol-2-ylidene)-4-oxo-thiazolidin-2-ylideneamino] benzonitrile;

4-ethylamino-3-[3-(3-pyridylmethyl)-5-(3-methyl-4,5-butylenylthiazol-2-ylidene)-4-oxo-thiazolidin-2-ylideneamino]benzonitrile; and 3-(4-methoxycarbonylbenzyl)-5-(3-methyl-4,5-butylenyl]thiazol-2-ylidene)-2-(2-ethylamino-5-acetylphenyl)imino-thiazolidine-4-one.

In certain embodiments herein, the compounds provided herein are FXR or LXR antagonists. In these embodiments, the compounds have formulae I, where A and G are each independently substituted or unsubstituted phenyl, substituted or unsubstituted naphthyl, or substituted or unsubstituted methyl, substituted or unsubstituted ethyl or together form substituted or unsubstituted butadienylene where there are 0 to 4 substituents, in one embodiment 0 or 1 substituents, selected from methylcarbonylamino, hydroxy, trifluoromethoxy, trifluorocarbonylamino, aminocarbonylmethoxy, 2-hydroxyethoxy, 3-hydroxypropoxy, dimethylaminocarbonyloxy, 2-(1-piperidinyl)ethoxy, 2-(4-(1-methylpiperazin)yl)ethoxy, 2-(4-morpholinyl)ethoxy, 2-dimethylaminoethoxy and hydroxycarbonylmethoxy; D and E form a bond; $X^1$ and $X^2$ are both S; $X^3$ is O; $R^1$ is methyl; $R^2$ is benzyl; and $R^3$ is 5-cyano-2-ethylaminophenyl.

In certain embodiments, FXR or LXR antagonists provided herein are selected from the following compounds. All isomer of these compounds are within the scope of the disclosure herein:

3-(3'-Benzyl-3,5-dimethyl-4'-oxo-4-phenyl-3',4'-dihydro-3H-[2,5']bithiazolyliden-2'-ylideneamino)-4-ethylamino-benzonitrile;

3-(3'-Benzyl-5-ethyl-3-methyl-4'-oxo-4-phenyl-3',4'-dihydro-3H-[2,5']bithiazolyliden-2'-ylideneamino)-4-ethylamino-benzonitrile;

3-(3'-Benzyl-3-methyl-4-naphthalen-2-yl-4'-oxo-3',4'-dihydro-3H-[2,5']bithiazolyliden-2'-ylideneamino)-4-ethylamino-benzonitrile;

3-[3'-Benzyl-4-(4-bromophenyl)-3-methyl-4'-oxo-3',4'-dihydro-3H-[2,5']bithiazolyliden-2'-ylideneamino]-4-ethylamino-benzonitrile;

3-[3'-Benzyl-4-(2-methoxyphenyl)-3-methyl-4'-oxo-3',4'-dihydro-3H-[2,5']bithiazolyliden-2'-ylideneamino]-4-ethylamino-benzonitrile;

3-[3'-Benzyl-4-(3-fluorophenyl)-3-methyl-4'-oxo-3',4'-dihydro-3H-[2,5']bithiazolyliden-2'-ylideneamino]-4-ethylamino-benzonitrile;

3-[3'-Benzyl-4-(2,4-dimethoxyphenyl)-3-methyl-4'-oxo-3',4'-dihydro-3H-[2,5']bithiazolyliden-2'-ylideneamino]-4-ethylamino-benzonitrile;

N-{2-[3-Benzyl-2-(5-cyano-2-ethylamino-phenylimino)-4-oxo-thiazolidin-5-ylidene]-3-methyl-2,3-dihydrobenzothiazol-6-yl}-acetamide;

3-[3-Benzyl-5-(6-hydroxy-3-methyl-3H-benzothiazol-2-ylidene)-4-oxo-thiazolidin-2-ylideneamino]-4-ethylamino-benzonitrile;

3-[3-Benzyl-5-(3-methyl-6-trifluoromethoxy-3H-benzothiazol-2-ylidene)-4-oxo-thiazolidin-2-ylideneamino]-4-ethylamino-benzonitrile;

N-{2-[3-Benzyl-2-(5-cyano-2-ethylamino-phenylimino)-4-oxo-thiazolidin-5-ylidene]-3-methyl-2,3-dihydrobenzothiazol-6-yl}-2,2,2-trifluoroacetamide;

2-{2-[3-Benzyl-2-(5-cyano-2-ethylamino-phenylimino)-4-oxothiazolidin-5-ylidene]-3-methyl-2,3-dihydrobenzothiazol-5-yloxy}-acetamide;

3-{3-Benzyl-5-[5-(2-hydroxyethoxy)-3-methyl-3H-benzothiazol-2-ylidene]-4-oxothiazolidin-2-ylideneamino}-4-ethylamino-benzonitrile;

3-{3-Benzyl-5-[5-(3-hydroxypropoxy)-3-methyl-3H-benzothiazol-2-ylidene]-4-oxothiazolidin-2-ylideneamino}-4-ethylamino-benzonitrile;

Dimethylcarbamic acid 2-[3-benzyl-2-(5-cyano-2-ethylamino-phenylimino)-4-oxothiazolidin-5-ylidene]-3-methyl-2,3-dihydrobenzothiazol-5-yl ester;

3-{3-Benzyl-5-[3-methyl-5-(2-piperidin-1-ylethoxy)-3H-benzothiazol-2-ylidene]-4-oxothiazolidin-2-ylideneamino}-4-ethylamino-benzonitrile;

3-(3-Benzyl-5-{3-methyl-5-[2-(4-methylpiperazin-1-yl)-ethoxy]-3H-benzothiazol-2-ylidene}-4-oxothiazolidin-2-ylideneamino)-4-ethylamino-benzonitrile;

3-{3-Benzyl-5-[3-methyl-5-(2-morpholin-4-ylethoxy)-3H-benzothiazol-2-ylidene]-4-oxothiazolidin-2-ylideneamino}-4-ethylamino-benzonitrile;

3-{3-Benzyl-5-[5-(2-dimethylaminoethoxy)-3-methyl-3H-benzothiazol-2-ylidene]-4-oxothiazolidin-2-ylideneamino}-4-ethylamino-benzonitrile; and {2-[3-Benzyl-2-(5-cyano-2-ethylamino-phenylimino)-4-oxothiazolidin-5-ylidene]-3-methyl-2,3-dihydrobenzothiazol-5-yloxy}-acetic acid.

In another embodiment, the compounds for use in the compositions and methods provided herein are shown in the Examples. All isomers of these compounds are within the scope of this disclosure.

C. Preparation of the Compounds

Starting materials in the synthesis examples provided herein are either available from commercial sources or via literature procedures. All commercially available compounds were used without further purification unless otherwise indicated. $CDCl_3$ (99.8% D, Cambridge Isotope Laboratories) was used in all experiments as indicated. Proton ($^1H$) nuclear magnetic resonance (NMR) spectra were recorded on a Bruker Avance 400 MHz NMR spectrometer. Significant peaks are tabulated and typically include: number of protons, and multiplicity (s, singlet; d, double; t, triplet; q, quartet; m, multiplet; br s, broad singlet). Chemical shifts are reported as parts per million (δ) relative to tetramethylsilane. Low-resolution mass spectra (MS) were obtained as electrospray ionization (ESI) mass spectra, which were recorded on a Perkin-Elmer SCIEX HPLC/MS instrument using reverse-phase conditions (acetonitrile/water, 0.05% trifluoroacetic acid). Flash chromatography was performed using Merck Silica Gel 60 (230–400 mesh) following standard protocol (Still et al. (1978) *J. Org. Chem.* 43, 2923).

The following illustrations depict general preparations of compounds claimed herein and consist of reactions typically known to one skilled in the art of chemical synthesis. The substituents A, D, E, G, $R^1$–$R^3$ and $X^1$–$X^3$ have been previously described. Also it will be apparent to one skilled in the art that many of the products could exist as one or more isomers, that is E/Z isomers, enantiomers and/or diastereomers.

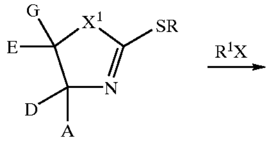

1

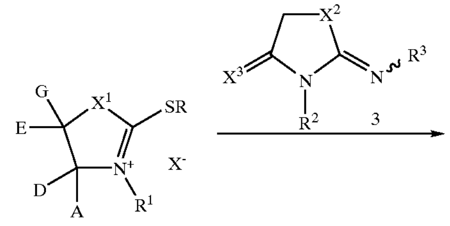

2

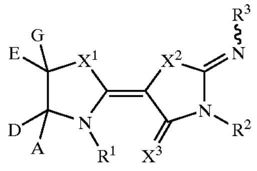

and/or

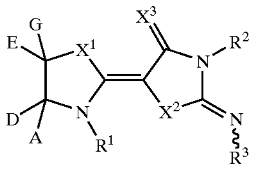

4a 4b

As shown above, treatment of 2-(alkylthio)azole (1) with an alkylating agent ($R^1X$) affords the corresponding 2-(alkylthio)azolium complex (2), which then is condensed with 2-iminoazolidine (3) in the presence of a base to yield heterocycle (4). Thus, for example, when 1 is a 1,3-heterocycle such as thiazole ($X^1$=S; E and D form a bond) that is alkylated with methyl p-toluenesulfonate, an intermediate N-methyl thiazolium complex 2 is prepared (see, e.g., U.S. Pat. Nos. 5,707,794 and 2,388,963). Subsequently, for example, when 3 is an 2-iminothiazolidinone ($X^2$=S and $X^3$=O), an 2-imino-5-(thiazol-2-ylidene)thiazolidin-4-one 4 is generated. Likewise, other heterocycles 1, such as but not limited to thiazoles, thiazolines, benzimidazoles, benzoxazoles, quinolines, pyridines and indoles, should undergo this transformation when bearing a 2-alkylthio or 2-mercapto substituent.

The synthesis of intermediate 2 is alternatively prepared from the corresponding thione precursor (5) upon alkylation with RX. For example, when 5 is thiazolin-2-thione ($X^1$=S) that is alkylated with methyl p-toluenesulfonate (RX), an intermediate N-alkyl 2-(thiomethyl)thiazolinium complex 2 is generated.

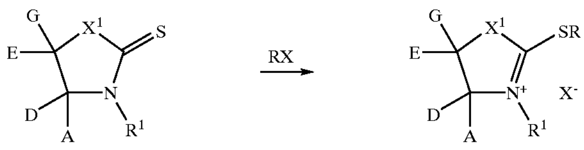

5 2

Furthermore, for example, when the thione precursor 5 is thiazole-2-thione ($X^1$=S; E and D form a bond), it can be prepared by the condensation of a dithiocarbamate salt ($X^1$=S) with a α-haloketone, as depicted below (see, e.g., Bellec et al. (1999) *Chem. Mater.* 11:3147; Humphlett et al. (1964) *J. Org. Chem.* 29:2146). Various dithiocarbamate salts are synthesized, for example, by reacting a primary amine, e.g., methylamine, with carbon disulfide in the presence of a base such as $Et_3N$ (see, e.g., Humphlett et al. (1964) *J. Org. Chem.* 29:2146). The thiazole-2-thione 5 can then be transformed into the corresponding thiazolium complex 2.

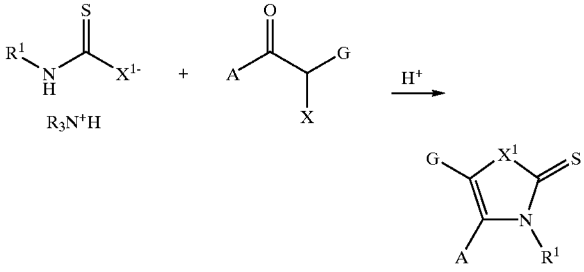

5

Alternatively, as depicted below, reaction of intermediate 2 with azolidin-2-thione (6) in the presence of base gives another azolidin-2-thione (7). Treatment of intermediate 7 with an alkylating agent (RX) affords the 2-(alkylthio) azolium complex (8), which reacts with an amine in the presence of base to yield heterocycle 4. Thus, for example, when 6 is a 1,3-heterocycle such as rhodanine ($X^2$=S and $X^3$=O) that is condensed with an intermediate N-methyl benzothiazolium complex 2 ($X^1$=S; E and D form a bond; A and G form a fused benzene), a 5-(benzothiazol-2-ylidene) thiazolidin-4-one-2-thione 7 is generated (see, e.g., U.S. Pat. Nos. 5,618,831 and 2,454,629). Subsequently intermediate 7 is alkylated with, for example, methyl p-toluenesulfonate to give a 5-(benzothiazol-2-ylidene)-2-methylthio-4-oxothiazolidinium complex 8, which can react with, for example, an aniline to yield an 2-imino-5-(benzothiazol-2-ylidene)thiazolidin-4-one 4 (see, e.g., U.S. Pat. No. 5,618,831).

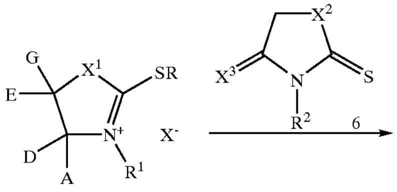

2

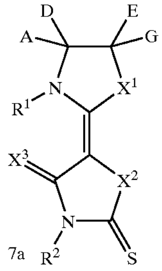

and/or

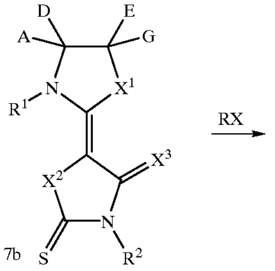

7a 7b

-continued

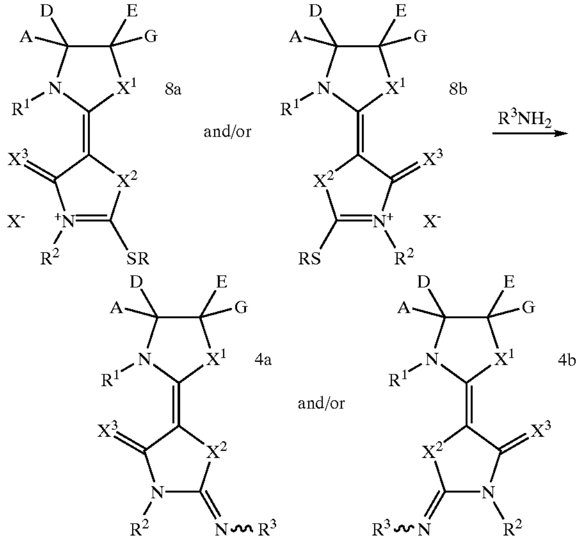

8a and/or 8b 4a and/or 4b

In general, 2-iminoazolidines 3 may be prepared as depicted below. Thus, for example, when 3 is an 2-imino-4-thiazolidinone ($X^2$=S and $X^3$=O), it can be prepared by condensing a thiourea ($X^2$=S) with a 2-haloester ($X^3$=O) in the presence of base, in which $R^3$ is typically aryl or heteroaryl (see, e.g., Seada et al. (1993) *Indian J. Heterocycl. Chem.* 3:81; and International Patent Application Publication No. WO 00/42031).

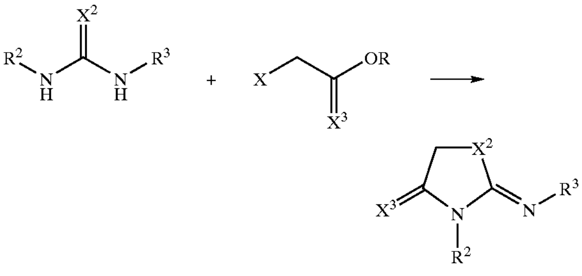

3

Likewise 2-iminoazolidines 3 may be prepared from a carbodiimide as depicted below. For example, when 3 is an 2-imino-4-imidazolidinone ($X^2$=NR and $X^3$=O), it can be prepared by reacting a carbodiimide with a 2-aminoester ($X^2$=NR and $X^3$=O). Also an 2-imino-4-oxazolidinones ($X^2$ and $X^3$=O) can be prepared from a carbodiimide and a 2-hydroxyester.

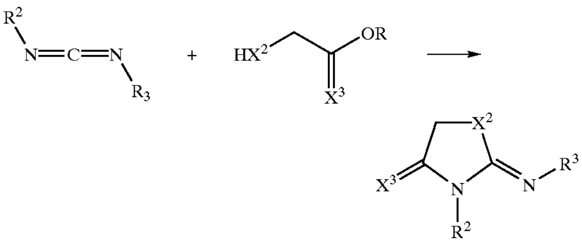

3

Similarly azolidine-2-thiones 6 may be prepared as depicted below. Thus, for example, when 6 is a rhodanine ($X^2$=S and $X^3$=O), it can be prepared by condensing an isothiocyanate with a 2-mercaptoester (see, e.g., Dogan et al. (1992) *Tetrahedron* 48:7157; and Drobnica et al. (1972) *Chem. Zvesti* 26:538). Also imidazolidin-4-one-2-thiones ($X^2$=NR and $X^3$=O) or oxazolidin-4-one-2-thiones ($X^2$ and $X^3$=O) can be prepared by reacting an isothiocyanate with 2-aminoester or 2-hydroxyester, respectively.

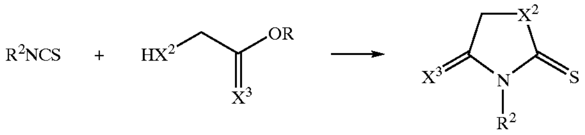

6

Alkyl and aryl isothiocyanates, aryl amines, rhodanines, unsymmetrical carbodiimides and thioureas may be synthesized utilizing known methodology (see, e.g., Katritzky et al. (1984) *Comprehensive Heterocyclic Chemistry*; Pergamon Press: Oxford, UK; Katritzky et al. (2000) *Handbook of Heterocyclic Chemistry*, $2^{nd}$ Ed.; Pergamon Press: Oxford, UK; March *Advanced Organic Chemistry*, $4^{th}$ Ed.; John Wiley: New York (1992); and International Patent Application Publication No. WO 00/42031). For example, alkyl and aryl isothiocyanates are readily prepared from reaction of an amine with thiophosgene or a thiophosgene equivalent, e.g. thiocarbonyl diimidazole. Many isothiocyanates also are commercially available. Unsymmetrical thioureas are prepared from reaction of an isothiocyanate with an amine.

D. Formulation of Pharmaceutical Compositions

The pharmaceutical compositions provided herein contain therapeutically effective amounts of one or more of the nuclear receptor activity modulators provided herein that are useful in the prevention, treatment, or amelioration of one or more of the symptoms of diseases or disorders associated with nuclear receptor activity, including FXR, LXR and/or orphan nuclear receptor activity. Such diseases or disorders include, but are not limited to, hypercholesterolemia, hyperlipoproteinemia, hypertriglyceridemia, lipodystrophy, hyperglycemia, diabetes mellitus, dyslipidemia, atherosclerosis, gallstone disease, acne vulgaris, acneiform skin conditions, diabetes, Parkinson's disease, cancer, Alzheimer's disease, inflammation, immunological disorders, lipid disorders, obesity, conditions characterized by a perturbed epidermal barrier function, hyperlipidemia, cholestasis, peripheral occlusive disease, ischemic stroke, conditions of disturbed differentiation or excess proliferation of the epidermis or mucous membrane, and cardiovascular disorders.

The compositions contain one or more compounds provided herein. The compounds are preferably formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see, e.g., Ansel *Introduction to Pharmaceutical Dosage Forms*, Fourth Edition 1985, 126).

In the compositions, effective concentrations of one or more compounds or pharmaceutically acceptable derivatives is (are) mixed with a suitable pharmaceutical carrier or vehicle. The compounds may be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with nuclear receptor activity or in which nuclear receptor activity is implicated. Such diseases or disorders include, but are not limited to, hypercholesterolemia, hyperlipoproteinemia, hypertriglyceridemia, lipodystrophy, hyperglycemia, diabetes mellitus, dyslipidemia, atherosclerosis, gallstone disease, acne vulgaris, acneiform skin conditions, diabetes, Parkinson's disease, cancer, Alzheimer's disease, inflammation, immunological disorders, lipid disorders, obesity, conditions characterized by a perturbed epidermal barrier function, hyperlipidemia, cholestasis, peripheral occlusive disease, ischemic stroke, conditions of disturbed differentiation or excess proliferation of the epidermis or mucous membrane, and cardiovascular disorders.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and in International Patent Application Publication Nos. 99/27365 and 00/25134 (see, e.g., EXAMPLES 53 and 54) and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with nuclear receptor activity or in which nuclear receptor activity is implicated, as described herein.

Typically a therapeutically effective dosage should produce a serum concentration of active ingredient of from about 0.1 ng/ml to about 50–100 μg/ml. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and preferably from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing diseases or disorders associated with nuclear receptor activity or in which nuclear receptor activity is implicated, as described herein. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including orally, parenterally, rectally, topically and locally. For oral administration, capsules and tablets are presently preferred. The compositions are in liquid, semi-liquid or solid form and are formulated in a manner suitable for each route of administration. Preferred modes of administration include parenteral and oral modes of administration. Oral administration is presently most preferred.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain along with the active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount sufficient to alleviate the symptoms of the treated subject.

Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%–100% active ingredient, preferably 0.1–85%, typically 75–95%.

The active compounds or pharmaceutically acceptable derivatives may be prepared with carriers that protect the compound against rapid elimination from the body, such as time release formulations or coatings. The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as diseases or disorders associated with nuclear receptor activity or in which nuclear receptor activity is implicated. It is to be understood that such combination therapy constitutes a further aspect of the compositions and methods of treatment provided herein.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, preferably capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action', such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect., Injectables are designed for local and systemic administration. Typically a therapeutically effective dosage is formulated to contain a concentration of at least about 0.1% w/w up to about 90% w/w or more, preferably more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10–1000 mg, preferably 100–500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1–50 mg, preferably 5–35 mg, more preferably about 9–30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%–10% isotonic solutions, pH about 5–7, with appropriate salts.

5. Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Articles of Manufacture

The compounds or pharmaceutically acceptable derivatives may be packaged as articles of manufacture containing packaging material, a compound or pharmaceutically acceptable derivative thereof provided herein, which is effective for modulating the activity of nuclear receptors, including FXR, LXR and/or orphan nuclear receptors, or for treatment, prevention or amelioration of one or more symptoms of nuclear receptor, including FXR, LXR and/or orphan nuclear receptor, mediated diseases or disorders, or diseases or disorders in which nuclear receptor activity, including FXR, LXR and/or orphan nuclear receptor activity, is implicated, within the packaging material, and a label that indicates that the compound or composition, or pharmaceutically acceptable derivative thereof, is used for modulating the activity of nuclear receptors, including FXR, LXR and/or orphan nuclear receptors, or for treatment, prevention or amelioration of one or more symptoms of nuclear receptor, including FXR, LXR and/or orphan nuclear receptor, mediated diseases or disorders, or diseases or disorders in which nuclear receptor activity, including FXR, LXR and/or orphan nuclear receptor activity, is implicated.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder in which nuclear receptor activity, including FXR, LXR and/or orphan nuclear receptor activity, is implicated as a mediator or contributor to the symptoms or cause.

E. Evaluation of the Activity of the Compounds

Standard physiological, pharmacological and biochemical procedures are available for testing the compounds to identify those that possess biological activities that modulate the activity or nuclear receptors, including the FXR. Such assays include, for example, biochemical assays such as binding assays, fluorescence polarization assays, FRET based coactivator recruitment assays (see generally Glickman et al., *J. Biomolecular Screening*, 7 No. 13-10 (2002)), as well as cell based assays including the co-transfection assay, the use of LBD-Gal 4 chimeras and protein-protein interaction assays (see, Lehmann. et al., *J. Biol Chem.*, 272(6) 3137–3140 (1997).

High throughput screening systems are commercially available (see, e.g., Zymark Corp., Hopkinton, Mass.; Air Technical Industries, Mentor, Ohio; Beckman Instruments Inc., Fullerton, Calif.; Precision Systems, Inc., Natick, Mass.) that enable these assays to be run in a high throughput mode. These systems typically automate entire procedures, including all sample and reagent pipetting, liquid dispensing timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

Assays that do not require washing or liquid separation steps are preferred for such high throughput screening systems and include biochemical assays such as fluorescence polarization assays (see for example, Owicki, J., Biomol Screen 2000 October;5(5):297) scintillation proximity assays (SPA) (see for example, Carpenter et al., Methods Mol Biol 2002; 190:31–49) and fluorescence resonance energy transfer energy transfer (FRET) or time resolved FRET based coactivator recruitment assays (Mukherjee et al., J Steroid Biochem Mol Biol 2002 July;81 (3):217–25; (Zhou et al., Mol Endocrinol. 1998 October; 12(10):1594–604). Generally such assays can be preformed using either the full length receptor, or isolated ligand binding domain (LBD). In the case of FXR, the LBD comprises amino acids 244 to 472 of the full length sequence.

If a fluorescently labeled ligand is available, fluorescence polarization assays provide a way of detecting binding of compounds to the nuclear receptor of interest by measuring changes in fluorescence polarization that occur as a result of the displacement of a trace amount of the label ligand by the compound. Additionally this approach can also be used to monitor the ligand dependent association of a fluorescently labeled coactivator peptide to the nuclear receptor of interest to detect ligand binding to the nuclear receptor of interest.

The ability of a compound to bind to a receptor, or heterodimer complex with RXR, can also be measured in a homogeneous assay format by assessing the degree to which the compound can compete off a radiolabelled ligand with known affinity for the receptor using a scintillation proximity assay (SPA). In this approach, the radioactivity emitted by a radiolabelled compound generates an optical signal when it is brought into close proximity to a scintillant such as a Ysi-copper containing bead, to which the nuclear receptor is bound. If the radiolabelled compound is displaced from the nuclear receptor the amount of light emitted from the nuclear receptor bound scintillant decreases, and this can be readily detected using standard microplate liquid scintillation plate readers such as, for example, a Wallac MicroBeta reader.

The heterodimerization of FXR with RXRα can also be measured by fluorescence resonance energy transfer (FRET), or time resolved FRET, to monitor the ability of the compounds provided herein to bind to FXR or other nuclear receptors. Both approaches rely upon the fact that energy transfer from a donor molecule to an acceptor molecule only occurs when donor and acceptor are in close proximity. Typically the purified LBD of the nuclear receptor of interest is labeled with biotin then mixed with stoichiometric amounts of europium labeled streptavidin (Wallac Inc.), and the purified LBD of RXRα is labeled with a suitable fluorophore such as CY5™. Equimolar amounts of each modified LBD are mixed together and allowed to equilibrate for at least 1 hour prior to addition to either variable or constant concentrations of the sample for which the affinity is to be determined. After equilibration, the time-resolved fluorescent signal is quantitated using a fluorescent plate reader. The affinity of the compound can then be estimated from a plot of fluorescence versus concentration of compound added.

This approach can also be exploited to measure the ligand dependent interaction of a co-activator peptide with a nuclear receptor in order to characterize the agonist or antagonist activity of the compounds disclosed herein. Typically the assay in this case involves the use a recombinant Glutathione-S-transferase (GST)-nuclear receptor ligand binding domain (LBD) fusion protein and a synthetic biotinylated peptide sequenced derived from the receptor interacting domain of a co-activator peptide such as the steroid receptor coactivator 1 (SRC-1). Typically GST-LBD is labeled with a europium chelate (donor) via a europium-tagged anti-GST antibody, and the coactivator peptide is labeled with allophycocyanin via a streptavidin-biotin linkage.

In the presence of an agonist for the nuclear receptor, the peptide is recruited to the GST-LBD bringing europium and allophycocyanin into close proximity to enable energy transfer from the europium chelate to the allophycocyanin. Upon excitation of the complex with light at 340 nm excitation energy absorbed by the europium chelate is transmitted to the allophycocyanin moiety resulting in emission at 665 nm. If the europium chelate is not brought in to close proximity to the allophycocyanin moiety there is little or no energy transfer and excitation of the europium chelate results in emission at 615 nm. Thus the intensity of light emitted at 665 nm gives an indication of the strength of the protein-protein interaction. The activity of a nuclear receptor antagonist can be measured by determining the ability of a compound to competitively inhibit (i.e., $IC_{50}$) the activity of an agonist for the nuclear receptor.

In addition a variety of cell based assay methodologies may be successfully used in screening assays to identify and profile the specificity of compounds of the present invention. These approaches include the co-transfection assay, translocation assays, complementation assays and the use of gene activation technologies to over express endogenous nuclear receptors.

Three basic variants of the co-transfection assay strategy exist, co-transfection assays using full-length nuclear receptor, co transfection assays using chimeric nuclear receptors comprising the ligand binding domain of the nuclear receptor of interest fused to a heterologous DNA binding domain, and assays based around the use of the mammalian two hybrid assay system.

The basic co-transfection assay is based on the co-transfection into the cell of an expression plasmid to express the nuclear receptor of interest in the cell with a reporter plasmid comprising a reporter gene whose expression is under the control of DNA sequence that is capable of interacting with that nuclear receptor. (See for example U.S. Pat. Nos. 5,071,773; 5,298,429 and 6,416,957).Treatment of the transfected cells with an agonist for the nuclear receptor increases the transcriptional activity of that receptor which is reflected by an increase in expression of the reporter gene, which may be measured by a variety of standard procedures.

For those receptors that function as heterodimers with RXR, such as FXR, the co-transfection assay typically includes the use of expression plasmids for both the nuclear receptor of interest and RXR. Typical co-transfection assays require access to the full length nuclear receptor and suitable response elements that provide sufficient screening sensitivity and specificity to the nuclear receptor of interest.

Genes encoding the following full-length previously described proteins, which are suitable for use in the co-transfection studies and profiling the compounds described herein, include rat FXR (SEQ ID NO. 5), human FXR (SEQ ID NO.7), human RXR α (SEQ ID NO. 9), human RXR β (SEQ ID NO. 17), human RXR.γ (SEQ ID NO. 15), human LXR α (SEQ ID NO. 1), human LXR β (SEQ ID NO. 3),human PPARα (SEQ ID NO. 11) and human PPAR δ (SEQ ID NO. 13).

Reporter plasmids may be constructed using standard molecular biological techniques by placing cDNA encoding for the reporter gene downstream from a suitable minimal promoter. For example luciferase reporter plasmids may be constructed by placing cDNA encoding firefly luciferase immediately down stream from the herpes virus thymidine kinase promoter (located at nucleotides residues-105 to +51 of the thymidine kinase nucleotide sequence) which is linked in turn to the various response elements.

Numerous methods of co-transfecting the expression and reporter plasmids are known to those of skill in the art and may be used for the co-transfection assay to introduce the plasmids into a suitable cell type. Typically such a cell will not endogenously express nuclear receptors that interact with the response elements used in the reporter plasmid.

Numerous reporter gene systems are known in the art and include, for example, alkaline phosphatase Berger, J., et al. (1988) Gene 66 1–10; Kain, S. R. (1997) Methods. Mol. Biol. 63 49–60), β-galactosidase (See, U.S. Pat. No. 5,070, 012, issued Dec., 3, 1991 to Nolan et al., and Bronstein, I., et al., (1989) J. Chemilum. Biolum. 4 99–111), chloramphenicol acetyltransferase (See Gorman et al., Mol Cell Biol. (1982) 2 1044–51), β-glucuronidase, peroxidase, β-lactamase (U.S. Pat. Nos. 5,741,657 and 5,955,604), catalytic antibodies, luciferases (U.S. Pat. Nos. 5,221,623; 5,683,888; 5,674,713; 5,650,289; 5,843,746) and naturally fluorescent proteins (Tsien, R. Y. (1998) Annu. Rev. Biochem. 67 509–44).

The use of chimeras comprising the ligand binding domain (LBD) of the nuclear receptor of interest to a heterologous DNA binding domain (DBD) expands the versatility of cell based assays by directing activation of the nuclear receptor in question to defined DNA binding elements recognized by defined DNA binding domain (see WO95/18380). This assay expands the utility of cell based co-transfection assays in cases where the biological response or screening window using the native DNA binding domain is not satisfactory.

In general the methodology is similar to that used with the basic co-transfection assay, except that a chimeric construct is used in place of the full length nuclear receptor. As with the full length nuclear receptor, treatment of the transfected cells with an agonist for the nuclear receptor LBD increases the transcriptional activity of the heterologous DNA binding domain which is reflected by an increase in expression of the reporter gene as described above. Typically for such chimeric constructs, the DNA binding domains from defined nuclear receptors, or from yeast or bacterially derived transcriptional. regulators such as members of the GAL 4 and Lex A/Umud super families are used.

A third cell based assay of utility for screening compounds of the present invention is a mammalian two-hybrid assay that measures the ability of the nuclear hormone receptor to interact with a cofactor in the presence of a ligand. (See for example, U.S. Pat. Nos. 5,667,973, 5,283, 173 and 5,468,614). The basic approach is to create three plasmid constructs that enable the interaction of the nuclear receptor with the interacting protein to be coupled to a transcriptional readout within a living cell. The first construct is an expression plasmid for expressing a fusion protein comprising the interacting protein, or a portion of that protein containing the interacting domain, fused to a GAL4 DNA binding domain. The second expression plasmid comprises DNA encoding the nuclear receptor of interest fused to a strong transcription activation domain such as VP16, and the third construct comprises the reporter plasmid comprising a reporter gene with a minimal promoter and GAL4 upstream activating sequences.

Once all three plasmids are introduced into a cell, the GAL4 DNA binding domain encoded in the first construct allows for specific binding of the fusion protein to GAL4 sites upstream of a minimal promoter. However because the GAL4 DNA binding domain typically has no strong transcriptional activation properties in isolation, expression of the reporter gene occurs only at a low level. In the presence of a ligand, the nuclear receptor-VP16 fusion protein can bind to the GAL4-interacting protein fusion protein bringing the strong transcriptional activator VP16 in close proximity to the GAL4 binding sites and minimal promoter region of the reporter gene. This interaction significantly enhances the transcription of the reporter gene, which can be measured for various reporter genes as described above. Transcription of the reporter gene is thus driven by the interaction of the interacting protein and nuclear receptor of interest in a ligand dependent fashion.

Any compound which is a candidate for activation of FXR may be tested by these methods. Generally, compounds are tested at several different concentrations to optimize the chances that activation of the receptor will be detected and recognized if present. Typically assays are performed in triplicate and vary within experimental error by less than 15%. Each experiment is typically repeated three or more times with similar results.

Activity of the reporter gene can be conveniently normalized to the internal control and the data plotted as fold activation relative to untreated cells. A positive control compound (agonist) may be included along with DMSO as high and low controls for normalization of the assay data. Similarly, antagonist activity can be measured by determining the ability of a compound to competitively inhibit the activity of an agonist.

Additionally the compounds and compositions can be evaluated for their ability to increase or decrease the expression of genes known to be modulated by FXR and other nuclear receptors in vivo, using Northern-blot, RT PCR or oligonucleotide microarray analysis to analyze RNA levels. Western-blot analysis can be used to measure expression of proteins encoded by FXR target genes. Genes that are known to be regulated by the FXR include cholesterol 7 a-hydroxylase (CYP7A1), the rate limiting enzyme in the conversion of cholesterol to bile acids, the small heterodimer partner-1 (SHP-1), the bile salt export pump (BSEP, ABCB11), canalicular bile acid export protein, sodium taurocholate cotransporting polypeptide (NTCP, SLC10A1) and intestinal bile acid binding protein (I-BABP).

Established animal models exist for a number of diseases of direct relevance to the claimed compounds and these can be used to further profile and characterize the claimed compounds. These model systems include diabetic dislipidemia using Zucker (fa/fa) rats or (db/db) mice, spontaneous hyperlipidemia using apolipoprotein E deficient mice (ApoE$^{-/-}$), diet-induced hyperlipidemia, using low density lipoprotein receptor deficient mice (LDR$^{-/-}$) and atherosclerosis using both the Apo E($^{-/-}$) and LDL($^{-/-}$) mice fed a western diet. (21% fat, 0.05% cholesterol). Additionally FXR or LXR animal models (e.g., knockout mice) can be used to further evaluate the present compounds and compositions in vivo (see, for example, Sinal, et al., *Cell*, 102: 731–744 (2000), Peet, et al., *Cell*, 93:693–704 (1998)).

F. Methods of Use of the Compounds and Compositions

Methods of use of the compounds and compositions provided herein are also provided. The methods involve both in vitro and in vivo uses of the compounds and compositions for altering nuclear receptor activity, including FXR, LXR and/or orphan nuclear receptor activity, and for treatment, prevention, or amelioration of one or more symptoms of diseases or disorder that are modulated by nuclear receptor activity, including FXR, LXR and/or orphan nuclear receptor activity, or in which nuclear receptor activity, including FXR, LXR and/or orphan nuclear receptor activity, is implicated.

Methods of reducing cholesterol levels and of modulating cholesterol metabolism are provided. As described above, FXR is implicated in modulating cholesterol metabolism, catabolism and absorption of dietary cholesterol. See, e.g., International Patent Application Publication No. 00/40965.

Method of altering nuclear receptor activity, including FXR, LXR and/or orphan nuclear receptor activity, by contacting the receptor with one or more compounds or compositions provided herein, are provided.

Methods of treatment, prevention, or amelioration of one or more symptoms of a disease or disorder which is affected by cholesterol, triglyceride, or bile acid levels are provided.

Methods of treatment, prevention, or amelioration of one or more symptoms of hypercholesterolemia (see, e.g., International Patent Application Publication No. WO 00/57915); hyperlipoproteinemia (see, e.g., International Patent Application Publication No. WO 01/60818); hypertriglyceridemia, lipodystrophy, hyperglycemia or diabetes mellitus (see, e.g., International Patent Application Publication No. WO 01/82917); dyslipidemia, obesity, atherosclerosis, lipid disorders, cardiovascular disorders, or gallstone disease (see, e.g., International Patent Application Publication No. WO 00/37077); acne vulgaris or acneiform skin conditions (see, e.g., International Patent Application Publication No. WO 00/49992); atherosclerosis, diabetes, Parkinson's disease, inflammation, immunological disorders, obesity, cancer or Alzheimer's disease (see, e.g., International Patent Application Publication No. WO 00/17334); conditions characterized by a perturbed epidermal barrier function, hyperlipidemia, cholestasis, peripheral occlusive disease, ischemic stroke, or conditions of disturbed differentiation or excess proliferation of the epidermis or mucous membrane (see, e.g., U.S. Pat. Nos. 6,184,215 and 6,187,814, and International Patent Application Publication No. WO 98/32444) are provided.

Methods of increasing cholesterol efflux from mammalian cells using the compounds and compositions provided herein are provided (see, e.g., International Patent Application Publication No. WO 00/78972).

Methods of increasing the expression of ATP-Binding Cassette (ABC1) in mammalian cells using the compounds and compositions provided herein are provided (see, e.g., International Patent Application Publication No. WO 00/78972).

Further provided herein are methods for the treatment, prevention, or amelioration of one or more symptoms of cholestasis, as well as treating the complications of cholestasis by administering a compound provided herein.

Cholestasis is typically caused by factors within the liver (intrahepatic) or outside the liver (extrahepatic) and leads to the accumulation of bile salts, bile pigment bilirubin, and lipids in the blood stream instead of being eliminated normally.

Intrahepatic cholestasis is characterized by widespread blockage of small ducts or by disorders, such as hepatitis, that impair the body's ability to eliminate bile. Intrahepatic cholestasis may also be caused by alcoholic liver disease, primary biliary cirrhosis, cancer that has spread (metastasized) from another part of the body, primary sclerosing cholangitis, gallstones, biliary colic and acute cholecystitis. It can also occur as a complication of surgery, serious injury, infection, or intravenous feeding or be drug induced. Cholestasis may also occur as a complication of pregnancy and often develops during the second and third trimesters.

Extrahepatic cholestasis is most often caused by choledocholithiasis (Bile Duct Stones), benign biliary strictures (non-cancerous narrowing of the common duct), cholangiocarcinoma (ductal carcinoma) and pancreatic carcinoma. Extrahepatic cholestasis can occur as a side effect of many medications.

Accordingly, compounds provided herein may be used for the treatment, prevention, or amelioration of one or more symptoms of intrahepatic or extrahepatic cholestasis, including without limitation, biliary artesia, obstetric cholestasis, neonatal cholestasis, drug induced cholestasis, cholestasis arising from Hepatitis C infection, chronic cholestatic liver disease such as primary biliary cirrhosis (PBC) and primary sclerosing cholangitis (PSC).

Methods of treating, preventing, or ameliorating one or more symptoms of hypocholesterolemia using the compounds and compositions provided herein are also provided.

G. Combination Therapy

Also contemplated herein is combination therapy using a compound provided herein, or a pharmaceutically acceptable derivative thereof, in combination with one or more of the following: antihyperlipidemic agents, plasma HDL-raising agents, antihypercholesterolemic agents, cholesterol biosynthesis inhibitors (such as HMG CoA reductase inhibitors, such as lovastatin, simvastatin, pravastatin, fluvastatin, atorvastatin and rivastatin), acyl-coenzyme A:cholesterol acytransferase (ACAT) inhibitors, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives. The compound provided herein, or pharmaceutically acceptable derivative thereof, is administered simultaneously with, prior to, or after administration of one or more of the above agents. Pharmaceutical compositions containing a compound provided herein and one or more of the above agents are also provided.

Combination therapy includes administration of a single pharmaceutical dosage formulation which contains a FXR selective compound and one or more additional active agents, as well as administration of the FXR selective compound and each active agent in its own separate pharmaceutical dosage formulation. For example, a FXR agonist or antagonist of the present invention and an HMG-CoA reductase inhibitor can be administered to the patient together in a single oral dosage composition such as a tablet or capsule, or each agent administered in separate oral dosage formulations. Where separate dosage formulations are used, the compounds described herein and one or more additional active agents can be administered at essentially the same time, i.e., concurrently, or at separately staggered times, i.e., sequentially; combination therapy is understood to include all these regimens.

The compound is preferably administered with a cholesterol biosynthesis inhibitor, particularly an HMG-CoA reductase inhibitor. The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art. For instance, suitable assays are described or disclosed in U.S. Pat. No. 4,231,938 and WO 84/02131. Examples of suitable HMG-CoA reductase inhibitors include, but are not limited to, lovastatin (MEVACOR®; see, U.S. Pat. No. 4,231,938); simvastatin (ZOCOR®; see, U.S. Pat. No. 4,444,784); pravastatin sodium (PRAVACHOL®; see, U.S. Pat. No. 4,346,227); fluvastatin sodium (LESCOL®; see, U.S. Pat. No. 5,354,772); atorvastatin calcium (LIPITOR®; see, U.S. Pat. No. 5,273,995) and rivastatin (also known as cerivastatin; see, U.S. Pat. No. 5,177,080). The structural formulas of these and additional HMG-CoA reductase inhibitors that can be used in the methods of the present invention are described at page 87 of M. Yalpani, "Cholesterol Lowering Drugs," *Chemistry & Industry*, pp. 85–89 (5 February 1996). In presently preferred embodiments, the HMG-CoA reductase inhibitor is selected from lovastatin and simvastatin.

Dosage information for HMG-CoA reductase inhibitors is well known in the art, since several HMG-CoA reductase inhibitors are marketed in the U.S. In particular, the daily dosage amounts of the HMG-CoA reductase inhibitor may be the same or similar to those amounts which are employed for anti-hypercholesterolemic treatment and which are described in the *Physicians' Desk Reference* (PDR). For example, see the 50th Ed. of the PDR, 1996 (Medical Economics Co); in particular, see at page 216 the heading "Hypolipidemics," sub-heading "HMG-CoA Reductase Inhibitors," and the reference pages cited therein. Preferably, the oral dosage amount of HMG-CoA reductase inhibitor is from about 1 to 200 mg/day and, more preferably, from about 5 to 160 mg/day. However, dosage amounts will vary depending on the potency of the specific HMG-CoA reductase inhibitor used as well as other factors as noted above. An HMG-CoA reductase inhibitor which has sufficiently greater potency may be given in sub-milligram daily dosages.

As examples, the daily dosage amount for simvastatin may be selected from 5 mg, 10 mg, 20 mg, 40 mg, 80 mg and 160 mg for lovastatin, 10 mg, 20 mg, 40 mg and 80 mg; for fluvastatin sodium, 20 mg, 40 mg and 80 mg; and for pravastatin sodium, 10 mg, 20 mg, and 40 mg. The daily dosage amount for atorvastatin calcium may be in the range of from 1 mg to 160 mg and, more particularly, from 5 mg to 80 mg. Oral administration may be in a single or divided doses of two, three, or four times daily, although a single daily dose of the HMG-CoA reductase inhibitor is preferred.

The compounds of the present invention can be utilized in methods for decreasing hyperglycemia and insulin resistance or for methods of treating type II diabetes. The compounds can be identified, formulated, and administered as described above.

Diabetes mellitus, commonly called diabetes, refers to a disease process derived from multiple causative factors and characterized by elevated levels of plasma glucose, referred to as hyperglycemia. See, e.g., LeRoith, D. et al., (eds.), DIABETES MELLITUS (Lippincott-Raven Publishers, Philadelphia, Pa. U.S.A. 1996). According to the American Diabetes Association, diabetes mellitus is estimated to affect approximately 6% of the world population. Uncontrolled hyperglycemia is associated with increased and premature mortality due to an increased risk for macrovascular and macrovascular diseases, including nephropathy, neuropathy, retinopathy, hypertension, cerebrovascular disease and coronary heart disease. Therefore, control of glucose homeostasis is a critically important approach for the treatment of diabetes.

There are two major forms of diabetes: type 1 diabetes (formerly referred to as insulin-dependent diabetes or IDEM); and type 2 diabetes (formerly referred to as noninsulin dependent diabetes or NIDDM).

Type 2 diabetes is a disease characterized by insulin resistance accompanied by relative, rather than absolute, insulin deficiency. Type 2 diabetes can range from predominant insulin resistance with relative insulin deficiency to predominant insulin deficiency with some insulin resistance. Insulin resistance is the diminished ability of insulin to exert its biological action across a broad range of concentrations. In insulin resistant individuals, the body secretes abnormally high amounts of insulin to compensate for this defect. When inadequate amounts of insulin are present to compensate for insulin resistance and adequate control of glucose, a state of impaired glucose tolerance develops. In a significant number of individuals, insulin secretion declines further and the plasma glucose level rises, resulting in the clinical state of diabetes. Type 2 diabetes can be due to a profound resistance to insulin stimulating regulatory effects on glucose and lipid metabolism in the main insulin-sensitive tissues: muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. In Type 2 diabetes, free fatty acid levels are often elevated in obese and some non-obese patients and lipid oxidation is increased.

Premature development of atherosclerosis and increased rate of cardiovascular and peripheral vascular diseases are characteristic features of patients with diabetes. Hyperlipidemia is an important precipitating factor for these diseases. Hyperlipidemia is a condition generally characterized by an abnormal increase in serum lipids in the bloodstream and is an important risk factor in developing atherosclerosis and heart disease. For a review of disorders of lipid metabolism, see, e.g., Wilson, J. et al., (ed.), Disorders of Lipid Metabolism, Chapter 23, Textbook of Endocrinology, 9th Edition, (W.B. Sanders Company, Philadelphia, Pa. U.S.A. 1998). Hyperlipidemia is usually classified as primary or secondary hyperlipidemia. Primary hyperlipidemia is generally caused by genetic defects, while secondary hyperlipidemia is generally caused by other factors, such as various disease states, drugs, and dietary factors. Alternatively, hyperlipidemia can result from both a combination of primary and secondary causes of hyperlipidemia. Elevated cholesterol levels are associated with a number of disease states, including coronary artery disease, angina pectoris, carotid artery disease, strokes, cerebral arteriosclerosis, and xanthoma.

Dyslipidemia, or abnormal levels of lipoproteins in blood plasma, is a frequent occurrence among diabetics, and has been shown to be one of the main contributors to the increased incidence of coronary events and deaths among diabetic subjects (see, e.g., Joslin, E. Ann. Chim. Med. (1927) 5: 1061–1079). Epidemiological studies since then have confirmed the association and have shown a several-fold increase in coronary deaths among diabetic subjects when compared with nondiabetic subjects (see, e.g., Garcia, M. J. et al., Diabetes (1974) 23: 105–11 (1974); and Laakso, M. and Lehto, S., Diabetes Reviews (1997) 5(4): 294–315). Several lipoprotein abnormalities have been described among diabetic subjects (Howard B., et al., Arteriosclerosis (1978) 30: 153–162).

The term "insulin resistance" can be defined generally as a disorder of glucose metabolism. More specifically, insulin resistance can be defined as the diminished ability of insulin to exert its biological action across a broad range of concentrations producing less than the expected biologic effect. (see, e.g., Reaven, G. M., J. Basic & Clin. Phys. & Pharm. (1998) 9: 387–406 and Flier, J. Ann Rev. Med. (1983) 34:145–60). Insulin resistant persons have a diminished ability to properly metabolize glucose and respond poorly, if at all, to insulin therapy. Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, Impaired Glucose Tolerance (IGT), gestational diabetes, hypertension, obesity, atherosclerosis and a variety of other disorders. Eventually, the insulin resistant individuals can progress to a point where a diabetic state is reached. The association of insulin resistance with glucose intolerance, an increase in plasma triglyceride and a decrease in high-density lipoprotein cholesterol concentrations, high blood pressure, hyperuricemia, smaller denser low-density lipoprotein particles, and higher circulating levels of plasminogen activator inhibitor-1), has been referred to as "Syndrome X" (see, e.g., Reaven, G. M., Physiol. Rev. (1995) 75: 473–486).

The term "diabetes mellitus" or "diabetes" means a disease or condition that is generally characterized by metabolic defects in production and utilization of glucose which result in the failure to maintain appropriate blood sugar levels in the body. The result of these defects is elevated blood glucose, referred to as "hyperglycemia." Type 2 diabetes often occurs in the face of normal, or even elevated, levels of insulin and can result from the inability of tissues to respond appropriately to insulin. Most type 2 diabetic patients are insulin resistant and have a relative deficiency of insulin, in that insulin secretion can not compensate for the resistance of peripheral tissues to respond to insulin. In addition, many type 2 diabetics are obese. Other types of disorders of glucose homeostasis include Impaired Glucose Tolerance, which is a metabolic stage intermediate between normal glucose homeostasis and diabetes, and Gestational Diabetes Mellitus, which is glucose intolerance in pregnancy in women with no previous history of type 1 or type 2 diabetes.

The term "complication" of diabetes includes, but is not limited to, microvascular complications and macrovascular complications. Microvascular complications are those complications which generally result in small blood vessel damage. These complications include, e.g., retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys). macrovascular complications are those complications which generally result from large blood vessel damage. These complications include, e.g., cardiovascular disease and peripheral vascular disease. Cardiovascular disease refers to diseases of blood vessels of the heart. See. e.g., Kaplan, R. M., et al., "Cardiovascular diseases" in HEALTH AND HUMAN BEHAVIOR, pp. 206–242 (McGraw-Hill, New York 1993). Cardiovascular disease is generally one of several forms, including, e.g., hypertension (also referred to as high blood pressure), coronary heart disease, stroke, and rheumatic heart disease. Peripheral vascular disease refers to diseases of any of the blood vessels outside of the heart. It is often a narrowing of the blood vessels that carry blood to leg and arm muscles.

The term "hyperlipidemia" refers to the presence of an abnormally elevated level of lipids in the blood. Hyperlipidemia can appear in at least three forms: (1) hypercholesterolemia, i.e., an elevated cholesterol level; (2) hypertriglyceridemia, i.e., an elevated triglyceride level; and (3) combined hyperlipidemia, i.e., a combination of hypercholesterolemia and hypertriglyceridemia.

The term "cholesterol" refers to a steroid alcohol that is an essential component of cell membranes and myelin sheaths and, as used herein, incorporates its common usage. Cholesterol also serves as a precursor for steroid hormones and bile acids.

The term "triglyceride(s)" ("TGs"), as used herein, incorporates its common usage. TGs consist of three fatty acid molecules esterified to a glycerol molecule and serve to store fatty acids which are used by muscle cells for energy production or are taken up and stored in adipose tissue.

The term "dyslipidemia" refers to abnormal levels of lipoproteins in blood plasma including both depressed and/or elevated levels of lipoproteins (e.g., elevated levels of LDL, VLDL and depressed levels of HDL).

Exemplary Primary Hypedipidemia include, but are not limited to, the following: (1) Familial Hyperchylomicronemia, a rare genetic disorder which causes a deficiency in an enzyme, LP lipase, that breaks down fat molecules. The LP lipase deficiency can cause the accumulation of large quantities of fat or lipoproteins in the blood;

(2) Familial Hypercholesterolemia, a relatively common genetic disorder caused where the underlying defect is a series of mutations in the LDL receptor gene that result in malfunctioning LDL receptors and/or absence of the LDL receptors. This brings about ineffective clearance of LDL by the LDL receptors resulting in elevated LDL and total cholesterol levels in the plasma;

(3) Familial Combined Hypedipidemia, also known as multiple lipoprotein-type hyperlipidemia; an inherited disorder where patients and their affected first-degree relatives can at various times manifest high cholesterol and high triglycerides. Levels of HDL cholesterol are often moderately decreased;

(4) Familial Defective Apolipoprotein B-100 is a relatively common autosomal dominant genetic abnormality. The defect is caused by a single nucleotide mutation that produces a substitution of glutamine for arginine which can cause reduced affinity of LDL particles for the LDL receptor. Consequently, this can cause high plasma LDL and total cholesterol levels;

(5) Familial Dysbetaliproteinemia, also referred to as Type III Hyperlipoproteinemia, is an uncommon inherited disorder resulting in moderate to severe elevations of serum TG and cholesterol levels with abnormal apolipoprotein E function. HDL levels are usually normal; and (6) Familial Hypertriglyceridemia, is a common inherited disorder in which the concentration of plasma VLDL is elevated. This can cause mild to moderately elevated triglyceride levels (and usually not cholesterol levels) and can often be associated with low plasma HDL levels.

Risk factors in exemplary Secondary Hyperlipidemia include, but are not limited to, the following: (1) disease risk factors, such as a history of type 1 diabetes, type 2 diabetes, Cushing's syndrome, hypothyroidism and certain types of renal failure; (2) drug risk factors, which include, birth control pills; hormones, such as estrogen, and corticosteroids; certain diuretics; and various .beta. blockers; (3) dietary risk factors include dietary fat intake per total calories greater than 40%; saturated fat intake per total calories greater than 10%; cholesterol intake greater than 300 mg per day; habitual and excessive alcohol use; and obesity; and (4) non-genetic dyslipidemias.

The methods of the present invention can be used effectively in combination with one or more additional active diabetes agents depending on the desired target therapy (see, e.g., Turner, N. et al. Prog. Drug Res. (1998) 51: 33–94; Haffner, S. Diabetes Care (1998) 21: 160–178; and DeFronzo, R. et al. (eds.), Diabetes Reviews (1997) Vol. 5 No. 4). A number of studies have investigated the benefits of combination therapies with oral agents (see, e.g., Mahler, R., J. Clin. Endocrinol. Metab. (1999) 84: 1165–71; United Kingdom Prospective Diabetes Study Group: UKPDS 28, Diabetes Care (1998) 21: 87–92; Bardin, C. W.,(ed.), CURRENT THERAPY IN ENDOCRINOLOGY AND METABOLISM, 6th Edition (Mosby—Year Book, Inc., St. Louis, Mo. 1997); Chiasson, J. et al., Ann. Intern. Med. (1994) 121: 928–935; Coniff, R. et al., Clin. Ther. (1997) 19:16–26; Coniff, R. et al., Am. J. Med. (1995) 98: 443–451; and Iwamoto, Y. et al, Diabet. Med. (1996) 13 365–370; Kwiterovich, P. Am. J. Cardiol (1998) 82(12A): 3U–17U). These studies indicate that diabetes and hyperlipidemia modulation can be further improved by the addition of a second agent to the therapeutic regimen.

An example of combination therapy that modulates (prevents the onset of the symptoms or complications associated) atherosclerosis, is administered with one or more of the following active agents: an antihyperlipidemic agent; a plasma HDL-raising agent; an antihypercholesterolemic agent, such as a cholesterol biosynthesis inhibitor, e.g., an hydroxymethylglutaryl (HMG) CoA reductase inhibitor (also referred to as statins, such as lovastatin, simvastatin, pravastatin, fluvastatin, and atorvastatin), an HMG-CoA synthase inhibitor, a squalene epoxidase inhibitor, or a squalene synthetase inhibitor (also known as squalene synthase inhibitor); an acyl-coenzyme A cholesterol acyltransferase (ACAT) inhibitor, such as melinamide; probucol; nicotinic acid and the salts thereof and niacinamide; a cholesterol absorption inhibitor, such as β-sitosterol; a bile acid sequestrant anion exchange resin, such as cholestyramine, colestipol or dialkylaminoalkyl derivatives of a cross-linked dextran; an LDL (low density lipoprotein) receptor inducer; fibrates, such as clofibrate, bezafibrate, fenofibrate, and gemfibrizol; vitamin $B_6$ (also known as pyridoxine) and the pharmaceutically acceptable salts thereof, such as the HCl salt; vitamin $B_{12}$ (also known as cyanocobalamin); vitamin $B_3$ (also known as nicotinic acid and niacinamide, supra); anti-oxidant vitamins, such as vitamin C and E and beta carotene; a beta-blocker; an angiotensin II antagonist; an angiotensin converting enzyme inhibitor; and a platelet aggregation inhibitor, such as fibrinogen receptor antagonists (i.e., glycoprotein IIb/IIIa fibrinogen receptor antagonists) and aspirin.

Still another example of combination therapy can be seen in modulating diabetes (or treating diabetes and its related symptoms, complications, and disorders) with, for example, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone); and related insulin sensitizers, such as selective and non-selective activators of PPARα, PPARβ and PPARγ; dehydroepiandrosterone (also referred to as DHEA or its conjugated sulphate ester, DHEA-$SO_4$); antiglucocorticoids; TNFαinhibitors; α-glucosidase inhibitors (such as acarbose, miglitol, and voglibose), pramlintide (a synthetic analog of the human hormone amylin), other insulin secretogogues (such as repaglinide, gliquidone, and nateglinide), insulin, as well as the active agents discussed above for treating atherosclerosis.

Further provided by this invention are methods for treating obesity, as well as treating the complications of obesity, by administering a compound of the present invention. The antagonists can be identified, formulated, and administered similarly to the information described above. A FXR selective antagonist includes a partial agonist/antagonist or antagonist that exhibits about a two to about a ten-fold preference for FXR compared to another nuclear receptor such as, for example LXR α or β with respect to potency ($IC_{50}$, the concentration of compound that achieves 50% of the maximum reduction in the transcription activity achieved by the compound of interest observed in the presence of a sub-maximal concentration of FXR agonist) and/or efficacy (the maximum percent inhibition of transcription observed with the compound in question).

The terms "obese" and "obesity" refers to, according to the World Health Organization, a Body Mass Index (BMI) greater than 27.8 $kg/m^2$ for men and 27.3 $kg/m^2$ for women (BMI equals weight (kg)/height ($m^2$). Obesity is linked to a variety of medical conditions including diabetes and hyperlipidemia. Obesity is also a known risk factor for the development of type 2 diabetes (See, e.g., Barrett-Conner, E., Epidemol. Rev. (1989) 11: 172–181; and Knowler, et al., Am. J Clin. Nutr. (1991) 53:1543–1551).

Another example of combination therapy can be seen in treating obesity or obesity-related disorders, wherein the methods can be effectively used in combination with, for example, phenylpropanolamine, phentermine, diethylpropion, mazindol; fenfluramine, dexfenfluramine, phentiramine, $\beta_3$ adrenoceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptors, melanocyte stimulating hormone, corticotrophin releasing factor, galanin and gamma amino butyric acid (GABA).

Another example of a combination therapy can be seen in treating cholestasis, where the compounds of the invention can be combined with Actigall (Ursodeoxycholic acid—UDCA), corticosteroids, anti-infective agents (Rifampin, Rifadin, Rimactane), anti-viral agents, Vitamin D, Vitamin A, phenobarbital, cholestyramine, UV light, antihistamines, oral opiate receptor antagonists and biphosphates, for the treatment, prevention, or amelioration of one or more symptoms of intrahepatic or extrahepatic cholestasis. Dosage information for these agents is well known in the art.

The following examples are included for illustrative purposes only and are not intended to limit the scope of the subject matter claimed herein.

EXAMPLE 1

A. Preparation of 3-Benzyl-5-(3-methyl-3H-benzothiazol-2-ylidene)-2-thioxothiazolidin-4-one

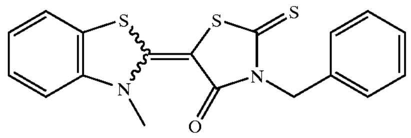

To a 100 mL flask was added anhydrous anisole (14 mL), 2-(methylthio)benzothiazole (10.0 g, 55.2 mmol) and methyl p-toluenesulfonate (12.5 mL, 82.7 mmol). After heating the mixture at 120° C. for 30 min, a crystalline solid precipitated. Anisole (14 mL) was added and the mixture was further heated at 120° C. for 4 h.

After cooling to room temperature, the mixture was then transferred to a 1000 mL flask and diluted with anhydrous MeCN (200 mL). To the well-stirred mixture was added N-benzyl rhodanine (12.3 g, 55.1 mmol) and then dropwise TEA (12.5 mL, 90 mmol). The resulting yellow slurry was diluted with MeCN (200 mL) and stirred 2 h. The yellow precipitates were filtered under reduced pressure, washed first with MeCN (50 mL) and then MeOH (150 mL) to give the crude product.

To a three-neck 1 L flask fitted with a reflux condenser was added the crude product, acetone (100 mL) and MeOH (200 mL). The mixture was stirred under reflux for 15 min, cooled to room temperature, filtered under reduced pressure, washed with MeOH (100 mL) and dried under vacuum for 24 h to yield the title product (17.4 g, 85%) as a yellow solid, which was used without further purification. $^1$H-NMR ($CDCl_3$): δ 7.61 (1H, dd), 7.55 (2H, m), 7.44 (1H, m), 7.25–7.34 (4H, m), 7.21 (1H, d), 5.37 (2H, s), 3.91 (3H, s); MS(ESI): 371 ($MH^+$).

B. Preparation of 3-Benzyl-5-(3-methyl-3H-benzothiazol-2-ylidene)-2-methylthio4-oxo-2-thiazolium p-Toluenesulfonate

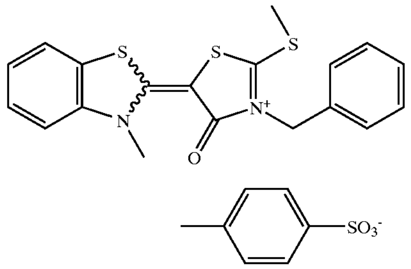

To a 200 mL flask was added 3-benzyl-5-(3-methylbenzothiazolin-2-ylidene)-2-thioxothiazolidin-4-one (5.00 g, 13.5 mmol), methyl p-toluenesulfonate (7.34 mL, 48.6 mmol) and anhydrous DMF(40 mL). After heating at 120° C. for 3 h, the mixture was allowed to cool to 60° C., transferred to a 1 L flask and diluted with acetone (400 mL). After cooling to room temperature, the precipitate was filtered under reduced pressure, washed first with acetone (50 mL) and then $Et_2O$ (100 mL), and dried under vacuum for 12 h to give the title product (6.25 g, 83%) as a yellow crystalline solid, which was used without further purification. $^1$H-NMR ($CDCl_3$): δ 7.83 (1H, d), 7.75 (2H, m), 7.59–7.66 (2H, m), 7.50 (1H, m), 7.37–7.43 (5H, m), 7.06 (2H, d), 5.31 2H, s), 4.52 (3H, s), 3.22 (3H, s), 2.28 (3H, s).

C. Preparation of 3-Benzyl-5-(3-methyl-3H-benzothiazol-2-ylidene)-2-phenylimino-thiazolidine-4-one

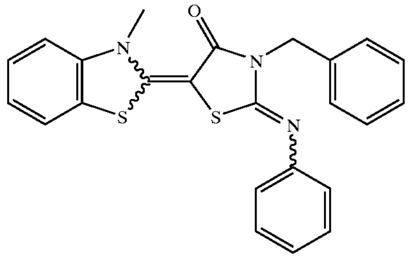

To an 8 mL vial was added 3-benzyl-5-(3-methyl-3H-benzothiazol-2-ylidene)-2-methylthio-4-oxo-2-thiazolium p-toluenesulfonate (100 mg, 0.18 mmol), aniline (16 μL, 0.18 mmol) and anhydrous MeCN (1 mL). After warming the mixture to 50° C., TEA (0.10 mL, 0.56 mmol) was added and continued heating the mixture at 50° C. for 12 h. After cooling to room temperature, the resulting precipitates were filtered under reduced pressure, washed with MeCN (2 mL) and dried under vacuum to yield the title product (22.3 mg, 29%) as a yellow solid. $^1$H-NMR ($CDCl_3$): δ 7.59 (2H, m), 7.48 (1H, dd), 7.26–7.39 (6H, m), 7.10–7.18 (2H, m) 7.01 (3H, m), 5.16 (2H, s), 3.71 (3H, s); MS(ESI): 430 ($MH^+$).

EXAMPLE 2

Preparation of 3-Benzyl-2-(4-methoxyphenylimino)-5-(3-methyl-3H-benzothiazol-2-ylidene)thiazolidine-4-one

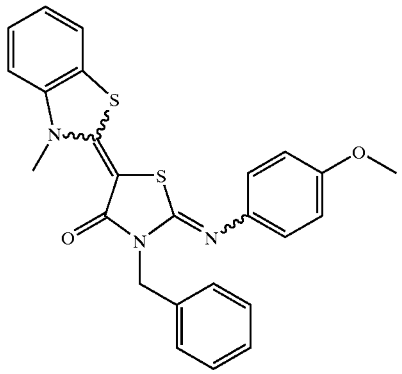

The title compound was prepared in a manner similar to that described in Example 1 by replacing aniline with 4-anisidine. $^1$H-NMR ($CDCl_3$): δ 7.58 (2H, d), 7.48 (1H, d), 7.26–7.35 (4H, m), 7.15 (1H, t), 7.01 (1H, d), 6.96 (2H, d), 6.90 (2H, d), 5.16 (2H, s), 3.82 (3H, s), 3.73 (3H, s); MS(ESI): 460 ($MH^+$).

EXAMPLE 3

Preparation of 3-Benzyl-2-(4-dimethylaminophenylimino)-5-(3-methyl-3H-benzothiazol-2-ylidene)thiazolidine-4-one

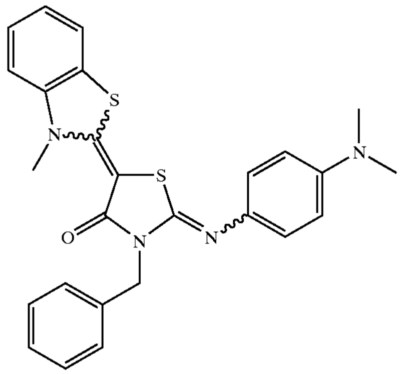

The title compound was prepared in a manner similar to that described in Example 1 by replacing aniline with N,N-dimethyl-1,4-phenylendiamine. $^1$H-NMR ($CDCl_3$): δ 7.59 (2H, d), 7.47 (1H, d), 7.24–7.35 (4H, m), 7.14 (1H, t), 6.99 (1H, d), 6.95 (2H, dd), 6.76 (2H, dd), 5.15 (2H, s), 3.73 (3H, s), 2.95 (6H, s); MS(ESI): 473 ($MH^+$).

EXAMPLE 4

Preparation of 2-(4-Aminophenylimino)-3-benzyl-5-(3-methyl-3H-benzothiazol-2-ylidene)thiazolidine-4-one

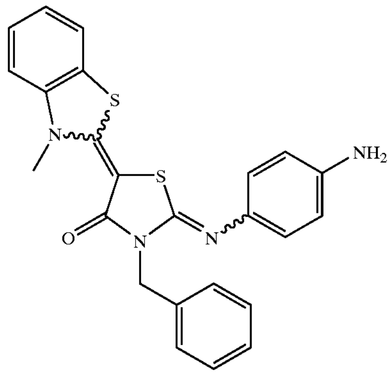

The title compound was prepared in a manner similar to that described in Example 1 by replacing aniline with 1,4-phenylenediamine. $^1$H-NMR ($CDCl_3$): δ 7.58 (2H, m), 7.47 (1H, dd), 7.27–7.34 (4H, m), 7.14 (1H, m), 6.99 (1H, d), 6.85 (2H, dd), 6.70 (2H, dd), 5.14 (2H, s), 3.72 (3H, s), 3.60 (2H, br); MS(ESI): 445 ($MH^+$).

EXAMPLE 5

Preparation of 3-Benzyl-5-(3-methyl-3H-benzothiazol-2-ylidene)-2-(quinolin6-ylimino)-thiazolidine-4-one

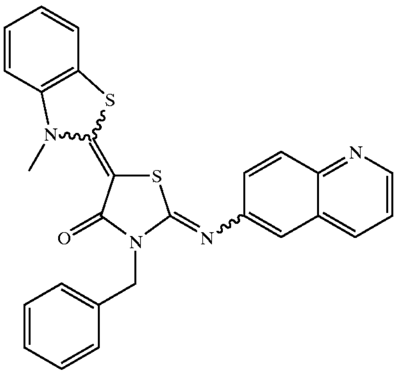

The title compound was prepared in a manner similar to that described in Example 1 by replacing aniline with 6-aminoquinoline. $^1$H-NMR ($CDCl_3$): δ 8.84 (1H, dd), 8.09 (2H, d), 7.62 (2H, m), 7.50 (1H, d), 7.43 (1H, dd), 7.27–7.40 (6H, m), 7.16 (1H, m), 7.01 (1H, d), 5.20 (2H, s), 3.69 (3H, s); MS(ESI): 481 ($MH^+$).

EXAMPLE 6

Preparation of 2-(2-Aminophenylimino)-3-benzyl-5-(3-methyl-3H-benzothiazol-2-ylidene)thiazolidine-4-one

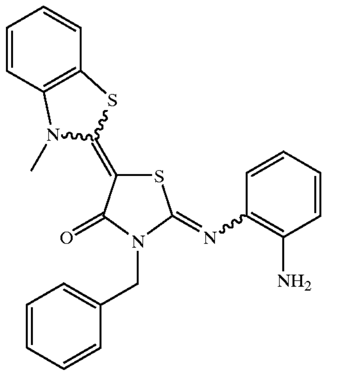

The title compound was prepared in a manner similar to that described in Example 1 by replacing aniline with 1,2-phenylenediamine. $^1$H-NMR ($CDCl_3$): δ 7.48–7.56 (3H, m), 7.30–7.36 (3H, m), 7.26–29 (1H, m), 7.17 (1H, t), 7.03 (1H, d), 6.91–6.99 (2H, m), 6.69–6.77 (2H, m), 5.19 (2H, s), 3.75 (3H, s), 3.49 (2H, s); MS(ESI): 445 ($MH^+$).

EXAMPLE 7

Preparation of 3-Benzyl-2-(4-benzyloxyphenylimino)-5-(3-methyl-3H-benzothiazol-2-ylidene)thiazolidine-4-one

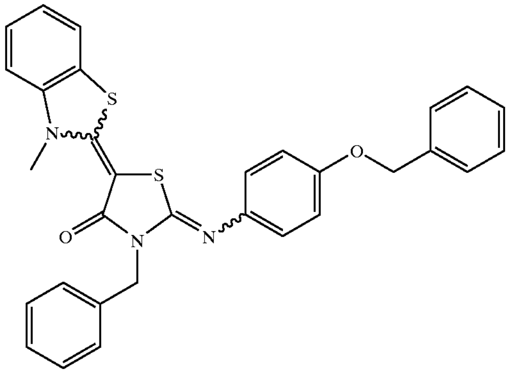

The title compound was prepared in a manner similar to that described in Example 1 by replacing aniline with 4-benzyloxyaniline. $^1$H-NMR ($CDCl_3$): δ 7.58 (2H, d), 7.43–7.50 (3H, m), 7.40 (2H, t), 7.26–7.36 (5H, m), 7.15 (1H, t), 6.93–7.03 (5H, m), 5.14 (2H, s), 5.07 (2H, s), 3.73 (3H, s); MS(ESI): 536 ($MH^+$).

EXAMPLE 8

Preparation of 3-Benzyl-2-(2-hydroxy-1-naphthylimino)-5-(3-methyl-3H-benzothiazol-2-ylidene)thiazolidine-4-one

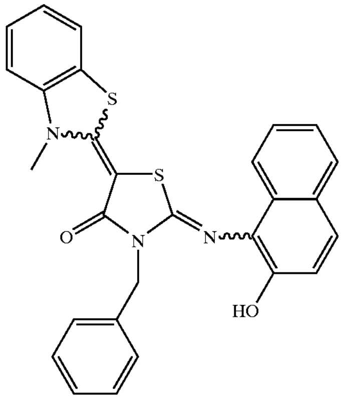

The title compound was prepared in a manner similar to that described in Example 1 by replacing aniline with 1-amino-2-naphthol hydrochloride. $^1$H-NMR ($CDCl_3$): δ 7.79 (1H, d), 7.56–7.64 (3H, m), 7.51 (2H, t), 7.28–7.44 (6H, m), 7.21 (1H, d), 7.18 (1H, t), 6.99 (1H, d), 5.34 (2H, s), 5.00 (1H, s), 3.57 (3H, s); MS(ESI): 496 ($MH^+$).

EXAMPLE 9

Preparation of 3-[3-Benzyl-5-(3-methyl-3H-benzothiazol-2-ylidene)-4-oxothiazolidin-2-ylideneamino]benzonitrile

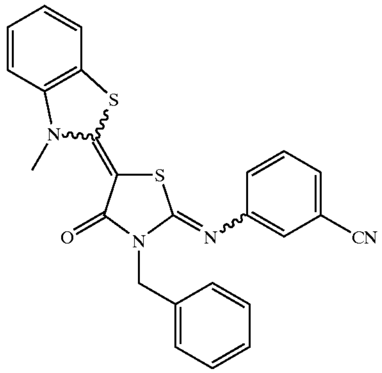

The title compound was prepared in a manner similar to that described in Example 1 by replacing aniline with 3-aminobenzonitrile. $^1$H-NMR (DMSO-$d_6$): δ 7.72 (1H, d), 7.54 (2H, d), 7.23–7.41 (9H, m), 7.16–7.22 (1H, m), 5.02 (2H, s), 3.74 (3H, s); MS(ESI): 455 ($MH^+$).

EXAMPLE 10

Preparation of 3-Benzyl-2-(4-hydroxy-5-isopropyl-2-methylphenylimino)-5-(3-methyl-3H-benzothiazol-2-ylidene)thiazolidine-4-one

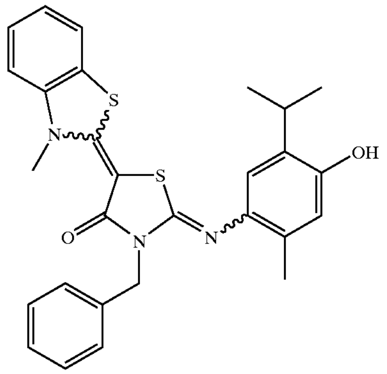

The title compound was prepared in a manner similar to that described in Example 1 by replacing aniline with 4-aminothymol hydrochloride. $^1$H-NMR ($CDCl_3$): δ 7.55–7.60 (2H, m), 7.48 (1H, d), 7.26–7.34 (4H, m), 7.14 (1H, m), 6.99 (1H, d), 6.76 (1H, s), 6.62 (1H, s), 5.17 (2H, s), 4.49 (1H, s), 3.71 (3H, s), 3.17 (1H, m), 1.96 (3H, s), 1.24 (6H, d); MS(ESI): 502 ($MH^+$).

EXAMPLE 11

Preparation of 3-Benzyl-2-(2-ethylamino-5-nitrophenylimino)-5-(3-methyl-3H-benzothiazol-2-ylidene)thiazolidine-4-one

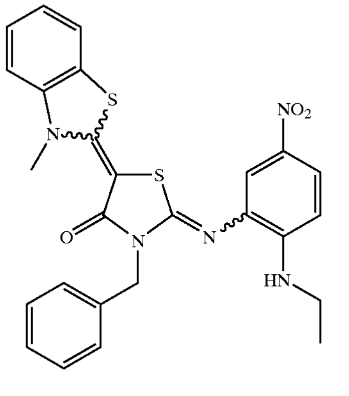

The title compound was prepared in a manner similar to that described in Example 1 by replacing aniline with $N^1$-ethyl-4-nitrobenzene-1,2-diamine. $^1$H-NMR ($CDCl_3$): δ 7.98 (1H, dd), 7.93 (1H, d), 7.55 (1H, d), 7.44 (2H, d), 7.19–7.42 (6H, m), 7.11 (1H, d), 6.46 (1H, d), 5.20 (2H, s), 4.55 (1H, br), 3.83 (3H, s), 3.07 (2H, m), 1.05 (3H, t); MS(ESI): 518 ($MH^+$).

EXAMPLE 12

Preparation of 3-Benzyl-543-methyl-3H-benzothiazol-2-ylidene)-2-[3-(trifluoromethyl)-phenylimino]thiazolidine-4-one

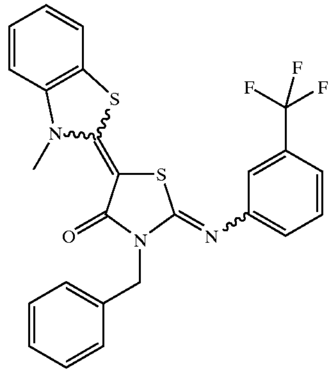

The title compound was prepared in a manner similar to that described in Example 1 by replacing aniline with 3-(trifluoromethyl)aniline. $^1$H-NMR ($CDCl_3$): δ 7.57 (2H, m), 7.50 (1H, d), 7.46 (1H, t), 7.24–7.42 (6H, m), 7.15–7.21 (2H, m), 7.03 (1H, d), 5.15 (2H, s), 3.73 (3H, s); MS(ESI): 498 ($MH^+$).

EXAMPLE 13

Preparation of 2-(3-Acetylphenylimino)-3-benzyl-5-(3-methyl-3H-benzothiazol-2-ylidene)thiazolidine-4-one

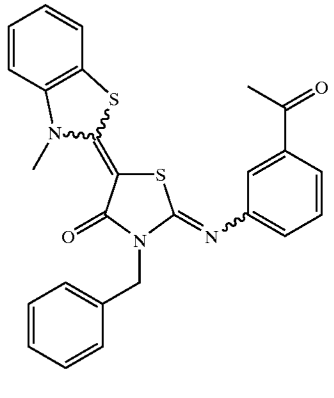

The title compound was prepared in a manner similar to that described in Example 1 by replacing aniline with 3'-aminoacetophenone. $^1$H-NMR ($CDCl_3$): δ 7.72 (1H, m), 7.56–7.60 (3H, m), 7.50 (1H, dd), 7.45 (1H, t), 7.27–7.37 (4H, m), 7.21 (1H, ddd), 7.17 (1H, m), 7.02 (1H, d), 5.16 (2H, s), 3.72 (3H, s), 2.61 (3H, s); MS(ESI): 472 ($MH^+$).

EXAMPLE 14

Preparation of 3-Benzyl-2-(3chlorophenylimino)-5-(3-methyl-3H-benzothiazol-2-ylidene)thiazolidine-4-one

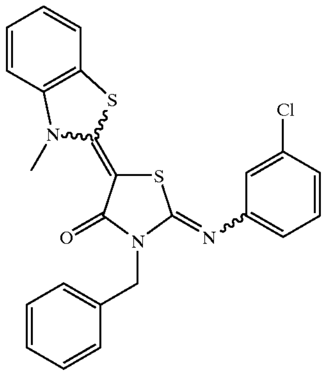

The title compound was prepared in a manner similar to that described in Example 1 by replacing aniline with 3-chloroaniline. $^1$H-NMR ($CDCl_3$): δ 7.54–7.58 (2H, m), 7.49 (1H, dd), 7.26–7.36 (5H, m), 7.17 (1H, m), 7.09 (1H, ddd), 7.03 (1H, d), 7.01 (1H, t), 6.89 (1H, ddd), 5.13 (2H, s), 3.74 (3H, s); MS(ESI): 464 ($MH^+$).

EXAMPLE 15

Preparation of 3-Benzyl-5-(3-methyl-3H-benzothiazol-2-ylidene)-2-(2-propyl-phenylimino) thiazolidine-4-one

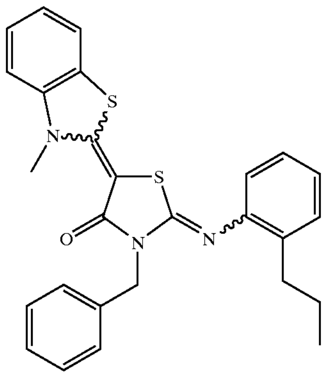

The title compound was prepared in a manner similar to that described in Example 1 by replacing aniline with 2-propylaniline. $^1$H-NMR ($CDCl_3$): δ 7.49 (1H, d), 7.27–7.37 (4H, m), 7.12–7.23 (3H, m), 7.06 (1H, m), 7.00 (1H, d), 6.92 (1H, d), 5.17 (2H, s), 3.71 (3H, s), 2.37 (2H, t), 1.42 (2H, s), 0.79 (3H, t); MS(ESI): 472 ($MH^+$).

EXAMPLE 16

Preparation of 3-Benzyl-5-(3-methyl-3H-benzothiazol-2-ylidene)-2-(quinolin-5-ylimino)-thiazolidine-4-one

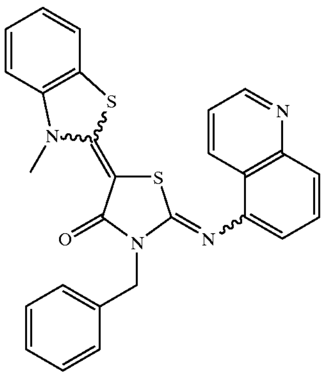

The title compound was prepared in a manner similar to that described in Example 1 by replacing aniline with 5-aminoquinoline. $^1$H-NMR ($CDCl_3$): δ 8.86 (1H, d), 8.02 (1H, d), 7.81 (1H, d), 7.68 (1H, t), 7.42–7.50 (3H, m), 7.25–7.35 (5H, m), 7.20 (1H, d), 7.12 (1H, t), 7.07 (1H, d), 5.19 (2H, s), 3.67 (3H, s); MS(ESI): 481 ($MH^+$).

EXAMPLE 17

Preparation of 3-Benzyl-2-(2-ethoxyphenylimino)-5-(3-methyl-3H-benzothiazol-2-ylidene)thiazolidine-4-one

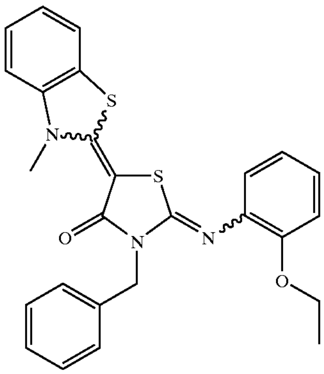

The title compound was prepared in a manner similar to that described in Example 1 by replacing aniline with o-phenetidine. $^1$H-NMR ($CDCl_3$): δ 7.66 (2H, m), 7.46 (2H, d), 7.24–7.34 (3H, m), 7.07–7.16 (2H, m), 6.94–7.00 (4H, m), 5.19 (2H, s), 4.01 (2H, q), 3.69 (3H, s), 1.36 (3H, t); MS(ESI): 474 ($MH^+$).

EXAMPLE 18

Preparation of N-{3-[3-Benzyl-5-(3-methyl-3H-benzothiazol-2-ylidene)-4-oxothiazolidin-2-ylideneamino]phenyl}acetamide

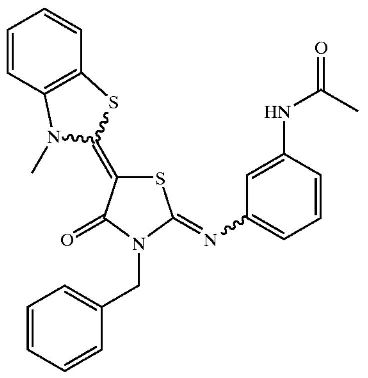

The title compound was prepared in a manner similar to that described in Example 1 by replacing aniline with 3'-aminoacetanilide. $^1$H-NMR ($CDCl_3$): δ 7.57 (2H, d), 7.48 (1H, d), 7.27–7.39 (6H, m), 7.15 (2H, m), 7.06 (1H, br s), 7.01 (1H, d), 6.76 (1H, d), 5.14 (2H, s), 3.72 (3H, s), 2.18 (3H, s); MS(ESI): 487 ($MH^+$).

EXAMPLE 19

Preparation of 3-[3-Benzyl-5-(3-methyl-3H-benzothiazol-2-ylidene)-4-oxothiazolidin-2-ylideneamino]benzamide

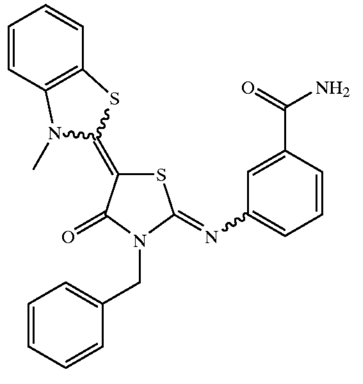

The title compound was prepared in a manner similar to that described in Example 1 by replacing aniline with 3-aminobenzamide. $^1$H-NMR (DMSO-$d_6$): δ 7.98 (1H, br s), 7.74 (1H, d), 7.62 (1H, d), 7.34–7.48 (9H, m), 7.30 (1H, m), 7.21 (1H, m), 7.12 (1H, d), 5.06 (2H, s), 3.75 (3H, s); MS(ESI): 473 ($MH^+$).

EXAMPLE 20

Preparation of 3-[3-Benzyl-5-(3-methyl-3H-benzothiazol-2-ylidene)-4-oxothiazolidin-2-ylideneamino]benzoic Acid, Methyl Ester

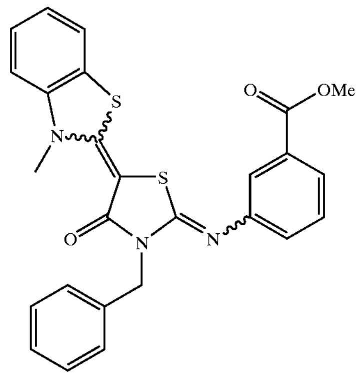

The title compound was prepared in a manner similar to that described in Example 1 by replacing aniline with methyl 3-aminobenzoate. $^1$H-NMR ($CDCl_3$): δ 7.80 (1H, m), 7.68 (1H, m), 7.56–7.60 (2H, m), 7.49 (1H, dd), 7.42 (1H, m), 7.27–7.36 (4H, m), 7.14–7.20 (2H, m), 7.01 (1H, d), 5.16 (2H, s), 3.92 (3H, s), 3.71 (3H, s); MS(ESI): 488 ($MH^+$).

EXAMPLE 21

Preparation of 3-Benzyl-5-(3-methyl-3H-benzothiazol-2-ylidene)-2-(pyridin-3-ylimino)-thiazolidine-4-one

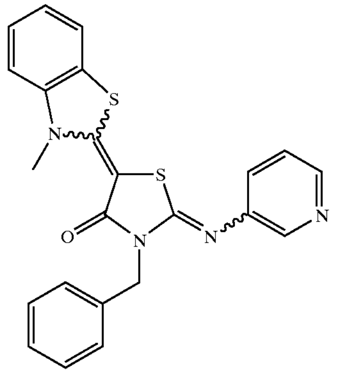

The title compound was prepared in a manner similar to that described in Example 1 by replacing aniline with 3-aminopyridine. $^1$H-NMR ($CDCl_3$): δ 8.37 (1H, dd), 8.35 (1H, dd), 7.56–7.60 (2H, m), 7.51 (1H, dd), 7.27–7.37 (6H, m), 7.18 (1H, m), 7.04 (1H, d), 5.16 (2H, s), 3.73 (3H, s); MS(ESI): 431 ($MH^+$).

EXAMPLE 22

Preparation of N-{3-[3-Benzyl-5-(3-methyl-3H-benzothiazol-2-ylidene)-4-oxothiazolidin-2-ylideneamino]-4-ethoxyphenyl}acetamide

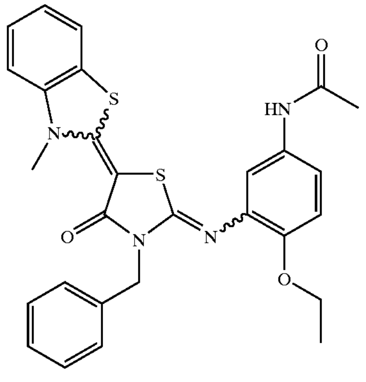

The title compound was prepared in a manner similar to that described in Example 1 by replacing aniline with N-(4-amino-3-ethoxyphenyl)acetamide. $^{1}$H-NMR ($CDCl_3$): δ 7.63 (2H, d), 7.48 (1H, d), 7.28–7.36 (5H, m), 7.15 (1H, t), 7.10 (1H, s), 7.00 (1H, d), 6.96 (1H, d), 6.91 (1H, d), 5.18 (2H, s), 3.97 (2H, q), 3.70 (3H, s), 2.16 (3H, s), 1.33 (3H, t); MS(ESI): 531 ($MH^+$).

EXAMPLE 23

Preparation of 3-Benzyl-5-(3-methyl-3H-benzothiazol-2-ylidene)-2-(pyridin-4-ylimino)-thiazolidine-4-one

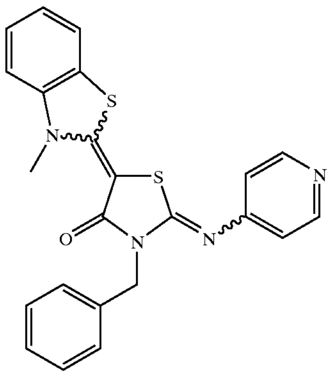

The title compound was prepared in a manner similar to that described in Example 1 by replacing aniline with 4-aminopyridine. $^{1}$H-NMR ($CDCl_3$): δ 8.53 (2H, dd), 7.56 (2H, m), 7.52 (1H, dd), 7.28–7.38 (4H, m), 7.19 (1H, m), 7.06 (1H, d), 6.93 (2H, dd), 5.14 (2H, s), 3.75 (3H, s); MS(ESI): 431 ($MH^+$).

EXAMPLE 24

Preparation of 4-[3-Benzyl-5-(3-methyl-3H-benzothiazol-2-ylidene)-4-oxothiazolidin-2-ylideneamino]benzoic Acid, Methyl Ester

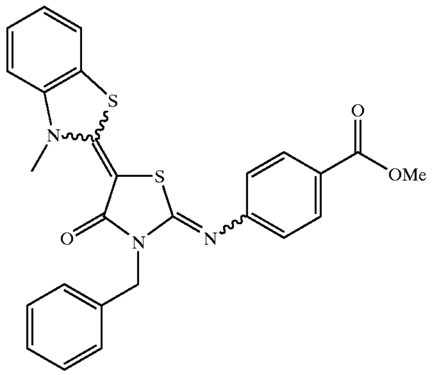

The title compound was prepared in a manner similar to that described in Example 1 by replacing aniline with methyl 4-aminobenzoate. $^{1}$H-NMR ($CDCl_3$): δ 8.04 (2H, m), 7.58 (2H, m), 7.50 (1H, d), 7.27–7.38 (4H, m), 7.17 (1H, t), 7.01–7.08 (3H, m), 5.15 (2H, s), 3.92 (3H, s), 3.72 (3H, s); MS(ESI): 488 ($MH^+$).

EXAMPLE 25

Preparation of 3-Benzyl-5-(3-methyl-3H-benzothiazol-2-ylidene)-2-[4-(trifluoro-methoxy)phenylimino]thiazolidine-4-one

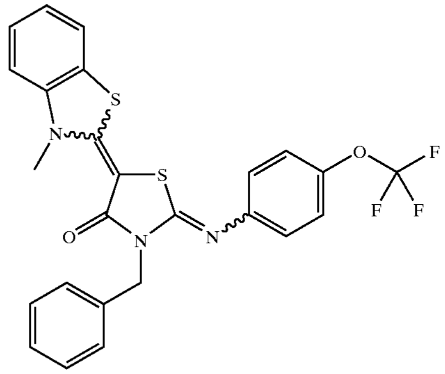

The title compound was prepared in a manner similar to that described in Example 1 by replacing aniline with 4-(trifluoromethoxy)aniline. $^{1}$H-NMR ($CDCl_3$): δ 7.57 (2H, m), 7.50 (1H, dd), 7.27–7.36 (4H, .m), 7.14–7.22 (3H, m), 7.03 (1H, d), 7.00 (2H, dd), 5.14 (2H, s), 3.75 (3H, s); MS(ESI): 514 ($MH^+$).

EXAMPLE 26

Preparation of 3-Benzyl-2-(1H-indazol-5-ylimino)-5-(3-methyl-3H-benzothiazol-2-ylidene)-thiazolidin-4-one

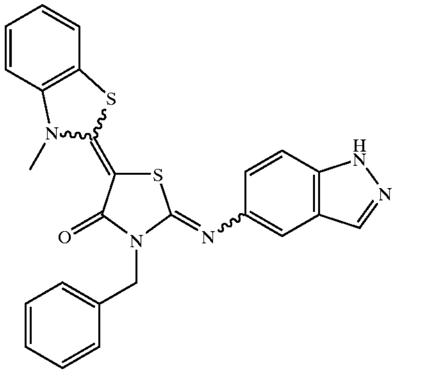

The title compound was prepared in a manner similar to that described in Example 1 by replacing aniline with 5-aminoindazole. $^1$H-NMR ($CDCl_3$): δ 10.05 (1H, br s), 8.08 (1H, d), 7.64–7.67 (2H, m), 7.51–7.55 (2H, m), 7.32–7.41 (5H, m), 7.20 (1H, m), 7.14 (1H, dd), 7.04 (1H, d), 5.23 (2H, s), 3.74 (3H, s); MS(ESI): 470 ($MH^+$).

EXAMPLE 27

Preparation of 3-Benzyl-2-(4-imidazol-1-ylphenylimino)-5-(3-methyl-3H-benzothiazol-2-ylidene)thiazolidine-4-one

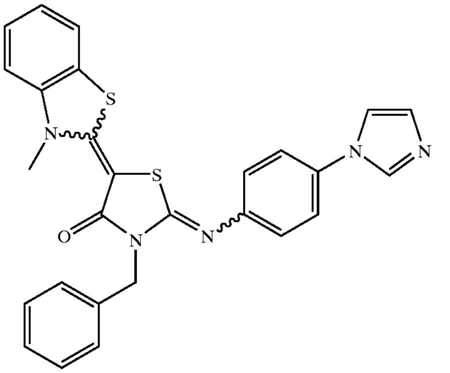

The title compound was prepared in a manner similar to that described in Example 1 by replacing aniline with 4-(1H-imidazol-1-yl)aniline. $^1$H-NMR ($CDCl_3$): δ 7.93 (1H, s), 7.66 (2H, d), 7.58 (1H, d), 7.35–7.46 (7H, m), 7.29 (1H, s), 7.25 (1H, t), 7.18 (2H, m), 7.11 (1H, d), 5.24 (2H, s), 3.82 (3H, s); MS(ESI): 496 ($MH^+$).

EXAMPLE 28

Preparation of 2-(Benzo[1,3]dioxol-5-ylimino)-3-benzyl-5-(3-methyl-3H-benzothiazol-2-ylidene) thiazolidin-4-one

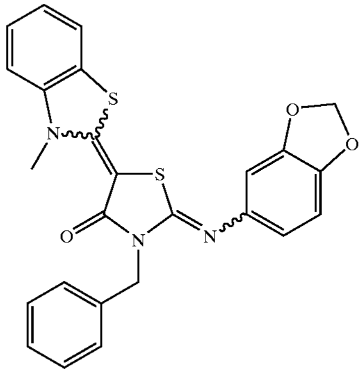

The title compound was prepared in a manner similar to that described in Example 1 by replacing aniline with 3,4-(methylenedioxy)aniline. $^1$H-NMR ($CDCl_3$): δ 7.56–7.60 (2H, m), 7.49 (1H, dd), 7.28–7.36 (4H, m), 7.16 (1H, m), 7.02 (1H, d), 6.80 (1H, d), 6.56 (1H, d), 6.48 (1H, dd), 5.98 (2H, s), 5.14 (2H, s), 3.75 (3H, s); MS(ESI): 474 ($MH^+$).

EXAMPLE 29

Preparation of 3-[3-Benzyl-5-(3-methyl-3H-benzothiazol-2-ylidene)-4-oxothiazolidin-2-ylideneamino]benzoic Acid

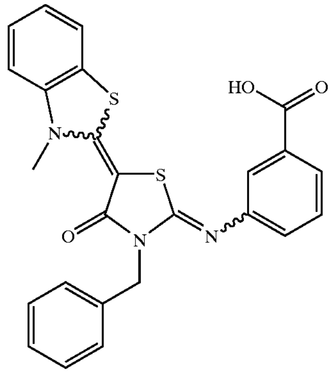

An aqueous solution of lithium hydroxide (1 M, 5 mL) was added to a solution of compound I-20 (0.13 g, 0.27 mmol) in THF (20 mL). After stirring at room temperature for 12 h, the reaction mixture was concentrated under reduced pressure. The resulting residue was acidified with hydrochloric acid (1 M, 10 mL) and extracted with EtOAc. The combined organic extracts were dried (anhydrous magnesium sulfate), concentrated under reduced pressure and chromatographed (silica gel, MeOH/DCM, 1:19) to yield the title compound (0.12 g, 95%) as a yellow solid. $^1$H-NMR ($MeOD-d_3$): δ 7.81 (1H, d), 7.63–7.68 (2H, m), 7.55 (1H, d), 7.50 (2H, d), 7.44 (1H, t), 7.31–7.40 (3H, m), 7.28 (1H, d), 7.16–7.23 (3H, m), 5.15 (2H, s), 3.79 (3H, s); MS(ESI): 474 ($MH^+$).

EXAMPLE 30

Preparation of N-Ethyl-1,2-phenylenediamine

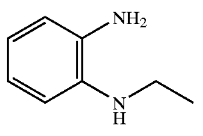

N-Ethyl-2-nitroaniline (0.97 g, 5.8 mmol) was dissolved in EtOAc (60 mL) and placed in a closed vessel. 10% Pd/C (0.4 g, 7 mol %) was added and the mixture was hydrogenated under 50 psi $H_2$ for 2 h. The mixture was filtered through celite and the filtrate was concentrated under reduced pressure to yield the title product (0.79 g, 99%) as a brown liquid, which was used without further purification. $^1$H-NMR ($CDCl_3$): δ 6.83 (1H, m), 6.64–6.74 (3H, m), 3.29 (3H, br s), 3.15 (2H, q), 1.30 (3H, t); TLC (2:98 MeOH/DCM $R_f$ 0.24).

Preparation of 3-Benzyl-2-[2-(ethylamino) phenylimino]-5-(3-methyl-3H-benzothiazol-2-ylidene)thiazolidine-4-one

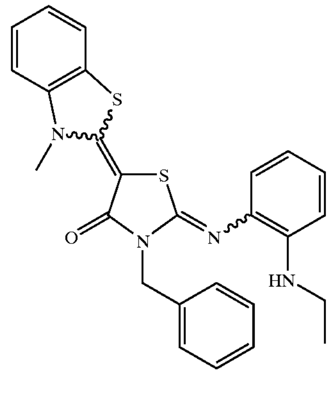

The title compound was then prepared in a manner similar to that described in Example 1 by replacing aniline with N-ethyl-1,2-phenylenediamine. $^1$H-NMR ($CDCl_3$): δ 7.47–7.54 (3H, m), 7.30–7.37 (3H, m), 7.28 (1H, m), 7.17 (1H, t), 7.00–7.06 (2H, m), 6.96 (1H, dd), 6.64 (1H, m), 6.60 (1H, d), 5.19 (2H, s), 3.76 (3H, s), 3.68 (1H, br s), 3.01 (2H, q), 1.05 (3H, t); MS(ESI): 473 ($MH^+$).

EXAMPLE 31

Preparation of 4-Methylamino-3-nitrobenzonitrile

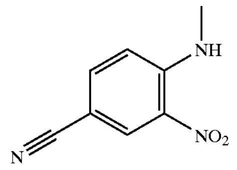

4-Fluoro-3-nitrobenzonitrile (0.25 g, 1.5 mmol) was cautiously added to a solution of methylamine (2.0 M, 5.0 mL) in THF. The mixture was stirred at room temperature for 8 h, concentrated under reduced pressure, and chromatographed (silica gel, DCM) to give the title product (0.18 g, 68%) as a yellow solid. $^1$H-NMR ($CDCl_3$): δ 8.52 (1H, d), 8.41 (1H, br s), 7.64 (1H, dd), 6.92 (1H, d), 3.10 (3H, d).

Preparation of 3-Amino-4-methylamino)benzonitrile

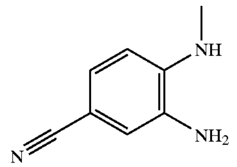

4-Methylamino-3-nitrobenzonitrile (0.18 g, 1.0 mmol) was dissolved in EtOAc (10 mL) and placed in a closed vessel. 10% Pd/C (50 mg, 5 mol %) was added and the mixture was hydrogenated via a hydrogen-filled balloon that was affixed to the vessel. After 2 h the mixture was filtered through celite and the filtrate was concentrated under reduced pressure to yield the title product (0.14 g, 93%) as an off-white solid, which was used without further purification. $^1$H-NMR ($CDCl_3$): δ 7.19 (1H, dd), 6.92 (1H, d), 6.57 (1H, d), 4.04 (1H, br s), 3.30 (2H, br s), 2.91 (3H, br s); TLC (5:95 MeOH/DCM $R_f$ 0.33).

Preparation of 3-[3-Benzyl-5-(3-methyl-3H-benzothiazol-2-ylidene)-4-oxothiazolidin-2-ylideneamino]-4-(methylamino)benzonitrile

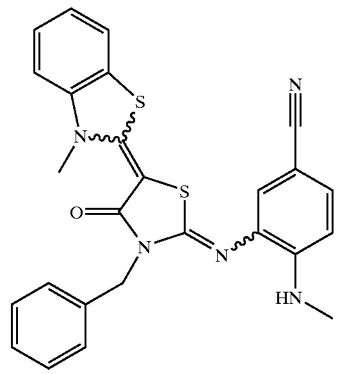

The title compound was then prepared in a manner similar to that described in Example 1 by replacing aniline with 3-amino-4-methylamino)benzonitrile. $^1$H-NMR ($CDCl_3$): δ 7.55 (1H, d), 7.42–7.47 (2H, m, 7.34–7.41 (3H, m), 7.28–7.34 (2H, m), 7.21 (1H, m), 7.18 (1H, d), 7.11 (1H, d, 6.45 (1H, d), 5.17 (2H, s), 4.15 (1H, br s), 3.83 (3H, s), 2.63 (3H, br s); MS(ESI): 484 ($MH^+$).

EXAMPLE 32

Preparation of 3-[3-Benzyl-5-(3-methyl-3H-benzothiazol-2-ylidene)-4-oxothiazolidin-2-ylideneamino]-4-(ethylamino)benzonitrile

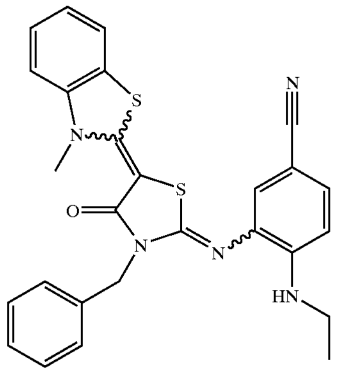

The title compound was prepared in a manner similar to that described in Example 31 by replacing methylamine with ethylamine. $^1$H-NMR ($CDCl_3$): δ 7.54 (1H, d), 7.41–7.46 (2H, m), 7.27–7.40 (5H, m), 7.18–7.24 (2H, m), 7.11 (1H, d), 6.49 (1H, d), 5.18 (2H, s), 4.23 (1H, t), 3.83 (3H, s), 3.01 (2H, m), 1.02 (3H, t); MS(ESI): 498 ($MH^+$).

EXAMPLE 33

Preparation of 3-[3-Benzyl-5-(3-methyl-3H-benzothiazol-2-ylidene)-4-oxothiazolidin-2-ylideneamino]-4-(isopropylamino)benzonitrile

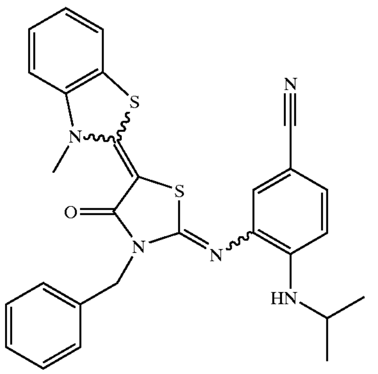

The title compound was prepared in a manner similar to that described in Example 31 by replacing methylamine with isopropylamine. $^1$H-NMR ($CDCl_3$): δ 7.54 (1H, d), 7.45 (2H, d), 7.27–7.40 (5H, m), 7.18–7.24 (2H, m), 7.11 (1H, d), 6.53 (1H, d), 5.18 (2H, s), 4.29 (1H, d), 3.83 (3H, s), 3.54 (1H, m), 1.02 (6H, d); MS(ESI): 512 ($MH^+$).

EXAMPLE 34

Preparation of 3-[3-Benzyl-5-(3-methyl-3H-benzothiazol-2-ylidene)-4-oxothiazolidin-2-ylideneamino]-4-(dimethylamino)benzonitrile

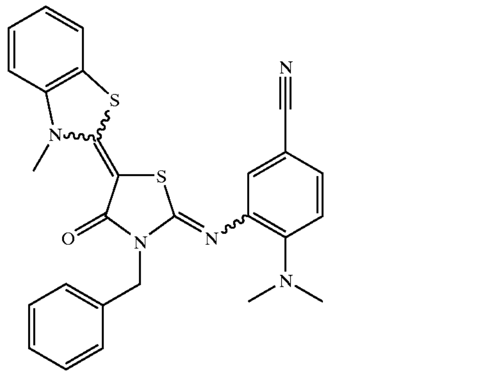

The title compound was prepared in a manner similar to that described in Example 31 by replacing methylamine with dimethylamine. $^1$H-NMR ($CDCl_3$): δ 7.49–7.53 (3H, m), 7.27–7.37 (5H, m), 7.18 (1H, t), 7.13 (1H, d), 7.06 (1H, d), 6.85 (1H, d), 5.18 (2H, s), 3.76 (3H, s), 2.68 (6H, s); MS(ESI): 498 ($MH^+$).

EXAMPLE 35

Preparation of 3-[3-Benzyl-5-(3-methyl-3H-benzothiazol-2-ylidene)-4-oxothiazolidin-2-ylideneamino]-4-(tert-butylamino)benzonitrile

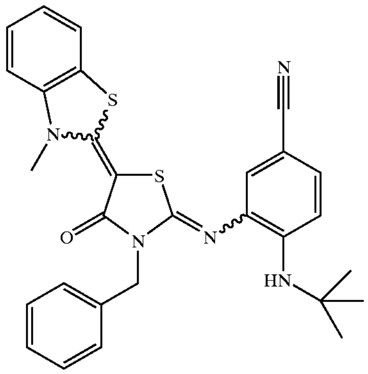

The title compound was prepared in a manner similar to that described in Example 31 by replacing methylamine with tert-butylamine. $^1$H-NMR ($CDCl_3$): δ 7.54 (1H, d), 7.44 (2H, d), 7.27–7.40 (5H, m), 7.18–7.24 (2H, m), 7.11 (1H, d), 6.80 (1H, d), 5.18 (2H, s), 4.67 (1H, br s), 3.83 (3H, s), 1.22 (9H, s); MS(ESI): 526 ($MH^+$).

EXAMPLE 36

Preparation of 3-[3-Benzyl-5-(3-methyl-3H-benzothiazol-2-ylidene)-4-oxothiazolidin-2-ylideneamino]-4-(2,2,2-trifluoroethylamino) benzonitrile

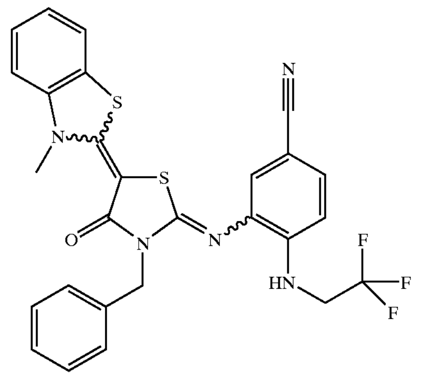

The title compound was prepared in a manner similar to that described in Example 31 by replacing methylamine with 2,2,2-trifluoroethylamine. $^1$H-NMR ($CDCl_3$): δ 7.57 (1H, d), 7.27–7.44 (8H, m), 7.23 (1H, t), 7.14 (1H, d), 6.62 (1H, d), 5.17 (2H, s), 4.49 (1H, t), 3.86 (3H, s), 3.50 (2H, m); MS(ESI): 552 (MH$^+$).

EXAMPLE 37

Preparation of 3-[3-Benzyl-5-(3-methyl-3H-benzothiazol-2-ylidene)-4-oxothiazolidin-2-ylideneamino]-4-piperidin-1-ylbenzonitrile

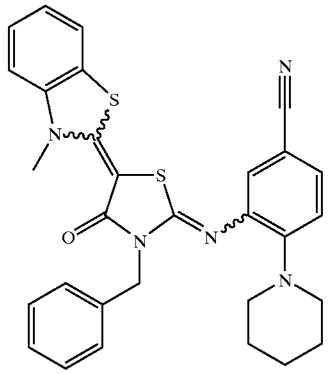

The title compound was prepared in a manner similar to that described in Example 31 by replacing methylamine with piperidine. $^1$H-NMR ($CDCl_3$): δ 7.50–7.54 (3H, m), 7.27–7.37 (5H, m), 7.18 (1H, t), 7.15 (1H, d), 7.05 (1H, d), 6.92 (1H, d), 5.17 (2H, s), 3.75 (3H, s), 2.98 (4H, m), 1.44 (6H, m); MS(ESI): 538 (MH$^+$).

EXAMPLE 38

Preparation of 2-[5-Acetyl-2-(ethylamino) phenylimino]-3-benzyl-5-(3-ethyl-3H-benzothiazol-2-ylidene)thiazolidin-4-one

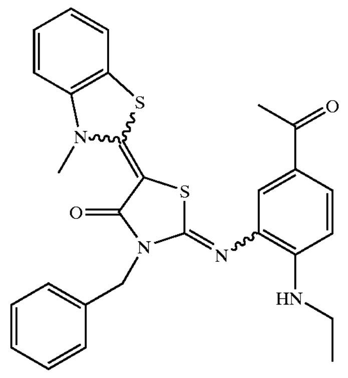

The title compound was prepared in a manner similar to that described in Example 31 by replacing methylamine with ethylamine and by replacing 4-fluoro-3-nitrobenzonitrile with 4'-chloro-3'-nitroacetophenone. $^1$H-NMR ($CDCl_3$): δ 7.68 (1H, dd), 7.65 (1H, d), 7.53 (1H, d), 7.45–7.49 (2H, m), 7.32–7.38 (3H, m), 7.28–7.31 (1H, m), 7.19 (1H, m), 7.06 (1H, d), 6.52 (1H, d), 5.19 (2H, s), 4.24 (1H, t), 3.78 (3H, s), 3.06 (2H, m), 2.51 (3H, s), 1.05 (3H, t); MS(ESI): 515 (MH$^+$).

EXAMPLE 39

Preparation of 3-Ethyl-5-(3-methyl-3H-benzothiazol-2-ylidene)-2-thioxothiazolidin-4-one

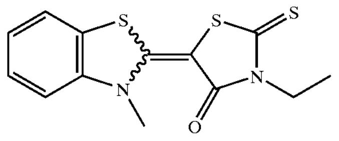

The title compound was prepared in a manner similar to that described in Example 1 by replacing N-benzyl rhodanine with N-ethyl rhodanine. $^1$H-NMR ($CDCl_3$): δ 7.63 (1H, d), 7.45 (1H, m), 7.30 (1H, m), 7.22 (1H, d), 4.24 (2H, q), 3.91 (3H, s), 1.32 (3H, t); MS(ESI): 309 (MH$^+$).

Preparation 3-Ethyl-5-(3-methyl-3H-benzothiazol-2-ylidene)-2-methylthio-4-oxo-2-thiazolium p-toluenesulfonate

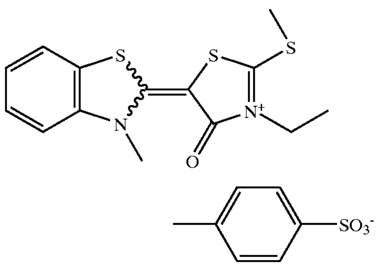

The title compound was prepared from 3-ethyl-5-(3-methyl-3H-benzothiazol-2-ylidene)-2-thioxothiazolidin-4- one and methyl p-toluenesulfonate in a manner similar to that described in Example 1. $^1$H-NMR ($CDCl_3$): δ 7.82 (1H, d), 7.77 (2H, d), 7.58–7.66 (2H, m), 7.49 (1H, m), 7.08 (2H, d), 4.52 (3H, s), 4.21 (2H, q), 3.29 (3H, s), 2.29 (3H, s), 1.45 (3H, t).

Preparation of 3-Ethyl-5-(3-methyl-3H-benzothiazol-2-ylidene)-2-(quinolin-6-ylimino)-thiazolidin-4-one

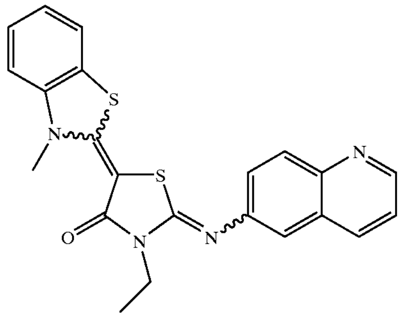

The title compound was prepared from 3-ethyl-5-(3-methyl-3H-benzothiazol-2-ylidene)-2-methylthio-4-oxo-2-thiazolium p-toluenesulfonate and 6-aminoquinoline in a manner similar to that described in Example 1. $^1$H-NMR ($CDCl_3$): δ 8.85 (1H, dd), 8.11 (1H, d), 8.10 (1H, d), 7.51 (1H, dd) 7.46 (1H, dd), 7.40 (1H, d), 7.38 (1H, dd), 7.32 (1H, m), 7.16 (1H, m), 7.01 (1H, d), 4.10 (2H, q), 3.70 (3H, s), 1.41 (3H, t); MS(ESI): 419 ($MH^+$).

EXAMPLE 40

Preparation of 3-Ethyl-5-(3-methyl-3H-benzothiazol-2-ylidene)-2-(4-morpholin-4-yl-phenylimino)thiazolidin-4-one

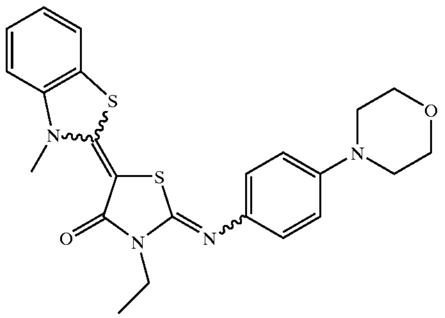

The title compound was prepared in a manner similar to that described in Example 39 by replacing 6-aminoquinoline with 4-morpholin-4-ylaniline. $^1$H-NMR ($CDCl_3$): δ 7.49 (1H, dd), 7.31 (1H, m), 7.15 (1H, m), 6.91–7.02 (5H, m), 4.03 (2H, q), 3.88 (4H, m), 3.73 (3H, s), 3.17 (4H, m), 1.36 (3H, t); MS(ESI): 453 ($MH^+$).

EXAMPLE 41

Preparation of 3-[3-Ethyl-5-(3-methyl-3H-benzothiazol-2-ylidene)-4-oxothiazolidin-2-ylideneamino]-4-(methylamino)benzonitrile

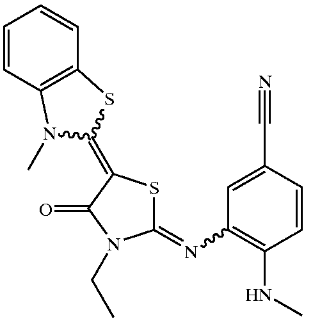

The title compound was prepared in a manner similar to that described in Example 39 by replacing 6-aminoquinoline with 3-amino-4-(methylamino)benzonitrile. $^1$H-NMR ($CDCl_3$): δ 7.53 (1H, d), 7.36 (1H, m), 7.36 (1H, dd), 7.25 (1H, m), 7.20 (1H, m), 7.09 (1H, d), 6.60 (1H, d), 4.86 (1H, q), 4.07 (2H, q), 3.81 (3H, s), 2.92 (3H, d), 1.37 (3H, t); MS(ESI): 422 ($MH^+$).

EXAMPLE 42

Preparation of 4-Dimethylamino-3-[3-ethyl-5-(3-methyl-3H-benzothiazol-2-ylidene)-4-oxothiazolidin-2-ylideneamino]benzonitrile

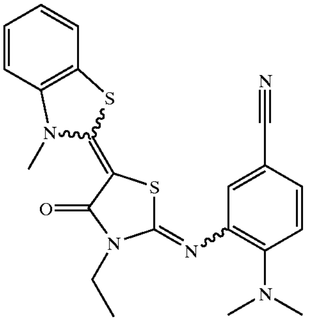

The title compound was prepared in a manner similar to that described in Example 39 by replacing 6-aminoquinoline with 3-amino-4-(dimethylamino)benzonitrile. $^1$H-NMR ($CDCl_3$): δ 7.52 (1H, dd), 7.34 (1H, m), 7.34 (1H, dd), 7.20 (1H, d), 7.18 (1H, m), 7.06 (1H, d), 6.92 (1H, d), 4.08 (2H, q), 3.76 (3H, s), 2.90 (6H, s), 1.38 (3H, t); MS(ESI): 436 ($MH^+$).

EXAMPLE 43

Preparation of 4-Ethylamino-3-[3-ethyl-5-(3-methyl-3H-benzothiazol-2-ylidene)-4-oxo-thiazolidin-2-ylideneamino]benzonitrile

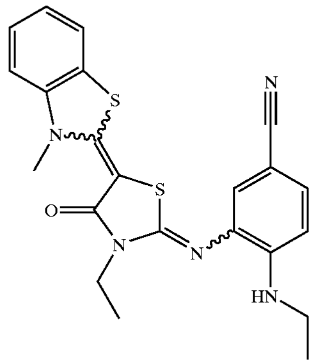

The title compound was prepared in a manner similar to that described in Example 39 by,replacing 6-aminoquinoline with 3-amino-4-(ethylamino)benzonitrile. $^{1}$H-NMR ($CDCl_3$): δ 7.53 (1H, d), 7.32–7.40 (2H, m), 7.26 (1H, m), 7.20 (1H, m), 7.10 (1H, d), 6.60 (1H, d), 4.75 (1H, t), 4.08 (2H, q), 3.81 (3H, s), 3.22 (2H, m), 1.37 (3H, t), 1.29 (3H, t); MS(ESI): 436 ($MH^+$).

EXAMPLE 44

Preparation of 3-[3-Ethyl-5-(3-methyl-3H-benzothiazol-2-ylidene)-4-oxothiazolidin-2-ylideneamino]-4-(isopropylamino)benzonitrile

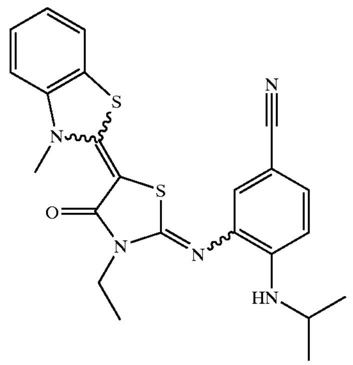

The title compound was prepared in a manner similar to that described in Example 39 by replacing 6-aminoquinoline with 3-amino-4-(isopropylamino)benzonitrile. $^{1}$H-NMR ($CDCl_3$): δ 7.53 (1H, dd), 7.36 (1H, m), 7.32 (1H, dd), 7.25 (1H, d), 7.20 (1H, m), 7.10 (1H, d), 6.60 (1H, d), 4.74 (1H, d), 4.08 (2H, q), 3.81 (3H, s), 3.67 (1H, m), 1.37 (3H, t), 1.25 (6H, d); MS(ESI): 450 ($MH^+$).

EXAMPLE 45

Preparation of 3-(3-Butyl-4-oxothiazolidin-2-ylideneamino)benzonitrile

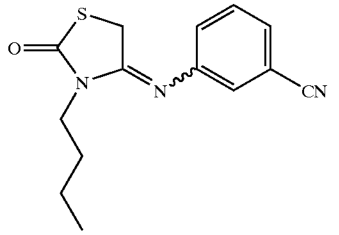

To a 250 mL flask was added 3-aminobenzonitrile (0.59 g, 5.0 mmol), $CHCl_3$ (25 mL) and saturated sodium bicarbonate (25 mL). To the well-stirred mixture was added dropwise thiophosgene (0.39 mL, 5.1 mmol). After 2 h butylamine (0.50 mL, 5.1 mmol) was added dropwise and stirred 1 h. The reaction mixture was then extracted with $CHCl_3$, concentrated under reduced pressure, and chromatographed (silica gel, 2:98 MeOH/DCM) to yield 1-butyl-3-(3-cyanophenyl)thiourea (1.02 g, 87%) as a white solid: TLC (2:98 MeOH/DCM $R_f$ 0.47).

To a 100 mL flask was added anhydrous EtOH (25 mL), 1-butyl-3-(3-cyanophenyl)thiourea (0.99 g, 4.2 mmol), ethyl chloroacetate (0.51 mL, 5.0 mmol), and anhydrous pyridine (0.5 mL, 5 mmol). After heating under reflux 16 h, the product mixture was concentrated under reduced pressure and chromatographed (silica gel, 2:98 MeOH/DCM) to afford the title product (0.78 g, 67%) as a colorless oil. $^{1}$H-NMR ($CDCl_3$): δ 7.40–7.47 (2H, m), 7.25 (1H, m), 7.19 (1H, m), 3.84 (2H, t), 3.84 (2H, s), 1.69 (2H, m), 1.39 (2H, m), 0.97 (3H, t); MS(ESI): 274 ($MH^+$).

Preparation of 3-[3-Butyl-5-(3-methyl-3H-benzothiazol-2-ylidene)-4-oxothiazolidin-2-ylideneamino]benzonitrile

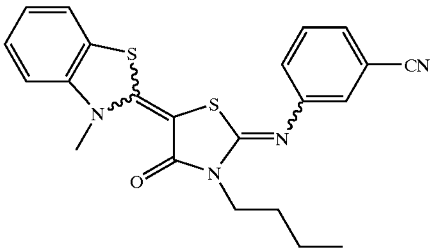

To a 8 mL vial was added 3-(3-butyl-4-oxothiazolidin-2-ylideneamino)benzonitrile (55 mg, 0.20 mmol), 3-methyl-2-(methylthio)benzothiazol-3-ium p-toluenesulfonate (73 mg, 0.20 mmol), anhydrous MeCN (2 mL) and TEA (70 μL, 0.50 mmol). The reaction mixture was first Warmed to 50° C. and the resulting solution was allowed to stir at room temperature for 16 h. The product mixture was concentrated under reduced pressure, chromatographed (silica gel, 1:99 MeOH/DCM) and then recrystallized from MeCN to give the title product (11.8 mg) as a yellow solid. $^{1}$H-NMR ($CDCl_3$): δ 7.52 (1H, dd), 7.38–7.48 (2H, m), 7.32–7.37 (2H, m), 7.25 (1H, m), 7.18 (1H, m), 7.06 (1H, d), 3.96 (2H, t), 3.75 (3H, s), 1.77 (2H, m), 1.44 (2H, m), 0.98 (3H, t); MS(ESI): 421 ($MH^+$).

EXAMPLE 46

Preparation of 3-Benzyl-5-(3-methyl-3H-benzoxazol-2-ylidene)-2-thioxothiazolidin-4-one

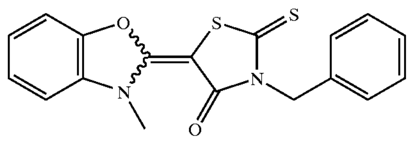

The title compound was prepared in a manner similar to that described in Example 1 by replacing 2-(methylthio) benzothiazole with 2-mercaptobenzoxazole. $^1$H-NMR ($CDCl_3$): δ 7.49 (2H, d), 7.24–7.41 (6H, m), 7.18 (1H, d), 5.31(2H, s), 4.17 (3H, s); MS(ESI): 377 ($MNa^+$).

Preparation of 3-Benzyl-5-(3-methyl-3H-benzoxazol-2-ylidene)-2-(quinolin-5-ylimino)-thiazolidin-4-one

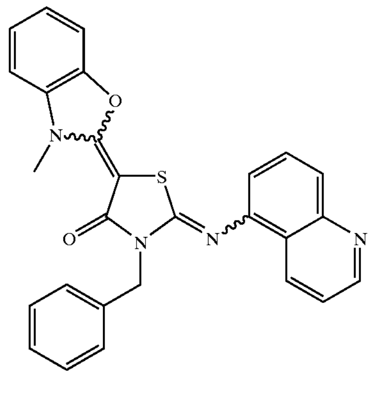

To a 10 mL flask was added 3-benzyl-5-(3-methyl-3H-benzoxazol-2-ylidene)-2-thioxothiazolidin-4-one (100 mg, 0.28 mmol), anhydrous $CHCl_3$ (2 mL) and methyl p-toluenesulfonate (53 μL, 0.35 mmol). After heating at reflux 10 min, the reaction mixture was heated at 120° C. for 2 h to yield a red oil. The desired intermediate, 3-benzyl-5-(3-methyl-3H-benzoxazol-2-ylidene)-2-methylthio-4-oxo-2-thiazolium p-toluenesulfonate, was not isolated successfully in previous experiments similar to Example 1 and, thus, the crude reaction mixture was diluted with anhydrous $CHCl_3$ (4 mL) and used without purification in the next step.

To a 8 mL vial was added the crude reaction mixture (2 mL) and 5-aminoquinoline (29 mg, 0.20 mmol). After warming the mixture to 55° C., TEA (0.10 mL, 0.56 mmol) was added and the mixture was heated at 60° C. for 16 h. After cooling to room temperature, the resulting product mixture was concentrated under reduced pressure and chromatographed (silica gel, 2:98 MeOH/DCM) to yield the title product (21 mg) as a yellow solid. $^1$H-NMR ($CDCl_3$): δ 8.86 (1H, dd), 7.97 (1H, dd), 7.85 (1H, d), 7.66 (1H, dd), 7.56 (2H, m), 7.30–7.42 (3H, m), 7.19–7.25 (3H, m), 7.11–7.17 (2H, m), 7.05 (1H, d), 5.24 (2H, s), 4.11 (3H, s); MS(ESI): 465 ($MH^+$).

EXAMPLE 47

Preparation of 3'-Benzyl-3-methyl-4-phenyl-2'-thioxo-2',3'-dihydro-3H-[2,5']bithiazol-yliden-4'-one

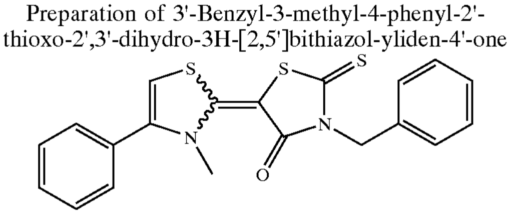

The title compound was prepared in a manner similar to that described in Example 1 by replacing 2-(methylthio) benzothiazole with 2-mercapto-4-phenylthiazole. $^1$H-NMR ($CDCl_3$): δ 7.49–7.56 (5H, m), 7.34–7.38 (2H, m), 7.24–7.33 (3H, m), 6.54 (1H, s), 5.39 (2H, s), 3.68 (3H, s); MS(ESI): 397 ($MH^+$).

Preparation 3'-Benzyl-3-methyl-2'-methylthio-4'-oxo-4-phenyl-3H,4'H-[2,5']bithiazol-yliden-3'-ium p-Toluenesulfonate

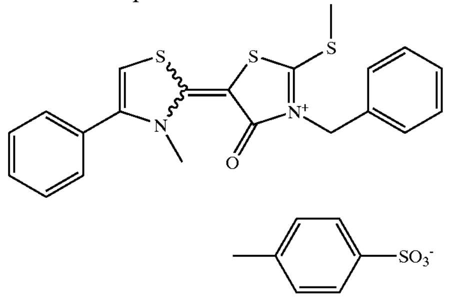

The title compound was prepared from 3'-benzyl-3-methyl-4-phenyl-2'-thioxo-2',3'-dihydro-3H-[2,5'] bithiazolyliden-4'-one and methyl p-toluenesulfonate in a manner similar to that described in Example 1. $^1$H-NMR ($CDCl_3$): δ 7.72 (2H, d), 7.49–7.56 (3H, m), 7.42–7.47 (2H, m), 7.36–7.41 (5H, m), 7.05 (2H, d), 6.99 (1H, s), 5.29 (2H, s), 4.26 (3H, s), 3.14 (3H, s), 2.29 (3H, s).

Preparation of N-[4-(3'-Benzyl-3-methyl-4'-oxo-4-phenyl-3',4'-dihydro-3H-[2,5']-bithiazolyliden-2'-ylideneamino)phenyl]acetamide

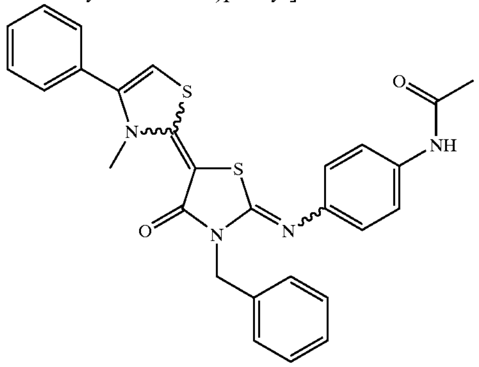

The title compound was prepared from 3'-benzyl-3-methyl-2'-methylthio-4'-oxo-4-phenyl-3H,4'H-[2,5'] bithiazolyliden-3'-ium p-toluenesulfonate and 4'-aminoacetanilide in a manner similar to that described in Example 1. $^1$H-NMR ($CDCl_3$): δ 7.56 (2H, d), 7.42–7.47 (5H, m), 7.24–7.34 (5H, m), 7.12 (1H, s), 6.97 (2H, d), 6.30 (1H, s), 5.15 (2H, s), 3.49 (3H, s), 2.17 (3H, s); MS(ESI): 513 ($MH^+$).

EXAMPLE 48

Preparation of 2'-[5-Acetyl-2-(ethylamino) phenylimino]-3'-benzyl-3-methyl-4-phenyl-2',3'-dihydro-3H-[2,5']bithiazolyliden-4'-one

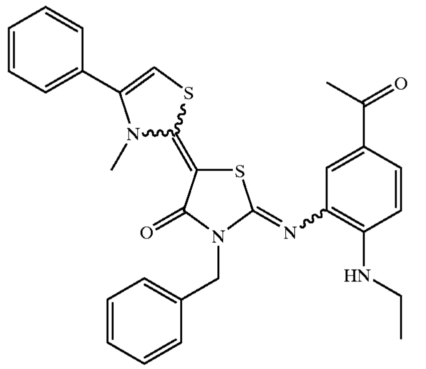

The title compound was prepared in a manner similar to that described in Example 47 by replacing 4'-aminoacetanilide with 3'-amino-4'-(ethylamino) acetophenone. $^1$H-NMR ($CDCl_3$): δ 7.63–7.67 (2H, m), 7.44–7.48 (5H, m), 7.27–7.37 (5H, m), 6.50 (1H, d), 6.37 (1H, s), 5.20 (2H, s), 4.29 (1H, t), 3.55 (3H, s), 3.05 (2H, m), 2.49 (3H, s), 1.04 (3H, t); MS(ESI): 541 ($MH^+$).

EXAMPLE 49

Preparation of 3-(3'-Benzyl-3-methyl-4'-oxo-4-phenyl-3',4'-dihydro-3H-[2,5']bithiazol-yliden-2'-ylideneamino)-4-(ethylamino)benzonitrile

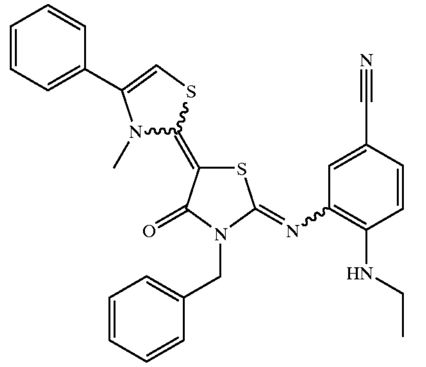

The title compound was prepared in a manner similar to that described in Example 47 by replacing 4'-aminoacetanilide with 3-amino-4-(ethylamino) benzonitrile. $^1$H-NMR ($CDCl_3$): δ 7.46–7.50 (3H, m), 7.41–7.45 (2H, m), 7.23–7.40 (6H, m), 7.21 (1H, d), 6.47 (1H, d), 6.40 (1H, s), 5.18 (2H, s), 4.27 (1H, t), 3.59 (3H, s), 3.00 (2H, m), 1.01 (3H, t); MS(ESI): 524 ($MH^+$).

EXAMPLE 50

Preparation of N-[4-(3'-Benzyl-3-methyl-4'-oxo-3',4'-dihydro-3H-[2,5']bithiazolyliden-2'-ylideneamino) phenyl]acetamide

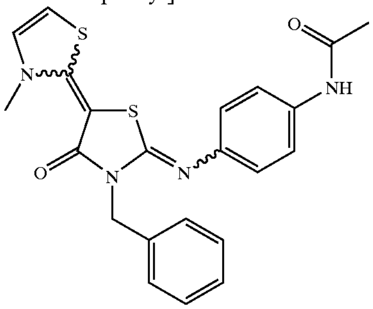

The title compound was prepared in a manner similar to that described in Example 47 by replacing 2-mercapto-4-phenylthiazole with 2-mercaptothiazole. $^1$H-NMR ($CDCl_3$): δ 7.55 (2H, d), 7.44 (2H, d), 7.24–7.33 (3H, m), 7.13 (1H, s), 6.95 (2H, d), 6.52 (1H, d), 6.37 (1H, d), 5.12 (2H, s), 3.68 (3H, s), 2.17 (3H, s); MS(ESI): 437 ($MH^+$).

EXAMPLE 51

Preparation of N-[4-(3'-Benzyl-3-methyl-4'-oxo-[2,5']bithiazolidinyliden-2'-ylidene-amino)phenyl] acetamide

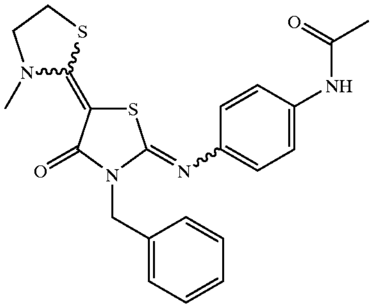

The title compound was prepared in a manner similar to that described in Example 47 by replacing 2-mercapto-4-phenylthiazole with 2-methylthio-2-thiazoline. $^1$H-NMR ($CDCl_3$): δ 7.53 (2H, d), 7.44 (2H, d), 7.23–7.32 (3H, m), 7.14 (1H, s), 6.93 (2H, d), 5.07 (2H, s), 3.63 (2H, t), 3.16 (3H, s), 3.09 (2H, t), 2.17 (3H, s); MS(ESI): 439 ($MH^+$).

EXAMPLE 52

Preparation of 1-Benzyl-345-cyano-2-ethylaminophenyl)thiourea

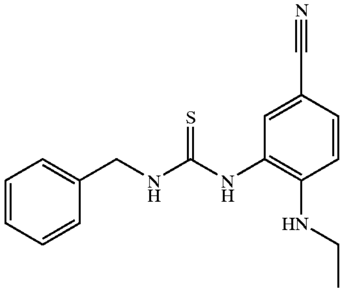

To a 100 mL flask was added 3-amino-4-(ethylamino) benzonitrile (1.0 g, 6.2 mmol), anhydrous THF (50 mL) and benzylisothiocyanate (0.92 g, 6.2 mmol). The reaction mixture was heated at 50° C. with stirring for 6 h. After cooling to room temperature, the reaction mixture was concentrated under reduced pressure and chromatographed (silica gel, 1:1 EtOAc/Hex) to yield the title product (1.78 g, 93 %). $^1$H-NMR ($CDCl_3$): δ 7.48 (1H, dd), 7.37 (1H, d), 7.31 (3H, m), 7.24 (1H, s), 7.18 (1H, br), 6.67 (1H, d), 5.95 (1H, br), 4.81 (2H, d), 4.68 (1H, br), 3.19 (2H, m), 1.23 (3H, t).

Preparation of 3-(3-Benzyl-4-oxothiazolidin-2-ylideneamino)-4-ethylamino)benzo-nitrile

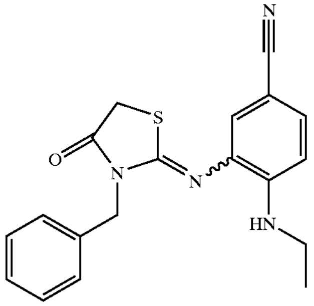

To a 100 mL flask was added 1-benzyl-3-(5-cyano-2-ethylaminophenyl)thiourea (1.0 g, 3.2 mmol), anhydrous ethanol (40 mL), ethyl chloroacetate (0.39 g, 3.2 mmol) and then DBU (0.58 g, 3.8 mmol). The reaction was heated at 80° C. for 30 min. After cooling to room temperature, the reaction mixture was concentrated under reduced pressure and chromatographed (silica gel, 1:1 EtOAc/Hex) to afford the title product (0.98 g, 87%). $^1$H-NMR ($CDCl_3$): δ 7.38 (6H, m), 7.11 (1H, d), 6.50 (1H, d), 5.05 (2H, s), 3.96 (2H, s), 3.01 (2H, m), 1.03 (3H, t).

Preparation of 3,5-Dimethyl-4-phenyl-3H-thiazole-2-thione

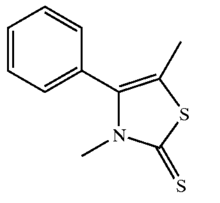

To a 100 mL flask was added freshly prepared triethylammonium methydithiocarbamate (2.0 g, 9.5 mmol), anhydrous MeCN (50 mL), and 2-bromopropiophenone (2.04 g, 9.5 mmol). The reaction mixture was stirred at room temperature for 3 h. The reaction mixture was concentrated under reduced pressure and the resulting crude residue was treated with conc $H_2SO_4$ (5 mL) with stirring at room temperature. After 20 min, the reaction mixture was diluted with water (75 mL) and then mixed with DCM (75 mL). The layers were separated and the aqueous layer extracted once more with DCM (75 mL). The combined organic layers were washed with water (3x50 mL) and then brine (50 mL), dried over anhydrous $MgSO_4$ and concentrated under reduced pressure to afford the title product (1.95 g, 92%) as an off-white solid, which was used without further purification. $^1$H-NMR ($CDCl_3$): δ 7.50 (2H, m), 7.27 (2H,m), 3.45 (3H, s), 2.06 (3H, s).

Preparation of 3-(3'-Benzyl-3,5-dimethyl-4'-oxo-4-phenyl-3',4'-dihydro-3H-[2,5']-bithiazolyliden-2'-ylideneamino)-4-(ethylamino)benzonitrile

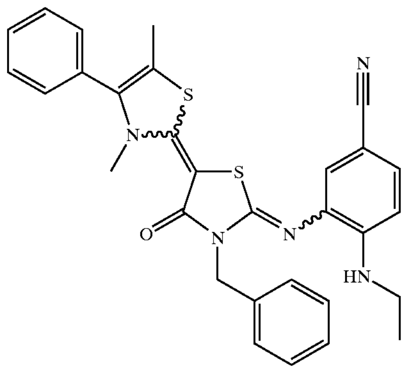

To an 8 mL vial was added 3,5-dimethyl-4-phenyl-3H-thiazole-2-thione (100 mg, 0.45 mmol), methyl p-toluenesulfonate (126 mg, 0.68 mmol) and anhydrous anisole (0.5 mL). The reaction was heated to 120° C. and stirred for 3 h. The cooled reaction mixture was diluted with anhydrous MeCN (3 mL) and then treated with 3-(3-benzyl-4-oxothiazolidin-2-ylideneamino)-4-(ethylamino) benzonitrile (50 mg, 0.14 mmol) and TEA (70 μL, 0.50 mmol). The reaction mixture was warmed to 80° C. and the resulting solution was allowed to stir for 16 h. The product mixture was concentrated under reduced pressure and chromatographed (silica gel, 1:1 EtOAc/Hex) to yield the title product (48.3 mg, 64%) as a yellow solid. $^1$H-NMR ($CDCl_3$): δ 7.40 (5H, m) 7.33 (2H, m), 7.25 (3H, m), 7.23 (2H, m), 6.46 (1H, d), 5.15 (2H, s), 4.28 (1H, m), 3.46 (3H, s), 2.99 (2H, m), 2.28 (3H, s), 1.01 (3H, t); MS(ESI): 538 ($MH^+$).

EXAMPLE 53

Time Resolved Fluorescence Resonance Energy Transfer (TR-FRET) Assay

The FRET assay was performed by incubating 8 nM of GST-FXR-LBD, 8 nM of Europium-labeled anti-GST antibody (Wallac), 16 nM biotin-SRC-1 peptide [5'-biotin-CPSSHSSLTERHKILHRLLQEGSPS-CONH2], 20 nM APC-SA [allophycocyanin conjugated streptavidin] (Wallac) in FRET assay buffer (20 mM $KH_2PO_4/K_2HPO_4$ (pH 7.3), 150 mM NaCl, 2 mM CHAPS, 2 mM EDTA, 1 mM DTT) in the presence of the test compound(s) for 2–4 hours at room temperature. Data was collected using an LJL Analyst with readings at 615 nm and 665 nm.

EXAMPLE 54

FXR Co-transfection Assay

The basic co-transfection protocol for measuring FXR activity is as follows. CV-1 African Green Monkey Kidney cells are plated 24 hours before transfection to achieve approximately 70–80 percent confluency. Cells are transfected with CMX-hFXR, CMX-RXRα, Luc12 reporter (ECREx7-Tk-Luciferase), and a CMX-β-Galactosidase expression vector. The transfection reagent used is DOTAP. Cells are incubated with the DOTAP/DNA mixture for 5 hours after which the cells are harvested and plated onto either 96 well or 384 well plates containing the appropriate concentration of test compound. The assay is allowed to continue for an additional 18–20 hours, after which the cells are lysed, and the luciferase activity is measured on a standard plate reader.

Results of Examples 53 and 54

Both the FXR/ECREx7 co-transfection assay (Example 54) and the TR-FRET assay (Example 53) can be used to establish the $EC_{50}/IC_{50}$ values for potency and percent activity or inhibition for efficacy. Efficacy defines the activity of a compound relative to a high control (chenodeoxycholic acid, CDCA) or a low control (DMSO/vehicle). The dose response curves are generated from an 8 point curve with concentrations differing by ½ LOG units. Each point represents the average of 4 wells of data from a 384 well plate. The curve for the data is generated by using the equation:

$$Y=\text{Bottom}+(\text{Top}-\text{Bottom})/(1+10\hat{}((\text{LogEC50}-X)*\text{HillSlope}))$$

The $EC_{50}/IC_{50}$ is therefore defined as the concentration at which an agonist or antagonist elicits a response that is half way between the Top (maximum) and Bottom (baseline) values. The $EC_{50}/IC_{50}$ values represented are the averages of at least 3 independent experiments. The determination of the relative efficacy or % control for an agonist is by comparison to the maximum response achieved by chenodeoxycholic acid that is measured individually in each dose response experiment.

For the antagonist assay, 40 $\mu$M CDCA is added to each well of a 384 well plate to elicit a response. The % inhibition for each antagonist is therefore a measurement of the inhibition of the activity of 40 $\mu$M CDCA. In this example 100% inhibition would indicate that the activity of 40 $\mu$M CDCA has been reduced to baseline levels, defined as the activity of the assay in the presence of DMSO only.

Most of the compounds disclosed herein and tested exhibited activity in at least one of the above assays ($EC_{50}$ or $IC_{50}$ less than 10 $\mu$M). Most showed activity at below 1 $\mu$M. Some showed activity below 100 nM. For example, 3-[3-benzyl-5-(3-methyl-3H-benzothiazol-2-ylidene)-4-oxothiazolidin-2-ylideneamino]-4-(ethylamino)benzonitrile (Example 32) shows an $EC_{50}$ of about 0.010 $\mu$M and a % efficacy of about 150% in the co-transfection assay; and 3-(3'-benzyl-3,5-dimethyl-4'-oxo-4-phenyl-3',4'-dihydro-3H-[2,5']-bithiazolyliden-2'-ylideneamino)-4-(ethylamino)benzonitrile (Example 52) shows an $EC_{50}$ of about 0.056 $\mu$M and a % efficacy of about 32% in the co-transfection assay; and an $IC_{50}$ of about 0.042 $\mu$M and a % inhibition of about 48% in a FRET assay.

EXAMPLE 55

Preparation of 3-{3-Benzyl-5-[3-methyl-5-(trifluoromethyl)-3H-benzothiazol-2-ylidene]-4-oxothiazolidin-2-ylideneamino}4-(ethylamino) benzonitrile

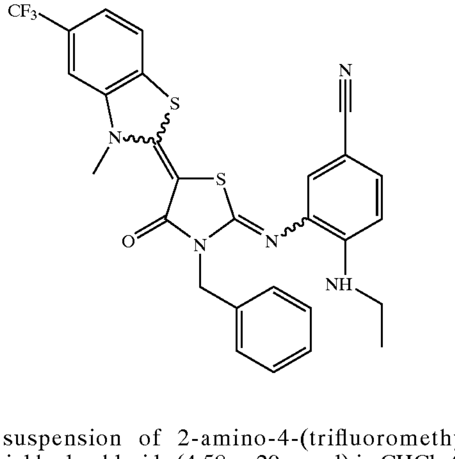

To a suspension of 2-amino-4-(trifluoromethyl) benzenethiol hydrochloride (4.58 g, 20 mmol) in $CHCl_3$ (50 mL) was added satd aqueous $Na_2CO_3$ (50 mL). To this stirred biphasic mixture was added $CSCl_2$ (1.57 mL, 20 mmol) dropwise. After the addition was complete, the mixture was stirred for 72 h at 20° C. The organic layer was separated and the aqueous layer was extracted by $CHCl_3$ (3×20 mL). The combined organic layer was washed by water and dried over $MgSO_4$. Evaporation of solvent gave 2-mercapto-5-(trifluoromethyl)benzothiazole (1.27 g), which was used in the next step without further purification. $^1$H-NMR ($CDCl_3$): δ 7.23 (1H, d), 6.94 (1H, s), 6.81 (1H, d), 4.53 (s, 1H).

To a suspension of the above compound in anisole (10 mL) was added methyl tosylate (MeOTs) (2.5 mL, 2 equiv) and the suspension was heated to 130° C. for 3 h. After cooling to 20° C., acetonitrile and 3-benzylrhodanine were added. To this suspension was added TEA (3 mL, 4 equiv) dropwise, yellow precipitate appeared immediately. The suspension was stirred for 5 h at 20° C. The yellow solid was collected by filtration and washed by acetonitrile and dried under high vacuum to give the product (360 mg).

To a suspension of the above compound in DMF (4 mL) was added MeOTs (0.45 mL, 3 equiv) and the resulted suspension was heated to 130° C. for 5 h. After cooling to 20° C., acetone was added to precipitate the product. Solid was collected by filtration and washed by acetone and dried under high vacuum to afford the tosylate salt (110 mg).

A mixture of the above compound (56 mg, 0.1 mmol), 3-amino-4-(ethylamino)benzonitrile (16 mg, 0.1 mmol) and TEA (28 $\mu$L, 0.2 mmol) was shaken at 60° C. overnight. Evaporation of solvent gave a crude, which was purified by trituration with MeOH to afford the title compound (27 mg). $^1$H-NMR indicated one isomer. $^1$H-NMR ($CDCl_3$): δ 7.61 (1H, d), 7.44 (2H, m), 7.35 (2H, m), 7.27–7.31 (4H, m), 7.18 (1H), 6.5 (1H), 5.19 (2H, s), 4.19 (1H, t), 3.84 (3H, s), 3.01 (2H, m), 1.03 (3H, t); MS (ESI): 566 ($MH^+$).

EXAMPLE 56

Preparation of 3-[3-Benzyl-5-(3-methyl-5-methoxy-3H-benzothiazol-2-ylidene)-4-oxothiazolidin-2-ylideneamino]-4-(ethylamino)benzonitrile

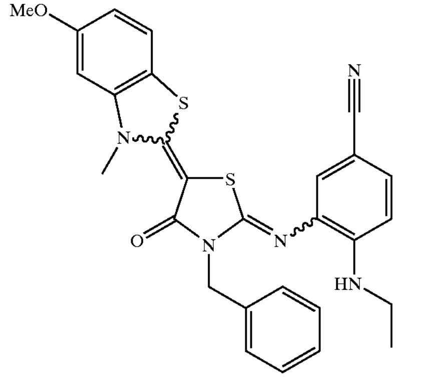

The title compound was prepared in a manner similar to that described in Example 55 by starting from 2-mercapto-5-methoxy-benzothiazole. $^1$H-NMR indicated one isomer. $^1$H-NMR (DMSO-$d_3$): δ 7.47 (1H, d), 7.13–7.21 (5H, m), 6.98 (1H, d), 6.86 (1H, d), 6.67 (1H, dd), 6.46 (1H, d), 4.96 (2H, s), 4.81 (1H, m), 3.66 (3H, s), 3.65 (3H, s), 2.89 (2H, m), 0.83 (3H, t); MS (ESI): 528 ($MH^+$).

EXAMPLE 57

Preparation of 3-[3-Benzyl-5-(5-hydroxy-3-methyl-3H-benzothiazol-2-ylidene)-4-oxothiazolidin-2-ylideneamino]-4-(ethylamino)benzonitrile

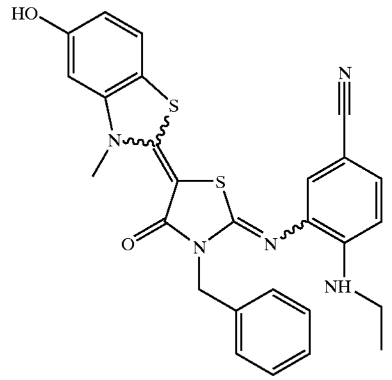

To a suspension of the product of Example 56 (1.06 g, 2 mmol) in DCM (10 mL) was added $BBr_3$ (1.0 M in DCM, 2 mL) dropwise at −78° C. It was warmed to 20° C. slowly and the suspension was stirred for 72 h at 20° C. under $N_2$. MeOH was added to decompose $BBr_3$ at 0° C. Solvent was removed to give a crude, which was purified by chromatography on silica gel eluting with MeOH-DCM (2.5:97.5) to afford the title compound (0.6 g). $^1$H-NMR indicated one isomer. $^1$H-NMR (DMSO-$d_6$): δ 9.66 (1H, s), 7.35 (1H, d), 7.13–7.24 (5H, m), 6.99 (1H, d), 6.60 (1H, d), 6.53 (1H, dd), 6.46 (1H, d), 4.96 (2H, s), 4.82(1H, t), 3.58 (3H, s), 2.89 (2H, m), 0.84 (3H, t); MS (ESI): 514 ($MH^+$).

EXAMPLE 58

Preparation of Dimethylcarbamic Acid 2-[3-Benzyl-2-(5-cyano-2-ethylamino-phenylimino)-4-oxothiazolidin-5-ylidene]-3-methyl-2,3-dihydrobenzothiazol-5-yl Ester

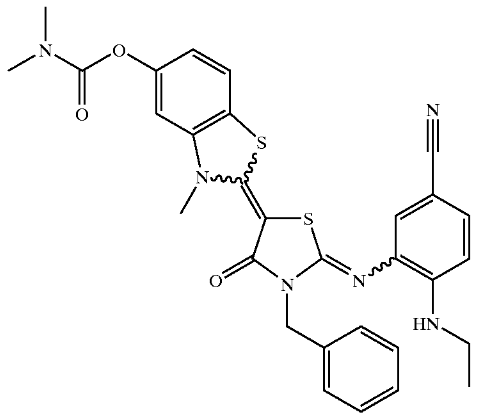

To a suspension of the product of Example 57 in $CHCl_3$ was added TEA (84 μL, 0.6 mmol) and dimethylcarbamoyl chloride (56 μL, 0.6 mmol). The resulted suspension was heated to 65° C. overnight with shaking. Solvent was removed under vacuum to give a crude, which was purified by chromatography on silica gel, eluting by MeOH-DCM (5:95) to afford the title compound (38.6 mg). $^1$H-NMR indicated one isomer. $^1$H-NMR (DMSO-$d_6$): δ 97.73 (1H, d), 7.28–7.39 (7H, m), 7.14 (1H, d), 6.97 (1H, dd), 6.63 (1H, dd), 5.12 (2H, s), 4.98 (1H, t), 3.78 (3H, s), 3.05 (6H, m), 2.91 (3H, s), 0.99 (3H, t); MS (ESI): 585 ($MH^+$).

EXAMPLE 59

Preparation of 3-{3-Benzyl-5-[5-(2-hydroxyethoxy)-3-methyl-3H-benzothiazol-2-ylidene]-4-oxothiazolidin-2-ylideneamino}-4-(ethylamino) benzonitrile

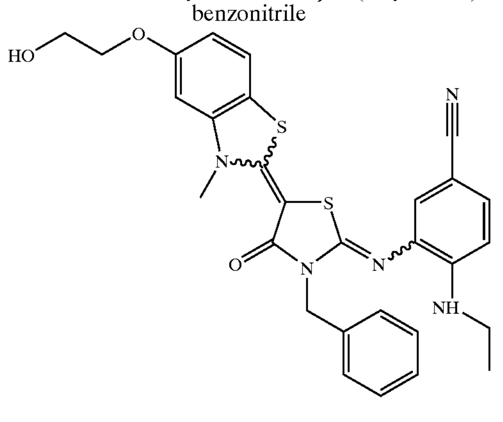

To a solution of the product of Example 57 in DMF were added $K_2CO_3$ and 3-bromoethanol and the resulting suspension was heated to 75° C. with stirring under nitrogen for 72 h. Solid was removed by filtration and washed by DMF. Evaporation of solvent gave a crude, which was purified by chromatography on silica gel eluting with MeOH-DCM (5:95) to afford the title compound (0.58 g). $^1$H-NMR indicated one isomer. $^1$H-NMR (DMSO-$d_6$): δ 7.62 (1H, d), 7.29–7.39 (5H, m), 7.14 (1H, d), 7.02 (1H, d), 6.84 (1H, dd), 5.75 (1H, d), 5.11 (2H, s), 4.97 (1H, t), 4.87 (1H, t), 4.05 (2H, t), 3.80 (3H, s, 3.71 (2H, m), 3.05 (2H, m), 0.99 (3H, t); MS (ESI): 558 ($MH^+$).

EXAMPLE 60

Preparation of 3-{3-Benzyl-5-[3-methyl-(2-morpholin-4-ylethoxy)-3H-benzothiazol-2-ylidene]-4-oxothiazolidin-2-ylideneamino}-4-(ethylamino) benzonitrile

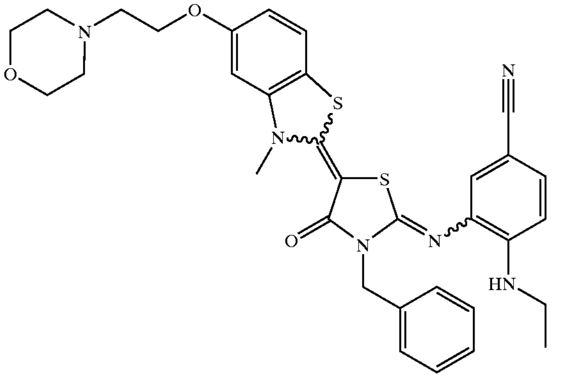

To a suspension of the product of Example 59 (56 mg, 0.1 mmol) in anhydrous DCM (2 mL) was added triflic anhydride ($Tf_2O$) at −10° C. under nitrogen. The suspension was stirred for 1 h at −10° C. Morpholine (44 μL, 0.5 mmol) was added and the reaction mixture was stirred overnight at 20° C. Evaporation of solvent gave a crude, which was purified by chromatography on silica gel eluting with MeOH-DCM to give the title compound (18 mg). $^1$H-NMR indicated one isomer. $^1$H-NMR ($CDCl_3$): δ 7.44 (2H, m), 7.39 (1H, d), 7.32–7.36 (2H, m), 7.27–7.30 (2H, m), 7.20 (1H, d), 6.78 (1H, dd), 6.67 (1H, d), 6.49 (1H, d), 5.17 (2H, s), 4.22 (1H, t), 4.15 (2H, t), 3.78 (3H, s), 3.75 (4H, m), 3.01 (2 H, m), 2.83 (2H, t), 2.59 (2 H, t), 1.02 (3 H, t); MS (ESI): 627 ($MH^+$).

EXAMPLE 61

3-[3-Benzyl-5-(1,3-dimethyl-1,3-dihydrobenzoimidazol-2-ylidene)-4-oxothiazolidin-2-ylideneamino]-4-(ethylamino)benzonitrile

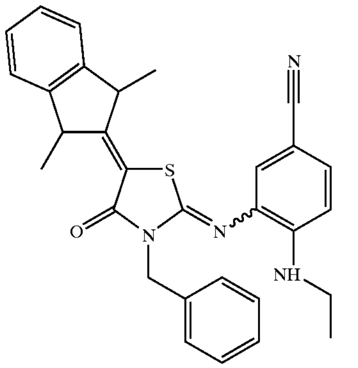

To suspension of 2-mercaptobenzimidazole (15.02 g, 100 mmol) in aqueous $NaHCO_3$ (25.2 g, 300 mmol in 40 mL of $H_2O$) was added $Me_2SO_4$ (47.4 mL, 500 mmol) dropwise at 20° C. A clear solution was obtained. The solution was stirred for 17 h at 20° C. NaI (3.2 g, 200 mmol) was added. After the solution was cooled in an ice-water bath, yellowish precipitate appeared. Solid was collected by filtration and washed by cold water and ether. Drying under high vacuum afford the iodide salt (6.5 g).

To a solution of the above salt (66 mg, 0.2 mmol) and 3-(3-benzyl-4-oxothiazolidin-2-ylideneamino)-4-(ethylamino)benzonitrile (70 mg, 0.2 mmol) in DMF was added DBU (62 mL, 2 equiv) and the solution was heated to 100° C. for 48 h. Evaporation of solvent under high vacuum gave a crude, which was purified by chromatography on silica gel eluting with EtOAc-hexane (1:1) to give the title compound (3.6 mg). $^1$H-NMR indicated one isomer. $^1$H-NMR ($CDCl_3$): δ 7.46 (2H, m), 7.22–7.36 (8H, m), 6.46 (1H,d), 5.17 (2H, s), 4.44 (1H, t), 3.79 (3H, s), 3.01 (2 H, m), 0.88 (3 H, t); MS (ESI): 495 ($MH^+$).

EXAMPLE 62

Preparation of 3-Benzyl-5-(3-methyl-3H-benzothiazol-2-ylidene)-2-(quinolin-8-ylimino) thiazolidin-4-one

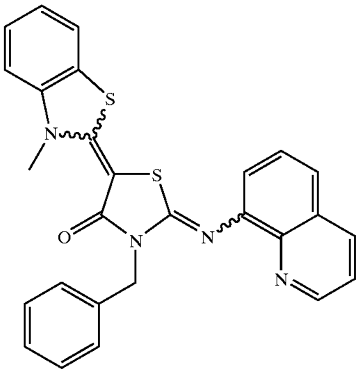

The title compound was prepared in a manner similar to that described in Example 1 by replacing aniline with 8-aminoquinoline. MS(ESI): 481 ($MH^+$).

EXAMPLE 63

Preparation of 3-Benzyl-2-(8-hydroxyquinolin-5-ylimino)-5-(3-methyl-3H-benzothiazol-2-ylidene) thiazolidin-4-one

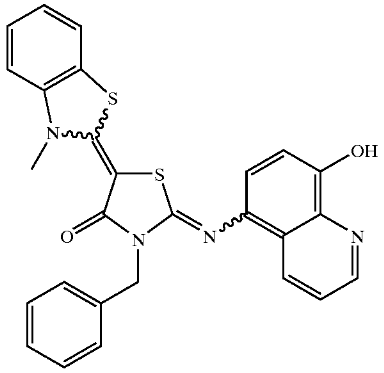

The title compound was prepared in a manner similar to that described in Example 1 by replacing aniline with 5-aminoquinolin-8-ol. MS(ESI): 497 ($MH^+$).

EXAMPLE 64

Preparation of 3-[3-Benzyl-5-(3-methyl-3H-benzothiazol-2-ylidene)-4-oxothiazolidin-2-ylideneamino]-4-butylaminobenzonitrile

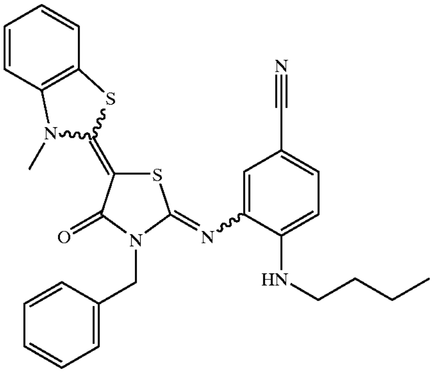

The title compound was prepared in a manner similar to that described in Example 31 by replacing methylamine with butylamine. MS(ESI): 526 ($MH^+$).

EXAMPLE 65

Preparation of 4-Benzylamino-3-[3-benzyl-5-(3-methyl-3H-benzothiazol-2-ylidene)-4-oxothiazolidin-2-ylideneamino]benzonitrile

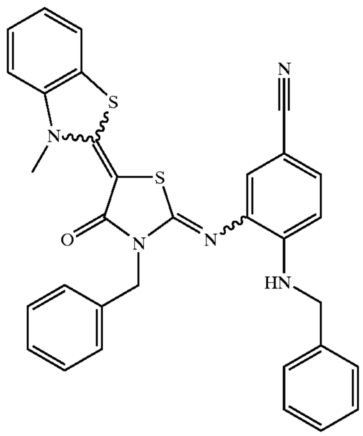

The title compound was prepared in a manner similar to that described in Example 31 by replacing methylamine with benzylamine. MS(ESI): 560 ($MH^+$).

EXAMPLE 66

Preparation of 3-[3-Benzyl-5-(3-methyl-3H-benzothiazol-2-ylidene)-4-oxothiazolidin-2-ylideneamino]-4-cyclopentylaminobenzonitrile

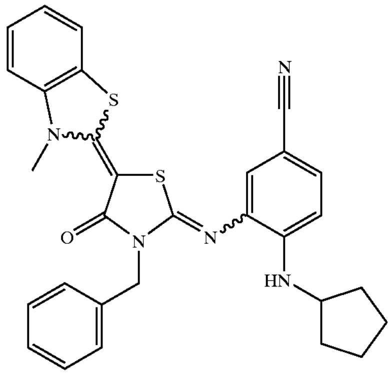

The title compound was prepared in a manner similar to that described in Example 31 by replacing methylamine with cyclopentylamine. MS(ESI): 538 ($MH^+$).

EXAMPLE 67

Preparation of 3-[3-Benzyl-5-(3-methyl-3H-benzothiazol-2-ylidene)-4-oxothiazolidin-2-ylideneamino]-4-(pyrrolidin-1-ylamino)benzonitrile

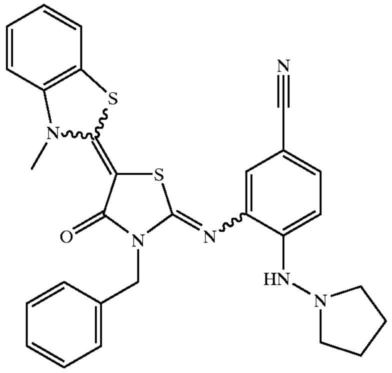

The title compound was prepared in a manner similar to that described in Example 31 by replacing methylamine with 1-aminopyrrolidine. MS(ESI): 539 ($MH^+$).

EXAMPLE 68

Preparation of 3-[3-Benzyl-5-(3-methyl-3H-benzothiazol-2-ylidene)-4-oxothiazolidin-2-ylideneamino]-4-pyrrolidin-1-ylbenzonitrile

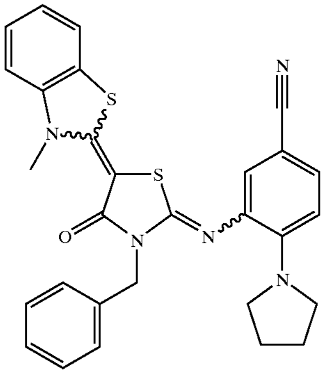

The title compound was prepared in a manner similar to that described in Example 31 by replacing methylamine with pyrrolidine. MS(ESI): 524 ($MH^+$).

EXAMPLE 69

Preparation of 3-Benzyl-2-(isoquinolin-5-ylimino)-5-(3-methyl-3H-benzothiazol-2-ylidene)thiazolidin-4-one

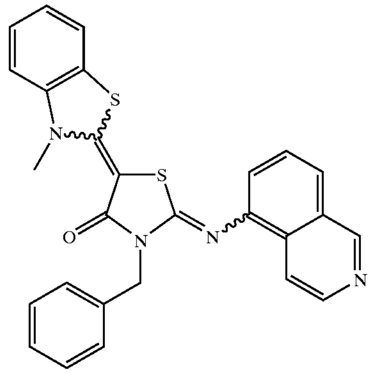

The title compound was prepared in a manner similar to that described in Example 1 by replacing aniline with 5-aminoisoquinoline. MS(ESI): 481 ($MH^+$).

EXAMPLE 70

Preparation of 3-Benzyl-2-(isoquinolin-1-ylimino)-5-(3-methyl-3H-benzothiazol-2-ylidene)thiazolidin-4-one

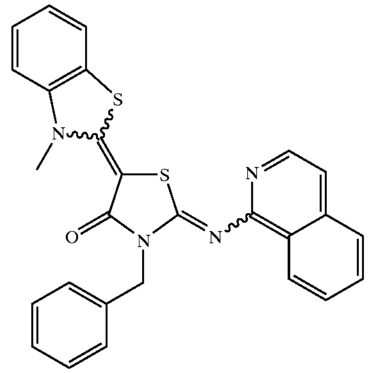

The title compound was prepared in a manner similar to that described in Example 1 by replacing aniline with 1-aminoisoquinoline. MS(ESI): 481 ($MH^+$).

EXAMPLE 71

Preparation of N-{4-[3-Benzyl-5-(3-methyl-3H-benzothiazol-2-ylidene)-4-oxothiazolidin-2-ylideneamino]phenyl}acetamide

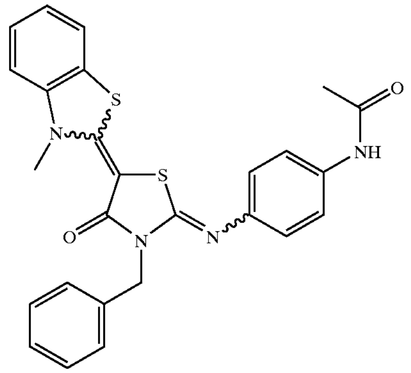

The title compound was prepared in a manner similar to that described in Example 1 by replacing aniline with 4'-aminoacetanilide. MS(ESI): 487 ($MH^+$).

EXAMPLE 72

Preparation of 2-(4-Acetylphenylimino)-3-benzyl-5-(3-methyl-3H-benzothiazol-2-ylidene)thiazolidin-4-one

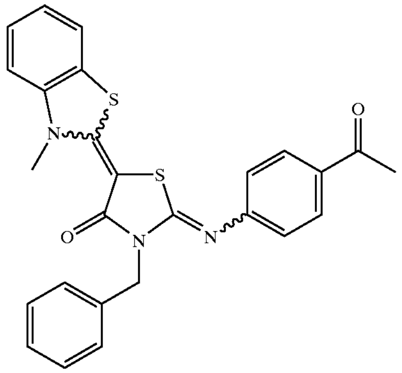

The title compound was prepared in a manner similar to that described in Example 1 by replacing aniline with 4'-aminoacetophenone. MS(ESI): 482 ($MH^+$).

EXAMPLE 73

Preparation of 4-[3-Benzyl-5-(3-methyl-3H-benzothiazol-2-ylidene)-4-oxothiazolidin-2-ylideneamino]benzamide

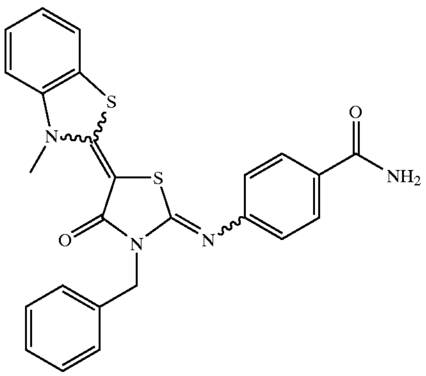

The title compound was prepared in a manner similar to that described in Example 1 by replacing aniline with 4-aminobenzamide. MS(ESI): 473 ($MH^+$).

EXAMPLE 74

Preparation of 3-Benzyl-5-(3-methyl-3H-benzothiazol-2-ylidene)-2-(naphthalen-1-ylimino) thiazolidin-4-one

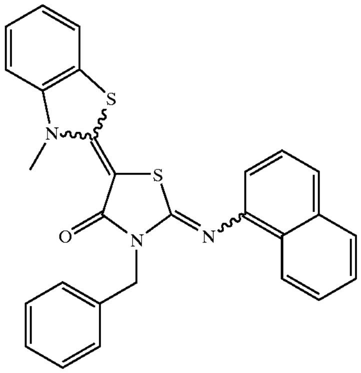

The title compound was prepared in a manner similar to that described in Example 1 by replacing aniline with 1-naphthylamine. MS(ESI): 480 ($MH^+$).

EXAMPLE 75

Preparation of 3-Benzyl-5-(3-methyl-3H-benzothiazol-2-ylidene)-2-(naphthalen-2-ylimino) thiazolidin-4-one

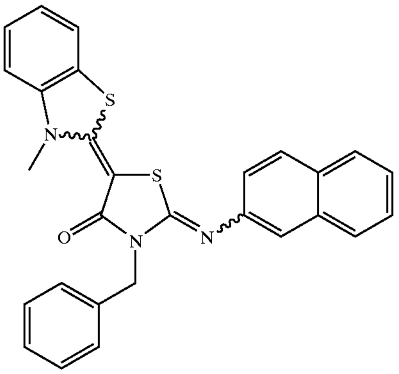

The title compound was prepared in a manner similar to that described in Example 1 by replacing aniline with 2-naphthylamine. MS(ESI): 480 ($MH^+$).

EXAMPLE 76

Preparation of 3-Benzyl-5-(3-methyl-3H-benzothiazol-2-ylidene)-2-(pyridin-2-ylimino) thiazolidin-4-one

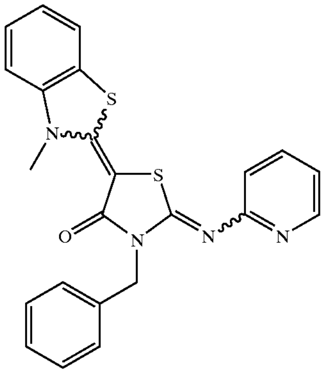

The title compound was prepared in a manner similar to that described in Example 1 by replacing aniline with 1-aminopyridine. MS(ESI): 431 ($MH^+$).

EXAMPLE 77

Preparation of 4-[3-Benzyl-5-(3-methyl-3H-benzothiazol-2-ylidene)-4-oxothiazolidin-2-ylideneamino]benzenesulfonamide

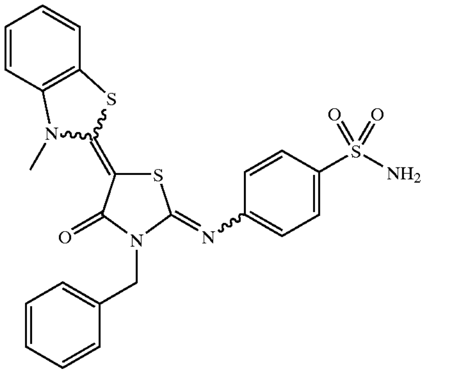

The title compound was prepared in a manner similar to that described in Example 1 by replacing aniline with 4'-aminoacetophenone. MS(ESI): 509 ($MH^+$).

EXAMPLE 78

Preparation of N-Acetyl-4-[3-benzyl-5-(3-methyl-3H-benzothiazol-2-ylidene)-4-oxothiazolidin-2-ylideneamino]benzenesulfonamide

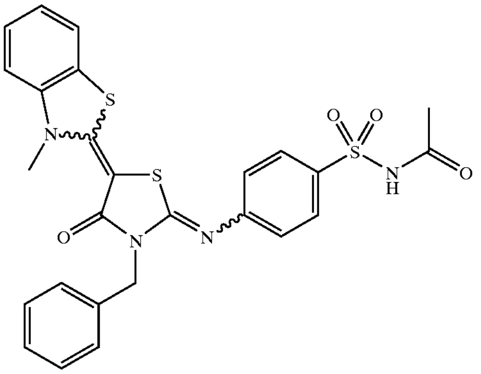

The title compound was prepared in a manner similar to that described in Example 1 by replacing aniline with N-acetyl-4-aminobenzenesulfonamide. MS(ESI): 551 ($MH^+$).

EXAMPLE 79

A. Preparation of 2-(3-Acetylphenylimino)-3-pyridin-3-ylmethylthiazolidin-4-one

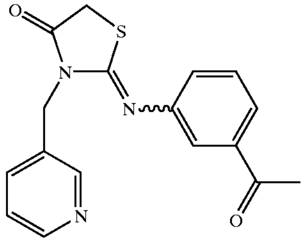

The title compound was prepared from 3-picolyl isothiocyanate hydrobromide and 3'-aminoacetophenone in a manner similar to Example 52. $^1H$-NMR ($CDCl_3$): δ 8.80 (1H, d), 8.58 (1H, dd), 7.85 (1H, m), 7.74 (1H, m), 7.54 (1H, m), 7.45 (1H, m), 7.29 (1H, m), 7.15 (1H, m), 5.05 (2H, s), 3.86 (2H, s), 2.60 (3H, s).

B. Preparation of 2-(3-Acetylphenylimino)-5-(3-methyl-3H-(benzothiazol-2-ylidene)-3-pyridin-3-ylmethylthiazolidin-4-one

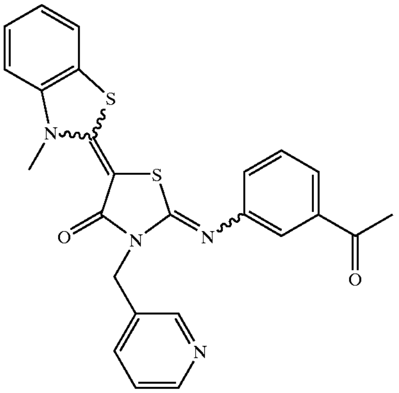

The title compound was prepared from intermediate 2-(3-acetylphenylimino)-3-pyridin-3-ylmethylthiazolidin-4-one and 3-methyl-2-(methylthio)benzothiazol-3-ium p-toluenesulfonate as described in Example 45. $^1H$-NMR ($CDCl_3$): δ 8.87 (1H, d), 8.56 (1H, dd), 7.93 (1H, m), 7.74 (1H, m), 7.60 (1H, m), 7.53 (1H, d), 7.46 (1H, m), 7.27–7.38 (2H, m), 7.17–7.23 (2H, m), 7.05 (1H, d), 5.18 (2H, s), 3.74 (3H, s), 2.62 (3H, s); MS(ESI): 473 ($MH^+$).

EXAMPLE 80

A. Preparation of N-(5-Aminopyridin-2-yl) acetamide

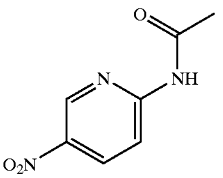

To a hot solution of 2-amino-5-nitropyridine (1.4 g, 10 mmol) in acetic anhydride (5 mL) at 100° C. was added conc. $H_2SO_4$ (0.1 mL). The resulting mixture was heated at 130° C. for 2 h, cooled and partitioned between EtOAc (200 mL) and water (100 mL). The layers were separated and the aqueous layer was washed once with EtOAc (100 mL). The combined organic layers were washed with water (100 mL), saturated aqueous $NaHCO_3$ (100 mL) and then brine (50 mL); dried over anhydrous $MgSO_4$ and concentrated under reduced pressure to afford N-(5-nitropyridin-2-yl)acetamide (1.8 g, 98%), which was used without further purification. $^1$H-NMR ($CDCl_3$): δ 9.14 (1H, d), 8.50 (1H, dd), 8.40 (1H, d), 8.23 (1H, br s), 2.29 (3H, s).

B. Preparation of N-{5-[3-Benzyl-5-(3-methyl-3H-benzothiazol-2-ylidene)-4-oxothiazolidin-2-ylideneamino]pyridin-2-yl}acetamide

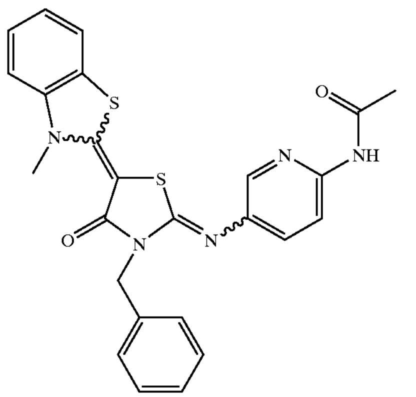

In a manner similar to Example 30, intermediate N-(5-nitropyridin-2-yl)acetamide was hydrogenated and then condensed with 3-benzyl-5-(3-methyl-3H-benzothiazol-2-ylidene)-2-methylthio-4-oxo-2-thiazolium p-toluenesulfonate to afford the title compound. $^1$H-NMR (DMSO-$d_6$): δ 10.45 (1H, s), 8.07 (1H, d), 7.97 (1H, d), 7.75 (1H, d), 7.33–7.46 (7H, m), 7.29 (1H, m), 7.22 (1H, m), 5.06 (2H, s), 3.79 (3H, s), 2.09 (3H, s); MS(ESI): 488 (MH$^+$).

EXAMPLE 81

Preparation of N-{5-[3-Benzyl-5-(3-methyl-3H-benzothiazol-2-ylidene)-4-oxothiazolidin-2-ylideneamino]-2-cyanophenyl}acetamide

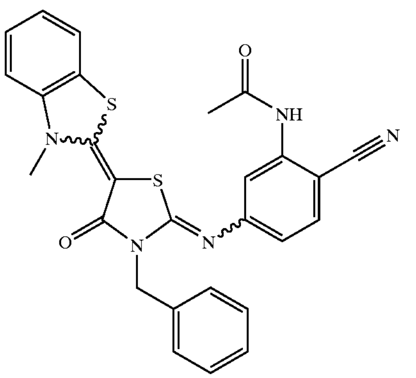

The title compound was prepared in a manner similar to that described in Example 1 by replacing aniline with 5'-amino-2'-cyanoacetanilide. MS(ESI): 512 (MH$^+$).

EXAMPLE 82

Preparation of 2-(5-Acetyl-2-ethylaminophenylimino)-5-(3-methyl-3H-benzothiazol-2-ylidene)-3-pyridin-3-ylmethylthiazolidin-4-one

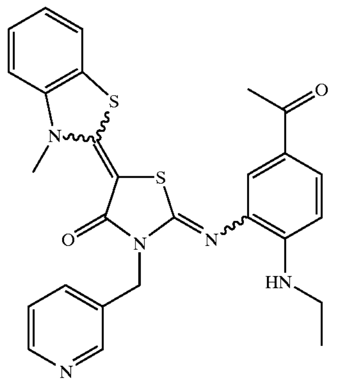

The title compound was prepared in a manner similar to that described in Example 79 by replacing 3'-aminoacetophenone with 3'-amino-4'-(ethylamino) acetophenone. MS(ESI): 516 (MH$^+$). Recrystallization of the product from hot ethanol afforded crystals suitable for single-crystal X-ray diffraction. Structural analysis showed that the E-isomer had been obtained.

EXAMPLE 83

Preparation of 4-Ethylamino-3-[5-(3-methyl-3H-benzothiazol-2-ylidene)-4-oxo-3-pyridin-3-ylmethylthiazolidin-2-ylideneamino]benzonitrile

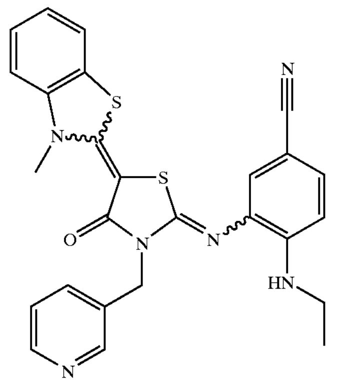

The title compound was prepared in a manner similar to that described in Example 79 by replacing 3'-aminoacetophenone with 3-amino-4-(ethylamino) benzonitrile. MS(ESI): 499 (MH$^+$).

EXAMPLE 84

Preparation of 4-Ethylamino-3-[3-furan-2-ylmethyl-5-(3-methyl-3H-benzothbiazol-2-ylidene)-4-oxothiazolidin-2-ylideneamino]benzonitrile

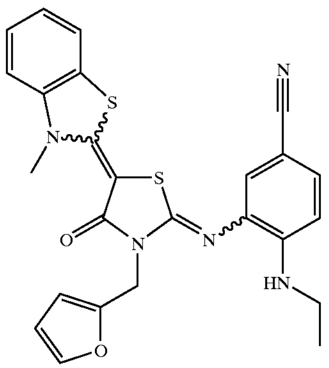

The title compound was prepared in a manner similar to that described in Example 83 by replacing 3-picolyl isothiocyanate hydrobromide with 2-furfuryl isothiocyanate. MS(ESI): 488 ($MH^+$).

EXAMPLE 85

Preparation of 2-(5-Acetyl-2-methylaminophenylimino)-3-benzyl-5-(3-methyl-3H-benzothiazol-2-ylidene)thiazolidin-4-one

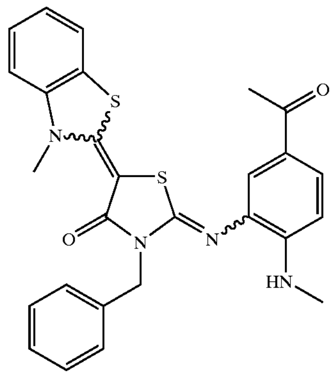

The title compound was prepared in a manner similar to that described in Example 31 by replacing 4-fluoro-3-nitrobenzonitrile with 4'-chloro-3'-nitroacetophenone. MS(ESI): 501 ($MH^+$).

EXAMPLE 86

Preparation of N-{4-[3-Benzyl-5-(3-methyl-3H-benzothiazol-2-ylidene)-4-oxothiazolidin-2-ylideneamino]phenyl}-2,2,2-trifluoroacetamide

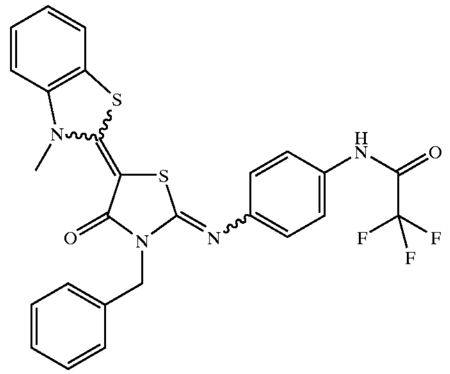

The product of Example 4 was treated with trifluoroacetic anhydride in anhydrous DCM. After 1 h the product mixture was diluted with EtOAc, washed with water and satd aqueous $NaHCO_3$, dried over anhydrous $Na_2SO_4$ and concentrated under reduced pressure to afford the title compound as a yellow solid. $^1$H-NMR ($CDCl_3$): δ 7.81 (1H, br s), 7.53–7.59 (4H, m), 7.49 (1H, d), 7.27–7.36 (4H, m), 7.17 (1H, m), 7.01–7.06 (3H, m), 5.15 (2H, s), 3.73 (3H, s); MS(ESI): 541 ($MH^+$).

EXAMPLE 87

A. Preparation of 4-Ethylamino-3-nitrobenzoic Acid Methyl Ester

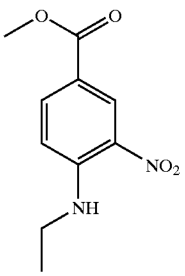

In a manner similar to Example 31, 4-fluoro-3-nitrobenzoic acid was treated with ethylamine to give 4-ethylamino-3-nitrobenzoic acid, which was then esterified with anhydrous hydrogen chloride in methanol to give the title compound. $^1$H-NMR ($CDCl_3$): δ 8.89 (1H, d), 8.28 (1H, br s), 8.06 (1H, dd), 6.87 (1H, d), 3.90 (3H, s), 3.42 (2H, m), 1.40 (3H, t).

B. Preparation of 3-[3-Benzyl-5-(3-methyl-3H-benzothiazol-2-ylidene)-4-oxothiazolidin-2-ylideneamino]-4-ethylaminobenzoic Acid Methyl Ester

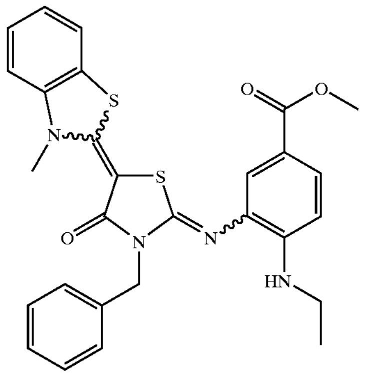

In a manner similar to Example 30, intermediate 4-ethylamino-3-nitrobenzoic acid methyl ester was hydrogenated and then condensed with 3-benzyl-5-(3-methyl-3H-benzothiazol-2-ylidene)-2-methylthio-4-oxo-2-thiazolium p-toluenesulfonate to afford the title compound. $^1$H-NMR ($CDCl_3$): δ 7.73 (1H, dd), 7.65 (1H, d), 7.52 (1H, dd), 7.45–7.49 (2H, m), 7.27–7.38 (4H, m), 7.18 (1H, m), 7.06 (1H, d), 6.52 (1H, d), 5.19 (2H, s), 4.14 (1H, br t), 3.85 (3H, s), 3.78 (3H, s), 3.04 (2H, m), 1.04 (3H, t); MS(ESI): 531 ($MH^+$).

EXAMPLE 88

Preparation of 4-Ethylamino-3-[5-(3-methyl-3H-benzothiazol-2-ylidene)-4-oxo-3-phenethylthiazolidin-2-ylideneamino]benzonitrile

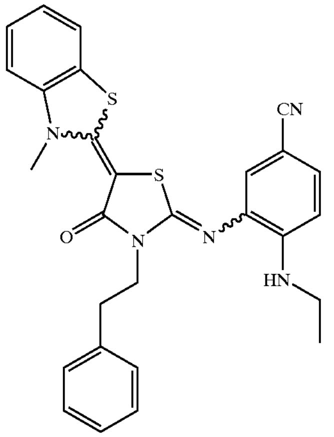

The title compound was prepared in a manner similar to that described in Example 83 by replacing 3-picolyl isothiocyanate hydrobromide with phenethyl isothiocyanate. MS(ESI): 512 ($MH^+$).

EXAMPLE 89

Preparation of 2-[3-Benzyl-5-(3-methyl-3H-benzothiazol-2-ylidene)-4-oxothiazolidin-2-ylideneamino]benzoic Acid

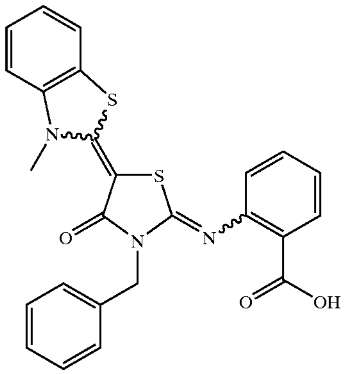

The title compound was prepared in a manner similar to that described in Example 1 by replacing aniline with anthranilic acid. MS(ESI): 474 ($MH^+$).

EXAMPLE 90

A. Preparation of 4-Ethylamino-3-nitrobenzoic Acid tert-Butyl Ester

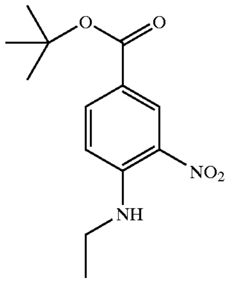

4-Chloro-3-nitrobenzoic acid tert-butyl ester (3.0 g, 11.6 mmol), prepared according to a published procedure [WO 9707101], was cautiously added to a solution of 2.0 M $EtNH_2$/THF (20 mL, 40 mmol) and TEA (2.0 mL, 14 mmol) in anhydrous THF (30 mL). The resulting mixture was heated at 65° C. for 3 h, cooled, concentrated under reduced pressure, diluted with DCM (200 mL), washed with water (2×100 mL) and brine (50 mL), dried over anhydrous $Na_2SO_4$ and concentrated to give the title compound (3.1 g, 99%) as a yellow solid, which was used without further purification. $^1$H-NMR ($CDCl_3$): δ 8.80 (1H, d), 8.24 (1H, br s), 8.02 (1H, dd), 6.84 (1H, d), 3.41 (2H, m), 1.59 (9H, s), 1.40 (3H, t).

B. Preparation of 3-[3-Benzyl-5-(3-methyl-3H-benzothiazol-2-ylidene)-4-oxothiazolidin-2-ylideneamino]-4-ethylaminobenzoic Acid tert-Butyl

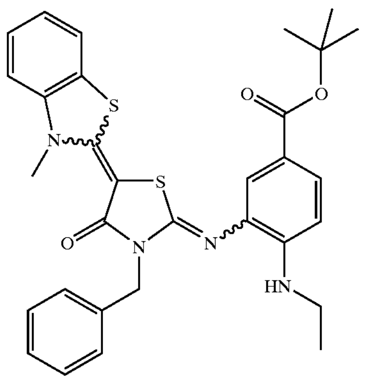

In a manner similar to Example 30, intermediate 4-ethylamino-3-nitrobenzoic acid tert-butyl ester was hydrogenated and then condensed with 3-benzyl-5-(3-methyl-3H-benzothiazol-2-ylidene)-2-methylthio-4-oxo-2-thiazolium p-toluenesulfonate to afford the title compound. $^1$H-NMR ($CDCl_3$): δ 7.69 (1H, dd), 7.61 (1H, d), 7.52 (1H, dd), 7.45–7.49 (2H, m), 7.27–7.37 (4H, m), 7.18 (1H, m), 7.06 (1H, d), 6.51 (1H, d), 5.19 (2H, s), 4.11 (1H, br t), 3.79 (3H, s), 3.04 (2H, m), 1.57 (9H, s), 1.04 (3H, t); MS(ESI): 573 ($MH^+$).

EXAMPLE 91

Preparation of 3-[3-Benzyl-5-(3-methyl-3H-benzothiazol-2-ylidene)-4-oxothiazolidin-2-ylideneamino]-4-ethylaminobenzoic Acid

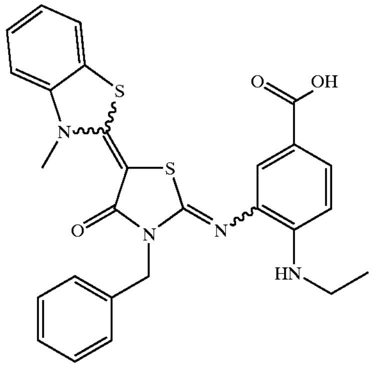

The product of Example 90 was treated with 55% TFA/DCM for 1 h, concentrated under reduced pressure, diluted with DCM, concentrated once again, diluted with DCM, allowed to stand over solid $NaHCO_3$, filtered and concentrated to afford the title product. MS(ESI): 517 ($MH^+$).

EXAMPLE 92

Preparation of 3-[3-Benzyl-5-(3-methyl-3H-benzothiazol-2-ylidene)-4-oxothiazolidin-2-ylideneamino]-4-(2-hydroxyethylamino)benzonitrile

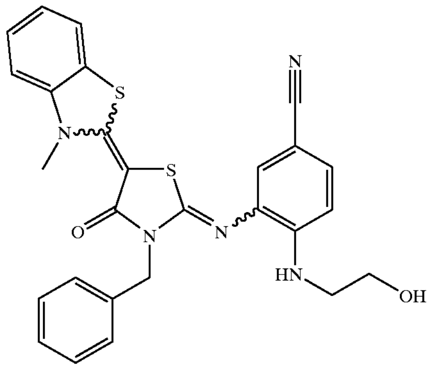

The title compound was prepared in a manner similar to that described in Example 31 by replacing methylamine with 2-aminoethanol. $^1$H-NMR ($CDCl_3$): δ 7.52 (1H, d), 7.42–7.49 (4H, m), 7.27–7.37 (4H, m), 7.19 (1H, m), 7.05 (1H, d), 6.57 (1H, d), 5.94 (1H, br t), 5.19 (2H, s), 3.76 (3H, s), 3.48 (2H, m), 3.03 (2H, q), 1.23 (3H, t), 1.04 (3H, t); MS(ESI): 514 ($MH^+$).

EXAMPLE 93

Preparation of {2-[3-Benzyl-5-(3-methyl-3H-benzothiazol-2-ylidene)-4-oxdthiazolidin-2-ylideneamino]-4-cyanophenylamino}acetic Acid Methyl

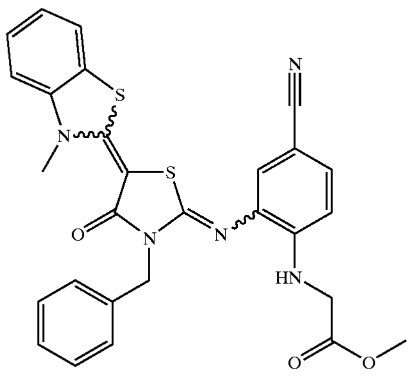

The title compound was prepared in a manner similar to that described in Example 31 by replacing methylamine with glycine methyl ester. MS(ESI): 542 ($MH^+$).

EXAMPLE 94

A. Preparation of N-Ethyl-4-ethylamino-3-nitrobenzamide

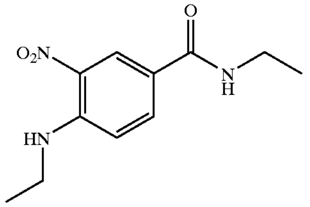

In a manner similar to Example 31, the title compound was prepared from 4-fluoro-3-nitrobenzoic acid (as a mixed anhydride) and ethylamine. $^1$H-NMR ($CDCl_3$): δ 8.52 (1H, d), 8.21 (1H, br s), 7.98 (1H, dd), 6.90 (1H, d), 6.06 (1H, br s), 3.46–3.57 (2H, m), 3.38–3.45 (2H, m), 1.40 (3H, t), 1.27 (3H, t).

B. Preparation of 3-[3-Benzyl-5-(3-methyl-3H-benzothiazol-2-ylidene)-4-oxothiazolidin-2-ylideneamino]-N-ethyl-4-ethylaminobenzamide

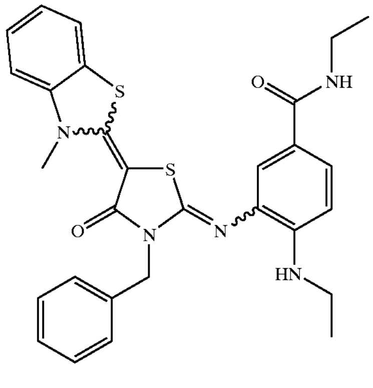

In a manner similar to Example 30, intermediate N-ethyl-4-ethylamino-3-nitrobenzamide was hydrogenated and then condensed with 3-benzyl-5-(3-methyl-3H-benzothiazol-2-ylidene)-2-methylthio-4-oxo-2-thiazolium p-toluenesulfonate to afford the title compound. MS(ESI): 544 ($MH^+$).

EXAMPLE 95

Preparation of {2-[3-Benzyl-5-(3-methyl-3H-benzothiazol-2-ylidene)-4-oxothiazolidin-2-ylideneamino]-4-cyanophenylamino}acetic Acid

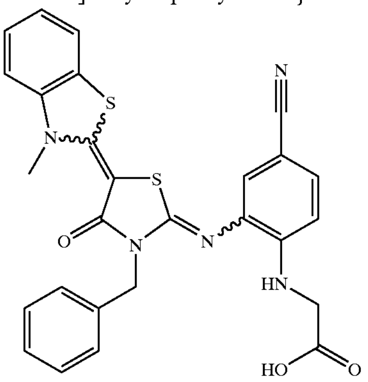

The product of Example 93 was saponified under conditions similar to that described in Example 29 to afford the title compound. MS(ESI): 528 ($MH^+$).

EXAMPLE 96

A. Preparation of 4-Ethylamino-3-nitropyridine

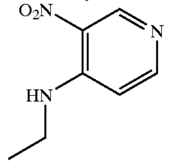

In a manner similar to example 31, the title compound was prepared from 4-chloro-3-nitropyridine, prepared according to published procedure [*J. Med. Chem.* 1996, 39, 487–493], and ethylamine. $^1$H-NMR ($CDCl_3$): δ 9.22 (1H, s), 8.30 (1H, d), 8.10 (1H, br s), 6.71 (1H, d), 3.40 (2H, m), 1.39 (3H, t).

B. Preparation of 3-Benzyl-2-(4-ethylaminopyridin-3-ylimino)-5-(3-methyl-3H-benzothiazol-2-ylidene)thiazolidin-4-one

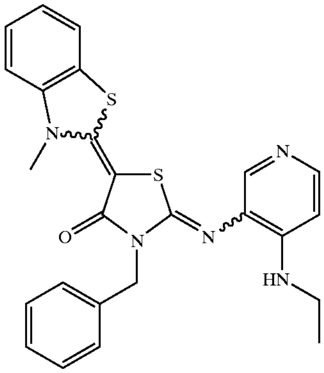

In a manner similar to Example 30, intermediate 4-ethylamino-3-nitropyridine was hydrogenated and then condensed with 3-benzyl-5-(3-methyl-3H-benzothiazol-2-ylidene)-2-methylthio-4-oxo-2-thiazolium p-toluenesulfonate to afford the title compound. $^1$H-NMR ($CDCl_3$): δ 8.04–8.09 (2H, m), 7.53 (1H, d), 7.44–7.48 (2H, m), 7.27–7.38 (4H, m), 7.19 (1H, m), 7.07 (1H, d), 6.42 (1H, d), 5.19 (2H, s), 4.12 (1H, br t), 3.79 (3H, s), 3.02 (2H, m), 1.05 (3H, t); MS(ESI): 474 ($MH^+$).

EXAMPLE 97

A. Preparation of 3'-Fluoro-4'-nitroacetanilide

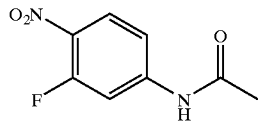

Added 3'-fluoroacetanilide (3.06 g, 20 mmol) cautiously to conc sulfuric acid (6 mL) at 5° C. To the resulting solution, added fuming nitric acid (1.05 mL, 25 mmol) dropwise while maintaining temperature at 5–10° C. After 30 min, added ice (50 g), later diluted with water (100 mL) and extracted with EtOAc (2×100 mL). The combined organic layers were washed with saturated $NaHCO_3$ and brine, dried ($Na_2SO_4$) and concentrated to give the crude product (4.0 g) as a mixture of isomers (1:1.4 ratio of 4'-nitro/2'-nitro). The desired isomer, 3'-flouro-4'-nitroacetanilide, was isolated by flash chromatography (DCM-5% MeOH/DCM) in low yield (1.2 g, 30%) as a yellow solid. $^1H$-NMR ($CDCl_3$): δ 8.08 (1H, app t), 7.82 (1H, dd), 7.41 (1H, br s), 7.21 (1H, m), 2.25 (3H, s).

B. Preparation of 3'-Ethylamino-4'-nitroacetanilide

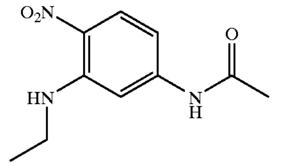

In a manner similar to Example 31, the title compound was prepared from 3'-fluoro-4'-nitroacetanilide and ethylamine. $^1H$-NMR ($CDCl_3$): δ 8.17 (1H, br s), 8.13 (1H, d), 7.57 (1H, br d), 7.33 (1H, br s), 6.38 (1H, dd), 3.36 (2H, m), 2.22 (3H, s), 1.37 (3H, t).

C. Preparation of N-{4-[3-Benzyl-5-(3-methyl-3H-benzothiazol-2-ylidene)-4-oxothiazolidin-2-ylideneamino]-3-ethylaminophenyl}acetamide

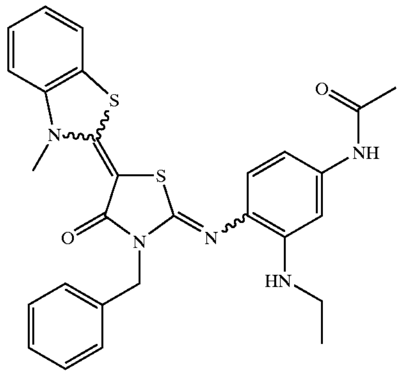

In a manner similar to Example 30, intermediate 3'-ethylamino-4'-nitroacetanilide was hydrogenated and then condensed with 3-benzyl-5-(3-methyl-3H-benzothiazol-2-ylidene)-2-methylthio-4-oxo-2-thiazolium p-toluenesulfonate to afford the title compound. $^1H$-NMR ($CDCl_3$): δ 7.45–7.53 (3H, m), 7.27–7.37 (4H, m), 7.17 (1H, m), 7.03–7.09 (2H, m), 6.91 (1H, d), 6.83 (1H, br d), 6.75 (1H, br s), 5.18 (2H, s), 3.78 (3H, s), 2.99 (2H, m), 2.15 (3H, s), 1.03 (3H, t); MS(ESI): 530 ($MH^+$).

EXAMPLE 98

Preparation of 3-[3-Benzyl-5-(3-methyl-3H-benzothiazol-2-ylidene)-4-oxothiazolidin-2-ylideneamino]-4-(2-dimethylaminoethylamino)benzonitrile

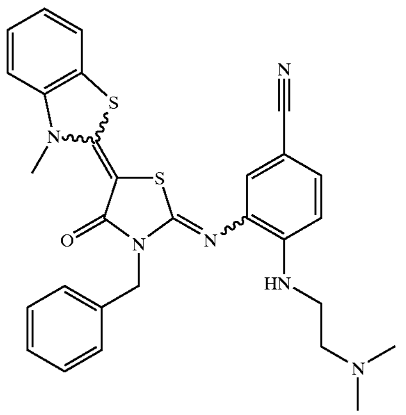

The title compound was prepared in a manner similar to that described in Example 31 by replacing methylamine with N,N-dimethylethylenediamine. MS(ESI): 541 ($MH^+$).

EXAMPLE 99

A. Preparation of N-Ethyl-3-ethylamino-4-nitrobenzamide

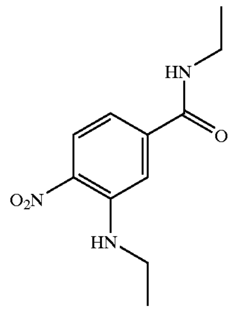

To a chilled solution (10° C.) of 3-fluoro4-nitrobenzoyl chloride (1.0 g, 4.9 mmol) in anhydrous THF (30 mL) added dropwise 2.0 M solution of ethylamine in THF (10 mL, 20 mmol). After stirring 16 h at 25° C., combine with satd $NaHCO_3$ (50 mL) and extracted with EtOAc (3×80 mL). The combined organic layers were washed with 1 N NaOH (50 mL) and brine (50 mL), dried ($MgSO_4$) and concentrated under reduced pressure to yield the title compound (0.66 g, 57%) as an orange-yellow solid that was used without further purification. $^1H$-NMR ($CDCl_3$): δ 8.20 (1H, d), 7.98 (1H, br s), 7.36 (1H, d), 6.81 (1H, dd), 6.13 (1H, br s), 3.51 (2H, m), 3.42 (2H, m), 1.39 (3H, t), 1.27 (3H, t).

B. Preparation of 4-[3-Benzyl-5-(3-methyl-3H-benzothiazol-2-ylidene)-4-oxothiazolidin-2-ylideneamino]-N-ethyl-3-ethylaminobenzamide

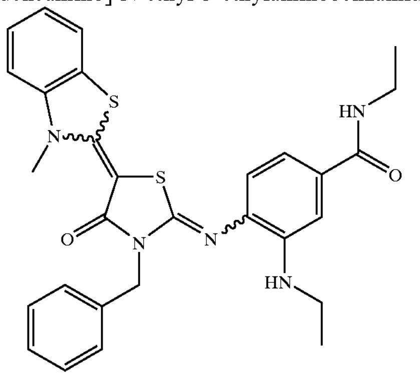

In a manner similar to Example 30, intermediate N-ethyl-3-ethylamino-4-nitrobenzamide was hydrogenated and then condensed with 3-benzyl-5-(3-methyl-3H-benzothiazol-2-ylidene)-2-methylthio-4-oxo-2-thiazolium p-toluenesulfonate to afford the title compound. $^1$H-NMR ($CDCl_3$): δ 7.46–7.54 (3H, m), 7.27–7.38 (4H, m), 7.19 (1H, m), 6.96–7.08 (4H, m), 6.04 (1H, br t), 5.19 (2H, s), 3.76 (3H, s), 3.49 (2H, m), 3.06 (2H, q), 1.25 (3H, t), 1.05 (3H, t); MS(ESI): 544 ($MH^+$).

EXAMPLE 100

A. Preparation of 4-Chloro-N-(2-dimethylaminoethyl)-3-nitrobenzamide

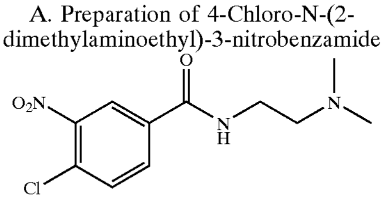

To a chilled solution (−10° C.) of 4-chloro-3-nitrobenzoyl chloride (0.92 g, 4.2 mmol) in anhydrous THF (20 mL) added dropwise a solution of N,N-dimethylethylenediamine (0.44 mL, 4.0 mmol) in THF (20 mL). After stirring 30 min combined with a 1:1 mixture of ice and satd $NaHCO_3$ (50 mL) and then extracted with EtOAc (3x80 mL). The combined organic layers were dried ($Na_2SO_4$), concentrated and chromatographed (silica gel, MeOH/DCM, 3:22) to yield the title compound (0.40 g, 37%) as a pale yellow solid. $^1$H-NMR ($CDCl_3$): δ 8.28 (1H, d), 7.96 (1H, dd), 7.63 (1H, d), 6.98 (1H, br s), 3.54 (2H, m), 2.56 (2H, t), 2.30 (6H, s).

B. Preparation of N-(2-Dimethylaminoethyl)-4-ethylamino-3-nitrobenzamide

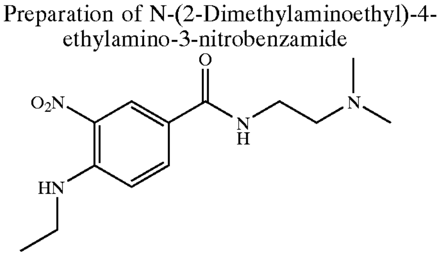

To 2.0 M solution of ethylamine in THF (8 mL, 16 mmol) slowly added 4-chloro-N-(2-dimethylaminoethyl)-3-nitrobenzamide (0.40 g, 1.5 mmol). After heating at 65° C. for 16 h, the reaction mixture was cooled, concentrated and chromatographed (silica gel, MeOH/DCM, 3:22) to afford the title compound (0.30 g, 73%) as a yellow solid. $^1$H-NMR ($CD_3OD$): δ 8.75 (1H, d), 8.32 (1H, br s), 7.98 (1H, dd), 7.08 (1H, d), 3.58–3.64 (3H, m), 3.43–3.51 (2H, m), 2.94 (2H, br t), 2.62 (6H, s), 1.35 (3H, t).

C. Preparation of 3-[3-Benzyl-5-(3-methyl-3H-benzothiazol-2-ylidene)-4-oxothiazolidin-2-ylideneamino]-N-2-dimethylaminoethyl)-4-ethylaminobenzamide

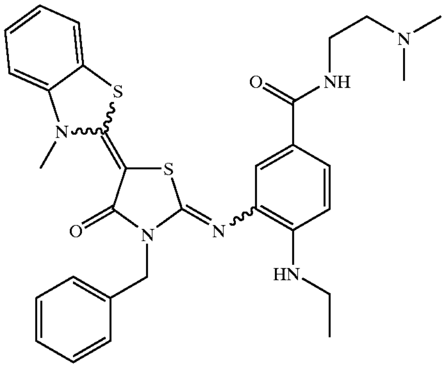

In a manner similar to Example 30, intermediate N-(2-dimethylaminoethyl)-4-ethylamino-3-nitrobenzamide was hydrogenated and then condensed with 3-benzyl-5-(3-methyl-3H-benzothiazol-2-ylidene)-2-methylthio-4-oxo-2-thiazolium p-toluenesulfonate to afford the title compound. $^1$H-NMR ($CDCl_3$): δ 7.44–7.54 (5H, m), 7.28–7.38 (4H, m), 7.18 (1H, m), 7.04 (1H, d), 6.89 (1H, br s), 6.52 (1H, d), 5.19 (2H, s), 3.99 (1H, br t), 3.76 (3H, s), 3.59 (2H, m), 3.02 (2H, m), 2.68 (2H, br s), 2.40 (6H, s), 1.03 (3H, t); MS(ESI): 587 ($MH^+$).

EXAMPLE 101

A. Preparation of 4-(4,5-Dihydrooxazol-2-yl)-$N^1$-ethylbenzene-1,2-diamine

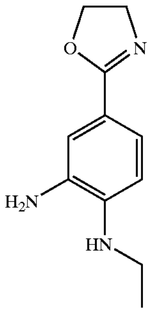

To a chilled solution (−10° C.) of 4-chloro-3-nitrobenzoyl chloride (1.85 g, 8.4 mmol) in anhydrous THF (60 mL) was added dropwise a solution of ethanolamine (0.48 mL, 8.0 mmol) in THF (20 mL) followed by TEA (1.1 mL, 8.0 mmol). After stirring 1 h while temperature was maintained at −10° C., the solution was combined with a 1:1 mixture of ice and satd $NaHCO_3$ (100 mL) and then extracted with EtOAc (3x100 mL). The combined organic layers were washed with brine, dried ($Na_2SO_4$), and concentrated to give 4-chloro-N-(2-hydroxyethyl)-3-nitrobenzamide (1.74 g, 89%) as a white solid, which was used without purification. TLC (3:22 MeOH/DCM $R_f$ 0.36).

To a solution of intermediate 4-chloro-N-(2-hydroxyethyl)-3-nitrobenzamide (0.40 g, 1.6 mmol) in anhydrous DCM (20 mL) added dropwise thionyl chloride (0.29 mL, 4.0 mmol). After stirring 2 h the reaction mixture was diluted with chloroform and concentrated. The resulting yellow oil was diluted cautiously with 2.0 M solution of ethylamine in THF (10 mL, 20 mmol) and heated in a sealed tube at 65° C. After 2 h the reaction mixture was cooled, concentrated and diluted with THF (20 mL). This solution was combined with an aqueous solution of 20% KOH (5 mL) and tetrabutylammonium bromide (20 mg). After stirring rapidly 2 h the mixture was extracted with $Et_2O$ (2×100 mL). The combined organic layers were washed with water and brine, dried ($MgSO_4$), concentrated and chromatographed (silica gel, MeOH/DCM, 1:19) to yield [4-(4,5-dihydrooxazol-2-yl)-2-nitrophenyl]ethylamine (0.17 g, 45%) as a yellow solid. TLC (1:19 MeOH/DCM $R_f$ 0.56).

To a solution of this oxazoline intermediate (71 mg, 0.30 mmol) in ethanol (2 mL) was added zinc dust (0.20 g) and HOAc (0.20 mL). Observed initial exotherm and continued stirring 30 min. The reaction mixture was diluted with $Et_2O$ (20 mL), filtered, combined cautiously with 15% $NH_4OH$ (10 mL), and extracted again with $Et_2O$. The organic layers were combined, washed with brine, dried ($Na_2SO4$), and concentrated under reduced pressure to yield the title compound (60 mg, 97%) as an off-white solid, which was used without purification. $^1$H-NMR ($CDCl_3$): δ 7.45 (1H, dd), 7.35 (1H, d), 6.60 (1H, d), 4.38 (2H, t), 4.01 (2H, t), 3.69 (1H, br s), 3.26 (2H, br s), 3.21 (2H, m), 1.32 (3H, t); TLC (1:19 MeOH/DCM $R^f$ 0.12).

B. Preparation of 3-Benzyl-2-[5-(4,5-dihydrooxazol-2-yl)-2-ethylaminophenylimino]-5-(3-methyl-3H-benzothiazol-2-ylidene)thiazolidin-4-one

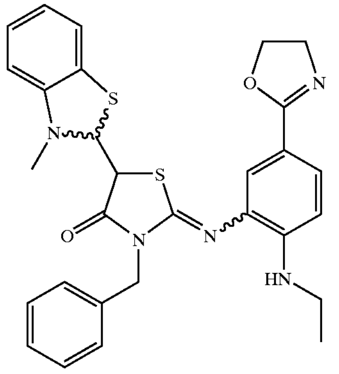

The title compound was prepared in a manner similar to Example 1 by replacing aniline with intermediate 4-(4,5-dihydrooxazol-2-yl)-N$^1$-ethylbenzene-1,2-diamine. $^1$H-NMR ($CDCl_3$): δ 7.64 (1H, d), 7.55 (1H, d), 7.52 (1H, d), 7.45–7.49 (2H, m), 7.27–7.37 (4H, m), 7.18 (1H, m), 7.04 (1H, d), 6.55 (1H, d), 5.19 (2H, s), 4.38 (2H, t), 4.02 (2H, t), 3.77 (3H, s), 3.04 (2H, m), 1.05 (3H, s); MS(ESI): 542 (MH$^+$).

EXAMPLE 102

A. Preparation of 1-Methyl-2-methylthioquinolinium p-Toluenesulfonate

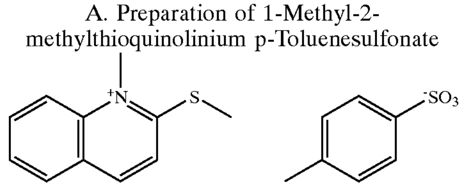

A mixture of 1-methylquinolin-2-thione (175 mg, 1.0 mmol) and methyl p-toluenesulfonate (186 mg, 1.0 mmol) were heated at 130° C. After 30 min the resulting solid was cooled, crushed, triturated with $Et_2O$ (4×1 mL) and dried under high vacuum to give the title compound (0.35 g, 97%) as a white solid. $^1$H-NMR (DMSO-$d_6$): δ 8.96 (1H, d), 8.46 (1H, d), 8.35 (1H, dd), 8.16 (1H, m), 8.08 (1H, d), 7.91 (1H, m), 7.47 (2H, d), 7.10 (2H, d), 4.40 (3H, s), 3.02 (3H, s), 2.28 (3H, s).

B. Preparation of 3-[3-Benzyl-5-(1-methyl-1H-quinolin-2-ylidene)-4-oxothiazolidin-2-ylideneamino]-4-ethylaminobenzonitrile

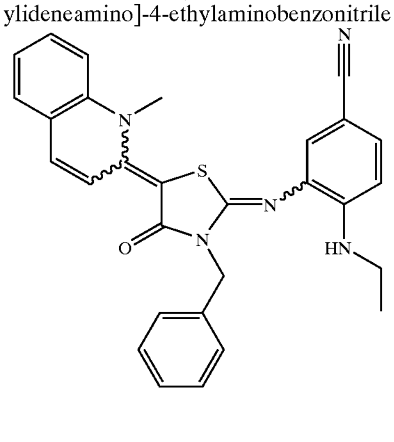

In a manner similar to Example 45, intermediate 1-methyl-2-methylthioquinolinium p-toluenesulfonate was condensed with 3-(3-benzyl-4-oxothiazolidin-2-ylideneamino)-4-ethylaminobenzonitrile to afford the title compound. $^1$H-NMR ($CDCl_3$): δ 7.41–7.58 (4H, m), 7.20–7.38 (9H, m), 6.49 (1H, d), 5.16 (2H, s), 3.79 (3, br s), 3.01 (2H, q), 1.02 (3H, t); MS(ESI): 492 (MH$^+$).

EXAMPLE 103

Preparation of 2-(5-Acetyl-2-ethylaminophenylimino)-3-benzyl-5-(1-methyl-1H-quinolin-2-ylidene)thiazolidin-4-one

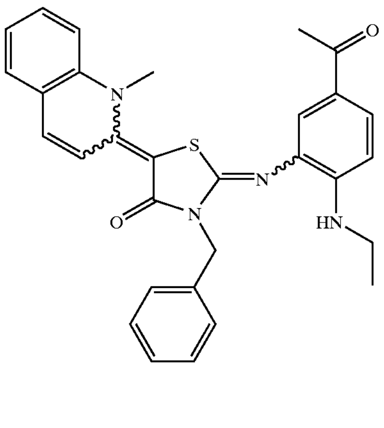

In a manner similar to Example 102, 1-methyl-2-methylthioquinolinium p-toluenesulfonate was condensed with 2-(5-acetyl-2-ethylaminophenylimino)-3-benzylthiazolidin-4-one to afford the title compound. $^1$H-NMR ($CDCl_3$): δ 7.66–7.71 (2H, m), 7.43–7.56 (4H, m), 7.20–7.38 (7H, m), 6.53 (1H, d), 5.20 (2H, s), 3.78 (3H, br s), 3.07 (2H, q), 2.51 (3H, s), 1.06 (3H, t); MS(ESI): 509 (MH$^+$).

EXAMPLE 104

Preparation of 3-Benzyl-2-benzylimino-5-(3-methyl-3H-benzothiazol-2-ylidene)thiazolidin-4-one

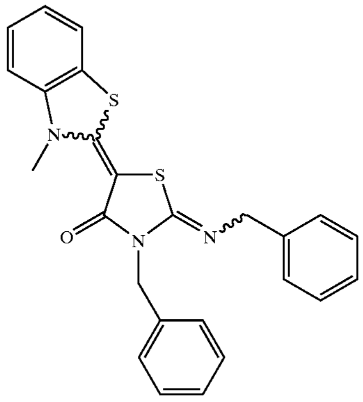

The title compound was prepared in a manner similar to that described in Example 1 by replacing aniline with benzylamine. $^1$H-NMR ($CDCl_3$): δ 7.46–7.57 (3H, m), 7.22–7.37 (9H, m), 7.15 (1H, m), 7.03 (1H, br d), 5.09 (2H, br s), 4.49 (2H, br s), 3.85 (3H, s); MS(ESI): 444 ($MH^+$).

EXAMPLE 105

Preparation of 2-(3-Acetylphenylimino)-3-furan-2-ylmethyl-5-(3-methyl-3H-benzothiazol-2-ylidene) thiazolidin-4-one

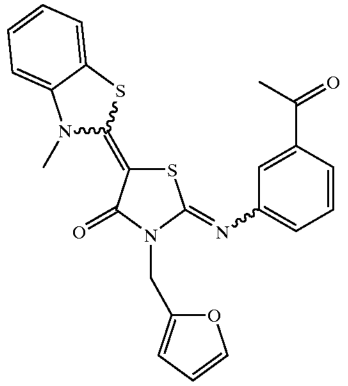

The title compound was prepared in a manner similar to that described in Example 79 by replacing 3-picolyl isothiocyanate hydrobromide with 2-furfuryl isothiocyanate. MS(ESI): 462 ($MH^+$).

EXAMPLE 106

Preparation of N-{4-[3-Furan-2-ylmethyl-5-(3-methyl-3H-benzothiazol-2-ylidene)-4-oxothiazolidin-2-ylideneamino]phenyl}acetamide

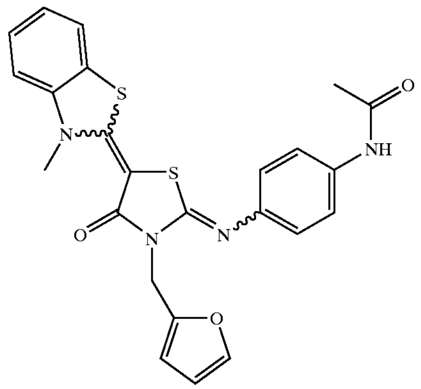

The title compound was prepared in a manner similar to that described in Example 105 by replacing 3'-aminoacetophenone with 4'-aminoacetanilide. MS(ESI): 477 ($MH^+$).

EXAMPLE 107

Preparation of [2-(5-Acetyl-2-ethylaminophenylimino)-5-(3-methyl-3H-benzothiazol-2-ylidene)-4-oxothiazolidin-3-yl]acetic Acid Methyl Ester

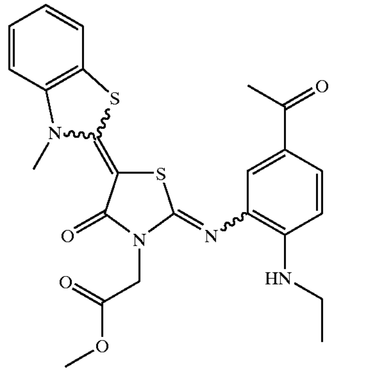

The title compound was prepared in a manner similar to Example 1 by replacing 3-benzylrhodanine with rhodanine-3-acetic acid methyl ester. MS(ESI): 497 ($MH^+$).

EXAMPLE 108

A. Preparation of 2-cyano-4-nitroacetanilide

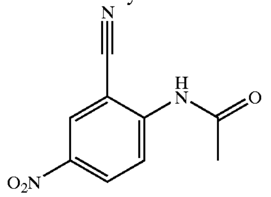

The title compound was prepared in a manner similar to Example 80 by replacing 2-amino-5-nitropyridine with 5-nitroanthranilonitrile. $^1$H-NMR ($CDCl_3$): δ 8.78 (1H, d), 8.49 (1H, d), 8.44 (1H, dd), 7.88 (1H, br s), 2.35 (3H, s).

B. Preparation of N-{4-[3-Benzyl-5-(3-methyl-3H-benzothiazol-2-ylidene)-4-oxothiazolidin-2-ylideneamino]-2-cyanophenyl}acetamide

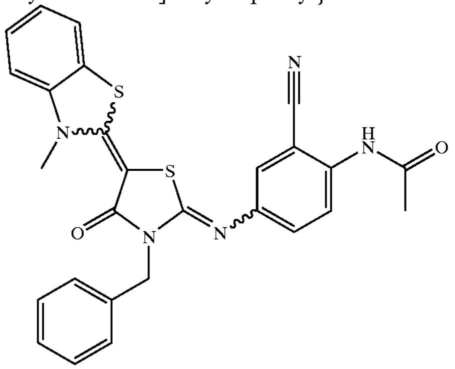

In a manner similar to Example 30, intermediate 2-cyano-4-nitroacetanilide was hydrogenated and then condensed with 3-benzyl-5-(3-methyl-3H-benzothiazol-2-ylidene)-2-methylthio-4-oxo-2-thiazolium p-toluenesulfonate to afford the title compound. $^1$H-NMR ($CDCl_3$): δ 8.30 (1H, d), 7.49–7.57 (4H, m), 7.27–7.38 (5H, m), 7.22 (1H, d), 7.19 (1H, m), 7.07 (1H, d), 5.14 (2H, s), 3.76 (3H, s), 2.27 (3H, s); MS(ESI): 512 ($MH^+$).

EXAMPLE 109

A. Preparation of 4'-Ethoxy-3'-nitroacetophenone

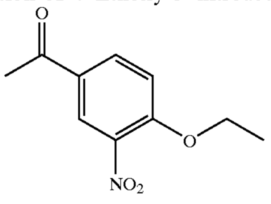

To a solution of 4'-hydroxy-3'-nitroacetophenone (1.0 g, 5.5 mmol) in anhydrous DMF (20 mL) was added anhydrous $K_2CO_3$ (3.0 g, 22 mmol) and then bromoethane (0.49 mL, 6.6 mmol). After heating at 80° C. for 20 h, the reaction mixture was cooled, combined with satd aqueous $NH_4Cl$ (50 mL) and extracted with $Et_2O$ (2×100 mL). The combined organic layers were washed with water (3×50 mL), 1 N NaOH (50 mL) and then brine (50 mL), dried ($Na_2SO_4$) and concentrated under reduced pressure to afford the title compound (1.1 g, 96%) as a light brown solid, which was used without further purification. $^1$H-NMR ($CDCl_3$): δ 8.41 (1H, d), 8.15 (1H, dd), 7.14 (1H, d), 4.28 (2H, q), 2.61 (3H, s), 1.52 (3H, t).

B. Preparation of 2-(5-Acetyl-2-ethoxyphenylimino)-3-benzyl-5-(3-methyl-3H-benzothiazol-2-ylidene)thiazolidin-4-one

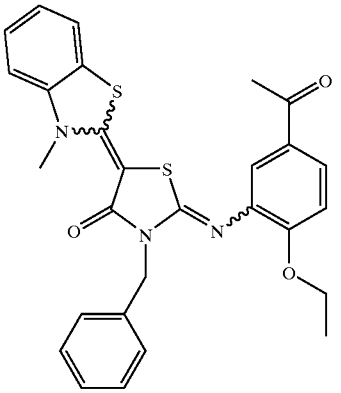

In a manner similar to Example 30, intermediate 4'-ethoxy-3'-nitroacetophenone was hydrogenated and then condensed with 3-benzyl-5-(3-methyl-3H-benzothiazol-2-ylidene)-2-methylthio-4-oxo-2-thiazolium p-toluenesulfonate to afford the title compound. $^1$H-NMR ($CDCl_3$): δ 7.77 (1H, dd), 7.64–7.68 (2H, m), 7.61 (1H, d), 7.48 (1H, m), 7.25–7.36 (4H, m), 7.15 (1H, m), 6.99 (1H, d), 6.98 (1H, d), 5.20 (2H, s), 4.11 (2H, q), 3.69 (3H, s), 2.57 (3H, s), 1.43 (3H, t); MS(ESI): 516 ($MH^+$).

EXAMPLE 110

Preparation of 2-(5-Acetyl-2-hydroxyphenylimino)-3-benzyl-5-(3-methyl-3H-benzothiazol-2-ylidene) thiazolidin-4-one

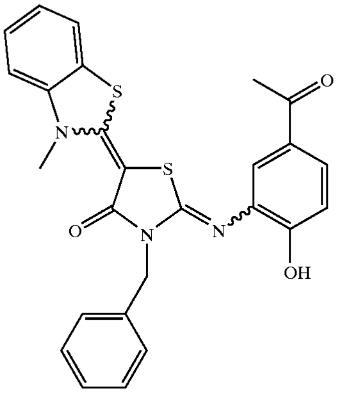

In a manner similar to Example 30, 4'-hydroxy-3'-nitroacetophenone was hydrogenated and then condensed with 3-benzyl-5-(3-methyl-3H-benzothiazol-2-ylidene)-2-methylthio-4-oxo-2-thiazolium p-toluenesulfonate to afford the title compound. MS(ESI): 488 ($MH^+$).

EXAMPLE 111

A. Preparation of 3-Benzyl-1-methyl-2-thioxoimidazolidin-4-one

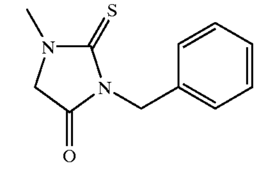

To a solution of sarcosine methyl ester hydrochloride (0.56 g, 4.0 mmol) and DBU (0.60 mL, 4.0 mmol) in anhydrous ethanol added benzyl isothiocyanate (0.53 mL, 4.0 mmol). The resulting solution was heated at reflux 16 h, cooled, concentrated and chromatographed (silica gel, DCM) to give the title compound (0.88 g, quant.). $^1$H-NMR ($CDCl_3$): δ 7.49–7.53 (2H, m), 7.28–7.35 (3H, m), 5.02 (2H, s), 4.03 (2H, s), 3.34 (3H, s).

B. Preparation of 3-Benzyl-1-methyl-5-(3-methyl-3H-benzothiazol-2-ylidene)-2-thioxoimidazolidin-4-one

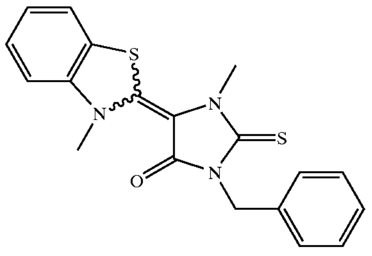

To a mixture of intermediate 3-benzyl-1-methyl-2-thioxoimidazolidin-4-one (0.33 g, 1.5 mmol) and 3-methyl-2-methylthiobenzothiazol-3-ium p-toluenesulfonate 0.66 g, 1.8 mmol) in anhydrous MeCN (10 mL) added dropwise TEA (0.28 mL, 2.0 mmol). After 2 h the resulting product mixture was concentrated and chromatographed (silica gel, DCM) to afford the title compound (0.47 g, 85%) as an orange-yellow solid. $^1$H-NMR ($CDCl_3$): δ 7.54–7.61 (3H, m), 7.46 (1H, m), 7.21–7.33 (5H, m), 5.19 (2H; s), 3.86 (3H, s), 3.77 (3H, s).

C. Preparation of 2-(5-Acetyl-2-ethylaminophenylimino)-3-benzyl-1-methyl-5-(3-methyl-3H-benzothiazol-2-ylidene)imidazolidin-4-one

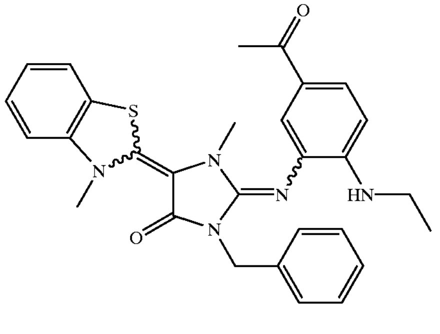

In a manner similar to Example 1, intermediate 3-benzyl-1-methyl-5-(3-methyl-3H-benzothiazol-2-ylidene)-2-thioxoimidazolidin-4-one was alkylated with methyl p-toluenesulfonate and condensed with 3'-amino-4'-ethylaminoacetophenone to yield the title compound. $^1$H-NMR ($CDCl_3$): δ 8.11 (1H, d), 7.84 (1H, dd), 7.51 (1H, dd), 7.31 (1H, m), 7.16 (1H, m), 6.95–7.12 (7H, m), 6.08 (1H, br t), 4.46 (2H, hs m), 3.99 (2H, m), 3.78 (3H, s), 3.50 (3H, s), 2.65 (3H, s), 1.06 (3H, t); MS(ESI): 512 ($MH^+$).

EXAMPLE 112

Preparation of 4-Ethylamino-3-[5-(3-methyl-3H-benzothiazol-2-ylidene)-3-(2-morpholin-4-ylethyl)-4-oxothiazolidin-2-ylideneamino]benzonitrile

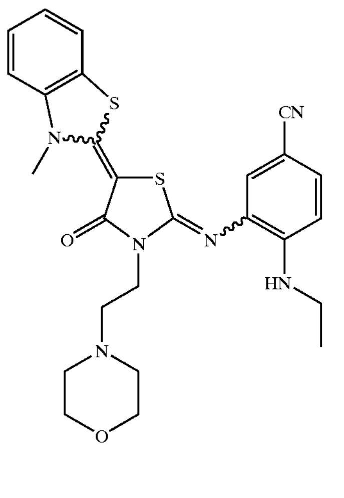

The title compound was prepared in a manner similar to that described in Example 83 by replacing 3-picolyl isothiocyanate hydrobromide with N-(2-ethylisothiocyanate) morpholine, synthesized from N-(2-aminoethyl)morpholine and thiophosgene. $^1$H-NMR ($CDCl_3$): δ 7.52 (1H, d), 7.32–7.37 (2H, m), 7.18–7.23 (2H, m), 7.09 (1H, d), 6.60 (1H, d), 4.75 (1H, br s), 4.16 (1H, t), 3.81 (3H, s), 3.71 (4H, br s), 3.23 (2H, q), 2.76 (2H, br s), 2.60 (4H, br s), 1.29 (3H, t); MS(ESI): 521 ($MH^+$).

EXAMPLE 113

Preparation of 4-Ethylamino-3-[3-(4-methoxybenzyl)-5-(3-methyl-3H-benzothiazol-2-ylidene)-4-oxothiazolidin-2-ylideneamino] benzonitrile

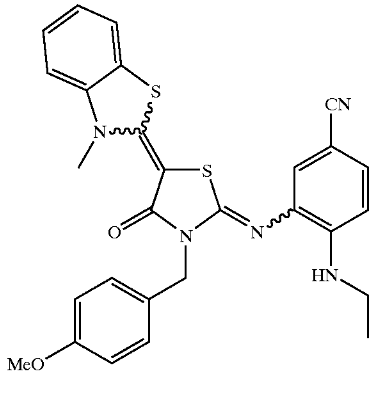

The title compound was prepared in a manner similar to that described in Example 83 by replacing 3-picolyl isothiocyanate hydrobromide with 4-methoxybenzylisothiocyanate. MS(ESI): 528 ($MH^+$).

EXAMPLE 114

Preparation of 4-Ethylamino-3-[3-(3-methoxybenzyl)-5-(3-methyl-3H-benzothiazol-2-ylidene)-4-oxothiazolidin-2-ylideneamino] benzonitrile

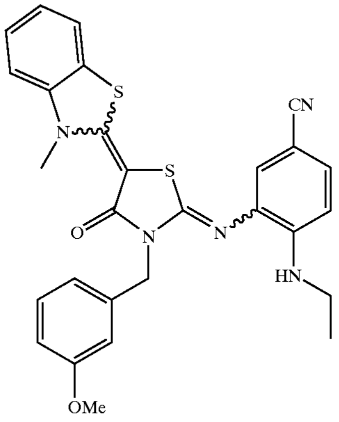

The title compound was prepared in a manner similar to that described in Example 83 by replacing 3-picolyl isothiocyanate hydrobromide with 3-methoxybenzylisothiocyanate. $^{1}$H-NMR ($CDCl_3$): δ 7.55 (1H, d), 7.37 (1H, t), 7.22–7.32 (4H, m), 7.12 (1H, d), 7.01 (2H, m), 6.86 (1H, d), 6.51 (1H, d), 5.16 (2H, s), 4.32 (1H, t), 3.84 (3H, s), 3.81 (3H, s), 3.03 (2H, q), 1.05 (3H, t); MS(ESI): 528 ($MH^+$). Recrystallization of the product from hot MeCN afforded crystals suitable for single-crystal X-ray diffraction. Structural analysis showed that the E-isomer had been obtained.

EXAMPLE 115

Preparation of 4-Ethylamino-3-[3-(2-methoxybenzyl)-5-(3-methyl-3H-benzothiazol-2-ylidene)-4-oxothiazolidin-2-ylideneamino] benzonitrile

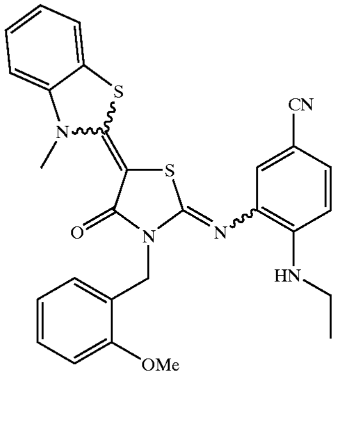

The title compound was prepared in a manner similar to that described in Example 83 by replacing 3-picolyl isothiocyanate hydrobromide with 2-methoxybenzylisothiocyanate. MS(ESI): 528 ($MH^+$).

EXAMPLE 116

A. Preparation of 2-(3-Aminophenylimino)-3-benzyl-5-(3-methyl-3H-benzothiazol-2-ylidene) thiazoiidine-4-one

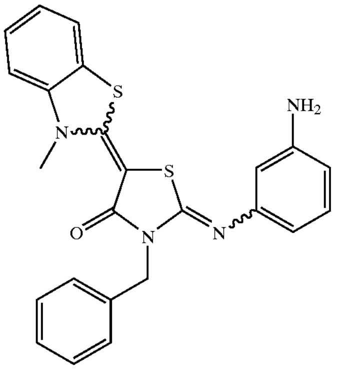

The title compound was prepared in a manner similar to that described in Example 1 by replacing aniline with 1,3-phenylenediamine. MS(ESI): 445 ($MH^+$).

B. Preparation of N-{3-[3-Benzyl-5-(3-methyl-3H-benzothiazol-2-ylidene)-4-oxothiazolidin-2-ylideneamino]phenyl}succinamic Acid

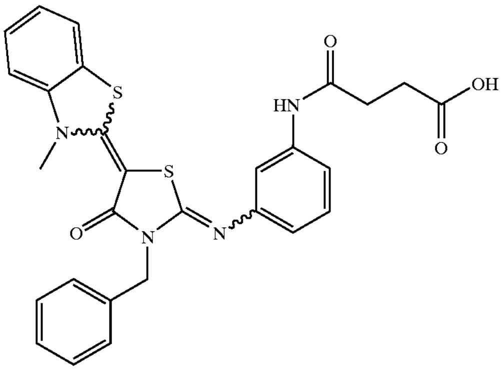

To a 25 mL flask was added 2-(3-aminophenylimino)-3-benzyl-5-(3-methyl-3H-benzothiazol-2-ylidene) thiazolidine-4-one (100 mg, 225 μmol), anhydrous DCM (5 mL) and $CHCl_3$ (3 mL). To the solution was added succinic anhydride (23 mg, 239 μmol). The reaction solution was allowed to stir at 50° C. for 1.5 h. The white precipitates were collected by filtration under reduced pressure, washed with DCM (10 mL) and hexanes (20 mL), and then dried under vacuum to give the title compound (75 mg, 61%). MS(ESI): 545 ($MH^+$).

EXAMPLE 117

Preparation of N-{3-[3-Benzyl-5-(3-methyl-3H-benzothiazol-2-ylidene)-4-oxothiazolidin-2-ylideneamino]phenyl}benzenesulfonamide

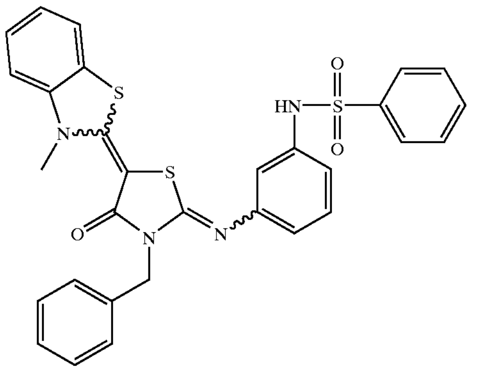

To a 25 mL flask was added 2-(3-aminophenylimino)-3-benzyl-5-(3-methyl-3H-benzothiazol-2-ylidene)thiazolidine-4-one (0.18 g, 0.40 mmol), anhydrous $CHCl_3$ (7 mL), benzenesulfonyl chloride (56 $\mu$L, 0.44 mmol), and TEA (0.10 mL, 0.80 mmol). The solution was stirred at 50° C. for 20 h. The yellow precipitates were collected by filtration under reduced pressure, washed with hexanes (30 mL), and dried under vacuum to give the title compound (49 mg, 21%) as a yellow solid. $^1$H-NMR (DMSO-$d_6$): δ 7.97 (1H, s), 7.76 (2H, d), 7.53 (2H, m), 7.45 (2H, t), 7.37 (2H, d), 7.09–7.31 (8H, m), 6.81 (1H, d), 6.74 (1H, s), 6.57 (1H, d), 4.99 (2H, s), 3.72 (3H, s); MS(ESI): 585 ($MH^+$).

EXAMPLE 118

Preparation of Thiophene-2-sulfonic Acid {3-[3-Benzyl-5-(3-methyl-3H-benzothiazol-2-ylidene)-4-oxothiazolidin-2-ylideneamino]phenyl}amide

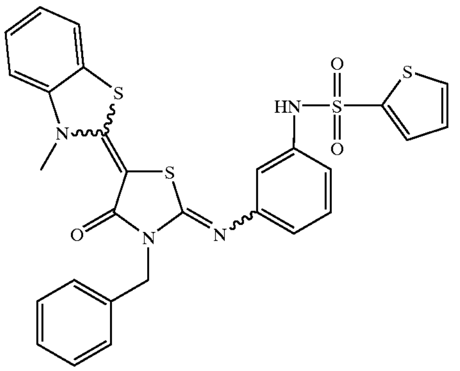

The title compound was prepared in a manner similar to that described in Example 117 by replacing benzenesulfonyl chloride with 2-(thiophene)sulfonyl chloride. MS(ESI): 591 ($MH^+$).

EXAMPLE 119

Preparation of N-{3-[3-Benzyl-5-(3-methyl-3H-benzothiazol-2-ylidene)-4-oxothiazolidin-2-ylideneamino]phenyl}-3-methoxybenzamide

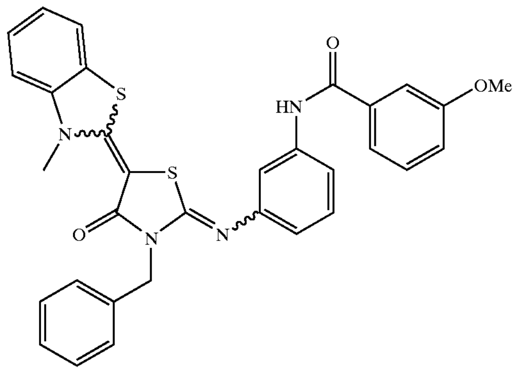

The title compound was prepared in a manner similar to that described in Example 117 by replacing benzenesulfonyl chloride with 3-methoxybenzoyl chloride. MS(ESI): 579 ($MH^+$).

EXAMPLE 120

Preparation of N-{3-[3-Benzyl-5-(3-methyl-3H-benzothiazol-2-ylidene)-4-oxothiazolidin-2-ylideneamino]phenyl}methanesulfonamide

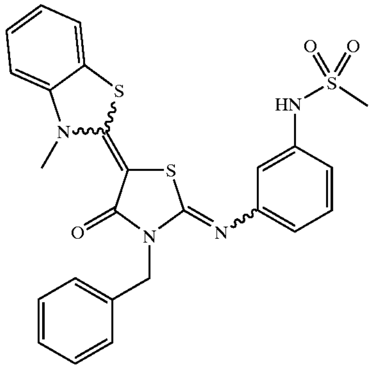

The title compound was prepared in a manner similar to that described in Example 117 by replacing benzenesulfonyl chloride with methanesulfonyl choride. $^1$H-NMR ($CDCl_3$): δ 8.88 (1H, s), 7.48 (2H, d), 7.41 (1H, d), 7.16–7.26 (5H, m), 7.09 (1H, t), 6.96 (2H, t), 6.89 (1H, m), 6.70 (1H, d), 5.05 (2H, s), 3.67 (3H, s), 2.92 (3H, s); MS(ESI): 532 ($MH^+$).

EXAMPLE 121

Preparation of {3-[3-Benzyl-5-(3-methyl-3H-benzothiazol-2-ylidene)-4-oxothiazolidin-2-ylideneamino]phenyl}carbamic Acid Ethyl Ester

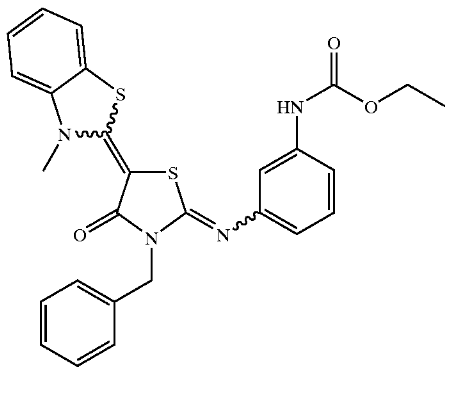

The title compound was prepared in a manner similar to the described in Example 117 by replacing benzenesulfonyl chloride with ethyl chloroformate. MS(ESI): 517 ($MH^+$).

EXAMPLE 122

Preparation of 3-{3-[3-Benzyl-5-(3-methyl-3H-benzothiazol-2-ylidene)-4-oxothiazolidin-2-ylideneamino]phenyl}-1,1-dimethylurea

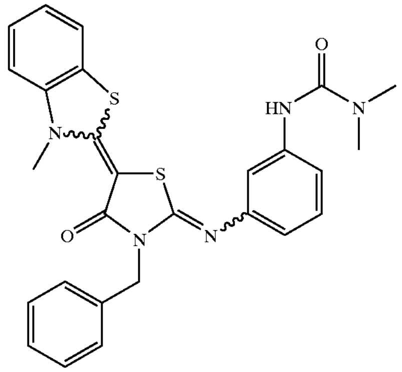

The title compound was prepared in a manner similar to the described in Example 117 by replacing benzenesulfonyl chloride with dimethylcarbamyl chloride. MS(ESI): 523 ($MH^+$).

EXAMPLE 123

A. Preparation of Morpholin4-ylacetyl Chloride Hydrochloride

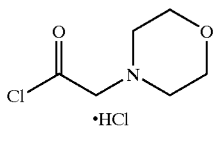

To a 100 mL flask was added morpholine (5.5 g, 63 mmol), benzene (20 mL), and ethyl chloroacetate (3.2 mL, 30 mmol). The reaction solution was allowed to stir 1 h at ambient temperature. The resulting white crystalline solids were collected by filtration under reduced pressure and then transferred to a 100 mL flask along with dioxane (20 mL) and 1 N NaOH (33 mL). The solution was allowed to stir at 80° C. for 16 h, cooled and then neutralized with 1N HCl. The aqueous solution was frozen and lyophilized to isolate the crude morpholinylacetic acid. The crude acid (2.6 g, 20 mmol) and thionyl chloride (15 mL) was added to a $N_2$-purged 100 mL flask. After stirring 3 h the reaction solution was filtered and concentrated under reduced pressure to provide the title compound (3.1 g, 78%) as a white powder. $^1$H-NMR (DMSO-$d_6$): δ 7.58 (1H, s), 3.48 (2H, s), 3.37 (4H, m), 2.76 (4H, m); $^{13}$C-NMR (DMSO-$d_6$): δ 166.0, 63.5, 55.5, 51.8.

B. Preparation of N-{3-[3-Benzyl-5-(3-methyl-3H-benzothiazol-2-ylidene)-4-oxothiazolidin-2-ylideneamino]phenyl}-2-morpholin-4-ylacetamide

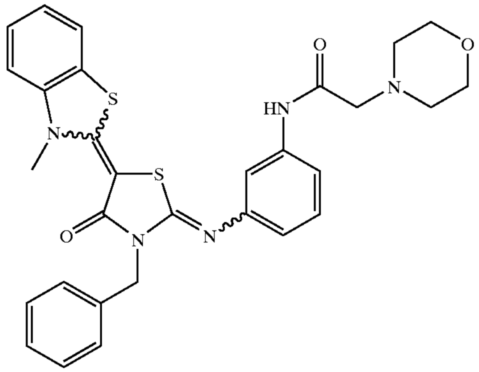

The title compound was prepared in a manner similar to that described in Example 117 by replacing benzenesulfonyl chloride with morpholin-4-ylacetyl chloride hydrochloride. $^1$H-NMR ($CDCl_3$): δ 8.98 (1H, s), 7.51 (2H, d), 7.41 (1H, d), 7.34 (1H, d), 7.19–7.27 (5H, m), 7.08 (2H, m), 6.91 (1H, d), 6.70 (1H, d), 5.06 (2H, s), 3.70 (4H, t), 3.63 (3H, s), 3.07 (2H, s), 2.55 (4H, t); MS(ESI): 572 ($MH^+$).

EXAMPLE 124

Preparation of N-{4-[3-Benzyl-5-(3-methyl-3H-benzothiazol-2-ylidene)-4-oxothiazolidin-2-ylideneamino]phenyl}-2-morpholin-4-ylacetamide

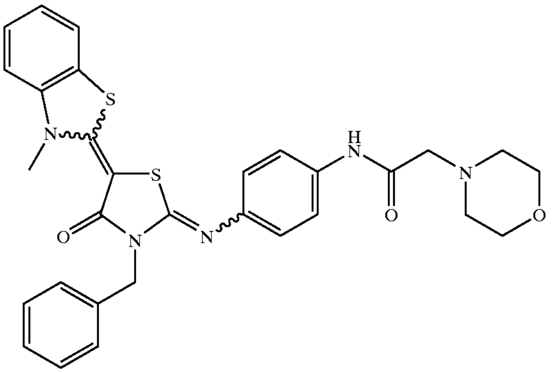

The title compound was prepared from the product of Example 4 in a manner similar to that described in Example 123. MS(ESI): 572 ($MH^+$).

EXAMPLE 125

Preparation of N-{3-[3-Benzyl-5-(3-methyl-3H-benzothiazol-2-ylidene)-4-oxothiazolidin-2-ylideneamino]phenyl}-2-dimethylaminoacetamide

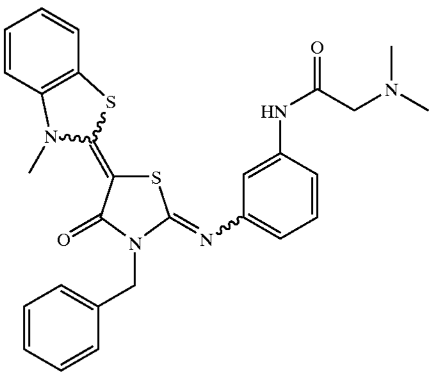

To a 25 mL flask was added N,N-dimethylglycine (500 mg, 4.85 mmol) and thionyl chloride (5 mL). The resulting solution was allowed to stir at ambient temperature under $N_2$ for 3 h. The excess thionyl chloride was removed in vacuo to provide N,N-dimethylaminoacetyl chloride hydrochloride as a white powder.

To a solution of 2-(3-aminophenylimino)-3-benzyl-5-(3-methyl-3H-benzothiazol-2-ylidene)thiazolidine-4-one (160 mg, 360 μmol) in chloroform (8 mL) was added N,N-dimethylaminoacetyl chloride hydrochloride (90 mg, 0.58 mmol) and TEA (150 μL, 1.1 mmol). The reaction solution was heated at reflux for 20 h, cooled, and concentrated in vacuo. The crude material was chromatographed (silica gel, 0–50% EtOAc/Hex) to give the title compound (34 mg, 18%) as a yellow solid. $^1$H-NMR ($CDCl_3$): δ 9.03 (1H, s), 7.50 (2H, d), 7.37 (2H, t), 7.17–7.26 (5H, m), 7.11 (1H, m), 7.05 (1H, t), 6.88 (1H, d), 6.68 (1H, d), 5.03 (2H), 3.60 (3H, s), 3.00 (2H, s), 2.28 (6H, s); MS(ESI): 530 ($MH^+$).

EXAMPLE 126

Preparation of {4-[3-Benzyl-5-(3-methyl-3H-benzothiazol-2-ylidene)-4-oxothiazolidin-2-ylideneamino]phenyl}carbamic Acid Ethyl Ester

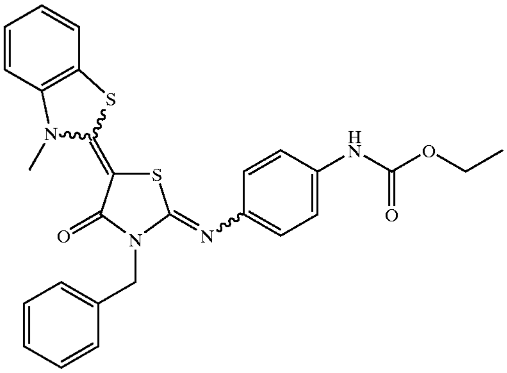

The title compound was prepared from the product of Example 4 in a manner similar to that described in Example 121. $^1$H-NMR ($CDCl_3$): δ 7.49 (2H, d), 7.37 (1H, d), 7.20–7.29 (5H, m), 7.07 (1H, t), 6.87–6.95 (3H, m), 6.54 (1H, br s), 5.07 (2H, s), 4.15 (2H, q), 3.61 (3H, s), 1.24 (3H, t); MS(ESI): 517 ($MH^+$).

EXAMPLE 127

Preparation of N-{4-[3-Benzyl-5-(3-methyl-3H-benzothiazol-2-ylidene)-4-oxothiazolidin-2-ylideneamino]phenyl}-2-dimethylaminoacetamide

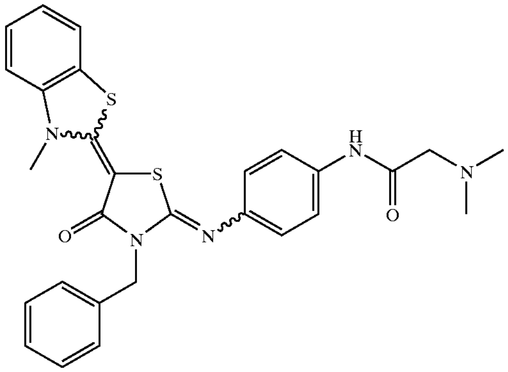

The title compound was prepared from the product of Example 4 in a manner similar to that described in Example 125. MS(ESI) 530 ($MH^+$).

EXAMPLE 128

Preparation of N-{4-[3-Benzyl-5-(3-methyl-3H-benzothiazol-2-ylidene)-4-oxothiazolidin-2-ylideneamino]phenyl}methanesulfonamide

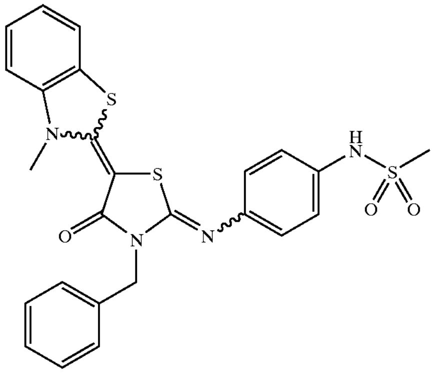

The title compound was prepared from the product of Example 4 in a manner similar to that described in Example 120. MS(ESI): 523 ($MH^+$).

EXAMPLE 129

Preparation of 4-Ethylamino-3-[3-(3-hydroxybenzyl)-5-(3-methyl-3H-benzothiazol-2-ylidene)-4-oxothiazolidin-2-ylideneamino] benzonitrile

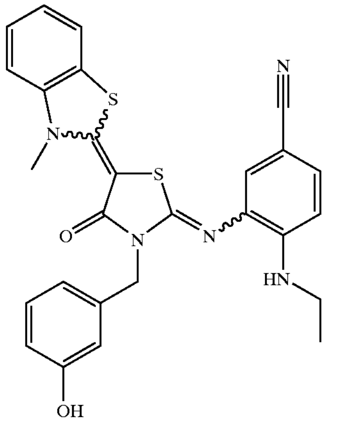

To a $N_2$-purged flask was added the product of Example 114 (60 mg, 0.11 mmol) and anhydrous DCM (5 mL). The solution was cooled to −78° C. prior to the addition of a 1.0M solution of $BBr_3$ in DCM (0.50 mL). The solution was allowed to warm to ambient temperature with stirring. After 7 h the solution was quenched by addition of MeOH (10 mL) and then concentrated under reduced pressure. The crude material was purified by reverse-phase HPLC (C18 column), eluting with 0.05% TFA in MeCN—$H_2O$ (1:9 to 9:1) to provide the title compound (15 mg, 26%). $^1$H-NMR ($CDCl_3$): δ 7.40 (1H, d), 7.35 (1H, t), 7.29 (1H, dd), 7.13–7.25 (3H, m), 6.95–7.01 (3H, m), 6.76 (1H, dd), 6.49 (1H, d), 5.08 (2H, s), 3.56 (3H, s), 3.02 (2H, q), 1.05 (3H, t); MS(ESI): 514 ($MH^+$).

EXAMPLE 130

Preparation of 4'-Ethylamino-3'-nitroacetanilide

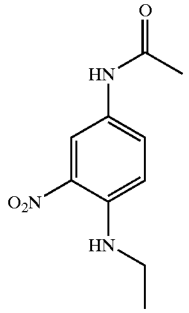

To a solution of 4-fluoro-3-nitroaniline (2.5 g, 16 mmol) in DCM (35 mL) was added acetic anhydride (2.3 mL, 24 mmol). The solution was stirred 15 min, and the resulting off-white precipitates were collected by filtration under reduced pressure. To a solution of the intermediate acetanilide in anhydrous THF (15 mL) was added a 2.0M solution of ethylamine in THF (8.0 mL). The solution was stirred at ambient temperature 14 h, and the resulting precipitates were collected by filtration under reduced pressure and dried under vacuum to provide the title compound (2.4 g, 68%). $^1$H-NMR ($CDCl_3$): δ 8.08 (1H, d), 7.90 (1H, br s), 7.78 (1H, dd), 7.32 (1H, br s), 6.82 (1H, d), 3.35 (2H, q), 2.16 (3H, s), 1.36 (3H, t).

B. Preparation of 4-Ethylamino-3-[3-(3-fluorobenzyl)-5-(3-methyl-3H-benzothiazol-2-ylidene)-4-oxothiazolidin-2-ylideneamino] benzonitrile

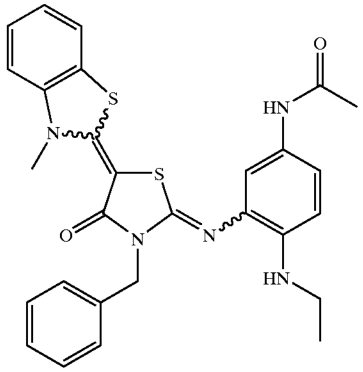

In a manner similar to Example 30, intermediate 4'-ethylamino-3'-nitroacetanilide was hydrogenated and then condensed with 3-benzyl-5-(3-methyl-3H-benzothiazol-2-ylidene)-2-methylthio-4-oxo-2-thiazolium p-toluenesulfonate to afford the title compound. $^1$H-NMR ($CDCl_3$): δ 9.58 (1H, s), 7.76 (1H, d), 7.18–7.46 (9H, m), 7.12 (1H, d), 6.47 (1H, d), 5.09 (2H, s), 3.82 (1H, br s), 3.79 (3H, s), 2.92 (2H, t), 1.98 (3H, s), 0.97 (3H, t); MS(ESI): 530 ($MH^+$).

EXAMPLE 131

Preparation of 4-Ethylamino-3-[3-(3-fluorobenzyl)-5-(3-methyl-3H-benzothiazol-2-ylidene)-4-oxothiazolidin-2-ylideneamino]benzonitrile

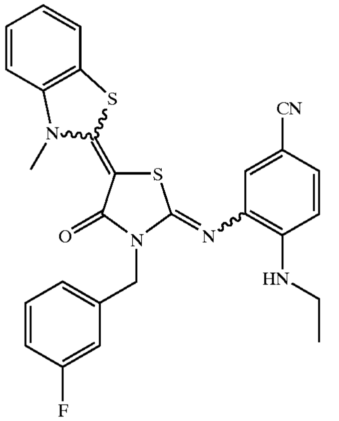

The title compound was synthesized in a manner similar or to that described in Example 83 by replacing 3-picolyl isothiocyanate hydrobromide with 3-fluorobenzylisothiocyanate. MS(ESI): 516 ($MH^+$).

EXAMPLE 132

Preparation of 4-Ethylamino-3-[5-(3-methyl-3H-benzothiazol-2-ylidene)-4-oxo-3-(3-trifluoromethylbenzyl)thiazolidin-2-ylideneamino]benzonitrile

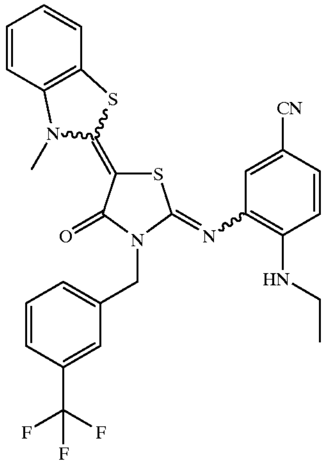

The title compound was synthesized in a manner similar to that described in Example 83 by replacing 3-picolyl isothiocyanate hydrobromide with 3-(trifluoromethyl)benzylisothiocyanate. MS(ESI): 566 ($MH^+$).

EXAMPLE 133

Preparation of 4-Ethylamino-3-[5-(3-methyl-3H-benzothiazol-2-ylidene)-4-oxo-3-(2-trifluoromethylbenzyl)thiazolidin-2-ylideneamino]benzonitrile

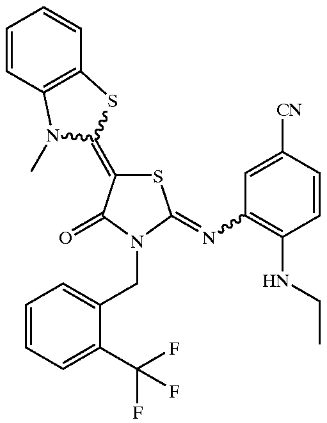

The title compound was synthesized in a manner similar to that described in Example 83 by replacing 3-picolyl isothiocyanate hydrobromide with 2-(trifluoromethyl)benzylisothiocyanate. MS(ESI): 566 ($MH^+$).

EXAMPLE 134

Preparation of 4-Ethylamino-3-[5-(3-methyl-3H-benzothiazol-2-ylidene)-3-(3-methylbenzyl)-4-oxothiazolidin-2-ylideneamino]benzonitrile

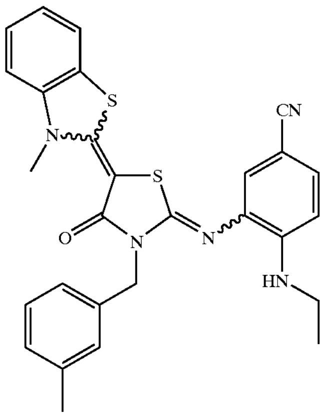

The title compound was prepared in a manner similar to that described in Example 83 by replacing 3-picolyl isothiocyanate hydrobromide with 3-methylbenzylisothiocyanate. MS(ESI): 512 ($MH^+$).

EXAMPLE 135

A. Preparation of 4'-Ethylamino-2-(morpholin-4-yl)-3'-nitroacetanilide

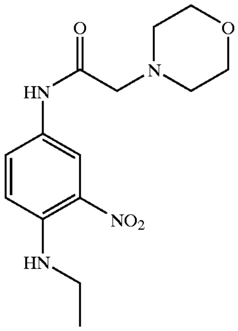

The title compound was synthesized in a manner similar to Example 130 by replacing acetic anhydride with morpholin-4-ylacetyl chloride hydrochloride. $^1H$-NMR ($CDCl_3$): δ 8.94 (1H, s), 8.11 (1H, d), 7.88 (1H, dd), 6.83 (1H, d), 3.78 (4H, t), 3.34 (2H, q), 3.13 (2H, s), 2.62 (4H, t), 1.31 (3H, t).

B. Preparation of N-{3-[3-Benzyl-5-(3-methyl-3H-benzothiazol-2-ylidene)-4-oxothiazolidin-2-ylideneamino]-4-ethylaminophenyl}-2-morpholin-4-ylacetamide

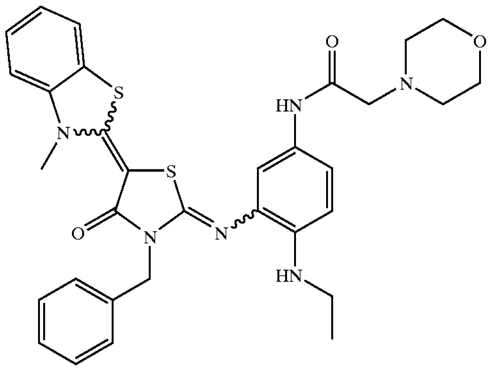

In a manner similar to Example 30, intermediate 4'-ethylamino-2-(morpholin-4-yl)-3'-nitroacetanilide was hydrogenated and then condensed with 3-benzyl-5-(3-methyl-3H-benzothiazol-2-ylidene)-2-methylthio-4-oxo-2-thiazolium p-toluenesulfonate to afford the title compound. $^1$H-NMR ($CDCl_3$): δ 8.87 (1H, s), 7.49–7.53 (3H, m), 7.28–7.37 (5H, m), 7.19 (1H, t), 7.12 (1H, dd), 7.04 (1H, d), 6.57 (1H, d), 5.19 (2H, s), 3.79 (8H, br s), 3.16 (2H, s), 3.01 (2H, q), 2.66 (4H, br s), 1.06 (3H, t); MS(ESI): 615 ($MH^+$).

EXAMPLE 136

Preparation of 3-[3-(3-Chlorobenzyl)-5-(3-methyl-3H-benzothiazol-2-ylidene)-4-oxothiazolidin-2-ylideneamino]-4-ethylaminobenzonitrile

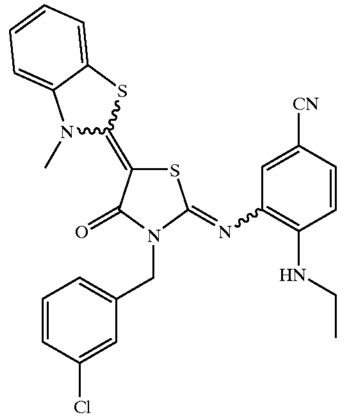

The title compound was synthesized in a manner similar to that described in Example 83 by replacing 3-picolyl isothiocyanate hydrobromide with 3-chlorobenzylisothiocyanate. MS(ESI): 533 ($MH^+$).

EXAMPLE 137

Preparation of 3-[3-(3-Bromobenzyl)-5-(3-methyl-3H-benzothiazol-2-ylidene)-4-oxothiazolidin-2-ylideneamino]-4-ethylaminobenzonitrile

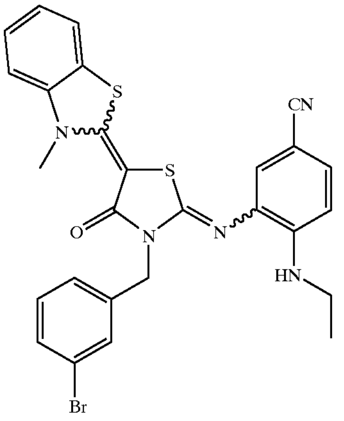

The title compound was synthesized in a manner similar to that described in Example 83 by replacing 3-picolyl isothiocyanate hydrobromide with 3-bromobenzylisothiocyanate. MS(ESI): 578 ($MH^+$).

EXAMPLE 138

A. Preparation of 4'-Ethylamino-3'-nitro-2,2,2-trifluoroacetanilide

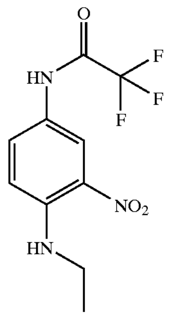

The title compound was prepared in a manner similar to that described in Example 130 by replacing acetic anhydride with trifluoroacetic anhydride (TFAA). TLC (1:1 Hex/EtOAc) $R_f$=0.5; MS(ESI): 278 ($MH^+$).

B. Preparation of N-{3-[3-Benzyl-5-(3-methyl-3H-benzothiazol-2-ylidene)-4-oxothiazolidin-2-ylideneamino]-4-ethylaminophenyl}-2,2,2-trifluoroacetamide

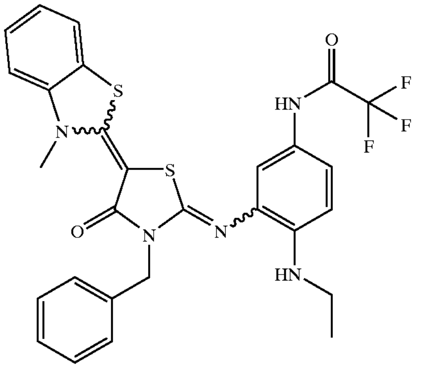

In a manner similar to Example 30, intermediate 4'-ethylamino-3'-nitro-2,2,2-trifluoroacetanilide was hydrogenated and then condensed with 3-benzyl-5-(3-methyl-3H-benzothiazol-2-ylidene)-2-methylthio-4-oxo-2-thiazolium p-toluenesulfonate to afford the title compound. MS(ESI): 584 ($MH^+$).

EXAMPLE 139

A. Preparation of 2-Dimethylamino-4'-ethylamino-3'-nitroacetanilide

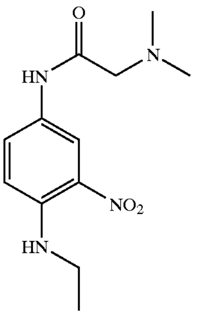

The title compound was prepared in a similar manner as that described in Example 130 by replacing acetic anhydride with N,N-dimethylaminoacetyl chloride hydrochloride. $^1$H-NMR ($CDCl_3$): δ 9.04 (1H, s), 8.16 (1H, d), 7.95 (1H, dd), 7.89 (1H, br s), 6.84 (1H, d), 3.35.(2H,.q), 3.09 (2H, s), 2.39 (6H, s), 1.36 (3H, t); MS(ESI): 267 ($MH^+$).

B. Preparation of N-{3-[3-Benzyl-5-(3-methyl-3H-benzothiazol-2-ylidene)-4-oxothiazolidin-2-ylideneamino]-4-ethylaminophenyl}-2-dimethylaminoacetamide

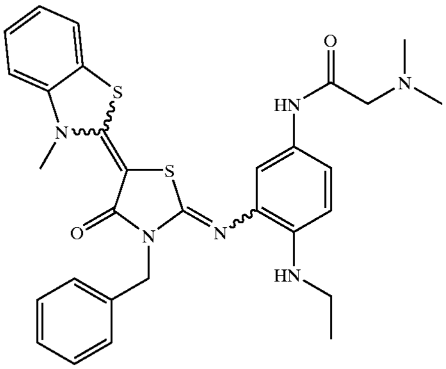

In a manner similar to Example 30, intermediate 2-dimethylamino-4'-ethylamino-3'-nitroacetanilide was hydrogenated and then condensed with 3-benzyl-5-(3-methyl-3H-benzothiazol-2-ylidene)-2-methylthio-4-oxo-2-thiazolium p-toluenesulfonate to afford the title compound. $^1$H-NMR ($CDCl_3$): δ 8.85 (1H, s), 7.43 (3H, t), 7.18–7.28 (5H, m), 7.10 (2H, t), 6.95 (1H, d), 6.48 (1H, d), 5.10 (2H, s), 3.71 (3H, s), 3.03 (2H, s), 2.93 (2H, q), 2.33 (6H, s), 0.97 (3H, t); MS(ESI): 584($MH^+$).

EXAMPLE 140

A. Preparation of 4-Ethylamino-3-nitroaniline

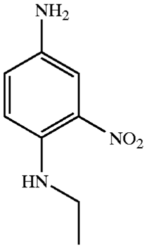

To a pressure tube was added 4-fluoro-3-nitroaniline (550 mg, 3.50 mmol) and a 2.0 M solution of ethylamine in THF (8 mL). The sealed tube was heated at 120° C. for 24 h. The reaction solution was cooled, diluted with EtOAc (30 mL), washed with satd $NaHCO_3$ (2×25 mL), dried over $Na_2SO_4$, and concentrated under reduced pressure to provide the title compound (625 mg, 98%) as a purple solid. $^1$H-NMR ($CDCl_3$): δ 7.72 (1H, br s), 7.49 (1H, d), 6.96 (1H, dd), 6.74 (1H, d), 3.45 (2H, br s), 3.30 (2H, m), 1.33 (3H, t).

B. Preparation of 4-Methylpiperazine-1-carboxylic Acid (4-Ethylamino-3-nitro-phenyl)amide

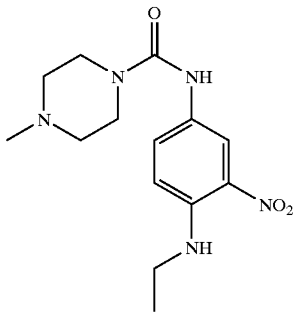

To a 100 mL flask was added 4-ethylamino-3-nitroaniline (625 mg, 3.45 mmol), chloroform (30 mL), and triphosgene (341 mg, 1.15 mmol). To the solution was added satd $NaHCO_3$ (30 mL), and the biphasic mixture was stirred for 30 min. The organic phase was partitioned, dried over $Na_2SO_4$, filtered, and concentrated under reduced pressure. The residue was dissolved in anhydrous THF (16 mL), and 4-methylpiperizine (291 mg, 2.90 mmol) was added. The solution was stirred at 40° C. for 1 h, cooled and concentrated under reduced pressure to provide the title compound (1.0 g, 94%) as a red solid. $^1$H-NMR ($CDCl_3$): δ 7.91 (1H, d), 7.84 (1H, t), 7.61 (1H, dd), 6.95 (1H, s), 6.73 (1H, d) 3.52 (4H, t), 3.31 (2H, m), 2.42 (4H, t), 2.32 (3H, s), 1.34 (3H, t); MS(ESI): 308 ($MH^+$).

C. Preparation of 4-Methylpiperazine-1-carboxylic Acid {3-[3-Benzyl-5-(3-methyl-3H-benzothiazol-2-ylidene)-4-oxothiazolidin-2-ylideneamino]-4-ethylaminophenyl}amide

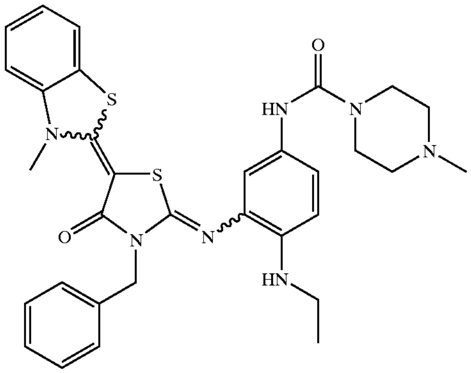

In a manner similar to Example 30, intermediate 4-methylpiperazine-1-carboxylic acid (4-ethylamino-3-nitro-phenyl)amide was hydrogenated and then condensed with 3-benzyl-5-(3-methyl-3H-benzothiazol-2-ylidene)-2-methylthio-4-oxo-2-thiazolium p-toluenesulfonate to afford the title compound. MS(ESI): 614 ($MH^+$).

EXAMPLE 141

Preparation of 2-(5-Amino-2-ethylaminophenylimino)-3-benzyl-5-(3-methyl-3H-benzothiazol-2-ylidene)thiazolidin-4-one

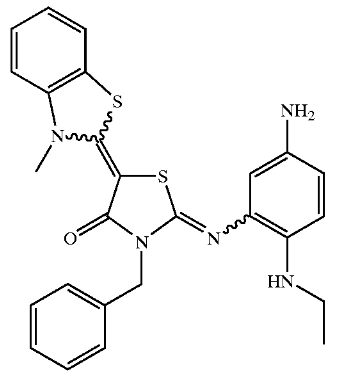

To the product of Example 138 (0.15 g, 0.26 mmol) in MeOH (30 mL) was added $H_2O$ (6 mL) and fine mesh $K_2CO_3$ (0.30 g, 1.5 mmol), and the solution was stirred 24 h at 55° C. The reaction mixture was cooled, diluted with EtOAc (30 mL), washed with $H_2O$ (20 mL), dried over $Na_2SO_4$, filtered, and concentrated under reduced pressure. The crude material was purified by reverse-phase HPLC (C18 column), eluting with 0.05% TFA in MeCN—$H_2O$ (1:9 to 9:1) to provide the title compound (2 mg). MS(ESI): 488 ($MH^+$).

EXAMPLE 142

A. Preparation of 4'-Ethylamino-2-(4-methylpiperazin-1-yl)-3'-nitroacetanilide

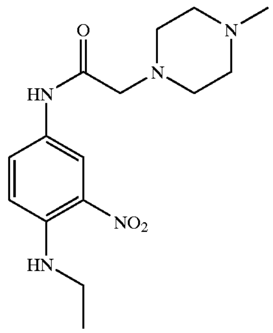

To a 100 mL flask was added 4-fluoro-3-nitroaniline (0.83 g, 5.3 mmol), DCM (30 mL), bromoacetyl chloride (0.53 mL, 6.4 mmol), and TEA (0.74 mL, 5.3 mmol). The reaction solution was stirred at room temperature 2 h and then quenched with satd $NaHCO_3$ (20 mL). The organic phase was partitioned, dried over $Na_2SO_4$, filtered under vacuum, and concentrated under reduced pressure. The resulting amide (1.31 g, 4.73 mmol) was added to a 100 mL flask along with MeCN (20 mL), 4-methylpiperizine (0.53 mL, 4.7 mmol), and $K_2CO_3$ (655 mg, 4.74 mmol). The reaction slurry was stirred 14 h at 35° C. prior to removal of excess $K_2CO_3$ by vacuum filtration. The filtrate was concentrated under reduced pressure, and the crude residue was chromatographed ($SiO_2$, hexane/EtOAc) to provide 400 mg of intermediate amide. In a manner similar to that described in Example 31, the intermediate amide was treated with ethylamine to afford the title compound. $^1$H-NMR ($CDCl_3$): δ 9.66 (1H, s), 8.44 (1H, m), 8.05 (1H, m), 7.17 (1H, t), 3.25 (2H, s), 3.19 (4H, m), 3.14 (2H, m), 2.88 (4H, m), 2.53 (3H, 2), 1.38 (3H, t); MS(ESI): 322 ($MH^+$).

B. Preparation of N-{3-[3-Benzyl-5-(3-methyl-3H-benzothiazol-2-ylidene)-4-oxothiazolidin-2-ylideneamino]-4-ethylaminophenyl}-2-(4-methylpiperazin-1-yl)acetamide

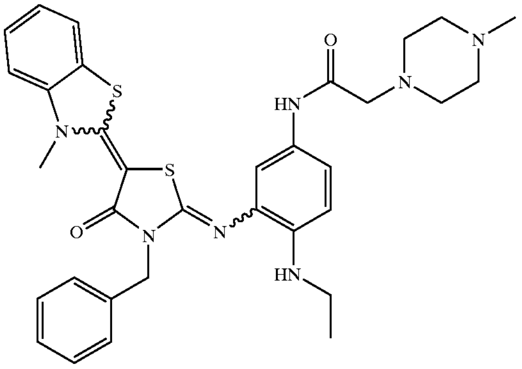

In a manner similar to Example 30, intermediate 4'-ethylamino-2-(4-methylpiperazin-1-yl)-3'-nitroacetanilide was hydrogenated and then condensed with 3-benzyl-5-(3-methyl-3H-benzothiazol-2-ylidene)-2-methylthio-4-oxo-2-thiazolium p-toluene sulfonate to afford the title compound. MS(ESI): 628 ($MH^+$).

EXAMPLE 143

Preparation of N-{3-[3-Benzyl-5-(5-methoxy-3-methyl-3H-benzothiazol-2-ylidene)-4-oxothiazolidin-2-ylideneamino]-4-ethylaminophenyl}-2-dimethylaminoacetamide

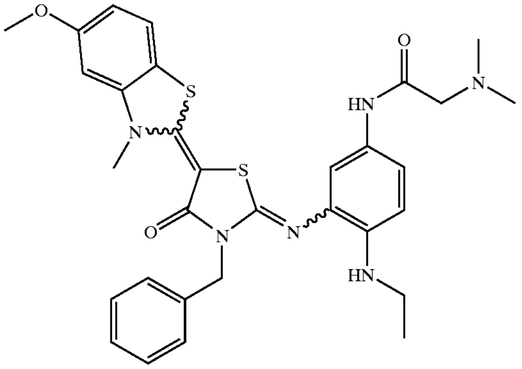

The title compound was prepared in a manner similar to Example 1 by replacing 2-(methylthio)benzothiazole with 2-mercapto-5-methoxybenzothiazole and by replacing aniline with 3'-amino-2-dimethylamino-4'-ethylaminoacetanilide. MS(ESI): 603 ($MH^+$).

EXAMPLE 144

Preparation of N-{3-[3-Benzyl-5-(5-hydroxy-3-methyl-3H-benzothiazol-2-ylidene)-4-oxothiazolidin-2-ylideneamino]-4-ethylaminophenyl}-2-dimethylaminoacetamide

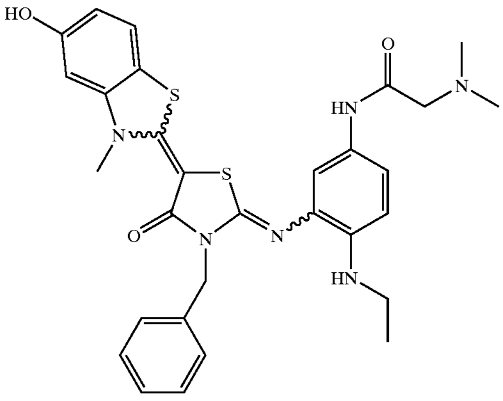

The title compound was prepared from the product of Example 143 in a manner similar to that described in Example 129. MS(ESI): 589 ($MH^+$).

EXAMPLE 145

A. Preparation of 5-(2-Chloroethoxy)-2-methylthiobenzothiazole

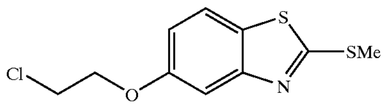

To a 250 mL flask was added 2-mercapto-5-methoxybenzothiazole (5.1 g, 26 mmol), MeCN (63 mL), methyl p-toluenesulfonate (4.8 g, 26 mmol) and TEA (4.4 mL, 31 mmol). After stirring 16 h at ambient temperature, the solution was concentrated under reduced pressure. The crude material was diluted with EtOAc (200 mL), washed with water (2x75 mL), dried over $Na_2SO_4$, filtered, and concentrated. The resulting viscous oil was dissolved in DCM (40 mL), and transferred to an argon-purged 250 mL flask. The solution was cooled to −78° C. prior to the addition of a 1.0 M $BBr_3$ solution in DCM (64 mL). The reaction suspension was allowed to warm to room temperature. After 16 h the reaction solution was cooled to −78° C. and quenched by addition of MeOH (100 mL). The resulting precipitates were isolated by vacuum filtration to yield 5-hydroxy-2-methylthio-benzothiazole (3.9 g, 76%) as a white solid.

To a solution of 5-hydroxy-2-methylthio-benzothiazole (2.1 g, 11 mmol) in anhydrous DMF (25 mL) was added bromo-2-chloroethane (4.4 mL, 53 mmol) and powdered $K_2CO_3$ (7.3 g, 53 mmol). The reaction slurry was heated at 70° C. for 13 h. The slurry was filtered under vacuum and the filtrate was concentrated under reduced pressure. The crude material was chromatographed ($SiO_2$, 0–20% EtOAc/Hex) to afford the title compound (1.2 g, 46%). $^1$H-NMR ($CDCl_3$): δ 7.62 (1H, d), 7.39 (1H, d), 6.97 (1H, dd), 4.29 (2H, t), 3.85 (2H, t), 2.79 (3H, s); MS(ESI): 259 ($MH^+$).

B. Preparation of 3-Benzyl-5-[5-(2-chloroethoxy)-3-methylbenzothiazol-2-ylidene]-2-methylthio-4-oxo-2-thiazolium p-Toluenesulfonate

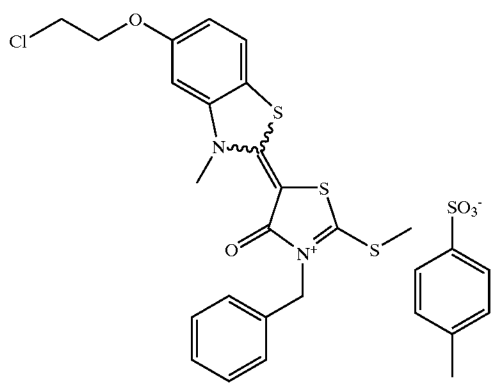

The title compound was prepared in a manner similar to that described in Example 1 by replacing 2-(methylthio) benzothiazole with 5-(2-chloroethoxy)-2-methylthio-benzothiazole. $^1$H-NMR (DMSO-d$_6$): δ 8.08 (1H, d), 7.65 (1H, d), 7.36–7.53 (7H, m), 7.22 (1H, dd), 7.09 (1H, d), 5.38 (2H, s), 4.45 (2H, t), 4.25 (3H, s), 4.03 (2H, t), 3.01 (3H, s), 2.28 (3H, s) MS(ESI): 463 ($M^+$–p-toluenesulfonate).

C. Preparation of N-(3-{3-Benzyl-5-[5-(2-chloroethoxy)-3-methyl-3H-benzothiazol-2-ylidene]-4-oxothiazolidin-2-ylideneamino}-4-ethylaminophenyl)-2-dimethylaminoacetamide

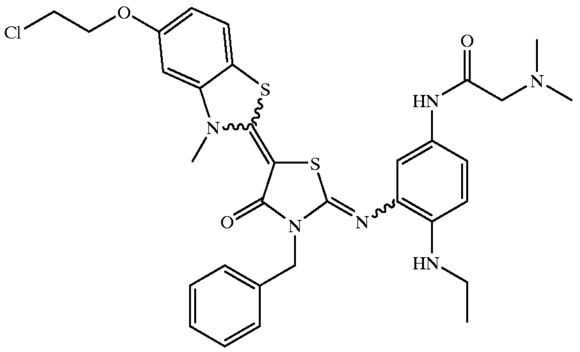

In a manner similar to Example 30, intermediate 2-dimethylamino-4'-ethylamino-3'-nitroacetanilide was hydrogenated and then condensed with 3-benzyl-5-[5-(2-chloroethoxy)-3-methylbenzothiazol-2-ylidene]-2-methylthio-4-oxo-2-thiazolium p-toluenesulfonate to afford the title compound. MS(ESI): 651 ($MH^+$).

EXAMPLE 146

A. Preparation of 3-Benzyl-5-[5-(2-methoxyethoxy)-3-methylbenzothiazol-2-ylidene]-2-methylthio-4-oxo-2-thiazolium p-Toluenesulfonate

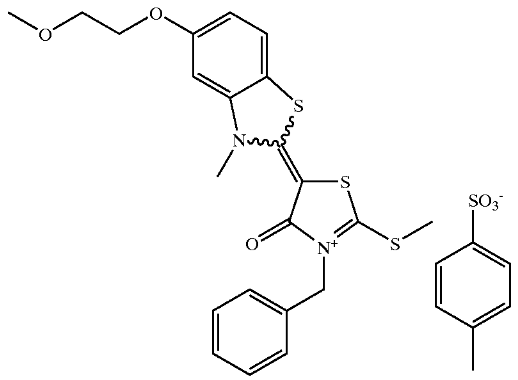

The title compound was synthesized in a manner similar to that described in Example 145 by replacing bromo-2-chloroethane with 2-chloroethyl methylether. MS(ESI): 459 ($M^+$–p-toluenesulfonate).

B. Preparation of N-(3-{3-Benzyl-5-[5-(2-methoxyethoxy)-3-methyl-3H-benzothiazol-2-ylidene]-4-oxothiazolidin-2-ylideneamino}-4-ethylaminophenyl)-2-dimethylaminoacetamide

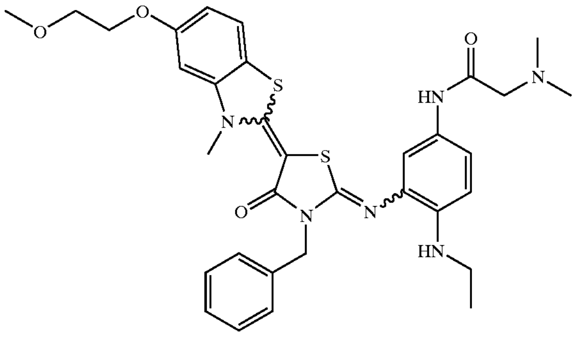

In a manner similar to Example 30, intermediate 2-dimethylamino-4'-ethylamino-3'-nitroacetanilide was hydrogenated and then condensed with 3-benzyl-5-[5-(2-methoxyethoxy)-3-methylbenzothiazol-2-ylidene]-2-methylthio-4-oxo-2-hiazolium p-toluenesulfonate to afford the title compound. $^1$H-NMR ($CDCl_3$): δ 9.08 (11H, s), 7.46 (2H, d), 7.27–7.35 (5H, m), 7.16 (1H, dd), 6.69 (1H, dd), 6.62 (1H, d), 6.51 (1H, d), 5.14 (2H, s), 4.13 (2H, t), 3.75 (2H, t), 3.71 (2H, s), 3.44 (3H, s), 3.19 (2H, s), 2.94 (2H, q), 2.46 (6H, s), 1.02 (3H, t); MS(ESI): 647 ($MH^+$).

EXAMPLE 147

A. Preparation of 4'-Ethylamino-2-methoxy-3'-nitroacetanilide

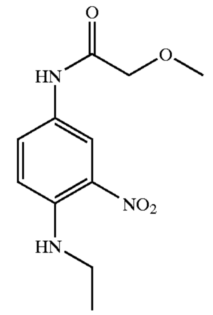

The title compound was prepared in a similar manner as that described in Example 130 by replacing acetic anhydride with methoxyacetyl chloride. $^1$H-NMR ($CDCl_3$): δ 8.20 (1H, d), 8.17 (1H, br s), 7.88 (1H, dd), 6.68 (1H, d), 4.03 (2H, s), 3.52 (3H, s), 3.37 (2H, q), 1.62 (2H, br s), 1.38 (3H, t).

B. Preparation of N-{3-[3-Benzyl-5-(3-methyl-3H-benzothiazol-2-ylidene)-4-oxothiazolidin-2-ylideneamino]-4-ethylaminophenyl}-2-methoxyacetamide

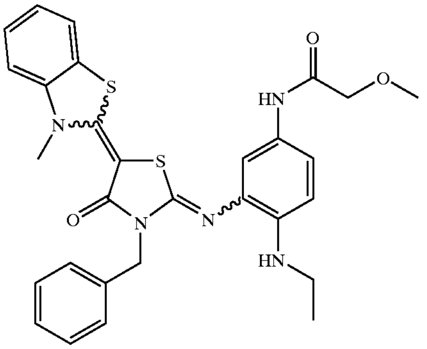

In a manner similar to Example 30, intermediate 4'-ethylamino-2-methoxy-3'-nitroacetanilide was hydrogenated and then condensed with 3-benzyl-5-(3-methyl-3H-benzothiazol-2-ylidene)-2-methylthio-4-oxo-2-thiazolium p-toluenesulfonate to afford the title compound. $^1$H-NMR ($CDCl_3$): δ 7.99 (1H, s), 7.39–7.44 (3H, m), 7.17–7.28 (5H, m), 7.05–7.11 (2H, m), 694 (1H, d), 6.50 (1H, d), 5.08 (2H, s), 3.92 (2H, s), 3.66 (3H, s), 3.41 (3H, s), 2.91 (2H, q), 0.96 (3H, t); MS(ESI): 560 ($MH^+$).

EXAMPLE 148

Preparation of N-(3-{3-Benzyl-5-[5-(2-dimethylaminoethoxy)-3-methyl-3H-benzothiazol-2-ylidene]-4-oxothiazolidin-2-ylideneamino}-4-ethylaminophenyl)-2-dimethylaminoacetamide

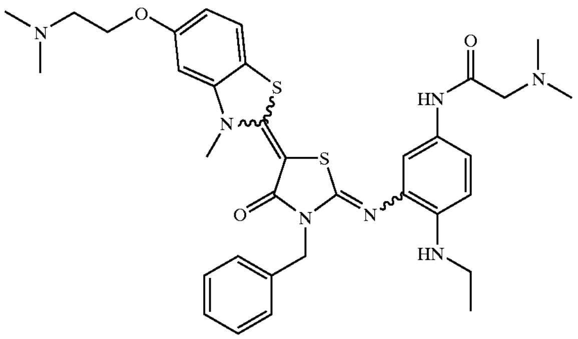

To a pressure tube was added the product of Example 145 (150 mg, 0.23 mmol), tetra-n-butylammonium iodide (85 mg, 0.23 mmol), and 2.0 M solution of dimethylamine in THF (6 mL). The tube was sealed and heated at 65° C. for 14 h. The solution was cooled and concentrated under reduced pressure, and the crude material was purified by chromatography (silica gel, 0–20% MeOH/DCM) to provide the title compound (30 mg, 20%). $^1$H-NMR ($CDCl_3$): δ 8.83 (1H, s), 7.45 (2H, d), 7.22–7.34 (5H, m), 7.11 (1H, dd), 6.71 (1H, dd), 6.63 (1H, d), 6.52 (1H, d), 5.14 (2H, s), 4.12 (2H, t), 3.70 (3H, s), 3.04 (2H, s), 2.97 (2H, q), 2.82 (2H, t), 2.40 (6H, s), 2.35 (6H, s), 1.02 (3H, t); MS(ESI): 660 ($MH^+$).

EXAMPLE 149

Preparation of N-(3-{3-Benzyl-5-[5-(2-hydroxyethoxy)-3-methyl-3H-benzothiazol-2-ylidene]-4-oxothiazolidin-2-ylideneamino}-4-ethylaminophenyl)-2-dimethylamino-acetamide

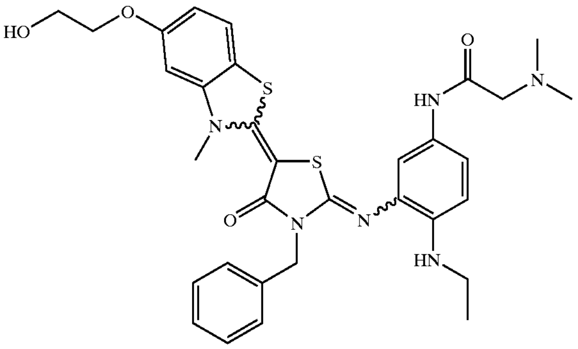

To an 8 mL vial was added the product of Example 145 (100 mg, 0.15 mmol), anhydrous DMF (5 mL), and tetra-n-butylammonium iodide (570 mg, 1.54 mmol). The solution was heated at 75° C. for 4 h prior to the addition of sodium acetate (250 mg, 3.08 mmol). The reaction solution was then heated 16 h at 75° C. To the solution was added MeOH (2 mL), 5M aqueous NaOH (1 mL) and $H_2O$ (1 mL). After heating at 50° C. for 5 h, the reaction mixture was cooled, neutralized with conc HCl and concentrated under reduced pressure. The residue was taken up into DCM (50 mL), and the organic phase was washed with water (2×25 mL), dried over $Na_2SO_4$, filtered, and concentrated under reduced pressure. The crude material was chromatographed ($SiO_2$, 0–10% MeOH/DCM) to provide the title compound (5 mg, 5%). $^1$H NMR (MeOH-$d_4$): δ 8.92 (1H, s), 7.11–7.26 (7H, m), 6.97 (1H, dd), 6.66 (1H, dd), 6.60 (1H, d), 6.44 (1H, d), 5.01 (2H, s), 3.96 (2H, t), 3.77 (2H, t), 3.62 (3H, s), 3.00 (2H, s), 2.82 (2H, q), 2.28 (6H, s), 0.89 (3H, t); MS(ESI) 633 ($MH^+$).

EXAMPLE 150

A. Preparation of 2-(5-Acetyl-2-ethylaminophenylimino)-3-furan-2-ylmethyl-thiazolidin-4-one

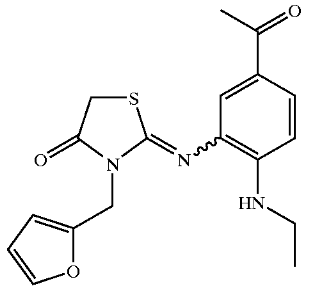

The title compound was prepared from furfuryl isothiocyanate and 3'-amino-4'-(ethylamino)acetophenone in a manner similar to that described in Example 52. $^1$H-NMR ($CDCl_3$): δ 7.73 (1H, dd), 7.61 (1H, s), 7.38 (1H, s), 6.59 (1H, d), 6.43 (1H, d), 6.36 (1H, m), 5.06 (2H, s), 3.88 (2H, s), 3.21 (2H, q), 2.50 (3H, s), 1.27 (3H, t); MS(ESI): 358 ($MH^+$).

B. Preparation of 2-(5-Acetyl-2-ethylaminophenylimino)-5-[5-(2-chloroethoxy)-3-methyl-3H-benzothiazol-2-ylidene]-3-furan-2-ylmethylthiazolidin-4-one

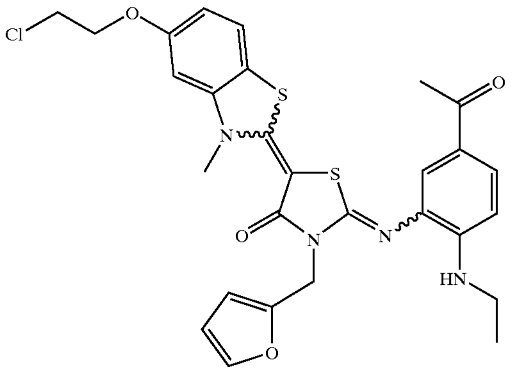

In a manner similar to Example 45, intermediate 5-(2-chloroethoxy)-2-(methylthio)benzothiazole was alkylated with menthyl p-toluenesulfonate and then condensed with the above 2-(5-acetyl-2-ethylaminophenylimino)-3-furan-2-ylmethyl-thiazolidin-4-one. MS(ESI): 583 ($MH^+$).

EXAMPLE 151

Preparation of 2-(5-Acetyl-2-ethylaminophenylimino)-3-furan-2-ylmethyl-5-(3-methyl-3H-benzothiazol-2-ylidene)thiazolidin-4-one

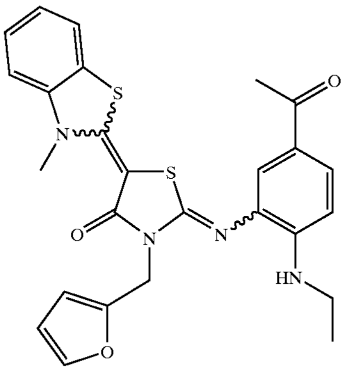

The title compound was synthesized in a manner similar to that described in Example 82 by replacing 3-picolyl isothiocyanate hydrobromide with 2-furfuryl isothiocyanate. $^1$H-NMR ($CDCl_3$): δ 7.70–7.74 (2H, m), 7.52 (1H, d), 7.33–7.39 (2H, m), 7.20 (1H, t), 7.06 (1H, d), 6.68 (1H, d), 6.50 (1H, d), 6.35 (1H, m), 5.24 (2H, s), 3.76 (3H, s), 3.23 (2H, q), 2.49 (3H, s), 1.28 (3H, t); MS(ESI): 505 ($MH^+$).

EXAMPLE 152

Preparation of N-(3-{3-Benzyl-5-[5-(2-chloroethoxy)-3-methyl-3H-benzothiazol-2-ylidene]-4-oxothiazolidin-2-ylideneamino}-4-ethylaminophenyl)-2-methoxyacetamide

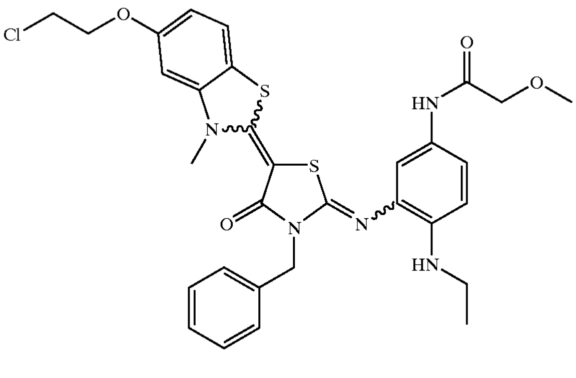

In a manner similar to Example 30, intermediate 4'-ethylamino-2-methoxy-3'-nitroacetanilide was hydrogenated and then condensed with 3-benzyl-5-[5-(2-chloroethoxy)-3-methyl benzothiazol-2-ylidene]-2-methylthio-4-oxo-2-thiazolium p-toluenesulfonate to afford the title compound. MS(ESI): 638 (M H+).

EXAMPLE 153

Preparation of N-{4-Ethylamino-3-[3-furan-2-ylmethyl-5-(3-methyl-3H-benzothiazol-2-ylidene)-4-oxothiazolidin-2-ylideneamino]phenyl}-2-methoxyacetamide

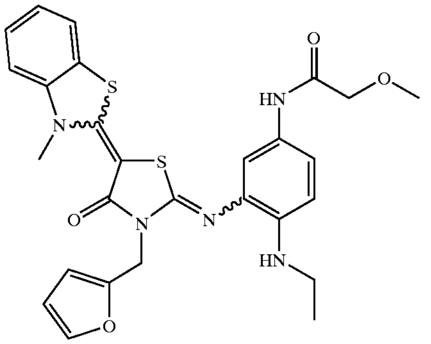

The title compound was prepared in a manner similar to that described in Example 84 by replacing 3-amino-4-(ethylamino)benzonitrile with 3'-amino-4'-ethylamino-2-methoxyacetanilide. $^1$H-NMR ($CDCl_3$): δ 8.07 (1H, s), 7.50 (1H, dd), 7.37 (1H, d), 7.29–7.34 (2H, m), 7.16 (2H, m), 7.02 (1H, d), 6.66 (1H, br s), 6.45 (1H, d), 6.32 (1H, m), 5.15 (2H, s), 3.99 (2H, s), 3.75 (3H, s), 3.51 (3H, s), 3.13 (2H, q), 1.23 (3H, t); MS(ESI): 550 (MH$^+$).

EXAMPLE 154

Preparation of N-(3-{3-Benzyl-5-[5-(2-dimethylaminoethoxy)-3-methyl-3H-benzothiazol-2-ylidene]-4-oxothiazolidin-2-ylideneamino}-4-ethylaminophenyl)-2-methoxyacetamide

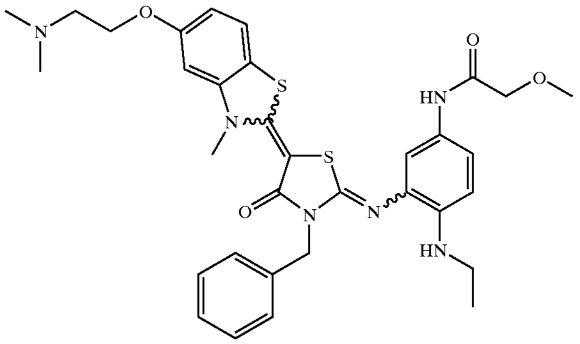

The title compound was prepared from the product of Example 152 in a manner similar to that described in Example 148. $^1$H-NMR ($CDCl_3$): δ 8.03 (1H, s), 7.48 (2H, d), 7.24–7.37 (5H, m), 7.14 (1H, dd), 6.74 (1H, dd), 6.65 (1H, d), 6.53 (1H, d), 5.16 (2H, s), 4.13 (2H, t), 4.00 (2H, s), 3.72 (3H, s), 3.48 (3H, s), 2.99 (2H, q), 2.81 (2H, t), 2.39 (6H, s), 1.03 (3H, t); MS(ESI): 647 (MH$^+$).

EXAMPLE 155

Preparation of 2-(5-Acetyl-2-ethylaminophenylimino)-5-[5-(2-dimethylamino-ethoxy)-3-methyl-3H-benzothiazol-2-ylidene]-3-furan-2-ylmethylthiazolidin-4-one

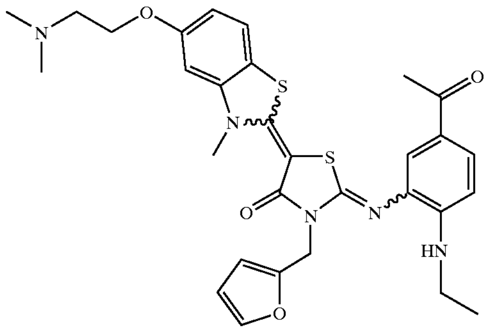

The title compound was prepared from the product of Example 150 in a manner similar to that described in Example 148. $^1$H-NMR ($CDCl_3$): δ 7.67–7.72 (2H, m), 7.37 (1H, s), 7.35 (1H, d), 6.76 (1H, dd), 6.64 (1H, d), 6.57 (1H, d), 6.45 (1H, d), 6.34 (1H, dd), 5.18 (2H, s), 4.89 (1H, t), 4.10 (2H, t), 3.71 (3H, s), 3.22 (2H, m), 2.75 (2H, m), 2.51 (3H, s), 2.35 (6H, s), 0.97 (3H, t); MS(ESI): 592 (MH$^+$).

EXAMPLE 156

A. Preparation of N-[4-Ethylamino-3-(3-furan-2-ylmethyl-4-oxothiazolidin-2-ylideneamino)phenyl]-2-methoxyacetamide

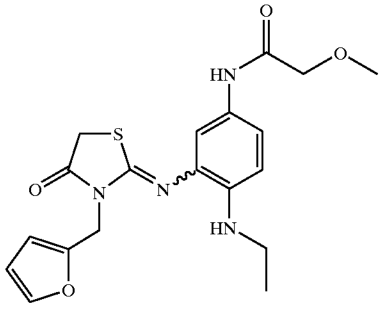

The title compound was synthesized from 2-furfuryl isothiocyanate and 3'-amino-4'-ethylamino-2-methoxyacetanilide in a manner similar to that described in Example 52. MS(ESI): 403 (MH$^+$).

B. Preparation of N-(3-{5-[5-(2-Dimethylaminoethoxy)-3-methyl-3H-benzothiazol-2-ylidene]-3-furan-2-ylmethyl-4-oxothiazolidin-2-ylideneamino}-4-ethylaminophenyl)-2-methoxyacetamide

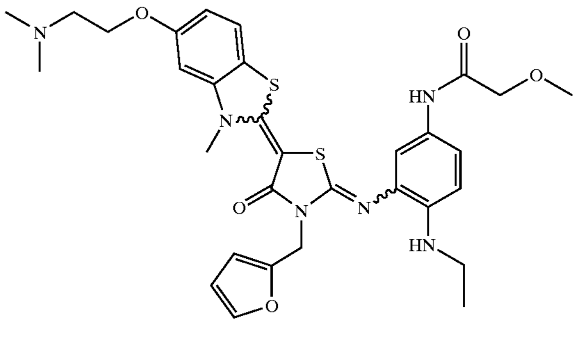

In a manner similar to Example 45, intermediate 5-(2-chloroethoxy)-2-(methylthio)benzothiazole was alkylated with methyl p-toluenesulfonate and then condensed with the above N-[4-ethylamino-3-(3-furan-2-ylmethyl-4-oxothiazolidin-2-ylideneamino)phenyl]-2-methoxyacetamide. The resulting product was transformed into the title compound following the procedure outlined in Example 148. MS(ESI): 583 ($MH^+$).

EXAMPLE 157

A. Preparation of 2-Acetoxy-4'-ethylamino-3'-nitroacetanilide

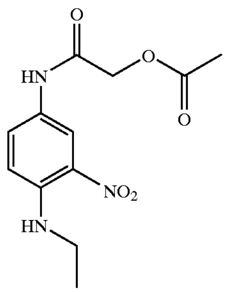

To a 100 mL flask was added 4-ethylamino-3-nitroaniline (1.1 g, 6.3 mmol) and anhydrous $CHCl_3$ (45 mL). The solution was cooled to 0° C. prior to the addition of bromoacetyl chloride (0.62 mL, 7.5 mmol) and TEA (1.7 mL, 13 mmol) under a nitrogen atmosphere. The reaction mixture was allowed to warm to ambient temperature over 1 h before the solvent was removed under reduced pressure. The crude material was chromatographed ($SiO_2$, 0–40% EtOAc/Hex) to provide the intermediate acetanilide (540 mg, 1.8 mmol) as a red solid. To a solution of the intermediate in anhydrous DMF (25 mL) was added sodium acetate (1.41 g, 17.2 mmol). The suspension was heated at 100° C. for 4 h. After cooling, the reaction mixture was diluted with EtOAc (25 mL), and the excess sodium acetate was removed by filtration under reduced pressure. The filtrate was concentrated under reduced pressure to provide the title compound (420 mg). $^1$H-NMR ($CDCl_3$): δ 8.13 (1H, br s), 8.11 (1H, d), 7.90 (1H, br s), 7.79 (1H, dd), 6.80 (1H, d), 4.68 (2H, s), 3.33 (2H, m), 2.21 (3H, s), 1.35 (3H, t); MS(ESI): 282 ($MH^+$).

B. Preparation of Acetic Acid {3-[3-Benzyl-5-(3-methyl-3H-benzothiazol-2-ylidene)-4-oxothiazolidin-2-ylideneamino]-4-ethylaminophenylcarbamoyl}methyl Ester

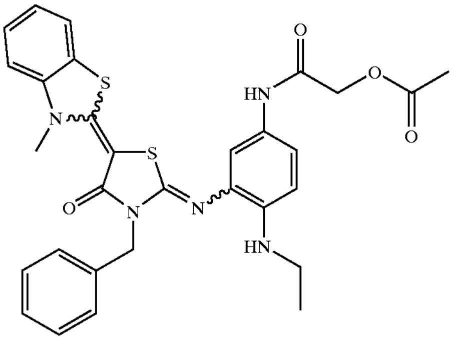

In a manner similar to Example 30, intermediate 2-acetoxy-4'-ethylamino-3'-nitroacetanilide was hydrogenated and then condensed with 3-benzyl-5-(3-methyl-3H-benzothiazol-2-ylidene)-2-methylthio-4-oxo-2-thiazolium p-toluenesulfonate to afford the title compound. $^1$H-NMR ($CDCl_3$): δ 7.73 (1H, br s), 7.44–7.51 (3H, m), 7.23–7.34 (5H, m), 7.16 (1H, t), 7.08 (1H, dd), 7.00 (1H, d), 6.56 (1H, d), 5.15 (2H, s), 4.67 (2H, s), 3.74 (3H, s), 2.98 (2H, q), 2.20 (3H, s), 1.00 (3H, t); MS(ESI): 588 ($MH^+$).

EXAMPLE 158

Preparation of N-{3-[3-Benzyl-5-(3-methyl-3H-benzothiazol-2-ylidene)-4-oxothiazolidin-2-ylideneamino]-4-ethylaminophenyl}-2-hydroxyacetamide

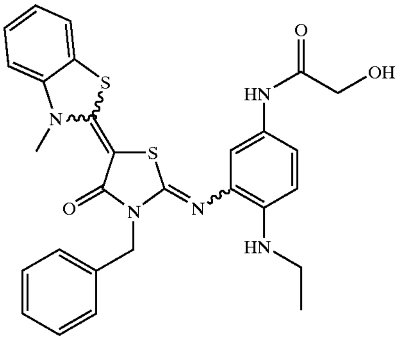

To a 50 mL flask was added the product of Example 157 (0.19 g, 0.32 mmol), $CHCl_3$ (5 mL), MeOH (10 mL), water (2 mL), and potassium carbonate (0.22 g, 1.6 mmol). After 4 h the reaction mixture was diluted with $CHCl_3$ (40 mL), and the organic phase was partitioned, washed with water (20 mL), dried over $Na_2SO_4$, filtered, and concentrated under reduced pressure. The crude sample was chromatographed (silica gel, 0–10% MeOH/DCM) to afford the title compound (37 mg, 21%). $^1$H-NMR ($CDCl_3$): δ 8.14 (1H, s), 7.42–7.48 (3H, m), 7.27–7.33 (5H, m), 7.15 (1H, t), 7.09 (1H, dd), 6.99 (1H, d), 6.56 (1H, d), 5.15 (2H, s), 4.14 (2H, s), 3.71 (3H, s), 2.95 (2H, q), 0.99 (3H, t); MS(ESI): 546 ($MH^+$).

EXAMPLE 159

Preparation of N-(3-{3-Benzyl-5-[5-(2-methoxyethoxy)-3-methyl-3H-benzothiazol-2-ylidene]-4-oxothiazolidin-2-ylideneamino}-4-ethylaminophenyl)-2-hydroxyacetamide

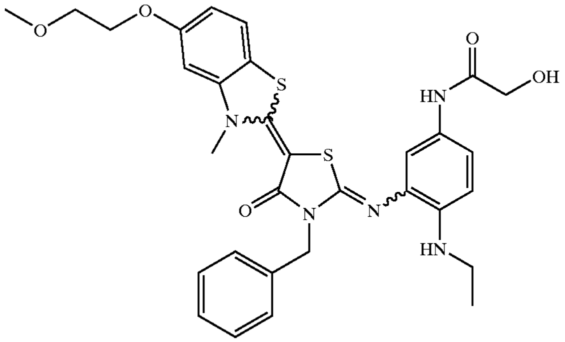

In a manner similar to Example 30, intermediate 2-acetoxy-4'-ethylamino-3'-nitroacetanilide was hydrogenated and then condensed with 3-benzyl-5-[5-(2-methoxyethoxy)-3-methylbenzothiazol-2-ylidene]-2-methylthio-4-oxo-2-thiazolium p-toluenesulfonate to afford an intermediate thiazolidinone, which was hydrolyzed in a manner similar to Example 158 to provide the title compound. MS(ESI): 620 ($MH^+$).

EXAMPLE 160

Preparation of 2-(3-Acetylphenylimino)-3-benzyl-5-[5-(2-methoxyethoxy)-3-methyl-3H-benzothiazol-2-ylidene]thiazolidin-4-one

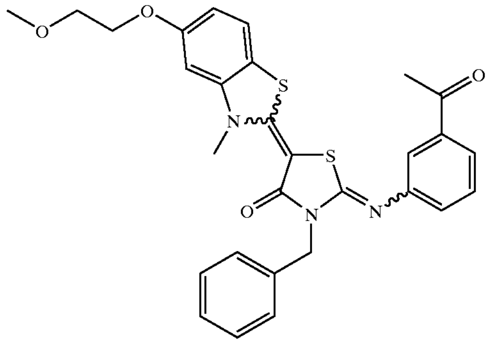

The title compound was synthesized in a manner similar to that described in Example 146 by condensing 3'-aminoacetophenone with 3-benzyl-5-[5-(2-methoxyethoxy)-3-methylbenzothiazol-2-ylidene]-2-methylthio-4-oxo-2-thiazolium p-toluenesulfonate. $^1$H-NMR ($CDCl_3$): δ 7.75 (1H, d), 7.60–7.64 (3H, m), 7.28–7.50 (6H, m), 7.24 (1H, d), 6.85 (1H, m), 5.21 (2H, s), 4.18 (2H, m), 3.80 (2H, m), 3.70 (3H, s), 3.48 (3H, s), 2.65 (3H, s); MS(ESI): 546 ($MH^+$).

EXAMPLE 161

Preparation of 2-(5-Acetyl-2-ethylaminophenylimino)-3-furan-2-ylmethyl-5-[5-(2-methoxyethoxy)-3-methyl-3H-benzothiazol-2-ylidene]thiazolidin-4-one

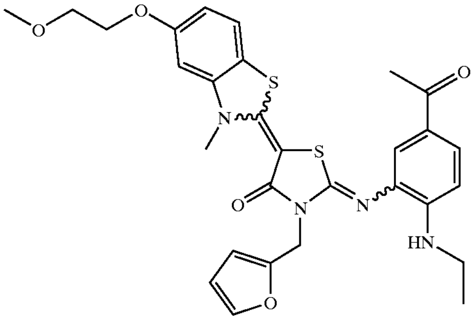

The title compound was prepared in a manner similar to that described in Example 150 by replacing 5-(2-chloroethoxy)-2-(methylthio)benzothiazole with 5-(2-methoxyethoxy)-2-(methylthio)benzothiazole. $^1$H-NMR ($CDCl_3$): δ 7.69 (1H, dd), 7.66 (1H, d), 7.34–7.37 (2H, m), 6.76 (1H, dd), 6.65 (1H, d), 6.59 (1H, d), 6.45 (1H, d), 6.33 (1H, m), 5.18 (2H, s), 4.14 (2H, m), 3.75 (2H, m), 3.70 (3H, s), 3.44 (3H, s), 3.20 (2H, q), 2.51 (3H, s), 1.26 (3H, t); MS(ESI): 579 ($MH^+$).

EXAMPLE 162

Preparation of N-(4-Ethylamino-3-{3-furan-2-ylmethyl-5-[5-(2-methoxyethoxy)-3-methyl-3H-benzothiazol-2-ylidene]-4-oxothiazolidin-2-ylideneamino}phenyl)-2-methoxyacetamide

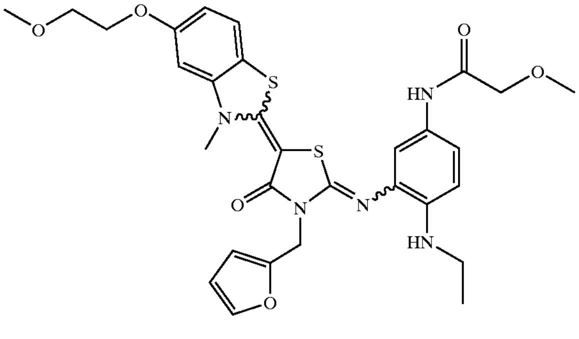

In a manner similar to Example 156, 5-(2-methoxyethoxy)-2-(methylthio)benzothiazole was alkylated with methyl p-toluenesulfonate and then condensed with intermediate N-[4-ethylamino-3-(3-furan-2-ylmethyl-4-oxothiazolidin-2-ylideneamino)phenyl]-2-methoxyacetamide. $^1$H-NMR ($CDCl_3$): δ 8.09 (1H, s), 7.28–7.38 (3H, m), 7.15 (1H, dd), 6.76 (1H, dd), 6.64 (1H, d), 6.44 (1H, d), 6.33 (1H, m), 5.16 (2H, s), 4.14 (2H, m), 4.01 (2H, s), 3.77 (2H, m), 3.72 (3H, s), 3.51 (3H, s), 3.44 (3H, s), 3.15 (2H, q), 1.23 (3H, t); MS(ESI): 624 ($MH^+$).

EXAMPLE 163

Preparation of 2-(5-Acetyl-2-ethylaminophenylimino)-3-benzyl-5-[5-(2-methoxyethoxy)-3-methyl-3H-benzothiazol-2-ylidene]thiazolidin-4-one

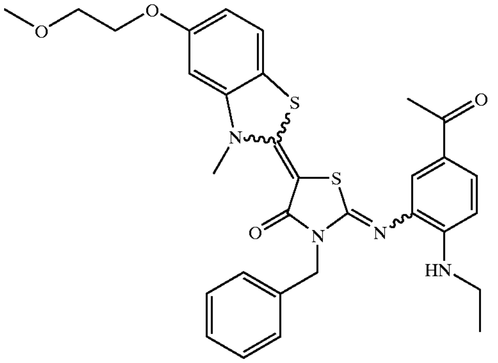

The title compound was synthesized in a manner similar to that described in Example 146 by condensing 3'-amino-4'-(ethylamino)acetophenone with 3-benzyl-5-[5-(2-methoxyethoxy)-3-methylbenzothiazol-2-ylidene]-2-methylthio-4-oxo-2-thiazolium p-toluenesulfonate. MS(ESI): 546 ($MH^+$).

EXAMPLE 164

Preparation of N-(3-{3-Benzyl-5-[5-(2-methoxyethoxy)-3-methyl-3H-benzothiazol-2-ylidene]-4-oxothiazolidin-2-ylideneamino}-4-ethylaminophenyl)-2-methoxyacetamide

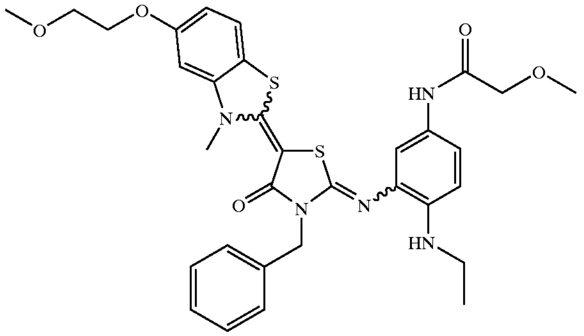

The title compound was synthesized in a manner similar to that described in Example 146 by replacing 2-dimethylamino-4'-ethylamino-3'-nitroacetanilide with 4'-ethylamino-2-methoxy-3'-nitroacetanilide. MS(ESI): 634 ($MH^+$).

EXAMPLE 165

A. Preparation of N-(3-{5-[5-(2-Azidoethoxy)-3-methyl-3H-benzothiazol-2-ylidene]-3-benzyl-4-oxothiazolidin-2-ylideneamino}-4-ethylaminophenyl)-2-dimethylaminoacetamide

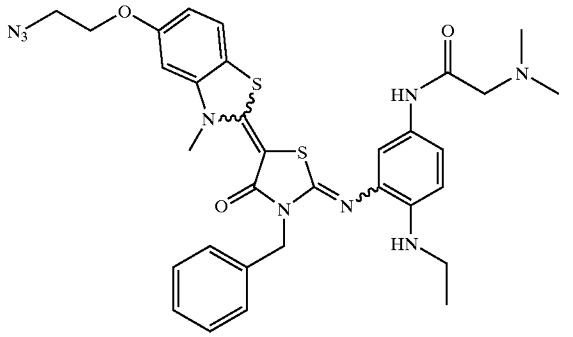

To a 50 mL flask was added the product of Example 145 (225 mg, 345 μmol), anhydrous DMF (8 mL), sodium azide (112 mg, 1.73 mmol), and sodium iodide (15 mg, 103 μmol). The reaction slurry was heated at 70° C. for 6 h under $N_2$. The reaction mixture was diluted with EtOAc (70 mL), washed with $H_2O$ (2×30 mL), dried over $Na_2SO_4$, filtered, and concentrated under reduced pressure to provide the title compound. MS(ESI): 658 ($MH^+$).

B. Preparation of N-(3-{5-[5-(2-Aminoethoxy)-3-methyl-3H-benzothiazol-2-ylidene]-3-benzyl-4-oxothiazolidin-2-ylideneamino}-4-ethylaminophenyl)-2-dimethylaminoacetamide

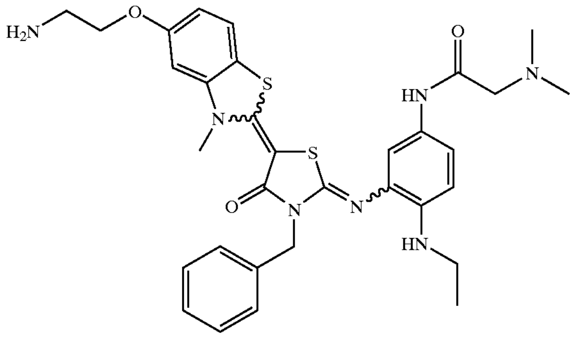

To a solution of the above N-(3-{5-[5-(2-azidoethoxy)-3-methyl-3H-benzothiazol-2-ylidene]-3-benzyl-4-oxothiazolidin-2-ylideneamino}-4-ethylamino-phenyl)-2-dimethylaminoacetamide (0.34 mmol) in THF (13 mL) was added triphenylphosphine (100 mg, 380 mmol) and $H_2O$ (20 mL). The solution was stirred 48 h at room temperature. The solvent was removed under reduced pressure, and the crude material was chromatographed (silica gel, 0–5% MeOH/DCM) to afford the title compound (157 mg, 72% overall).

$^1$H-NMR ($CDCl_3$): δ 8.85 (1H, s), 7.48 (2H, d), 7.27–7.37 (5H, m), 7.13 (1H, dd), 6.74 (1H, dd), 6.60 (1H, d), 6.55 (1H, d), 5.17 (2H, s), 4.03 (2H, t), 3.73 (3H, s), 3.11 (2H, t), 3.06 (2H, s), 3.00 (2H, q), 2.37 (6H, s), 1.39 (2H, t), 1.04 (3H, t); MS(ESI): 631 ($MH^+$).

EXAMPLE 166

A. Preparation of 2-Dimethylamino-3'-nitroacetanilide

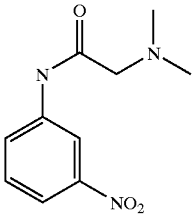

The title compound was prepared from 3-nitroaniline in a manner similar to that described in Example 139. $^{1}$H-NMR ($CDCl_3$): δ 9.04 (1H, br s), 8.39 (1H, t), 8.06 (1H, dd), 7.96 (1H, dd), 7.50 (1H, t), 3.13 (2H, s), 2.41 (6H, s).

B. Preparation of 2-Dimethylamino-N-[3-(3-furan-2-ylmethyl-4-oxothiazolidin-2-ylideneamino)phenyl] acetamide

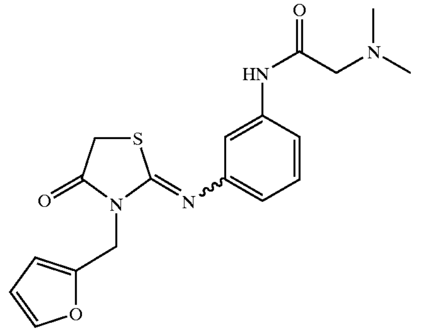

In a manner similar to that described in Example 52, the title compound was prepared from 2-furfuryl isothiocyanate and 3'-amino-2-(dimethylamino)acetanilide, derived from 2-dimethylamino-3'-nitroacetanilide. MS(ESI): 373 ($MH^+$).

C. Preparation of 2-Dimethylamino-N-{3-[3-furan-2-ylmethyl-5-(5-methoxy-3-methyl-3H-benzothiazol-2-ylidene)-4-oxothiazolidin-2-ylideneamino]-phenyl}acetamide

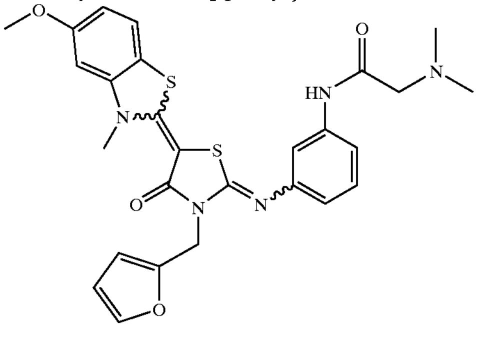

In a manner similar to Example 45, 2-mercapto-5-methoxybenzothiazole was alkylated with methyl p-toluenesulfonate and then condensed with 2-dimethylamino-N-[3-(3-furan-2-ylmethyl-4-oxothiazolidin-2-ylideneamino)-phenyl]acetamide. MS(ESI): 550 ($MH^+$).

EXAMPLE 167

Preparation of 3-(3'-Benzyl-3,4,5-trimethyl-4'-oxo-3',4'-dihydro-3H-[2,5']bithiazolyliden-2'-ylideneamino)-4-ethylaminobenzonitrile

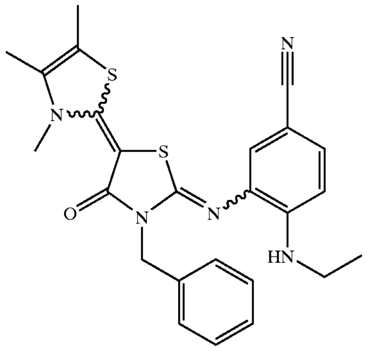

The title compound was prepared in a manner similar to that described in Example 52 by replacing 2-bromopropiophenone with 3-chloro-2-butanone.

MS(ESI): 476 ($MH^+$).

EXAMPLE 168

Preparation of 3-[3-Benzyl-5-(3-methyl-4,5,6,7-tetrahydro-3H-benzothiazol-2-ylidene)-4-oxothiazolidin-2-ylideneamino]-4-ethylaminobenzonitrile

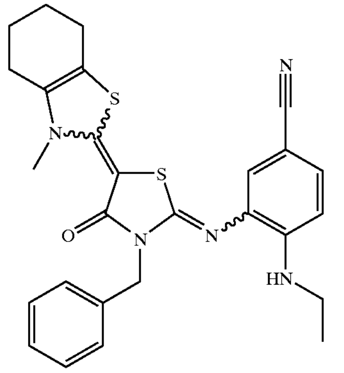

The title compound was prepared in a manner similar to that described in Example 52 by replacing 2-bromopropiophenone with 2-chlorocyclohexanone. MS(ESI): 502 ($MH^+$).

EXAMPLE 169

Preparation of 3-(3'-Benzyl-4-ethyl-3-methyl-4'-oxo-3',4'-dihydro-3H-[2,5']bithiazolyliden-2'-ylideneamino)-4-ethylaminobenzonitrile

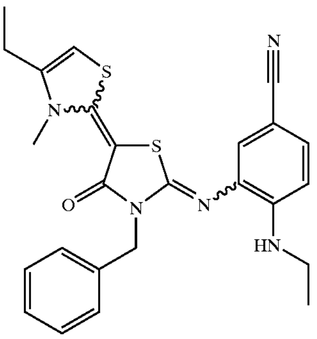

The title compound was prepared in a manner similar to that described in Example 52 by replacing 2-bromopropiophenone with 1-bromo-2-butanone.

MS(ESI): 476 ($MH^+$).

EXAMPLE 170

Preparation of 3-[3'-Benzyl-3-methyl-4-(4-nitrophenyl)-4'-oxo-3',4'-dihydro-3H-[2,5']bithiazolyliden-2'-ylideneamino]-4-ethylaminobenzonitrile

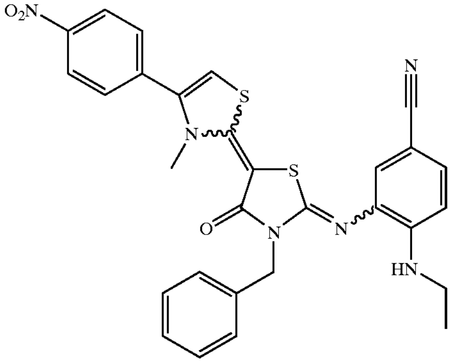

The title compound was prepared in a manner similar to that described in Example 52 by replacing 2-bromopropiophenone with 2-bromo-4'-nitroacetophenone. MS(ESI): 569 ($MH^+$).

EXAMPLE 171

Preparation of 3-[3'-Benzyl-4-(4-fluorophenyl)-3-methyl-4'-oxo-3',4'-dihydro-3H-[2,5']bithiazolyliden-2'-ylideneamino]-4-ethylaminobenzonitrile

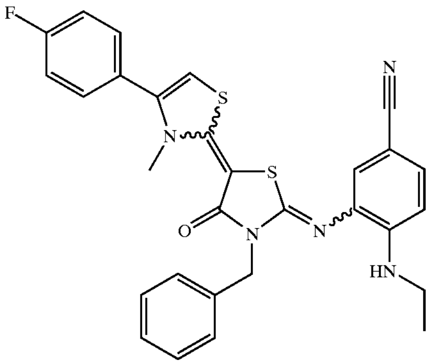

The title compound was prepared in a manner similar to that described in Example 52 by replacing 2-bromopropiophenone with 2-bromo-4'-fluoroacetophenone. MS(ESI): 542 ($MH^+$).

EXAMPLE 172

Preparation of 3-[3'-Benzyl-4-(4-chloro-phenyl)-3-methyl-4'-oxo-3',4'-dihydro-3H-[2,5']bithiazolyliden-2'-ylideneamino]-4-ethylaminobenzonitrile

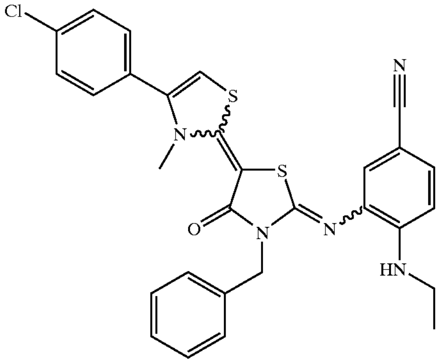

The title compound was prepared in a manner similar to that described in Example 52 by replacing 2-bromopropiophenone with 2-bromo-4'-chloroacetophenone. MS(ESI): 558 ($MH^+$).

EXAMPLE 173

Preparation of 3-(3'-Benzyl-3-methyl-4'-oxo-4-p-tolyl-3',4'-dihydro-3H-[2,5']bithiazolyliden-2'-ylideneamino)-4-ethylaminobenzonitrile

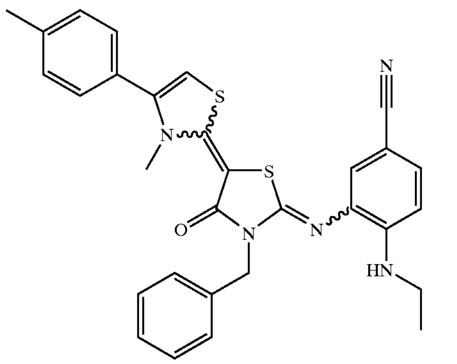

The title compound was prepared in a manner similar to that described in Example 52 by replacing 2-bromopropiophenone with 2-bromo-4'-methylacetophenone. MS(ESI): 538 ($MH^+$).

EXAMPLE 174

Preparation of 3-[3'-Benzyl-4-(4-methoxyphenyl)-3-methyl-4'-oxo-3',4'-dihydro-3H-[2,5']bithiazolyliden-2'-ylideneamino]-4-ethylaminobenzonitrile

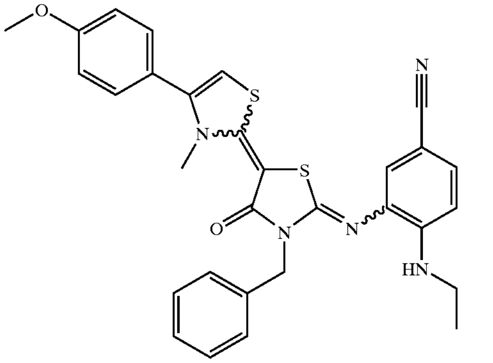

The title compound was prepared in a manner similar to that described in Example 52 by replacing 2-bromopropiophenone with 2-bromo-4'-methoxyacetophenone. MS(ESI): 554 ($MH^+$).

EXAMPLE 175

Preparation of 3-(5-Acetyl-3'-benzyl-3,4-dimethyl-4'-oxo-3',4'-dihydro-3H-[2,5']bithiazolyliden-2'-ylideneamino)-4-ethylaminobenzonitrile

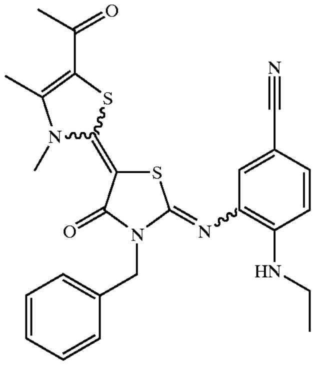

The title compound was prepared in a manner similar to that described in Example 52 by replacing 2-bromopropiophenone with 3-chloro-2,4-pentanedione. MS(ESI): 504 ($MH^+$).

EXAMPLE 176

Preparation of 3-[3-Benzyl-5-(3-methyl-3,4,5,6-tetrahydrocyclopentathiazol-2-ylidene)-4-oxothiazolidin-2-ylideneamino]-4-ethylaminobenzonitrile

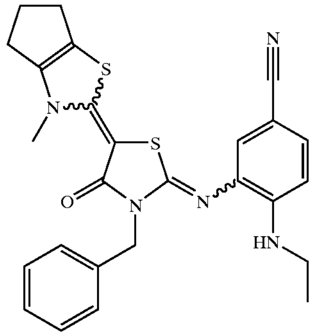

The title compound was prepared in a manner similar to that described in Example 52 by replacing 2-bromopropiophenone with 2-chlorocyclopentanone. MS(ESI): 488 ($MH^+$).

EXAMPLE 177

Preparation of 3-(3'-Benzyl-3-methyl-4'-oxo-4,5-diphenyl-3',4'-dihydro-3H-[2,5']bithiazolyliden-2'-ylideneamino)-4-ethylaminobenzonitrile

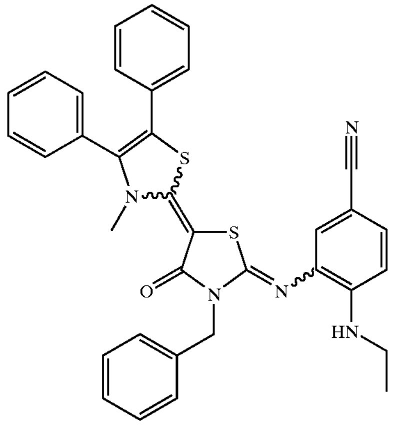

The title compound was prepared in a manner similar to that described in Example 52 by replacing 2-bromopropiophenone with 2-chloro-2-phenylacetophenone. MS(ESI): 600 ($MH^+$).

EXAMPLE 178

Preparation of 3-(3'-Benzyl-3,4-dimethyl-4'-oxo-3',4'-dihydro-3H-[2,5']bithiazolyliden-2'-ylideneamino)-4-ethylaminobenzonitrile

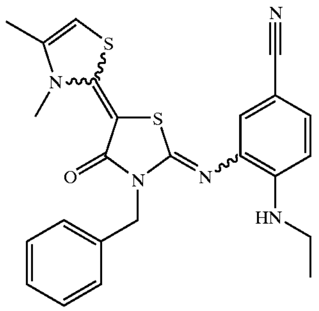

The title compound was prepared in a manner similar to that described in Example 52 by replacing 2-bromopropiophenone with chloroacetone.

MS(ESI): 462 ($MH^+$).

EXAMPLE 179

Preparation of 4-Ethylamino-3-[5-(3-methyl-4,5,6,7-tetrahydro-3H-benzothiazol-2-ylidene)-4-oxo-3-pyridin-3-ylmethylthiazolidin-2-ylideneamino] benzonitrile

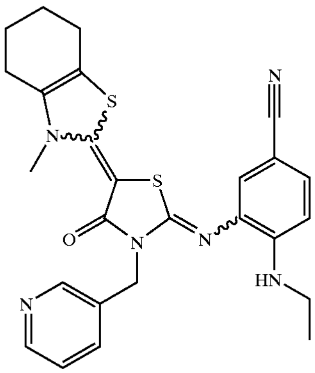

The title compound was prepared in a manner similar to Example 168 by condensing intermediate 3-methyl-2-methylthio-4,5,6,7-tetrahydrobenzothiazol-3-ium p-toluenesulfonate with 4-ethylamino-3-(4-oxo-3-pyridin-3-ylmethylthiazolidin-2-ylideneamino)benzonitrile. MS(ESI): 503 ($MH^+$).

EXAMPLE 180

A. Preparation of Methyl 4-[2-(5-Acetyl-2-ethylaminophenylimino)-4-oxothiazolidin-3-ylmethyl]benzoate

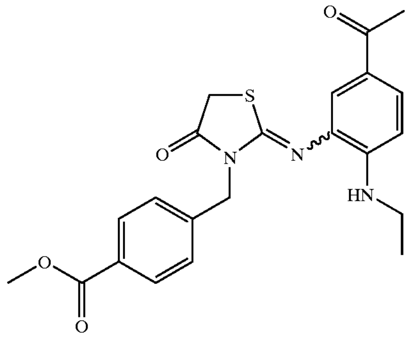

In a manner similar to Example 52, the title compound was prepared from 3'-amino-4'-ethylaminoacetophenone and methyl 4-(isothiocyantomethyl)benzoate—generated from methyl 4-(aminomethyl)benzoate hydrochloride and thiophosgene. $^1H$-NMR ($CDCl_3$): δ 8.04 (2H, d), 7.69 (1H, m), 7.58 (1H, s), 7.47 (2H, d), 6.52 (1H, d), 5.10 (2H, s), 3.96 (2H, s), 3.92 (3H, s), 3.05 (2H, q), 2.49 (3H, s), 1.03 (3H, t).

B. Preparation of Methyl 4-[2-(5-Acetyl-2-ethylaminophenylimino)-5-(3-methyl-3H-benzothiazol-2-ylidene)-4-oxothiazolidin-3-ylmethyl]benzoate

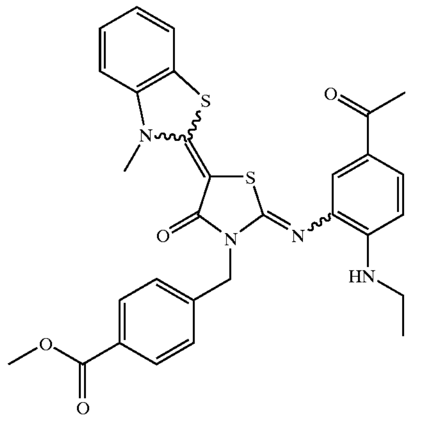

The title compound was prepared from intermediate 4-[2-(5-acetyl-2-ethylaminophenylimino)-4-oxothiazolidin-3-ylmethyl]benzoic acid methyl ester and 3-methyl-2-(methylthio)benzothiazol-3-ium p-toluenesulfonate in a manner similar to Example 45. $^1$H-NMR ($CDCl_3$): δ 8.03 (2H, d), 7.64–7.70 (2H, m), 7.49–7.55 (3H, m), 7.36 (1H, m), 7.20 (1H, m), 7.08 (1H, d), 6.51 (1H, d), 5.24 (2H, s), 4.15 (1H, br t), 3.91 (3H, s), 3.80 (3H, s), 3.04 (2H, m), 2.51 (3H, s), 1.01 (3H, s); MS(ESI): 573 ($MH^+$).

EXAMPLE 181

Preparation of Methyl 4-[2-(5-Acetyl-2-ethylamino-phenylimino)-5-(3-methyl-4,5,6,7-tetrahydro-3H-benzothiazol-2-ylidene)-4-oxothiazolidin-3-ylmethyl]benzoate

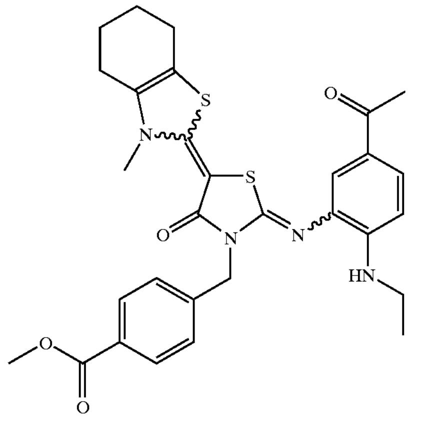

The title compound was prepared in a manner similar to Example 168 by condensing intermediate 3-methyl-2-methylthio-4,5,6,7-tetrahydrobenzothiazol-3-ium p-toluenesulfonate with 4-[2-(5-acetyl-2-ethylaminophenylimino)-4-oxothiazolidin-3-yl methyl] benzoic acid methyl ester.

MS(ESI): 577 ($MH^+$).

EXAMPLE 182

Preparation of 4-[2-(5-Acetyl-2-ethylaminophenylimino)-5-(3-methyl-3H-benzothiazol-2-ylidene)-4-oxothiazolidin-3-ylmethyl]benzoic Acid

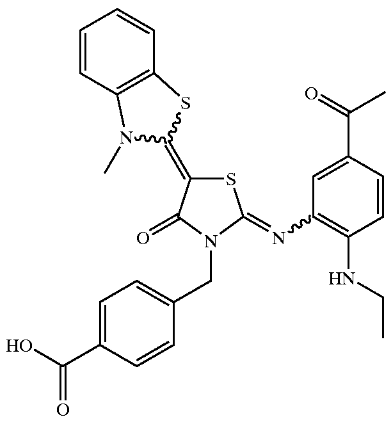

The product of Example 180 was saponified under conditions similar to that described in Example 29 to afford the title compound. MS(ESI): 559 ($MH^+$).

EXAMPLE 183

Preparation of 3-[3-Benzyl-5-(1-methyl-4,5,6,7-tetrahydro-1H-thiazolo[5,4-c]pyridin-2-ylidene)-4-oxothiazolidin-2-ylideneamino]-4-ethylaminobenzonitrile

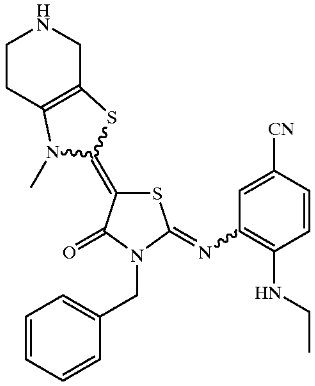

The title compound was prepared in a manner similar to that described in Example 52 by replacing 2-bromopropiophenone with 3-bromo-4-oxopiperidine-1-carboxylic acid 9H-fluoren-9-ylmethyl ester—synthesized according to a published procedure [*J. Med. Chem.* 1998, 41, 1409–1416].

$^1$H-NMR ($CDCl_3$): δ 7.39–7.43 (2H, m), 7.33 (2H, m), 7.24–7.29 (2H, m), 7.20 (1H, d), 6.47 (1H, d), 5.15 (2H, s), 4.28 (1H, br t), 3.81 (2H, br s), 3.63 (3H, s), 3.22 (2H, br s), 2.99 (2H, q), 2.49 (2H, br s), 1.01 (3H, t); MS(ESI): 503 ($MH^+$).

EXAMPLE 184

Preparation of Methyl 3-[2-(5-Acetyl-2-ethylaminophenylimino)-5-(3-methyl-3H-benzothiazol-2-ylidene)-4-oxothiazolidin-3-ylmethyl]benzoate

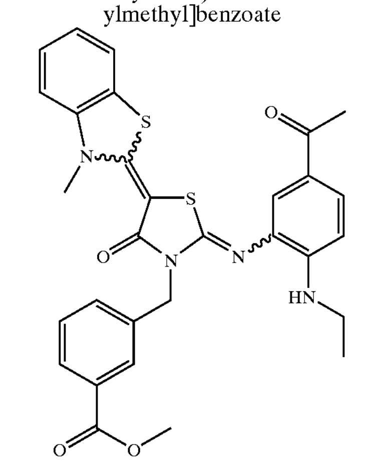

To a solution of methyl 3-(bromomethyl)benzoate (1.0 g, 4.4 mmol) in anhydrous DMF (10 mL) was added sodium azide (285 mg, 4.4 mmol). The resulting mixture was heated at 50° C. for 2 h, cooled, diluted with $CHCl_3$ (100 mL), washed with water (5×50 mL), dried ($MgSO_4$) and concentrated under reduced pressure to yield methyl 3-(azidomethyl)benzoate (0.84 g, quant.), which was used without purification. $^1$H-NMR ($CDCl_3$): δ 8.01 (2H, m), 7.44–7.54 (2H, m), 4.42 (2H, s), 3.94 (3H, s).

Methyl 3-(azidomethyl)benzoate was transformed into its amine (Staudinger conditions) and then converted into its isocyanate in a manner similar to Example 45. The title compound then was prepared in a manner similar to that described in Example 180 by replacing methyl 4-(isothiocyantomethyl)benzoate with methyl 3-(isothiocyantomethyl)benzoate.

$^1$H-NMR ($CDCl_3$): δ 8.13 (1H, br s), 7.98 (1H, d), 7.60–7.70 (3H, m), 7.53 (1H, d), 7.43 (1H, m), 7.36 (1H, m), 7.20 (1H, m), 7.07 (1H, d), 6.52 (1H, d), 5.24 (2H, s), 4.20 (1H, br t), 3.90 (3H, s), 3.79 (3H, s), 3.05 (2H, m), 2.51 (3H, s), 1.01 (3H, t); MS(ESI): 573 (MH$^+$).

EXAMPLE 185

Preparation of 3-[2-(5-Acetyl-2-ethylaminophenylimino)-5-(3-methyl-3H-benzothiazol-2-ylidene)-4-oxothiazolidin-3-ylmethyl]benzoic Acid

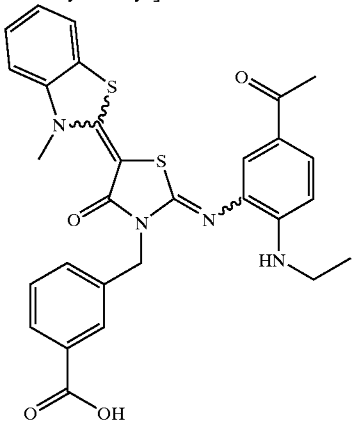

The product of Example 184 was saponified under conditions similar to that described in Example 29 to afford the title compound. MS(ESI): 559 (MH$^+$).

EXAMPLE 186

Preparation of 2-(5-Acetyl-2-ethylaminophenylimino)-3-benzyl-5-(3-methyl-4,5,6,7-tetrahydro-3H-benzothiazol-2-ylidene)thiazolidin-4-one

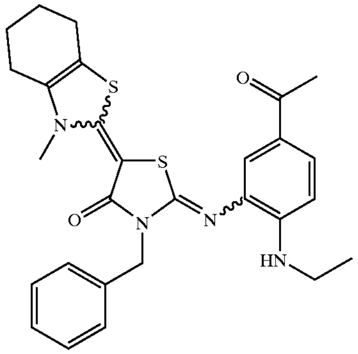

The title compound was prepared in a manner similar to Example 168 by condensing intermediate 3-methyl-2-methylthio-4,5,6,7-tetrahydrobenzothiazol-3-ium p-toluenesulfonate with 2-(5-acetyl-2-ethylaminophenylimino)-3-benzylthiazolidin-4-one. MS(ESI): 519 (MH$^+$).

EXAMPLE 187

Preparation of 3-(3'-Benzyl-4-biphenyl-4-yl-3-methyl-4'-oxo-3',4'-dihydro-3H-[2,5']bithiazolyliden-2'-ylideneamino)-4-ethylaminobenzonitrile

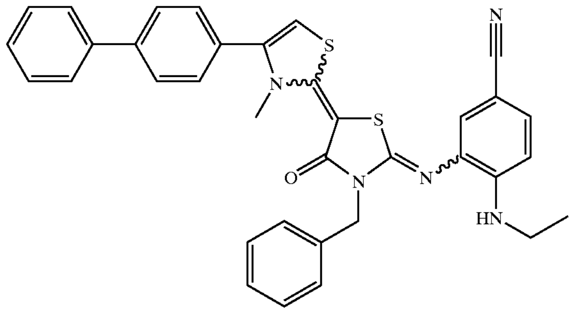

The title compound was prepared in a manner similar to that described in Example 52 by replacing 2-bromopropiophenone with 2-bromo-4'-phenylacetophenone. MS(ESI): 600 (MH$^+$).

EXAMPLE 188

Preparation of 3-(3'-Benzyl-3-methyl-4-naphthalen-2-yl-4'-oxo-3',4'-dihydro-3H-[2,5']bithiazolyliden-2'-ylideneamino)-4-ethylaminobenzonitrile

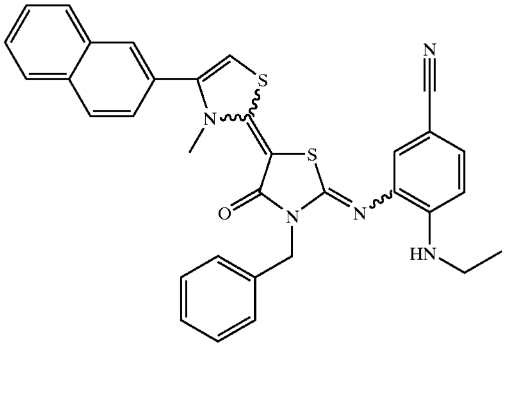

The title compound was prepared in a manner similar to that described in Example 52 by replacing 2-bromopropiophenone with 2-bromo-2'-acetonaphthone. MS(ESI): 574 ($MH^+$).

EXAMPLE 189

Preparation of 3-[3'-Benzyl-4-(4-bromophenyl)-3-methyl-4'-oxo-3',4'-dihydro-3H-[2,5']bithiazolyliden-2'-ylideneamino]-4-ethylaminobenzonitrile

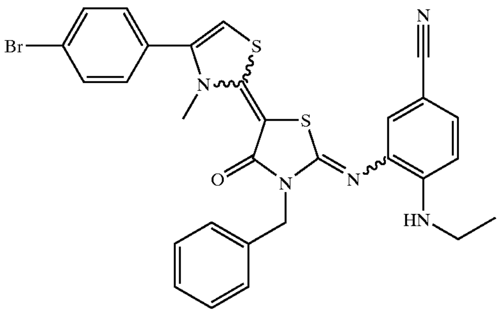

The title compound was prepared in a manner similar to that described in Example 52 by replacing 2-bromopropiophenone with 2,4'-dibromoacetophenone. MS(ESI): 602 ($MH^+$).

EXAMPLE 190

Preparation of 3-[3'-Benzyl-3-methyl-4-(2-nitrophenyl)-4'-oxo-3',4'-dihydro-3H-[2,5'] bithiazolyliden-2'-ylideneamino]-4-ethylaminobenzonitrile

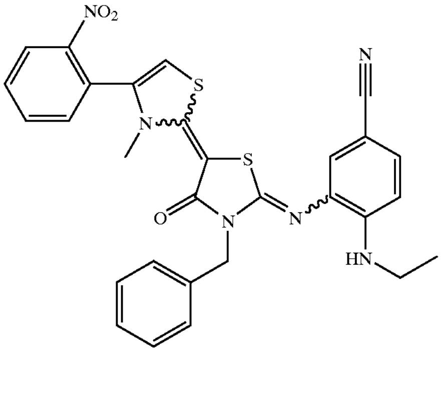

The title compound was prepared in a manner similar to that described in Example 52 by replacing 2-bromopropiophenone with 2-bromo-2'-nitroacetophenone. MS(ESI): 569 ($MH^+$).

EXAMPLE 191

Preparation of 2-(5-Acetyl-2-ethylaminophenylimino)-5-(3-methyl-4,5,6,7-tetrahydro-3H-benzothiazol-2-ylidene)-3-pyridin-3-ylmethylthiazolidin-4-one

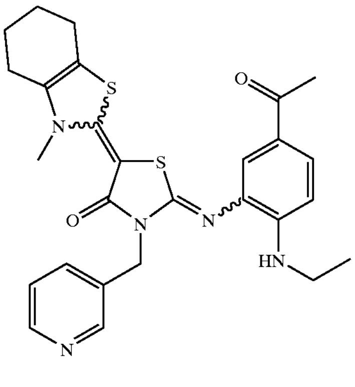

The title compound was prepared in a manner similar to Example 168 by condensing intermediate 3-methyl-2-methylthio-4,5,6,7-tetrahydrobenzothiazol-3-ium p-toluenesulfonate with 2-(5-acetyl-2-ethylaminophenylimino)-3-pyridin-3-ylmethyl-thiazolidin-4-one. MS(ESI): 520 ($MH^+$).

EXAMPLE 192

Preparation of 3-[3'-Benzyl-4-(2-methoxyphenyl)-3-methyl-4'-oxo-3',4'-dihydro-3H-[2,5']bithiazolyliden-2'-ylideneamino]-4-ethylaminobenzonitrile

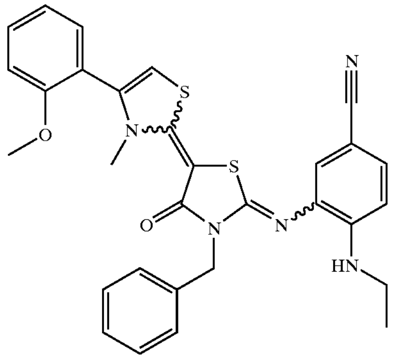

The title compound was prepared in a manner similar to that described in Example 52 by replacing 2-bromopropiophenone with 2-bromo-2'-methoxyacetophenone. MS(ESI): 554 ($MH^+$).

EXAMPLE 193

Preparation of 3-[3'-Benzyl-4-(3-fluorophenyl)-3-methyl-4'-oxo-3',4'-dihydro-3H-[2,5']bithiazolyliden-2'-ylideneamino]-4-ethylaminobenzonitrile

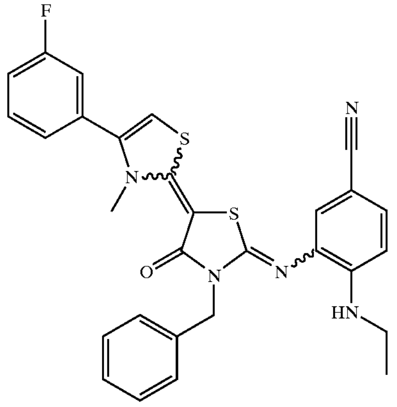

The title compound was prepared in a manner similar to that described in Example 52 by replacing 2-bromopropiophenone with 2-bromo-3'-fluoroacetophenone. MS(ESI): 542 ($MH^+$).

EXAMPLE 194

Preparation of 3-[3'-Benzyl-3-methyl-4'-oxo-4-(4-trifluoromethylphenyl)-3',4'-dihydro-3H-[2,5']bithiazolyliden-2'-ylideneamino]-4-ethylaminobenzonitrile

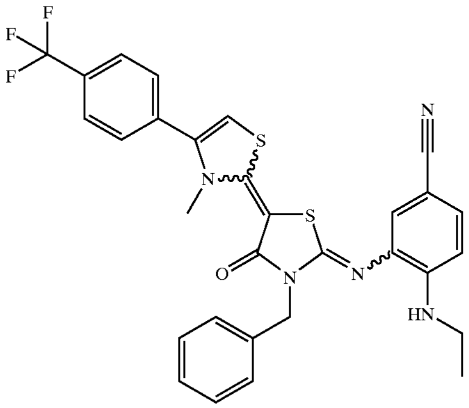

The title compound was prepared in a manner similar to that described in Example 52 by replacing 2-bromopropiophenone with 2-bromo-4'-trifluoromethyl-acetophenone. MS(ESI): 592 ($MH^+$).

EXAMPLE 195

Preparation of 3-[3'-Benzyl-3-methyl-4'-oxo-4-(4-trifluoromethoxyphenyl)-3',4'-dihydro-3H-[2,5']bithiazolyliden-2'-ylideneamino]-4-ethylaminobenzonitrile

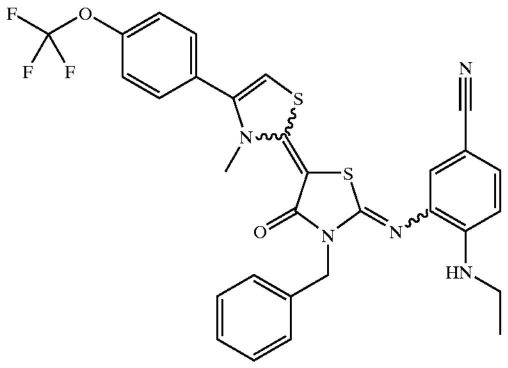

The title compound was prepared in a manner similar to that described in Example 52 by replacing 2-bromopropiophenone with 2-bromo-4'-(trifluoromethoxy) acetophenone. MS(ESI): 608 ($MH^+$).

EXAMPLE 196

Preparation of 3-[3'-Benzyl-4-(2,4-dimethoxyphenyl)-3-methyl-4'-oxo-3',4'-dihydro-3H-[2,5']bithiazolyliden-2'-ylideneamino]-4-ethylaminobenzonitrile

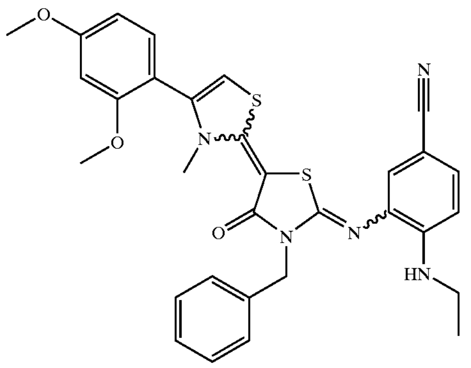

The title compound was prepared in a manner similar to that described in Example 52 by replacing 2-bromopropiophenone with 2-bromo-2',4'-dimethoxyacetophenone. MS(ESI): 584 ($MH^+$).

EXAMPLE 197

Preparation of 3-(3'-Benzyl-5-ethyl-3-methyl-4'-oxo-4-phenyl-3',4'-dihydro-3H-[2,5']bithiazolyliden-2'-ylideneamino)-4-ethylaminobenzonitrile

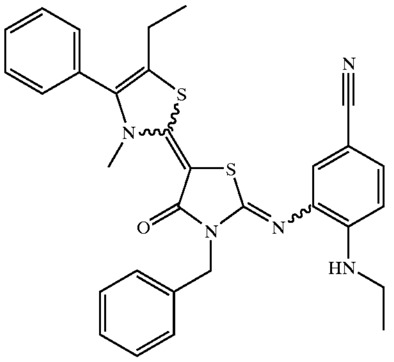

The title compound was prepared in a manner similar to that described in Example 52 by replacing 2-bromopropiophenone with 2-bromobutyrophenone. MS(ESI): 552 ($MH^+$).

EXAMPLE 198

Preparation of 3-[3'-Benzyl-3-methyl-4'-oxo-4-(2-trifluoromethylphenyl)-3',4'-dihydro-3H-[2,5'] bithiazolyliden-2'-ylideneamino]-4-ethylaminobenzonitrile

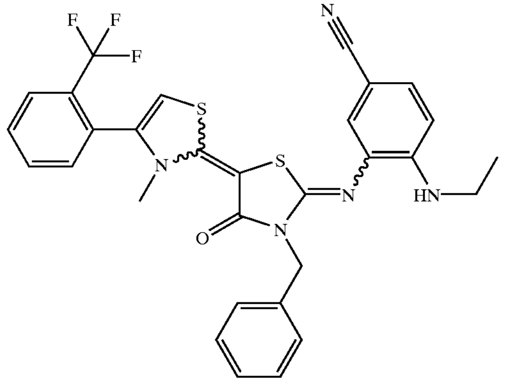

The title compound was prepared in a manner similar to that described in Example 52 by replacing 2-bromopropiophenone with 2-bromo-2'-(trifluoromethyl) acetophenone. MS(ESI): 592 ($MH^+$).

EXAMPLE 199

Preparation of 3-[3'-Benzyl-4-(3-bromophenyl)-3,5-dimethyl-4'-oxo-3',4'-dihydro-3H-[2,5'] bithiazolyliden-2'-ylideneamino]-4-ethylaminobenzonitrile

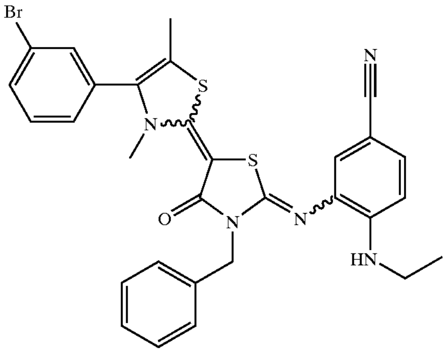

The title compound was prepared in a manner similar to that described in Example 52 by replacing 2-bromopropiophenone with 2,3'-dibromopropiophenone. MS(ESI): 617 ($MH^+$).

EXAMPLE 200

Preparation of 3-[3'-Benzyl-4-(3-methoxyphenyl)-3-methyl-4'-oxo-3',4'-dihydro-3H-[2,5']bithiazolyliden-2'-ylideneamino]-4-ethylaminobenzonitrile

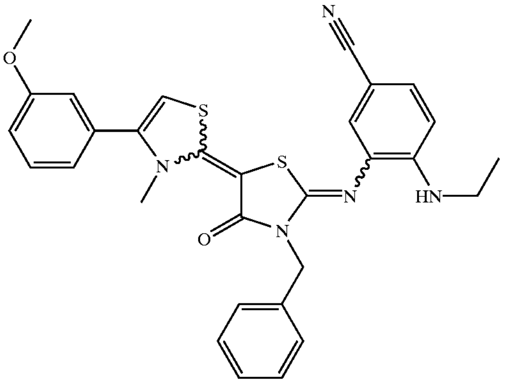

The title compound was prepared in a manner similar to that described in Example 52 by replacing 2-bromopropiophenone with 2-bromo-3'-methoxyacetophenone. MS(ESI): 554 ($MH^+$).

EXAMPLE 201

Preparation of 3-Benzyl-2-[4-(1,1,1,3,3,3-hexafluoro-2-hydroxyisopropyl)-phenylimino]-5-(3-methyl-3H-benzothiazol-2-ylidene)thiazolidin-4-one

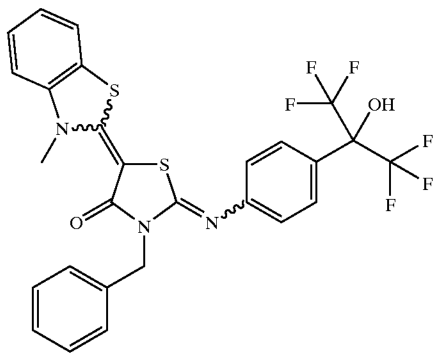

The title compound was prepared in a manner similar to that described in Example 52 by replacing aniline with 4-(1,1,1,3,3,3-hexafluoro-2-hydroxyisopropyl)aniline. MS(ESI): 596 ($MH^+$).

EXAMPLE 202

Preparation of 3-(3'-Benzyl-4-chloromethyl-3-methyl-4'-oxo-3',4'-dihydro-3H-[2,5']bithiazolyliden-2'-ylideneamino)-4-ethylaminobenzonitrile

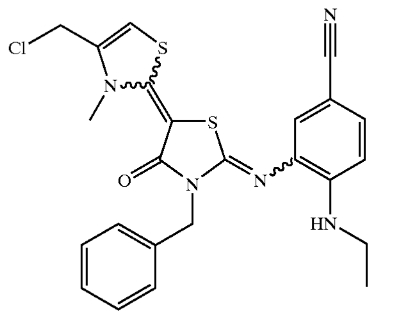

The title compound was prepared in a manner similar to that described in Example 52 by replacing 2-bromopropiophenone with 1,3-dichloroacetone.

MS(ESI): 496 ($MH^+$).

EXAMPLE 203

Preparation of 3'-Benzyl-2'-(5-cyano-2-ethylaminophenylimino)-3-methyl-4'-oxo-3',4'-dihydro-3H,2'H-[2,5']bithiazolylidene-4-carboxylic Acid Ethyl Ester

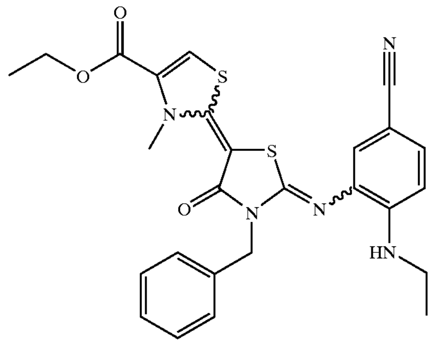

The title compound was prepared in a manner similar to that described in Example 52 by replacing 2-bromopropiophenone with ethyl bromopyruvate.

MS(ESI): 520 ($MH^+$).

EXAMPLE 204

Preparation of 3-(4,3'-Dibenzyl-3-methyl-4'-oxo-3',4'-dihydro-3H-[2,5']bithiazolyliden-2'-ylideneamino)-4-ethylaminobenzonitrile

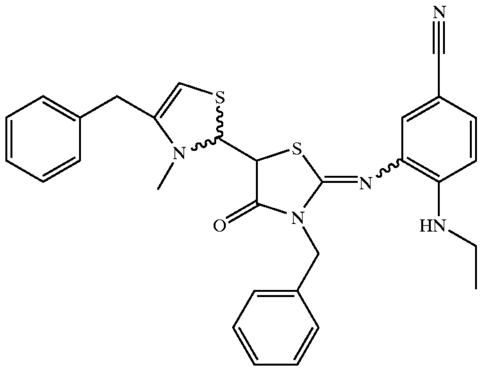

The title compound was prepared in a manner similar to that described in Example 52 by replacing 2-bromopropiophenone with 1-chloro-3-phenylpropan-2-one. MS(ESI): 538 ($MH^+$).

EXAMPLE 205

Preparation of 3'-Benzyl-2'-(5-cyano-2-ethylaminophenylimino)-3-methyl-4'-oxo-3',4'-dihydro-3H,2'H-[2,5']bithiazolylidene-4-carboxylic Acid

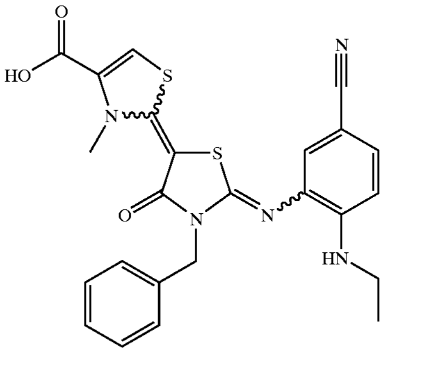

The product of Example 203 was saponified under conditions similar to that described in Example 29 to afford the title compound. MS(ESI): 492 ($MH^+$).

EXAMPLE 206

Preparation of 3-Benzyl-2-[2-ethylamino-5-(1-hydroxyethyl)phenylimino]-5-(3-methyl-3H-benzothiazol-2-ylidene)thiazolidin-4-one

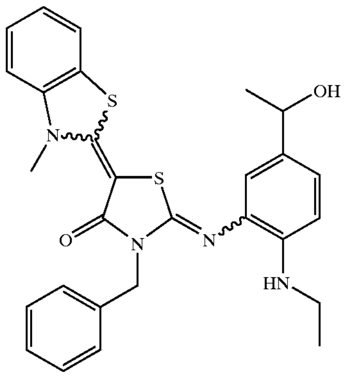

The product of Example 38 was reduced with sodium borohydride in 1:1 MeOH/THF and chromatographed (TEA-washed silica gel, 0–10% MeOH/DCM) to afford the title compound. $^1$H-NMR ($CDCl_3$): δ 7.47–7.54 (3H, m), 7.28–7.37 (4H, m), 7.17 (1H, m), 6.99–7.06 (3H, m), 6.57 (1H, d), 5.19 (2H, s), 4.80 (1H, q), 3.76 (3H, s), 3.01 (2H, q), 1.48 (3H, d), 1.04 (3H, s); MS(ESI): 517 ($MH^+$).

EXAMPLE 207

Preparation of 3-[3'-Benzyl-4-(2-hydroxyphenyl)-3-methyl-4'-oxo-3',4'-dihydro-3H-[2,5']bithiazolyliden-2'-ylideneamino]-4-ethylaminobenzonitrile

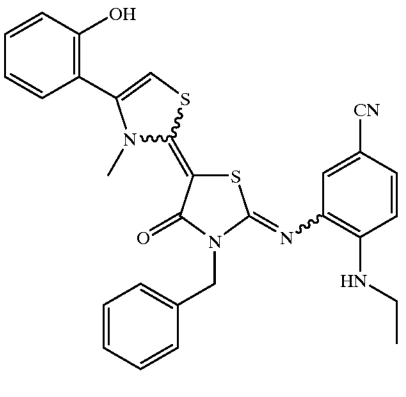

The product of Example 192 was treated with boron tribromide in DCM at 25° C. After 15 min the product mixture was quenched with brine, concentrated and chromatographed (silica gel, 0–10% MeOH/DCM) to yield the title compound. MS(ESI): 540 ($MH^+$).

EXAMPLE 208

Preparation of 3-Benzyl-2-[2-ethylamino-5-(1-hydroxyiminoethyl)phenylimino]-5-(3-methyl-3H-benzothiazol-2-ylidene)thiazolidin-4-one

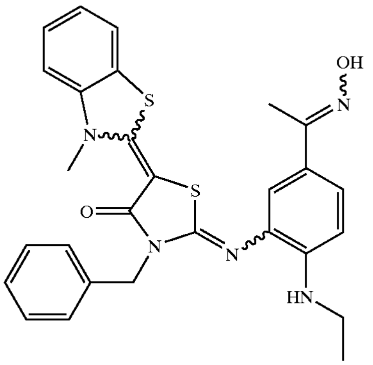

To the product of Example 38 was added hydroxylamine hydrochloride (2 equiv) and pyridine. The resulting mixture was heated at 80° C. for 24 h, cooled, concentrated and chromatographed (TEA-washed silica gel, 0–50% EtOAc/Hex) to give the title compound. $^1$H-NMR (DMSO-$d_6$): δ 11.07 (1H, s), 7.88 (1H, s), 7.67 (2H, m), 7.53 (1H, d), 7.39 (2H, m), 7.21–7.33 (5H, m), 7.09–7.14 (1H, m), 5.05 (2H, s), 3.92 (2H, q), 3.27 (3H, s), 2.23 (3H, s), 1.03 (3H, t); MS(ESI): 530 ($MH^+$).

EXAMPLE 209

Preparation of 3-Benzyl-2-[2-ethylamino-5-(1-methoxyiminoethyl)phenylimino]-5-(3-methyl -3H-benzothiazol-2-ylidene)thiazolidin-4-one

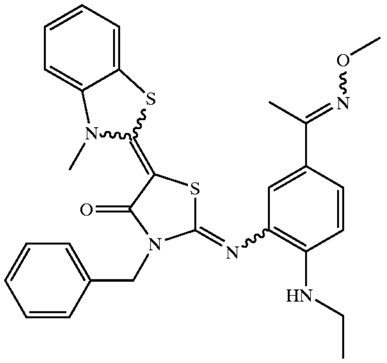

The title compound was prepared in a manner similar to that described in Example 208 by replacing hydroxylamine hydrochloride with O-methylhydroxylamine hydrochloride. MS(ESI): 544 ($MH^+$).

EXAMPLE 210

Preparation of 3-Benzyl-2-[5-(1-benzyloxyiminoethyl)-2-ethylaminophenylimino]-5-(3-methyl-3H-benzothiazol-2-ylidene)thiazolidin-4-one

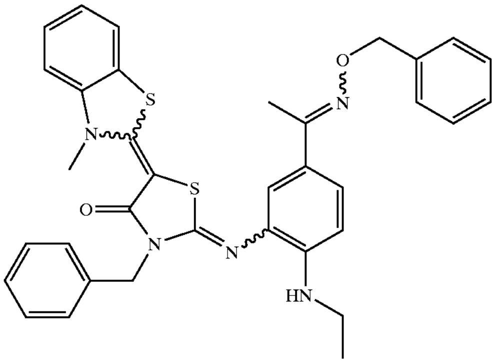

The title compound was prepared in a manner similar to that described in Example-208 by replacing hydroxylamine hydrochloride with O-benzylhydroxylamine hydrochloride. MS(ESI): 620 ($MH^+$).

EXAMPLE 211

Preparation of 3-Benzyl-2-{2-ethylamino-5-[1-(phenylhydrazono)ethyl]-phenylimino}-5-(3-methyl-3H-benzothiazol-2-ylidene)thiazolidin-4-one

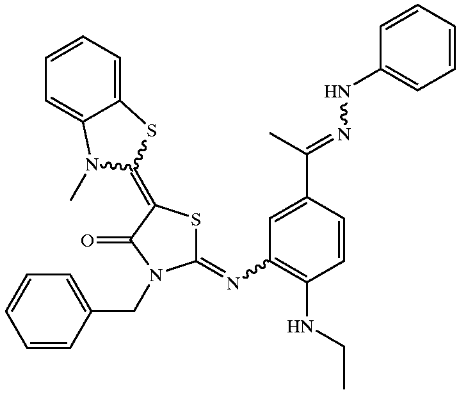

The title compound was prepared in a manner similar to that described in Example 208 by replacing hydroxylamine hydrochloride with phenylhydrazine. MS(ESI): 605 ($MH^+$).

EXAMPLE 212

Preparation of 3-(4,3'-Dibenzyl-3,5-dimethyl-4'-oxo-3',4'-dihydro-3H-[2,5']bithiazolyliden-2'-ylideneamino)-4-ethylaminobenzonitrile

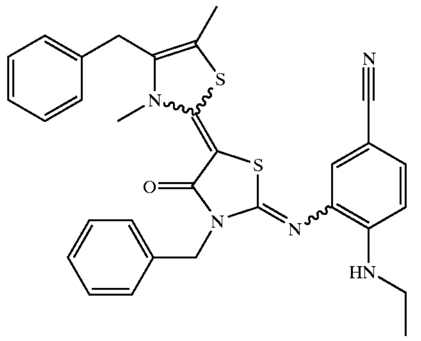

The title compound was prepared in a manner similar to that described in Example 52 by replacing 2-bromopropiophenone with 3-chloro-1-phenylbutan-2-one. MS(ESI): 552 ($MH^+$).

EXAMPLE 213

Preparation of 3-[3-Cyclohexylmethyl-5-(3-methyl-3H-benzothiazol-2-ylidene)-4-oxothiazolidin-2-ylideneamino]-4-ethylaminobenzonitrile

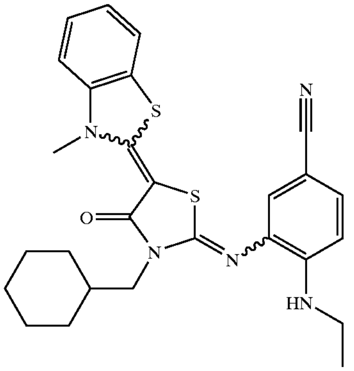

The title compound was prepared in a manner similar to that described in Example 83 by replacing 3-picolyl isothiocyanate hydrobromide with cyclohexylmethyl isothiocyanate. MS(ESI): 504 ($MH^+$).

EXAMPLE 214

Preparation of 3-[3'-Benzyl-4-(3-hydroxyphenyl)-3-methyl-4'-oxo-3',4'-dihydro-3H-[2,5']bithiazolyliden-2'-ylideneamino]-4-ethylaminobenzonitrile

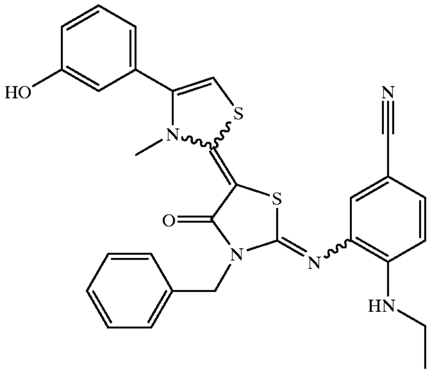

The title compound was prepared from the product of Example 200 in a manner similar to that described in Example 207. MS(ESI): 540 ($MH^+$).

EXAMPLE 215

Preparation of 3-[3'-Benzyl-4-(4-hydroxyphenyl)-3-methyl-4'-oxo-3',4'-dihydro-3H-[2,5']bithiazolyliden-2'-ylideneamino]-4-ethylaminobenzonitrile

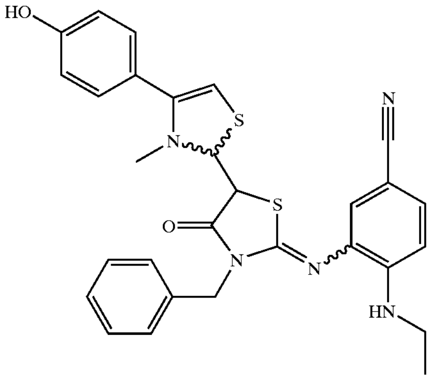

The title compound was prepared from the product of Example 174 in a manner similar to that described in Example 207. MS(ESI): 540 ($MH^+$).

EXAMPLE 216

Preparation of 3-(3'-Benzyl-3,4-dimethyl-4'-oxo-5-phenyl-3',4'-dihydro-3H-[2,5']bithiazolyliden-2'-ylideneamino)-4-ethylaminobenzonitrile

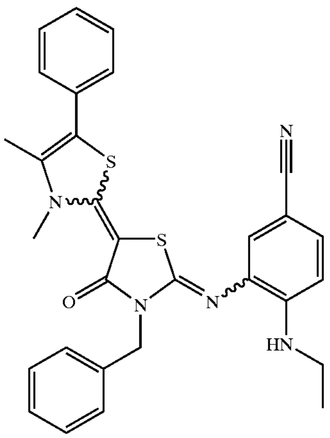

The title compound was prepared in a manner similar to that described in Example 52 by replacing 2-bromopropiophenone with 1-chloro-1-phenylpropan-2-one—generated in situ by addition of methylmagnesium chloride to chlorophenylacetyl chloride (−78 to 25° C.). MS(ESI): 538 ($MH^+$).

EXAMPLE 217

Preparation of 2'-(5-Acetyl-2-ethylaminophenylimino)-3'-benzyl-3,5-dimethyl-4-phenyl-2',3'-dihydro-3H-[2,5']bithiazolyliden-4'-one

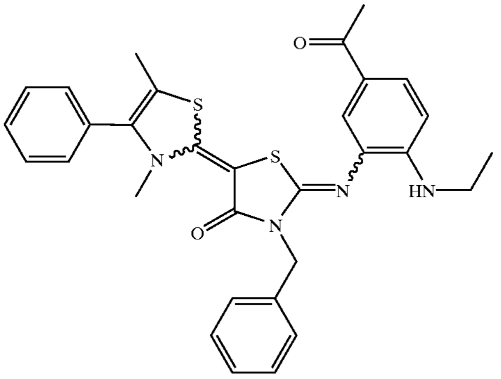

The title compound was prepared in a manner similar to that described in Example 52 by replacing 3-amino-4-ethylaminobenzonitrile with 3'-amino-4'-ethylaminoacetophenone. MS(ESI): 555 ($MH^+$).

EXAMPLE 218

Preparation of 2'-(5-Acetyl-2-ethylaminophenylimino)-3'-benzyl-3,4-dimethyl-5-phenyl-2',3'-dihydro-3H-[2,5']bithiazolyliden-4'-one

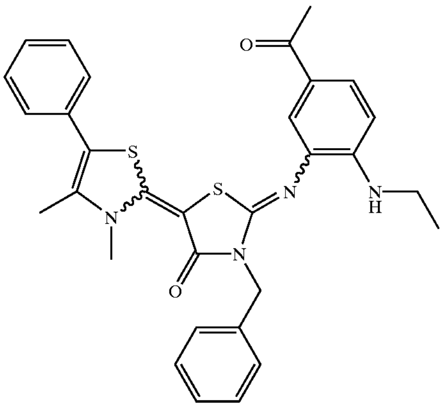

The title compound was prepared in a manner similar to that described in Example 217 by replacing 2-bromopropiophenone with 1-chloro-1-phenylpropan-2-one. MS(ESI): 555 ($MH^+$).

EXAMPLE 219

Preparation of 2'-(5-Acetyl-2-ethylaminophenylimino)-3'-benzyl-4-(4-methoxyphenyl)-3,5-dimethyl-2',3'-dihydro-3H-[2,5']bithiazolyliden-4'-one

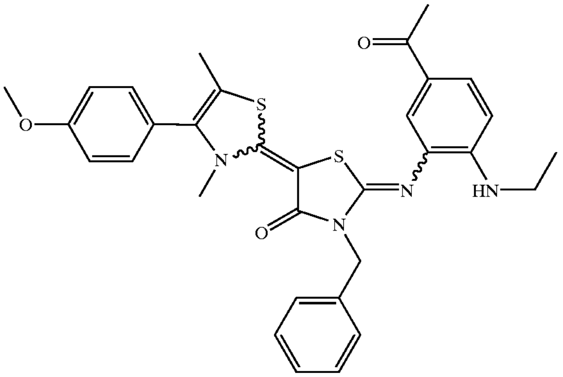

The title compound was prepared in a manner similar to that described in Example 217 by replacing 2-bromopropiophenone with 2-bromo-4'-methoxypropiophenone. MS(ESI): 585 ($MH^+$).

EXAMPLE 220

Preparation of 2'-(5-Acetyl-2-ethylaminophenylimino)-4,3'-dibenzyl-3-methyl-2',3'-dihydro-3H-[2,5']bithiazolyliden-4'-one

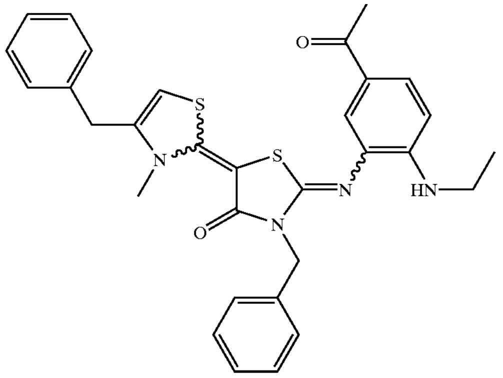

The title compound was prepared in a manner similar to that described in Example 217 by replacing 2-bromopropiophenone with 1-chloro-3-phenylpropan-2-one. MS(ESI): 555 ($MH^+$).

EXAMPLE 221

Preparation of 2'-(5-Acetyl-2-ethylaminophenylimino)-3'-benzyl-4-(2-methoxyphenyl)-3,5-dimethyl-2',3'-dihydro-3H-[2,5']bithiazolyliden-4'-one

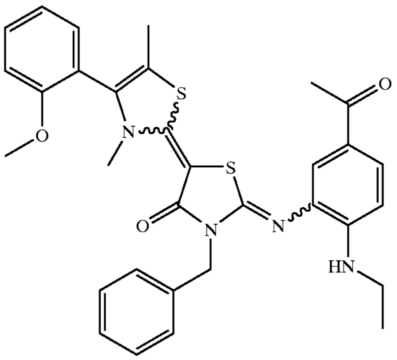

The title compound was prepared in a manner similar to that described in Example 217 by replacing 2-bromopropiophenone with 2-bromo-2'-methoxypropiophenone. MS(ESI): 585 ($MH^+$).

EXAMPLE 222

Preparation of 3-{3-Benzyl-5-[5-(2-dimethylaminoacetyl)-1-methyl-4,5,6,7-tetrahydro-1H-thiazolo[5,4-c]pyridin-2-ylidene]-4-oxothiazolidin-2-ylideneamino}-4-ethylaminobenzonitrile

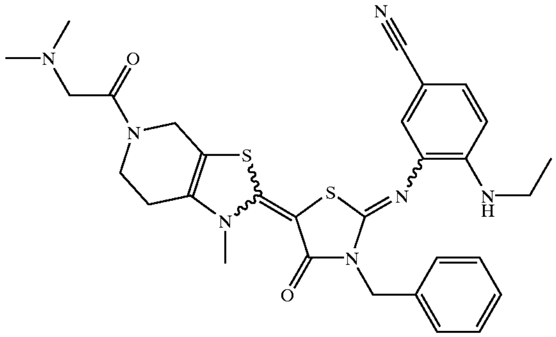

To the product of Example 183 in $CHCl_3$ was added N,N-dimethylaminoacetyl chloride and TEA. After 4 h the product mixture was concentrated and chromatographed (silica gel, 0–40% EtOAc/Hex) to yield the title compound. $^1$H-NMR ($CDCl_3$): δ 7.39–7.44 (2H, m), 7.33 (2H, m), 7.23–7.30 (2H m), 7.19 (1H, br s), 6.47 (1H, d), 5.15 (2H, s), 4.61 (1H, br s), 4.51 (1H, br s), 4.27 (1H, m), 3.92 (2H, m), 3.64 (3H, br s), 3.22 (1H, br s), 3.16 (1H, br s), 2.99 (2H, m), 2.63 (1H, br s), 2.56 (1H, br s), 2.31 (3H, s), 2.28 (3H, s), 1.01 (3H, t); MS(ESI): 588 ($MH^+$).

EXAMPLE 223

Preparation of 2'-5-Acetyl-2-ethylaminophenylimino)-3'-benzyl-4-(3-methoxyphenyl)-3,5-dimethyl-2',3'-dihydro-3H-[2,5']bithiazolyliden-4'-one

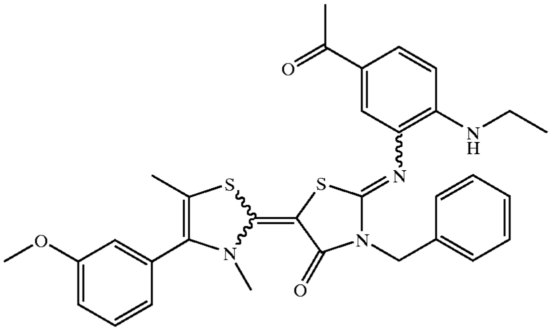

The title compound was prepared in a manner similar to that described in Example 217 by replacing 2-bromopropiophenone with 2-bromo-3'-methoxypropiophenone. MS(ESI): 585 ($MH^+$).

EXAMPLE 224

Preparation of 2'-(5-Acetyl-2-ethylaminophenylimino)-3'-benzyl-4-(3-hydroxyphenyl)-3,5-dimethyl-2',3'-dihydro-3H-[2,5'] bithiazolyliden-4'-one

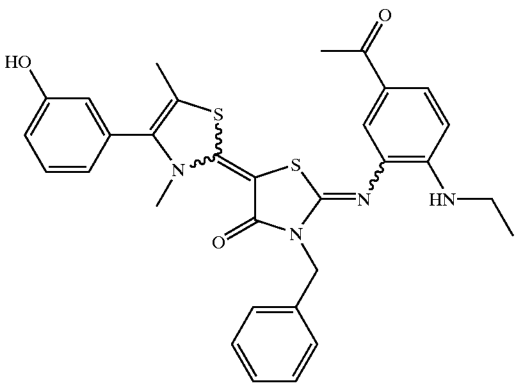

The title compound was prepared from the product of Example 223 in a manner similar to that described in Example 207. MS(ESI): 571 ($MH^+$).

EXAMPLE 225

Preparation of 2'-(5-Acetyl-2-ethylaminophenylimino)-3,3'-dibenzyl-5-methyl-4-phenyl-2',3'-dihydro-3H-[2,5']bithiazolyliden-4'-one

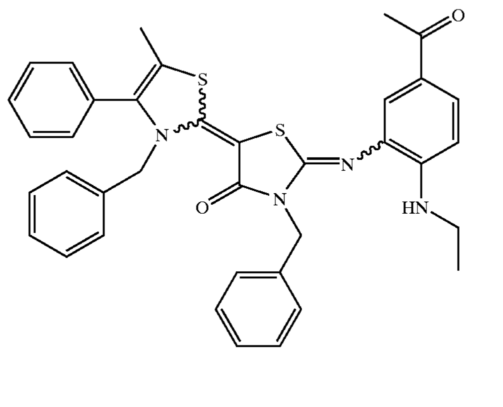

The title compound was prepared in a manner similar to that described in Example 52 by replacing triethylammonium methyldithiocarbamate with triethylammonium benzyldithiocarbamate—generated from benzylamine, carbon disulfide and TEA. MS(ESI): 631 ($MH^+$).

EXAMPLE 226

Preparation of N-(3-{3-Benzyl-5-[5-(2-acetoxyethoxy)-3-methyl-3H-benzothiazol-2-ylidene]-4-oxothiazolidin-2-ylideneamino}-4-ethylaminophenyl)-2-dimethylamino-acetamide

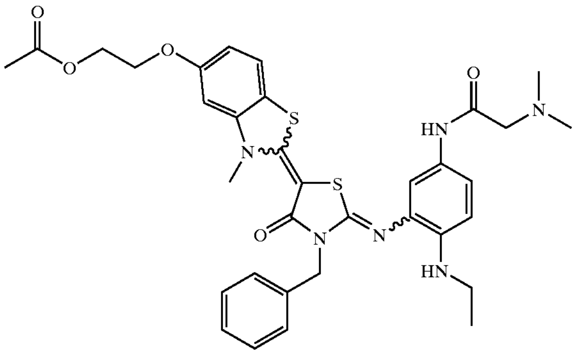

To the product of Example 145 (21 mg, 32 μmol) in acetone (2 mL) was added tetra-n-butylammonium iodide (24 mg, 65 μmol). The solution was stirred at 40° C. for 17 h prior to the addition of sodium acetate (50 mg, 0.64 mmol). The reaction solution was heated at 75° C. for 48 h. After cooling the solution was diluted with EtOAc (25 mL), washed with satd $NaHCO_3$ (20 mL) and water (2×20 mL), dried over $Na_2SO_4$, and concentrated under reduced pressure. The crude sample was chromatographed (silica gel, DCM) to provide the title compound (7 mg, 33%). $^1$H-NMR ($CDCl_3$) δ 7.87 (1H, s), 7.60 (1H, dd), 7.30–7.35 (3H, m), 7.17–7.22 (3H, m), 6.60 (1H, dd), 6.48 (1H, d), 5.27 (2H, s), 4.72 (1H, s), 4.39 (2H, t), 4.16 (2H, t), 3.69 (2H, q), 3.16 (2H, s), 3.08 (3H, s), 2.43 (6H, s), 2.06 (3H, s), 0.91 (3H, t); MS(ESI): 675 ($MH^+$).

EXAMPLE 227

Preparation of 2'-(5-Acetyl-2-ethylaminophenylimino)-3'-benzyl-3-(2-methoxyethyl)-5-methyl-4-phenyl-2',3'-dihydro-3H-[2,5']bithiazolyliden-4'-one

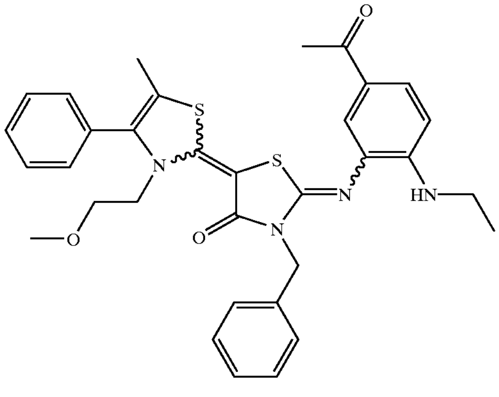

The title compound was prepared in a manner similar to that described in Example 52 by replacing triethylammonium methyldithiocarbamate with triethylammonium 2-methoxyethyldithiocarbamate—generated from 2-methoxy-ethylamine, carbon disulfide and TEA. MS(ESI): 599 ($MH^+$).

EXAMPLE 228

Preparation of 2'-(5-Acetyl-2-ethylaminophenylimino)-3'-benzyl-3-(3-methoxypropyl)-5-methyl-4-phenyl-2',3'-dihydro-3H-[2,5']bithiazolyliden-4'-one

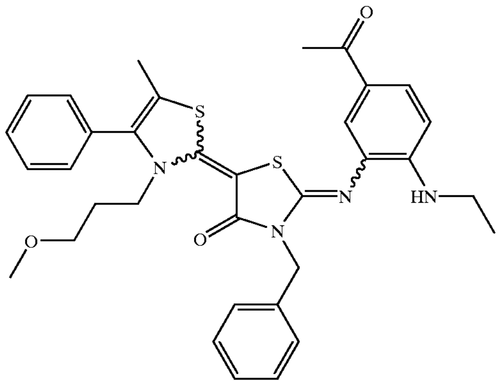

The title compound was prepared in a manner similar to that described in Example 52 by replacing triethylammonium methyldithiocarbamate with triethylammonium 3-methoxypropyldithiocarbamate—generated from 2-methoxy-propylamine, carbon disulfide and TEA. MS(ESI): 613 ($MH^+$).

EXAMPLE 229

Preparation of [2'-(5-Acetyl-2-ethylaminophenylimino)-3'-benzyl-5-methyl-4'-oxo-4-phenyl-3',4'-dihydro-2'H-[2,5']bithiazolyliden-3-yl]acetic Acid Methyl Ester

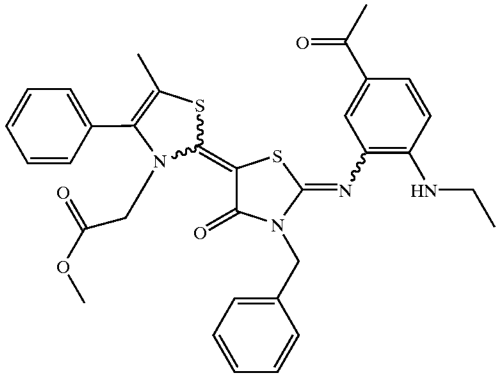

The title compound was prepared in a manner similar to that described in Example 52 by replacing triethylammonium methyldithiocarbamate with triethylammonium methoxycarbonylmethyldithiocarbamate—generated from glycine methyl ester, carbon disulfide and TEA. MS(ESI): 613 ($MH^+$).

EXAMPLE 230

Preparation of [2'-(5-Acetyl-2-ethylaminophenylimino)-3'-benzyl-5-methyl-4'-oxo-4-phenyl-3',4'-dihydro-2'H-[2,5']bithiazolyliden-3-yl]acetic Acid

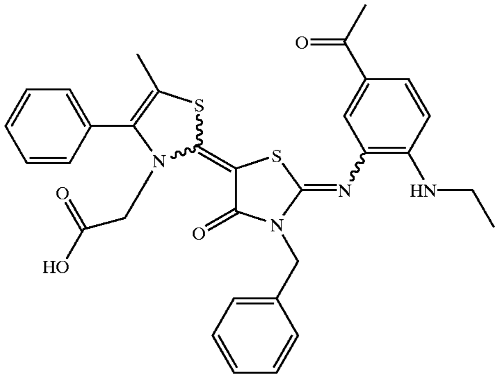

The product of Example 229 was saponified under conditions similar to that described in Example 29 to afford the title compound. MS(ESI): 599 ($MH^+$).

EXAMPLE 231

A. Preparation of 2-(5-Methyl-4-phenyl-2-thioxothiazol-3-yl)ethyl Acetate

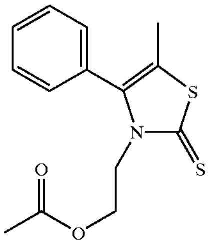

3-(2-Hydroxyethyl)-5-methyl-4-phenyl-3H-thiazole-2-thione was prepared in a manner similar to that described in Example 52 by replacing triethylammonium methyldithiocarbamate with triethylammonium 2-hydroxyethyldithiocarbamate—generated from ethanolamine, carbon disulfide and TEA.

Intermediate 3-(2-hydroxyethyl)-5-methyl-4-phenyl-3H-thiazole-2-thione was treated with acetic anhydride (1 equiv) and TEA (2 equiv) in $CHCl_3$. After 12 h the product mixture was concentrated and chromatographed (silica gel, 0–40% EtOAc/Hex) to afford the title compound. $^1$H-NMR ($CDCl_3$): δ 7.50–7.55 (3H, m), 7.28–7.32 (2H, m), 4.32 (2H, t), 4.26 (2H, t), 2.03 (3H, s), 1.93 (3H, s).

B. Preparation of 2-[2'-(5-Acetyl-2-ethylaminophenylimino)-3'-benzyl-5-methyl-4'-oxo-4-phenyl-3',4'-dihydro-2'H-[2,5']bithiazolyliden-3-yl]ethyl Acetate

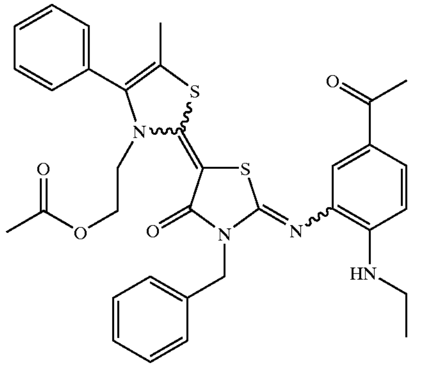

In a manner similar to that described in Example 52, intermediate 2-(5-methyl-4-phenyl-2-thioxothiazol-3-yl) ethyl acetate was alkylated with methyl p-toluenesulfonate and condensed with 2-(5-acetyl-2-ethylaminophenylimino)-3-benzylthiazolidin-4-one to yield the title compound. $^{1}$H-NMR ($CDCl_3$): δ 7.63–7.67 (2H, m), 7.44–7.51 (5H, m), 7.28–7.37 (5H, m), 6.50 (1H, d), 5.19 (2H, s), 4.30 (1H, br t), 4.03 (4H, m), 3.06 (2H, m), 2.48 (3H, s), 2.05 (3H, s), 1.89 (3H, s), 1.05 (3H, t); MS(ESI): 627 ($MH^+$).

EXAMPLE 232

Preparation of 2'-(5-Acetyl-2-ethylaminophenylimino)-3'-benzyl-3-(2-hydroxyethyl)-5-methyl-4-phenyl-2',3'-dihydro-3H-[2,5']bithiazolyliden-4'-one

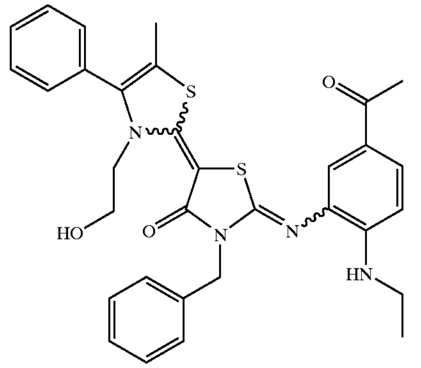

The product of Example 231 was saponified under conditions similar to that described in Example 29 to afford the title compound. MS(ESI): 585 ($MH^+$).

EXAMPLE 233

A. Preparation of 3'-Benzyl-3,5-dimethyl-4-phenyl-2'-thioxo-2',3'-dihydro-3H-[2,5']bithiazolyliden-4'-one

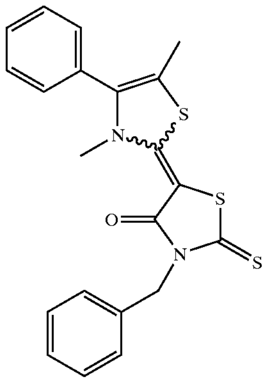

The title compound was prepared in a manner similar to that described in Example 1 by replacing 2-methylthiobenzothiazole with 3,5-dimethyl-4-phenyl-3H-thiazole-2-thione. $^{1}$H-NMR ($CDCl_3$): δ 7.50–7.58 (5H, m), 7.23–7.32 (5H, m), 5.39 (2H, s), 3.54 (3H, s), 2.11 (3H, s).

B. Preparation of N-[3-(3'-Benzyl-3,5-dimethyl-4'-oxo-4-phenyl-3',4'-dihydro-3H-[2,5']bithiazolyliden-2'-ylideneamino)-4-ethylaminophenyl]-2-methoxyacetamide

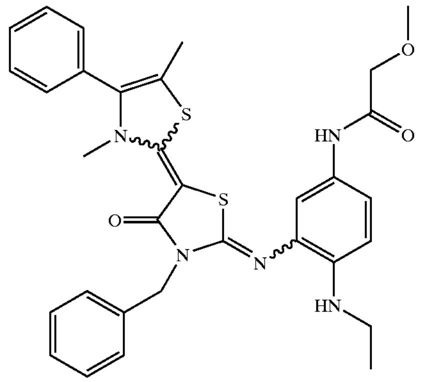

Likewise as described in Example 1, intermediate 3'-benzyl-3,5-dimethyl-4-phenyl-2'-thioxo-2',3'-dihydro-3H-[2,5']bithiazolyliden-4'-one was alkylated with methyl p-toluenesulfonate and condensed with N-(3-amino-4-ethylaminophenyl)-2-methoxyacetamide to afford the title compound. $^{1}$H-NMR ($CDCl_3$): δ 8.00 (1H, br s), 7.42–7.51 (5H, m), 7.30–7.37 (3H, m), 7.19–7.26 (3H, m), 7.11 (1H, d), 6.53 (1H, br s), 5.18 (2H, s), 3.97 (2H, s), 3.47 (3H, s), 3.42 (3H, s), 2.98 (2H, m), 2.06 (3H, s), 1.02 (3H, br t); MS(ESI): 600 ($MH^+$).

EXAMPLE 234

Preparation of N-[3-(3'-Benzyl-3,5-dimethyl-4'-oxo-4-phenyl-3',4'-dihydro-3H-[2,5']bithiazolyliden-2'-ylideneamino)-4-ethylaminophenyl]-2-dimethylaminoacetamide

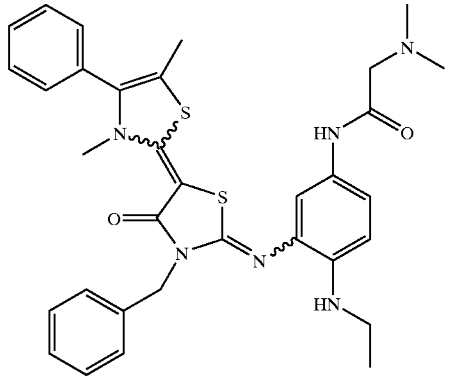

The title compound was prepared in a manner similar to that described in Example 233 by replacing N-(3-amino-4-ethylaminophenyl)-2-methoxyacetamide with N-(3-amino-4-ethylaminophenyl)-2-dimethylaminoacetamide. MS(ESI): 613 ($MH^+$).

EXAMPLE 235

Preparation of 3-[3-Cyclohexyl-5-(3-methyl-3H-benzothiazol-2-ylidene)-4-oxothiazolidin-2-ylideneamino]-4-ethylaminobenzonitrile

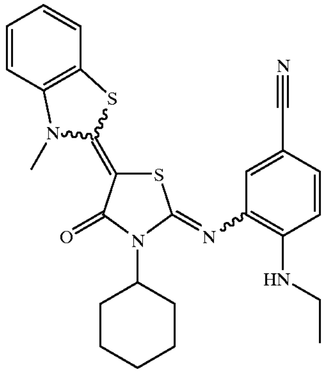

To a biphasic mixture of cyclohexylamine (2.3 mL, 20 mmol) in $CHCl_3$ (60 mL) and satd aqueous $NaHCO_3$ (40 mL) was added a solution of $CSCl_2$ (1.57 mL, 20 mmol) in $CHCl_3$ (5 mL) dropwise at 5° C. The mixture was stirred 1 h at 5° C. Methyl thioglycolate (1.9 mL, 20 mmol) was added, and the mixture was stirred overnight at 20° C. The organic layer was separated, and the aqueous layer was extracted with $CHCl_3$. The combined organic layers were washed with water, 1N HCl, water, satd aqueous $NaHCO_3$ and then dried over $MgSO_4$. Evaporation of solvent under reduced pressure gave a crude material, which was used in the next step without purification.

To a solution of the above product in toluene (80 mL) was added TsOH (100 mg), and the mixture was heated at reflux for 8 h with a dropping funnel containing 4 Å molecular sieves attached to the flask. After cooling, solid was removed by filtration. Evaporation of the filtrate gave a crude, which was purified by column chromatography on silica gel, eluting with EtOAc-Hex (0:100 to 3:7) to afford 3-cyclohexylrhodanine (1.24 g). $^1$H-NMR ($CDCl_3$): δ 4.86 (1H, m), 3.82 (2H, s), 2.30 (2H, q), 1.86 (2H, m), 1.58–1.72 (3H, m), 1.16–1.42 (3H, m).

The title compound was prepared in a manner similar to that described in Example 32 by replacing 3-benzylrhodanine with 3-cyclohexylrhodanine.

MS(ESI): 490 ($MH^+$).

EXAMPLE 236

Preparation of 3-[3-Allyl-5-(3-methyl-3H-benzothiazol-2-ylidene)-4-oxothiazolidin-2-ylideneamino]-4-ethylaminobenzonitrile

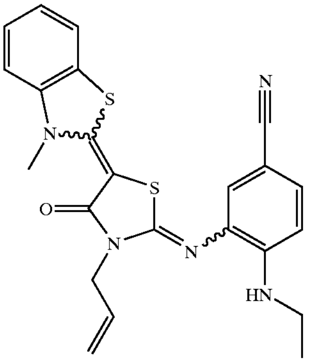

The title compound was prepared in a manner similar to that described in Example 235 by replacing cyclohexylamine with allylamine. MS(ESI): 448 ($MH^+$).

EXAMPLE 237

Preparation of 3-Allyl-5-(3-methyl-3H-benzothiazol-2-ylidene)-2-(quinolin-5-ylimino) thiazolidin-4-one

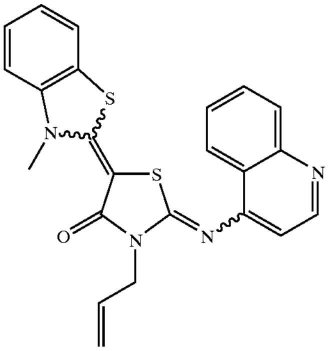

The title compound was prepared in a manner similar to that described in Example 236 by replacing 3-amino-4-ethylaminobenzonitrile with 5-aminoquinoline. MS(ESI): 431 ($MH^+$).

EXAMPLE 238

Preparation of 3-Allyl-2-(4-hydroxy-5-isopropyl-2-methylphenylimino)-5-(3-methyl-3H-benzothiazol-2-ylidene)thiazolidin-4-one

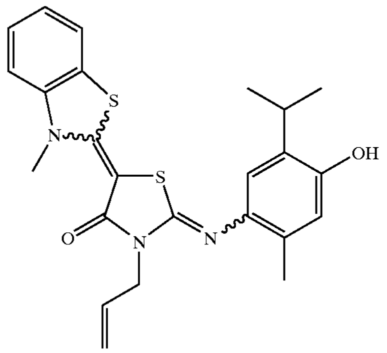

The title compound was prepared in a manner similar to that described in Example 236 by replacing 3-amino-4-ethylaminobenzonitrile with 4-aminothymol hydrochloride. MS(ESI): 452 ($MH^+$).

EXAMPLE 239

Preparation of 4-Ethylamino-3-[5-(3-methyl-3H-benzothiazol-2-ylidene)-4-oxo-3-phenylthiazolidin-2-ylideneamino]benzonitrile

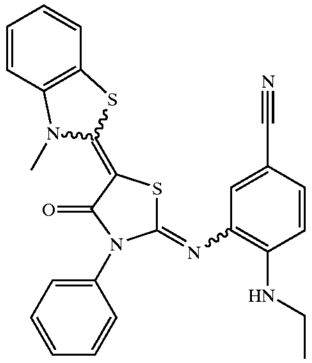

The title compound was prepared in a manner similar to that described in Example 235 by replacing cyclohexylamine with aniline. MS(ESI): 484 ($MH^+$).

EXAMPLE 240

Preparation of 3-Cyclohexyl-2-(2-hydroxynaphthalen-1-ylimino)-5-(3-methyl-3H-benzothiazol-2-ylidene)thiazolidin-4-one

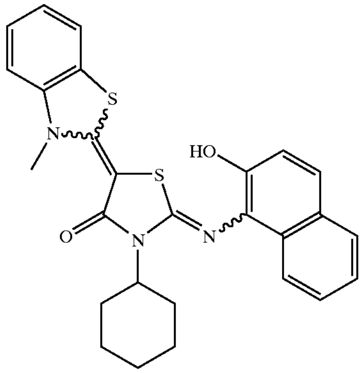

The title compound was prepared in a manner similar to that described in Example 235 by replacing 3-amino-4-ethylaminobenzonitrile with 1-amino-2-naphthol hydrochloride. MS(ESI): 488 ($MH^+$).

EXAMPLE 241

Preparation of 3-Allyl-2-(2-hydroxynaphthalen-1-ylimino)-5-(3-methyl-3H-benzothiazol-2-ylidene)thiazolidin-4-one

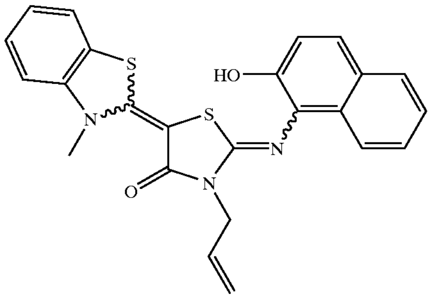

The title compound was prepared in a manner similar to that described in Example 236 by replacing 3-amino-4-ethylaminobenzonitrile with 1-amino-2-naphthol hydrochloride. MS(ESI): 446 ($MH^+$).

EXAMPLE 242

Preparation of 2-(4-Cyclohexylphenylimino)-5-(3-methyl-3H-benzothiazol-2-ylidene)-3-phenylthiazolidin-4-one

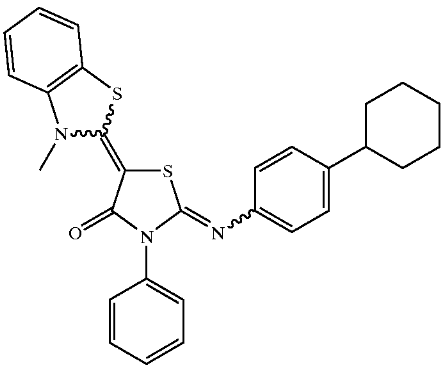

The title compound was prepared in a manner similar to that described in Example 239 by replacing 3-amino-4-ethylaminobenzonitrile with 4-cyclohexylaniline. MS(ESI): 498 ($MH^+$).

EXAMPLE 243

Preparation of 3-[3-Benzyl-5-(6-fluoro-3-methyl-3H-benzothiazol-2-ylidene)-4-oxothiazolidin-2-ylideneamino]-4-ethylaminobenzonitrile

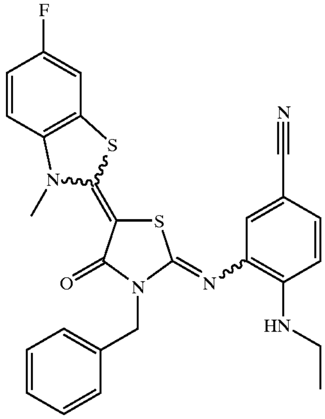

The title compound was prepared in a manner similar to that described in Example 55 by replacing 2-mercapto-5-trifluoromethylbenzothiazole with 6-fluoro-2-mercaptobenzothiazole. MS(ESI): 516 ($MH^+$).

EXAMPLE 244

Preparation of 3-[3-Benzyl-5-(5-chloro-3-methyl-3H-benzothiazol-2-ylidene)-4-oxothiazolidin-2-ylideneamino]-4-ethylaminobenzonitrile

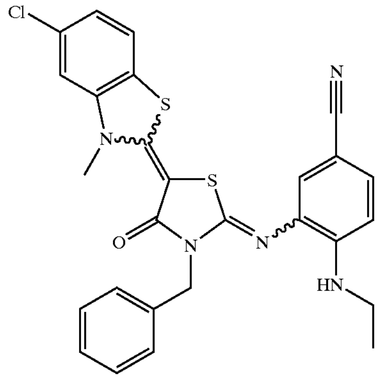

The title compound was prepared in a manner similar to that described in Example 55 by replacing 2-mercapto-5-trifluoromethylbenzothiazole with 5-chloro-2-mercaptobenzothiazole. MS(ESI): 532 ($MH^+$).

EXAMPLE 245

Preparation of 3-[3-Benzyl-5-(6-ethoxy-3-methyl-3H-benzothiazol-2-ylidene)-4-oxothiazolidin-2-ylideneamino]-4-ethylaminobenzonitrile

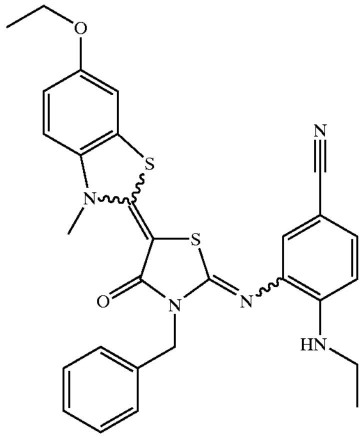

The title compound was prepared in a manner similar to that described in Example 55 by replacing 2-mercapto-5-trifluoromethylbenzothiazole with 6-ethoxy-2-mercaptobenzothiazole. MS(ESI): 542 ($MH^+$).

EXAMPLE 246

Preparation of 4-Ethylamino-3-[5-(3-methyl-3H-benzothiazol-2-ylidene)-4-oxo-3-propylthiazolidin-2-ylideneamino]benzonitrile

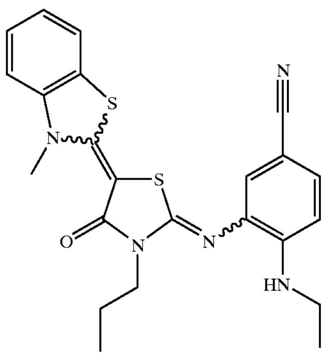

The title compound was prepared in a manner similar to that described in Example 235 by replacing cyclohexylamine with propylamine. MS(ESI): 450 ($MH^+$).

EXAMPLE 247

Preparation of 3-[3-Benzyl-5-(3-methyl-6-nitro-3H-benzothiazol-2-ylidene)-4-oxothiazolidin-2-ylideneamino]-4-ethylaminobenzonitrile

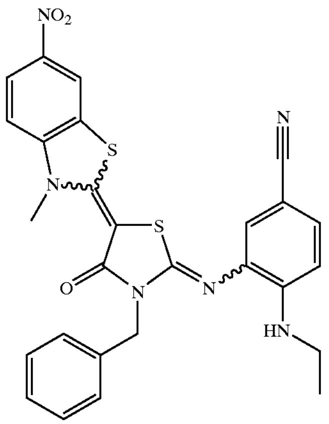

The title compound was prepared in a manner similar to that described in Example 55 by replacing 2-mercapto-5-trifluoromethylbenzothiazole with 2-mercapto-6-nitrobenzothiazole. MS(ESI): 543 ($MH^+$).

EXAMPLE 248

Preparation of N-{2-[3-Benzyl-2-(5-cyano-2-ethylaminophenylimino)-4-oxothiazolidin-5-ylidene]-3-methyl-2,3-dihydrobenzothiazol-6-yl}acetamide

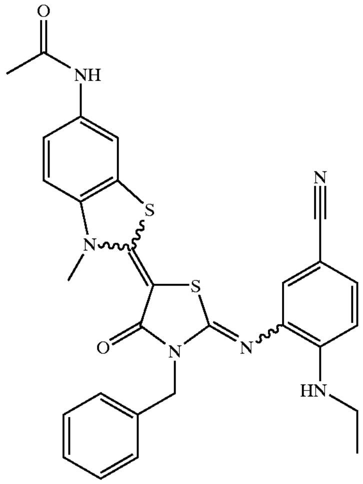

The title compound was prepared in a manner similar to that described in Example 55 by replacing 2-mercapto-5-trifluoromethylbenzothiazole with 2-mercapto-6-acetamidobenzothiazole. MS(ESI): 555 ($MH^+$).

EXAMPLE 249

Preparation of 3-[3-Benzyl-5-(6-hydroxy-3-methyl-3H-benzothiazol-2-ylidene)-4-oxothiazolidin-2-ylideneamino]-4-ethylaminobenzonitrile

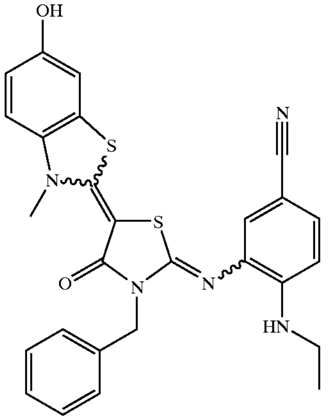

The title compound was prepared from the product of Example 245 in a manner similar to that described in Example 57. MS(ESI): 514 ($MH^+$).

EXAMPLE 250

Preparation of Ethylcarbamic Acid 2-[3-Benzyl-2-(5-cyano-2-ethylaminophenylimino)-4-oxothiazolidin-5-ylidene]-3-methyl-2,3-dihydrobenzothiazol-5-yl Ester

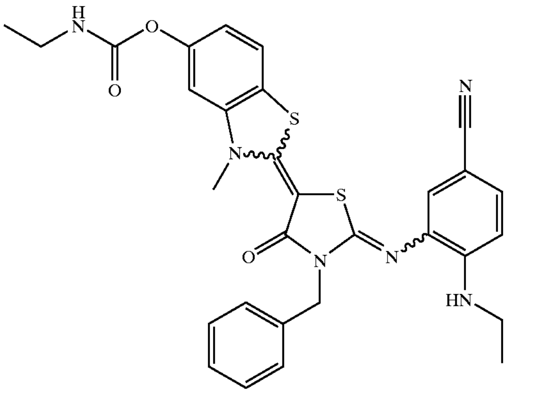

The title compound was prepared in a manner similar to that described in Example 58 by replacing dimethylcarbamoyl chloride with ethyl isocyanate.

MS(ESI): 585 ($MH^+$).

EXAMPLE 251

Preparation of {2-[3-Benzyl-2-(5-cyano-2-ethylaminophenylimino)-4-oxothiazolidin-5-ylidene]-3-methyl-2,3-dihydrobenzothiazol-5-yloxy}acetic Acid Methyl Ester

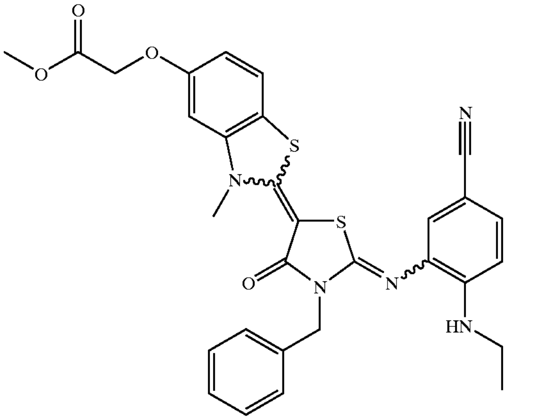

To a suspension of $K_2CO_3$ (41 mg, 5 equiv) in 2-butanone (2 mL) were added the product of Example 57 (31 mg, 0.06 mmol) and methyl 2-bromoacetate (7 μL, 1.2 equiv). The resulting suspension was heated at 75° C. overnight. After cooling, the reaction mixture was filtered, and the filtrate was evaporated to give a crude material, which was purified by chromatography on silica gel, eluting with MeOH-DCM (0:100 to 3:97) to give the title compound (5 mg). $^1H$-NMR ($CDCl_3$): δ 7.63 (1H, d), 7.28–7.39 (6H, m), 7.13 (1H, d), 7.08 (1H, d), 6.84 (1H, dd), 6.62 (1H, d), 5.13 (2H, s), 4.98 (1H, t), 4.88 (2H, s), 3.79 (3H, s), 3.68 (3H, s), 3.05 (2H, m), 0.99 (3H, t); MS(ESI): 586 ($MH^+$).

EXAMPLE 252

Preparation of 2-{2-[3-Benzyl-2-(5-cyano-2-ethylaminophenylimino)-4-oxothiazolidin-5-ylidene]-3-methyl-2,3-dihydrobenzothiazol-5-yloxy}acetamide

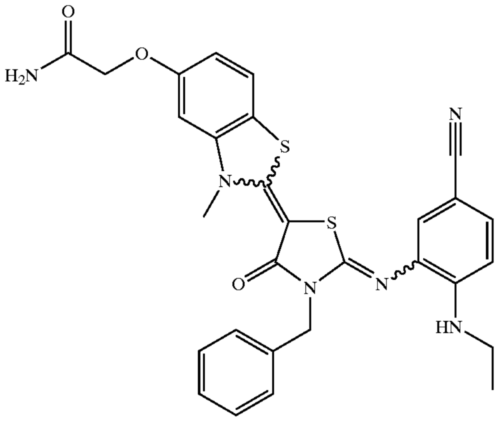

The title compound was prepared in a manner similar to that described in Example 251 by replacing methyl 2-bromoacetate with 2-bromoacetamide.

MS(ESI): 571 ($MH^+$).

EXAMPLE 253

Preparation of (2-Chloroethyl)carbamic Acid 2-[3-Benzyl-2-(5-cyano-2-ethylaminophenylimino)-4-oxothiazolidin-5-ylidene]-3-methyl-2,3-dihydrobenzothiazol-5-yl Ester

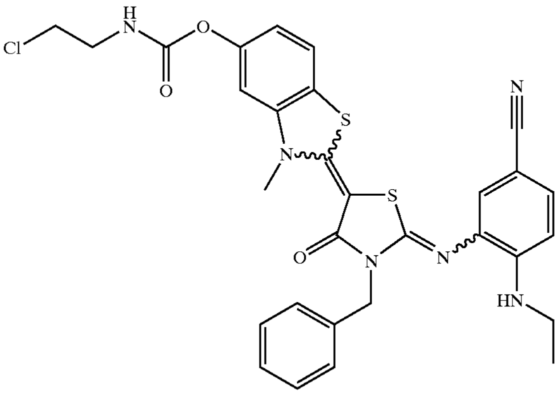

The title compound was prepared in a manner similar to that described in Example 250 by replacing ethyl isocyanate with 2-chloroethylisocyanate.

MS(ESI): 619 ($MH^+$).

EXAMPLE 254

Preparation of 3-{3-Benzyl-5-[3-methyl-5-(2-methylaminoethoxy)-3H-benzothiazol-2-ylidene]-4-oxothiazolidin-2-ylideneamino}-4-ethylaminobenzonitrile

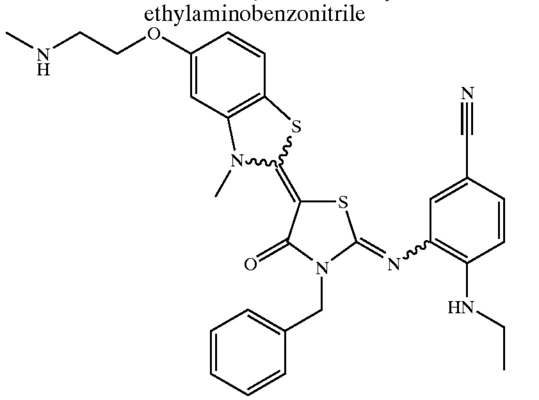

To the product of Example 57 (62 mg, 0.12 mmol) in anhydrous DMF (2 mL) were added 1,2-dibromoethane (100 mL, 10 equiv) and anhydrous $K_2CO_3$ (166 mg, 10 equiv). The suspension was shaken overnight at 60° C. in a sealed tube. After cooling, the reaction mixture was concentrated under reduced pressure, diluted with DCM and acetone, and filtered. The filtrate was concentrated to give a residue, which was purified by chromatography on silica gel, eluting with MeOH-DCM (1:19) to give a yellow solid, which was used in the next step without further purification.

The above material was dissolved in 2M solution of methylamine in THF (3 mL) and the solution was heated in a sealed tube for 40 h at 60° C. After cooling, the product mixture was concentrated to give a residue, which was purified by chromatography on silica gel, eluting with MeOH-DCM (1:19 to 1:9) to give the title compound (10 mg). $^1$H-NMR ($CDCl_3$): δ 7.63 (1H, d), 7.28–7.39 (6H, m), 7.13 (1H, d), 7.03 (1H, d), 6.85 (1H, dd), 6.62 (1H, d), 5.13 (2H, s), 4.98 (1H, t), 4.12 (2H, t), 3.79 (3H, s), 3.05 (3H, m), 2.93 (2H, t), 2.3 (3H, s), 0.99 (3H, t); MS(ESI): 571 ($MH^+$).

EXAMPLE 255

Preparation of 3-{3-Benzyl-5-[5-(3-hydroxypropoxy)-3-methyl-3H-benzothiazol-2-ylidene]-4-oxothiazolidin-2-ylideneamino}-4-ethylaminobenzonitrile

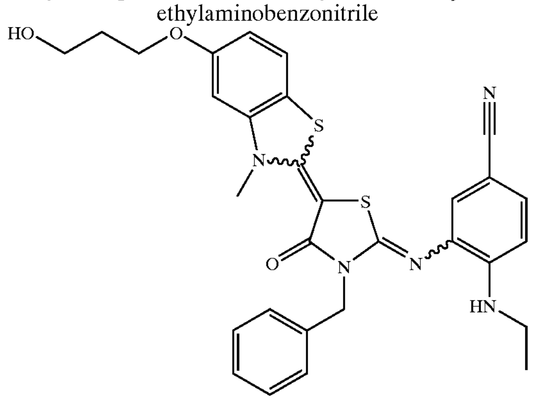

The title compound was prepared in a manner similar to that described in Example 59 by replacing 2-bromoethanol with 3-bromopropanol. MS(ESI): 572 ($MH^+$).

EXAMPLE 256

Preparation of (3-Chloropropyl)carbamic Acid 2-[3-Benzyl-2-(5-cyano-2-ethylaminophenylimino)-4-oxothiazolidin-5-ylidene]-3-methyl-2,3-dihydrobenzothiazol-5-yl Ester

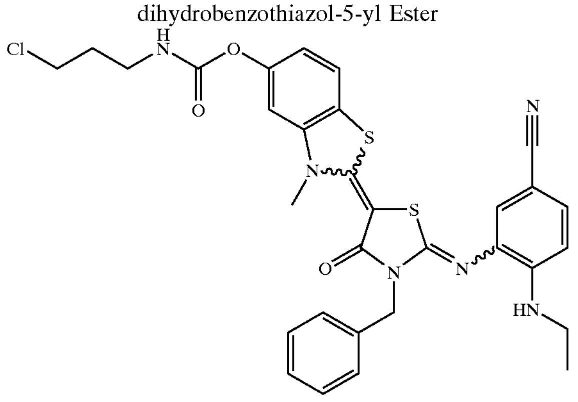

The title compound was prepared in a manner similar to that described in Example 250 by replacing ethyl isocyanate with 3-chloropropylisocyanate.

MS(ESI): 633 ($MH^+$).

EXAMPLE 257

Preparation of 3-(3-Benzyl-5-{3-methyl-5-[2-(4-methylpiperazin-1-yl)-ethoxy]-3H-benzothiazol-2-ylidene}-4-oxothiazolidin-2-ylideneamino)-4-ethylaminobenzonitrile

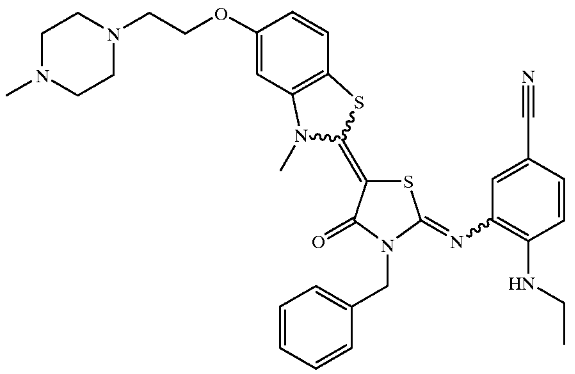

The title compound was prepared in a manner similar to that described in Example 60 by replacing morpholine with 1-methylpiperizine. MS(ESI): 640 ($MH^+$).

EXAMPLE 258

Preparation of 3-{3-Benzyl-5-[3-methyl-5-(2-piperidin-4-ylethoxy)-3H-benzothiazol-2-ylidene]-4-oxothiazolidin-2-ylideneamino}-4-ethylaminobenzonitrile

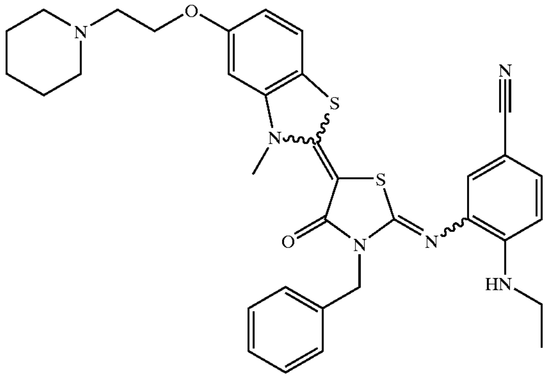

The title compound was prepared in a manner similar to that described in Example 60 by replacing morpholine with piperidine. MS(ESI): 625 ($MH^+$).

EXAMPLE 259

Preparation of 3-{3-Benzyl-5-[5-(2-dimethylaminoethoxy)-3-methyl-3H-benzothiazol-2-ylidene]-4-oxothiazolidin-2-ylideneamino}-4-ethylaminobenzonitrile

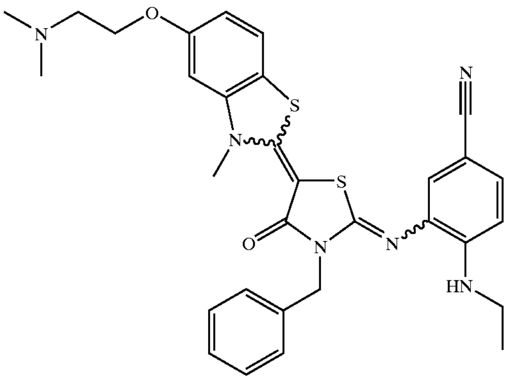

The title compound was prepared in a manner similar to that described in Example 60 by replacing morpholine with dimethylamine. $^1$H-NMR ($CDCl_3$): δ 7.43 (2H, m), 7.33 (1H, d), 7.29 (2H, m), 7.25–7.27 (5H, m), 7.20 (1H, d), 6.80 (1H, dd), 6.70 (1H, d), 6.49 (1H, d), 5.18 (2H, s), 4.22 (1H, t), 4.11 (2H, t), 3.77 (3H, s), 3.00 (2H, m), 2.75 (2H, t), 2.35 (6H, s), 1.02 (3H, t), MS(ESI): 585 ($MH^+$).

EXAMPLE 260

Preparation of {2-[3-Benzyl-2-(5-cyano-2-ethylaminophenylimino)-4-oxothiazolidin-5-ylidene]-3-methyl-2,3-dihydrobenzothiazol-5-yloxy}acetic Acid

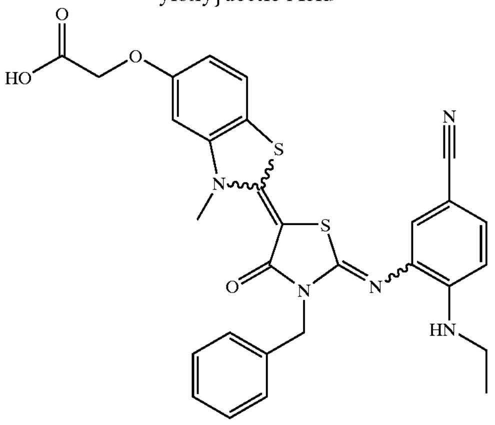

To the product of Example 57 (158 mg, 0.31 mmol) in anhydrous DMF (5 mL) were added tert-butyl bromoacetate (460 μL, 10 equiv) and anhydrous $K_2CO_3$ (425 mg, 10 equiv). The suspension was heated at 80° C. under nitrogen for 16 h. After cooling, resulting solids were removed by filtration. The filtrate was concentrated to give a residue, which was purified by chromatography on silica gel, eluting with MeOH-DCM (5:95) to give the product, which was used in the next step without further purification.

The above product was dissolved in a 1:1 mixture of TFA/DCM (2 mL) and the solution was stirred for 1 h at 20° C. Evaporation of solvent gave a residue, which was purified by chromatography on silica gel, eluting with MeOH-DCM (5:95) to give the title compound (35 mg, 75%). $^1$H-NMR ($CDCl_3$): δ 7.61 (1H, m), 7.28–7.39 (6H, m), 7.13 (1H, d), 7.05 (1H, d), 6.82 (1H, dd), 6.62 (1H, d), 5.14 (2H, s), 4.95 (1H, t), 4.76 (2H, t), 3.79 (3H, s), 3.05 (2H, m), 0.99 (3H, t), MS(ESI): 572 ($MH^+$).

EXAMPLE 261

Preparation of 3-{3-Benzyl-5-[6-(2-hydroxyethoxy)-3-methyl-3H-benzothiazol-2-ylidene]-4-oxothiazolidin-2-ylideneamino}-4-ethylaminobenzonitrile

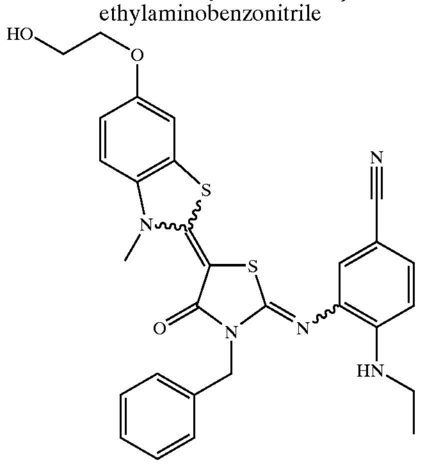

The title compound was prepared in a manner similar to that described in Example 59 by replacing the product of Example 57 with the product of Example 249. MS(ESI): 558 ($MH^+$).

EXAMPLE 262

Preparation of 3-{3-Benzyl-5-[6-(2-methoxyethoxy)-3-methyl-3H-benzothiazol-2-ylidene]-4-oxothiazolidin-2-ylideneamino}-4-ethylaminobenzonitrile

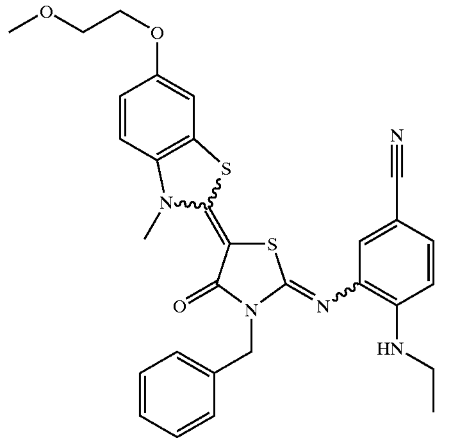

The title compound was prepared in the same manner as described in Example 261 in the presence of excess methyl p-toluenesulfonate. MS(ESI): 572 ($MH^+$).

EXAMPLE 263

Preparation of 3-{3-Benzyl-5-[3-methyl-6-(2-morpholin-4-ylethoxy)-3H-benzothiazol-2-ylidene]-4-oxothiazolidin-2-ylideneamino}-4-ethylaminobenzonitrile

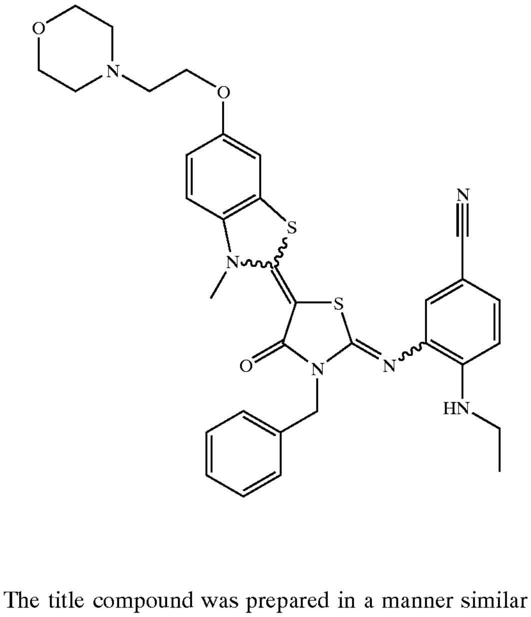

The title compound was prepared in a manner similar to that described in Example 60 by replacing the product of Example 60 with the product of Example 261. MS(ESI): 627 ($MH^+$).

EXAMPLE 264

Preparation of 3-{3-Benzyl-5-[5-(2-methoxyethoxy)-3-methyl-3H-benzothiazol-2-ylidene]-4-oxothiazolidin-2-ylideneamino}-4-ethylaminobenzonitrile

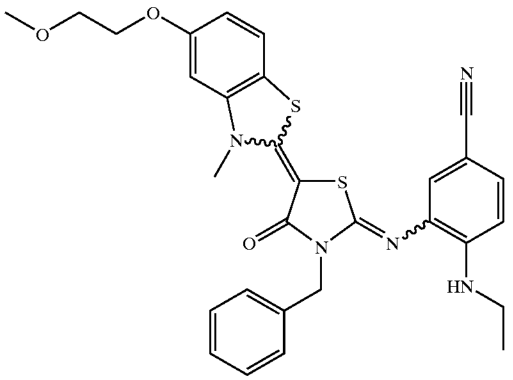

The title compound was prepared in the same manner as described in Example 59 in the presence of excess methyl p-toluenesulfonate. MS(ESI): 572 ($MH^+$).

EXAMPLE 265

A. Preparation of 4-Methoxy-2-methylthiobenzothiazole

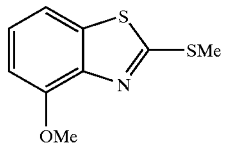

2-Amino-4-methoxybenzothiazole (3.6 g, 20 mmol) was dissolved in warm $H_3PO_4$ (120 mL). The resulting homogeneous solution was cooled to −8° C., and a solution of $NaNO_2$ (8.28 g, 120 mmol) in $H_2O$ (50 mL) was added dropwise with stirring such that the temperature was not allowed to rise above −4° C. The resulting dark-red syrup was added slowly to $H_3PO_2$ (50% in $H_2O$, 60 mL) at 0° C. with stirring. After the addition was complete, the mixture was allowed to warm to ambient temperature until gas evolution had ceased. The solution was diluted with ice-water, cautiously neutralized with solid $Na_2CO_3$, and extracted with $CHCl_3$ (3×200 mL). The combined extracts were washed with water (2×200 mL), dried over $Na_2SO_4$, and concentrated under reduced pressure to give a red solid (2.87 g), which was purified by chromatography on silica gel, eluting with EtOAc-Hex (0:100 to 30:70) to yield 4-methoxybenzothiazole (2.14 g, 65%) as a yellow solid. $^1H$-NMR ($CDCl_3$): δ 8.90 (1H, s), 7.52 (1H, d), 7.38 (1H, t), 6.93 (1H, d), 4.06 (3H, s).

To a solution of 4-methoxybenzothiazole (495 mg, 3.0 mmol) in anhydrous THF (12 mL) at −78° C. was added BuLi (2.5 mL, 1.6M in hexanes, 4.0 mmol) dropwise. The resulting red solution was stirred at −78° C. for 2 h under $N_2$. Methyl disulfide (0.55 mL, 6.0 mmol) was added dropwise at −78° C. and the mixture was allowed to warm to ambient temperature overnight. The reaction mixture was combined with water and then extracted with EtOAc. The combined extracts were washed with brine, dried over $Na_2SO_4$, and concentrated under reduced pressure to afford the title compound as a yellow oil (632 mg, 100%), which solidified upon standing and was used without purification. $^1$H-NMR ($CDCl_3$): δ 7.35 (1H, d), 7.24 (1H, q), 6.86 (1H, d), 4.06 (3H, s), 2.79 (3H, s).

B. Preparation of 3-{3-Benzyl-5-[3-methyl-4-methoxy-3H-benzothiazol-2-ylidene]-4-oxothiazolidin-2-ylideneamino}4-ethylaminobenzonitrile

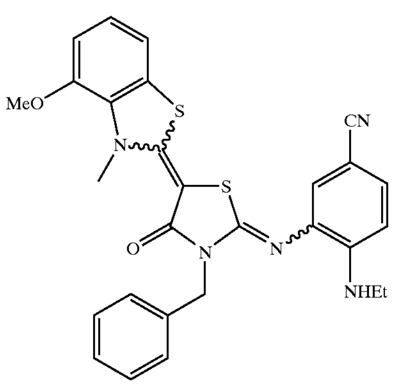

To a suspension of the 4-methoxy2-methylthiobenzothiazole (0.60 g, 2.8 mmol) in anhydrous anisole (8 mL) was added methyl p-toluenesulfonate (1.4 mL, 9.0 mmol) and the suspension was heated at 130° C. for 3.5 h. After cooling to 20° C., MeCN (5 mL), 3-(3-benzyl-4-oxothiazolidin-2-ylideneamino)-4-ethylaminobenzonitrile (119 mg, 0.34 mmol) and TEA (2.0 mL, 14 mmol) were added. The suspension was stirred for 5 h at 80° C. After cooling to ambient temperature, yellow solids were collected by filtration, washed with MeCN and dried under high vacuum to afford the title compound (123 mg, 69%). $^1$H-NMR ($CDCl_3$): δ 7.45–7.11 (9H, m), 6.88–6.85 (1H, m), 6.48 (1H, d), 5.17 (2H, s), 4.08 (3H, s), 3.92 (3H, s), 3.02–2.97 (2H, m), 1.02 (3H, t); MS(ESI): 528 ($MH^+$).

EXAMPLE 266

Preparation of 3-{3-Benzyl-5-[3-methyl-4-methyl-3H-benzothiazol-2-ylidene]-4-oxothiazolidin-2-ylideneamino}-4-ethylaminobenzonitrile

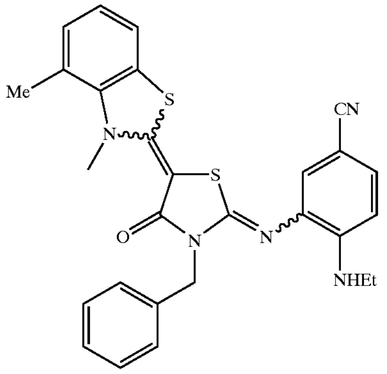

The title compound was prepared in a manner similar to that described in Example 265 by starting from 2-amino-4-methylbenzothiazole. $^1$H-NMR ($CDCl_3$): δ 7.46–7.06 (10H, m), 6.49 (1H, d), 5.17 (2H, s), 3.88 (3H, s), 3.04–2.97 (2H, m), 2.62 (3H, s), 1.03 (3H, t); MS(ESI): 512 ($MH^+$).

EXAMPLE 267

Preparation of 3-{3-Benzyl-5-[3-methyl-4-chloro-3H-benzothiazol-2-ylidene]-4-oxothiazolidin-2-ylideneamino}-4-ethylaminobenzonitrile

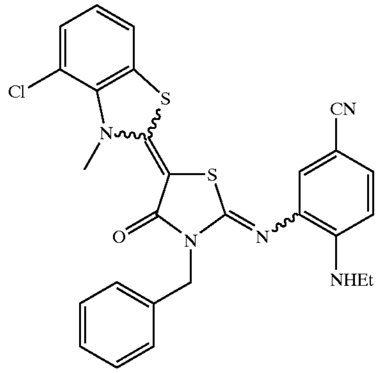

The title compound was prepared in a manner similar to that described in Example 265 by starting from 2-amino-4-chlorobenzothiazole. $^1$H-NMR ($CDCl_3$): δ 7.45–7.08 (10H, m), 6.50 (1H, d), 5.17 (2H, s), 4.01 (3H, s), 3.04–2.98 (2H, m), 1.03 (3H, t); MS(ESI): 532 ($MH^+$).

EXAMPLE 268

Preparation of 3-{3-Benzyl-5-[3-methyl-6-trifluoromethoxy-3H-benzothiazol-2-ylidene]-4-oxothiazolidin-2-ylideneamino}-4-ethylaminobenzonitrile

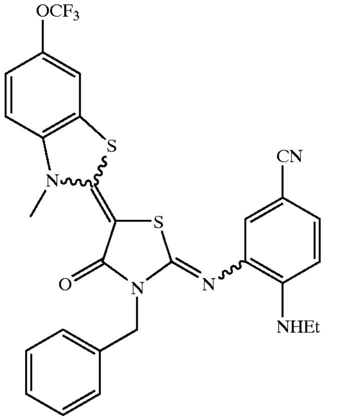

The title compound was prepared in a manner similar to that described in Example 265 by starting from 2-amino-6-(trifluoromethoxy)benzothiazole.

$^1$H-NMR ($CDCl_3$): δ 7.44–7.18 (9H, m), 7.06 (1H, d), 6.49 (1H, d), 5.17 (2H, s), 3.81 (3H, s), 3.04–2.97 (2H, m), 1.03 (3H, t); MS(ESI): 582 ($MH^+$).

EXAMPLE 269

Preparation of 3-[3-Benzyl-5-(3,5,6-trimethyl-3H-benzothiazol-2-ylidene)-4-oxothiazolidin-2-ylideneamino]-4-ethylaminobenzonitrile

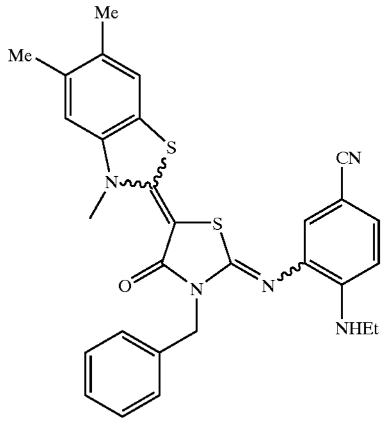

The title compound was prepared in a manner similar to that described in Example 265 by starting from 2-amino-5,6-dimethylbenzothiazole. $^1$H-NMR ($CDCl_3$): δ 7.44–7.20 (8H, m), 6.90 (1H, s), 6.48 (1H, d), 5.17 (2H, s), 3.80 (3H, s), 3.03–2.97 (2H, m), 2.35 (3H, s), 2.31 (3H, s), 1.02 (3H, t); MS(ESI): 526 ($MH^+$).

EXAMPLE 270

A. Preparation of 5-Acetamidobenzothiazole

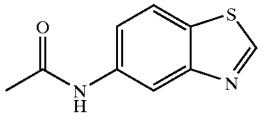

To a stirred solution of 4-chloro-3-nitroaniline (17.3 g, 100 mmol) in DCM (150 mL) was added dropwise acetic anhydride (14 mL, 150 mmol) at ambient temperature. The mixture was stirred at ambient temperature for 2.5 h. The solvent was removed in vacuo, and $Et_2O$ was added to the residue. The precipitate was collected by filtration, washed with $Et_2O$, and dried in vacuo to give N-(4-chloro-3-nitrophenyl)acetamide (20.7 g, 96%), which was used without further purification.

A suspension of the above compound (13.8 g, 64.3 mmol) and $Na_2S.9H_2O$ (18.6 g, 77.2 mmol) in DMF (100 mL) was stirred at ambient temperature under $N_2$ overnight. The reaction mixture was filtered, and the filtrate was diluted with water (400 mL) and then acidified with conc HCl to pH 3. The resulting yellow solids were collected by filtration, washed with water and dried under high vacuum to afford 4'-mercapto-3'-nitroacetanilide (12.0 g, 88%).

A suspension of 4'-mercapto-3'-nitroacetanilide (3.0 g, 14 mmol) and 10% Pd/C (0.6 g) in MeOH (200 mL) was hydrogenated at 60 psi overnight. The catalyst was removed by filtration, and the filtrate was concentrated to give 3'-amino-4'-mercaptoacetanilide (2.5 g, 13 mmol), which was used in the next reaction immediately.

To a solution of intermediate 3'-amino-4'-mercaptoacetanilide in HOAc (50 mL) was added ethoxymethylene malononitrile (1.95 g, 16 mmol) and the resulting mixture was refluxed at 125° C. for 5 h. After cooling, the product mixture was concentrated under reduced pressure, and the residue was partitioned between satd aqueous $NaHCO_3$ and EtOAc. The aqueous phase was extracted with EtOAc, and the combined extracts were washed with brine, dried over $Na_2SO_4$ and concentrated. The residue was purified by chromatography on silica gel, eluting with EtOAc-Hex (0:100 to 50:50) to give the title compound (508 mg, 17%) as a yellow solid. $^1$H-NMR (DMSO-$d_6$): δ 9.35 (1H, s), 8.53(1H, s), 8.10 (1H, d), 7.63 (1H, d), 2.15 (3H, s).

B. Preparation of 3-[3-Benzyl-5-(3-methyl-5-acetamido-3H-benzothiazol-2-ylidene)-4-oxothiazolidin-2-ylideneamino]-4-ethylaminobenzonitrile

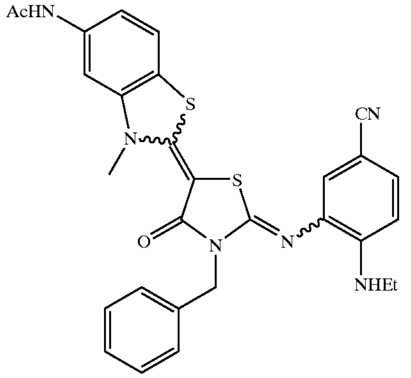

The title compound was prepared using the above 5-acetamidobenzothiazole as the starting material in a manner similar to that described in Example 265. $^1$H-NMR ($CDCl_3$): δ 7.45–7.21 (8H, m), 6.62 (1H, dd), 6.48 (1H, d), 6.34 (1H, d), 5.17 (2H, s), 3.79 (3H, s), 3.02 (3H,s), 3.00 (2H, m), 1.02 (3H, t); MS(ESI): 555 ($MH^+$).

EXAMPLE 271

A. Preparation of 2-Methylthio-6-(trifluoroacetoamido)benzothiazole

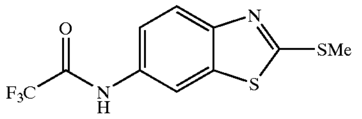

To a suspension of 6-amino-2-mercaptobenzothiazole (550 mg, 3.0 mmol) in anhydrous MeCN (15 mL) was added TEA (0.9 mL) and methyl p-toluenesulfonate (0.45 mL, 3.0 mmol) at ambient temperature. The mixture turned to a clear solution after a few minutes and was stirred at ambient temperature for 3 h. To the above solution was added dropwise TFAA (0.65 mL, 4.6 mmol). After 12 h the solution was concentrated under reduced pressure, diluted with EtOAc, washed with water and brine, dried over $Na_2SO_4$ and concentrated. The resulting residue was purified by chromatography on silica gel, eluting with EtOAc-Hex (0:100 to 10:90) to give the title compound (575 mg, 66%) as a white solid. $^1$H-NMR ($CDCl_3$): δ 8.31 (1H, d), 7.99 (1H, br s), 7.84 (1H, d), 7.35 (1H, dd), 2.80 (3H, s).

B. Preparation of N-{2-[3-Benzyl-2-(5-cyano-2-ethylaminophenylimino)-4-oxothiazilidin-4-ylidene]-3-methyl-2,3-dihydrobenzothiazol-5-yl}-2,2,2-trifluoroacetamide

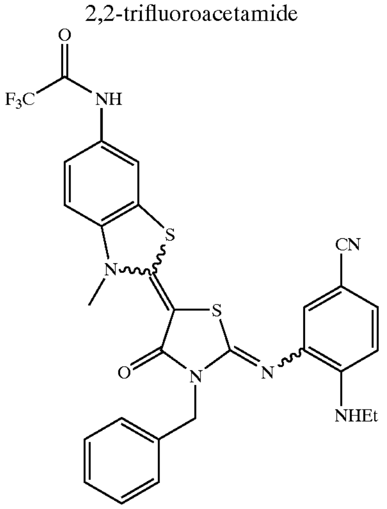

The title compound was prepared in a manner similar to that described in Example 265 by starting with 2-methylthio-6-(trifluoroacetamido)benzothiazole. $^1$H-NMR (DMSO-d$_6$): δ 7.82 (1H, d), 7.40–7.06 (8H, m), 6.90 (1H, d), 6.48 (1H, d), 6.40 (1H, d), 4.89 (2H, s), 3.57 (3H, s), 2.83 (2H, m), 0.77 (3H, t); MS(ESI): 609 (MH$^+$).

EXAMPLE 272

Preparation of 3-[5-(6-Amino-3-methyl-3H-benzothiazol-2-ylidene)-4-oxothiazolidin-2-ylideneamino]-4-ethylaminobenzonitrile

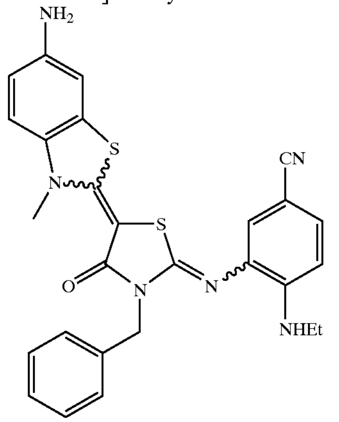

To the product of Example 271 (400 mg, 0.66 mmol) in a mixture of MeOH/$H_2O$ (12 mL, 5:1 v/v) was added potassium carbonate (553 mg, 4.0 mmol). The reaction mixture was stirred at 60° C. for 16 h, and then concentrated under reduced pressure. The resulting residue was partitioned between $CHCl_3$ and water. The aqueous phase was extracted with $CHCl_3$, and the combined extracts were washed with brine, dried over $Na_2SO_4$, and concentrated to give the title compound (326 mg, 97%) as a yellow solid. $^1$H-NMR (DMSO-d$_6$): δ 7.40–7.28 (6H, m), 7.15–7.13 (2H, m), 6.88 (1H, d), 6.66–6.61 (2H, m), 5.23 (2H, br s), 5.11 (2H, s), 3.75 (3H, s), 3.09–3.02 (2H, m), 1.01 (3H, t); MS(ESI): 513 (MH$^+$).

EXAMPLE 273

Preparation of N-{2-[3-Benzyl-2-(5-cyano-2-ethylaminophenylimino)-4-oxothiazolidin-5-ylidene]-3-methyl-2,3-dihydrobenzothiazol-6-yl}-N',N"-di(tert-butoxycarbonyl)guanidine

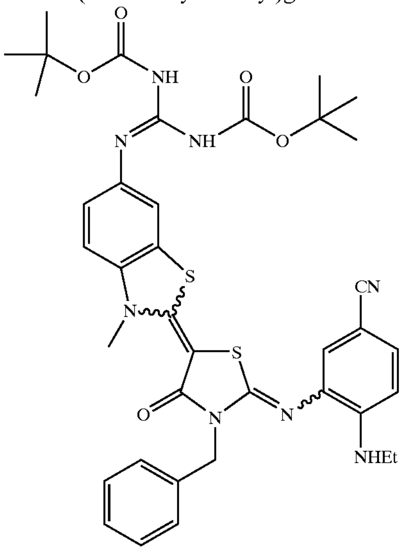

To a stirred mixture of the product of Example 272 (77 mg, 0.15 mmol), N,N'-di-(tert-butoxycarbonyl)thiourea (50 mg, 0.18 mmol) and TEA (70 μL, 0.5 mmol) in anhydrous DMF (1.5 mL) at 0° C. was added $HgCl_2$ (49 mg, 0.18 mmol). The resulting mixture was stirred at 0° C. for 30 min, then at ambient temperature overnight. The mixture was diluted with $CHCl_3$, washed with water and brine, dried over $Na_2SO_4$, and concentrated in vacuo. The residue was purified by chromatography on silica gel, eluting with MeOH-DCM (0:100 to 20:80) to afford the title compound (98 mg, 87%). $^1$H-NMR ($CDCl_3$): δ 11.62 (1H, br s), 10.43 (1H, br s), 8.02 (2H, m), 7.45–7.20 (7H, m), 7.02 (1H, d), 6.49 (1H, t), 5.16 (2H, s), 3.82 (3H, s), 3.04–2.96 (2H, m), 1.43 (9H, s), 1.35 (9H, s), 1.02 (3H, t); MS(ESI): 756 (MH$^+$).

EXAMPLE 274

Preparation of 2-{2-[3-Benzyl-2-(5-cyano-2-ethylaminophenylimino)-4-oxothiazilidin-5-ylidene]-3-methyl-2,3-dihydrobenzothiazol-6-yl}-1,1,-dimethylurea

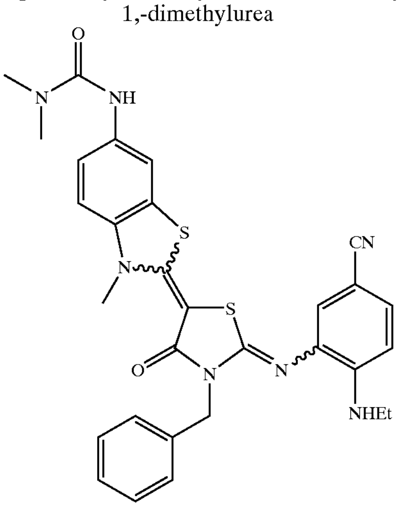

To the product of Example 272 (89 mg, 0.174 mmol) in anhydrous $CHCl_3$ (5 mL) were added TEA (0.3 mL, 2.4 mmol) and dimethylcarbamyl chloride (0.2 mL, 2.0 mmol). The resulting mixture was stirred at ambient temperature overnight. After diluting with $CHCl_3$, the mixture was washed with satd $NaHCO_3$ and brine, dried over $Na_2SO_4$, and concentrated in vacuo. The residue was purified by chromatography on silica gel, eluting with MeOH-DCM (0:100 to 5:95) to afford the title compound (48 mg, 47%). $^1$H-NMR ($CDCl_3$): δ 7.70 (1H, d), 7.44–7.26 (8H, m), 7.20 (1H, d), 7.00 (1H, d), 6.48 (1H, d), 6.38 (1H, s), 5.16 (2H, s), 3.79 (3H, s), 3.06 (6H, s), 3.05–2.97 (2H, m), 1.02 (3H, t); MS(ESI): 584 ($MH^+$).

EXAMPLE 275

A. Preparation of 5-Acetamido-2-mercaptobenzothiazole

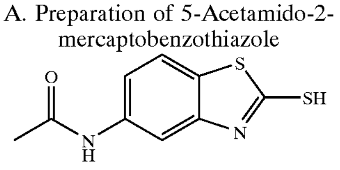

To a stirred solution of 4-chloro-3-nitroaniline (51.8 g, 0.36 mol) in anhydrous DCM (300 mL) was added dropwise acetic anhydride (45 mL, 0.48 mol) at room temperature, and the resulting solution was stirred at room temperature for 3 h. The solvent was removed in vacuo, and $Et_2O$ was added to the residue. The precipitates were collected by filtration, washed thoroughly with $Et_2O$, and dried under high vacuum to give 4'-chloro-3'-nitroacetanilide (78.7 g, 100%).

A mixture of $Na_2S.9H_2O$ (65 g, 0.28 mol), sulfur (25 g, 0.78 mol) and water (150 mL) were heated with stirring at 90° C. for 10 min, and then poured into a flask charged with the above 4'-chloro-3'-nitroacetanilide (21.5 g, 0.10 mol). The resulting mixture was heated at 80° C. for 10 min, and then $CS_2$ (12 mL, 0.2 mol) was added dropwise while maintaining a gentle reflux. The resulting mixture was heated at 90° C. for 7 h. The solids were collected by filtration, washed with water and dilute HCl solution. The solids were taken up in water, and the solution was made alkaline with solid NaOH. The solution was filtered, and the filtrate was acidified with conc HCl. The precipitates were collected by filtration, washed with water, and dried under high vacuum. The crude product was suspended in cold water (200 mL) and solid $Na_2CO_3$ was added to obtain pH 13. Dimethyl sulfate was added to the above milky solution, and the resulting mixture was stirred at ambient temperature for 3 h. The solids were collected by filtration, washed with water, and dried under high vacuum to yield the title compound (12.4 g, 55%).

B. Preparation of 2-Methylthio-5-(2,2,2-trifluoroacetamido)benzothiazole

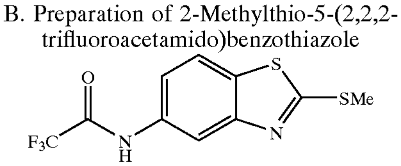

A suspension of 5-acetamido-2-mercaptobenzothiazole (12.9 g, 54 mmol) in a mixture of conc HCl (30 mL) and water (60 mL) was heated at reflux for 3 h. After cooling, the mixture was extracted with $CHCl_3$, and the aqueous phase was diluted with ice-water. To the aqueous layer was added portionwise solid NaOH to achieve pH 6, and then solid $K_2CO_3$ to obtain pH 8. The precipitates were collected by filtration, washed with water, and dried under high vacuum to yield 5-amino-2-methylthiobenzothiazole (7.65 g, 72%).

To a stirred solution of 5-amino-2-methylthiobenzothiazole (3.93 g, 20 mmol) in anhydrous MeCN were added dropwise at 0° C. TFM (4.0 mL, 28 mmol) and TEA (5 mL, 36 mmol) under $N_2$. The mixture was stirred at room temperature for 3 h. The solvent was removed in vacuo, and the residue was taken up in EtOAc, washed with water and brine, dried with $Na_2SO_4$, and concentrated in vacuo. The crude material was purified by chromatography on silica gel, eluting with EtOAc-Hex (0:100 to 20:80) to afford the title, compound (3.9 g, 67%) as a pale white solid. $^1$H-NMR ($CDCl_3$): δ 8.10 (1H, d), 7.98 (1H, br s), 7.75 (1H, d), 7.53–7.51 (1H, dd), 2.80 (3H, s).

C. Preparation of N-{2-[3-Benzyl-2-(5-cyano-2-ethylaminophenylimino)-4-oxothiazilidin-5-ylidene]-3-methyl-2,3-dihydrobenzothiazol-5-yl}-2,2,2-trifluoroacetamide

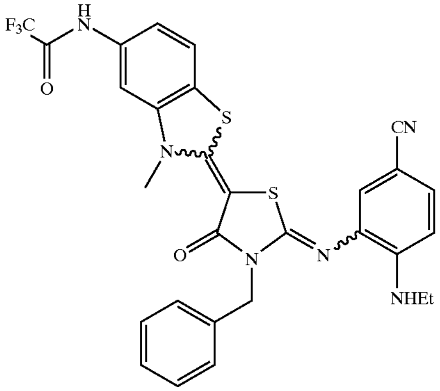

The title compound was prepared from 2-methylthio-5-trifluoroacetoamido-benzothiazole in a manner similar to that described in Example 265. $^1$H-NMR (DMSO-$d_6$): δ 7.82 (1H, d), 7.56–7.26 (8H, m), 7.16 (1H, d), 6.51 (1H, d), 5.16 (2H, s), 3.83 (3H, s), 3.03–2.96 (2H, m), 1.02 (3H, t); MS(ESI): 609 ($MH^+$).

EXAMPLE 276

Preparation of 3-[5-(5-Amino-3-methyl-3H-benzothiazol-2-ylidene)-4-oxothiazolidin-2-ylideneamino]-4-ethylaminobenzonitrile

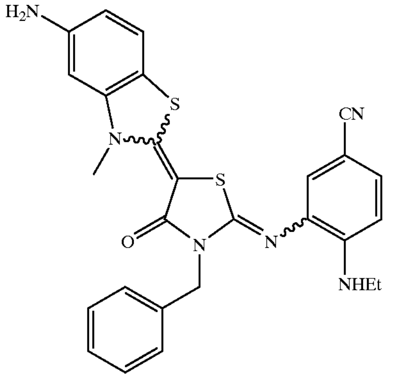

The title compound was prepared-from the product of Example 275 in a manner similar to that described in Example 272. $^1$H-NMR (DMSO-$d_6$): δ 8.38 (1H, s), 7.47–7.36 (6H, m), 7.21 (1H, d), 6.69 (1H, d), 6.61–6.56 (2H, m), 4.45 (2H, br s), 5.18 (2H, s), 3.78 (3H, s), 3.12 (2H, m), 1.06 (3H, t) MS(ESI): 513 ($MH^+$).

EXAMPLE 277

Preparation of {2-[3-Benzyl-2-(5-cyano-2-ethylaminophenylimino)-4-oxothiazilidin-5-ylidene]-3-methyl-2,3-dihydrobenzothiazol-6-yl}carbamic Acid Ethyl Ester

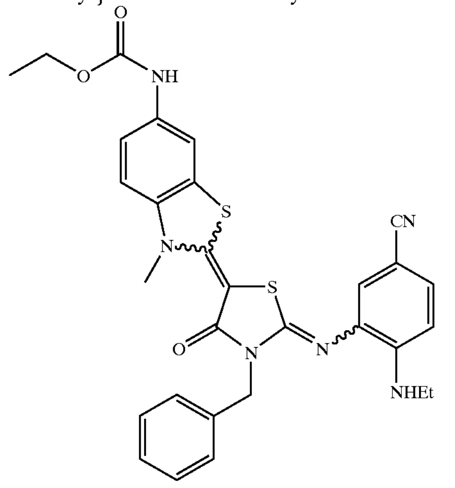

The title compound was prepared in a manner similar to that described in Example 274 by replacing dimethylcarbamyl chloride with ethyl choroformate. $^1$H-NMR (DMSO-$d_6$): δ 9.64 (1H, s), 7.75 (1H, d), 7.29–7.16 (8H, m), 7.02 (1H, d), 6.51 (1H, d), 5.00 (2H, s), 4.04–3.98 (2H, q), 3.68 (3H, s), 2.97–2.91 (2H, m), 1.26 (3H, t), 0.88 (3H, t); MS(ESI): 585 ($MH^+$).

EXAMPLE 278

Preparation of N-[2-(3-Benzyl-2-{5-cyano-2-[ethyl-2-morpholin-ylethyl)amino]phenylimino}-4-oxothiazilidin-5-ylidene)-3-methyl-2,3-dihydrobenzothiazol-6-yl]-2,2,2-trifluoroacetamide

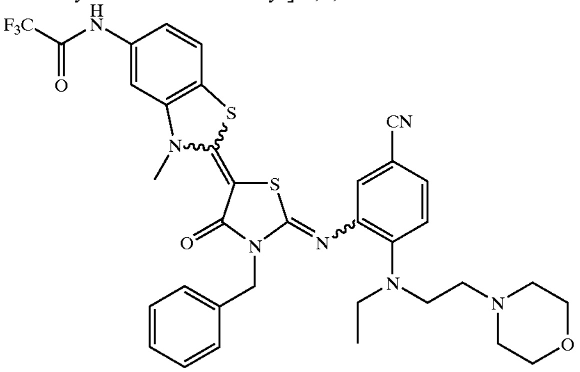

Sodium hydride (8 mg, 60% w/w in mineral oil, 0.2 mmol) was added at 0° C. to a stirred solution of the product of Example 271 (52 mg, 0.1 mmol) in anhydrous DMF under $N_2$. The mixture was stirred at 0° C. for 5 min, then at ambient temperature for 15 min. 4-(2-Chloroethyl) morpholine hydrochloride 24 mg, 0.15 mmol) was added to the above red solution at 0° C., and the mixture was stirred at ambient temperature under $N_2$ for 21 h. The reaction mixture was diluted with $CHCl_3$, washed thoroughly with water, dried over $Na_2SO_4$, and concentrated under reduced pressure. The residue was purified by chromatography on silica gel, eluting with MeOH-DCM (0:100 to 20:80) to afford the title compound (42 mg, 58%) as a yellow solid. $^1$H-NMR ($CDCl_3$): δ 8.98 (1H, br s), 7.92 (1H, s), 7.68 (1H, s), 7.51–7.22 (7H, m), 6.81 (1H, d), 5.12 (2H, s), 4.04 (2H, m), 3.64 (5H, m), 3.36 (2H, m), 2.54–2.17 (8H, m), 1.26 (3H, m); MS(ESI): 722 ($MH^+$).

EXAMPLE 279

Preparation of N-{2-[3-Benzyl-2-(5-cyano-2-ethylaminophenylimino)-4-oxothiazilidin-5-ylidene]-3-methyl-2,3-dihydrobenzothiazol-6-yl}-2,2,2-trifluoro-N-(2-morpholin-4ylethyl)acetamide

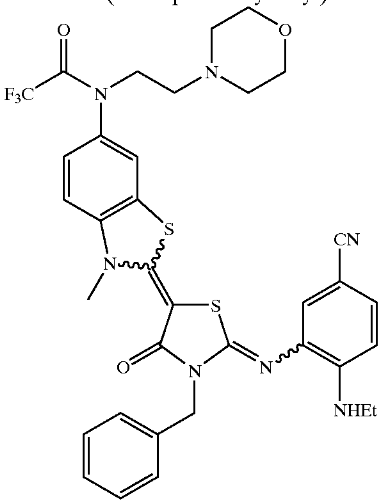

To the product of Example 271 (65 mg, 0.11 mmol) in anhydrous DMF were added 4-(2-chloroethyl)morpholine hydrochloride (50 mg, 0.3 mmol), $K_2CO_3$ (30 mg, 0.21 mmol) and KI (10 mg). The reaction mixture was heated at 90° C. for 30 h, cooled, and diluted with $CHCl_3$. The solution was washed with water, dried over $Na_2SO_4$, and concentrated in vacuo. The crude material was purified by chromatography on silica gel, eluting with MeOH-DCM (0:100 to 20:80) to afford the title compound (72 mg, 94%) as a yellow solid. $^1$H-NMR ($CDCl_3$): δ 7.51 (1H, s), 7.44–7.42 (2H, m), 7.38–7.28 (5H, m), 7.19 (1H, d), 7.09 (1H, d), 5.18 (2H, s), 4.21 (2H, br s), 3.85 (3H, s), 3.68 (4H, br s), 3.05–2.96 (2H, m), 2.52–2.45 (6H, m), 1.03 (3H, t); MS(ESI): 722 ($MH^+$).

EXAMPLE 280

Preparation of 3-{3-Benzyl-5-[3-methyl-6-(2-morpholin-4-yl-ethylamino)-3H-benzothiazol-2-ylidene]-4-oxothiazolidin-2-ylideneamino}-4-ethylaminobenzonitrile

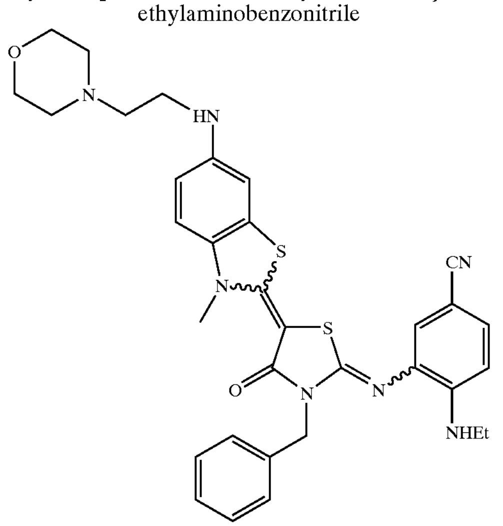

The title compound was prepared from the product of Example 279 in a manner similar to that described in Example 272. $^1$H-NMR ($CDCl_3$): δ 7.44–7.21 (7H, m), 6.93 (1H, d), 6.78 (1H, d), 6.65 (1H, m), 6.48 (1H, d), 5.17 (2H, s), 3.81 (3H, s), 3.80–3.74 (4H, m), 3.20–3.17 (2H, m), 3.03–2.96 (2H, m), 2.67 (2H, br s), 2.49 (4H, br s), 1.02 (3H, t); MS(ESI): 626 ($MH^+$).

EXAMPLE 281

Preparation of 3-{3-Benzyl-5-[3-methyl-6-(2-piperidin-1-yl-ethylamino)-3H-benzothiazol-2-ylidene]-4-oxothiazolidin-2-ylideneamino}-4-ethylaminobenzonitrile

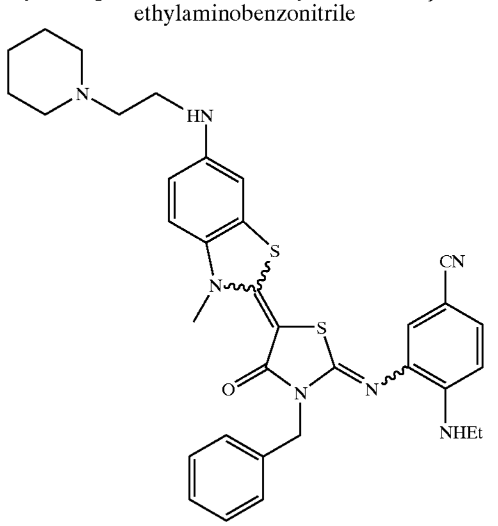

The title compound was prepared in a manner similar to that described in Examples 279 and 280 by replacing 4-(2-chloroethyl)morpholine hydrochloride with 4-(2-chloroethyl)piperidine hydrochloride. $^1$H-NMR ($CDCl_3$): δ 7.44–7.19 (7H, m), 6.93 (1H, d), 6.77–6.71 (2H, m), 6.48 (1H, d), 5.16 (2H, s), 3.77 (3H, s), 3.28 (2H, br s), 3.03–2.96 (2H, m), 2.81 (2H, br s), 2.48 (2H, br s), 2.04 (4H, br s), 1.02 (3H, t); MS(ESI): 624 ($MH^+$).

EXAMPLE 282

Preparation of N-{2-[3-Benzyl-2-(5-cyano-2-ethylaminophenylimino)-4-oxothiazilidin-5-ylidene]-3-methyl-2,3-dihydrobenzothiazol-5-yl}-2,2,2-trifluoro-N-(2-morpholin-4ylethyl)acetamide

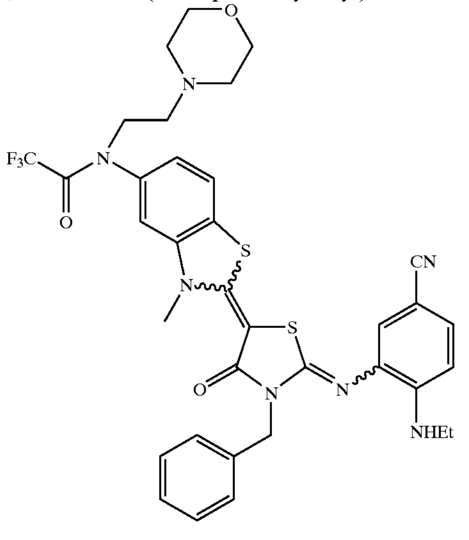

The title compound was prepared from the product of Example 275 in a manner similar to that described in Example 279. $^1$H-NMR ($CDCl_3$): δ 7.54 (1H, d), 7.44–7.11 (9H, m), 6.50 (1H, d), 5.18 (2H, s), 3.95 (2H, m), 3.79 (3H, s), 3.70 (4H, m), 3.04–2.98 (2H, m), 2.49 (6H, m), 1.03 (3H, t); MS(ESI): 722 ($MH^+$).

EXAMPLE 283

Preparation of 3-{3-Benzyl-5-[3-methyl-5-(2-morpholin-4-yl-ethylamino)-3H-benzothiazol-2-ylidene]-4-oxothiazolidin-2-ylideneamino}-4-ethylaminobenzonitrile

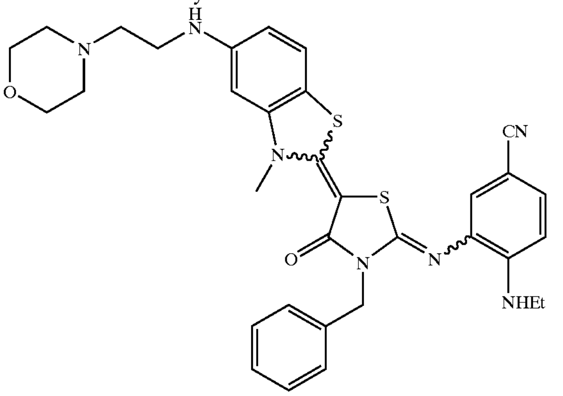

The title compound was prepared from the product of Example 282 in a manner similar to that described in Example 272. $^1$H-NMR ($CDCl_3$): δ 7.54 (1H, d), 7.44–7.11 (9H, m), 6.50 (1H, d), 5.18 (2H, s), 3.80 (2H, s), 3.70 (4H, br s), 3.04–2.98 (2H, m), 2.49 (6H, br s), 1.03 (3H, t); MS(ESI): 626 ($MH^+$).

EXAMPLE 284

Preparation of N-{2-[3-Benzyl-2-(5-cyano-2-ethylaminophenylimino)-4-oxothiazolidin-5-ylidene]-3-methyl-2,3-dihydrobenzothiazol-6-yl}guanidine

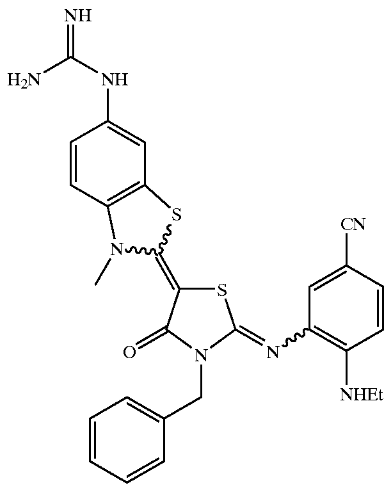

To a stirred solution of the product of Example 273 (116 mg, 0.15 mmol) in anhydrous DCM (6 mL) was added TFA (3 mL) at 0° C. The reaction mixture was stirred at 0° C. for 30 min, then at ambient temperature for 14 h. The solvent was removed in vacuo, and the residue was purified by reverse-phase HPLC (C18 column), eluting with 0.05% TFA in MeCN—$H_2O$ (1:9 to 9:1) to afford the title compound (25 mg, 30%) as a yellow solid. $^1$H-NMR (DMSO-$d_6$): δ 9.65 (1H, s), 7.72 (1H, d), 7.48 (1H, d), 7.41–7.25 (8H, m), 7.15 (1H, d), 6.65 (1H, d), 5.14 (2H, s), 3.84 (3H, s), 3.07 (2H, m), 1.01 (3H, t); MS(ESI): 555 (MH$^+$).

EXAMPLE 285

Preparation of 3-{3-Benzyl-5-[3-methyl-6-(4-trifluoromethylbenzylamino)-3H-benzothiazol-2-ylidene]-4-oxothiazolidin-2-ylideneamino}-4-ethylaminobenzonitrile

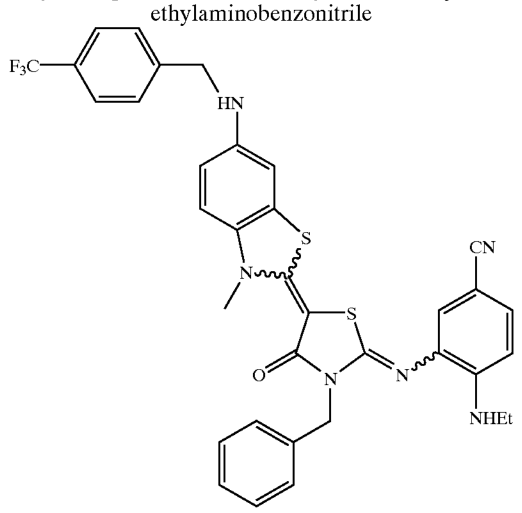

The title compound was prepared in a manner similar to that described in Examples 279 and 280 by replacing 4-(2-chloroethyl)morpholine hydrochloride with 4-(trifluoromethyl)benzyl bromide. $^1$H-NMR (DMSO-$d_6$): δ 7.69 (2H, d), 7.58 (2H, d), 7.38–7.32 (6H, m), 7.17 (1H, d), 7.14 (1H, d), 6.94 (1H, d), 6.63 (1H, dd), 6.61 (1H, d), 5.10 (2H, s), 4.40 (2H, s), 3.73 (3H, s), 3.05 (2H, m), 1.00 (3H, t); MS(ESI): 671 (MH$^+$).

EXAMPLE 286

Preparation of N-{2-[3-Benzyl-2-(5-cyano-2-ethylaminophenylimino)-4-oxothiazilidin-5-ylidene]-3-methyl-2,3-dihydrobenzothiazol-6-yl}-N-(3-fluoropropyl)-2,2,2-trifluoroacetamide

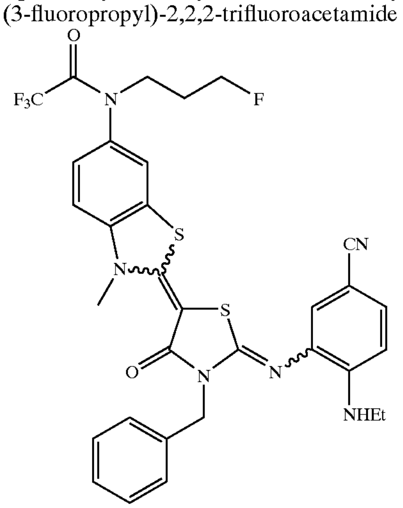

The title compound was prepared in a manner similar to that described in Example 279 by replacing 4-(2-chloroethyl)morpholine hydrochloride with 1-bromo-3-fluoropropane. $^1$H-NMR ($CDCl_3$): δ 7.44–7.19 (9H, m), 7.10 (1H, d), 6.50 (1H, d), 5.18 (2H, s), 4.60 (1H, m), 4.48 (1H, m), 4.20 (1H, m), 3.91 (1H, m), 3.83 (3H, s), 3.01 (2H, m), 2.09–1.99 (2H, m), 1.03 (3H, t); MS(ESI): 669 (MH$^+$).

EXAMPLE 287

Preparation of N-{2-[3-Benzyl-2-(5-cyano-2-ethylaminophenylimino)-4-oxothiazilidin-5-ylidene]-3-methyl-2,3-dihydrobenzothiazol-6-yl}-N-(3-cyanopropyl)-2,2,2-trifluoroacetamide

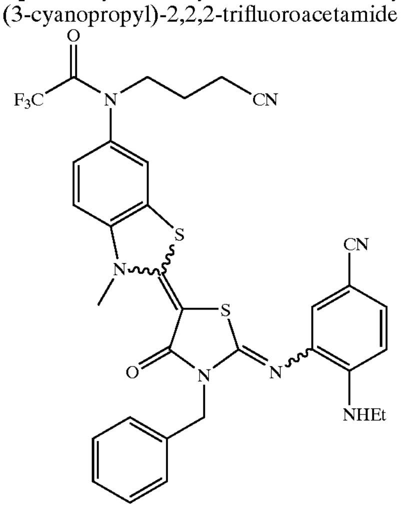

The title compound was prepared in a manner similar to that described in Example 279 by replacing 4-(2-chloroethyl)morpholine hydrochloride with 4-bromobutyronitrile. $^1$H-NMR ($CDCl_3$): δ 7.44–7.19 (9H, m), 7.11 91H, d), 6.51 91H, d), 5.19 (2H, s), 3.86 (3H, s), 3.85–3.77 (2H, m), 3.05–2.98 (2H, m), 2.53–2.44 (2H, m), 2.04–1.88 (2H, m), 1.03 (3H, t); MS(ESI): 676 (MH$^+$).

EXAMPLE 288

Preparation of 3-{3-Benzyl-5-[6-(3-cyanopropylamino)-3-methyl-3H-benzothiazol-2-ylidene]-4-oxothiazolidin-2-ylideneamino}-4-(ethylamino)benzonitrile

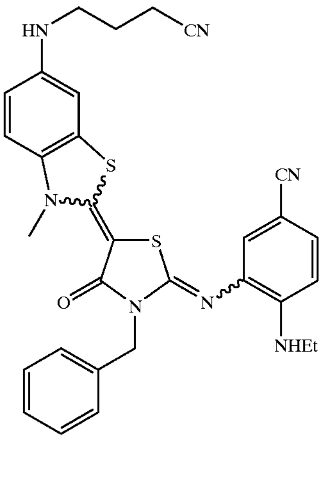

The title compound was prepared from the product of Example 287 in a manner similar to that described in Example 272. $^1$H-NMR ($CDCl_3$): δ 7.44–7.20 (7H, m), 6.94 (1H, d), 6.77 (1H, d), 6.65 (1H, dd), 6.48 (1H, d), 5.17 (2H, s), 3.77 (3H, s), 3.34 (2H, m), 3.01 (2H, m), 2.49 (2H, m), 2.01 (2H, m), 1.02 (3H, t); MS(ESI): 580 ($MH^+$).

EXAMPLE 289

Preparation of 3-{3-Benzyl-5-[6-(3-hydroxypropylamino)-3-methyl-3H-benzothiazol-2-ylidene]-4-oxothiazolidin-2-ylideneamino}-4-(ethylamino)benzonitrile

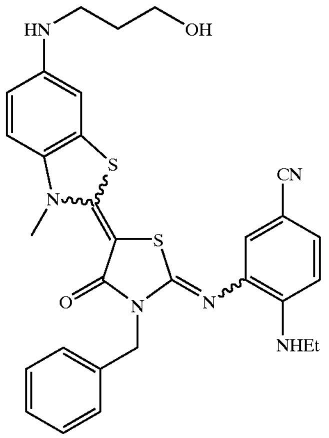

The title compound was prepared in a manner similar to that described in Examples 279 and 280 by replacing 4-(2-chloroethyl)morpholine hydrochloride with 3-bromopropanol. $^1$H-NMR ($CDCl_3$): δ 7.44–7.21 (8H, m), 6.93 (1H, d), 6.79 (1H, d), 6.65 (1H, dd), 6.48 (1H, d), 5.17 (2H, s), 3.85 (2H, m), 3.77 (3H, s), 3.30 (2H, t), 3.01 (2H, m), 1.92 (2H, m), 1.02 (3H, t); MS(ESI): 571 ($MH^+$).

EXAMPLE 290

Preparation of 3-{3-Benzyl-5-[6-(2-methoxyethylamino)-3-methyl-3H-benzothiazol-2-ylidene]-4-oxothiazolidin-2-ylideneamino}4-(ethylamino)benzonitrile

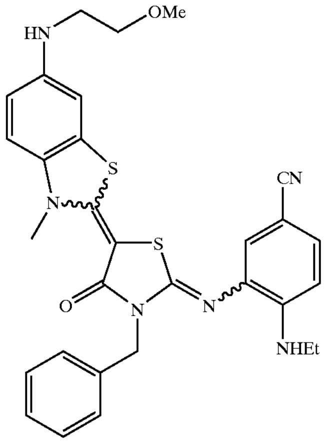

The title compound was prepared in a manner similar to that described in Examples 279 and 280 by replacing 4-(2-chloroethyl)morpholine hydrochloride with 2-bromoethyl methyl ether. $^1$H-NMR ($CDCl_3$): δ 7.44–7.21 (7H, m), 6.93 (1H, d), 6.79 (1H, d), 6.66 (1H, dd), 6.48 (1H, d), 5.17 (2H, s), 3.77 (3H, s), 3.63 (2H, m), 3.41 (3H, s), 3.30 (2H, m), 3.00 (2H, m), 1.02 (3H, t); MS(ESI): 571 ($MH^+$).

EXAMPLE 291

In Vivo Studies

In order to evaluate direct regulation of key target genes by the compounds of the invention, animals are administered a single oral dose of the test compound and tissues collected at six or fifteen hours after dose. Male C57BL/6 mice (n=8) are dosed by oral gavage with vehicle or compound. At six and fifteen hours after the dose, animals are bled via the retro orbital sinus for plasma collection. Animals are then euthanized and tissues, such as liver and intestinal mucosa are collected and snap frozen for further analysis. Plasma is analyzed for lipid parameters, such as total cholesterol, HDL cholesterol and triglyceride levels. RNA is extracted for frozen tissues and can be analyzed by quantitative real time PCR for regulation of key target genes. To identify specificity of target gene regulation by FXR, knock out mice ($FXR^{-/-}$) and C57BL/6 wild-type controls maybe used in this same protocol.

Plasma Lipid Evaluation

To compare the effects of compounds on plasma cholesterol and triglycerides, animals are dosed with compound for one week and plasma lipid levels are monitored throughout the study. Male C57BL/6 mice (n=8) are dosed daily by oral gavage with vehicle or compound. Plasma samples are taken on day-1 (in order to group animals), day 1, 3, and 7. Samples are collected three hours after the daily dose. On day 7 of the study, following plasma collection, animals are euthanized and tissues, such as liver and intestinal mucosa are collected and snap frozen for further analysis. Plasma is analyzed for lipid parameters, such as total cholesterol, HDL cholesterol and triglyceride levels. RNA is extracted for frozen tissues and can be analyzed by quantitative real time PCR for regulation of key target genes. To identify specificity of target gene regulation by FXR knockout mice and C57BL/6 wild-type controls maybe used in this same protocol.

Cholesterol Absorption

Evaluation of compounds to inhibit cholesterol absorption is done via measurement of labeled cholesterol in feces. Male A129 mice (n=7) are dosed daily by oral gavage with vehicle or compound for 7 days. On day 7 of the study, animals are administered [$^{14}$C]-cholesterol and [$^3$H]-sitostanol by oral gavage. Animals are individually housed on wire racks for the next 24 hours in order to collect feces. Feces are then dried and ground to a fine powder. Labeled cholesterol and sitostanol are extracted from the feces and ratios of the two are counted on a liquid scintillation counter in order to evaluate the amount of cholesterol absorbed by the individual animal.

Since modifications will be apparent to those of skill in this art, it is intended that the subject matter claimed herein be limited only by the scope of the appended claims.

What is claimed is:

1. A compound that has formulae I:

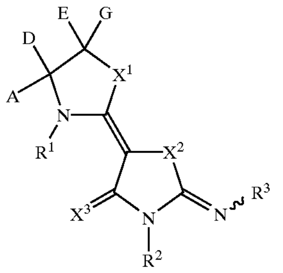

or

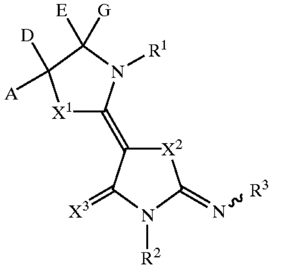

or a pharmaceutically acceptable derivative thereof, wherein:

$X^1$, $X^2$ and $X^3$ are selected from (i) or (ii) as follows:

(i) $X^1$, $X^2$ and $X^3$ are each independently S, O or $NR^5$; or (ii) $X^1$ is —$CR^8$═$CR^9$—, where $R^8$ and $R^9$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo, pseudohalo, $OR^{10}$, $NR^{14}R^{15}$ and C(═J)$R^{13}$; and $X^2$ and $X^3$ are each independently S, O or $NR^5$;

$R^1$ is substituted or unsubstituted alkyl;

$R^2$ is substituted or unsubstituted aralkyl, substituted or unsubstituted aryl, substituted or unsubstituted alkenyl, substituted or unsubstituted alkyl, substituted or unsubstituted cycloalkyl, substituted or unsubstituted heteroaralkyl, or substituted or unsubstituted heterocyclylalkyl;

$R^3$ is substituted or unsubstituted heteroaryl, substituted or unsubstituted aryl, or substituted or unsubstituted aralkyl;

A and G are selected from (i), (ii) or (iii) as follows:

(i) A and G are each independently selected from hydrogen, substituted or unsubstituted aryl, substituted or unsubstituted alkyl, substituted or unsubstituted alkoxycarbonyl, hydroxycarbonyl, and substituted or unsubstituted alkylcarbonyl, where the substituents, when present, are each selected independently from $Q^1$, with the proviso that when $R^1$ is Et, $X^1$ and $X^2$ are S, $X^3$ is O, $R^3$ is 3-methylphenyl, $R^2$ is allyl, and D and E form a bond, then A and G are not both methyl; or (ii) A and G together form substituted or unsubstituted alkylene, or substituted or unsubstituted azaalkylene, where the substituents, when present, are each selected independently from $Q^1$; or (iii) A and G together form substituted butadienyl, where there are 1 to 4 substituents selected from $Q^1$, with the provisos that (a) when $X^1$ and $X^2$ are S and $X^3$ is O, then the resulting benzothiazolyl group is not mono-substituted at the 5-position with methoxy or chloro or at the 6-position with methoxy, and (b) when $X^1$ is —$CR^8$═$CR^9$—, $X^2$ is S and $X^3$ is O, then the resulting quinolyl group is not mono-substituted at the 6-position with methoxy or methyl;

D and E are each hydrogen, or together form a bond; and $R^5$ is hydrogen, substituted or unsubstituted alkyl substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo, pseudohalo, $OR^{10}$, $SR^{10}$, S(═O)$R^{13}$, S(═O)$_2R^{13}$, $NR^{14}R^{15}$ or C(═J)$R^{13}$;

$R^{10}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl or C(═J)$R^{13}$;

J is O, S or $NR^{14}$;

$R^{13}$ is selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, pseudohalo, $OR^{16}$ and $NR^{14}R^{15}$;

$R^{14}$, $R^{15}$ and $R^{16}$ are each independently selected from hydrogen, alkyl, alkenyl, alkynyl, cycloalkyl, heterocyclyl, cycloalkylalkyl, heterocyclylalkyl, aryl, heteroaryl, aralkyl and heteroaralkyl;

wherein the alkyl, alkenyl, alkynyl, cycloalkyl, heterocyclyl, cycloalkylalkyl, heterocyclylalkyl, aryl, heteroaryl, aralkyl and heteroaralkyl moieties of $R^1$, $R^2$, $R^3$, $R^5$, $R^{10}$, $R^{13}$, A and G, when substituted, are substituted with one or more substituents each independently selected from $Q^1$, where $Q^1$ is halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, imino, hydroxyimino, alkoxyimino, aralkoxyimino, arylazo, haloalkylcarbonylamino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{51}R^{52}R^{53}$, $P(R^{50})_2$, $P({=}O)(R^{50})_2$, $OP({=}O)(R^{50})_2$, $—NR^{60}C({=}O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy, thioalkylenoxy or alkylenedithioxy; or two $Q^1$ groups, which substitute the same atom, together form alkylene;

each $Q^1$ is independently unsubstituted or substituted with one or more substituents each independently selected from $Q^2$;

each $Q^2$ is independently halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{51}R^{52}R^{53}$, $P(R^{50})_2$, $P({=}O)(R^{50})_2$, $OP({=}O)(R^{50})_2$, $—NR^{60}C({=}O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^2$ groups, which substitute atoms in a 1,2 or 1,3 arrangement, together form alkylenedioxy, thioalkylenoxy or alkylenedithioxy where y is 1 or 2; or two $Q^2$ groups, which substitute the same atom, together form alkylene;

$R^{50}$ is hydroxy, alkoxy, aralkoxy, alkyl, heteroaryl, heterocyclyl, aryl or —$NR^{70}R^{71}$, where $R^{70}$ and $R^{71}$ are each independently hydrogen, alkyl, aralkyl, aryl, heteroaryl, heteroaralkyl or heterocyclyl, or $R^{70}$ and $R^{71}$ together form alkylene, azaalkylene, oxaalkylene or thiaalkylene;

$R^{51}$, $R^{52}$ and $R^{53}$ are each independently hydrogen, alkyl, aryl, aralkyl, heteroaryl, heteroaralkyl, heterocyclyl or heterocyclylalkyl;

$R^{60}$ is hydrogen, alkyl, aryl, aralkyl, heteroaryl, heteroaralkyl, heterocyclyl or heterocyclylalkyl; and $R^{63}$ is alkoxy, aralkoxy, alkyl, heteroaryl, heterocyclyl, aryl or —$NR^{70}R^{71}$.

2. The compound of claim 1, wherein $X^1$ is S.

3. The compound of claim 1, wherein $X^2$ is S.

4. The compound of claim 1, wherein $X^3$ is O.

5. The compound of claim 1 that has formulae II:

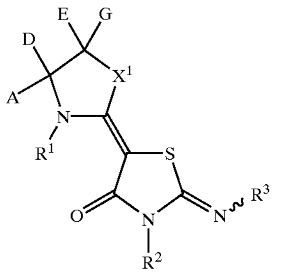

or

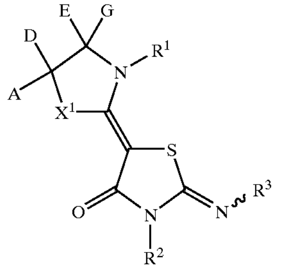

6. The compound of claim 1, wherein $R^1$ is unsubstituted alkyl.

7. The compound of claim 1, wherein $R^1$ is methyl.

8. The compound of claim 1, wherein $R^2$ is benzyl, phenyl, allyl, ethyl, butyl, cyclohexyl, propyl, 3-pyridylmethyl, 2-furylmethyl, 4-methoxycarbonylbenzyl, 4-hydroxycarbonylbenzyl, 2-phenethyl, 2-pyridylmethyl, 4-pyridylmethyl or 2-(4-morpholinyl)ethyl.

9. The compound of claim 1, wherein $R^2$ is benzyl, 3-pyridylmethyl or 2-furylmethyl.

10. The compound of claim 1, wherein $R^3$ is substituted or unsubstituted quinolyl, substituted or unsubstituted phenyl, substituted or unsubstituted naphthyl, substituted or unsubstituted isoquinolyl, substituted or unsubstituted pyridyl, or substituted or unsubstituted indazolyl.

11. The compound of claim 1, wherein $R^3$ is substituted or unsubstituted phenyl.

12. The compound of claim 1, wherein $R^3$ is substituted with 0 to 5 substituents selected from ethylamino, cyano, cyclohexyl, hydroxy, methoxy, dimethylamino, amino, 4-morpholinyl, methylamino, isopropylamino, benzyloxy, methyl, isopropyl, nitro, trifluoromethyl, methylcarbonyl, chloro, propyl, ethoxy, methylcarbonylamino, aminocarbonyl, methoxycarbonyl, butylamino, benzylamino, cyclopentylamino, 1-pyrrolidinylamino, pyrrolidinyl, t-butylamino, 2,2,2-trifluoroethylamino, piperidinyl, trifluoromethoxy, hydroxycarbonyl, aminosulfonyl, methylcarbonylaminosulfonyl, trifluoromethylcarbonylamino and t-butoxycarbonyl, or any two substituents, which substitute atoms in a 1,2 arrangement, together form methylenedioxy.

13. The compound of claim 1, wherein $R^3$ is 5-quinolyl, 2-ethylamino-5-cyanophenyl, 4-cyclohexylphenyl, 2-hydroxy-1-naphthyl, 6-quinolyl, 3-methoxyphenyl, 4-dimethylaminophenyl, 4-aminophenyl, 4-(4-morpholinyl) phenyl, 2-methylamino-5-cyanophenyl, 2-dimethylamino-5-cyanophenyl, 2-ethylaminophenyl, 3-cyanophenyl, 2-aminophenyl, 2-isopropylamino-5-cyanophenyl, 4-benzyloxyphenyl, 2-methyl-4-hydroxy-5-isopropylphenyl, 2-ethylamino-5-nitrophenyl, 3-trifluoromethylphenyl, 3-methylcarbonylphenyl, 3-chlorophenyl, 2-propylphenyl, 2-ethoxyphenyl, 3-methylcarbonylaminophenyl, 3-aminocarbonylphenyl, 3-methoxycarbonylphenyl, 8-quinolyl, 8-hydroxy-5-quinolyl, 2-butylamino-5-cyanophenyl, 2-benzylamino-5-cyanophenyl, 2-cyclopentylamino-5-cyanophenyl, 2-(1-pyrrolidinyl)amino-5-cyanophenyl, 5-isoquinolyl, 1-isoquinolyl, 4-methylcarbonylaminophenyl, 2-t-butylamino-5-cyanophenyl, 2-(2,2,2-trifluoroethyl)amino-5-cyanophenyl, 2-piperidinyl-5-cyanophenyl, 4-methylcarbonylphenyl, 4-aminocarbonylphenyl, 1-naphthyl, 2-naphthyl, 2-pyridyl, 3-pyridyl, 2-ethoxy-5-methylcarbonylaminophenyl, 4-pyridyl, 4-methoxycarbonylphenyl, 4-trifluoromethoxyphenyl, 5-indazolyl, 4-(imidazol-1-yl)phenyl, 3,4-methylenedioxyphenyl, 3-hydroxycarbonylphenyl, 2-ethylamino-5-methylcarbonylphenyl, 4-aminosulfonylphenyl, 4-methylcarbonylaminosulfonylphenyl, 3-methylcarbonylphenyl, 2-methylcarbonylamino-5-pyridyl, 4-cyano-3-methylcarbonylaminophenyl, 2-methylamino-5-methylcarbonylphenyl, 4-trifluoromethylcarbonylaminophenyl, 2-ethylamino-5-methoxycarbonylphenyl, 2-hydroxycarbonylphenyl or 2-ethylamino-5-t-butoxycarbonylphenyl.

14. The compound of claim 1, wherein A and G are each independently selected from hydrogen, substituted or unsubstituted phenyl, substituted or unsubstituted naphthyl, substituted or unsubstituted methyl and substituted or unsubstituted methylcarbonyl, or A and G together from substituted or unsubstituted butylene, or substituted or unsubstituted propylene.

15. The compound of claim 1, wherein A and G are each independently selected from hydrogen, substituted or unsubstituted phenyl, substituted or unsubstituted naphthyl, substituted or unsubstituted methyl and substituted or unsubstituted methylcarbonyl, and are substituted with 0 to 4 substituents selected from chloro, bromo, methoxy, fluoro, ethoxy, nitro, trifluoromethyl, trifluoromethoxy, trifluoromethylcarbonylamino, dimethylaminocarbonyloxy, 2-(1-piperidinyl)ethoxy, 2-(1-methyl-4-piperazinyl)ethoxy, 2-(N-morpholinyl)ethoxy, 2-dimethylaminoethoxy, hydroxycarbonylmethoxy, methylcarbonylamino, hydroxy, ethylaminocarbonyloxy, methoxycarbonylmethoxy, aminocarbonylmethoxy, 2-hydroxyethoxy, 2-hydroxypropoxy, methyl, 2-chloroethylaminocarbonyloxy and 2-methylaminoethoxy.

16. The compound of claim 1, wherein A and G are each independently selected from hydrogen, 4-nitrophenyl, 4-fluorophenyl, 4-chlorophenyl, 2-naphthyl, 4-bromophenyl, 2-methoxyphenyl, 3-fluorophenyl, 2,4-dimethoxyphenyl, 4-methylphenyl, 4-methoxyphenyl, methyl, phenyl and methylcarbonyl.

17. The compound of claim 1, wherein D and E are each hydrogen or together form a bond.

18. The compound of claim 1 that has formulae VI:

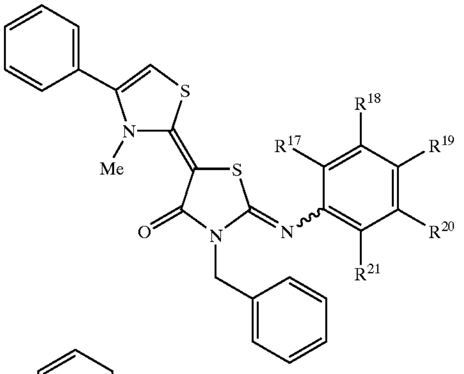

or

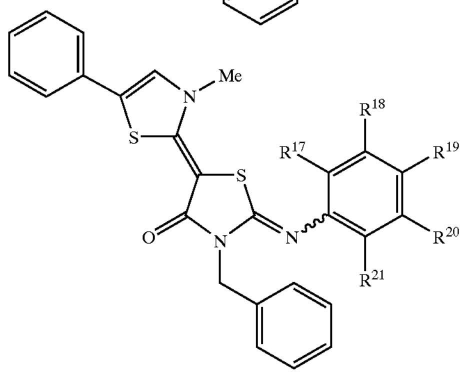

or a pharmaceutically acceptable derivative thereof, wherein $R^{17}$, $R^{18}$, $R^{19}$, $R^{20}$ and $R^{21}$ are each independently selected from hydrogen, ethylamino, cyano, cyclohexyl, hydroxy, methoxy, dimethylamino, amino, 4-morpholinyl, methylamino, isopropylamino, benzyloxy, methyl, isopropyl, nitro, trifluoromethyl, methylcarbonyl, chloro, propyl, ethoxy, methylcarbonylamino, aminocarbonyl, methoxycarbonyl, butylamino, benzylamino, cyclopentylamino, 1-pyrrolidinylamino, pyrrolidinyl, t-butylamino, 2,2,2-trifluoroethylamino, piperidinyl, trifluoromethoxy, hydroxycarbonyl, aminosulfonyl, methylcarbonylaminosulfonyl, trifluoromethylcarbonylamino and t-butoxycarbonyl, or any two substituents, which substitute atoms in a 1,2 arrangement, together form methylenedioxy.

19. The compound of claim 1 that has formulae VII:

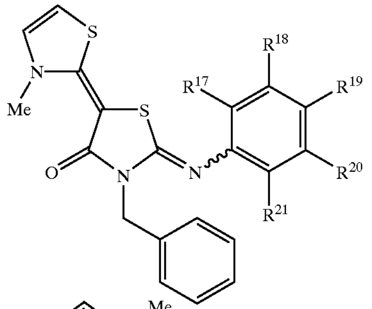

or

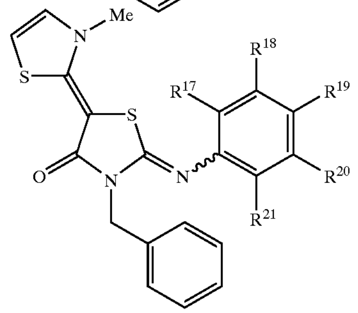

or a pharmaceutically acceptable derivative thereof, wherein $R^{17}$, $R^{18}$, $R^{19}$, $R^{20}$ and $R^{21}$ are each independently selected from hydrogen, ethylamino, cyano, cyclohexyl, hydroxy, methoxy, dimethylamino, amino, 4-morpholinyl, methylamino, isopropylamino, benzyloxy, methyl, isopropyl, nitro, trifluoromethyl, methylcarbonyl, chloro, propyl, ethoxy, methylcarbonylamino, aminocarbonyl, methoxycarbonyl, butylamino, benzylamino, cyclopentylamino, 1-pyrrolidinylamino, pyrrolidinyl, t-butylamino, 2,2,2-trifluoroethylamino, piperidinyl, trifluoromethoxy, hydroxycarbonyl, aminosulfonyl, methylcarbonylaminosulfonyl, trifluoromethylcarbonylamino and t-butoxycarbonyl, or any two substituents, which substitute atoms in a 1,2 arrangement, together form methylenedioxy.

20. The compound of claim 1 that has formulae VIII:

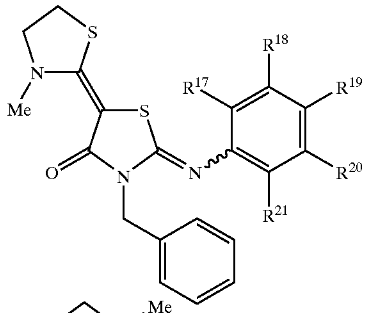

or

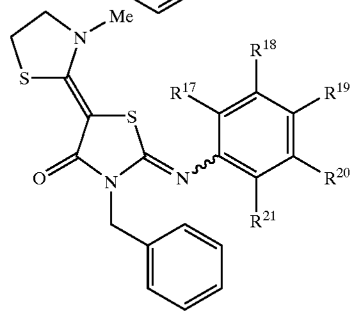

or a pharmaceutically acceptable derivative thereof, wherein $R^{17}$, $R^{18}$, $R^{19}$, $R^{20}$ and $R^{21}$ are each independently selected from hydrogen, ethylamino, cyano, cyclohexyl, hydroxy, methoxy, dimethylamino, amino, 4-morpholinyl, methylamino, isopropylamino, benzyloxy, methyl, isopropyl, nitro, trifluoromethyl, methylcarbonyl, chloro, propyl, ethoxy, methylcarbonylamino, aminocarbonyl, methoxycarbonyl, butylamino, benzylamino, cyclopentylamino, 1-pyrrolidinylamino, pyrrolidinyl, t-butylamino, 2,2,2-trifluoroethylamino, piperidinyl, trifluoromethoxy, hydroxycarbonyl, aminosulfonyl, methylcarbonylaminosulfonyl, trifluoromethylcarbonylamino and t-butoxycarbonyl, or any two substituents, which substitute atoms in a 1,2 arrangement, together form methylenedioxy.

21. The compound of claim 1 that has formulae IX:

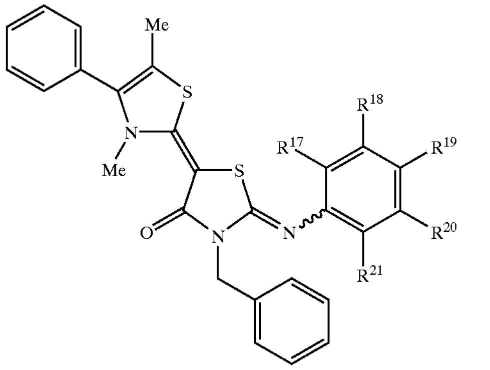

or

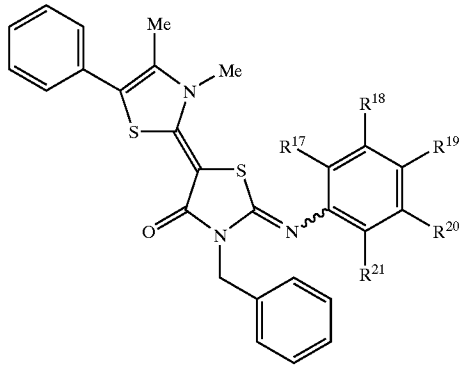

or a pharmaceutically acceptable derivative thereof, wherein $R^{17}$, $R^{18}$, $R^{19}$, $R^{20}$ and $R^{21}$ are each independently selected from hydrogen, ethylamino, cyano, cyclohexyl, hydroxy, methoxy, dimethylamino, amino, 4-morpholinyl, methylamino, isopropylamino, benzyloxy, methyl, isopropyl, nitro, trifluoromethyl, methylcarbonyl, chloro, propyl, ethoxy, methylcarbonylamino, aminocarbonyl, methoxycarbonyl, butylamino, benzylamino, cyclopentylamino, 1-pyrrolidinylamino, pyrrolidinyl, t-butylamino, 2,2,2-trifluoroethylamino, piperidinyl, trifluoromethoxy, hydroxycarbonyl, aminosulfonyl, methylcarbonylaminosulfonyl, trifluoromethylcarbonylamino and t-butoxycarbonyl, or any two substituents, which substitute atoms in a 1,2 arrangement, together form methylenedioxy.

22. The compound of claim 18, wherein $R^{17}$, $R^{18}$, $R^{19}$, $R^{20}$ and $R^{21}$ are each independently selected from (i) or (ii) as follows:

(i) $R^{21}$ is ethylamino; $R^{18}$ is cyano; and $R^{17}$, $R^{19}$ and $R^{20}$ are each hydrogen; or (ii) $R^{17}$ is ethylamino; $R^{20}$ is cyano; and $R^{18}$, $R^{19}$ and $R^{21}$ are each hydrogen.

23. A compound selected from:

3-benzyl-2-(4-methoxyphenylimino)-5-(3-methyl-3H-benzothiazol-2-ylidene)thiazolidine-4-one;

3-benzyl-2-(4-dimethylaminophenylimino)-5-(3-methyl-3H-benzothiazol-2-ylidene)thiazolidine-4-one;

2-(4-aminophenylimino)-3-benzyl-5-(3-methyl-3H-benzothiazol-2-ylidene)thiazolidine-4-one;

3-benzyl-5-(3-methyl-3H-benzothiazol-2-ylidene)-2-(quinolin-6-ylimino)-thiazolidine-4-one;

2-(2-aminophenylimino)-3-benzyl-5-(3-methyl-3H-benzothiazol-2-ylidene)thiazolidine-4-one;

3-benzyl-2-(4-benzyloxyphenylimino)-5-(3-methyl-3H-benzothiazol-2-ylidene)thiazolidine-4-one;

3-benzyl-2-(2-hydroxy- 1-naphthylimino)-5-(3-methyl-3H-benzothiazol-2-ylidene)thiazolidine-4-one;

3-[3-benzyl-5-(3-methyl-3H-benzothiazol-2-ylidene)-4-oxothiazolidin-2-ylideneamino]benzonitrile;

3-benzyl-2-(4-hydroxy-5-isopropyl-2-methylphenylimino)-5-(3-methyl-3H-benzothiazol-2-ylidene)thiazolidine-4-one;

3-benzyl-2-(2-ethylamino-5-nitrophenylimino)-5-(3-methyl-3H-benzothiazol-2-ylidene)thiazolidine-4-one;

3-benzyl-5-(3-methyl-3H-benzothiazol-2-ylidene)-2-[3-(trifluoromethyl)phenylimino]thiazolidine-4-one;

2-(3-acetylphenylimino)-3-benzyl-5-(3-methyl-3H-benzothiazol-2-ylidene)thiazolidine-4-one;

3-benzyl-2-(3-chlorophenylimino)-5-(3-methyl-3H-benzothiazol-2-ylidene)thiazolidine-4-one;

3-benzyl-5-(3-methyl-3H-benzothiazol-2-ylidene)-2-(2-propylphenylimino)thiazolidine-4-one;

3-benzyl-5-(3-methyl-3H-benzothiazol-2-ylidene)-2-(quinolin-5-ylimino)-thiazolidine-4-one;

3-benzyl-2-(2-ethoxyphenylimino)-5-(3-methyl-3H-benzothiazol-2-ylidene)thiazolidine-4-one;

N-{3-[3-benzyl-5-(3-methyl-3H-benzothiazol-2-ylidene)-4-oxothiazolidin-2-ylideneamino]phenyl}acetamide;

3-[3-benzyl-5-(3-methyl-3H-benzothiazol-2-ylidene)-4-oxothiazolidin-2-ylideneamino]benzamide;

3-[3-benzyl-5-(3-methyl-3H-benzothiazol-2-ylidene)-4-oxothiazolidin-2-ylideneamino]benzoic acid, methyl ester;

3-benzyl-5-(3-methyl-3H-benzothiazol-2-ylidene)-2-(pyridin-3-ylimino)thiazolidine-4-one;

N-{3-[3-benzyl-5-(3-methyl-3H-benzothiazol-2-ylidene)-4-oxothiazolidin-2-ylideneamino]-4-ethoxyphenyl}acetamide;

3-benzyl-5-(3-methyl-3H-benzothiazol-2-ylidene)-2-(pyridin-4-ylimino)thiazolidine-4-one;

4-[3-benzyl-5-(3-methyl-3H-benzothiazol-2-ylidene)-4-oxothiazolidin-2-ylideneamino]benzoic acid, methyl ester;

3-benzyl-5-(3-methyl-3H-benzothiazol-2-ylidene)-2-[4-(trifluoromethoxy)phenylimino]thiazolidine-4-one;

3-benzyl-2-(1H-indazol-5-ylimino)-5-(3-methyl-3H-benzothiazol-2-ylidene)thiazolidin-4-one;

3-benzyl-2-(4-imidazol-1-ylphenylimino)-5-(3-methyl-3H-benzothiazol-2-ylidene)thiazolidine-4-one;

2-(benzo[1,3]dioxol-5-ylimino)-3-benzyl-5-(3-methyl-3H-benzothiazol-2-ylidene)thiazolidin-4-one;

3-[3-benzyl-5-(3-methyl-3H-benzothiazol-2-ylidene)-4-oxothiazolidin-2-ylideneamino]benzoic acid;

3-benzyl-2-[2-(ethylamino)phenylimino]-5-(3-methyl-3H-benzothiazol-2-ylidene)thiazolidine-4-one;

3-[3-benzyl-5-(3-methyl-3H-benzothiazol-2-ylidene)-4-oxothiazolidin-2-ylideneamino]-4-(methylamino) benzonitrile;

3-[3-benzyl-5-(3-methyl-3H-benzothiazol-2-ylidene)-4-oxothiazolidin-2-ylideneamino]-4-(isopropylamino) benzonitrile;

3-[3-benzyl-5-(3-methyl-3H-benzothiazol-2-ylidene)-4-oxothiazolidin-2-ylideneamino]-4-(dimethylamino) benzonitrile;

3-[3-benzyl-5-(3-methyl-3H-benzothiazol-2-ylidene)-4-oxothiazolidin-2-ylideneamino]-4-(tert-butylamino) benzonitrile;

3-[3-benzyl-5-(3-methyl-3H-benzothiazol-2-ylidene)-4-oxothiazolidin-2-ylideneamino]-4-(2,2,2-trifluoroethylamino)benzonitrile;

3-[3-benzyl-5-(3-methyl-3H-benzothiazol-2-ylidene)-4-oxothiazolidin-2-ylideneamino]-4-piperidin-1-ylbenzonitrile;

2-[5-acetyl-2-(ethylamino)phenylimino]-3-benzyl-5-(3-methyl-3H-benzothiazol-2-ylidene)thiazolidin-4-one;

3-ethyl-5-(3-methyl-3H-benzothiazol-2-ylidene)-2-(4-morpholin-4-yl-phenylimino)thiazolidin-4-one;

3-[3-ethyl-5-(3-methyl-3H-benzothiazol-2-ylidene)-4-oxothiazolidin-2-ylideneamino]-4-(methylamino) benzonitrile;

4-dimethylamino-3-[3-ethyl-5-(3-methyl-3H-benzothiazol-2-ylidene)-4-oxothiazolidin-2-ylideneamino]benzonitrile;

3-[3-ethyl-5-(3-methyl-3H-benzothiazol-2-ylidene)-4-oxothiazolidin-2-ylideneamino]-4-(isopropylamino) benzonitrile;

3-[3-butyl-5-(3-methyl-3H-benzothiazol-2-ylidene)-4-oxothiazolidin-2-ylideneamino]benzonitrile;

3-benzyl-5-(3-methyl-3H-benzoxazol-2-ylidene)-2-(quinolin-5-ylimino)thiazolidin-4-one;

N-[4-(3'-benzyl-3-methyl-4'-oxo-4-phenyl-3',4'-dihydro-3H-[2,5']-bithiazolyliden-2'-ylideneamino)phenyl] acetamide;

2'-[5-acetyl-2-(ethylamino)phenylimino]-3'-benzyl-3-methyl-4-phenyl-2',3'-dihydro-3H-[2,5] bithiazolyliden-4'-one;

3-(3'-benzyl-3-methyl-4'-oxo-4-phenyl-3',4'-dihydro-3H-[2,5']bithiazol-yliden-2'-ylideneamino)-4-(ethylamino) benzonitrile;

N-[4-(3'-benzyl-3-methyl-4'-oxo-3',4'-dihydro-3H-[2,5'] bithiazolyliden-2'-ylideneamino)phenyl]acetamide;

N-[4-(3'-benzyl-3-methyl-4'-oxo-[2,5'] bithiazolidinyliden-2'-ylideneamino)phenyl] acetamide;

3-(3'-benzyl-3,5-dimethyl-4'-oxo-4-phenyl-3',4'-dihydro-3H-[2,5']-bithiazolyliden-2'-ylideneamino)-4-(ethylamino)benzonitrile;

3-phenyl-5-(3-methyl-3H-benzothiazol-2-ylidene)-2-benzylimino-thiazolidine-4-one;

3-benzyl-5-(3-methyl-3H-benzothiazol-2-ylidene)-2-(8-quinolyl)imino-thiazolidine-4-one;

3-benzyl-5-(3-methyl-3H-benzothiazol-2-ylidene)-2-(8-hydroxy-5-quinolyl)imino-thiazolidine-4-one;

3-benzyl-5-(3-methyl-3H-benzothiazol-2-ylidene)-2-(5-isoquinolyl)imino-thiazolidine-4-one;

3-benzyl-5-(3-methyl-3H-benzothiazol-2-ylidene)-2-(1-isoquinolyl)imino-thiazolidine-4-one;

3-benzyl-5-(3-methyl-3H-benzothiazol-2-ylidene)-2-(4-methylcarbonylamino)phenylimino-thiazolidine-4-one;

3-benzyl-5-(3-methyl-3H-benzothiazol-2-ylidene)-2-(4-methylcarbonyl)phenylimino-thiazolidine-4-one;

3-benzyl-5-(3-methyl-3H-benzothiazol-2-ylidene)-2-(4-aminocarbonyl)phenylimino-thiazolidine-4-one;

3-benzyl-5-(3-methyl-3H-benzothiazol-2-ylidene)-2-(1-naphthyl)imino-thiazolidine-4-one;

3-benzyl-5-(3-methyl-3H-benzothiazol-2-ylidene)-2-(2-naphthyl)imino-thiazolidine-4-one;

3-benzyl-5-(3-methyl-3H-benzothiazol-2-ylidene)-2-(2-pyridyl)imino-thiazolidine-4-one;

3-benzyl-5-(3-methyl-3H-benzothiazol-2-ylidene)-2-(4-aminosulfonyl)phenylimino-thiazolidine-4-one;

3-benzyl-5-(3-methyl-3H-benzothiazol-2-ylidene)-2-(4-methylcarbonylaminosulfonyl)phenylimino-thiazolidine-4-one;

3-benzyl-5-(3-methyl-3H-benzothiazol-2-ylidene)-2-(3-methylcarbonyl)phenylimino-thiazolidine-4-one;

3-benzyl-5-(3-methyl-3H-benzothiazol-2-ylidene)-2-(2-methylcarbonylamino-5-pyridyl)imino-thiazolidine-4-one;

3-benzyl-5-(3-methyl-3H-benzothiazol-2-ylidene)-2-(4-cyano-3-methylcarbonylaminophenyl)imino-thiazolidine-4-one;

3-benzyl-5-(3-methyl-3H-benzothiazol-2-ylidene)-2-(2-ethylamino-5-methylcarbonylphenyl)imino-thiazolidine-4-one;

3-benzyl-5-(3-methyl-3H-benzothiazol-2-ylidene)-2-(2-methylamino-5-methylcarbonylphenyl)imino-thiazolidine-4-one;

3-benzyl-5-(3-methyl-3H-benzothiazol-2-ylidene)-2-(4-trifluoromethylcarbonylaminophenyl)imino-thiazolidine-4-one;

3-benzyl-5-(3-methyl-3H-benzothiazol-2-ylidene)-2-(2-ethylamino-5-methoxycarbonylphenyl)imino-thiazolidine-4-one;

3-benzyl-5-(3-methyl-3H-benzothiazol-2-ylidene)-2-(2-hydroxycarbonylphenyl)imino-thiazolidine-4-one;

3-benzyl-5-(3-methyl-3H-benzothiazol-2-ylidene)-2-(2-ethylamino-5-tert-butoxycarbonylphenyl)imino-thiazolidine-4-one;

4-butylamino-3-[3-benzyl-5-(3-methyl-3H-benzothiazol-2-ylidene)-4-oxo-thiazolidin-2-ylideneamino] benzonitrile;

4-benzylamino-3-[3-benzyl-5-(3-methyl-3H-benzothiazol-2-ylidene)-4-oxo-thiazolidin-2-ylideneamino]benzonitrile;

4-cyclopentylamino-3-[3-benzyl-5-(3-methyl-3H-benzothiazol-2-ylidene)-4-oxo-thiazolidin-2-ylideneamino]benzonitrile;

4-pyrrolidinylamino-3-[3-benzyl-5-(3-methyl-3H-benzothiazol-2-ylidene)-4-oxo-thiazolidin-2-ylideneamino]benzonitrile;

4-pyrrolidinyl-3-[3-benzyl-5-(3-methyl-3H-benzothiazol-2-ylidene)-4-oxo-thiazolidin-2-ylideneamino]benzonitrile;

4-ethylamino-3-[3-cyclohexyl-5-(3-methyl-3H-benzothiazol-2-ylidene)-4-oxo-thiazolidin-2-ylideneamino]benzonitrile;

3-allyl-5-(3-methyl-3H-benzothiazol-2-ylid ene)-2-(4-hydroxy-2-methyl-5-isopropylphenyl)imino-thiazolidine-4-one;

3-cyclohexyl-5-(3-methyl-3H-benzothiazol-2-ylidene)-2-(2-hydroxy-1-naphthyl)imino-thiazolidine-4-one;

4-ethylamino-3-[3-benzyl-5-(6-fluoro-3-methyl-3H-benzothiazol-2-ylidene)-4-oxo-thiazolidin-2-ylideneamino]benzonitrile;

4-ethylamino-3-[3-benzyl-5-(6-ethoxy-3-methyl-3H-benzothiazol-2-ylidene)-4-oxo-thiazolidin-2-ylideneamino]benzonitrile;

4-ethylamino-3-[3-benzyl-5-(6-nitro-3-methyl-3H-benzothiazol-2-ylidene)-4-oxo-thiazolidin-2-ylideneamino]benzonitrile;

4-ethylamino-3-[3-benzyl-5-(5-trifluoromethyl-3-methyl-3H-benzothiazol-2-ylidene)-4-oxo-thiazolidin-2-ylideneamino]benzonitrile;

4-ethylamino-3-[3-benzyl-5-(6-methylcarbonylamino-3-methyl-3H-benzothiazol-2-ylidene)-4-oxo-thiazolidin-2-ylideneamino]benzonitrile;

4-ethylamino-3-[3-benzyl-5-(5-hydroxy-3-methyl-3H-benzothiazol-2-ylidene)-4-oxo-thiazolidin-2-ylideneamino]benzonitrile;

4-ethylamino-3-[3-benzyl-5-(6-hydroxy-3-methyl-3H-benzothiazol-2-ylidene)-4-oxo-thiazolidin-2-ylideneamino]benzonitrile;

4-ethylamino-3-[3-benzyl-5-(5-ethylaminocarbonyloxy-3-methyl-3H-benzothiazol-2-ylidene)-4-oxo-thiazolidin-2-ylideneamino]benzonitrile;

4-ethylamino-3-[3-benzyl-5-(5-methoxycarbonylmethoxy-3-methyl-3H-benzothiazol-2-ylidene)-4-oxo-thiazolidin-2-ylideneamino]benzonitrile;

4-ethylamino-3-[3-benzyl-5-(5-aminocarbonylmethoxy-3-methyl-3H-benzothiazol-2-ylidene)-4-oxo-thiazolidin-2-ylideneamino]benzonitrile;

4-ethylamino-3-[3-benzyl-5-(5-(2-hydroxyethoxy)-3-methyl-3H-benzothiazol-2-ylidene)-4-oxo-thiazolidin-2-ylideneamino]benzonitrile;

4-ethylamino-3-[3-benzyl-5-(4-methoxy-3-methyl-3H-benzothiazol-2-ylidene)-4-oxo-thiazolidin-2-ylideneamino]benzonitrile;

4-ethylamino-3-[3-benzyl-5-(4-methyl-3-methyl-3H-benzothiazol-2-ylidene)-4-oxo-thiazolidin-2-ylideneamino]benzonitrile;

4-ethylamino-3-[3-benzyl-5-(4-chloro-3-methyl-3H-benzothiazol-2-ylidene)-4-oxo-thiazolidin-2-ylideneamino]benzonitrile;

4-ethylamino-3-[3-benzyl-5-(5-(2-chloroethylaminocarbonyloxy)-3-methyl-3H-benzothiazol-2-ylidene)-4-oxo-thiazolidin-2-ylideneamino]benzonitrile;

4-ethylamino-3-[3-benzyl-5-(5-(2-methylaminoethoxy)-3-methyl-3H-benzothiazol-2-ylidene)-4-oxo-thiazolidin-2-ylideneamino]benzonitrile;

4-ethylamino-3-[3-propyl-5-(3-methyl-3H-benzothiazol-2-ylidene)-4-oxo-thiazolidin-2-ylideneamino]benzonitrile;

3-(3-pyridylmethyl)-5-(3-methyl-3H-benzothiazol-2-ylidene)-2-(3-acetylphenyl)imino-thiazolidine-4-one;

3-(3-pyridylmethyl)-5-(3-methyl-3H-benzothiazol-2-ylidene)-2-(2-ethylamino-5-acetylphenyl)imino-thiazolidine-4-one;

4-ethylamino-3-[3-(3-pyridylmethyl)-5-(3-methyl-3H-benzothiazol-2-ylidene)-4-oxo-thiazolidin-2-ylideneamino]benzonitrile;

4-ethylamino-3-[3-(2-furylmethyl)-5-(3-methyl-3H-benzothiazol-2-ylidene)-4-oxo-thiazolidin-2-ylideneamino]benzonitrile;

3-(4-methoxycarbonylbenzyl)-5-(3-methyl-3H-benzothiazol-2-ylidene)-2-(2-ethylamino-5-acetylphenyl)imino-thiazolidine-4-one;

3-(4-hydroxycarbonylbenzyl)-5-(3-methyl-3H-benzothiazol-2-ylidene)-2-(2-ethylamino-5-acetylphenyl)imino-thiazolidine-4-one;

4-ethylamino-3-[3-(2-phenylethyl)-5-(3-methyl-3H-benzothiazol-2-ylidene)-4-oxo-thiazolidin-2-ylideneamino]benzonitrile;

4-ethylamino-3-[3-(2-(4-morpholinyl)-1-ethyl)-5-(3-methyl-3H-benzothiazol-2-ylidene)-4-oxo-thiazolidin-2-ylideneamino]benzonitrile;

3-benzyl-5-(3-methylthiazolin-2-ylidene)-2-(4-methylcarbonylaminophenyl)imino-thiazolidine-4-one;

3-benzyl-5-(3-methyl-4-phenylthiazol-2-ylidene)-2-(4-methylcarbonylaminophenyl)imino-thiazolidine-4-one;

3-benzyl-5-(3-methyl-4-phenylthiazol-2-ylidene)-2-(2-ethylamino-5-acetylphenyl)imino-thiazolidine-4-one;

3-benzyl-5-(3-methylthiazol-2-ylidene)-2-(4-methylcarbonylaminophenyl)imino-thiazolidine-4-one;

4-ethylamino-3-[3-benzyl-5-(3-methyl-4-phenylthiazol-2-ylidene)-4-oxo-thiazolidin-2-ylideneamino]benzonitrile;

4-ethylamino-3-[3-benzyl-5-(3-methyl-4,5-dimethylthiazol-2-ylidene)-4-oxo-thiazolidin-2-ylideneamino]benzonitrile;

4-ethylamino-3-[3-benzyl-5-(3-methyl-4-phenyl-5-methylthiazol-2-ylidene)-4-oxo-thiazolidin-2-ylideneamino]benzonitrile;

4-ethylamino-3-[3-benzyl-5-(3-methyl-4,5-butylenylthiazol-2-ylidene)-4-oxo-thiazolidin-2-ylideneamino]benzonitrile;

4-ethylamino-3-[3-benzyl-5-(3-methyl-4-ethylthiazol-2-ylidene)-4-oxo-thiazolidin-2-ylideneamino]benzonitrile;

4-ethylamino-3-[3-benzyl-5-(3-methyl-4-(4-nitrophenyl)thiazol-2-ylidene)-4-oxo-thiazolidin-2-ylideneamino]benzonitrile;

4-ethylamino-3-[3-benzyl-5-(3-methyl-4-(4-fluorophenyl)thiazol-2-ylidene)-4-oxo-thiazolidin-2-ylideneamino]benzonitrile;

4-ethylamino-3-[3-benzyl-5-(3-methyl-4-(4-chlorophenyl)thiazol-2-ylidene)-4-oxo-thiazolidin-2-ylideneamino]benzonitrile;

4-ethylamino-3-[3-benzyl-5-(3-methyl-4-(4-methylphenyl)thiazol-2-ylidene)-4-oxo-thiazolidin-2-ylideneamino]benzonitrile;

4-ethylamino-3-[3-benzyl-5-(3-methyl-4-(4-methoxyphenyl)thiazol-2-ylidene)-4-oxo-thiazolidin-2-ylideneamino]benzonitrile;

4-ethylamino-3-[3-benzyl-5-(3-methyl-4-methyl-5-acetylthiazol-2-ylidene)-4-oxo-thiazolidin-2-ylideneamino]benzonitrile;

4-ethylamino-3-[3-benzyl-5-(3-methyl-4,5-propylenylthiazol-2-ylidene)-4-oxo-thiazolidin-2-ylideneamino]benzonitrile;

4-ethylamino-3-[3-benzyl-5-(3-methyl-4,5-diphenylthiazol-2-ylidene)-4-oxo-thiazolidin-2-ylideneamino]benzonitrile;

4-ethylamino-3-[3-benzyl-5-(3-methyl-4-methylthiazol-2-ylidene)-4-oxo-thiazolidin-2-ylideneamino]benzonitrile;

4-ethylamino-3-[3-(3-pyridylmethyl)-5-(3-methyl-4,5-butylenylthiazol-2-ylidene)-4-oxo-thiazolidin-2-ylideneamino]benzonitrile; and 3-(4-methoxycarbonylbenzyl)-5-(3-methyl-4,5-butylenylthiazol-2-ylidene)-2-(2-ethylamino-5-acetylphenyl)imino-thiazolidine-4-one.

24. A compound selected from:

3-benzyl-5-(3-methyl-3H-benzothiazol-2-ylidene)-2-(quinolin-8-ylimino)thiazolidin-4-one;

3-benzyl-2-(8-hydroxyquinolin-5-ylimino)-5-(3-methyl-3H-benzothiazol-2-ylidene)thiazolidin-4-one;

3-[3-benzyl-5-(3-methyl-3H-benzothiazol-2-ylidene)-4-oxothiazolidin-2-ylideneamino]-4-butylaminobenzonitrile;

4-benzylamino-3-[3-benzyl-5-(3-methyl-3H-benzothiazol-2-ylidene)-4-oxothiazolidin-2-ylideneamino]benzonitrile;

3-[3-benzyl-5-(3-methyl-3H-benzothiazol-2-ylidene)-4-oxothiazolidin-2-ylideneamino]-4-cyclopentylaminobenzonitrile;

3-[3-benzyl-5-(3-methyl-3H-benzothiazol-2-ylidene)-4-oxothiazolidin-2-ylideneamino]-4-(pyrrolidin-1-ylamino)benzonitrile;

3-[3-benzyl-5-(3-methyl-3H-benzothiazol-2-ylidene)-4-oxothiazolidin-2-ylideneamino]-4-pyrrolidin-1-ylbenzonitrile;

3-benzyl-2-(isoquinolin-5-ylimino)-5-(3-methyl-3H-benzothiazol-2-ylidene)thiazolidin-4-one;

3-benzyl-2-(isoquinolin-1-ylimino)-5-(3-methyl-3H-benzothiazol-2-ylidene)thiazolidin-4-one;

N-{4-[3-benzyl-5-(3-methyl-3H-benzothiazol-2-ylidene)-4-oxothiazolidin-2-ylideneamino]phenyl}acetamide;

3-(4-acetylphenylimino)-3-benzyl-5-(3-methyl-3H-benzothiazol-2-ylidene)thiazolidin-4-one;

4-[3-benzyl-5-(3-methyl-3H-benzothiazol-2-ylidene)-4-oxothiazolidin-2-ylideneamino]benzamide;

3-benzyl-5-(3-methyl-3H-benzothiazol-2-ylidene)-2-(naphthalen-1-ylimino)thiazolidin-4-one;

3-benzyl-5-(3-methyl-3H-benzothiazol-2-ylidene)-2-(naphthalen-2-ylimino)thiazolidin-4-one;

3-benzyl-5-(3-methyl-3H-benzothiazol-2-ylidene)-2-(pyridin-2-ylimino)thiazolidin-4-one;

4-[3-benzyl-5-(3-methyl-3H-benzothiazol-2-ylidene)-4-oxothiazolidin-2-ylideneamino]benzenesulfonamide;

N-acetyl-4-[3-benzyl-5-(3-methyl-3H-benzothiazol-2-ylidene)-4-oxothiazolidin-2-ylideneamino]benzenesulfonamide;

2-(3-acetylphenylimino)-5-(3-methyl-3H-benzothiazol-2-ylidene)-3-pyridin-3-ylmethylthiazolidin-4-one;

N-{5-[3-benzyl-5-(3-methyl-3H-benzothiazol-2-ylidene)-4-oxothiazolidin-2-ylideneamino]pyridin-2-yl}acetamide;

N-{5-[3-benzyl-5-(3-methyl-3H-benzothiazol-2-ylidene)-4-oxothiazolidin-2-ylideneamino]-2-cyanophenyl}acetamide;

2-(5-acetyl-2-ethylaminophenylimino)-5-(3-methyl-3H-benzothiazol-2-ylidene)-3-pyridin-3-ylmethylthiazolidin-4-one;

4-ethylamino-3-[5-(3-methyl-3H-benzothiazol-2-ylidene)-4-oxo-3-pyridin-3-ylmethylthiazolidin-2-ylideneamino]benzonitrile;

4-ethylamino-3-[3-furan-2-ylmethyl-5-(3-methyl-3H-benzothiazol-2-ylidene)-4-oxothiazolidin-2-ylideneamino]benzonitrile;

2-(5-acetyl-2-methylaminophenylimino)-3-benzyl-5-(3-methyl-3H-benzothiazol-2-ylidene)thiazolidin-4-one;

N-{4-[3-benzyl-5-(3-methyl-3H-benzothiazol-2-ylidene)-4-oxothiazolidin-2-ylideneamino]phenyl}-2,2,2-trifluoroacetamide;

3-[3-benzyl-5-(3-methyl-3H-benzothiazol-2-ylidene)-4-oxothiazolidin-2-ylideneamino]-4-ethylaminobenzoic acid methyl ester;

4-ethylamino-3-[5-(3-methyl-3H-benzothiazol-2-ylidene)-4-oxo-3-phenethylthiazolidin-2-ylideneamino]benzonitrile;

2-[3-benzyl-5-(3-methyl-3H-benzothiazol-2-ylidene)-4-oxothiazolidin-2-ylideneamino]benzoic acid;

3-[3-benzyl-5-(3-methyl-3H-benzothiazol-2-ylidene)-4-oxothiazolidin-2-ylideneamino]-4-ethylaminobenzoic acid tert-butyl ester;

3-[3-benzyl-5-(3-methyl-3H-benzothiazol-2-ylidene)-4-oxothiazolidin-2-ylideneamino]-4-ethylaminobenzoic acid;

3-[3-benzyl-5-(3-methyl-3H-benzothiazol-2-ylidene)-4-oxothiazolidin-2-ylideneamino]-4-(2-hydroxyethylamino)benzonitrile;

{2-[3-benzyl-5-(3-methyl-3H-benzothiazol-2-ylidene)-4-oxothiazolidin-2-ylideneamino]-4-cyanophenylamino}acetic acid methyl ester;

3-[3-benzyl-5-(3-methyl-3H-benzothiazol-2-ylidene)-4-oxothiazolidin-2-ylideneamino]-N-ethyl-4-ethylaminobenzamide;

{2-[3-benzyl-5-(3-methyl-3H-benzothiazol-2-ylidene)-4-oxothiazolidin-2-ylideneamino]-4-cyanophenylamino}acetic acid;

3-benzyl-2-(4-ethylaminopyridin-3-ylimino)-5-(3-methyl-3H-benzothiazol-2-ylidene)thiazolidin-4-one;

N-{4-[3-benzyl-5-(3-methyl-3H-benzothiazol-2-ylidene)-4-oxothiazolidin-2-ylideneamino]-3-ethylaminophenyl}acetamide;

3-[3-benzyl-5-(3-methyl-3H-benzothiazol-2-ylidene)-4-oxothiazolidin-2-ylideneamino]-4-(2-dimethylaminoethylamino)benzonitrile;

4-[3-benzyl-5-(3-methyl-3H-benzothiazol-2-ylidene)-4-oxothiazolidin-2-ylideneamino]-N-ethyl-3-ethylaminobenzamide;

3-[3-benzyl-5-(3-methyl-3H-benzothiazol-2-ylidene)-4-oxothiazolidin-2-ylideneamino]-N-(2-dimethylaminoethyl)-4-ethylaminobenzamide;

3-benzyl-2-[5-(4,5-dihydrooxazol-2-yl)-2-ethylamino-phenylimino]-5-(3-methyl-3H-benzothiazol-2-ylidene)thiazolidin-4-one;

3-[3-benzyl-5-(1-methyl-1H-quinolin-2-ylidene)-4-oxothiazolidin-2-ylideneamino]-4-ethylaminobenzonitrile;

2-(5-acetyl-2-ethylaminophenylimino)-3-benzyl-5-(1-methyl-1H-quinolin-2-ylidene)thiazolidin-4-one;

3-benzyl-2-benzylimino-5-(3-methyl-3H-benzothiazol-2-ylidene)thiazolidin-4-one;

2-(3-acetylphenylimino)-3-furan-2-ylmethyl-5-(3-methyl-3H-benzothiazol-2-ylidene)thiazolidin-4-one;

N-{4-[3-furan-2-ylmethyl-5-(3-methyl-3H-benzothiazol-2-ylidene)-4-oxothiazolidin-2-ylideneamino]phenyl}acetamide;

[2-(5-acetyl-2-ethylaminophenylimino)-5-(3-methyl-3H-benzothiazol-2-ylidene)-4-oxothiazolidin-3-yl]acetic acid methyl ester;

N-{4-[3-benzyl-5-(3-methyl-3H-benzothiazol-2-ylidene)-4-oxothiazolidin-2-ylideneamino]-2-cyanophenyl}acetamide;

2-(5-acetyl-2-ethoxyphenylimino)-3-benzyl-5-(3-methyl-3H-benzothiazol-2-ylidene)thiazolidin-4-one;

2-(5-acetyl-2-hydroxyphenylimino)-3-benzyl-5-(3-methyl-3H-benzothiazol-2-ylidene)thiazolidin-4-one;

2-(5-acetyl-2-ethylaminophenylimino)-3-benzyl-1-methyl-5-(3-methyl-3H-benzothiazol-2-ylidene)imidazolidin-4-one;

4-ethylamino-3-[5-(3-methyl-3H-benzothiazol-2-ylidene)-3-(2-morpholin-4-ylethyl)-4-oxothiazolidin-2-ylideneamino]benzonitrile;

4-ethylamino-3-[3-(4-methoxybenzyl)-5-(3-methyl-3H-benzothiazol-2-ylidene)-4-oxothiazolidin-2-ylideneamino]benzonitrile;

4-ethylamino-3-[3-(3-methoxybenzyl)-5-(3-methyl-3H-benzothiazol-2-ylidene)-4-oxothiazolidin-2-ylideneamino]benzonitrile;

4-ethylamino-3-[3-(2-methoxybenzyl)-5-(3-methyl-3H-benzothiazol-2-ylidene)-4-oxothiazolidin-2-ylideneamino]benzonitrile;

N-{3-[3-benzyl-5-(3-methyl-3H-benzothiazol-2-ylidene)-4-oxothiazolidin-2-ylideneamino]phenyl}succinamic acid;

N-{3-[3-benzyl-5-(3-methyl-3H-benzothiazol-2-ylidene)-4-oxothiazolidin-2-ylideneamino]phenyl}benzenesulfonamide;

thiophene-2-sulfonic acid {3-[3-benzyl-5-(3-methyl-3H-benzothiazol-2-ylidene)-4-oxothiazolidin-2-ylideneamino]phenyl}amide;

N-{3-[3-benzyl-5-(3-methyl-3H-benzothiazol-2-ylidene)-4-oxothiazolidin-2-ylideneamino]phenyl}-3-methoxybenzamide;

N-{3-[3-benzyl-5-(3-methyl-3H-benzothiazol-2-ylidene)-4-oxothiazolidin-2-ylideneamino]phenyl}methanesulfonamide;

{3-[3-benzyl-5-(3-methyl-3H-benzothiazol-2-ylidene)-4-oxothiazolidin-2-ylideneamino]phenyl}carbamic acid ethyl ester;

3-{3-[3-benzyl-5-(3-methyl-3H-benzothiazol-2-ylidene)-4-oxothiazolidin-2-ylideneamino]phenyl}-1,1-dimethylurea;

N-{3-[3-benzyl-5-(3-methyl-3H-benzothiazol-2-ylidene)-4-oxothiazolidin-2-ylideneamino]phenyl}-2-morpholin-4-ylacetamide;

N-{4-[3-benzyl-5-(3-methyl-3H-benzothiazol-2-ylidene)-4-oxothiazolidin-2-ylideneamino]phenyl}-2-morpholin-4-ylacetamide;

N-{3-[3-benzyl-5-(3-methyl-3H-benzothiazol-2-ylidene)-4-oxothiazolidin-2-ylideneamino]phenyl}-2-dimethylaminoacetamide;

{4-[3-benzyl-5-(3-methyl-3H-benzothiazol-2-ylidene)-4-oxothiazolidin-2-ylideneamino]phenyl}carbamic acid ethyl ester;

N-{4-[3-benzyl-5-(3-methyl-3H-benzothiazol-2-ylidene)-4-oxothiazolidin-2-ylideneamino]phenyl}-2-dimethylaminoacetamide;

N-{4-[3-benzyl-5-(3-methyl-3H-benzothiazol-2-ylidene)-4-oxothiazolidin-2-ylideneamino]phenyl}methanesulfonamide;

4-ethylamino-3-[3-(3-hydroxybenzyl)-5-(3-methyl-3H-benzothiazol-2-ylidene)-4-oxothiazolidin-2-ylideneamino]benzonitrile;

4-ethylamino-3-[3-(3-fluorobenzyl)-5-(3-methyl-3H-benzothiazol-2-ylidene)-4-oxothiazolidin-2-ylideneamino]benzonitrile;

4-ethylamino-3-[3-(3-fluorobenzyl)-5-(3-methyl-3H-benzothiazol-2-ylidene)-4-oxothiazolidin-2-ylideneamino]benzonitrile;

4-ethylamino-3-[5-(3-methyl-3H-benzothiazol-2-ylidene)-4-oxo-3-(3-trifluoromethylbenzyl)thiazolidin-2-ylideneamino]benzonitrile;

4-ethylamino-3-[5-(3-methyl-3H-benzothiazol-2-ylidene)-4-oxo-3-(2-trifluoromethylbenzyl)thiazolidin-2-ylideneamino]benzonitrile;

4-ethylamino-3-[5-(3-methyl-3H-benzothiazol-2-ylidene)-3-(3-methylbenzyl)-4-oxothiazolidin-2-ylideneamino]benzonitrile;

N-{3-[3-benzyl-5-(3-methyl-3H-benzothiazol-2-ylidene)-4-oxothiazolidin-2-ylideneamino]-4-ethylaminophenyl}-2-morpholin-4-ylacetamide;

3-[3-(3-chlorobenzyl)-5-(3-methyl-3H-benzothiazol-2-ylidene)-4-oxothiazolidin-2-ylideneamino]-4-ethylaminobenzonitrile;

3-[3-(3-bromobenzyl)-5-(3-methyl-3H-benzothiazol-2-ylidene)-4-oxothiazolidin-2-ylideneamino]-4-ethylaminobenzonitrile;

N-{3-[3-benzyl-5-(3-methyl-3H-benzothiazol-2-ylidene)-4-oxothiazolidin-2-ylideneamino]-4-ethylaminophenyl}-2,2,2-trifluoroacetamide;

N-{3-[3-benzyl-5-(3-methyl-3H-benzothiazol-2-ylidene)-4-oxothiazolidin-2-ylideneamino]-4-ethylaminophenyl}-2-dimethylaminoacetamide;

4-methylpiperazine-1-carboxylic acid {3-[3-benzyl-5-(3-methyl-3H-benzothiazol-2-ylidene)-4-oxothiazolidin-2-ylideneamino]-4-ethylaminophenyl}amide;

2-(5-amino-2-ethylaminophenylimino)-3-benzyl-5-(3-methyl-3H-benzothiazol-2-ylidene)thiazolidin-4-one;

N-{3-[3-benzyl-5-(3-methyl-3H-benzothiazol-2-ylidene)-4-oxothiazolidin-2-ylideneamino]-4-ethylaminophenyl}-2-(4-methylpiperazin-1-yl)acetamide;

N-{3-[3-benzyl-5-(5-methoxy-3-methyl-3H-benzothiazol-2-ylidene)-4-oxothiazolidin-2-ylideneamino]-4-ethylaminophenyl}-2-dimethylaminoacetamide;

N-{3-[3-benzyl-5-(5-hydroxy-3-methyl-3H-benzothiazol-2-ylidene)-4-oxothiazolidin-2-ylideneamino]-4-ethylaminophenyl}-2-dimethylaminoacetamide;

N-(3-{3-benzyl-5-[5-(2-chloroethoxy)-3-methyl-3H-benzothiazol-2-ylidene]-4-oxothiazolidin-2-ylideneamino}-4-ethylamino-phenyl)-2-dimethylaminoacetamide;

N-(3-{3-benzyl-5-[5-(2-methoxyethoxy)-3-methyl-3H-benzothiazol-2-ylidene]-4-oxothiazolidin-2-ylideneamino}-4-ethylamino-phenyl)-2-dimethylaminoacetamide;

N-{3-[3-benzyl-5-(3-methyl-3H-benzothiazol-2-ylidene)-4-oxothiazolidin-2-ylideneamino]-4-ethylaminophenyl}-2-methoxyacetamide;

N-(3-{3-benzyl-5-[5-(2-dimethylaminoethoxy)-3-methyl-3H-benzothiazol-2-ylidene]-4-oxothiazolidin-2-ylideneamino}-4-ethylaminophenyl)-2-dimethylaminoacetamide;

N-(3-{3-benzyl-5-[5-(2-hydroxyethoxy)-3-methyl-3H-benzothiazol-2-ylidene]-4-oxothiazolidin-2-ylideneamino}-4-ethylaminophenyl)-2-dimethylaminoacetamide;

2-(5-acetyl-2-ethylaminophenylimino)-5-[5-(2-chloroethoxy)-3-methyl-3H-benzothiazol-2-ylidene]-3-furan-2-ylmethylthiazolidin-4-one;

2-(5-acetyl-2-ethylaminophenylimino)-3-furan-2-ylmethyl-5-(3-methyl-3H-benzothiazol-2-ylidene)thiazolidin-4-one;

N-(3-{3-benzyl-5-[5-(2-chloroethoxy)-3-methyl-3H-benzothiazol-2-ylidene]-4-oxothiazolidin-2-ylideneamino}-4-ethylaminophenyl)-2-methoxyacetamide;

N-{4-ethylamino-3-[3-furan-2-ylmethyl-5-(3-methyl-3H-benzothiazol-2-ylidene)-4-oxothiazolidin-2-ylideneamino]phenyl}-2-methoxyacetamide;

N-(3-{3-benzyl-5-[5-(2-dimethylaminoethoxy)-3-methyl-3H-benzothiazol-2-ylidene]-4-oxothiazolidin-2-ylideneamino}-4-ethylaminophenyl)-2-methoxyacetamide;

2-(5-acetyl-2-ethylaminophenylimino)-5-[5-(2-dimethylamino-ethoxy)-3-methyl-3H-benzothiazol-2-ylidene]-3-furan-2-ylmethylthiazolidin-4-one;

N-(3-{5-[5-(2-dimethylaminoethoxy)-3-methyl-3H-benzothiazol-2-ylidene]-3-furan-2-ylmethyl-4-oxothiazolidin-2-ylideneamino}-4-ethylaminophenyl)-2-methoxyacetamide;

acetic acid {3-[3-benzyl-5-(3-methyl-3H-benzothiazol-2-ylidene)-4-oxothiazolidin-2-ylideneamino]-4-ethylaminophenylcarbamoyl}methyl ester;

N-{3-[3-benzyl-5-(3-methyl-3H-benzothiazol-2-ylidene)-4-oxothiazolidin-2-ylideneamino]-4-ethylaminophenyl}-2-hydroxyacetamide;

N-(3-{3-benzyl-5-[5-(2-methoxyethoxy)-3-methyl-3H-benzothiazol-2-ylidene]-4-oxothiazolidin-2-ylideneamino}-4-ethylaminophenyl)-2-hydroxyacetamide;

2-(3-acetylphenylimino)-3-benzyl-5-[5-(2-methoxyethoxy)-3-methyl-3H-benzothiazol-2-ylidene]thiazolidin-4-one;

2-(5-acetyl-2-ethylaminophenylimino)-3-furan-2-ylmethyl-5-[5-(2-methoxyethoxy)-3-methyl-3H-benzothiazol-2-ylidene]thiazolidin-4-one;

N-(4-ethylamino-3-{3-furan-2-ylmethyl-5-[5-(2-methoxyethoxy)-3-methyl-3H-benzothiazol-2-ylidene]-4-oxothiazolidin-2-ylideneamino}phenyl)-2-methoxyacetamide;

2-(5-acetyl-2-ethylaminophenylimino)-3-benzyl-5-[5-(2-methoxyethoxy)-3-methyl-3H-benzothiazol-2-ylidene]thiazolidin-4-one;

N-(3-{3-benzyl-5-[5-(2-methoxyethoxy)-3-methyl-3H-benzothiazol-2-ylidene]-4-oxothiazolidin-2-ylideneamino}-4-ethylaminophenyl)-2-methoxyacetamide;

N-(3-{5-[5-(2-aminoethoxy)-3-methyl-3H-benzothiazol-2-ylidene]-3-benzyl-4-oxothiazolidin-2-ylideneamino}-4-ethylaminophenyl)-2-dimethylaminoacetamide;

2-dimethylamino-N-{3-[3-furan-2-ylmethyl-5-(5-methoxy-3-methyl-3H-benzothiazol-2-ylidene)-4-oxothiazolidin-2-ylideneamino]-phenyl}acetamide;

3-(3'-benzyl-3,4,5-trimethyl-4'-oxo-3',4'-dihydro-3H-[2,5']bithiazolyliden-2'-ylideneamino)-4-ethylaminobenzonitrile;

3-[3-benzyl-5-(3-methyl-4,5,6,7-tetrahydro-3H-benzothiazol-2-ylidene)-4-oxothiazolidin-2-ylideneamino]-4-ethylaminobenzonitrile;

3-(3'-benzyl-4-ethyl-3-methyl-4'-oxo-3',4'-dihydro-3H-[2,5']bithiazolyliden-2'-ylideneamino)-4-ethylaminobenzonitrile;

3-[3'-benzyl-3-methyl-4-(4-nitrophenyl)-4'-oxo-3',4'-dihydro-3H-[2,5']bithiazolyliden-2'-ylideneamino]-4-ethylaminobenzonitrile;

3-[3'-benzyl-4-(4-fluorophenyl)-3-methyl-4'-oxo-3',4'-dihydro-3H-[2,5']bithiazolyliden-2'-ylideneamino]-4-ethylaminobenzonitrile;

3-[3'-benzyl-4-(4-chloro-phenyl)-3-methyl-4'-oxo-3',4'-dihydro-3H-[2,5']bithiazolyliden-2'-ylideneamino]-4-ethylaminobenzonitrile;

3-(3'-benzyl-3-methyl-4'-oxo-4-p-tolyl-3',4'-dihydro-3H-[2,5']bithiazolyliden-2'-ylideneamino)-4-ethylaminobenzonitrile;

3-[3'-benzyl-4-(4-methoxyphenyl)-3-methyl-4'-oxo-3',4'-dihydro-3H-[2,5']bithiazolyliden-2'-ylideneamino]-4-ethylaminobenzonitrile;

3-(5-acetyl-3'-benzyl-3,4-dimethyl-4'-oxo-3',4'-dihydro-3H-[2,5']bithiazolyliden-2'-ylideneamino)-4-ethylaminobenzonitrile;

3-[3-benzyl-5-(3-methyl-3,4,5,6-tetrahydrocyclopentathiazol-2-ylidene)-4-oxothiazolidin-2-ylideneamino]-4-ethylaminobenzonitrile;

3-(3'-benzyl-3-methyl-4'-oxo-4,5-diphenyl-3',4'-dihydro-3H-[2,5']bithiazolyliden-2'-ylideneamino)-4-ethylaminobenzonitrile;

3-(3'-benzyl-3,4-dimethyl-4'-oxo-3',4'-dihydro-3H-[2,5']bithiazolyliden-2'-ylideneamino)-4-ethylaminobenzonitrile;

4-ethylamino-3-[5-(3-methyl-4,5,6,7-tetrahydro-3H-benzothiazol-2-ylidene)-4-oxo-3-pyridin-3-ylmethylthiazolidin-2-ylideneamino]benzonitrile;

methyl 4-[2-(5-acetyl-2-ethylaminophenylimino)-5-(3-methyl-3H-benzothiazol-2-ylidene)-4-oxothiazolidin-3-ylmethyl]benzoate;

methyl 4-[2-(5-acetyl-2-ethylamino-phenylimino)-5-(3-methyl-4,5,6,7-tetrahydro-3H-benzothiazol-2-ylidene)-4-oxothiazolidin-3-ylmethyl]benzoate;

4-[2-(5-acetyl-2-ethylaminophenylimino)-5-(3-methyl-3H-benzothiazol-2-ylidene)-4-oxothiazolidin-3-ylmethyl]benzoic acid;

3-[3-benzyl-5-(1-methyl-4,5,6,7-tetrahydro-1H-thiazolo[5,4-c]pyridin-2-ylidene)-4-oxothiazolidin-2-ylideneamino]-4-ethylaminobenzonitrile;

methyl 3-[2-(5-acetyl-2-ethylaminophenylimino)-5-(3-methyl-3H-benzothiazol-2-ylidene)-4-oxothiazolidin-3-ylmethyl]benzoate;

3-[2-(5-acetyl-2-ethylaminophenylimino)-5-(3-methyl-3H-benzothiazol-2-ylidene)-4-oxothiazolidin-3-ylmethyl]benzoic acid;

2-(5-acetyl-2-ethylaminophenylimino)-3-benzyl-5-(3-methyl-4,5,6,7-tetrahydro-3H-benzothiazol-2-ylidene)thiazolidin-4-one;

3-(3'-benzyl-4-biphenyl-4-yl-3-methyl-4'-oxo-3',4'-dihydro-3H-[2,5']bithiazolyliden-2'-ylideneamino)-4-ethylaminobenzonitrile;

3-(3'-benzyl-3-methyl-4-naphthalen-2-yl-4'-oxo-3',4'-dihydro-3H-[2,5']bithiazolyliden-2'-ylideneamino)-4-ethylaminobenzonitrile;

3-[3'-benzyl-4-(4-bromophenyl)-3-methyl-4'-oxo-3',4'-dihydro-3H-[2,5']bithiazolyliden-2'-ylideneamino]-4-ethylaminobenzonitrile;

3-[3'-benzyl-3-methyl-4-(2-nitrophenyl)-4'-oxo-3',4'-dihydro-3H-[2,5']bithiazolyliden-2'-ylideneamino]-4-ethylaminobenzonitrile;

2-(5-acetyl-2-ethylaminophenylimino)-5-(3-methyl-4,5,6,7-tetrahydro-3H-benzothiazol-2-ylidene)-3-pyridin-3-ylmethylthiazolidin-4-one;

3-[3'-benzyl-4-(2-methoxyphenyl)-3-methyl-4'-oxo-3',4'-dihydro-3H-[2,5']bithiazolyliden-2'-ylideneamino]-4-ethylaminobenzonitrile;

3-[3'-benzyl-4-(3-fluorophenyl)-3-methyl-4'-oxo-3',4'-dihydro-3H-[2,5']bithiazolyliden-2'-ylideneamino]-4-ethylaminobenzonitrile;

3-[3'-benzyl-3-methyl-4'-oxo-4-(4-trifluoromethylphenyl)-3',4'-dihydro-3H-[2,5']bithiazolyliden-2'-ylideneamino]-4-ethylaminobenzonitrile;

3-[3'-benzyl-3-methyl-4'-oxo-4-(4-trifluoromethoxyphenyl)-3',4'-dihydro-3H-[2,5']bithiazolyliden-2'-ylideneamino]-4-ethylaminobenzonitrile;

3-[3'-benzyl-4-(2,4-dimethoxyphenyl)-3-methyl-4'-oxo-3',4'-dihydro-3H-[2,5']bithiazolyliden-2'-ylideneamino]-4-ethylaminobenzonitrile;

3-(3'-benzyl-5-ethyl-3-methyl-4'-oxo-4-phenyl-3',4'-dihydro-3H-[2,5']bithiazolyliden-2'-ylideneamino)-4-ethylaminobenzonitrile;

3-[3'-benzyl-3-methyl-4'-oxo-4-(2-trifluoromethylphenyl)-3',4'-dihydro-3H-2,5']bithiazolyliden-2'-ylideneamino]-4-ethylaminobenzonitrile;

3-[3'-benzyl-4-(3-bromophenyl)-3,5-dimethyl-4'-oxo-3',4'-dihydro-3H-[2,5']bithiazolyliden-2'-ylideneamino]-4-ethylaminobenzonitrile;

3-[3'-benzyl-4-(3-methoxyphenyl)-3-methyl-4'-oxo-3',4'-dihydro-3H-[2,5']bithiazolyliden-2'-ylideneamino]-4-ethylaminobenzonitrile;

3-benzyl-2-[4-(1,1,1,3,3,3-hexafluoro-2-hydroxyisopropyl)-phenylimino]-5-(3-methyl-3H-benzothiazol-2-ylidene)thiazolidin-4-one;

3-(3'-benzyl-4-chloromethyl-3-methyl-4'-oxo-3',4'-dihydro-3H-[2,5']bithiazolyliden-2'-ylideneamino)-4-ethylaminobenzonitrile;

3'-benzyl-2'-(5-cyano-2-ethylaminophenylimino)-3-methyl-4'-oxo-3',4'-dihydro-3H,2'H-[2,5']bithiazolylidene-4-carboxylic acid ethyl ester;

3-(4,3'-dibenzyl-3-methyl-4'-oxo-3',4'-dihydro-3H-[2,5']bithiazolyliden-2'-ylideneamino)-4-ethylaminobenzonitrile;

3'-benzyl-2'-(5-cyano-2-ethylaminophenylimino)-3-methyl-4'-oxo-3',4'-dihydro-3H,2'H-[2,5']bithiazolylidene-4-carboxylic acid;

3-benzyl-2-[2-ethylamino-5-(1-hydroxyethyl)phenylimino]-5-(3-methyl-3H-benzothiazol-2-ylidene)thiazolidin-4-one;

3-[3'-benzyl-4-(2-hydroxyphenyl)-3-methyl-4'-oxo-3',4'-dihydro-3H-[2,5']bithiazolyliden-2'-ylideneamino]-4-ethylaminobenzonitrile;

3-benzyl-2-[2-ethylamino-5-(1-hydroxyiminoethyl)phenylimino]-5-(3-methyl-3H-benzothiazol-2-ylidene)thiazolidin-4-one;

3-benzyl-2-[2-ethylamino-5-(1-methoxyiminoethyl)phenylimino]-5-(3-methyl-3H-benzothiazol-2-ylidene)thiazolidin-4-one;

3-benzyl-2-[5-(1-benzyloxyiminoethyl)-2-ethylaminophenylimino]-5-(3-methyl-3H-benzothiazol-2-ylidene)thiazolidin-4-one;

3-benzyl-2-{2-ethylamino-5-[1-(phenylhydrazono)ethyl]-phenylimino}-5-(3-methyl-3H-benzothiazol-2-ylidene)thiazolidin-4-one;

3-(4,3'-dibenzyl-3,5-dimethyl-4'-oxo-3',4'-dihydro-3H-[2,5']bithiazolyliden-2'-ylideneamino)-4-ethylaminobenzonitrile;

3-[3-cyclohexylmethyl-5-(3-methyl-3H-benzothiazol-2-ylidene)-4-oxothiazolidin-2-ylideneamino]-4-ethylaminobenzonitrile;

3-[3'-benzyl-4-(3-hydroxyphenyl)-3-methyl-4'-oxo-3',4'-dihydro-3H-[2,5']bithiazolyliden-2'-ylideneamino]-4-ethylaminobenzonitrile;

3-[3'-benzyl-4-(4-hydroxyphenyl)-3-methyl-4'-oxo-3',4'-dihydro-3H-[2,5']bithiazolyliden-2'-ylideneamino]-4-ethylaminobenzonitrile;

3-(3'-benzyl-3,4-dimethyl-4'-oxo-5-phenyl-3',4'-dihydro-3H-[2,5']bithiazolyliden-2'-ylideneamino)-4-ethylaminobenzonitrile;

2'-(5-acetyl-2-ethylaminophenylimino)-3'-benzyl-3,5-dimethyl-4-phenyl-2',3'-dihydro-3H-[2,5']bithiazolyliden-4'-one;

2'-(5-acetyl-2-ethylaminophenylimino)-3'-benzyl-3,4-dimethyl-5-phenyl-2',3'-dihydro-3H-[2,5']bithiazolyliden-4'-one;

2'-(5-acetyl-2-ethylaminophenylimino)-3'-benzyl-4-(4-methoxyphenyl)-3,5-dimethyl-2',3'-dihydro-3H-[2,5']bithiazolyliden-4'-one;

2'-(5-acetyl-2-ethylaminophenylimino)-4,3'-dibenzyl-3-methyl-2',3'-dihydro-3H-[2,5']bithiazolyliden-4'-one;

2'-(5-acetyl-2-ethylaminophenylimino)-3'-benzyl-4-(2-methoxyphenyl)-3,5-dimethyl-2',3'-dihydro-3H-[2,5']bithiazolyliden-4'-one;

3-{3-benzyl-5-[5-(2-dimethylaminoacetyl)-1-methyl-4,5,6,7-tetrahydro-1H-thiazolo[5,4-c]pyridin-2-ylidene]-4-oxothiazolidin-2-ylideneamino}-4-ethylaminobenzonitrile;

2'-(5-acetyl-2-ethylaminophenylimino)-3'-benzyl-4-(3-methoxyphenyl)-3,5-dimethyl-2',3'-dihydro-3H-[2,5']bithiazolyliden-4'-one;

2'-(5-acetyl-2-ethylaminophenylimino)-3'-benzyl-4-(3-hydroxyphenyl)-3,5-dimethyl-2',3'-dihydro-3H-[2,5']bithiazolyliden-4'-one;

2'-(5-acetyl-2-ethylaminophenylimino)-3,3'-dibenzyl-5-methyl-4-phenyl-2',3'-dihydro-3H-[2,5']bithiazolyliden-4'-one;

N-(3-{3-benzyl-5-[5-(2-acetoxyethoxy)-3-methyl-3H-benzothiazol-2-ylidene]-4-oxothiazolidin-2-ylideneamino}-4-ethylaminophenyl)-2-dimethylaminoacetamide;

2'-(5-acetyl-2-ethylaminophenylimino)-3'-benzyl-3-(2-methoxyethyl)-5-methyl-4-phenyl-2',3'-dihydro-3H-[2,5']bithiazolyliden-4'-one;

2'-(5-acetyl-2-ethylaminophenylimino)-3'-benzyl-3-(3-methoxypropyl)-5-methyl-4-phenyl-2',3'-dihydro-3H-[2,5']bithiazolyliden-4'-one;

[2'-(5-acetyl-2-ethylaminophenylimino)-3'-benzyl-5-methyl-4'-oxo-4-phenyl-3',4'-dihydro-2'H-[2,5']bithiazolyliden-3-yl]acetic acid methyl ester;

[2'-(5-acetyl-2-ethylaminophenylimino)-3'-benzyl-5-methyl-4'-oxo-4-phenyl-3',4'-dihydro-2'H-[2,5']bithiazolyliden-3-yl]acetic acid;

2-[2'-(5-acetyl-2-ethylaminophenylimino)-3'-benzyl-5-methyl-4'-oxo-4-phenyl-3',4'-dihydro-2'H-[2,5']bithiazolyliden-3-yl]ethyl acetate;

2'-(5-acetyl-2-ethylaminophenylimino)-3'-benzyl-3-(2-hydroxyethyl)-5-methyl-4-phenyl-2',3'-dihydro-3H-[2,5']bithiazolyliden-4'-one;

N-[3-(3'-benzyl-3,5-dimethyl-4'-oxo-4-phenyl-3',4'-dihydro-3H-[2,5']bithiazolyliden-2'-ylideneamino)-4-ethylaminophenyl]-2-methoxyacetamide;

N-[3-(3'-benzyl-3,5-dimethyl-4'-oxo-4-phenyl-3',4'-dihydro-3H-[2,5']bithiazolyliden-2'-ylideneamino)-4-ethylaminophenyl]-2-dimethylaminoacetamide;

3-[3-cyclohexyl-5-(3-methyl-3H-benzothiazol-2-ylidene)-4-oxothiazolidin-2-ylideneamino]-4-ethylaminobenzonitrile;

3-[3-allyl-5-(3-methyl-3H-benzothiazol-2-ylidene)-4-oxothiazolidin-2-ylideneamino]-4-ethylaminobenzonitrile;

3-allyl-5-(3-methyl-3H-benzothiazol-2-ylidene)-2-(quinolin-5-ylimino)thiazolidin-4-one;

3-allyl-2-(4-hydroxy-5-isopropyl-2-methylphenylimino)-5-(3-methyl-3H-benzothiazol-2-ylidene)thiazolidin-4-one;

4-ethylamino-3-[5-(3-methyl-3H-benzothiazol-2-ylidene)-4-oxo-3-phenylthiazolidin-2-ylideneamino]benzonitrile;

3-cyclohexyl-2-(2-hydroxynaphthalen-1-ylimino)-5-(3-methyl-3H-benzothiazol-2-ylidene)thiazolidin-4-one;

3-allyl-2-(2-hydroxynaphthalen-1-ylimino)-5-(3-methyl-3H-benzothiazol-2-ylidene)thiazolidin-4-one;

2-(4-cyclohexylphenylimino)-5-(3-methyl-3H-benzothiazol-2-ylidene)-3-phenylthiazolidin-4-one;

3-[3-benzyl-5-(6-fluoro-3-methyl-3H-benzothiazol-2-ylidene)-4-oxothiazolidin-2-ylideneamino]-4-ethylaminobenzonitrile;

3-[3-benzyl-5-(5-chloro-3-methyl-3H-benzothiazol-2-ylidene)-4-oxothiazolidin-2-ylideneamino]-4-ethylaminobenzonitrile;

3-[3-benzyl-5-(6-ethoxy-3-methyl-3H-benzothiazol-2-ylidene)-4-oxothiazolidin-2-ylideneamino]-4-ethylaminobenzonitrile;

4-ethylamino-3-[5-(3-methyl-3H-benzothiazol-2-ylidene)-4-oxo-3-propylthiazolidin-2-ylideneamino]benzonitrile;

3-[3-benzyl-5-(3-methyl-6-nitro-3H-benzothiazol-2-ylidene)-4-oxothiazolidin-2-ylideneamino]-4-ethylaminobenzonitrile;

N-{2-[3-benzyl-2-(5-cyano-2-ethylaminophenylimino)-4-oxothiazolidin-5-ylidene]-3-methyl-2,3-dihydrobenzothiazol-6-yl}acetamide;

3-[3-benzyl-5-(6-hydroxy-3-methyl-3H-benzothiazol-2-ylidene)-4-oxothiazolidin-2-ylideneamino]-4-ethylaminobenzonitrile;

ethylcarbamic acid 2-[3-benzyl-2-(5-cyano-2-ethylaminophenylimino)-4-oxothiazolidin-5-ylidene]-3-methyl-2,3-dihydrobenzothiazol-5-yl ester;

{2-[3-benzyl-2-(5-cyano-2-ethylaminophenylimino)-4-oxothiazolidin-5-ylidene]-3-methyl-2,3-dihydrobenzothiazol-5-yloxy}acetic acid methyl ester;

2-{2-[3-benzyl-2-(5-cyano-2-ethylaminophenylimino)-4-oxothiazolidin-5-ylidene]-3-methyl-2,3-dihydrobenzothiazol-5-yloxy}acetamide;

(2-chloroethyl)carbamic acid 2-[3-benzyl-2-(5-cyano-2-ethylaminophenylimino)-4-oxothiazolidin-5-ylidene]-3-methyl-2,3-dihydrobenzothiazol-5-yl ester;

3-{3-benzyl-5-[3-methyl-5-(2-methylaminoethoxy)-3H-benzothiazol-2-ylidene]-4-oxothiazolidin-2-ylideneamino}-4-ethylaminobenzonitrile;

3-{3-benzyl-5-[5-(3-hydroxypropoxy)-3-methyl-3H-benzothiazol-2-ylidene]-4-oxothiazolidin-2-ylideneamino}-4-ethylaminobenzonitrile;

(3-chloropropyl)carbamic acid 2-[3-benzyl-2-(5-cyano-2-ethylaminophenylimino)-4-oxothiazolidin-5-ylidene]-3-methyl-2,3-dihydrobenzothiazol-5-yl ester;

3-(3-benzyl-5-{3-methyl-5-[2-(4-methylpiperazin-1-yl)-ethoxy]-3H-benzothiazol-2-ylidene}-4-oxothiazolidin-2-ylideneamino)-4-ethylaminobenzonitrile;

3-{3-benzyl-5-[3-methyl-5-(2-piperidin-4-ylethoxy)-3H-benzothiazol-2-ylidene]-4-oxothiazolidin-2-ylideneamino}-4-ethylaminobenzonitrile;

3-{3-benzyl-5-[5-(2-dimethylaminoethoxy)-3-methyl-3H-benzothiazol-2-ylidene]-4-oxothiazolidin-2-ylideneamino}-4-ethylaminobenzonitrile;

{2-[3-benzyl-2-(5-cyano-2-ethylaminophenylimino)-4-oxothiazolidin-5-ylidene]-3-methyl-2,3-dihydrobenzothiazol-5-yloxy}acetic acid;

3-{3-benzyl-5-[6-(2-hydroxyethoxy)-3-methyl-3H-benzothiazol-2-ylidene]-4-oxothiazolidin-2-ylideneamino}-4-ethylaminobenzonitrile;

3-{3-benzyl-5-[6-(2-methoxyethoxy)-3-methyl-3H-benzothiazol-2-ylidene]-4-oxothiazolidin-2-ylideneamino}-4-ethylaminobenzonitrile;

3-{3-benzyl-5-[3-methyl-6-(2-morpholin-4-ylethoxy)-3H-benzothiazol-2-ylidene]-4-oxothiazolidin-2-ylideneamino}-4-ethylaminobenzonitrile;

3-{3-benzyl-5-[5-(2-methoxyethoxy)-3-methyl-3H-benzothiazol-2-ylidene]-4-oxothiazolidin-2-ylideneamino}-4-ethylaminobenzonitrile;

3-{3-benzyl-5-[3-methyl-4-methoxy-3H-benzothiazol-2-ylidene]-4-oxothiazolidin-2-ylideneamino}-4-ethylaminobenzonitrile;

3-{3-benzyl-5-[3-methyl-4-methyl-3H-benzothiazol-2-ylidene]-4-oxothiazolidin-2-ylideneamino}-4-ethylaminobenzonitrile;

3-{3-benzyl-5-[3-methyl-4-chloro-3H-benzothiazol-2-ylidene]-4-oxothiazolidin-2-ylideneamino}-4-ethylaminobenzonitrile;

3-{3-benzyl-5-[3-methyl-6-trifluoromethoxy-3H-benzothiazol-2-ylidene]-4-oxothiazolidin-2-ylideneamino}-4-ethylaminobenzonitrile;

3-[3-benzyl-5-(3,5,6-trimethyl-3H-benzothiazol-2-ylidene)-4-oxothiazolidin-2-ylideneamino]-4-ethylaminobenzonitrile;

3-[3-benzyl-5-(3-methyl-5-acetamido-3H-benzothiazol-2-ylidene)-4-oxothiazolidin-2-ylideneamino]-4-ethylaminobenzonitrile;

N-{2-[3-benzyl-2-(5-cyano-2-ethylaminophenylimino)-4-oxothiazilidin-6-ylidene]-3-methyl-2,3-dihydrobenzothiazol-5-yl}-2,2,2-trifluoroacetamide;

3-[5-(6-amino-3-methyl-3H-benzothiazol-2-ylidene)-4-oxothiazolidin-2-ylideneamino]-4-ethylaminobenzonitrile;

N-{2-[3-benzyl-2-(5-cyano-2-ethylaminophenylimino)-4-oxothiazolidin-5-ylidene]-3-methyl-2,3-dihydrobenzothiazol-6-yl}-N',N"-di(tert-butoxycarbonyl)guanidine;

2-{2-[3-benzyl-2-(5-cyano-2-ethylaminophenylimino)-4-oxothiazilidin-5-ylidene]-3-methyl-2,3-dihydrobenzothiazol-6-yl}-1,1,-dimethylurea;

N-{2-[3-benzyl-2-(5-cyano-2-ethylaminophenylimino)-4-oxothiazilidin-5-ylidene]-3-methyl-2,3-dihydrobenzothiazol-5-yl}-2,2,2-trifluoroacetamide;

3-[5-(5-amino-3-methyl-3H-benzothiazol-2-ylidene)-4-oxothiazolidin-2-ylideneamino]-4-ethylaminobenzonitrile;

{2-[3-benzyl-2-(5-cyano-2-ethylaminophenylimino)-4-oxothiazilidin-5-ylidene]-3-methyl-2,3-dihydrobenzothiazol-6-yl}carbamic acid ethyl ester;

N-[2-(3-benzyl-2-{5-cyano-2-[ethyl-(2-morpholin-ylethyl)amino]phenylimino}-4-oxothiazilidin-5-ylidene)-3-methyl-2,3-dihydrobenzothiazol-6-yl]-2,2,2-trifluoroacetamide;

N-{2-[3-benzyl-2-(5-cyano-2-ethylaminophenylimino)-4-oxothiazilidin-5-ylidene]-3-methyl-2,3-dihydrobenzothiazol-6-yl}-2,2,2-trifluoro-N-(2-morpholin-4ylethyl)acetamide;

3-{3-benzyl-5-[3-methyl-6-(2-morpholin-4-yl-ethylamino)-3H-benzothiazol-2-ylidene]-4-oxothiazolidin-2-ylideneamino}-4-ethylaminobenzonitrile;

3-{3-benzyl-5-[3-methyl-6-(2-piperidin-1-yl-ethylamino)-3H-benzothiazol-2-ylidene]-4-oxothiazolidin-2-ylideneamino}-4-ethylaminobenzonitrile;

N-{2-[3-benzyl-2-(5-cyano-2-ethylaminophenylimino)-4-oxothiazilidin-5-ylidene]-3-methyl-2,3-dihydrobenzothiazol-5-yl}-2,2,2-trifluoro-N-(2-morpholin-4ylethyl)acetamide;

3-{3-benzyl-5-[3-methyl-5-(2-morpholin-4-yl-ethylamino)-3H-benzothiazol-2-ylidene]-4-oxothiazolidin-2-ylideneamino}-4-ethylaminobenzonitrile;

N-{2-[3-benzyl-2-(5-cyano-2-ethylaminophenylimino)-4-oxothiazolidin-5-ylidene]-3-methyl-2,3-dihydrobenzothiazol-6-yl}guanidine;

3-{3-benzyl-5-[3-methyl-6-(4-trifluoromethylbenzylamino)-3H-benzothiazol-2-ylidene]-4-oxothiazolidin-2-ylideneamino}-4-ethylaminobenzonitrile;

N-{2-[3-benzyl-2-(5-cyano-2-ethylaminophenylimino)-4-oxothiazilidin-5-ylidene]-3-methyl-2,3-dihydrobenzothiazol-6-yl}-N-(3-fluoropropyl)-2,2,2-trifluoroacetamide;

N-{2-[3-benzyl-2-(5-cyano-2-ethylaminophenylimino)-4-oxothiazilidin-5-ylidene]-3-methyl-2,3-dihydrobenzothiazol-6-yl}-N-(3-cyanopropyl)-2,2,2-trifluoroacetamide;

3-{3-benzyl-5-[6-(3-cyanopropylamino)-3-methyl-3H-benzothiazol-2-ylidene]-4-oxothiazolidin-2-ylideneamino}-4-(ethylamino)benzonitrile;

3-{3-benzyl-5-[6-(3-hydroxypropylamino)-3-methyl-3H-benzothiazol-2-ylidene]-4-oxothiazolidin-2-ylideneamino}-4-(ethylamino)benzonitrile; and 3-{3-benzyl-5-[6-(2-methoxyethylamino)-3-methyl-3H-benzothiazol-2-ylidene]-4-oxothiazolidin-2-ylideneamino}-4-(ethylamino)benzonitrile.

25. A pharmaceutical composition, comprising, in a pharmaceutically acceptable carrier, a compound formulae I:

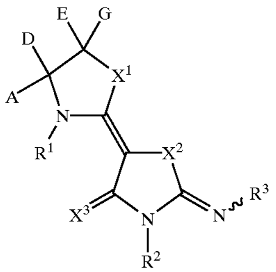

or

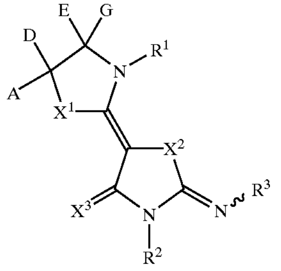

or a pharmaceutically acceptable derivative thereof, wherein:

A, D, E and G are selected from (i) or (ii) as follows:

(i) A and G are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted heteroarylium, substituted or unsubstituted heteroaryliumalkyl, halo, pseudohalo, $OR^{10}$, $SR^{10}$, $S(=O)R^{13}$, $S(=O)_2R^{13}$, $NR^{11}R^{12}$ and $C(=J)R^{13}$, or A and G together form substituted or unsubstituted alkylene, substituted or unsubstituted azaalkylene, substituted or unsubstituted oxaalkylene, substituted or unsubstituted thiaalkylene, substituted or unsubstituted alkenylene, substituted or unsubstituted alkynylene, substituted or unsubstituted 1,3-butadienylene, substituted or unsubstituted 1-aza-1,3-butadienylene, or substituted or unsubstituted 2-aza-1,3-butadienylene;

D and E are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo and pseudohalo or D and E together form a bond; or (ii) A and D; or E and G; together form substituted or unsubstituted alkylene, substituted or unsubstituted azaalkylene, substituted or unsubstituted oxaalkylene, or substituted or unsubstituted thiaalkylene; and the others of A, D, E and G are selected as in (i);

$X^1$ and $X^2$ are each independently selected from O, S, $S(=O)$, $S(=O)_2$, Se, $NR^5$, $CR^6R^7$ and $CR^8=CR^9$;

$X^3$ is O, S, Se, $NR^5$ or $CR^6R^7$;

$R^1$ and $R^2$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted heteroarylium, substituted or unsubstituted heteroaryliumalkyl, $OR^{10}$, $SR^{10}$, $S(=O)R^{13}$, $S(=O)_2R^{13}$, $NR^{11}R^{12}$ and $C(=J)R^{13}$;

$R^3$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted heteroarylium, substituted or unsubstituted aralkyl, substituted or unsubstituted heteroaralkyl, substituted or unsubstituted heteroaryliumalkyl, $OR^{10}$, $SR^{10}$, $S(=O)R^{13}$, $S(=O)_2R^{13}$, $NR^{11}R^{12}$ and $C(=J)R^{13}$;

where $R^5$, $R^6$, $R^7$, $R^8$ and $R^9$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo, pseudohalo, $OR^{10}$, $NR^{14}R^{15}$ and $C(=J)R^{13}$;

$R^{10}$, $R^{11}$ and $R^{12}$ are each independently hydrogen, substituted or unsubstituted alkyl, substituted or unsubstituted alkenyl, substituted or unsubstituted alkynyl, substituted or unsubstituted cycloalkyl, substituted or unsubstituted, heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl or $C(=J)R^{13}$;

J is O, S or $NR^{14}$;

$R^{13}$ is selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, pseudohalo, $OR^{16}$ and $NR^{14}R^{15}$;

$R^{14}$, $R^{15}$ and $R^{16}$ are each independently selected from hydrogen, alkyl, alkenyl, alkynyl, cycloalkyl, heterocyclyl, cycloalkylalkyl, heterocyclylalkyl, aryl, heteroaryl, aralkyl and heteroaralkyl;

where the alkyl, alkenyl, alkynyl, cycloalkyl, heterocyclyl, cycloalkylalkyl, heterocyclylalkyl, aryl, heteroaryl, heteroarylium, aralkyl, heteroaralkyl and heteroaryliumalkyl moieties of A, D, E, G, $R^1$, $R^2$, $R^3$, $R^5$, $R^6$, $R^7$, $R^8$, $R^9$, $R^{10}$, $R^{11}$, $R^{12}$ and $R^{13}$ are unsubstituted or substituted with one or more substituents each independently selected from $Q^1$, where $Q^1$ is halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, imino, hydroxyimino, alkoxyimino, aryloxyimino, aralkoxyimino, alkylazo, arylazo, aralkylazo, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{51}R^{52}R^{53}$, $P(R^{50})_2$, $P(=O)(R^{50})_2$, $OP(=O)(R^{50})_2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy, thioalkylenoxy or alkylenedithioxy where y is 1 or 2; or two $Q^1$ groups, which substitute the same atom, together form alkylene; and each $Q^1$ is independently unsubstituted or substituted with one or more substituents each independently selected from $Q^2$;

each $Q^2$ is independently halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{51}R^{52}R^{53}$, $P(R^{50})_2$, $P(=O)(R^{50})_2$, $OP(=O)(R^{50})_2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^2$ groups, which substitute atoms in a 1,2 or 1,3 arrangement, together form alkylenedioxy, thioalkylenoxy or alkylenedithioxy where y is 1 or 2; or two $Q^2$ groups, which substitute the same atom, together form alkylene;

each $Q^2$ is independently unsubstituted or substituted with one or more substituents each independently selected from alkyl, halo and pseudohalo;

$R^{50}$ is hydroxy, alkoxy, aralkoxy, alkyl, heteroaryl, heterocyclyl, aryl or $—NR^{70}R^{71}$, where $R^{70}$ and $R^{71}$ are each independently hydrogen, alkyl, aralkyl, aryl, heteroaryl, heteroaralkyl or heterocyclyl, or $R^{70}$ and $R^{71}$ together form alkylene, azaalkylene, oxaalkylene or thiaalkylene;

$R^{51}$, $R^{52}$ and $R^{53}$ are each independently hydrogen, alkyl, aryl, aralkyl, heteroaryl, heteroaralkyl, heterocyclyl or heterocyclylalkyl;

$R^{60}$ is hydrogen, alkyl, aryl, aralkyl, heteroaryl, heteroaralkyl, heterocyclyl or heterocyclylalkyl; and $R^{63}$ is alkoxy, aralkoxy, alkyl, heteroaryl, heterocyclyl, aryl or $—NR^{70}R^{71}$.

26. The pharmaceutical composition of claim 25, wherein the compound has formulae II:

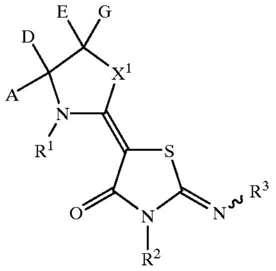

or

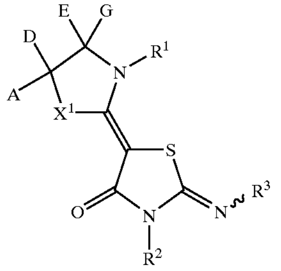

or a pharmaceutically acceptable derivative thereof, wherein:

A, D, E and G are selected from (i) or (ii) as follows:

(i) A and G are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted heteroarylium, substituted or unsubstituted heteroaryliumalkyl, halo, pseudohalo, $OR^{10}$, $SR^{10}$, $S({=}O)R^{13}$, $S({=}O)_2R^{13}$, $NR^{11}R^{12}$ and $C({=}J)R^{13}$, or A and G together form substituted or unsubstituted alkylene, substituted or unsubstituted azaalkylene, substituted or unsubstituted oxaalkylene, substituted or unsubstituted thiaalkylene, substituted or unsubstituted alkenylene, substituted or unsubstituted alkynylene, substituted or unsubstituted 1,3-butadienylene, substituted or unsubstituted 1-aza-1,3-butadienylene, or substituted or unsubstituted 2-aza-1,3-butadienylene;

D and E are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo and pseudohalo or D and E together form a bond; or (ii) A and D; or E and G; together form substituted or unsubstituted alkylene, substituted or unsubstituted azaalkylene, substituted or unsubstituted oxaalkylene, or substituted or unsubstituted thiaalkylene; and the others of A, D, E and G are selected as in (i);

$X^1$ is selected from O, S, Se, $NR^5$, $CR^6R^7$ and $CR^8{=}CR^9$;

$R^1$ and $R^2$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted heteroarylium, substituted or unsubstituted heteroaryliumalkyl, $OR^{10}$, $SR^{10}$, $S({=}O)R^{13}$, $S({=}O)_2R^{13}$, $NR^{11}R^{12}$ and $C({=}J)R^{13}$;

$R^3$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted heteroarylium, substituted or unsubstituted aralkyl, substituted or unsubstituted heteroaralkyl, substituted or unsubstituted heteroaryliumalkyl, $OR^{10}$, $SR^{10}$, $S({=}O)R^{13}$, $S({=}O)_2R^{13}$, $NR^{11}R^{12}$ and $C({=}J)R^{13}$;

where:

$R^5$, $R^6$, $R^7$, $R^8$ and $R^9$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo, pseudohalo, $OR^{10}$, $NR^{14}R^{15}$ and $C({=}J)R^{13}$;

$R^{10}$, $R^{11}$ and $R^{12}$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl or $C({=}J)R^{13}$;

J is O, S or $NR^{14}$;

$R^{13}$ is selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, pseudohalo, $OR^{16}$ and $NR^{14}R^{15}$;

$R^{14}$, $R^{15}$ and $R^{16}$ are each independently selected from hydrogen, alkyl, alkenyl, alkynyl, cycloalkyl, heterocyclyl, cycloalkylalkyl, heterocyclylalkyl, aryl, heteroaryl, aralkyl and heteroaralkyl;

where the alkyl, alkenyl, alkynyl, cycloalkyl, heterocyclyl, cycloalkylalkyl, heterocyclylalkyl, aryl, heteroaryl, heteroarylium, aralkyl, heteroaralkyl and heteroaryliumalkyl moieties of $R^1$, $R^2$, $R^3$, $R^5$, $R^6$, $R^7$, $R^8$, $R^9$, $R^{10}$, $R^{11}$, $R^{12}$ and $R^{13}$ are unsubstituted or substituted with one or more substituents each independently selected from $Q^1$, where $Q^1$ is halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'- diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{51}R^{52}R^{53}$, $P(R^{50})_2$, $P(=O)(R^{50})_2$, $OP(=O)(R^{50})_2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy, thioalkylenoxy or alkylenedithioxy; or two $Q^1$ groups, which substitute the same atom, together form alkylene;

each $Q^1$ is independently unsubstituted or substituted with one or more substituents each independently selected from $Q^2$;

each $Q^2$ is independently halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{51}R^{52}R^{53}$, $P(R^{50})_2$, $P(=O)(R^{50})_2$, $OP(=O)(R^{50})_2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^2$ groups, which substitute atoms in a 1,2 or 1,3 arrangement, together form alkylenedioxy (i.e., $—O—(CH_2)_y—O—$), thioalkylenoxy (i.e., $—S—(CH_2)_y—O—$)or alkylenedithioxy (i.e., $—S—(CH_2)_y—S—$) where y is 1 or 2; or two $Q^2$ groups, which substitute the same atom, together form alkylene;

$R^{50}$ is hydroxy, alkoxy, aralkoxy, alkyl, heteroaryl, heterocyclyl, aryl or $—NR^{70}R^{71}$, where $R^{70}$ and $R^{71}$ are each independently hydrogen, alkyl, aralkyl, aryl, heteroaryl, heteroaralkyl or heterocyclyl, or $R^{70}$ and $R^{71}$ together form alkylene, azaalkylene, oxaalkylene or thiaalkylene;

$R^{51}$, $R^{52}$ and $R^{53}$ are each independently hydrogen, alkyl, aryl, aralkyl, heteroaryl, heteroaralkyl, heterocyclyl or heterocyclylalkyl;

$R^{60}$ is hydrogen, alkyl, aryl, aralkyl, heteroaryl, heteroaralkyl, heterocyclyl or heterocyclylalkyl; and $R^{63}$ is alkoxy, aralkoxy, alkyl, heteroaryl, heterocyclyl, aryl or $—NR^{70}R^{71}$.

27. The pharmaceutical composition of claim 25, wherein A and G are each independently selected from hydrogen, substituted or unsubstituted alkyl, or substituted or unsubstituted aryl, or together form substituted or unsubstituted 1,3-butadienyl.

28. The pharmaceutical composition of claim 25, wherein A and G are each independently hydrogen, methyl or phenyl, or together form substituted or unsubstituted 1,3-butadienyl.

29. The pharmaceutical composition of claim 25, wherein A and G are both hydrogen.

30. The pharmaceutical composition of claim 25, wherein D and E are each hydrogen, or together form a bond.

31. The pharmaceutical composition of claim 25, wherein D and E together form a bond, and A and G together form substituted or unsubstituted 1,3-butadienyl.

32. The pharmaceutical composition of claim 25, wherein the compound has formulae III:

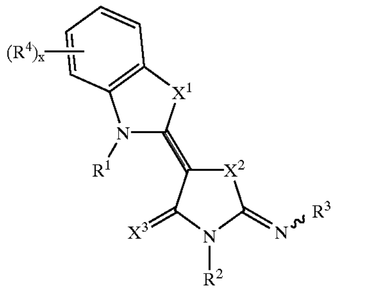

or

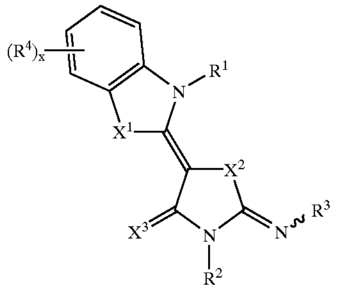

or a pharmaceutically acceptable derivative thereof, wherein:

each $R^4$ is independently substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted guanidino, substituted or unsubstituted isothioureido, halo, pseudohalo, $OR^{10}$, $SR^{10}$, $S(=O)R^{13}$, $S(=O)_2R^{13}$, $NR^{11}R^{12}$ or $C(=J)R^{13}$;

x is an integer from 0 to 4; and the amino, alkyl, alkenyl, alkynyl, cycloalkyl, heterocyclyl, cycloalkylalkyl, heterocyclylalkyl, aryl, heteroaryl, heteroarylium, aralkyl, heteroaralkyl and heteroaryliumalkyl moieties of $R^4$ are unsubstituted or substituted with one or more substituents each independently selected from $Q^2$.

33. The pharmaceutical composition of claim 32, wherein the compound has formulae IV:

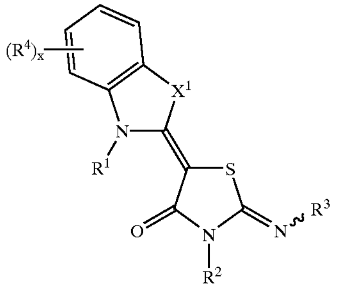

or

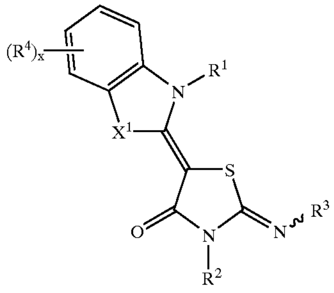

or a pharmaceutically acceptable derivative thereof, wherein:

each $R^4$ is independently substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted guanidino, substituted or unsubstituted isothioureido, halo, pseudohalo, $OR^{10}$, $SR^{10}$, $S(=O)R^{13}$, $S(=O)_2R^{13}$, $NR^{11}R^{12}$ or $C(=J)R^{13}$;

x is an integer from 0 to 4; and the amino, alkyl, alkenyl, alkynyl, cycloalkyl, heterocyclyl, cycloalkylalkyl, heterocyclylalkyl, aryl, heteroaryl, heteroarylium, aralkyl, heteroaralkyl and heteroaryliumalkyl moieties of $R^4$ are unsubstituted or substituted with one or more substituents each independently selected from $Q^2$.

34. The pharmaceutical composition of claim 25, wherein $X^1$ is O, S or $NR^5$.

35. The pharmaceutical composition of claim 25, wherein $X^1$ is O or S.

36. The pharmaceutical composition of claim 25, wherein $X^1$ is S.

37. The pharmaceutical composition of claim 25, wherein $R^1$ is substituted or unsubstituted alkyl.

38. The pharmaceutical composition of claim 25, wherein $R^1$ is methyl.

39. The pharmaceutical composition of claim 25, wherein $R^2$ is substituted or unsubstituted alkyl or substituted or unsubstituted aralkyl.

40. The pharmaceutical composition of claim 25, wherein $R^2$ is ethyl, n-butyl or benzyl.

41. The pharmaceutical composition of claim 25, wherein $R^2$ is benzyl.

42. The pharmaceutical composition of claim 25, wherein $R^3$ is substituted or unsubstituted aryl or substituted or unsubstituted heteroaryl.

43. The pharmaceutical composition of claim 25, wherein $R^3$ is substituted or unsubstituted phenyl, substituted or unsubstituted naphthyl, substituted or unsubstituted pyridyl, substituted or unsubstituted indazolyl, or substituted or unsubstituted quinolinyl.

44. The pharmaceutical composition of claim 25, wherein $R^3$ is substituted or unsubstituted phenyl.

45. The pharmaceutical composition of claim 25, wherein $Q^1$ is selected from halo, hydroxy, nitrile, nitro, hydroxycarbonyl, alkyl, haloalkyl, polyhaloalkyl, heteroaryl, alkylcarbonyl, alkoxycarbonyl, aminocarbonyl, alkoxy, perfluoroalkoxy, aralkoxy, amino, alkylamino, dialkylamino, haloalkylamino, alkylcarbonylamino, dialkylcarbonyloxy or heterocyclyl; or two $Q^1$ groups, which substitute atoms in a 1,2 arrangement, form alkylenedioxy.

46. The pharmaceutical composition of claim 25, wherein $Q^1$ is methoxy, dimethylamino, $NH_2$, benzyloxy, hydroxy, CN, isopropyl, methyl, nitro, ethylamino, trifluoromethyl, acetyl, chloro, n-propyl, ethoxy, methylcarbonylamino, $CONH_2$, methoxycarbonyl, methylamino, trifluoromethoxy, imidazolyl, hydroxycarbonyl, isopropylamino, tert-butylamino, 2,2,2-trifluoroethylamino, piperidinyl, dimethylaminocarbonyloxy, 2-hydroxyethoxy, 2-(N-morpholinyl)ethoxy or morpholinyl, or two $Q^1$ groups, which substitute atoms in a 1,2 arrangement, form methylenedioxy.

47. The pharmaceutical composition of claim 25, wherein the compound has formulae V:

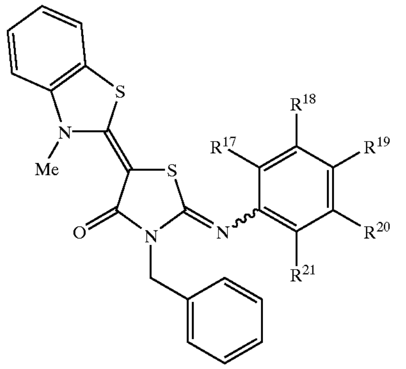

or

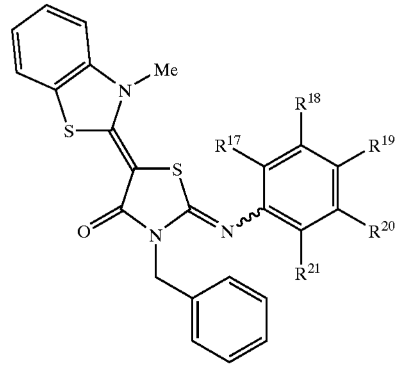

or a pharmaceutically acceptable derivative thereof, wherein:

$R^{17}$, $R^{18}$, $R^{19}$, $R^{20}$ and $R^{21}$ are each independently selected from hydrogen, halo, pseudohalo, hydroxyl, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{51}R^{52}R^{53}$, $P(R^{50})_2$, $P(=O)(R^{50})_2$, $OP(=O)(R^{50})_2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl, or any two of $R^{17}$, $R^{18}$, $R^{19}$, $R^{20}$ and $R^{21}$, which substitute adjacent carbons on the ring, together form alkylenedioxy; and the aryl and heteroaryl groups of $R^{17}$, $R^{18}$, $R^{19}$, $R^{20}$ and $R^{21}$ are unsubstituted or substituted with one or more substituents each independently selected from $R^{30}$, where $R^{30}$ is alkyl, halo, pseudohalo, alkoxy, aryloxy or alkylenedioxy.

48. The pharmaceutical composition of claim 25, wherein the compound has formulae VI:

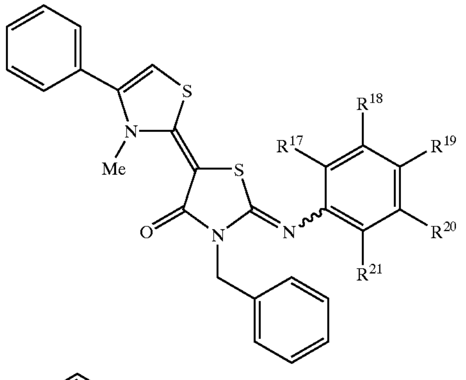

or

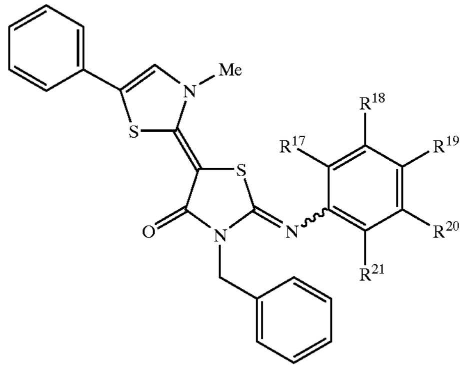

or a pharmaceutically acceptable derivative thereof, where $R^{17}$, $R^{18}$, $R^{19}$, $R^{20}$ and $R^{21}$ are each independently selected from hydrogen, halo, pseudohalo, hydroxyl, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^{+}R^{51}R^{52}R^{53}$, $P(R^{50})_2$, $P(=O)(R^{50})_2$, $OP(=O)(R^{50})_2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl, or any two of $R^{17}$, $R^{18}$, $R^{19}$, $R^{20}$ and $R^{21}$, which substitute adjacent carbons on the ring, together form alkylenedioxy; and the aryl and heteroaryl groups of $R^{17}$, $R^{18}$, $R^{19}$, $R^{20}$ and $R^{21}$ are unsubstituted or substituted with one or more substituents each independently selected from $R^{30}$, where $R^{30}$ is alkyl, halo, pseudohalo, alkoxy, aryloxy or alkylenedioxy.

49. The pharmaceutical composition of claim 25, wherein the compound has formulae VII:

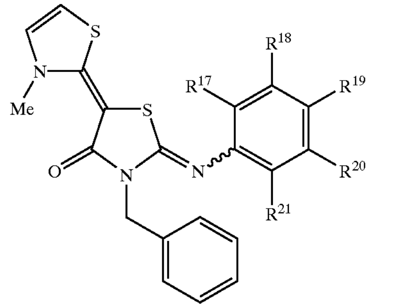

or

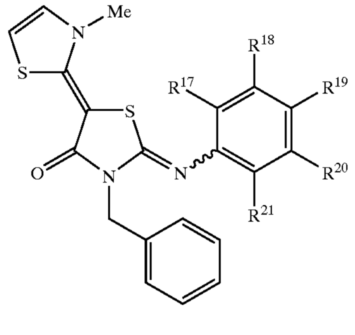

or a pharmaceutically acceptable derivative thereof, where $R^{17}$, $R^{18}$, $R^{19}$, $R^{20}$ and $R^{21}$ are each independently selected from hydrogen, halo, pseudohalo, hydroxyl, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —$N^+R^{51}R^{52}R^{53}$, $P(R^{50})_2$, P(=O)$(R^{50})_2$, OP(=O)$(R^{50})_2$, —$NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl, or any two of $R^{17}$, $R^{18}$, $R^{19}$, $R^{20}$ and $R^{21}$, which substitute adjacent carbons on the ring, together form alkylenedioxy; and the aryl and heteroaryl groups of $R^{17}$, $R^{18}$, $R^{19}$, $R^{20}$ and $R^{21}$ are unsubstituted or substituted with one or more substituents each independently selected from $R^{30}$, where $R^{30}$ is alkyl, halo, pseudohalo, alkoxy, aryloxy or alkylenedioxy.

50. The pharmaceutical composition of claim 25, wherein the compound has formulae VIII:

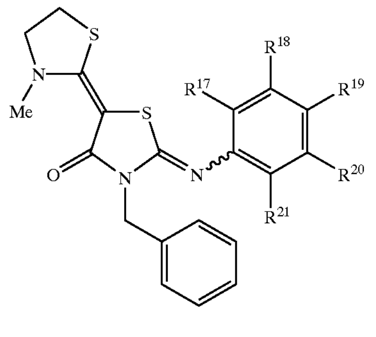

or

-continued

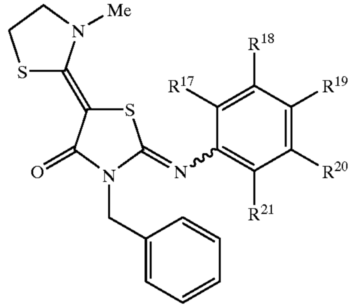

or a pharmaceutically acceptable derivative thereof, where $R^{17}$, $R^{18}$, $R^{19}$, $R^{20}$ and $R^{21}$ are each independently selected from hydrogen, halo, pseudohalo, hydroxyl, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —$N^+R^{51}R^{52}R^{53}$, $P(R^{50})_2$, P(=O)$(R^{50})_2$, OP(=O)$(R^{50})_2$, —$NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl, or any two of $R^{17}$, $R^{18}$, $R^{19}$, $R^{20}$ and $R^{21}$, which substitute adjacent carbons on the ring, together form alkylenedioxy; and the aryl and heteroaryl groups of $R^{17}$, $R^{18}$, $R^{19}$, $R^{20}$ and $R^{21}$ are unsubstituted or substituted with one or more substituents each independently selected from $R^{30}$, where $R^{30}$ is alkyl, halo, pseudohalo, alkoxy, aryloxy or alkylenedioxy.

51. The pharmaceutical composition of claim 25, wherein the compound has formulae IX:

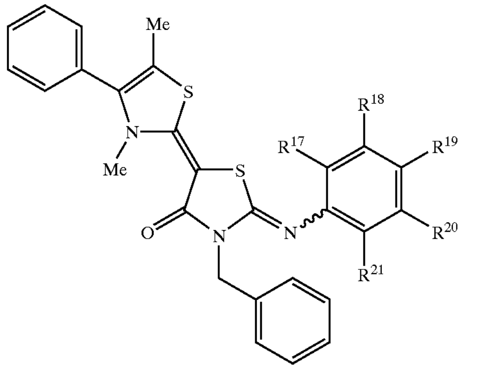

or

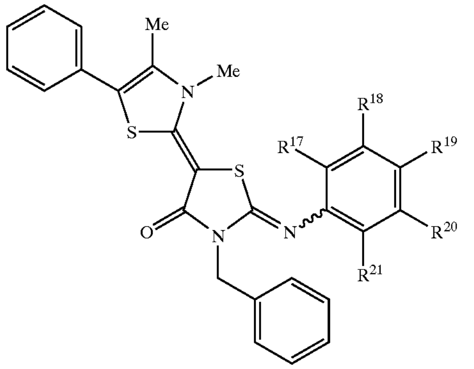

or a pharmaceutically acceptable derivative thereof, where $R^{17}$, $R^{18}$, $R^{19}$, $R^{20}$ and $R^{21}$ are each independently selected from hydrogen, halo, pseudohalo, hydroxyl, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{51}R^{52}R^{53}$, $P(R^{50})_2$, $P(=O)(R^{50})_2$, $OP(=O)(R^{50})_2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl, or any two of $R^{17}$, $R^{18}$, $R^{19}$, $R^{20}$ and $R^{21}$, which substitute adjacent carbons on the ring, together form alkylenedioxy; and the aryl and heteroaryl groups of $R^{17}$, $R^{18}$, $R^{19}$, $R^{20}$ and $R^{21}$ are unsubstituted or substituted with one or more substituents each independently selected from $R^{30}$, where $R^{30}$ is alkyl, halo, pseudohalo, alkoxy, aryloxy or alkylenedioxy.

52. The pharmaceutical composition of claim 48, wherein $R^{17}$, $R^{18}$, $R^{19}$, $R^{20}$ and $R^{21}$ are each independently selected from hydrogen, halo, hydroxy, nitrile, nitro, hydroxycarbonyl, alkyl, haloalkyl, polyhaloalkyl, heteroaryl, alkylcarbonyl, alkoxycarbonyl, aminocarbonyl, alkoxy, perfluoroalkoxy, aralkoxy, amino, alkylamino, dialkylamino, haloalkylamino, alkylcarbonylamino or heterocyclyl; or any two of $R^{17}$, $R^{18}$, $R^{19}$, $R^{20}$ and $R^{21}$, which substitute adjacent carbons on the ring, form alkylenedioxy.

53. The pharmaceutical composition of claim 48, wherein $R^{17}$, $R^{18}$, $R^{19}$, $R^{20}$ and $R^{21}$ are each independently hydrogen, methoxy, dimethylamino, $NH_2$, benzyloxy, hydroxy, CN, isopropyl, methyl, nitro, ethylamino, trifluoromethyl, acetyl, chloro, n-propyl, ethoxy, methylcarbonylamino, $CONH_2$, methoxycarbonyl, methylamino, trifluoromethoxy, imidazolyl, hydroxycarbonyl, isopropylamino, tert-butylamino, 2,2,2-trifluoroethylamino, piperidinyl or morpholinyl, or any two of $R^{17}$, $R^{18}$, $R^{19}$, $R^{20}$ and $R^{21}$, which substitute adjacent carbons on the ring, form methylenedioxy.

54. The pharmaceutical composition of claim 25, wherein the compound is selected from:

3-benzyl-5-(3-methyl-3H-benzothiazol-2-ylidene)-2-phenylimino-thiazolidine-4-one;

3-benzyl-2-(4-methoxyphenylimino)-5-(3-methyl-3H-benzothiazol-2-ylidene)thiazolidine-4-one;

3-benzyl-2-(4-dimethylaminophenylimino)-5-(3-methyl-3H-benzothiazol-2-ylidene)thiazolidine-4-one;

2-(4-aminophenylimino)-3-benzyl-5-(3-methyl-3H-benzothiazol-2-ylidene)thiazolidine-4-one;

3-benzyl-5-(3-methyl-3H-benzothiazol-2-ylidene)-2-(quinolin-6-ylimino)-thiazolidine-4-one;

2-(2-aminophenylimino)-3-benzyl-5-(3-methyl-3H-benzothiazol-2-ylidene)thiazolidine-4-one;

3-benzyl-2-(4-benzyloxyphenylimino)-5-(3-methyl-3H-benzothiazol-2-ylidene)thiazolidine-4-one;

3-benzyl-2-(2-hydroxy-1-naphthylimino)-5-(3-methyl-3H-benzothiazol-2-ylidene)thiazolidine-4-one;

3-[3-benzyl-5-(3-methyl-3H-benzothiazol-2-ylidene)-4-oxothiazolidin-2-ylideneamino]benzonitrile;

3-benzyl-2-(4-hydroxy-5-isopropyl-2-methylphenylimino)-5-(3-methyl-3H-benzothiazol-2-ylidene)thiazolidine-4-one;

3-benzyl-2-(2-ethylamino-5-nitrophenylimino)-5-(3-methyl-3H-benzothiazol-2-ylidene)thiazolidine-4-one;

3-benzyl-5-(3-methyl-3H-benzothiazol-2-ylidene)-2-[3-(trifluoromethyl)phenylimino]thiazolidine-4-one;

2-(3-acetylphenylimino)-3-benzyl-5-(3-methyl-3H-benzothiazol-2-ylidene)thiazolidine-4-one;

3-benzyl-2-(3-chlorophenylimino)-5-(3-methyl-3H-benzothiazol-2-ylidene)thiazolidine-4-one;

3-benzyl-5-(3-methyl-3H-benzothiazol-2-ylidene)-2-(2-propylphenylimino)thiazolidine-4-one;

3-benzyl-5-(3-methyl-3H-benzothiazol-2-ylidene)-2-(quinolin-5-ylimino)thiazolidine-4-one;

3-benzyl-2-(2-ethoxyphenylimino)-5-(3-methyl-3H-benzothiazol-2-ylidene)thiazolidine-4-one;

N-{3-[3-benzyl-5-(3-methyl-3H-benzothiazol-2-ylidene)-4-oxothiazolidin-2-ylideneamino]phenyl}acetamide;

3-[3-benzyl-5-(3-methyl-3H-benzothiazol-2-ylidene)-4-oxothiazolidin-2-ylideneamino]benzamide;

3-[3-benzyl-5-(3-methyl-3H-benzothiazol-2-ylidene)-4-oxothiazolidin-2-ylideneamino]benzoic acid, methyl ester;

3-benzyl-5-(3-methyl-3H-benzothiazol-2-ylidene)-2-(pyridin-3-ylimino)-thiazolidine-4-one;

N-{3-[3-benzyl-5-(3-methyl-3H-benzothiazol-2-ylidene)-4-oxothiazolidin-2-ylideneamino]-4-ethoxyphenyl}acetamide;

3-benzyl-5-(3-methyl-3H-benzothiazol-2-ylidene)-2-(pyridin-4-ylimino)thiazolidine-4-one;

4-[3-benzyl-5-(3-methyl-3H-benzothiazol-2-ylidene)-4-oxothiazolidin-2-ylideneamino]benzoic acid, methyl ester;

3-benzyl-5-(3-methyl-3H-benzothiazol-2-ylidene)-2-[4-(trifluoromethoxy)phenylimino]thiazolidine-4-one;

3-benzyl-2-(1H-indazol-5-ylimino)-5-(3-methyl-3H-benzothiazol-2-ylidene)thiazolidin-4-one;

3-benzyl-2-(4-imidazol-1-ylphenylimino)-5-(3-methyl-3H-benzothiazol-2-ylidene)thiazolidine-4-one;

2-(benzo[1,3]dioxol-5-ylimino)-3-benzyl-5-(3-methyl-3H-benzothiazol-2-ylidene)thiazolidin-4-one;

3-[3-benzyl-5-(3-methyl-3H-benzothiazol-2-ylidene)-4-oxothiazolidin-2-ylideneamino]benzoic acid;

3-benzyl-2-[2-(ethylamino)phenylimino]-5-(3-methyl-3H-benzothiazol-2-ylidene)thiazolidine-4-one;

3-[3-benzyl-5-(3-methyl-3H-benzothiazol-2-ylidene)-4-oxothiazolidin-2-ylideneamino]-4-(methylamino)benzonitrile;

3-[3-benzyl-5-(3-methyl-3H-benzothiazol-2-ylidene)-4-oxothiazolidin-2-ylideneamino]-4-(ethylamino)benzonitrile;

3-[3-benzyl-5-(3-methyl-3H-benzothiazol-2-ylidin-2-ylideneamino]-4-(isopropylamino)benzonitrile;

3-[3-benzyl-5-(3-methyl-3H-benzothiazol-2-ylidene)-4-oxothiazolidin-2-ylideneamino]-4-(dimethylamino)benzonitrile;

3-[3-benzyl-5-(3-methyl-3H-benzothiazol-2-ylidene)-4-oxothiazolidin-2-ylideneamino]-4-(tert-butylamino)benzonitrile;

3-[3-benzyl-5-(3-methyl-3H-benzothiazol-2-ylidene)-4-oxothiazolidin-2-ylideneamino]-4-(2,2,2-trifluoroethylamino)benzonitrile;

3-[3-benzyl-5-(3-methyl-3H-benzothiazol-2-ylidene)-4-oxothiazolidin-2-ylideneamino]-4-piperidin-1-ylbenzonitrile;

2-[5-acetyl-2-(ethylamino)phenylimino]-3-benzyl-5-(3-methyl-3H-benzothiazol-2-ylidene)thiazolidin-4-one;

3-ethyl-5-(3-methyl-3H-benzothiazol-2-ylidene)-2-(quinolin-6-ylimino)thiazolidin-4-one;

3-ethyl-5-(3-methyl-3H-benzothiazol-2-ylidene)-2-(4-morpholin-4-yl-phenylimino)thiazolidin-4-one;

3-[3-ethyl-5-(3-methyl-3H-benzothiazol-2-ylidene)-4-oxothiazolidin-2-ylideneamino]-4-(methylamino)benzonitrile;

4-dimethylamino-3-[3-ethyl-5-(3-methyl-3H-benzothiazol-2-ylidene)-4-oxothiazolidin-2-ylideneamino]benzonitrile;

4-ethylamino-3-[3-ethyl-5-(3-methyl-3H-benzothiazol-2-ylidene)-4-oxo-thiazolidin-2-ylideneamino]benzonitrile;

3-[3-ethyl-5-(3-methyl-3H-benzothiazol-2-ylidene)-4-oxothiazolidin-2-ylideneamino]-4-(isopropylamino)benzonitrile;

3-[3-butyl-5-(3-methyl-3H-benzothiazol-2-ylidene)-4-oxothiazolidin-2-ylideneamino]benzonitrile;

3-benzyl-5-(3-methyl-3H-benzoxazol-2-ylidene)-2-(quinolin-5-ylimino)thiazolidin-4-one;

N-[4-(3'-benzyl-3-methyl-4'-oxo-4-phenyl-3',4'-dihydro-3H-[2,5']-bithiazolyliden-2'-ylideneamino)phenyl]acetamide;

2'-[5-acetyl-2-(ethylamino)phenylimino]-3'-benzyl-3-methyl-4-phenyl-2',3'-dihydro-3H-[2,5']bithiazolyliden-4'-one;

3-(3'-benzyl-3-methyl-4'-oxo-4-phenyl-3',4'-dihydro-3H-[2,5']bithiazol-yliden-2'-ylideneamino)-4-(ethylamino)benzonitrile;

N-[4-(3'-benzyl-3-methyl-4'-oxo-3',4'-dihydro-3H-[2,5']bithiazolyliden-2'-ylideneamino)phenyl]acetamide;

N-[4-(3'-benzyl-3-methyl-4'-oxo-[2,5']bithiazolidinyliden-2'-ylideneamino)phenyl]acetamide;

3-(3'-benzyl-3,5-dimethyl-4'-oxo-4-phenyl-3',4'-dihydro-3H-[2,5']-bithiazolyliden-2'-ylideneamino)-4-(ethylamino)benzonitrile;

4-ethylamino-3-[3-benzyl-5-(3-methyl-5-chloro-3H-benzothiazol-2-ylidene)-4-oxo-thiazolidin-2-ylideneamino]benzonitrile;

3-phenyl-5-(3-methyl-3H-benzothiazol-2-ylidene)-2-(4-cyclohexylphenyl)imino-thiazolidine-4-one;

3-allyl-5-(3-methyl-3H-benzothiazol-2-ylidene)-2-(2-hydroxy-1-naphthyl)imino-thiazolidine-4-one;

4-ethylamino-3-[3-phenyl-5-(3-methyl-3H-benzothiazol-2-ylidene)-4-oxo-thiazolidin-2-ylideneamino]benzonitrile;

4-ethylamino-3-[3-benzyl-5-(3-methyl-5-methoxy-3H-benzothiazol-2-ylidene)-4-oxo-thiazolidin-2-ylideneamino]benzonitrile;

3-allyl-5-(3-methyl-3H-benzothiazol-2-ylidene)-2-(5-quinolyl)imino-thiazolidine-4-one;

4-ethylamino-3-[3-allyl-5-(3-methyl-3H-benzothiazol-2-ylidene)-4-oxo-thiazolidin-2-ylideneamino]benzonitrile;

3-phenyl-5-(3-methyl-3H-benzothiazol-2-ylidene)-2-benzylamino-thiazolidine-4-one;

3-benzyl-5-(3-methyl-3H-benzothiazol-2-ylidene)-2-(8-quinolyl)imino-thiazolidine-4-one;

3-benzyl-5-(3-methyl-3H-benzothiazol-2-ylidene)-2-(8-hydroxy-5-quinolyl)imino-thiazolidine-4-one;

3-benzyl-5-(3-methyl-3H-benzothiazol-2-ylidene)-2-(5-isoquinolyl)imino-thiazolidine-4-one;

3-benzyl-5-(3-methyl-3H-benzothiazol-2-ylidene)-2-(1-isoquinolyl)imino-thiazolidine-4-one;

3-benzyl-5-(3-methyl-3H-benzothiazol-2-ylidene)-2-(4-methylcarbonylamino)phenylimino-thiazolidine-4-one;

3-benzyl-5-(3-methyl-3H-benzothiazol-2-ylidene)-2-(4-methylcarbonyl)phenylimino-thiazolidine-4-one;

3-benzyl-5-(3-methyl-3H-benzothiazol-2-ylidene)-2-(4-aminocarbonyl)phenylimino-thiazolidine-4-one;

3-benzyl-5-(3-methyl-3H-benzothiazol-2-ylidene)-2-(1-naphthyl)imino-thiazolidine-4-one;

3-benzyl-5-(3-methyl-3H-benzothiazol-2-ylidene)-2-(2-naphthyl)imino-thiazolidine-4-one;

3-benzyl-5-(3-methyl-3H-benzothiazol-2-ylidene)-2-(2-pyridyl)imino-thiazolidine-4-one;

3-benzyl-5-(3-methyl-3H-benzothiazol-2-ylidene)-2-(4-aminosulfonyl)phenylimino-thiazolidine-4-one;

3-benzyl-5-(3-methyl-3H-benzothiazol-2-ylidene)-2-(4-methylcarbonylaminosulfonyl)phenylimino-thiazolidine-4-one;

3-benzyl-5-(3-methyl-3H-benzothiazol-2-ylidene)-2-(3-methylcarbonyl)phenylimino-thiazolidine-4-one;

3-benzyl-5-(3-methyl-3H-benzothiazol-2-ylidene)-2-(2-methylcarbonylamino-5-pyridyl)imino-thiazolidine-4-one;

3-benzyl-5-(3-methyl-3H-benzothiazol-2-ylidene)-2-(4-cyano-5-methylcarbonylaminophenyl)imino-thiazolidine-4-one;

3-benzyl-5-(3-methyl-3H-benzothiazol-2-ylidene)-2-(2-ethylamino-5-methylcarbonylphenyl)imino-thiazolidine-4-one;

3-benzyl-5-(3-methyl-3H-benzothiazol-2-ylidene)-2-(2-methylamino-5-methylcarbonylphenyl)imino-thiazolidine-4-one;

3-benzyl-5-(3-methyl-3H-benzothiazol-2-ylidene)-2-(4-trifluoromethylcarbonylaminophenyl)imino-thiazolidine-4-one;

3-benzyl-5-(3-methyl-3H-benzothiazol-2-ylidene)-2-(2-ethylamino-5-methoxycarbonylphenyl)imino-thiazolidine-4-one;

3-benzyl-5-(3-methyl-3H-benzothiazol-2-ylidene)-2-(2-hydroxycarbonylphenyl)imino-thiazolidine-4-one;

3-benzyl-5-(3-methyl-3H-benzothiazol-2-ylidene)-2-(2-ethylamino-5-tert-butoxycarbonylphenyl)imino-thiazolidine-4-one;

4-butylamino-3-[3-benzyl-5-(3-methyl-3H-benzothiazol-2-ylidene)-4-oxo-thiazolidin-2-ylideneamino]benzonitrile;

4-benzylamino-3-[3-benzyl-5-(3-methyl-3H-benzothiazol-2-ylidene)-4-oxo-thiazolidin-2-ylideneamino]benzonitrile;

4-cyclopentylamino-3-[3-benzyl-5-(3-methyl-3H-benzothiazol-2-ylidene)-4-oxo-thiazolidin-2-ylideneamino]benzonitrile;

4-pyrrolidinylamino-3-[3-benzyl-5-(3-methyl-3H-benzothiazol-2-ylidene)-4-oxo-thiazolidin-2-ylideneamino]benzonitrile;

4-pyrrolidinyl-3-[3-benzyl-5-(3-methyl-3H-benzothiazol-2-ylidene)-4-oxo-thiazolidin-2-ylideneamino]benzonitrile;

4-ethylamino-3-[3-cyclohexyl-5-(3-methyl-3H-benzothiazol-2-ylidene)-4-oxo-thiazolidin-2-ylideneamino]benzonitrile;

3-allyl-5-(3-methyl-3H-benzothiazol-2-ylidene)-2-(4-hydroxy-2-methyl-5-isopropylphenyl)imino-thiazolidine-4-one;

3-cyclohexyl-5-(3-methyl-3H-benzothiazol-2-ylidene)-2-(2-hydroxy-1-naphthyl)imino-thiazolidine-4-one;

4-ethylamino-3-[3-benzyl-5-(6-fluoro-3-methyl-3H-benzothiazol-2-ylidene)-4-oxo-thiazolidin-2-ylideneamino]benzonitrile;

4-ethylamino-3-[3-benzyl-5-(6-ethoxy-3-methyl-3H-benzothiazol-2-ylidene)-4-oxo-thiazolidin-2-ylideneamino]benzonitrile;

4-ethylamino-3-[3-benzyl-5-(6-nitro-3-methyl-3H-benzothiazol-2-ylidene)-4-oxo-thiazolidin-2-ylideneamino]benzonitrile;

4-ethylamino-3-[3-benzyl-5-(5-trifluoromethyl-3-methyl-3H-benzothiazol-2-ylidene)-4-oxo-thiazolidin-2-ylideneamino]benzonitrile;

4-ethylamino-3-[3-benzyl-5-(6-methylcarbonylamino-3-methyl-3H-benzothiazol-2-ylidene)-4-oxo-thiazolidin-2-ylideneamino]benzonitrile;

4-ethylamino-3-[3-benzyl-5-(5-hydroxy-3-methyl-3H-benzothiazol-2-ylidene)-4-oxo-thiazolidin-2-ylideneamino]benzonitrile;

4-ethylamino-3-[3-benzyl-5-(6-hydroxy-3-methyl-3H-benzothiazol-2-ylidene)-4-oxo-thiazolidin-2-ylideneamino]benzonitrile;

4-ethylamino-3-[3-benzyl-5-(5-ethylaminocarbonyloxy-3-methyl-3H-benzothiazol-2-ylidene)-4-oxo-thiazolidin-2-ylideneamino]benzonitrile;

4-ethylamino-3-[3-benzyl-5-(5-methoxycarbonylmethoxy-3-methyl-3H-benzothiazol-2-ylidene)-4-oxo-thiazolidin-2-ylideneamino]benzonitrile;

4-ethylamino-3-[3-benzyl-5-(5-aminocarbonylmethoxy-3-methyl-3H-benzothiazol-2-ylidene)-4-oxo-thiazolidin-2-ylideneamino]benzonitrile;

4-ethylamino-3-[3-benzyl-5-(5-(2-hydroxyethoxy)-3-methyl-3H-benzothiazol-2-ylidene)-4-oxo-thiazolidin-2-ylideneamino]benzonitrile;

4-ethylamino-3-[3-benzyl-5-(4-methoxy-3-methyl-3H-benzothiazol-2-ylidene)-4-oxo-thiazolidin-2-ylideneamino]benzonitrile;

4-ethylamino-3-[3-benzyl-5-(4-methyl-3-methyl-3H-benzothiazol-2-ylidene)-4-oxo-thiazolidin-2-ylideneamino]benzonitrile;

4-ethylamino-3-[3-benzyl-5-(4-chloro-3-methyl-3H-benzothiazol-2-ylidene)-4-oxo-thiazolidin-2-ylideneamino]benzonitrile;

4-ethylamino-3-[3-benzyl-5-(5-(2-chloroethylaminocarbonyloxy)-3-methyl-3H-benzothiazol-2-ylidene)-4-oxo-thiazolidin-2-ylideneamino]benzonitrile;

4-ethylamino-3-[3-benzyl-5-(5-(2-methylaminoethoxy)-3-methyl-3H-benzothiazol-2-ylidene)-4-oxo-thiazolidin-2-ylideneamino]benzonitrile;

4-ethylamino-3-[3-propyl-5-(3-methyl-3H-benzothiazol-2-ylidene)-4-oxo-thiazolidin-2-ylideneamino]benzonitrile;

3-(3-pyridylmethyl)-5-(3-methyl-3H-benzothiazol-2-ylidene)-2-(3-acetylphenyl)imino-thiazolidine-4-one;

3-(3-pyridylmethyl)-5-(3-methyl-3H-benzothiazol-2-ylidene)-2-(2-ethylamino-5-acetylphenyl)imino-thiazolidine-4-one;

4-ethylamino-3-[3-(3-pyridylmethyl)-5-(3-methyl-3H-benzothiazol-2-ylidene)-4-oxo-thiazolidin-2-ylideneamino]benzonitrile;

4-ethylamino-3-[3-(2-furylmethyl)-5-(3-methyl-3H-benzothiazol-2-ylidene)-4-oxo-thiazolidin-2-ylideneamino]benzonitrile;

3-(4-methoxycarbonylbenzyl)-5-(3-methyl-3H-benzothiazol-2-ylidene)-2-(2-ethylamino-5-acetylphenyl)imino-thiazolidine-4-one;

3-(4-hydroxycarbonylbenzyl)-5-(3-methyl-3H-benzothiazol-2-ylidene)-2-(2-ethylamino-5-acetylphenyl)imino-thiazolidine-4-one;

4-ethylamino-3-[3-(2-phenylethyl)-5-(3-methyl-3H-benzothiazol-2-ylidene)-4-oxo-thiazolidin-2-ylideneamino]benzonitrile;

4-ethylamino-3-[3-(2-(4-morpholinyl)-1-ethyl)-5-(3-methyl-3H-benzothiazol-2-ylidene)-4-oxo-thiazolidin-2-ylideneamino]benzonitrile;

3-benzyl-5-(3-methylthiazolin-2-ylidene)-2-(4-methylcarbonylaminophenyl)imino-thiazolidine-4-one;

3-benzyl-5-(3-methyl-4-phenylthiazol-2-ylidene)-2-(4-methylcarbonylaminophenyl)imino-thiazolidine-4-one;

3-benzyl-5-(3-methyl-4-phenylthiazol-2-ylidene)-2-(2-ethylamino-5-acetylphenyl)imino-thiazolidine-4-one;

3-benzyl-5-(3-methylthiazol-2-ylidene)-2-(4-methylcarbonylaminophenyl)imino-thiazolidine-4-one;

4-ethylamino-3-[3-benzyl-5-(3-methyl-4-phenylthiazol-2-ylidene)-4-oxo-thiazolidin-2-ylideneamino]benzonitrile;

4-ethylamino-3-[3-benzyl-5-(3-methyl-4,5-dimethylthiazol-2-ylidene)-4-oxo-thiazolidin-2-ylideneamino]benzonitrile;

4-ethylamino-3-[3-benzyl-5-(3-methyl-4-phenyl-5-methylthiazol-2-ylidene)-4-oxo-thiazolidin-2-ylideneamino]benzonitrile;

4-ethylamino-3-[3-benzyl-5-(3-methyl-4,5-butylenylthiazol-2-ylidene)-4-oxo-thiazolidin-2-ylideneamino]benzonitrile;

4-ethylamino-3-[3-benzyl-5-(3-methyl-4-ethylthiazol-2-ylidene)-4-oxo-thiazolidin-2-ylideneamino]benzonitrile;

4-ethylamino-3-[3-benzyl-5-(3-methyl-4-(4-nitrophenyl)thiazol-2-ylidene)-4-oxo-thiazolidin-2-ylideneamino]benzonitrile;

4-ethylamino-3-[3-benzyl-5-(3-methyl-4-(4-fluorophenyl)thiazol-2-ylidene)-4-oxo-thiazolidin-2-ylideneamino]benzonitrile;

4-ethylamino-3-[3-benzyl-5-(3-methyl-4-(4-chlorophenyl)thiazol-2-ylidene)-4-oxo-thiazolidin-2-ylideneamino]benzonitrile;

4-ethylamino-3-[3-benzyl-5-(3-methyl-4-(4-methylphenyl)thiazol-2-ylidene)-4-oxo-thiazolidin-2-ylideneamino]benzonitrile;

4-ethylamino-3-[3-benzyl-5-(3-methyl-4-(4-methoxyphenyl)thiazol-2-ylidene)-4-oxo-thiazolidin-2-ylideneamino]benzonitrile;

4-ethylamino-3-[3-benzyl-5-(3-methyl-4-methyl-5-acetylthiazol-2-ylidene)-4-oxo-thiazolidin-2-ylideneamino]benzonitrile;

4-ethylamino-3-[3-benzyl-5-(3-methyl-4,5-propylenylthiazol-2-ylidene)-4-oxo-thiazolidin-2-ylideneamino]benzonitrile;

4-ethylamino-3-[3-benzyl-5-(3-methyl-4,5-diphenylthiazol-2-ylidene)-4-oxo-thiazolidin-2-ylideneamino]benzonitrile;

4-ethylamino-3-[3-benzyl-5-(3-methyl-4-methylthiazol-2-ylidene)-4-oxo-thiazolidin-2-ylideneamino]benzonitrile;

4-ethylamino-3-[3-(3-pyridylmethyl)-5-(3-methyl-4,5-butylenylthiazol-2-ylidene)-4-oxo-thiazolidin-2-ylideneamino]benzonitrile; and 3-(4-methoxycarbonylbenzyl)-5-(3-methyl-4,5-butylenyllthiazol-2-ylidene)-2-(2-ethylamino-5-acetylphenyl)imino-thiazolidine-4-one.

55. The pharmaceutical composition of claim 25, wherein the compound is selected from:

3-benzyl-5-(3-methyl-3H-benzothiazol-2-ylidene)-2-(quinolin-8-ylimino)thiazolidin-4-one;

3-benzyl-2-(8-hydroxyquinolin-5-ylimino)-5-(3-methyl-3H-benzothiazol-2-ylidene)thiazolidin-4-one;

3-[3-benzyl-5-(3-methyl-3H-benzothiazol-2-ylidene)-4-oxothiazolidin-2-ylideneamino]-4-butylaminobenzonitrile;

4-benzylamino-3-[3-benzyl-5-(3-methyl-3H-benzothiazol-2-ylidene)-4-oxothiazolidin-2-ylideneamino]benzonitrile;

3-[3-benzyl-5-(3-methyl-3H-benzothiazol-2-ylidene)-4-oxothiazolidin-2-ylideneamino]-4-cyclopentylaminobenzonitrile;

3-[3-benzyl-5-(3-methyl-3H-benzothiazol-2-ylidene)-4-oxothiazolidin-2-ylideneamino]-4-(pyrrolidin-1-ylamino)benzonitrile;

3-[3-benzyl-5-(3-methyl-3H-benzothiazol-2-ylidene)-4-oxothiazolidin-2-ylideneamino]-4-pyrrolidin-1-ylbenzonitrile;

3-benzyl-2-(isoquinolin-5-ylimino)-5-(3-methyl-3H-benzothiazol-2-ylidene)thiazolidin-4-one;

3-benzyl-2-(isoquinolin-1-ylimino)-5-(3-methyl-3H-benzothiazol-2-ylidene)thiazolidin-4-one;

N-{4-[3-benzyl-5-(3-methyl-3H-benzothiazol-2-ylidene)-4-oxothiazolidin-2-ylideneamino]phenyl}acetamide;

2-(4-acetylphenylimino)-3-benzyl-5-(3-methyl-3H-benzothiazol-2-ylidene)thiazolidin-4-one;

4-[3-benzyl-5-(3-methyl-3H-benzothiazol-2-ylidene)-4-oxothiazolidin-2-ylideneamino]benzamide;

3-benzyl-5-(3-methyl-3H-benzothiazol-2-ylidene)-2-(naphthalen-1-ylimino)thiazolidin-4-one;

3-benzyl-5-(3-methyl-3H-benzothiazol-2-ylidene)-2-(naphthalen-2-ylimino)thiazolidin-4-one;

3-benzyl-5-(3-methyl-3H-benzothiazol-2-ylidene)-2-(pyridin-2-ylimino)thiazolidin-4-one;

4-[3-benzyl-5-(3-methyl-3H-benzothiazol-2-ylidene)-4-oxothiazolidin-2-ylideneamino]benzenesulfonamide;

N-acetyl-4-[3-benzyl-5-(3-methyl-3H-benzothiazol-2-ylidene)-4-oxothiazolidin-2-ylideneamino]benzenesulfonamide;

2-(3-acetylphenylimino)-5-(3-methyl-3H-benzothiazol-2-ylidene)-3-pyridin-3-ylmethylthiazolidin-4-one;

N-{5-[3-benzyl-5-(3-methyl-3H-benzothiazol-2-ylidene)-4-oxothiazolidin-2-ylideneamino]pyridin-2-yl}acetamide;

N-{5-[3-benzyl-5-(3-methyl-3H-benzothiazol-2-ylidene)-4-oxothiazolidin-2-ylideneamino]-2-cyanophenyl}acetamide;

2-(5-acetyl-2-ethylaminophenylimino)-5-(3-methyl-3H-benzothiazol-2-ylidene)-3-pyridin-3-ylmethylthiazolidin-4-one;

4-ethylamino-3-[5-(3-methyl-3H-benzothiazol-2-ylidene)-4-oxo-3-pyridin-3-ylmethylthiazolidin-2-ylideneamino]benzonitrile;

4-ethylamino-3-[3-furan-2-ylmethyl-5-(3-methyl-3H-benzothiazol-2-ylidene)-4-oxothiazolidin-2-ylideneamino]benzonitrile;

2-(5-acetyl-2-methylaminophenylimino)-3-benzyl-5-(3-methyl-3H-benzothiazol-2-ylidene)thiazolidin-4-one;

N-{4-[3-benzyl-5-(3-methyl-3H-benzothiazol-2-ylidene)-4-oxothiazolidin-2-ylideneamino]phenyl}-2,2,2-trifluoroacetamide;

3-[3-benzyl-5-(3-methyl-3H-benzothiazol-2-ylidene)-4-oxothiazolidin-2-ylideneamino]-4-ethylaminobenzoic acid methyl ester;

4-ethylamino-3-[5-(3-methyl-3H-benzothiazol-2-ylidene)-4-oxo-3-phenethylthiazolidin-2-ylideneamino]benzonitrile;

2-[3-benzyl-5-(3-methyl-3H-benzothiazol-2-ylidene)-4-oxothiazolidin-2-ylideneamino]benzoic acid;

3-[3-benzyl-5-(3-methyl-3H-benzothiazol-2-ylidene)-4-oxothiazolidin-2-ylideneamino]-4-ethylaminobenzoic acid tert-butyl ester;

3-[3-benzyl-5-(3-methyl-3H-benzothiazol-2-ylidene)-4-oxothiazolidin-2-ylideneamino]-4-ethylaminobenzoic acid;

3-[3-benzyl-5-(3-methyl-3H-benzothiazol-2-ylidene)-4-oxothiazolidin-2-ylideneamino]-4-(2-hydroxyethylamino)benzonitrile;

{2-[3-benzyl-5-(3-methyl-3H-benzothiazol-2-ylidene)-4-oxothiazolidin-2-ylideneamino]-4-cyanophenylamino}acetic acid methyl ester;

3-[3-benzyl-5-(3-methyl-3H-benzothiazol-2-ylidene)-4-oxothiazolidin-2-ylideneamino]-N-ethyl-4-ethylaminobenzamide;

{2-[3-benzyl-5-(3-methyl-3H-benzothiazol-2-ylidene)-4-oxothiazolidin-2-ylideneamino]-4-cyanophenylamino}acetic acid;

3-benzyl-2-(4-ethylaminopyridin-3-ylimino)-5-(3-methyl-3H-benzothiazol-2-ylidene)thiazolidin-4-one;

N-{4-[3-benzyl-5-(3-methyl-3H-benzothiazol-2-ylidene)-4-oxothiazolidin-2-ylideneamino]-3-ethylaminophenyl}acetamide;

3-[3-benzyl-5-(3-methyl-3H-benzothiazol-2-ylidene)-4-oxothiazolidin-2-ylideneamino]-4-(2-dimethylaminoethylamino)benzonitrile;

4-[3-benzyl-5-(3-methyl-3H-benzothiazol-2-ylidene)-4-oxothiazolidin-2-ylideneamino]-N-ethyl-3-ethylaminobenzamide;

3-[3-benzyl-5-(3-methyl-3H-benzothiazol-2-ylidene)-4-oxothiazolidin-2-ylideneamino]-N-(2-dimethylaminoethyl)-4-ethylaminobenzamide;

3-benzyl-2-[5-(4,5-dihydrooxazol-2-yl)-2-ethylamino-phenylimino]-5-(3-methyl-3H-benzothiazol-2-ylidene)thiazolidin-4-one;

3-[3-benzyl-5-(1-methyl-1H-quinolin-2-ylidene)-4-oxothiazolidin-2-ylideneamino]-4-ethylaminobenzonitrile;

2-(5-acetyl-2-ethylaminophenylimino)-3-benzyl-5-(1-methyl-1H-quinolin-2-ylidene)thiazolidin-4-one;

3-benzyl-2-benzylimino-5-(3-methyl-3H-benzothiazol-2-ylidene)thiazolidin-4-one;

2-(3-acetylphenylimino)-3-furan-2-ylmethyl-5-(3-methyl-3H-benzothiazol-2-ylidene)thiazolidin-4-one;

N-{4-[3-furan-2-ylmethyl-5-(3-methyl-3H-benzothiazol-2-ylidene)-4-oxothiazolidin-2-ylideneamino]phenyl}acetamide;

[2-(5-acetyl-2-ethylaminophenylimino)-5-(3-methyl-3H-benzothiazol-2-ylidene)-4-oxothiazolidin-3-yl]acetic acid methyl ester;

N-{4-[3-benzyl-5-(3-methyl-3H-benzothiazol-2-ylidene)-4-oxothiazolidin-2-ylideneamino]-2-cyanophenyl}acetamide;

2-(5-acetyl-2-ethoxyphenylimino)-3-benzyl-5-(3-methyl-3H-benzothiazol-2-ylidene)thiazolidin-4-one;

2-(5-acetyl-2-hydroxyphenylimino)-3-benzyl-5-(3-methyl-3H-benzothiazol-2-ylidene)thiazolidin-4-one;

2-(5-acetyl-2-ethylaminophenylimino)-3-benzyl-1-methyl-5-(3-methyl-3H-benzothiazol-2-ylidene)imidazolidin-4-one;

4-ethylamino-3-[5-(3-methyl-3H-benzothiazol-2-ylidene)-3-(2-morpholin-4-ylethyl)-4-oxothiazolidin-2-ylideneamino]benzonitrile;

4-ethylamino-3-[3-(4-methoxybenzyl)-5-(3-methyl-3H-benzothiazol-2-ylidene)-4-oxothiazolidin-2-ylideneamino]benzonitrile;

4-ethylamino-3-[3-(3-methoxybenzyl)-5-(3-methyl-3H-benzothiazol-2-ylidene)-4-oxothiazolidin-2-ylideneamino]benzonitrile;

4-ethylamino-3-[3-(2-methoxybenzyl)-5-(3-methyl-3H-benzothiazol-2-ylidene)-4-oxothiazolidin-2-ylideneamino]benzonitrile;

N-{3-[3-benzyl-5-(3-methyl-3H-benzothiazol-2-ylidene)-4-oxothiazolidin-2-ylideneamino]phenyl}succinamic acid;

N-{3-[3-benzyl-5-(3-methyl-3H-benzothiazol-2-ylidene)-4-oxothiazolidin-2-ylideneamino]phenyl}benzenesulfonamide;

thiophene-2-sulfonic acid {3-[3-benzyl-5-(3-methyl-3H-benzothiazol-2-ylidene)-4-oxothiazolidin-2-ylideneamino]phenyl}amide;

N-{3-[3-benzyl-5-(3-methyl-3H-benzothiazol-2-ylidene)-4-oxothiazolidin-2-ylideneamino]phenyl}-3-methoxybenzamide;

N-{3-[3-benzyl-5-(3-methyl-3H-benzothiazol-2-ylidene)-4-oxothiazolidin-2-ylideneamino]phenyl}methanesulfonamide;

{3-[3-benzyl-5-(3-methyl-3H-benzothiazol-2-ylidene)-4-oxothiazolidin-2-ylideneamino]phenyl}carbamic acid ethyl ester;

3-{3-[3-benzyl-5-(3-methyl-3H-benzothiazol-2-ylidene)-4-oxothiazolidin-2-ylideneamino]phenyl}-1,1-dimethylurea;

N-{3-[3-benzyl-5-(3-methyl-3H-benzothiazol-2-ylidene)-4-oxothiazolidin-2-ylideneamino]phenyl}-2-morpholin-4-ylacetamide;

N-{4-[3-benzyl-5-(3-methyl-3H-benzothiazol-2-ylidene)-4-oxothiazolidin-2-ylideneamino]phenyl}-2-morpholin-4-ylacetamide;

N-{3-[3-benzyl-5-(3-methyl-3H-benzothiazol-2-ylidene)-4-oxothiazolidin-2-ylideneamino]phenyl}-2-dimethylaminoacetamide;

{4-[3-benzyl-5-(3-methyl-3H-benzothiazol-2-ylidene)-4-oxothiazolidin-2-ylideneamino]phenyl}carbamic acid ethyl ester;

N-{4-[3-benzyl-5-(3-methyl-3H-benzothiazol-2-ylidene)-4-oxothiazolidin-2-ylideneamino]phenyl}-2-dimethylaminoacetamide;

N-{4-[3-benzyl-5-(3-methyl-3H-benzothiazol-2-ylidene)-4-oxothiazolidin-2-ylideneamino]phenyl}methanesulfonamide;

4-ethylamino-3-[3-(3-hydroxybenzyl)-5-(3-methyl-3H-benzothiazol-2-ylidene)-4-oxothiazolidin-2-ylideneamino]benzonitrile;

4-ethylamino-3-[3-(3-fluorobenzyl)-5-(3-methyl-3H-benzothiazol-2-ylidene)-4-oxothiazolidin-2-ylideneamino]benzonitrile;

4-ethylamino-3-[3-(3-fluorobenzyl)-5-(3-methyl-3H-benzothiazol-2-ylidene)-4-oxothiazolidin-2-ylideneamino]benzonitrile;

4-ethylamino-3-[5-(3-methyl-3H-benzothiazol-2-ylidene)-4-oxo-3-(3-trifluoromethylbenzyl)thiazolidin-2-ylideneamino]benzonitrile;

4-ethylamino-3-[5-(3-methyl-3H-benzothiazol-2-ylidene)-4-oxo-3-(2-trifluoromethylbenzyl)thiazolidin-2-ylideneamino]benzonitrile;

4-ethylamino-3-[5-(3-methyl-3H-benzothiazol-2-ylidene)-3-(3-methylbenzyl)-4-oxothiazolidin-2-ylideneamino]benzonitrile;

N-{3-[3-benzyl-5-(3-methyl-3H-benzothiazol-2-ylidene)-4-oxothiazolidin-2-ylideneamino]-4-ethylaminophenyl}-2-morpholin-4-ylacetamide;

3-[3-(3-chlorobenzyl)-5-(3-methyl-3H-benzothiazol-2-ylidene)-4-oxothiazolidin-2-ylideneamino]-4-ethylaminobenzonitrile;

3-[3-(3-bromobenzyl)-5-(3-methyl-3H-benzothiazol-2-ylidene)-4-oxothiazolidin-2-ylideneamino]-4-ethylaminobenzonitrile;

N-{3-[3-benzyl-5-(3-methyl-3H-benzothiazol-2-ylidene)-4-oxothiazolidin-2-ylideneamino]-4-ethylaminophenyl}-2,2,2-trifluoroacetamide;

N-{3-[3-benzyl-5-(3-methyl-3H-benzothiazol-2-ylidene)-4-oxothiazolidin-2-ylideneamino]-4-ethylaminophenyl}-2-dimethylaminoacetamide;

4-methylpiperazine-1-carboxylic acid {3-[3-benzyl-5-(3-methyl-3H-benzothiazol-2-ylidene)-4-oxothiazolidin-2-ylideneamino]-4-ethylaminophenyl}amide;

2-(5-amino-2-ethylaminophenylimino)-3-benzyl-5-(3-methyl-3H-benzothiazol-2-ylidene)thiazolidin-4-one;

N-{3-[3-benzyl-5-(3-methyl-3H-benzothiazol-2-ylidene)-4-oxothiazolidin-2-ylideneamino]-4-ethylaminophenyl}-2-(4-methylpiperazin-1-yl)acetamide;

N-{3-[3-benzyl-5-(5-methoxy-3-methyl-3H-benzothiazol-2-ylidene)-4-oxothiazolidin-2-ylideneamino]-4-ethylaminophenyl}-2-dimethylaminoacetamide;

N-{3-[3-benzyl-5-(5-hydroxy-3-methyl-3H-benzothiazol-2-ylidene)-4-oxothiazolidin-2-ylideneamino]-4-ethylaminophenyl}-2-dimethylaminoacetamide;

N-(3-{3-benzyl-5-[5-(2-chloroethoxy)-3-methyl-3H-benzothiazol-2-ylidene]-4-oxothiazolidin-2-ylideneamino}-4-ethylamino-phenyl)-2-dimethylaminoacetamide;

N-(3-{3-benzyl-5-[5-(2-methoxyethoxy)-3-methyl-3H-benzothiazol-2-ylidene]-4-oxothiazolidin-2-ylideneamino}-4-ethylamino-phenyl)-2-dimethylaminoacetamide;

N-{3-[3-benzyl-5-(3-methyl-3H-benzothiazol-2-ylidene)-4-oxothiazolidin-2-ylideneamino]-4-ethylaminophenyl}-2-methoxyacetamide;

N-(3-{3-benzyl-5-[5-(2-dimethylaminoethoxy)-3-methyl-3H-benzothiazol-2-ylidene]-4-oxothiazolidin-2-ylideneamino}-4-ethylaminophenyl)-2-dimethylaminoacetamide;

N-(3-{3-benzyl-5-[5-(2-hydroxyethoxy)-3-methyl-3H-benzothiazol-2-ylidene]-4-oxothiazolidin-2-ylideneamino}-4-ethylaminophenyl)-2-dimethylaminoacetamide;

2-(5-acetyl-2-ethylaminophenylimino)-5-[5-(2-chloroethoxy)-3-methyl-3H-enzothiazol-2-ylidene]-3-furan-2-ylmethylthiazolidin-4-one;

2-(5-acetyl-2-ethylaminophenylimino)-3-furan-2-ylmethyl-5-(3-methyl-3H-benzothiazol-2-ylidene) thiazolidin-4-one;

N-(3-{3-benzyl-5-[5-(2-chloroethoxy)-3-methyl-3H-benzothiazol-2-ylidene]-4-oxothiazolidin-2-ylideneamino}-4-ethylaminophenyl)-2-methoxyacetamide;

N-{4-ethylamino-3-[3-furan-2-ylmethyl-5-(3-methyl-3H-benzothiazol-2-ylidene)-4-oxothiazolidin-2-ylideneamino]phenyl}-2-methoxyacetamide;

N-(3-{3-benzyl-5-[5-(2-dimethylaminoethoxy)-3-methyl-3H-benzothiazol-2-ylidene]-4-oxothiazolidin-2-ylideneamino}-4-ethylaminophenyl)-2-methoxyacetamide;

2-(5-acetyl-2-ethylaminophenylimino)-5-[5-(2-dimethylamino-ethoxy)-3-methyl-3H-benzothiazol-2-ylidene]-3-furan-2-ylmethylthiazolidin-4-one;

N-(3-{5-[5-(2-dimethylaminoethoxy)-3-methyl-3H-benzothiazol-2-ylidene]-3-furan-2-ylmethyl-4-oxothiazolidin-2-ylideneamino}-4-ethylaminophenyl)-2-methoxyacetamide;

acetic acid {3-[3-benzyl-5-(3-methyl-3H-benzothiazol-2-ylidene)-4-oxothiazolidin-2-ylideneamino]-4-ethylaminophenylcarbamoyl}methyl ester;

N-{3-[3-benzyl-5-(3-methyl-3H-benzothiazol-2-ylidene)-4-oxothiazolidin-2-ylideneamino]-4-ethylaminophenyl}-2-hydroxyacetamide;

N-(3-{3-benzyl-5-[5-(2-methoxyethoxy)-3-methyl-3H-benzothiazo(-2-ylidene]-4-oxothiazolidin-2-ylideneamino}-4-ethylaminophenyl)-2-hydroxyacetamide;

2-(3-acetylphenylimino)-3-benzyl-5-[5-(2-methoxyethoxy)-3-methyl-3H-benzothiazol-2-ylidene] thiazolidin-4-one;

2-(5-acetyl-2-ethylaminophenylimino)-3-furan-2-ylmethyl-5-[5-(2-methoxyethoxy)-3-methyl-3H-benzothiazol-2-ylidene]thiazolidin-4-one;

N-(4-ethylamino-3-{3-furan-2-ylmethyl-5-[5-(2-methoxyethoxy)-3-methyl-3H-benzothiazol-2-ylidene]-4-oxothiazolidin-2-ylideneamino}phenyl)-2-methoxyacetamide;

2-(5-acetyl-2-ethylaminophenylimino)-3-benzyl-5-[5-(2-methoxyethoxy)-3-methyl-3H-benzothiazol-2-ylidene]thiazolidin-4-one;

N-(3-{3-benzyl-5-[5-(2-methoxyethoxy)-3-methyl-3H-benzothiazol-2-ylidene]-4-oxothiazolidin-2-ylideneamino}-4-ethylaminophenyl)-2-methoxyacetamide;

N-(3-{5-[5-(2-aminoethoxy)-3-methyl-3H-benzothiazol-2-ylidene]-3-benzyl-4-oxothiazolidin-2-ylideneamino}-4-ethylaminophenyl)-2-dimethylaminoacetamide;

2-dimethylamino-N-{3-[3-furan-2-ylmethyl-5-(5-methoxy-3-methyl-3H-benzothiazol-2-ylidene)-4-oxothiazolidin-2-ylideneamino]-phenyl}acetamide;

3-(3'-benzyl-3,4,5-trimethyl-4'-oxo-3',4'-dihydro-3H-[2,5']bithiazolyliden-2'-ylideneamino)-4-ethylaminobenzonitrile;

3-[3-benzyl-5-(3-methyl-4,5,6,7-tetrahydro-3H-benzothiazol-2-ylidene)-4-oxothiazolidin-2-ylideneamino]-4-ethylaminobenzonitrile;

3-(3'-benzyl-4-ethyl-3-methyl-4'-oxo-3',4'-dihydro-3H-[2,5']bithiazolyliden-2'-ylideneamino)-4-ethylaminobenzonitrile;

3-[3'-benzyl-3-methyl-4-(4-nitrophenyl)-4'-oxo-3',4'-dihydro-3H-[2,5']bithiazolyliden-2'-ylideneamino]-4-ethylaminobenzonitrile;

3-[3'-benzyl-4-(4-fluorophenyl)-3-methyl-4'-oxo-3',4'-dihydro-3H-[2,5']bithiazolyliden-2'-ylideneamino]-4-ethylaminobenzonitrile;

3-[3'-benzyl-4-(4-chloro-phenyl)-3-methyl-4'-oxo-3',4'-dihydro-3H-[2,5']bithiazolyliden-2'-ylideneamino]-4-ethylaminobenzonitrile;

3-(3'-benzyl-3-methyl-4'-oxo-4-p-tolyl-3',4'-dihydro-3H-[2,5']bithiazolyliden-2'-ylideneamino)-4-ethylaminobenzonitrile;

3-[3'-benzyl-4-(4-methoxyphenyl)3-methyl-4'-oxo-3',4'-dihydro-3H-[2,5']bithiazolyliden-2'-ylideneamino]-4-ethylaminobenzonitrile;

3-(5-acetyl-3'-benzyl-3,4-dimethyl-4'-oxo-3',4'-dihydro-3H-[2,5']bithiazolyliden-2'-ylideneamino)-4-ethylaminobenzonitrile;

3-[3-benzyl-5-(3-methyl-3,4,5,6-tetrahydrocyclopentathiazol-2-ylidene)-4-oxothiazolidin-2-ylideneamino]-4-ethylaminobenzonitrile;

3-(3'-benzyl-3-methyl-4'-oxo-4,5-diphenyl-3',4'-dihydro-3H-[2,5']bithiazolyliden-2'-ylideneamino)-4-ethylaminobenzonitrile;

3-(3'-benzyl-3,4-dimethyl-4'-oxo-3',4'-dihydro-3H-[2,5']bithiazolyliden-2'-ylideneamino)-4-ethylaminobenzonitrile;

4-ethylamino-3-[5-(3-methyl-4,5,6,7-tetrahydro-3H-benzothiazol-2-ylidene)-4-oxo-3-pyridin-3-ylmethylthiazolidin-2-ylideneamino]benzonitrile;

methyl 4-[2-(5-acetyl-2-ethylaminophenylimino)-5-(3-methyl-3H-benzothiazol-2-ylidene)-4-oxothiazolidin-3-ylmethyl]benzoate;

methyl 4-[2-(5-acetyl-2-ethylamino-phenylimino)-5-(3-methyl-4,5,6,7-tetrahydro-3H-benzothiazol-2-ylidene)-4-oxothiazolidin-3-ylmethyl]benzoate;

4-[2-(5-acetyl-2-ethylaminophenylimino)-5-(3-methyl-3H-benzothiazol-2-ylidene)-4-oxothiazolidin-3-ylmethyl]benzoic acid;

3-[3-benzyl-5-(1-methyl-4,5,6,7-tetrahydro-1H-thiazolo[5,4-c]pyridin-2-ylidene)-4-oxothiazolidin-2-ylideneamino]-4-ethylaminobenzonitrile;

methyl 3-[2-(5-acetyl-2-ethylaminophenylimino)-5-(3-methyl-3H-benzothiazol-2-ylidene)-4-oxothiazolidin-3-ylmethyl]benzoate;

3-[2-(5-acetyl-2-ethylaminophenylimino)-5-(3-methyl-3H-benzothiazol-2-ylidene)-4-oxothiazolidin-3-ylmethyl]benzoic acid;

2-(5-acetyl-2-ethylaminophenylimino)-3-benzyl-5-(3-methyl-4,5,6,7-tetrahydro-3H-benzothiazol-2-ylidene)thiazolidin-4-one;

3-(3'-benzyl-4-biphenyl4-yl-3-methyl-4'-oxo-3',4'-dihydro-3H-[2,5']bithiazolyliden-2'-ylideneamino)-4-ethylaminobenzonitrile;

3-(3'-benzyl-3-methyl-4-naphthalen-2-yl-4'-oxo-3',4'-dihydro-3H-[2,5']bithiazolyliden-2'-ylideneamino)-4-ethylaminobenzonitrile;

3-[3'-benzyl-4-(4-bromophenyl)-3-methyl-4'-oxo-3',4'-dihydro-3H-[2,5']bithiazolyliden-2'-ylideneamino]-4-ethylaminobenzonitrile;

3-[3'-benzyl-3-methyl-4-(2-nitrophenyl)-4'-oxo-3',4'-dihydro-3H-[2,5']bithiazolyliden-2'-ylideneamino]-4-ethylaminobenzonitrile;

2-(5-acetyl-2-ethylaminophenylimino)-5-(3-methyl-4,5,6,7-tetrahydro-3H-benzothiazol-2-ylidene)-3-pyridin-3-ylmethylthiazolidin-4-one;

3-[3'-benzyl-4-(2-methoxyphenyl)-3-methyl-4'-oxo-3',4'-dihydro-3H-[2,5']bithiazolyliden-2'-ylideneamino]-4-ethylaminobenzonitrile;

3-[3'-benzyl-4-(3-fluorophenyl)-3-methyl-4'-oxo-3',4'-dihydro-3H-[2,5']bithiazolyliden-2'-ylideneamino]-4-ethylaminobenzonitrile;

3-[3'-benzyl-3-methyl-4'-oxo-4-(4-trifluoromethylphenyl)-3',4'-dihydro-3H-[2,5']bithiazolyliden-2'-ylideneamino]-4-ethylaminobenzonitrile;

3-[3'-benzyl-3-methyl-4'-oxo-4-(4-trifluoromethoxyphenyl)-3',4'-dihydro-3H-[2,5']bithiazolyliden-2'-ylideneamino]-4-ethylaminobenzonitrile;

3-[3'-benzyl-4-(2,4-dimethoxyphenyl)-3-methyl-4'-oxo-3',4'-dihydro-3H-[2,5']bithiazolyliden-2'-ylideneamino]-4-ethylaminobenzonitrile;

3-(3'-benzyl-5-ethyl-3-methyl-4'-oxo-4-phenyl-3',4'-dihydro-3H-[2,5']bithiazolyliden-2'-ylideneamino)-4-ethylaminobenzonitrile;

3-[3'-benzyl-3-methyl-4'-oxo-4-(2-trifluoromethylphenyl)-3',4'-dihydro-3H-[2,5']bithiazolyliden-2'-ylideneamino]-4-ethylaminobenzonitrile;

3-[3'-benzyl-4-(3-bromophenyl)-3,5-dimethyl-4'-oxo-3',4'-dihydro-3H-[2,5']bithiazolyliden-2'-ylideneamino]-4-ethylaminobenzonitrile;

3-[3'-benzyl-4-(3-methoxyphenyl)-3-methyl-4'-oxo-3',4'-dihydro-3H-[2,5']bithiazolyliden-2'-ylideneamino]-4-ethylaminobenzonitrile;

3-benzyl-2-[4-(1,1,1,3,3,3-hexafluoro-2-hydroxyisopropyl)-phenylimino]-5-(3-methyl-3H-benzothiazol-2-ylidene)thiazolidin-4-one;

3-(3'-benzyl-4-chloromethyl-3-methyl-4'-oxo-3',4'-dihydro-3H-[2,5']bithiazolyliden-2'-ylideneamino)-4-ethylaminobenzonitrile;

3'-benzyl-2'-(5-cyano-2-ethylaminophenylimino)-3-methyl-4'-oxo-3',4'-dihydro-3H,2'H-[2,5']bithiazolylidene-4-carboxylic acid ethyl ester;

3-(4,3'-dibenzyl-3-methyl-4'-oxo-3',4'-dihydro-3H-[2,5']bithiazolyliden-2'-ylideneamino)-4-ethylaminobenzonitrile;

3'-benzyl-2'-(5-cyano-2-ethylaminophenylimino)-3-methyl-4'-oxo-3',4'-dihydro-3H,2'H-[2,5']bithiazolylidene-4-carboxylic acid;

3-benzyl-2-[2-ethylamino-5-(1-hydroxyethyl)phenylimino]-5-(3-methyl-3H-benzothiazol-2-ylidene)thiazolidin-4-one;

3-[3'-benzyl-4-(2-hydroxyphenyl)-3-methyl-4'-oxo-3',4'-dihydro-3H-[2,5']bithiazolyliden-2'-ylideneamino]-4-ethylaminobenzonitrile;

3-benzyl-2-[2-ethylamino-5-(1-hydroxyiminoethyl)phenylimino]-5-(3-methyl-3H-benzothiazol-2-ylidene)thiazolidin-4-one;

3-benzyl-2-[2-ethylamino-5-(1-methoxyiminoethyl)phenylimino]-5-(3-methyl-3H-benzothiazol-2-ylidene)thiazolidin-4-one;

3-benzyl-2-[5-(1-benzyloxyiminoethyl)-2-ethylaminophenylimino]-5-(3-methyl-3H-benzothiazol-2-ylidene)thiazolidin-4-one;

3-benzyl-2-{2-ethylamino-5-[1-(phenylhydrazono)ethyl]-phenylimino}-5-(3-methyl-3H-benzothiazol-2-ylidene)thiazolidin-4-one;

3-(4,3'-dibenzyl-3,5-dimethyl-4'-oxo-3',4'-dihydro-3H-[2,5']bithiazolyliden-2'-ylideneamino)-4-ethylaminobenzonitrile;

3-[3-cyclohexylmethyl-5-(3-methyl-3H-benzothiazol-2-ylidene)-4-oxothiazolidin-2-ylideneamino]-4-ethylaminobenzonitrile;

3-[3'-benzyl-4-(3-hydroxyphenyl)-3-methyl-4'-oxo-3',4'-dihydro-3H-[2,5']bithiazolyliden-2'-ylideneamino]-4-ethylaminobenzonitrile;

3-[3'-benzyl-4-(4-hydroxyphenyl)-3-methyl-4'-oxo-3',4'-dihydro-3H-[2,5']bithiazolyliden-2'-ylideneamino]-4-ethylaminobenzonitrile;

3-(3'-benzyl-3,4-dimethyl-4'-oxo-5-phenyl-3',4'-dihydro-3H-[2,5']bithiazolyliden-2'-ylideneamino)-4-ethylaminobenzonitrile;

2'-(5-acetyl-2-ethylaminophenylimino)-3'-benzyl-3,5-dimethyl-4-phenyl-2',3'-dihydro-3H-[2,5']bithiazolyliden-4'-one;

2'-(5-acetyl-2-ethylaminophenylimino)-3'-benzyl-3,4-dimethyl-5-phenyl-2',3'-dihydro-3H-[2,5']bithiazolyliden-4'-one;

2'-(5-acetyl-2-ethylaminophenylimino)-3'-benzyl-4-(4-methoxyphenyl)-3,5-dimethyl-2',3'-dihydro-3H-[2,5']bithiazolyliden-4'-one;

2'-(5-acetyl-2-ethylaminophenylimino)-4,3'-dibenzyl-3-methyl-2',3'-dihydro-3H-[2,5']bithiazolyliden-4'-one;

2'-(5-acetyl-2-ethylaminophenylimino)-3'-benzyl-4-(2-methoxyphenyl)-3,5-dimethyl-2',3'-dihydro-3H-[2,5']bithiazolyliden-4'-one;

3-{3-benzyl-5-[5-(2-dimethylaminoacetyl)-1-methyl-4,5,6,7-tetrahydro-1H-thiazolo[5,4-c]pyridin-2-ylidene]-4-oxothiazolidin-2-ylideneamino}-4-ethylaminobenzonitrile;

2'-(5-acetyl-2-ethylaminophenylimino)-3'-benzyl-4-(3-methoxyphenyl)-3,5-dimethyl-2',3'-dihydro-3H-[2,5']bithiazolyliden-4'-one;

2'-(5-acetyl-2-ethylaminophenylimino)-3'-benzyl-4-(3-hydroxyphenyl)-3,5-dimethyl-2',3'-dihydro-3H-[2,5']bithiazolyliden-4'-one;

2'-(5-acetyl-2-ethylaminophenylimino)-3,3'-dibenzyl-5-methyl-4-phenyl-2',3'-dihydro-3H-[2,5']bithiazolyliden-4'-one;

N-(3-{3-benzyl-5-[5-(2-acetoxyethoxy)-3-methyl-3H-benzothiazol-2-ylidene]-4-oxothiazolidin-2-ylideneamino}-4-ethylaminophenyl)-2-dimethylaminoacetamide;

2'-(5-acetyl-2-ethylaminophenylimino)-3'-benzyl-3-(2-methoxyethyl)-5-methyl-4-phenyl-2',3'-dihydro-3H-[2,5']bithiazolyliden-4'-one;

2'-(5-acetyl-2-ethylaminophenylimino)-3'-benzyl-3-(3-methoxypropyl)-5-methyl-4-phenyl-2',3'-dihydro-3H-[2,5']bithiazolyliden-4'-one;

[2'-(5-acetyl-2-ethylaminophenylimino)-3'-benzyl-5-methyl-4'-oxo-4-phenyl-3',4'-dihydro-2'H-[2,5']bithiazolyliden-3-yl]acetic acid methyl ester;

[2'-(5-acetyl-2-ethylaminophenylimino)-3'-benzyl-5-methyl-4'-oxo-4-phenyl-3',4'-dihydro-2'H-[2,5']bithiazolyliden-3-yl]acetic acid;

2-[2'-(5-acetyl-2-ethylaminophenylimino)-3'-benzyl-5-methyl-4'-oxo-4-phenyl-3',4'-dihydro-2'H-[2,5']bithiazolyliden-3-yl]ethyl acetate;

2'-(5-acetyl-2-ethylaminophenylimino)-3'-benzyl-3-(2-hydroxyethyl)-5-methyl-4-phenyl-2',3'-dihydro-3H-[2,5']bithiazolyliden-4'-one;

N-[3-(3'-benzyl-3,5-dimethyl-4'-oxo-4-phenyl-3',4'-dihydro-3H-[2,5']bithiazolyliden-2'-ylideneamino)-4-ethylaminophenyl]-2-methoxyacetamide;

N-[3-(3'-benzyl-3,5-dimethyl-4'-oxo-4-phenyl-3',4'-dihydro-3H-[2,5']bithiazolyliden-2'-ylideneamino)-4-ethylaminophenyl]-2-dimethylaminoacetamide;

3-[3-cyclohexyl-5-(3-methyl-3H-benzothiazol-2-ylidene)-4-oxothiazolidin-2-ylideneamino]-4-ethylaminobenzonitrile;

3-[3-allyl-5-(3-methyl-3H-benzothiazol-2-ylidene)-4-oxothiazolidin-2-ylideneamino]-4-ethylaminobenzonitrile;

3-allyl-5-(3-methyl-3H-benzothiazol-2-ylidene)-2-(quinolin-5-ylimino)thiazolidin-4-one;

3-allyl-2-(4-hydroxy-5-isopropyl-2-methylphenylimino)-5-(3-methyl-3H-benzothiazol-2-ylidene)thiazolidin-4-one;

4-ethylamino-3-[5-(3-methyl-3H-benzothiazol-2-ylidene)-4-oxo-3-phenylthiazolidin-2-ylideneamino]benzonitrile;

3-cyclohexyl-2-(2-hydroxynaphthalen- 1-ylimino)-5-(3-methyl-3H-benzothiazol-2-ylidene)thiazolidin-4-one;

3-allyl-2-(2-hydroxynaphthalen-1-ylimino)-5-(3-methyl-3H-benzothiazol-2-ylidene)thiazolidin-4-one;

3-(4-cyclohexylphenylimino)-5-(3-methyl-3H-benzothiazol-2-ylidene)-3-phenylthiazolidin-4-one;

3-[3-benzyl-5-(6-fluoro-3-methyl-3H-benzothiazol-2-ylidene)-4-oxothiazolidin-2-ylideneamino]-4-ethylaminobenzonitrile;

3-[3-benzyl-5-(5-chloro-3-methyl-3H-benzothiazol-2-ylidene)-4-oxothiazolidin-2-ylideneamino]-4-ethylaminobenzonitrile;

3-[3-benzyl-5-(6-ethoxy-3-methyl-3H-benzothiazol-2-ylidene)-4-oxothiazolidin-2-ylideneamino]-4-ethylaminobenzonitrile;

4-ethylamino-3-[5-(3-methyl-3H-benzothiazol-2-ylidene)-4-oxo-3-propylthiazolidin-2-ylideneamino] benzonitrile;

3-[3-benzyl-5-(3-methyl-6-nitro-3H-benzothiazol-2-ylidene)-4-oxothiazolidin-2-ylideneamino]-4-ethylaminobenzonitrile;

N-{2-[3-benzyl-2-(5-cyano-2-ethylaminophenylimino)-4-oxothiazolidin-5-ylidene]-3-methyl-2,3-dihydrobenzothiazol-6-yl}acetamide;

3-[3-benzyl-5-(6-hydroxy-3-methyl-3H-benzothiazol-2-ylidene)-4-oxothiazolidin-2-ylideneamino]-4-ethylaminobenzonitrile;

ethylcarbamic acid 2-[3-benzyl-2-(5-cyano-2-ethylaminophenylimino)-4-oxothiazolidin-5-ylidene]-3-methyl-2,3-dihydrobenzothiazol-5-yl ester;

{2-[3-benzyl-2-(5-cyano-2-ethylaminophenylimino)-4-oxothiazolidin-5-ylidene]-3-methyl-2,3-dihydrobenzothiazol-5-yloxy}acetic acid methyl ester;

2-{2-[3-benzyl-2-(5-cyano-2-ethylaminophenylimino)-4-oxothiazolidin-5-ylidene]-3-methyl-2,3-dihydrobenzothiazol-5-yloxy}acetamide;

(2-chloroethyl)carbamic acid 2-[3-benzyl-2-(5-cyano-2-ethylaminophenylimino)-4-oxothiazolidin-5-ylidene]-3-methyl-2,3-dihydrobenzothiazol-5-yl ester;

3-{3-benzyl-5-[3-methyl-5-(2-methylaminoethoxy)-3H-benzothiazol-2-ylidene]-4-oxothiazolidin-2-ylideneamino}-4-ethylaminobenzonitrile;

3-{3-benzyl-5-[5-(3-hydroxypropoxy)-3-methyl-3H-benzothiazol-2-ylidene]-4-oxothiazolidin-2-ylideneamino}-4-ethylaminobenzonitrile;

(3-chloropropyl)carbamic acid 2-[3-benzyl-2-(5-cyano-2-ethylaminophenylimino)-4-oxothiazolidin-5-ylidene]-3-methyl-2,3-dihydrobenzothiazol-5-yl ester;

3-(3-benzyl-5-{3-methyl-5-[2-(4-methylpiperazin-1-yl)-ethoxy]-3H-benzothiazol-2-ylidene}-4-oxothiazolidin-2-ylideneamino)-4-ethylaminobenzonitrile;

3-{3-benzyl-5-[3-methyl-5-(2-piperidin-4-ylethoxy)-3H-benzothiazol-2-ylidene]-4-oxothiazolidin-2-ylideneamino}-4-ethylaminobenzonitrile;

3-{3-benzyl-5-[5-(2-dimethylaminoethoxy)-3-methyl-3H-benzothiazol-2-ylidene]-4-oxothiazolidin-2-ylideneamino}-4-ethylaminobenzonitrile;

{2-[3-benzyl-2-(5-cyano-2-ethylaminophenylimino)-4-oxothiazolidin-5-ylidene]-3-methyl-2,3-dihydrobenzothiazol-5-yloxy}acetic acid;

3-{3-benzyl-5-[6-(2-hydroxyethoxy)-3-methyl-3H-benzothiazol-2-ylidene]-4-oxothiazolidin-2-ylideneamino}-4-ethylaminobenzonitrile;

3-{3-benzyl-5-[6-(2-methoxyethoxy)-3-methyl-3H-benzothiazol-2-ylidene]-4-oxothiazolidin-2-ylideneamino}-4-ethylaminobenzonitrile;

3-{3-benzyl-5-[3-methyl-6-(2-morpholin-4-ylethoxy)-3H-benzothiazol-2-ylidene]-4-oxothiazolidin-2-ylideneamino}-4-ethylaminobenzonitrile;

3-{3-benzyl-5-[5-(2-methoxyethoxy)-3-methyl-3H-benzothiazol-2-ylidene]-4-oxothiazolidin-2-ylideneamino}-4-ethylaminobenzonitrile;

3-{3-benzyl-5-[3-methyl-4-methoxy-3H-benzothiazol-2-ylidene]-4-oxothiazolidin-2-ylideneamino}-4-ethylaminobenzonitrile;

3-{3-benzyl-5-[3-methyl-4-methyl-3H-benzothiazol-2-ylidene]-4-oxothiazolidin-2-ylideneamino}-4-ethylaminobenzonitrile;

3-{3-benzyl-5-[3-methyl-4-chloro-3H-benzothiazol-2-ylidene]-4-oxothiazolidin-2-ylideneamino}-4-ethylaminobenzonitrile;

3-{3-benzyl-5-[3-methyl-6-trifluoromethoxy-3H-benzothiazol-2-ylidene]-4-oxothiazolidin-2-ylideneamino}-4-ethylaminobenzonitrile;

3-[3-benzyl-5-(3,5,6-trimethyl-3H-benzothiazol-2-ylidene)-4-oxothiazolidin-2-ylideneamino]-4-ethylaminobenzonitrile;

3-[3-benzyl-5-(3-methyl-5-acetamido-3H-benzothiazol-2-ylidene)-4-oxothiazolidin-2-ylideneamino]-4-ethylaminobenzonitrile;

N-{2-[3-benzyl-2-(5-cyano-2-ethylaminophenylimino)-4-oxothiazilidin-6-ylidene]-3-methyl-2,3-dihydrobenzothiazol-5-yl}-2,2,2-trifluoroacetamide;

3-[5-(6-amino-3-methyl-3H-benzothiazol-2-ylidene)-4-oxothiazolidin-2-ylideneamino]-4-ethylaminobenzonitrile;

N-{2-[3-benzyl-2-(5-cyano-2-ethylaminophenylimino)-4-oxothiazolidin-5-ylidene]-3-methyl-2,3-dihydrobenzothiazol-6-yl}-N',N"-di(tert-butoxycarbonyl)guanidine;

2-{2-[3-benzyl-2-(5-cyano-2-ethylaminophenylimino)-4-oxothiazilidin-5-ylidene]-3-methyl-2,3-dihydrobenzothiazol-6-yl}-1,1,-dimethylurea;

N-{2-[3-benzyl-2-(5-cyano-2-ethylaminophenylimino)-4-oxothiazilidin-5-ylidene]-3-methyl-2,3-dihydrobenzothiazol-5-yl}-2,2,2-trifluoroacetamide;

3-[5-(5-amino-3-methyl-3H-benzothiazol-2-ylidene)-4-oxothiazolidin-2-ylideneamino]-4-ethylaminobenzonitrile;

{2-[3-benzyl-2-(5-cyano-2-ethylaminophenylimino)-4-oxothiazilidin-5-ylidene]-3-methyl-2,3-dihydrobenzothiazol-6-yl}carbamic acid ethyl ester;

N-[2-(3-benzyl-2-{5-cyano-2-[ethyl-(2-morpholin-ylethylamino]phenylimino}-4-oxothiazilidin-5-ylidene)3-methyl-2,3-dihydrobenzothiazol-6-yl]-2,2,2-trifluoroacetamide;

N-{2-[3-benzyl-2-(5-cyano-2-ethylaminophenylimino)-4-oxothiazilidin-5-ylidene]-3-methyl-2,3-dihydrobenzothiazol-6-yl}-2,2,2-trifluoro-N-(2-morpholin-4ylethyl)acetamide;

3-{3-benzyl-5-[3-methyl-6-(2-morpholin-4-yl-ethylamino)-3H-benzothiazol-2-ylidene]-4-oxothiazolidin-2-ylideneamino}-4-ethylaminobenzonitrile;

3-{3-benzyl-5-[3-methyl-6-(2-piperidin-1-yl-ethylamino)-3H-benzothiazol-2-ylidene]-4-oxothiazolidin-2-ylideneamino}-4-ethylaminobenzonitrile;

N-{2-[3-benzyl-2-(5-cyano-2-ethylaminophenylimino)-4-oxothiazilidin-5-ylidene]-3-methyl-2,3-dihydrobenzothiazol-5-yl}-2,2,2-trifluoro-N-(2-morpholin-4ylethyl)acetamide;

3-{3-benzyl-5-[3-methyl-5-(2-morpholin-4-yl-ethylamino)-3H-benzothiazol-2-ylidene]-4-oxothiazolidin-2-ylideneamino}-4-ethylaminobenzonitrile;

N-{2-[3-benzyl-2-(5-cyano-2-ethylaminophenylimino)-4-oxothiazolidin-5-ylidene]-3-methyl-2,3-dihydrobenzothiazol-6-yl}guanidine;

3-{3-benzyl-5-[3-methyl-6-(4-trifluoromethylbenzylamino)-3H-benzothiazol-2-ylidene]-4-oxothiazolidin-2-ylideneamino}-4-ethylaminobenzonitrile;

N-{2-[3-benzyl-2-(5-cyano-2-ethylaminophenylimino)-4-oxothiazilidin-5-ylidene]-3-methyl-2,3-dihydrobenzothiazol-6-yl}-N-(3-fluoropropyl)-2,2,2-trifluoroacetamide;

N-{2-[3-benzyl-2-(5-cyano-2-ethylaminophenylimino)-4-oxothiazilidin-5-ylidene]-3-methyl-2,3-dihydrobenzothiazol-6-yl}-N-(3-cyanopropyl)-2,2,2-trifluoroacetamide;

3-{3-benzyl-5-[6-(3-cyanopropylamino)-3-methyl-3H-benzothiazol-2-ylidene]-4-oxothiazolidin-2-ylideneamino}-4-(ethylamino)benzonitrile;

3-{3-benzyl-5-[6-(3-hydroxypropylamino)-3-methyl-3H-benzothiazol-2-ylidene]-4-oxothiazolidin-2-ylideneamino}-4-(ethylamino)benzonitrile; and 3-{3-benzyl-5-[6-(2-methoxyethylamino)-3-methyl-3H-benzothiazol-2-ylidene]-4-oxothiazolidin-2-ylideneamino}-4-(ethylamino)benzonitrile.

56. An article of manufacture, comprising packaging material, a compound formulae I:

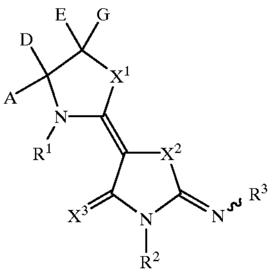

or

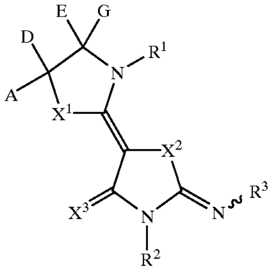

or a pharmaceutically acceptable derivative thereof, wherein:

A, D, E and G are selected from (i) or (ii) as follows:

(i) A and G are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted heteroarylium, substituted or unsubstituted heteroaryliumalkyl, halo, pseudohalo, $OR^{10}$, $SR^{10}$, $S(=O)R^{13}$, $S(=O)_2R^{13}$, $NR^{11}R^{12}$ and $C(=J)R^{13}$, or A and G together form substituted or unsubstituted alkylene, substituted or unsubstituted azaalkylene, substituted or unsubstituted oxaalkylene, substituted or unsubstituted thiaalkylene, substituted or unsubstituted alkenylene, substituted or unsubstituted alkynylene, substituted or unsubstituted 1,3-butadienylene, substituted or unsubstituted 1-aza-1,3-butadienylene, or substituted or unsubstituted 2-aza-1,3-butadienylene;

D and E are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo and pseudohalo or D and E together form a bond; or (ii) A and D; or E and G; together form substituted or unsubstituted alkylene, substituted or unsubstituted azaalkylene, substituted or unsubstituted oxaalkylene, or substituted or unsubstituted thiaalkylene; and the others of A, D, E and G are selected as in (i);

$X^1$ and $X^2$ are each independently selected from O, S, $S(=O)$, $S(=O)_2$, Se, $NR^5$, $CR^6R^7$ and $CR^8=CR^9$;

$X^3$ is O, S, Se, $NR^5$ or $CR^6R^7$;

$R^1$ and $R^2$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted heteroarylium, substituted or unsubstituted heteroaryliumalkyl, $OR^{10}$, $SR^{10}$, $S(=O)R^{13}$, $S(=O)_2R^{13}$, $NR^{11}R^{12}$ and $C(=J)R^{13}$;

$R^3$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted heteroarylium, substituted or unsubstituted aralkyl, substituted or unsubstituted heteroaralkyl, substituted or unsubstituted heteroaryliumalkyl, $OR^{10}$, $SR^{10}$, $S(=O)R^{13}$, $S(=O)_2R^{13}$, $NR^{11}R^{12}$ and $C(=J)R^{13}$;

where $R^5$, $R^6$, $R^7$, $R^8$ and $R^9$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo, pseudohalo, $OR^{10}$, $NR^{14}R^{15}$ and $C(=J)R^{13}$;

$R^{10}$, $R^{11}$ and $R^{12}$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl or C(=J)$R^{13}$;

J is O, S or $NR^{14}$;

$R^{13}$ is selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, pseudohalo, $OR^{16}$ and $NR^{14}R^{15}$;

$R^{14}$, $R^{15}$ and $R^{16}$ are each independently selected from hydrogen, alkyl, alkenyl, alkynyl, cycloalkyl, heterocyclyl, cycloalkylalkyl, heterocyclylalkyl, aryl, heteroaryl, aralkyl and heteroaralkyl;

where the alkyl, alkenyl, alkynyl, cycloalkyl, heterocyclyl, cycloalkylalkyl, heterocyclylalkyl, aryl, heteroaryl, heteroarylium, aralkyl, heteroaralkyl and heteroaryliumalkyl moieties of A, D, E, G, $R^1$, $R^2$, $R^3$, $R^5$, $R^6$, $R^7$, $R^8$, $R^9$, $R^{10}$, $R^{11}$, $R^{12}$ and $R^{13}$ are unsubstituted or substituted with one or more substituents each independently selected from $Q^1$, where $Q^1$ is halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, imino, hydroxyimino, alkoxyimino, aryloxyimino, aralkoxyimino, alkylazo, arylazo, aralkylazo, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —$N^+R^{51}R^{52}R^{53}$, $P(R^{50})_2$, $P(=O)(R^{50})_2$, $OP(=O)(R^{50})_2$, —$NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy, thioalkylenoxy or alkylenedithioxy where y is 1 or 2; or two $Q^1$ groups, which substitute the same atom, together form alkylene; and each $Q^1$ is independently unsubstituted or substituted with one or more substituents each independently selected from $Q^2$;

each $Q^2$ is independently halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{51}R^{52}R^{53}$, $P(R^{50})_2$, $P(=O)(R^{50})_2$, $OP(=O)(R^{50})_2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^2$ groups, which substitute atoms in a 1,2 or 1,3 arrangement, together form alkylenedioxy, thioalkylenoxy or alkylenedithioxy where y is 1 or 2; or two $Q^2$ groups, which substitute the same atom, together form alkylene;

each $Q^2$ is independently unsubstituted or substituted with one or more substituents each independently selected from alkyl, halo and pseudohalo;

$R^{50}$ is hydroxy, alkoxy, aralkoxy, alkyl, heteroaryl, heterocyclyl, aryl or $—NR^{70}R^{71}$, where $R^{70}$ and $R^{71}$ are each independently hydrogen, alkyl, aralkyl, aryl, heteroaryl, heteroaralkyl or heterocyclyl, or $R^{70}$ and $R^{71}$ together form alkylene, azaalkylene, oxaalkylene or thiaalkylene;

$R^{51}$, $R^{52}$ and $R^{53}$ are each independently hydrogen, alkyl, aryl, aralkyl, heteroaryl, heteroaralkyl, heterocyclyl or heterocyclylalkyl;

$R^{60}$ is hydrogen, alkyl, aryl, aralkyl, heteroaryl, heteroaralkyl, heterocyclyl or heterocyclylalkyl; and $R^{63}$ is alkoxy, aralkoxy, alkyl, heteroaryl, heterocyclyl, aryl or $—NR^{70}R^{71}$;

with the proviso that when $R^3$ is substituted or unsubstituted heteroarylium then the heteroatom substituent is not alkyl or aryl;

which is effective for modulating the activity of a nuclear receptor or for treatment, prevention or amelioration of one or more symptoms of nuclear receptor mediated diseases or disorders, or diseases or disorders in which nuclear receptor activity is implicated, within the packaging material, and a label that indicates that the compound or pharmaceutically acceptable derivative thereof is used for modulating the activity of a nuclear receptor or for treatment, prevention or amelioration of one or more symptoms of nuclear receptor mediated diseases or disorders, or diseases or disorders in which nuclear receptor activity is implicated.

57. A method of treating, preventing, or ameliorating the symptoms of a disease or disorder that is modulated or otherwise affected by nuclear receptor activity or in which nuclear receptor activity is implicated, comprising administering to a subject in need thereof an effective amount of a compound formulae I:

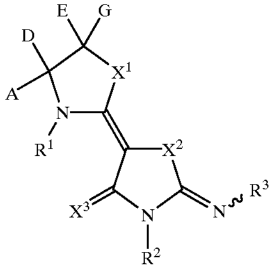

or

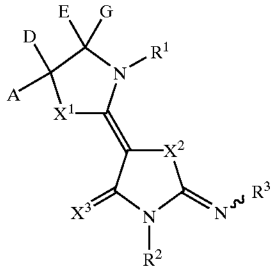

or a pharmaceutically acceptable derivative thereof, wherein:

A, D, E and G are selected from (i) or (ii) as follows:

(i) A and G are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted heteroarylium, substituted or unsubstituted heteroaryliumalkyl, halo, pseudohalo, $OR^{10}$, $SR^{10}$, $S(=O)R^{13}$, $S(=O)_2R^{13}$, $NR^{11}R^{12}$ and $C(=J)R^{13}$, or A and G together form substituted or unsubstituted alkylene, substituted or unsubstituted azaalkylene, substituted or unsubstituted oxaalkylene, substituted or unsubstituted thiaalkylene, substituted or unsubstituted alkenylene, substituted or unsubstituted alkynylene, substituted or unsubstituted 1,3-butadienylene, substituted or unsubstituted 1-aza-1,3-butadienylene, or substituted or unsubstituted 2-aza-1,3-butadienylene;

D and E are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo and pseudohalo or D and E together form a bond; or (ii) A and D; or E and G; together form substituted or unsubstituted alkylene, substituted or unsubstituted azaalkylene, substituted or unsubstituted oxaalkylene, or substituted or unsubstituted thiaalkylene; and the others of A, D, E and G are selected as in (i);

$X^1$ and $X^2$ are each independently selected from O, S, S(=O), $S(=O)_2$, Se, $NR^5$, $CR^6R^7$ and $CR^8=CR^9$;

$X^3$ is O, S, Se, $NR^5$ or $CR^6R^7$;

$R^1$ and $R^2$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted heteroarylium, substituted or unsubstituted heteroaryliumalkyl, $OR^{10}$, $SR^{10}$, $S(=O)R^{13}$, $S(=O)_2R^{13}$, $NR^{11}R^{12}$ and $C(=J)R^{13}$;

$R^3$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted heteroarylium, substituted or unsubstituted aralkyl, substituted or unsubstituted heteroaralkyl, substituted or unsubstituted heteroaryliumalkyl, $OR^{10}$, $SR^{10}$, $S(=O)R^{13}$, $S(=O)_2R^{13}$, $NR^{11}R^{12}$ and $C(=J)R^{13}$;

where $R^5$, $R^6$, $R^7$, $R^8$ and $R^9$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo, pseudohalo, $OR^{10}$, $NR^{14}R^{15}$ and $C(=J)R^{13}$;

$R^{10}$, $R^{11}$ and $R^{12}$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl or $C(=J)R^{13}$;

J is O, S or $NR^{14}$;

$R^{13}$ is selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, pseudohalo, $OR^{16}$ and $NR^{14}R^{15}$;

$R^{14}$, $R^{15}$ and $R^{16}$ are each independently selected from hydrogen, alkyl, alkenyl, alkynyl, cycloalkyl, heterocyclyl, cycloalkylalkyl, heterocyclylalkyl, aryl, heteroaryl, aralkyl and heteroaralkyl;

where the alkyl, alkenyl, alkynyl, cycloalkyl, heterocyclyl, cycloalkylalkyl, heterocyclylalkyl, aryl, heteroaryl, heteroarylium, aralkyl, heteroaralkyl and heteroaryliumalkyl moieties of A, D, E, G, $R^1$, $R^2$, $R^3$, $R^5$, $R^6$, $R^7$, $R^8$, $R^9$, $R^{10}$, $R^{11}$, $R^{12}$ and $R^{13}$ are unsubstituted or substituted with one or more substituents each independently selected from $Q^1$, where $Q^1$ is halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, imino, hydroxyimino, alkoxyimino, aryloxyimino, aralkoxyimino, alkylazo, arylazo, aralkylazo, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{51}R^{52}R^{53}$, $P(R^{50})_2$, $P(=O)(R^{50})_2$, $OP(=O)(R^{50})_2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy, thioalkylenoxy or alkylenedithioxy where y is 1 or 2; or two $Q^1$ groups, which substitute the same atom, together form alkylene; and each $Q^1$ is independently unsubstituted or substituted with one or more substituents each independently selected from $Q^2$;

each $Q^2$ is independently halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{51}R^{52}R^{53}$, $P(R^{50})_2$, $P(=O)(R^{15})_2$, $OP(=O)(R^{50})_2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^2$ groups, which substitute atoms in a 1,2 or 1,3 arrangement, together form alkylenedioxy, thioalkylenoxy or alkylenedithioxy where y is 1 or 2; or two $Q^2$ groups, which substitute the same atom, together form alkylene;

each $Q^2$ is independently unsubstituted or substituted with one or more substituents each independently selected from alkyl, halo and pseudohalo;

$R^{50}$ is hydroxy, alkoxy, aralkoxy, alkyl, heteroaryl, heterocyclyl, aryl or $—NR^{70}R^{71}$, where $R^{70}$ and $R^{71}$ are each independently hydrogen, alkyl, aralkyl, aryl, heteroaryl, heteroaralkyl or heterocyclyl, or $R^{70}$ and $R^{71}$ together form alkylene, azaalkylene, oxaalkylene or thiaalkylene;

$R^{51}$, $R^{52}$ and $R^{53}$ are each independently hydrogen, alkyl, aryl, aralkyl, heteroaryl, heteroaralkyl, heterocyclyl or heterocyclylalkyl;

$R^{60}$ is hydrogen, alkyl, aryl, aralkyl, heteroaryl, heteroaralkyl, heterocyclyl or heterocyclylalkyl; and $R^{63}$ is alkoxy, aralkoxy, alkyl, heteroaryl, heterocyclyl, aryl or $—NR^{70}R^{71}$.

58. The method of claim 57, wherein the disease or disorder is selected from hypercholesterolemia, hyperlipoproteinemia, hypertriglyceridemia, lipodystrophy, hyperglycemia, diabetes mellitus, dyslipidemia, atherosclerosis, gallstone disease, acne vulgaris, acneiforn skin conditions, diabetes, Parkinson's disease, cancer, Alzheimer's disease, inflammation, immunological disorders, lipid disorders, obesity, conditions characterized by a perturbed epidermal barrier function, hyperlipidemia, cholestasis, peripheral occlusive disease, ischemic stroke, conditions of disturbed differentiation or excess proliferation of the epidermis or mucous membrane, and cardiovascular disorders.

59. A method of treating, preventing, or ameliorating one or more symptoms of a disease or disorder which is affected by cholesterol, triglyceride, or bile acid levels, comprising administering to a subject in need thereof an effective amount of a compound formulae I:

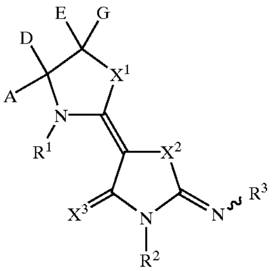

or

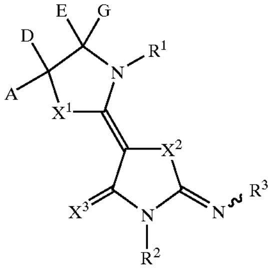

or a pharmaceutically acceptable derivative thereof, wherein:

A, D, E and G are selected from (i) or (ii) as follows:

(i) A and G are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted heteroarylium, substituted or unsubstituted heteroaryliumalkyl, halo, pseudohalo, $OR^{10}$, $SR^{10}$, $S(=O)R^{13}$, $S(=O)_2R^{13}$, $NR^{11}R^{12}$ and $C(=J)R^{13}$, or A and G together form substituted or unsubstituted alkylene, substituted or unsubstituted azaalkylene, substituted or unsubstituted oxaalkylene, substituted or unsubstituted thiaalkylene, substituted or unsubstituted alkenylene, substituted or unsubstituted alkynylene, substituted or unsubstituted 1,3-butadienylene, substituted or unsubstituted 1-aza-1,3-butadienylene, or substituted or unsubstituted 2-aza-1,3-butadienylene;

D and E are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo and pseudohalo or D and E together form a bond; or (ii) A and D; or E and G; together form substituted or unsubstituted alkylene, substituted or unsubstituted azaalkylene, substituted or unsubstituted oxaalkylene, or substituted or unsubstituted thiaalkylene;

and the others of A, D, E and G are selected as in (i);

$X^1$ and $X^2$ are each independently selected from O, S, S(=O), $S(=O)_2$, Se, $NR^5$, $CR^6R^7$ and $CR^8{=}CR^9$;

$X^3$ is O, S, Se, $NR^5$ or $CR^6R^7$;

$R^1$ and $R^2$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted heteroarylium, substituted or unsubstituted heteroaryliumalkyl, $OR^{10}$, $SR^{10}$, $S(=O)R^{13}$, $S(=O)_2R^{13}$, $NR^{11}R^{12}$ and $C(=J)R^{13}$;

$R^3$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted heteroarylium, substituted or unsubstituted aralkyl, substituted or unsubstituted heteroaralkyl, substituted or unsubstituted heteroaryliumalkyl, $OR^{10}$, $SR^{10}$, $S(=O)R^{13}$, $S(=O)_2R^{13}$, $NR^{11}R^{12}$ and $C(=J)R^{13}$;

where $R^5$, $R^6$, $R^7$, $R^8$ and $R^9$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo, pseudohalo, $OR^{10}$, $NR^{14}R^{15}$ and $C(=J)R^{13}$;

$R^{10}$, $R^{11}$ and $R^{12}$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl or $C(=J)R^{13}$;

J is O, S or $NR^{14}$;

$R^{13}$ is selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, pseudohalo, $OR^{16}$ and $NR^{14}R^{15}$;

$R^{14}$, $R^{15}$ and $R^{16}$ are each independently selected from hydrogen, alkyl, alkenyl, alkynyl, cycloalkyl, heterocyclyl, cycloalkylalkyl, heterocyclylalkyl, aryl, heteroaryl, aralkyl and heteroaralkyl;

where the alkyl, alkenyl, alkynyl, cycloalkyl, heterocyclyl, cycloalkylalkyl, heterocyclylalkyl, aryl, heteroaryl, heteroarylium, aralkyl, heteroaralkyl and heteroaryliumalkyl moieties of A, D, E, G, $R^1$, $R^2$, $R^3$, $R^5$, $R^6$, $R^7$, $R^8$, $R^9$, $R^{10}$, $R^{11}$, $R^{12}$ and $R^{13}$ are unsubstituted or substituted with one or more substituents each independently selected from $Q^1$, where $Q^1$ is halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N', N'-dialkylureido, N,N'-diaryl-N'-alkylureido, N,N', N'-triarylureido, amidino, alkylamidino, arylamidino, imino, hydroxyimino, alkoxyimino, aryloxyimino, aralkoxyimino, alkylazo, arylazo, aralkylazo, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $-N^+R^{51}R^{52}R^{53}$, $P(R^{50})_2$, $P(=O)(R^{50})_2$, $OP(=O)(R^{50})_2$, $-NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy, thioalkylenoxy or alkylenedithioxy where y is 1 or 2; or two $Q^1$ groups, which substitute the same atom, together form alkylene; and each $Q^1$ is independently unsubstituted or substituted with one or more substituents each independently selected from $Q^2$;

each $Q^2$ is independently halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —$N^+R^{51}R^{52}R^{53}$, $P(R^{50})_2$, $P(=O)(R^{50})_2$, $OP(=O)(R^{50})_2$, —$NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^2$ groups, which substitute atoms in a 1,2 or 1,3 arrangement, together form alkylenedioxy, thioalkylenoxy or alkylenedithioxy where y is 1 or 2; or two $Q^2$ groups, which substitute the same atom, together form alkylene;

each $Q^2$ is independently unsubstituted or substituted with one or more substituents each independently selected from alkyl, halo and pseudohalo;

$R^{50}$ is hydroxy, alkoxy, aralkoxy, alkyl, heteroaryl, heterocyclyl, aryl or —$NR^{70}R^{71}$, where $R^{70}$ and $R^{71}$ are each independently hydrogen, alkyl, aralkyl, aryl, heteroaryl, heteroaralkyl or heterocyclyl, or $R^{70}$ and $R^{71}$ together form alkylene, azaalkylene, oxaalkylene or thiaalkylene;

$R^{51}$, $R^{52}$ and $R^{53}$ are each independently hydrogen, alkyl, aryl, aralkyl, heteroaryl, heteroaralkyl, heterocyclyl or heterocyclylalkyl:

$R^{60}$ is hydrogen, alkyl, aryl, aralkyl, heteroaryl, heteroaralkyl, heterocyclyl or heterocyclylalkyl; and $R^{63}$ is alkoxy, aralkoxy, alkyl, heteroaryl, heterocyclyl, aryl or —$NR^{70}R^{71}$.

60. A method of modulating nuclear receptor activity, comprising contacting the nuclear receptor with a compound formulae I:

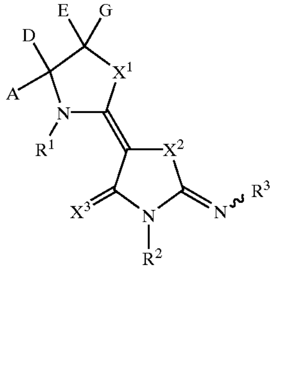

or

-continued

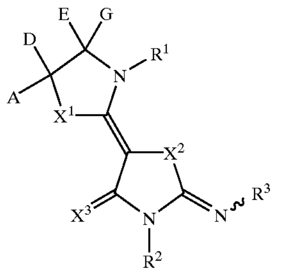

or a pharmaceutically acceptable derivative thereof, wherein:

A, D, E and G are selected from (i) or (ii) as follows:

(i) A and G are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted heteroarylium, substituted or unsubstituted heteroaryliumalkyl, halo, pseudohalo, $OR^{10}$, $SR^{10}$, $S(=O)R^{13}$, $S(=O)_2R^{13}$, $NR^{11}R^{12}$ and $C(=J)R^{13}$, or A and G together form substituted or unsubstituted alkylene, substituted or unsubstituted azaalkylene, substituted or unsubstituted oxaalkylene, substituted or unsubstituted thiaalkylene, substituted or unsubstituted alkenylene, substituted or unsubstituted alkynylene, substituted or unsubstituted 1,3-butadienylene, substituted or unsubstituted 1-aza-1,3-butadienylene, or substituted or unsubstituted 2-aza-1,3-butadienylene;

D and E are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo and pseudohalo or D and E together form a bond; or (ii) A and D; or E and G; together form substituted or unsubstituted alkylene, substituted or unsubstituted azaalkylene, substituted or unsubstituted oxaalkylene, or substituted or unsubstituted thiaalkylene;

and the others of A, D, E and G are selected as in (i);

$X^1$ and $X^2$ are each independently selected from O, S, S(=O), $S(=O)_2$, Se, $NR^5$, $CR^6R^7$ and $CR^8$=$CR^9$;

$X^3$ is O, S, Se, $NR^5$ or $CR^6R^7$;

$R^1$ and $R^2$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted heteroarylium, substituted or unsubstituted heteroaryliumalkyl, $OR^{10}$, $SR^{10}$, $S(=O)R^{13}$, $S(=O)_2R^{13}$, $NR^{11}R^{12}$ and $C(=J)R^{13}$;

$R^3$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted heteroarylium, substituted or unsubstituted aralkyl, substituted or unsubstituted heteroaralkyl, substituted or unsubstituted heteroaryliumalkyl, $OR^{10}$, $SR^{10}$, $S(=O)R^{13}$, $S(=O)_2R^{13}$, $NR^{11}R^{12}$ and $C(=J)R^{13}$;

where $R^5$, $R^6$, $R^7$, $R^8$ and $R^9$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo, pseudohalo, $OR^{10}$, $NR^{14}R^{15}$ and $C(=J)R^{13}$;

$R^{10}$, $R^{11}$ and $R^{12}$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl or $C(=J)R^{13}$;

J is O, S or $NR^{14}$;

$R^{13}$ is selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, pseudohalo, $OR^{16}$ and $NR^{14}R^{15}$;

$R^{14}$, $R^{15}$ and $R^{16}$ are each independently selected from hydrogen, alkyl, alkenyl, alkynyl, cycloalkyl, heterocyclyl, cycloalkylalkyl, heterocyclylalkyl, aryl, heteroaryl, aralkyl and heteroaralkyl;

where the alkyl, alkenyl, alkynyl, cycloalkyl, heterocyclyl, cycloalkylalkyl, heterocyclylalkyl, aryl, heteroaryl, heteroarylium, aralkyl, heteroaralkyl and heteroaryliumalkyl moieties of A, D, E, G, $R^1$, $R^2$, $R^3$, $R^5$, $R^6$, $R^7$, $R^8$, $R^9$, $R^{10}$, $R^{11}$, $R^{12}$ and $R^{13}$ are unsubstituted or substituted with one or more substituents each independently selected from $Q^1$, where $Q^1$ is halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, imino, hydroxyimino, alkoxyimino, aryloxyimino, aralkoxyimino, alkylazo, arylazo, aralkylazo, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{51}R^{52}R^{53}$, $P(R^{50})_2$, $P(=O)(R^{50})_2$, $OP(=O)(R^{50})_2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy, thioalkylenoxy or alkylenedithioxy where y is 1 or 2; or two $Q^1$ groups, which substitute the same atom, together form alkylene; and each $Q^1$ is independently unsubstituted or substituted with one or more substituents each independently selected from $Q^2$;

each $Q^2$ is independently halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^{+}R^{51}R^{52}R^{53}$, $P(R^{50})_2$, $P(=O)(R^{50})_2$, $OP(=O)(R^{50})_2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^2$ groups, which substitute atoms in a 1,2 or 1,3 arrangement, together form alkylenedioxy, thioalkylenoxy or alkylenedithioxy where y is 1 or 2; or two $Q^2$ groups, which substitute the same atom, together form alkylene;

each $Q^2$ is independently unsubstituted or substituted with one or more substituents each independently selected from alkyl, halo and pseudohalo;

$R^{50}$ is hydroxy, alkoxy, aralkoxy, alkyl, heteroaryl, heterocyclyl, aryl or $—NR^{70}R^{71}$, where $R^{70}$ and $R^{71}$ are each independently hydrogen, alkyl, aralkyl, aryl, heteroaryl, heteroaralkyl or heterocyclyl, or $R^{70}$ and $R^{71}$ together form alkylene, azaalkylene, oxaalkylene or thiaalkylene;

$R^{51}$, $R^{52}$ and $R^{53}$ are each independently hydrogen, alkyl, aryl, aralkyl, heteroaryl, heteroaralkyl, heterocyclyl or heterocyclylalkyl;

$R^{60}$ is hydrogen, alkyl, aryl, aralkyl, heteroaryl, heteroaralkyl, heterocyclyl or heterocyclylalkyl; and $R^{63}$ is alkoxy, aralkoxy, alkyl, heteroaryl, heterocyclyl, aryl or $—NR^{70}R^{71}$.

61. A method of treating, preventing, or ameliorating one or more symptoms of cholestasis in a subject in need thereof, comprising administrating an effective amount of a compound of formulae I:

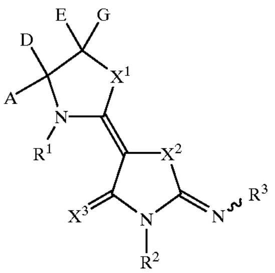

or

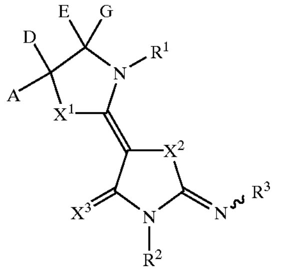

or a pharmaceutically acceptable derivative thereof, wherein:

A, D, E and G are selected from (i) or (ii) as follows:

(i) A and G are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted heteroarylium, substituted or unsubstituted heteroaryliumalkyl, halo, pseudohalo, $OR^{10}$, $SR^{10}$, $S(=O)R^{13}$, $S(=O)_2R^{13}$, $NR^{11}R^{12}$ and $C(=J)R^{13}$, or A and G together form substituted or unsubstituted alkylene, substituted or unsubstituted azaalkylene, substituted or unsubstituted oxaalkylene, substituted or unsubstituted thiaalkylene, substituted or unsubstituted alkenylene, substituted or unsubstituted alkynylene, substituted or unsubstituted 1,3-butadienylene, substituted or unsubstituted 1-aza-1,3-butadienylene, or substituted or unsubstituted 2-aza-1,3-butadienylene;

D and E are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo and pseudohalo or D and E together form a bond; or (ii) A and D; or E and G; together form substituted or unsubstituted alkylene, substituted or unsubstituted azaalkylene, substituted or unsubstituted oxaalkylene, or substituted or unsubstituted thiaalkylene;

and the others of A, D, E and G are selected as in (i);

$X^1$ and $X^2$ are each independently selected from O, S, $S(=O)$, $S(=O)_2$, Se, $NR^5$, $CR^6R^7$ and $CR^8{=}CR^9$;

$X^3$ is O, S, Se, $NR^5$ or $CR^6R^7$;

$R^1$ and $R^2$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, substituted or unsubstituted heteroarylium, substituted or unsubstituted heteroaryliumalkyl, $OR^{10}$, $SR^{10}$, $S(=O)R^{13}$, $S(=O)_2R^{13}$, $NR^{11}R^{12}$ and $C(=J)R^{13}$;

$R^3$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted heteroarylium, substituted or unsubstituted aralkyl, substituted or unsubstituted heteroaralkyl, substituted or unsubstituted heteroaryliumalkyl, $OR^{10}$, $SR^{10}$, $S(=O)R^{13}$, $S(=O)_2R^{13}$, $NR^{11}R^{12}$ and $C(=J)R^{13}$;

where $R^5$, $R^6$, $R^7$, $R^8$ and $R^9$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo, pseudohalo, $OR^{10}$, $NR^{14}R^{15}$ and $C(=J)R^{13}$;

$R^{10}$, $R^{11}$ and $R^{12}$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl or $C(=J)R^{13}$;

J is O, S or $NR^{14}$;

$R^{13}$ is selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, pseudohalo, $OR^{16}$ and $NR^{14}R^{15}$;

$R^{14}$, $R^{15}$ and $R^{16}$ are each independently selected from hydrogen, alkyl, alkenyl, alkynyl, cycloalkyl, heterocyclyl, cycloalkylalkyl, heterocyclylalkyl, aryl, heteroaryl, aralkyl and heteroaralkyl;

where the alkyl, alkenyl, alkynyl, cycloalkyl, heterocyclyl, cycloalkylalkyl, heterocyclylalkyl, aryl, heteroaryl, heteroarylium, aralkyl, heteroaralkyl and heteroaryliumalkyl moieties of A, D, E, G, $R^1$, $R^2$, $R^3$, $R^5$, $R^6$, $R^7$, $R^8$, $R^9$, $R^{10}$, $R^{11}$, $R^{12}$ and $R^{13}$ are unsubstituted or substituted with one or more substituents each independently selected from $Q^1$, where $Q^1$ is halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N', N'-dialkylureido, N,N'-diaryl-N'-alkylureido, N,N',N'-triarylureido, amidino, alkylamidino, arylamidino, imino, hydroxyimino, alkoxyimino, aryloxyimino, aralkoxyimino, alkylazo, arylazo, aralkylazo, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{51}R^{52}R^{53}$, $P(R^{50})_2$, $P(=O)(R^{50})_2$, $OP(=O)(R^{50})_2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy, thioalkylenoxy or alkylenedithioxy where y is 1 or 2; or two $Q^1$ groups, which substitute the same atom, together form alkylene; and each $Q^1$ is independently unsubstituted or substituted with one or more substituents each independently selected from $Q^2$;

each $Q^2$ is independently halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{51}R^{52}R^{53}$, $P(R^{50})_2$, $P(=O)(R^{50})_2$, $OP(=O)(R^{50})_2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^2$ groups, which substitute atoms in a 1,2 or 1,3 arrangement, together form alkylenedioxy, thioalkylenoxy or alkylenedithioxy where y is 1 or 2; or two $Q^2$ groups, which substitute the same atom, together form alkylene;

each $Q^2$ is independently unsubstituted or substituted with one or more substituents each independently selected from alkyl, halo and pseudohalo;

$R^{50}$ is hydroxy, alkoxy, aralkoxy, alkyl, heteroaryl, heterocyclyl, aryl or $—NR^{70}R^{71}$, where $R^{70}$ and $R^{71}$ are each independently hydrogen, alkyl, aralkyl, aryl, heteroaryl, heteroaralkyl or heterocyclyl, or $R^{70}$ and $R^{71}$ together form alkylene, azaalkylene, oxaalkylene or thiaalkylene;

$R^{51}$, $R^{52}$ and $R^{53}$ are each independently hydrogen, alkyl, aryl, aralkyl, heteroaryl, heteroaralkyl, heterocyclyl or heterocyclylalkyl;

$R^{60}$ is hydrogen, alkyl, aryl, aralkyl, heteroaryl, heteroaralkyl, heterocyclyl or heterocyclylalkyl; and $R^{63}$ is alkoxy, aralkoxy, alkyl, heteroaryl, heterocyclyl, aryl or $—NR^{70}R^{71}$.

62. The compound of claim 1 that has formulae I:

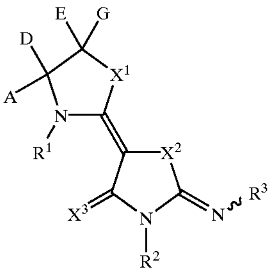

or

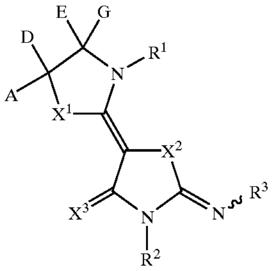

or a pharmaceutically acceptable derivative thereof, wherein:

$X^1$, $X^2$ and $X^3$ are selected from (i) or (ii) as follows:

(i) $X^1$, $X^2$ and $X^3$ are each independently S, O or $NR^5$; or (ii) $X^1$ is —$CR^8$═$CR^9$—, where $R^8$ and $R^9$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo, pseudohalo, $OR^{10}$, $NR^{14}R^{15}$ and C(═J)$R^{13}$, and $X^2$ and $X^3$ are each independently S, O or $NR^5$;

$R^1$ is substituted or unsubstituted alkyl, where there are 0 to 6 substituents selected from alkoxy, alkoxyalkyl, hydroxycarbonyl, alkylcarbonyloxy, hydroxy, halo, pseudohalo, aryl and heteroaryl;

$R^2$ is substituted or unsubstituted aralkyl, substituted or unsubstituted aryl, substituted or unsubstituted alkenyl, substituted or unsubstituted alkyl, substituted or unsubstituted cycloalkyl, substituted or unsubstituted heteroaralkyl, or substituted or unsubstituted heterocyclylalkyl; where there are 0 or 1 substituents selected from alkoxycarbonyl and hydroxycarbonyl;

$R^3$ is substituted or unsubstituted heteroaryl, substituted or unsubstituted aryl, or substituted or unsubstituted aralkyl; where there are 0 to 5 substituents selected from alkylamino, cyano, cycloalkyl, hydroxy, alkoxy, dialkylamino, amino, heterocyclyl, aralkoxy, alkyl, nitro, haloalkyl, alkylcarbonyl, halo, alkylcarbonylamino, alkoxyalkylcarbonyl-amino, dialkylaminoalkylcarbonylamino, aminocarbonyl, alkoxycarbonyl, aralkylamino, cycloalkylamino, heterocyclylamino, haloalkylamino, haloalkoxy, hydroxycarbonyl, aminosulfonyl, alkylcarbonylaminosulfonyl, or haloalkylcarbonylamino, or any two substituents, which substitute atoms in a 1,2 or 1,3 arrangement, together form alkylenedioxy;

A and G are each independently selected from hydrogen, substituted or unsubstituted aryl, substituted or unsubstituted alkyl, substituted or unsubstituted alkoxycarbonyl, hydroxycarbonyl, and substituted or unsubstituted alkylcarbonyl, where there are 0 to 5 substituents selected from aryl, haloalkyl, haloalkoxy, nitro, halo, pseudohalo, hydroxy, alkyl and alkoxy, or A and G together form substituted or unsubstituted alkylene, or substituted or unsubstituted azaalkylene, where there are 0 to 4 substituents selected from halo, pseudohalo, alkoxy, nitro, haloalkyl, alkylcarbonylamino, hydroxy, alkylaminocarbonyloxy, alkoxycarbonylalkoxy, aminocarbonylalkoxy, hydroxyalkoxy, alkyl, haloalkylaminocarbonyloxy and alkylaminoalkoxy;

D and E are each hydrogen, or together form a bond; and $R^5$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, halo, pseudohalo, $OR^{10}$, $SR^{10}$, S(═O)$R^{13}$, S(═O)$_2R^{13}$, $NR^{14}R^{15}$ or C(═J)$R^{13}$;

$R^{10}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl or C(═J)$R^{13}$;

J is O, S or $NR^{14}$;

$R^{13}$ is selected from hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, pseudohalo, $OR^{16}$ and $NR^{14}R^{15}$;

$R^{14}$, $R^{15}$ and $R^{16}$ are each independently selected from hydrogen, alkyl, alkenyl, alkynyl, cycloalkyl, heterocyclyl, cycloalkylalkyl, heterocyclylalkyl, aryl, heteroaryl, aralkyl and heteroaralkyl;

wherein the alkyl, alkenyl, alkynyl, cycloalkyl, heterocyclyl, cycloalkylalkyl, heterocyclylalkyl, aryl, heteroaryl, aralkyl and heteroaralkyl moieties of $R^5$, $R^{10}$ and $R^{13}$ are unsubstituted or substituted with one or more substituents each independently selected from $Q^1$, where $Q^1$ is halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, imino, hydroxyimino, alkoxyimino, aralkoxyimino, arylazo, haloalkylcarbonylamino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^{+}R^{51}R^{52}R^{53}$, $P(R^{50})_2$, $P(=O)(R^{50})_2$, $OP(=O)(R^{50})_2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy, thioalkylenoxy or alkylenedithioxy; or two $Q^1$ groups, which substitute the same atom, together form alkylene;

each $Q^1$ is independently unsubstituted or substituted with one or more substituents each independently selected from $Q^2$;

each $Q^2$ is independently halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^{+}R^{51}R^{52}R^{53}$, $P(R^{50})_2$, $P(=O)(R^{10})_2$, $OP(=O)(R^{50})_2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^2$ groups, which substitute atoms in a 1,2 or 1,3 arrangement, together form alkylenedioxy, thioalkylenoxy or alkylenedithioxy where y is 1 or 2; or two $Q^2$ groups, which substitute the same atom, together form alkylene;

$R^{50}$ is hydroxy, alkoxy, aralkoxy, alkyl, heteroaryl, heterocyclyl, aryl or —$NR^{70}R^{71}$, where $R^{70}$ and $R^{71}$ are each independently hydrogen, alkyl, aralkyl, aryl, heteroaryl, heteroaralkyl or heterocyclyl, or $R^{70}$ and $R^{71}$ together form alkylene, azaalkylene, oxaalkylene or thiaalkylene;

$R^{51}$, $R^{52}$ and $R^{53}$ are each independently hydrogen, alkyl, aryl, aralkyl, heteroaryl, heteroaralkyl, heterocyclyl or heterocyclylalkyl;

$R^{60}$ is hydrogen, alkyl, aryl, aralkyl, heteroaryl, heteroaralkyl, heterocyclyl or heterocyclylalkyl; and $R^{63}$ is alkoxy, aralkoxy, alkyl, heteroaryl, heterocyclyl, aryl or —$NR^{70}R^{71}$.

* * * * *

SEQUENCE LISTING

```
<160> NUMBER OF SEQ ID NOS: 18

<210> SEQ ID NO 1
<211> LENGTH: 1528
<212> TYPE: DNA
<213> ORGANISM: Homo Sapien
<220> FEATURE:
<221> NAME/KEY: CDS
<222> LOCATION: (36)...(1379)
<300> PUBLICATION INFORMATION:
<308> DATABASE ACCESSION NUMBER: GeneBank Nm_005693
<309> DATABASE ENTRY DATE: 2002-05-14

<400> SEQUENCE: 1

cagtgccttg gtaatgacca gggctccaga aagag atg tcc ttg tgg ctg ggg        53
                                       Met Ser Leu Trp Leu Gly
                                        1               5

gcc cct gtg cct gac att cct cct gac tct gcg gtg gag ctg tgg aag      101
Ala Pro Val Pro Asp Ile Pro Pro Asp Ser Ala Val Glu Leu Trp Lys
            10                  15                  20

cca ggc gca cag gat gca agc agc cag gcc cag gga ggc agc agc tgc      149
Pro Gly Ala Gln Asp Ala Ser Ser Gln Ala Gln Gly Gly Ser Ser Cys
        25                  30                  35

atc ctc aga gag gaa gcc agg atg ccc cac tct gct ggg ggt act gca      197
Ile Leu Arg Glu Glu Ala Arg Met Pro His Ser Ala Gly Gly Thr Ala
    40                  45                  50

ggg gtg ggg ctg gag gct gca gag ccc aca gcc ctg ctc acc agg gca      245
Gly Val Gly Leu Glu Ala Ala Glu Pro Thr Ala Leu Leu Thr Arg Ala
 55                  60                  65                  70

gag ccc cct tca gaa ccc aca gag atc cgt cca caa aag cgg aaa aag      293
Glu Pro Pro Ser Glu Pro Thr Glu Ile Arg Pro Gln Lys Arg Lys Lys
                75                  80                  85

ggg cca gcc ccc aaa atg ctg ggg aac gag cta tgc agc gtg tgt ggg      341
Gly Pro Ala Pro Lys Met Leu Gly Asn Glu Leu Cys Ser Val Cys Gly
            90                  95                  100

gac aag gcc tcg ggc ttc cac tac aat gtt ctg agc tgc gag ggc tgc      389
Asp Lys Ala Ser Gly Phe His Tyr Asn Val Leu Ser Cys Glu Gly Cys
        105                 110                 115

aag gga ttc ttc cgc cgc agc gtc atc aag gga gcg cac tac atc tgc      437
Lys Gly Phe Phe Arg Arg Ser Val Ile Lys Gly Ala His Tyr Ile Cys
    120                 125                 130

cac agt ggc ggc cac tgc ccc atg gac acc tac atg cgt cgc aag tgc      485
His Ser Gly Gly His Cys Pro Met Asp Thr Tyr Met Arg Arg Lys Cys
135                 140                 145                 150

cag gag tgt cgg ctt cgc aaa tgc cgt cag gct ggc atg cgg gag gag      533
Gln Glu Cys Arg Leu Arg Lys Cys Arg Gln Ala Gly Met Arg Glu Glu
                155                 160                 165

tgt gtc ctg tca gaa gaa cag atc cgc ctg aag aaa ctg aag cgg caa      581
Cys Val Leu Ser Glu Glu Gln Ile Arg Leu Lys Lys Leu Lys Arg Gln
            170                 175                 180

gag gag gaa cag gct cat gcc aca tcc ttg ccc ccc agg cgt tcc tca      629
Glu Glu Glu Gln Ala His Ala Thr Ser Leu Pro Pro Arg Arg Ser Ser
        185                 190                 195

ccc ccc caa atc ctg ccc cag ctc agc ccg gaa caa ctg ggc atg atc      677
Pro Pro Gln Ile Leu Pro Gln Leu Ser Pro Glu Gln Leu Gly Met Ile
    200                 205                 210

gag aag ctc gtc gct gcc cag caa cag tgt aac cgg cgc tcc ttt tct      725
Glu Lys Leu Val Ala Ala Gln Gln Gln Cys Asn Arg Arg Ser Phe Ser
215                 220                 225                 230

gac cgg ctt cga gtc acg cct tgg ccc atg gca cca gat ccc cat agc      773
```

-continued

```
Asp Arg Leu Arg Val Thr Pro Trp Pro Met Ala Pro Asp Pro His Ser
                235                 240                 245

cgg gag gcc cgt cag cag cgc ttt gcc cac ttc act gag ctg gcc atc      821
Arg Glu Ala Arg Gln Gln Arg Phe Ala His Phe Thr Glu Leu Ala Ile
            250                 255                 260

gtc tct gtg cag gag ata gtt gac ttt gct aaa cag cta ccc ggc ttc      869
Val Ser Val Gln Glu Ile Val Asp Phe Ala Lys Gln Leu Pro Gly Phe
        265                 270                 275

ctg cag ctc agc cgg gag gac cag att gcc ctg ctg aag acc tct gcg      917
Leu Gln Leu Ser Arg Glu Asp Gln Ile Ala Leu Leu Lys Thr Ser Ala
    280                 285                 290

atc gag gtg atg ctt ctg gag aca tct cgg agg tac aac cct ggg agt      965
Ile Glu Val Met Leu Leu Glu Thr Ser Arg Arg Tyr Asn Pro Gly Ser
295                 300                 305                 310

gag agt atc acc ttc ctc aag gat ttc agt tat aac cgg gaa gac ttt     1013
Glu Ser Ile Thr Phe Leu Lys Asp Phe Ser Tyr Asn Arg Glu Asp Phe
                315                 320                 325

gcc aaa gca ggg ctg caa gtg gaa ttc atc aac ccc atc ttc gag ttc     1061
Ala Lys Ala Gly Leu Gln Val Glu Phe Ile Asn Pro Ile Phe Glu Phe
            330                 335                 340

tcc agg gcc atg aat gag ctg caa ctc aat gat gcc gag ttt gcc ttg     1109
Ser Arg Ala Met Asn Glu Leu Gln Leu Asn Asp Ala Glu Phe Ala Leu
        345                 350                 355

ctc att gct atc agc atc ttc tct gca gac cgg ccc aac gtg cag gac     1157
Leu Ile Ala Ile Ser Ile Phe Ser Ala Asp Arg Pro Asn Val Gln Asp
    360                 365                 370

cag ctc cag gtg gag agg ctg cag cac aca tat gtg gaa gcc ctg cat     1205
Gln Leu Gln Val Glu Arg Leu Gln His Thr Tyr Val Glu Ala Leu His
375                 380                 385                 390

gcc tac gtc tcc atc cac cat ccc cat gac cga ctg atg ttc cca cgg     1253
Ala Tyr Val Ser Ile His His Pro His Asp Arg Leu Met Phe Pro Arg
                395                 400                 405

atg cta atg aaa ctg gtg agc ctc cgg acc ctg agc agc gtc cac tca     1301
Met Leu Met Lys Leu Val Ser Leu Arg Thr Leu Ser Ser Val His Ser
            410                 415                 420

gag caa gtg ttt gca ctg cgt ctg cag gac aaa aag ctc cca ccg ctg     1349
Glu Gln Val Phe Ala Leu Arg Leu Gln Asp Lys Lys Leu Pro Pro Leu
        425                 430                 435

ctc tct gag atc tgg gat gtg cac gaa tga ctgttctgtc cccatatttt       1399
Leu Ser Glu Ile Trp Asp Val His Glu  *
    440                 445

ctgttttctt ggccggatgg ctgaggcctg gtggctgcct cctagaagtg gaacagactg   1459

agaagggcaa acattcctgg gagctgggca aggagatcct cccgtggcat taaaagagag   1519

tcaaagggt                                                           1528


<210> SEQ ID NO 2
<211> LENGTH: 447
<212> TYPE: PRT
<213> ORGANISM: Homo Sapien

<400> SEQUENCE: 2

Met Ser Leu Trp Leu Gly Ala Pro Val Pro Asp Ile Pro Pro Asp Ser
 1               5                  10                  15

Ala Val Glu Leu Trp Lys Pro Gly Ala Gln Asp Ala Ser Ser Gln Ala
            20                  25                  30

Gln Gly Gly Ser Ser Cys Ile Leu Arg Glu Glu Ala Arg Met Pro His
        35                  40                  45

Ser Ala Gly Gly Thr Ala Gly Val Gly Leu Glu Ala Ala Glu Pro Thr
```

-continued

```
    50                  55                  60

Ala Leu Leu Thr Arg Ala Glu Pro Pro Ser Glu Pro Thr Glu Ile Arg
65                  70                  75                  80

Pro Gln Lys Arg Lys Lys Gly Pro Ala Pro Lys Met Leu Gly Asn Glu
                85                  90                  95

Leu Cys Ser Val Cys Gly Asp Lys Ala Ser Gly Phe His Tyr Asn Val
            100                 105                 110

Leu Ser Cys Glu Gly Cys Lys Gly Phe Phe Arg Arg Ser Val Ile Lys
        115                 120                 125

Gly Ala His Tyr Ile Cys His Ser Gly Gly His Cys Pro Met Asp Thr
    130                 135                 140

Tyr Met Arg Arg Lys Cys Gln Glu Cys Arg Leu Arg Lys Cys Arg Gln
145                 150                 155                 160

Ala Gly Met Arg Glu Glu Cys Val Leu Ser Glu Glu Gln Ile Arg Leu
                165                 170                 175

Lys Lys Leu Lys Arg Gln Glu Glu Glu Gln Ala His Ala Thr Ser Leu
            180                 185                 190

Pro Pro Arg Arg Ser Ser Pro Pro Gln Ile Leu Pro Gln Leu Ser Pro
        195                 200                 205

Glu Gln Leu Gly Met Ile Glu Lys Leu Val Ala Ala Gln Gln Gln Cys
    210                 215                 220

Asn Arg Arg Ser Phe Ser Asp Arg Leu Arg Val Thr Pro Trp Pro Met
225                 230                 235                 240

Ala Pro Asp Pro His Ser Arg Glu Ala Arg Gln Gln Arg Phe Ala His
                245                 250                 255

Phe Thr Glu Leu Ala Ile Val Ser Val Gln Glu Ile Val Asp Phe Ala
            260                 265                 270

Lys Gln Leu Pro Gly Phe Leu Gln Leu Ser Arg Glu Asp Gln Ile Ala
        275                 280                 285

Leu Leu Lys Thr Ser Ala Ile Glu Val Met Leu Leu Glu Thr Ser Arg
    290                 295                 300

Arg Tyr Asn Pro Gly Ser Glu Ser Ile Thr Phe Leu Lys Asp Phe Ser
305                 310                 315                 320

Tyr Asn Arg Glu Asp Phe Ala Lys Ala Gly Leu Gln Val Glu Phe Ile
                325                 330                 335

Asn Pro Ile Phe Glu Phe Ser Arg Ala Met Asn Glu Leu Gln Leu Asn
            340                 345                 350

Asp Ala Glu Phe Ala Leu Leu Ile Ala Ile Ser Ile Phe Ser Ala Asp
        355                 360                 365

Arg Pro Asn Val Gln Asp Gln Leu Gln Val Glu Arg Leu Gln His Thr
    370                 375                 380

Tyr Val Glu Ala Leu His Ala Tyr Val Ser Ile His His Pro His Asp
385                 390                 395                 400

Arg Leu Met Phe Pro Arg Met Leu Met Lys Leu Val Ser Leu Arg Thr
                405                 410                 415

Leu Ser Ser Val His Ser Glu Gln Val Phe Ala Leu Arg Leu Gln Asp
            420                 425                 430

Lys Lys Leu Pro Pro Leu Leu Ser Glu Ile Trp Asp Val His Glu
        435                 440                 445
```

<210> SEQ ID NO 3
<211> LENGTH: 1815
<212> TYPE: DNA
<213> ORGANISM: Homo Sapien -continued

```
<220> FEATURE:
<221> NAME/KEY: CDS
<222> LOCATION: (56)...(1438)
<300> PUBLICATION INFORMATION:
<308> DATABASE ACCESSION NUMBER: GeneBank XM_046419
<309> DATABASE ENTRY DATE: 2002-08-01

<400> SEQUENCE: 3

cgctgttgct tggagagggg cgggacctgg agagaggctg ctccgtgacc ccacc atg      58
                                                             Met
                                                              1

tcc tct cct acc acg agt tcc ctg gat acc ccc ctg cct gga aat ggc      106
Ser Ser Pro Thr Thr Ser Ser Leu Asp Thr Pro Leu Pro Gly Asn Gly
            5                  10                  15

ccc cct cag cct ggc gcc cct tct tct tca ccc act gta aag gag gag      154
Pro Pro Gln Pro Gly Ala Pro Ser Ser Ser Pro Thr Val Lys Glu Glu
        20                  25                  30

ggt ccg gag ccg tgg ccc ggg ggt ccg gac cct gat gtc cca ggc act      202
Gly Pro Glu Pro Trp Pro Gly Gly Pro Asp Pro Asp Val Pro Gly Thr
    35                  40                  45

gat gag gcc agc tca gcc tgc agc aca gac tgg gtc atc cca gat ccc      250
Asp Glu Ala Ser Ser Ala Cys Ser Thr Asp Trp Val Ile Pro Asp Pro
 50                  55                  60                  65

gaa gag gaa cca gag cgc aag cga aag aag ggc cca gcc ccg aag atg      298
Glu Glu Glu Pro Glu Arg Lys Arg Lys Lys Gly Pro Ala Pro Lys Met
                 70                  75                  80

ctg ggc cac gag ctt tgc cgt gtc tgt ggg gac aag gcc tcc ggc ttc      346
Leu Gly His Glu Leu Cys Arg Val Cys Gly Asp Lys Ala Ser Gly Phe
            85                  90                  95

cac tac aac gtg ctc agc tgc gaa ggc tgc aag ggc ttc ttc cgg cgc      394
His Tyr Asn Val Leu Ser Cys Glu Gly Cys Lys Gly Phe Phe Arg Arg
        100                 105                 110

agt gtg gtc cgt ggt ggg gcc agg cgc tat gcc tgc cgg ggt ggc gga      442
Ser Val Val Arg Gly Gly Ala Arg Arg Tyr Ala Cys Arg Gly Gly Gly
    115                 120                 125

acc tgc cag atg gac gct ttc atg cgg cgc aag tgc cag cag tgc cgg      490
Thr Cys Gln Met Asp Ala Phe Met Arg Arg Lys Cys Gln Gln Cys Arg
130                 135                 140                 145

ctg cgc aag tgc aag gag gca ggg atg agg gag cag tgc gtc ctt tct      538
Leu Arg Lys Cys Lys Glu Ala Gly Met Arg Glu Gln Cys Val Leu Ser
                150                 155                 160

gaa gaa cag atc cgg aag aag aag att cgg aaa cag cag cag gag tca      586
Glu Glu Gln Ile Arg Lys Lys Lys Ile Arg Lys Gln Gln Gln Glu Ser
            165                 170                 175

cag tca cag tcg cag tca cct gtg ggg ccg cag ggc agc agc agc tca      634
Gln Ser Gln Ser Gln Ser Pro Val Gly Pro Gln Gly Ser Ser Ser Ser
        180                 185                 190

gcc tct ggg cct ggg gct tcc cct ggt gga tct gag gca ggc agc cag      682
Ala Ser Gly Pro Gly Ala Ser Pro Gly Gly Ser Glu Ala Gly Ser Gln
    195                 200                 205

ggc tcc ggg gaa ggc gag ggt gtc cag cta aca gcg gct caa gaa cta      730
Gly Ser Gly Glu Gly Glu Gly Val Gln Leu Thr Ala Ala Gln Glu Leu
210                 215                 220                 225

atg atc cag cag ttg gtg gcg gcc caa ctg cag tgc aac aaa cgc tcc      778
Met Ile Gln Gln Leu Val Ala Ala Gln Leu Gln Cys Asn Lys Arg Ser
                230                 235                 240

ttc tcc gac cag ccc aaa gtc acg ccc tgg ccc ctg ggc gca gac ccc      826
Phe Ser Asp Gln Pro Lys Val Thr Pro Trp Pro Leu Gly Ala Asp Pro
            245                 250                 255

cag tcc cga gat gcc cgc cag caa cgc ttt gcc cac ttc acg gag ctg      874
Gln Ser Arg Asp Ala Arg Gln Gln Arg Phe Ala His Phe Thr Glu Leu
```

-continued

```
        260                 265                 270

gcc atc atc tca gtc cag gag atc gtg gac ttc gct aag caa gtg cct      922
Ala Ile Ile Ser Val Gln Glu Ile Val Asp Phe Ala Lys Gln Val Pro
    275                 280                 285

ggt ttc ctg cag ctg ggc cgg gag gac cag atc gcc ctc ctg aag gca      970
Gly Phe Leu Gln Leu Gly Arg Glu Asp Gln Ile Ala Leu Leu Lys Ala
290                 295                 300                 305

tcc act atc gag atc atg ctg cta gag aca gcc agg cgc tac aac cac     1018
Ser Thr Ile Glu Ile Met Leu Leu Glu Thr Ala Arg Arg Tyr Asn His
                310                 315                 320

gag aca gag tgt atc acc ttc ttg aag gac ttc acc tac agc aag gac     1066
Glu Thr Glu Cys Ile Thr Phe Leu Lys Asp Phe Thr Tyr Ser Lys Asp
            325                 330                 335

gac ttc cac cgt gca ggc ctg cag gtg gag ttc atc aac ccc atc ttc     1114
Asp Phe His Arg Ala Gly Leu Gln Val Glu Phe Ile Asn Pro Ile Phe
        340                 345                 350

gag ttc tcg cgg gcc atg cgg cgg ctg ggc ctg gac gac gct gag tac     1162
Glu Phe Ser Arg Ala Met Arg Arg Leu Gly Leu Asp Asp Ala Glu Tyr
    355                 360                 365

gcc ctg ctc atc gcc atc aac atc ttc tcg gcc gac cgg ccc aac gtg     1210
Ala Leu Leu Ile Ala Ile Asn Ile Phe Ser Ala Asp Arg Pro Asn Val
370                 375                 380                 385

cag gag ccg ggc cgc gtg gag gcg ttg cag cag ccc tac gtg gag gcg     1258
Gln Glu Pro Gly Arg Val Glu Ala Leu Gln Gln Pro Tyr Val Glu Ala
                390                 395                 400

ctg ctg tcc tac acg cgc atc aag agg ccg cag gac cag ctg cgc ttc     1306
Leu Leu Ser Tyr Thr Arg Ile Lys Arg Pro Gln Asp Gln Leu Arg Phe
            405                 410                 415

ccg cgc atg ctc atg aag ctg gtg agc ctg cgc acg ctg agc tct gtg     1354
Pro Arg Met Leu Met Lys Leu Val Ser Leu Arg Thr Leu Ser Ser Val
        420                 425                 430

cac tcg gag cag gtc ttc gcc ttg cgg ctc cag gac aag aag ctg ccg     1402
His Ser Glu Gln Val Phe Ala Leu Arg Leu Gln Asp Lys Lys Leu Pro
    435                 440                 445

cct ctg ctg tcg gag atc tgg gac gtc cac gag tga ggggctggcc          1448
Pro Leu Leu Ser Glu Ile Trp Asp Val His Glu  *
450                 455                 460

acccagcccc acagccttgc ctgaccaccc tccagcagat agacgccggc accccttcct   1508

cttcctaggg tggaaggggc cctgggccga gcctgtagac ctatcggctc tcatcccttg   1568

ggataagccc cagtccaggt ccaggaggct ccctccctgc ccagcgagtc ttccagaagg   1628

ggtgaaaggg ttgcaggtcc cgaccactga cccttcccgg ctgccctccc tccccagctt   1688

acacctcaag cccagcacgc agtgcacctt gaacagaggg aggggaggac ccatggctct   1748

ccccccctagc ccgggagacc agggccttcc tcttcctctg cttttattta ataaaaacta  1808

aaaacag                                                             1815


<210> SEQ ID NO 4
<211> LENGTH: 460
<212> TYPE: PRT
<213> ORGANISM: Homo Sapien

<400> SEQUENCE: 4

Met Ser Ser Pro Thr Thr Ser Ser Leu Asp Thr Pro Leu Pro Gly Asn
 1               5                  10                  15

Gly Pro Pro Gln Pro Gly Ala Pro Ser Ser Ser Pro Thr Val Lys Glu
            20                  25                  30

Glu Gly Pro Glu Pro Trp Pro Gly Gly Pro Asp Pro Asp Val Pro Gly
```

-continued

```
        35                  40                  45

Thr Asp Glu Ala Ser Ser Ala Cys Ser Thr Asp Trp Val Ile Pro Asp
    50                  55                  60

Pro Glu Glu Glu Pro Glu Arg Lys Arg Lys Lys Gly Pro Ala Pro Lys
65                  70                  75                  80

Met Leu Gly His Glu Leu Cys Arg Val Cys Gly Asp Lys Ala Ser Gly
                85                  90                  95

Phe His Tyr Asn Val Leu Ser Cys Glu Gly Cys Lys Gly Phe Phe Arg
            100                 105                 110

Arg Ser Val Val Arg Gly Gly Ala Arg Arg Tyr Ala Cys Arg Gly Gly
        115                 120                 125

Gly Thr Cys Gln Met Asp Ala Phe Met Arg Arg Lys Cys Gln Gln Cys
    130                 135                 140

Arg Leu Arg Lys Cys Lys Glu Ala Gly Met Arg Glu Gln Cys Val Leu
145                 150                 155                 160

Ser Glu Glu Gln Ile Arg Lys Lys Lys Ile Arg Lys Gln Gln Gln Glu
                165                 170                 175

Ser Gln Ser Gln Ser Gln Ser Pro Val Gly Pro Gln Gly Ser Ser Ser
            180                 185                 190

Ser Ala Ser Gly Pro Gly Ala Ser Pro Gly Gly Ser Glu Ala Gly Ser
        195                 200                 205

Gln Gly Ser Gly Glu Gly Glu Gly Val Gln Leu Thr Ala Ala Gln Glu
    210                 215                 220

Leu Met Ile Gln Gln Leu Val Ala Ala Gln Leu Gln Cys Asn Lys Arg
225                 230                 235                 240

Ser Phe Ser Asp Gln Pro Lys Val Thr Pro Trp Pro Leu Gly Ala Asp
                245                 250                 255

Pro Gln Ser Arg Asp Ala Arg Gln Gln Arg Phe Ala His Phe Thr Glu
            260                 265                 270

Leu Ala Ile Ile Ser Val Gln Glu Ile Val Asp Phe Ala Lys Gln Val
        275                 280                 285

Pro Gly Phe Leu Gln Leu Gly Arg Glu Asp Gln Ile Ala Leu Leu Lys
    290                 295                 300

Ala Ser Thr Ile Glu Ile Met Leu Leu Glu Thr Ala Arg Arg Tyr Asn
305                 310                 315                 320

His Glu Thr Glu Cys Ile Thr Phe Leu Lys Asp Phe Thr Tyr Ser Lys
                325                 330                 335

Asp Asp Phe His Arg Ala Gly Leu Gln Val Glu Phe Ile Asn Pro Ile
            340                 345                 350

Phe Glu Phe Ser Arg Ala Met Arg Arg Leu Gly Leu Asp Asp Ala Glu
        355                 360                 365

Tyr Ala Leu Leu Ile Ala Ile Asn Ile Phe Ser Ala Asp Arg Pro Asn
    370                 375                 380

Val Gln Glu Pro Gly Arg Val Glu Ala Leu Gln Gln Pro Tyr Val Glu
385                 390                 395                 400

Ala Leu Leu Ser Tyr Thr Arg Ile Lys Arg Pro Gln Asp Gln Leu Arg
                405                 410                 415

Phe Pro Arg Met Leu Met Lys Leu Val Ser Leu Arg Thr Leu Ser Ser
            420                 425                 430

Val His Ser Glu Gln Val Phe Ala Leu Arg Leu Gln Asp Lys Lys Leu
        435                 440                 445

Pro Pro Leu Leu Ser Glu Ile Trp Asp Val His Glu
    450                 455                 460
```

-continued

<210> SEQ ID NO 5
<211> LENGTH: 2070
<212> TYPE: DNA
<213> ORGANISM: Rattus norvegicus
<220> FEATURE:
<221> NAME/KEY: CDS
<222> LOCATION: (172)...(1581)
<300> PUBLICATION INFORMATION:
<308> DATABASE ACCESSION NUMBER: GeneBank U18374
<309> DATABASE ENTRY DATE: 1995-06-21

<400> SEQUENCE: 5

```
ctgagttctg agcgtctaca gcgaaagtgc tgggctttgg aaaggagacc tgggctccga      60

atcctctcag ggccttggac gtctctgacc caaaacaatc caaggttctt atttgaagac     120

caccatccca gaagcacatt ctcgagttga aaagttggag tggtgttcga a atg aat     177
                                                         Met Asn
                                                           1

ctg att ggg ccc tcc cat tta caa gcc acg gac gag ttt gct ctt tct      225
Leu Ile Gly Pro Ser His Leu Gln Ala Thr Asp Glu Phe Ala Leu Ser
        5                  10                  15

gaa aac tta ttt gga gtg cta aca gag cac gcg gca ggt cct ctg ggg      273
Glu Asn Leu Phe Gly Val Leu Thr Glu His Ala Ala Gly Pro Leu Gly
     20                  25                  30

cag aat ctg gac ttg gaa tcg tac tcc cca tac aac aat gtg cag ttt      321
Gln Asn Leu Asp Leu Glu Ser Tyr Ser Pro Tyr Asn Asn Val Gln Phe
 35                  40                  45                  50

cct caa gtt cag cca cag atc tcc tcc tcg tcc tat tat tcc aac ctg      369
Pro Gln Val Gln Pro Gln Ile Ser Ser Ser Ser Tyr Tyr Ser Asn Leu
                 55                  60                  65

ggt ttc tac ccg caa caa ccg gaa gac tgg tac tct cct gga ctc tat      417
Gly Phe Tyr Pro Gln Gln Pro Glu Asp Trp Tyr Ser Pro Gly Leu Tyr
             70                  75                  80

gaa ctc agg cga atg ccc act gag agt gtg tac cag gga gag act gag      465
Glu Leu Arg Arg Met Pro Thr Glu Ser Val Tyr Gln Gly Glu Thr Glu
         85                  90                  95

gta tcc gag atg cct gtg aca aag aag ccg cga atg gcc gcc tca tcg      513
Val Ser Glu Met Pro Val Thr Lys Lys Pro Arg Met Ala Ala Ser Ser
    100                 105                 110

gcg gga aga ata aaa ggg gat gag ctg tgt gtg gtc tgc gga gac agg      561
Ala Gly Arg Ile Lys Gly Asp Glu Leu Cys Val Val Cys Gly Asp Arg
115                 120                 125                 130

gcc tct ggg tac cat tac aac gcg ctc acc tgc gag ggc tgc aaa ggt      609
Ala Ser Gly Tyr His Tyr Asn Ala Leu Thr Cys Glu Gly Cys Lys Gly
                135                 140                 145

ttc ttc cga aga agc atc acc aaa aac gcc gtg tac aag tgt aag aac      657
Phe Phe Arg Arg Ser Ile Thr Lys Asn Ala Val Tyr Lys Cys Lys Asn
            150                 155                 160

ggg ggc aac tgc gtg atg gat atg tac atg cgt cgg aag tgc cag gat      705
Gly Gly Asn Cys Val Met Asp Met Tyr Met Arg Arg Lys Cys Gln Asp
        165                 170                 175

tgc cgg cta agg aag tgc aga gag atg gga atg ttg gct gaa tgt ttg      753
Cys Arg Leu Arg Lys Cys Arg Glu Met Gly Met Leu Ala Glu Cys Leu
    180                 185                 190

tta act gaa att cag tgt aaa tct aaa cgg cta agg aaa aat gtg aag      801
Leu Thr Glu Ile Gln Cys Lys Ser Lys Arg Leu Arg Lys Asn Val Lys
195                 200                 205                 210

cag cat gcg gat cag aca gtg aat gag gac agc gaa ggg cgt gac ttg      849
Gln His Ala Asp Gln Thr Val Asn Glu Asp Ser Glu Gly Arg Asp Leu
                215                 220                 225
```

-continued

```
cgg caa gtg acc tcc acg acc aag cta tgc agg gag aaa act gaa ctc      897
Arg Gln Val Thr Ser Thr Thr Lys Leu Cys Arg Glu Lys Thr Glu Leu
            230                 235                 240

act gta gac cag cag acc ctc ctg gat tat att atg gac tca tac agc      945
Thr Val Asp Gln Gln Thr Leu Leu Asp Tyr Ile Met Asp Ser Tyr Ser
        245                 250                 255

aaa cag aga atg cca cag gag atc aca aat aaa atc tta aaa gaa gaa      993
Lys Gln Arg Met Pro Gln Glu Ile Thr Asn Lys Ile Leu Lys Glu Glu
    260                 265                 270

ttt agt gca gaa gaa aat ttt ctc ata tta aca gaa atg gct acc agt     1041
Phe Ser Ala Glu Glu Asn Phe Leu Ile Leu Thr Glu Met Ala Thr Ser
275                 280                 285                 290

cac gta cag att ctc gta gaa ttc aca aaa aga ctt cca ggg ttt cag     1089
His Val Gln Ile Leu Val Glu Phe Thr Lys Arg Leu Pro Gly Phe Gln
                295                 300                 305

aca ctg gac cac gaa gac cag att gct ttg ctc aaa ggg tcc gca gtc     1137
Thr Leu Asp His Glu Asp Gln Ile Ala Leu Leu Lys Gly Ser Ala Val
            310                 315                 320

gag gcc atg ttc ctt cgt tca gcg gag att ttc aat aag aaa ctt cct     1185
Glu Ala Met Phe Leu Arg Ser Ala Glu Ile Phe Asn Lys Lys Leu Pro
        325                 330                 335

gcc gga cac gca gac ctg ttg gaa gaa aga att cga aag agc ggc atc     1233
Ala Gly His Ala Asp Leu Leu Glu Glu Arg Ile Arg Lys Ser Gly Ile
    340                 345                 350

tcc gat gag tac ata acc ccg atg ttt agt ttc tat aaa agt gtc ggg     1281
Ser Asp Glu Tyr Ile Thr Pro Met Phe Ser Phe Tyr Lys Ser Val Gly
355                 360                 365                 370

gag ctg aaa atg acc cag gaa gag tac gct ctg ctc aca gca att gtc     1329
Glu Leu Lys Met Thr Gln Glu Glu Tyr Ala Leu Leu Thr Ala Ile Val
                375                 380                 385

atc ctc tct cca gac aga caa tac ata aag gat aga gag gca gtg gag     1377
Ile Leu Ser Pro Asp Arg Gln Tyr Ile Lys Asp Arg Glu Ala Val Glu
            390                 395                 400

aag ctt cag gag cct ctg ctc gat gtc cta caa aaa ctc tgc aag atc     1425
Lys Leu Gln Glu Pro Leu Leu Asp Val Leu Gln Lys Leu Cys Lys Ile
        405                 410                 415

tac cag ccc gag aac cct cag cat ttc gcc tgc ctc ctg ggt cgc ctg     1473
Tyr Gln Pro Glu Asn Pro Gln His Phe Ala Cys Leu Leu Gly Arg Leu
    420                 425                 430

aca gaa ctc cgg aca ttc aac cat cac cac gct gag atg ctg atg tct     1521
Thr Glu Leu Arg Thr Phe Asn His His His Ala Glu Met Leu Met Ser
435                 440                 445                 450

tgg agg gtg aat gac cac aag ttc acc ccg ctc ctc tgt gag atc tgg     1569
Trp Arg Val Asn Asp His Lys Phe Thr Pro Leu Leu Cys Glu Ile Trp
                455                 460                 465

gat gtg cag tga aggacacggg gagaggctag ctccttgtcc tcctcagagc         1621
Asp Val Gln  *

agcaacctgg tattggactt cccttctttt catttgtacc aggtctcact caagaatctc   1681

aatgaatatt tatgtggcaa ttatacaatt cccacaactg taaatacagg ctccatagaa   1741

ttgcttcccc tacactgtat tttacaaggc ttcgggaaac cccactgaca cgcccttttt   1801

gcctcattaa atcaattgtt acttcaattt tgtcaactga gctagggacc gcctcgtttt   1861

atcctccatg cggcaacatt atatatatat atattttatc aaatagctgt tttctcttcc   1921

tttttttttt tttttttttt cggagctggg gactgaaccc agggccttgc gcttgctagg   1981

caagcgctct accactgagc taaatcccca acccctatta aatagctgtt ttcaactgag   2041

acaataaact gaacgtaatg ccaagagaa                                     2070
```

-continued

<210> SEQ ID NO 6
<211> LENGTH: 469
<212> TYPE: PRT
<213> ORGANISM: Rattus norvegicus

<400> SEQUENCE: 6

```
Met Asn Leu Ile Gly Pro Ser His Leu Gln Ala Thr Asp Glu Phe Ala
 1               5                  10                  15

Leu Ser Glu Asn Leu Phe Gly Val Leu Thr Glu His Ala Ala Gly Pro
            20                  25                  30

Leu Gly Gln Asn Leu Asp Leu Glu Ser Tyr Ser Pro Tyr Asn Asn Val
        35                  40                  45

Gln Phe Pro Gln Val Gln Pro Gln Ile Ser Ser Ser Ser Tyr Tyr Ser
    50                  55                  60

Asn Leu Gly Phe Tyr Pro Gln Gln Pro Glu Asp Trp Tyr Ser Pro Gly
65                  70                  75                  80

Leu Tyr Glu Leu Arg Arg Met Pro Thr Glu Ser Val Tyr Gln Gly Glu
                85                  90                  95

Thr Glu Val Ser Glu Met Pro Val Thr Lys Lys Pro Arg Met Ala Ala
            100                 105                 110

Ser Ser Ala Gly Arg Ile Lys Gly Asp Glu Leu Cys Val Val Cys Gly
        115                 120                 125

Asp Arg Ala Ser Gly Tyr His Tyr Asn Ala Leu Thr Cys Glu Gly Cys
    130                 135                 140

Lys Gly Phe Phe Arg Arg Ser Ile Thr Lys Asn Ala Val Tyr Lys Cys
145                 150                 155                 160

Lys Asn Gly Gly Asn Cys Val Met Asp Met Tyr Met Arg Arg Lys Cys
                165                 170                 175

Gln Asp Cys Arg Leu Arg Lys Cys Arg Glu Met Gly Met Leu Ala Glu
            180                 185                 190

Cys Leu Leu Thr Glu Ile Gln Cys Lys Ser Lys Arg Leu Arg Lys Asn
        195                 200                 205

Val Lys Gln His Ala Asp Gln Thr Val Asn Glu Asp Ser Glu Gly Arg
    210                 215                 220

Asp Leu Arg Gln Val Thr Ser Thr Thr Lys Leu Cys Arg Glu Lys Thr
225                 230                 235                 240

Glu Leu Thr Val Asp Gln Gln Thr Leu Leu Asp Tyr Ile Met Asp Ser
                245                 250                 255

Tyr Ser Lys Gln Arg Met Pro Gln Glu Ile Thr Asn Lys Ile Leu Lys
            260                 265                 270

Glu Glu Phe Ser Ala Glu Glu Asn Phe Leu Ile Leu Thr Glu Met Ala
        275                 280                 285

Thr Ser His Val Gln Ile Leu Val Glu Phe Thr Lys Arg Leu Pro Gly
    290                 295                 300

Phe Gln Thr Leu Asp His Glu Asp Gln Ile Ala Leu Leu Lys Gly Ser
305                 310                 315                 320

Ala Val Glu Ala Met Phe Leu Arg Ser Ala Glu Ile Phe Asn Lys Lys
                325                 330                 335

Leu Pro Ala Gly His Ala Asp Leu Leu Glu Glu Arg Ile Arg Lys Ser
            340                 345                 350

Gly Ile Ser Asp Glu Tyr Ile Thr Pro Met Phe Ser Phe Tyr Lys Ser
        355                 360                 365

Val Gly Glu Leu Lys Met Thr Gln Glu Glu Tyr Ala Leu Leu Thr Ala
    370                 375                 380
```

-continued

Ile Val Ile Leu Ser Pro Asp Arg Gln Tyr Ile Lys Asp Arg Glu Ala
385 390 395 400

Val Glu Lys Leu Gln Glu Pro Leu Leu Asp Val Leu Gln Lys Leu Cys
405 410 415

Lys Ile Tyr Gln Pro Glu Asn Pro Gln His Phe Ala Cys Leu Leu Gly
420 425 430

Arg Leu Thr Glu Leu Arg Thr Phe Asn His His His Ala Glu Met Leu
435 440 445

Met Ser Trp Arg Val Asn Asp His Lys Phe Thr Pro Leu Leu Cys Glu
450 455 460

Ile Trp Asp Val Gln
465

<210> SEQ ID NO 7
<211> LENGTH: 2218
<212> TYPE: DNA
<213> ORGANISM: Homo Sapien
<220> FEATURE:
<221> NAME/KEY: CDS
<222> LOCATION: (354)...(1772)
<300> PUBLICATION INFORMATION:
<308> DATABASE ACCESSION NUMBER: GeneBank NM_005123
<309> DATABASE ENTRY DATE: 2002-11-05

<400> SEQUENCE: 7
acgagactct ctcctcctcc tcacctcatt gtctccccga cttatcctaa tgcgaaattg 60
gattctgagc atttgtagca aaatcgctgg gatctggaga ggaagactca gtccagaatc 120
ctcccagggc cttgaaagtc catctctgac ccaaaacaat ccaaggaggt agaagacatc 180
gtagaaggag tgaaagaaga aaagaagact tagaaacata gctcaaagtg aacactgctt 240
ctcttagttt cctggatttc ttctggacat ttcctcaaga tgaaacttca gacactttgg 300 agttttttt gaagaccacc ataaagaaag tgcatttcaa ttgaaaaatt tgg atg 356
Met
1 gga tca aaa atg aat ctc att gaa cat tcc cat tta cct acc aca gat 404
Gly Ser Lys Met Asn Leu Ile Glu His Ser His Leu Pro Thr Thr Asp
5 10 15
gaa ttt tct ttt tct gaa aat tta ttt ggt gtt tta aca gaa caa gtg 452
Glu Phe Ser Phe Ser Glu Asn Leu Phe Gly Val Leu Thr Glu Gln Val
20 25 30 gca ggt cct ctg gga cag aac ctg gaa gtg gaa cca tac tcg caa tac 500
Ala Gly Pro Leu Gly Gln Asn Leu Glu Val Glu Pro Tyr Ser Gln Tyr
35 40 45 agc aat gtt cag ttt ccc caa gtt caa cca cag att tcc tcg tca tcc 548
Ser Asn Val Gln Phe Pro Gln Val Gln Pro Gln Ile Ser Ser Ser Ser
50 55 60 65 tat tat tcc aac ctg ggt ttc tac ccc cag cag cct gaa gag tgg tac 596
Tyr Tyr Ser Asn Leu Gly Phe Tyr Pro Gln Gln Pro Glu Glu Trp Tyr
70 75 80 tct cct gga ata tat gaa ctc agg cgt atg cca gct gag act ctc tac 644
Ser Pro Gly Ile Tyr Glu Leu Arg Arg Met Pro Ala Glu Thr Leu Tyr
85 90 95 cag gga gaa act gag gta gca gag atg cct gta aca aag aag ccc cgc 692
Gln Gly Glu Thr Glu Val Ala Glu Met Pro Val Thr Lys Lys Pro Arg
100 105 110 atg ggc gcg tca gca ggg agg atc aaa ggg gat gag ctg tgt gtt gtt 740
Met Gly Ala Ser Ala Gly Arg Ile Lys Gly Asp Glu Leu Cys Val Val
115 120 125 tgt gga gac aga gcc tct gga tac cac tat aat gca ctg acc tgt gag 788

-continued

```
Cys Gly Asp Arg Ala Ser Gly Tyr His Tyr Asn Ala Leu Thr Cys Glu
130                 135                 140                 145

ggg tgt aaa ggt ttc ttc agg aga agc att acc aaa aac gct gtg tac      836
Gly Cys Lys Gly Phe Phe Arg Arg Ser Ile Thr Lys Asn Ala Val Tyr
                150                 155                 160

aag tgt aaa aac ggg ggc aac tgt gtg atg gat atg tac atg cga aga      884
Lys Cys Lys Asn Gly Gly Asn Cys Val Met Asp Met Tyr Met Arg Arg
            165                 170                 175

aag tgt caa gag tgt cga cta agg aaa tgc aaa gag atg gga atg ttg      932
Lys Cys Gln Glu Cys Arg Leu Arg Lys Cys Lys Glu Met Gly Met Leu
        180                 185                 190

gct gaa tgc ttg tta act gaa att cag tgt aaa tct aag cga ctg aga      980
Ala Glu Cys Leu Leu Thr Glu Ile Gln Cys Lys Ser Lys Arg Leu Arg
    195                 200                 205

aaa aat gtg aag cag cat gca gat cag acc gtg aat gaa gac agt gaa     1028
Lys Asn Val Lys Gln His Ala Asp Gln Thr Val Asn Glu Asp Ser Glu
210                 215                 220                 225

ggt cgt gac ttg cga caa gtg acc tcg aca aca aag tca tgc agg gag     1076
Gly Arg Asp Leu Arg Gln Val Thr Ser Thr Thr Lys Ser Cys Arg Glu
                230                 235                 240

aaa act gaa ctc acc cca gat caa cag act ctt cta cat ttt att atg     1124
Lys Thr Glu Leu Thr Pro Asp Gln Gln Thr Leu Leu His Phe Ile Met
            245                 250                 255

gat tca tat aac aaa cag agg atg cct cag gaa ata aca aat aaa att     1172
Asp Ser Tyr Asn Lys Gln Arg Met Pro Gln Glu Ile Thr Asn Lys Ile
        260                 265                 270

tta aaa gaa gaa ttc agt gca gaa gaa aat ttt ctc att ttg acg gaa     1220
Leu Lys Glu Glu Phe Ser Ala Glu Glu Asn Phe Leu Ile Leu Thr Glu
    275                 280                 285

atg gca acc aat cat gta cag gtt ctt gta gaa ttc aca aaa aag cta     1268
Met Ala Thr Asn His Val Gln Val Leu Val Glu Phe Thr Lys Lys Leu
290                 295                 300                 305

cca gga ttt cag act ttg gac cat gaa gac cag att gct ttg ctg aaa     1316
Pro Gly Phe Gln Thr Leu Asp His Glu Asp Gln Ile Ala Leu Leu Lys
                310                 315                 320

ggg tct gcg gtt gaa gct atg ttc ctt cgt tca gct gag att ttc aat     1364
Gly Ser Ala Val Glu Ala Met Phe Leu Arg Ser Ala Glu Ile Phe Asn
            325                 330                 335

aag aaa ctt ccg tct ggg cat tct gac cta ttg gaa gaa aga att cga     1412
Lys Lys Leu Pro Ser Gly His Ser Asp Leu Leu Glu Glu Arg Ile Arg
        340                 345                 350

aat agt ggt atc tct gat gaa tat ata aca cct atg ttt agt ttt tat     1460
Asn Ser Gly Ile Ser Asp Glu Tyr Ile Thr Pro Met Phe Ser Phe Tyr
    355                 360                 365

aaa agt att ggg gaa ctg aaa atg act caa gag gag tat gct ctg ctt     1508
Lys Ser Ile Gly Glu Leu Lys Met Thr Gln Glu Glu Tyr Ala Leu Leu
370                 375                 380                 385

aca gca att gtt atc ctg tct cca gat aga caa tac ata aag gat aga     1556
Thr Ala Ile Val Ile Leu Ser Pro Asp Arg Gln Tyr Ile Lys Asp Arg
                390                 395                 400

gag gca gta gag aag ctt cag gag cca ctt ctt gat gtg cta caa aag     1604
Glu Ala Val Glu Lys Leu Gln Glu Pro Leu Leu Asp Val Leu Gln Lys
            405                 410                 415

ttg tgt aag att cac cag cct gaa aat cct caa cac ttt gcc tgt ctc     1652
Leu Cys Lys Ile His Gln Pro Glu Asn Pro Gln His Phe Ala Cys Leu
        420                 425                 430

ctg ggt cgc ctg act gaa tta cgg aca ttc aat cat cac cac gct gag     1700
Leu Gly Arg Leu Thr Glu Leu Arg Thr Phe Asn His His His Ala Glu
    435                 440                 445
```

-continued

```
atg ctg atg tca tgg aga gta aac gac cac aag ttt acc cca ctt ctc     1748
Met Leu Met Ser Trp Arg Val Asn Asp His Lys Phe Thr Pro Leu Leu
450                 455                 460                 465

tgt gaa atc tgg gac gtg cag tga tggggattac aggggagggg tctagctcct    1802
Cys Glu Ile Trp Asp Val Gln  *
                470

ttttctctct catattaatc tgatgtataa ctttccttta tttcacttgt acccagtttc   1862

actcaagaaa tcttgatgaa tatttatgtt gtaattacat gtgtaacttc cacaactgta   1922

aatattgggc tagatagaac aactttctct acattgtgtt ttaaaaggct ccagggaatc   1982

ctgcattcta attggcaagc cctgtttgcc taattaaatt gattgttact tcaattctat   2042

ctgttgaact agggaaaatc tcattttgct catcttacca tattgcatat attttattaa   2102

agagttgtat tcaatcttgg caataaagca aacataatgg caacagaaaa aaaaaaaaaa   2162

aaaaaaaaaa aaaaaaaaaa aaaaaaaaaa aaaaaaaaaa aaaaaaaaaa aaaaaa       2218


<210> SEQ ID NO 8
<211> LENGTH: 472
<212> TYPE: PRT
<213> ORGANISM: Homo Sapien

<400> SEQUENCE: 8

Met Gly Ser Lys Met Asn Leu Ile Glu His Ser His Leu Pro Thr Thr
 1               5                  10                  15

Asp Glu Phe Ser Phe Ser Glu Asn Leu Phe Gly Val Leu Thr Glu Gln
            20                  25                  30

Val Ala Gly Pro Leu Gly Gln Asn Leu Glu Val Glu Pro Tyr Ser Gln
        35                  40                  45

Tyr Ser Asn Val Gln Phe Pro Gln Val Gln Pro Gln Ile Ser Ser Ser
    50                  55                  60

Ser Tyr Tyr Ser Asn Leu Gly Phe Tyr Pro Gln Gln Pro Glu Glu Trp
65                  70                  75                  80

Tyr Ser Pro Gly Ile Tyr Glu Leu Arg Arg Met Pro Ala Glu Thr Leu
                85                  90                  95

Tyr Gln Gly Glu Thr Glu Val Ala Glu Met Pro Val Thr Lys Lys Pro
            100                 105                 110

Arg Met Gly Ala Ser Ala Gly Arg Ile Lys Gly Asp Glu Leu Cys Val
        115                 120                 125

Val Cys Gly Asp Arg Ala Ser Gly Tyr His Tyr Asn Ala Leu Thr Cys
    130                 135                 140

Glu Gly Cys Lys Gly Phe Phe Arg Arg Ser Ile Thr Lys Asn Ala Val
145                 150                 155                 160

Tyr Lys Cys Lys Asn Gly Gly Asn Cys Val Met Asp Met Tyr Met Arg
                165                 170                 175

Arg Lys Cys Gln Glu Cys Arg Leu Arg Lys Cys Lys Glu Met Gly Met
            180                 185                 190

Leu Ala Glu Cys Leu Leu Thr Glu Ile Gln Cys Lys Ser Lys Arg Leu
        195                 200                 205

Arg Lys Asn Val Lys Gln His Ala Asp Gln Thr Val Asn Glu Asp Ser
    210                 215                 220

Glu Gly Arg Asp Leu Arg Gln Val Thr Ser Thr Thr Lys Ser Cys Arg
225                 230                 235                 240

Glu Lys Thr Glu Leu Thr Pro Asp Gln Gln Thr Leu Leu His Phe Ile
                245                 250                 255

Met Asp Ser Tyr Asn Lys Gln Arg Met Pro Gln Glu Ile Thr Asn Lys
```

-continued

```
            260                 265                 270

Ile Leu Lys Glu Glu Phe Ser Ala Glu Glu Asn Phe Leu Ile Leu Thr
        275                 280                 285

Glu Met Ala Thr Asn His Val Gln Val Leu Val Glu Phe Thr Lys Lys
    290                 295                 300

Leu Pro Gly Phe Gln Thr Leu Asp His Glu Asp Gln Ile Ala Leu Leu
305                 310                 315                 320

Lys Gly Ser Ala Val Glu Ala Met Phe Leu Arg Ser Ala Glu Ile Phe
                325                 330                 335

Asn Lys Lys Leu Pro Ser Gly His Ser Asp Leu Leu Glu Glu Arg Ile
            340                 345                 350

Arg Asn Ser Gly Ile Ser Asp Glu Tyr Ile Thr Pro Met Phe Ser Phe
        355                 360                 365

Tyr Lys Ser Ile Gly Glu Leu Lys Met Thr Gln Glu Glu Tyr Ala Leu
    370                 375                 380

Leu Thr Ala Ile Val Ile Leu Ser Pro Asp Arg Gln Tyr Ile Lys Asp
385                 390                 395                 400

Arg Glu Ala Val Glu Lys Leu Gln Glu Pro Leu Leu Asp Val Leu Gln
                405                 410                 415

Lys Leu Cys Lys Ile His Gln Pro Glu Asn Pro Gln His Phe Ala Cys
            420                 425                 430

Leu Leu Gly Arg Leu Thr Glu Leu Arg Thr Phe Asn His His His Ala
        435                 440                 445

Glu Met Leu Met Ser Trp Arg Val Asn Asp His Lys Phe Thr Pro Leu
    450                 455                 460

Leu Cys Glu Ile Trp Asp Val Gln
465                 470


<210> SEQ ID NO 9
<211> LENGTH: 5449
<212> TYPE: DNA
<213> ORGANISM: Homo Sapien
<220> FEATURE:
<221> NAME/KEY: CDS
<222> LOCATION: (69)...(1457)
<300> PUBLICATION INFORMATION:
<308> DATABASE ACCESSION NUMBER: GeneBank NM_002957
<309> DATABASE ENTRY DATE: 2002-06-21

<400> SEQUENCE: 9

gcgccggggg ccgccgcgcc cgccgcccgc tgcctgcgcc gccggccggg catgagttag     60

tcgcagac atg gac acc aaa cat ttc ctg ccg ctc gat ttc tcc acc cag     110
         Met Asp Thr Lys His Phe Leu Pro Leu Asp Phe Ser Thr Gln
          1               5                  10

gtg aac tcc tcc ctc acc tcc ccg acg ggg cga ggc tcc atg gct gcc     158
Val Asn Ser Ser Leu Thr Ser Pro Thr Gly Arg Gly Ser Met Ala Ala
 15                  20                  25                  30

ccc tcg ctg cac ccg tcc ctg ggg cct ggc atc ggc tcc ccg gga cag     206
Pro Ser Leu His Pro Ser Leu Gly Pro Gly Ile Gly Ser Pro Gly Gln
                 35                  40                  45

ctg cat tct ccc atc agc acc ctg agc tcc ccc atc aac ggc atg ggc     254
Leu His Ser Pro Ile Ser Thr Leu Ser Ser Pro Ile Asn Gly Met Gly
             50                  55                  60

ccg cct ttc tcg gtc atc agc tcc ccc atg ggc ccc cac tcc atg tcg     302
Pro Pro Phe Ser Val Ile Ser Ser Pro Met Gly Pro His Ser Met Ser
         65                  70                  75

gtg ccc acc aca ccc acc ctg ggc ttc agc act ggc agc ccc cag ctc     350
Val Pro Thr Thr Pro Thr Leu Gly Phe Ser Thr Gly Ser Pro Gln Leu
```

-continued

```
    80                  85                  90

agc tca cct atg aac ccc gtc agc agc agc gag gac atc aag ccc ccc      398
Ser Ser Pro Met Asn Pro Val Ser Ser Ser Glu Asp Ile Lys Pro Pro
 95                 100                 105                 110

ctg ggc ctc aat ggc gtc ctc aag gtc ccc gcc cac ccc tca gga aac      446
Leu Gly Leu Asn Gly Val Leu Lys Val Pro Ala His Pro Ser Gly Asn
                115                 120                 125

atg gct tcc ttc acc aag cac atc tgc gcc atc tgc ggg gac cgc tcc      494
Met Ala Ser Phe Thr Lys His Ile Cys Ala Ile Cys Gly Asp Arg Ser
            130                 135                 140

tca ggc aag cac tat gga gtg tac agc tgc gag ggg tgc aag ggc ttc      542
Ser Gly Lys His Tyr Gly Val Tyr Ser Cys Glu Gly Cys Lys Gly Phe
        145                 150                 155

ttc aag cgg acg gtg cgc aag gac ctg acc tac acc tgc cgc gac aac      590
Phe Lys Arg Thr Val Arg Lys Asp Leu Thr Tyr Thr Cys Arg Asp Asn
    160                 165                 170

aag gac tgc ctg att gac aag cgg cag cgg aac cgg tgc cag tac tgc      638
Lys Asp Cys Leu Ile Asp Lys Arg Gln Arg Asn Arg Cys Gln Tyr Cys
175                 180                 185                 190

cgc tac cag aag tgc ctg gcc atg ggc atg aag cgg gaa gcc gtg cag      686
Arg Tyr Gln Lys Cys Leu Ala Met Gly Met Lys Arg Glu Ala Val Gln
                195                 200                 205

gag gag cgg cag cgt ggc aag gac cgg aac gag aat gag gtg gag tcg      734
Glu Glu Arg Gln Arg Gly Lys Asp Arg Asn Glu Asn Glu Val Glu Ser
            210                 215                 220

acc agc agc gcc aac gag gac atg ccg gtg gag agg atc ctg gag gct      782
Thr Ser Ser Ala Asn Glu Asp Met Pro Val Glu Arg Ile Leu Glu Ala
        225                 230                 235

gag ctg gcc gtg gag ccc aag acc gag acc tac gtg gag gca aac atg      830
Glu Leu Ala Val Glu Pro Lys Thr Glu Thr Tyr Val Glu Ala Asn Met
    240                 245                 250

ggg ctg aac ccc agc tcg ccg aac gac cct gtc acc aac att tgc caa      878
Gly Leu Asn Pro Ser Ser Pro Asn Asp Pro Val Thr Asn Ile Cys Gln
255                 260                 265                 270

gca gcc gac aaa cag ctt ttc acc ctg gtg gag tgg gcc aag cgg atc      926
Ala Ala Asp Lys Gln Leu Phe Thr Leu Val Glu Trp Ala Lys Arg Ile
                275                 280                 285

cca cac ttc tca gag ctg ccc ctg gac gac cag gtc atc ctg ctg cgg      974
Pro His Phe Ser Glu Leu Pro Leu Asp Asp Gln Val Ile Leu Leu Arg
            290                 295                 300

gca ggc tgg aat gag ctg ctc atc gcc tcc ttc tcc cac cgc tcc atc     1022
Ala Gly Trp Asn Glu Leu Leu Ile Ala Ser Phe Ser His Arg Ser Ile
        305                 310                 315

gcc gtg aag gac ggg atc ctc ctg gcc acc ggg ctg cac gtc cac cgg     1070
Ala Val Lys Asp Gly Ile Leu Leu Ala Thr Gly Leu His Val His Arg
    320                 325                 330

aac agc gcc cac agc gca ggg gtg ggc gcc atc ttt gac agg gtg ctg     1118
Asn Ser Ala His Ser Ala Gly Val Gly Ala Ile Phe Asp Arg Val Leu
335                 340                 345                 350

acg gag ctt gtg tcc aag atg cgg gac atg cag atg gac aag acg gag     1166
Thr Glu Leu Val Ser Lys Met Arg Asp Met Gln Met Asp Lys Thr Glu
                355                 360                 365

ctg ggc tgc ctg cgc gcc atc gtc ctc ttt aac cct gac tcc aag ggg     1214
Leu Gly Cys Leu Arg Ala Ile Val Leu Phe Asn Pro Asp Ser Lys Gly
            370                 375                 380

ctc tcg aac ccg gcc gag gtg gag gcg ctg agg gag aag gtc tat gcg     1262
Leu Ser Asn Pro Ala Glu Val Glu Ala Leu Arg Glu Lys Val Tyr Ala
        385                 390                 395

tcc ttg gag gcc tac tgc aag cac aag tac cca gag cag ccg gga agg     1310
```

-continued

```
Ser Leu Glu Ala Tyr Cys Lys His Lys Tyr Pro Glu Gln Pro Gly Arg
    400                 405                 410

ttc gct aag ctc ttg ctc cgc ctg ccg gct ctg cgc tcc atc ggg ctc     1358
Phe Ala Lys Leu Leu Leu Arg Leu Pro Ala Leu Arg Ser Ile Gly Leu
415                 420                 425                 430

aaa tgc ctg gaa cat ctc ttc ttc ttc aag ctc atc ggg gac aca ccc     1406
Lys Cys Leu Glu His Leu Phe Phe Phe Lys Leu Ile Gly Asp Thr Pro
                435                 440                 445

att gac acc ttc ctt atg gag atg ctg gag gcg ccg cac caa atg act     1454
Ile Asp Thr Phe Leu Met Glu Met Leu Glu Ala Pro His Gln Met Thr
            450                 455                 460

tag gcctgcgggc ccatcctttg tgcccacccg ttctggccac cctgcctgga          1507
 *

cgccagctgt tcttctcagc ctgagccctg tccctgccct tctctgcctg gcctgtttgg   1567

actttggggc acagcctgtc actgctctgc ctaagagatg tgttgtcacc ctccttattt   1627

ctgttactac ttgtctgtgg cccagggcag tggctttcct gaggcagcag ccttcgtggc   1687

aagaactagc gtgagcccag ccaggcgcct ccccaccggg ctctcaggac accctgccac   1747

accccacggg gcttgggcga ctacagggtc ttcgggcccc agccctggag ctgcaggagt   1807

tgggaacggg gcttttgttt ccgttgctgt ttatcgatgc tggttttcag aattcctgtg   1867

tggccctcct gtctggagtg acatcttcat ctgctctgaa tactggtgcc cagccagccc   1927

gtgacagctt ccccctaatc aggaggggac agctgggggc gcaagctggt gtgtcatcag   1987

caaagacctc agccgcctcg gggatgagag gggactcgtg gggcaagcaa gctgccctgt   2047

gctctgagtg agggggaagg tagccccttt ttccaaagat aactcacagt tttgccctcg   2107

agccaatgag aacatgagct gccctctgtg caaggtttcg gggccacctc caggctgcag   2167

gggcgggtca ctcacccccc tgttttctct ctgccttggt gttctggttt cagactcccg   2227

actccccgtt cagaccagag tgccccggcc cctccccagc ctgagtcttc tccttgctct   2287

gcggggtggg ctgaggcttg tccttgtttc ctgcagggct ggccctggct cgggcagggt   2347

ggggcatcac cacctcactg gccttgctgg aggcacaggg ctctgcggac ctgcagccat   2407

ctgtgaggcc cgcggggatg ggaggggagg agggtggcct gttggtttcc ctcagagggg   2467

gcaggtggcc tggagagaga ggggctcagg aactgggagc ctcgtgggtg gggcagatgc   2527

tccgcggcct ggagtggctc tgccggggca ttggtgggac ccctgctcag gccttctctc   2587

tggctgccag ttgtgtctaa aagactcttg gaatctgaga acccggagtc gcagcgccct   2647

cgggcctggg ccacacgcag gccctggtgg gaccacccag cctggtattg tccacggaca   2707

gcgttgttca cccagagcct tacttgggag cctcactgaa cgcctgctct ggttgaaggt   2767

ggggtggggg cggggcttgg ggcctccctg gctcagccca gtgcggcctg gcgctcctcc   2827

cgcaggctct gcccccgggc tccggtggtg cggggccctc tcaggttgaa ctcgcctctt   2887

ttgcactgga aggccctccc tttggcctga gtacttttcc cgttcacgcc tcagtcccgt   2947

ggacccagcc tttgtcagtg gcaggtgcct gaacagaggg tggatggggg ggataccgga   3007

gggggtcttg tcttcccagc cgcagtctag gaatgatgcg ggggggtgga cgccttctcc   3067

atagtctttc cccacctgga gcaggggctt cctcagtggt gaggggagct gcctacaggt   3127

tggaccggga ggcagtggct tggagaggca gctttccagc cttggtgggg aagaaagtgt   3187

ccattctttg ccttcctgga gctcccagcc agagctgagc ttaggcaccc gagtggagcc   3247

tgcagctgag tctgtgcccg agacaggctg tcagagattc cagaagcctc tcctccccgc   3307

cgccctccac ccctgccttt cagcgttgtg gatccctaga ggtggccccc tgcccgatcc   3367
```

-continued

```
accgtcctga ggcagagtgt tgagcctcat acctgtacca ggtccccggc cagctgggcc   3427

cctcccaggc actgccagga agccccagct gcccctggcg ggtgtggtgg aaatggcagg   3487

agggtgcagg tactcttggg gccccagcgg tgggagtgca aaagacccaa cgccaacacc   3547

tggtgccttt tgcagccagc gcccacccat ccgtgcccgg acccttggga atgcccgcgg   3607

ctccagagga aaaagcccag ggacggggcc tccgttgcgg ggggtcggct gcttcttggg   3667

aactttgtcg tttccggcgc tggctggctg gctggctgta aagcactgaa gcccccccggc   3727

cgccaacccc tgaaagcaga acctggcctc cctggccaca gcagccttac ccaccgctct   3787

acgtgtcccg ggcacttccc gcagccttcc cgtccctttc tcatcggcct tgtagttgta   3847

cagtgctgtt ggtttgaaaa ggtgatgtgt ggggagtgcg gctcatcact gagtagagag   3907

gtagaatttc tatttaacca gacctgtagt agtattacca atccagttca attaaggtga   3967

ttttttgtaa ttattattat tttggtggga caatctttaa ttttctaaag atagcactaa   4027

catcagctca ttagccacct gtgcctgtcc ccgccttggc ccggctggat gaagcggctt   4087

ccccgcaggg cccccacttc ccagtggctg cttcctgggg acccagggca ccccggcacc   4147

ttcaggcacg ctcctcagct ggtcacctcc cggctttgcc gttcagatgg ggctcctgag   4207

gctcaggagt gaagatgcca cagagccggg ctcccctagg ctgcgtcggg catgcttgga   4267

agctggcctg ccaggacctt ccaccctggg gcctgtgtca gccgccggcc ctccgcaccc   4327

tggaagcaca cggcctctgg gaaggacagc cctgaccttc ggttttccga gcacggtgtt   4387

tcccaagaat tctgggctgg cggcctggtg gcagtgctgg agatgacccc gagcccctcc   4447

ccgtggggca cccaggaggg ccctgccgga atgtgcagcc tgtgggtagt cggctggtgt   4507

ccctgtcgtg gagctggggt gcgtgatctg gtgctcgtcc acgcaggtgt gtggtgtaaa   4567

catgtatgtg ctgtacagag agacgcgtgt ggagagagcc gcacaccagc gccacccagg   4627

aaaggcggag cggttaccag tgttttgtgt ttattttttaa tcaagacgtt tcccctgttt   4687

tcctataaat ttgcttcgtg taagcaagta cataaggacc ctcctttggt gaaatccggg   4747

ttcgaatgaa tatctcaagg caggagatgc atctatttta agatgctttg gagcagacag   4807

ctttagccgt tcccaatcct tagcaatgcc ttagctggga cgcatagcta atactttaga   4867

gaggatgaca gatccataaa gagagtaaag ataagagaaa atgtctaaag catctggaaa   4927

ggtaaaaaaa aaaaatctat ttttgtacaa atgtaatttt atccctcatg tatacttgga   4987

tatggcgggg ggagggctgg gactgtttcg tttctgcttc tagagattga ggtgaaagct   5047

tcgtccgaga aacgccagga cagacgatgg cagaggagag ggctcctgtg acggcggcga   5107

ggcttgggag gaaaccgccg caatgggggt gtcttccctc ggggcaggag ggtgggcctg   5167

aggctttcaa gggttttctt ccctttcgag taatttttaa agccttgctc tgttgtgtcc   5227

tgttgccggc tctggccttc ctgtgactga ctgtgaagtg gcttctccgt acgattgtct   5287

ctgaaacatc gtggcctcag gtgccagggt ttgatggaca gtagcattag aattgtggaa   5347

aaggaacacg caaagggaga agtgtgagag gagaaacaaa atatgagcgt ttaaaataca   5407

tcgccattca gttcgttaaa aaaaaaaaaa aaaaaaaaaa aa                      5449
```

<210> SEQ ID NO 10
<211> LENGTH: 462
<212> TYPE: PRT
<213> ORGANISM: Homo Sapien

<400> SEQUENCE: 10

Met Asp Thr Lys His Phe Leu Pro Leu Asp Phe Ser Thr Gln Val Asn

-continued

```
1               5                   10                  15

Ser Ser Leu Thr Ser Pro Thr Gly Arg Gly Ser Met Ala Ala Pro Ser
            20                  25                  30

Leu His Pro Ser Leu Gly Pro Gly Ile Gly Ser Pro Gly Gln Leu His
        35                  40                  45

Ser Pro Ile Ser Thr Leu Ser Ser Pro Ile Asn Gly Met Gly Pro Pro
    50                  55                  60

Phe Ser Val Ile Ser Ser Pro Met Gly Pro His Ser Met Ser Val Pro
65                  70                  75                  80

Thr Thr Pro Thr Leu Gly Phe Ser Thr Gly Ser Pro Gln Leu Ser Ser
                85                  90                  95

Pro Met Asn Pro Val Ser Ser Ser Glu Asp Ile Lys Pro Pro Leu Gly
            100                 105                 110

Leu Asn Gly Val Leu Lys Val Pro Ala His Pro Ser Gly Asn Met Ala
        115                 120                 125

Ser Phe Thr Lys His Ile Cys Ala Ile Cys Gly Asp Arg Ser Ser Gly
    130                 135                 140

Lys His Tyr Gly Val Tyr Ser Cys Glu Gly Cys Lys Gly Phe Phe Lys
145                 150                 155                 160

Arg Thr Val Arg Lys Asp Leu Thr Tyr Thr Cys Arg Asp Asn Lys Asp
                165                 170                 175

Cys Leu Ile Asp Lys Arg Gln Arg Asn Arg Cys Gln Tyr Cys Arg Tyr
            180                 185                 190

Gln Lys Cys Leu Ala Met Gly Met Lys Arg Glu Ala Val Gln Glu Glu
        195                 200                 205

Arg Gln Arg Gly Lys Asp Arg Asn Glu Asn Glu Val Glu Ser Thr Ser
    210                 215                 220

Ser Ala Asn Glu Asp Met Pro Val Glu Arg Ile Leu Glu Ala Glu Leu
225                 230                 235                 240

Ala Val Glu Pro Lys Thr Glu Thr Tyr Val Glu Ala Asn Met Gly Leu
                245                 250                 255

Asn Pro Ser Ser Pro Asn Asp Pro Val Thr Asn Ile Cys Gln Ala Ala
            260                 265                 270

Asp Lys Gln Leu Phe Thr Leu Val Glu Trp Ala Lys Arg Ile Pro His
        275                 280                 285

Phe Ser Glu Leu Pro Leu Asp Asp Gln Val Ile Leu Leu Arg Ala Gly
    290                 295                 300

Trp Asn Glu Leu Leu Ile Ala Ser Phe Ser His Arg Ser Ile Ala Val
305                 310                 315                 320

Lys Asp Gly Ile Leu Leu Ala Thr Gly Leu His Val His Arg Asn Ser
                325                 330                 335

Ala His Ser Ala Gly Val Gly Ala Ile Phe Asp Arg Val Leu Thr Glu
            340                 345                 350

Leu Val Ser Lys Met Arg Asp Met Gln Met Asp Lys Thr Glu Leu Gly
        355                 360                 365

Cys Leu Arg Ala Ile Val Leu Phe Asn Pro Asp Ser Lys Gly Leu Ser
    370                 375                 380

Asn Pro Ala Glu Val Glu Ala Leu Arg Glu Lys Val Tyr Ala Ser Leu
385                 390                 395                 400

Glu Ala Tyr Cys Lys His Lys Tyr Pro Glu Gln Pro Gly Arg Phe Ala
                405                 410                 415

Lys Leu Leu Leu Arg Leu Pro Ala Leu Arg Ser Ile Gly Leu Lys Cys
            420                 425                 430
```

-continued

```
Leu Glu His Leu Phe Phe Phe Lys Leu Ile Gly Asp Thr Pro Ile Asp
        435                 440                 445

Thr Phe Leu Met Glu Met Leu Glu Ala Pro His Gln Met Thr
    450                 455                 460


<210> SEQ ID NO 11
<211> LENGTH: 2081
<212> TYPE: DNA
<213> ORGANISM: Mus musculus
<220> FEATURE:
<221> NAME/KEY: CDS
<222> LOCATION: (167)...(1573)
<300> PUBLICATION INFORMATION:
<308> DATABASE ACCESSION NUMBER: GeneBank X57638
<309> DATABASE ENTRY DATE: 1991-03-19

<400> SEQUENCE: 11

gtcacagcct aggctttgct ggggacctga gaaacgctgc cgccaagttg aagttcaagg     60

ccctgccttc cctgtgaact gacgtttgtg gctggtcaag ttcgggaaca agacgttgtc    120

atcacagctt agcgctctgt ggcctgcctg gccacatcca tccaac atg gtg gac       175
                                                   Met Val Asp
                                                    1

aca gag agc ccc atc tgt cct ctc tcc cca ctg gag gca gat gac ctg      223
Thr Glu Ser Pro Ile Cys Pro Leu Ser Pro Leu Glu Ala Asp Asp Leu
     5                  10                  15

gaa agt ccc tta tct gaa gaa ttc tta caa gaa atg gga aac att caa      271
Glu Ser Pro Leu Ser Glu Glu Phe Leu Gln Glu Met Gly Asn Ile Gln
 20                  25                  30                  35

gag att tct cag tcc atc ggt gag gag agc tct gga agc ttt ggt ttt      319
Glu Ile Ser Gln Ser Ile Gly Glu Glu Ser Ser Gly Ser Phe Gly Phe
                 40                  45                  50

gca gac tac cag tac tta gga agc tgt ccg ggc tcc gag ggc tct gtc      367
Ala Asp Tyr Gln Tyr Leu Gly Ser Cys Pro Gly Ser Glu Gly Ser Val
             55                  60                  65

atc aca gac acc ctc tct cca cgt tcc agc cct tcc tca gtc agc tgc      415
Ile Thr Asp Thr Leu Ser Pro Arg Ser Ser Pro Ser Ser Val Ser Cys
         70                  75                  80

ccc gtg atc ccc gcc agc acg gac gag tcc ccc ggc agt gcc ctg aac      463
Pro Val Ile Pro Ala Ser Thr Asp Glu Ser Pro Gly Ser Ala Leu Asn
     85                  90                  95

atc gag tgt cga ata tgt ggg gac aag gcc tca ggg tac cac tac gga      511
Ile Glu Cys Arg Ile Cys Gly Asp Lys Ala Ser Gly Tyr His Tyr Gly
100                 105                 110                 115

gtt cac gca tgt gaa ggc tgt aag ggc ttc ttt cgg cga act att cgg      559
Val His Ala Cys Glu Gly Cys Lys Gly Phe Phe Arg Arg Thr Ile Arg
                120                 125                 130

ctg aag ctg gtg tac gac aag tgt gat cgg agc tgc aag att cag aag      607
Leu Lys Leu Val Tyr Asp Lys Cys Asp Arg Ser Cys Lys Ile Gln Lys
            135                 140                 145

aag aac cgg aac aaa tgc cag tac tgc cgt ttt cac aag tgc ctg tct      655
Lys Asn Arg Asn Lys Cys Gln Tyr Cys Arg Phe His Lys Cys Leu Ser
        150                 155                 160

gtc ggg atg tca cac aat gca att cgc ttt gga aga atg cca aga tct      703
Val Gly Met Ser His Asn Ala Ile Arg Phe Gly Arg Met Pro Arg Ser
    165                 170                 175

gaa aaa gca aaa ctg aaa gca gaa att ctt acc tgt gaa cac gac ctg      751
Glu Lys Ala Lys Leu Lys Ala Glu Ile Leu Thr Cys Glu His Asp Leu
180                 185                 190                 195

aaa gat tcg gaa act gca gac ctc aaa tct ctg ggc aag aga atc cac      799
Lys Asp Ser Glu Thr Ala Asp Leu Lys Ser Leu Gly Lys Arg Ile His
```

-continued

```
            200                 205                 210

gaa gcc tac ctg aag aac ttc aac atg aac aag gtc aag gcc cgg gtc      847
Glu Ala Tyr Leu Lys Asn Phe Asn Met Asn Lys Val Lys Ala Arg Val
            215                 220                 225

ata ctc gcg gga aag acc agc aac aac ccg cct ttt gtc ata cat gac      895
Ile Leu Ala Gly Lys Thr Ser Asn Asn Pro Pro Phe Val Ile His Asp
        230                 235                 240

atg gag acc ttg tgt atg gcc gag aag acg ctt gtg gcc aag atg gtg      943
Met Glu Thr Leu Cys Met Ala Glu Lys Thr Leu Val Ala Lys Met Val
    245                 250                 255

gcc aac ggc gtc gaa gac aaa gag gca gag gtc cga ttc ttc cac tgc      991
Ala Asn Gly Val Glu Asp Lys Glu Ala Glu Val Arg Phe Phe His Cys
260                 265                 270                 275

tgc cag tgc atg tcc gtg gag acc gtc acg gag ctc aca gaa ttt gcc     1039
Cys Gln Cys Met Ser Val Glu Thr Val Thr Glu Leu Thr Glu Phe Ala
                280                 285                 290

aag gct atc cca ggc ttt gca aac ttg gac ttg aac gac caa gtc acc     1087
Lys Ala Ile Pro Gly Phe Ala Asn Leu Asp Leu Asn Asp Gln Val Thr
            295                 300                 305

ttg cta aag tac ggt gtg tat gaa gcc atc ttc acg atg ctg tcc tcc     1135
Leu Leu Lys Tyr Gly Val Tyr Glu Ala Ile Phe Thr Met Leu Ser Ser
        310                 315                 320

ttg atg aac aaa gac ggg atg ctg atc gcg tac ggc aat ggc ttt atc     1183
Leu Met Asn Lys Asp Gly Met Leu Ile Ala Tyr Gly Asn Gly Phe Ile
    325                 330                 335

aca cgc gag ttc ctt aag aac ctg agg aag ccg ttc tgt gac atc atg     1231
Thr Arg Glu Phe Leu Lys Asn Leu Arg Lys Pro Phe Cys Asp Ile Met
340                 345                 350                 355

gaa ccc aag ttt gac ttc gct atg aag ttc aat gcc tta gaa ctg gat     1279
Glu Pro Lys Phe Asp Phe Ala Met Lys Phe Asn Ala Leu Glu Leu Asp
                360                 365                 370

gac agt gac att tcc ctg ttt gtg gct gct ata att tgc tgt gga gat     1327
Asp Ser Asp Ile Ser Leu Phe Val Ala Ala Ile Ile Cys Cys Gly Asp
            375                 380                 385

cgg cct ggc ctt cta aac ata ggc tac att gag aag ttg cag gag ggg     1375
Arg Pro Gly Leu Leu Asn Ile Gly Tyr Ile Glu Lys Leu Gln Glu Gly
        390                 395                 400

att gtg cac gtg ctt aag ctc cac ctg cag agc aac cat cca gat gac     1423
Ile Val His Val Leu Lys Leu His Leu Gln Ser Asn His Pro Asp Asp
    405                 410                 415

acc ttc ctc ttc cca aag ctc ctt caa aaa atg gtg gac ctt cgg cag     1471
Thr Phe Leu Phe Pro Lys Leu Leu Gln Lys Met Val Asp Leu Arg Gln
420                 425                 430                 435

ctg gtc acg gag cat gcg cag ctc gta cag gtc atc aag aag acc gag     1519
Leu Val Thr Glu His Ala Gln Leu Val Gln Val Ile Lys Lys Thr Glu
                440                 445                 450

tcc gac gca gcg ctg cac cca ctg ttg caa gag atc tac aga gac atg     1567
Ser Asp Ala Ala Leu His Pro Leu Leu Gln Glu Ile Tyr Arg Asp Met
            455                 460                 465

tac tga tctttcctga gatggcaggc cattaccact gttcagggac ctccgaggcc     1623
Tyr  *

tgcggcccca tacaggagag cagggatttg cacagagggc ctccctccta cgcttgggga   1683

tgaagagggc tgagcgtagg taatgcgggc tctccccaca tcctttctga atgggcactt   1743

ctaagactac ctgctaccga aatgggggtg atcggaggct aataggattc agacagtgac   1803

agacaacggc agtccccagt ctggtcttaa ccggcccaat gttaatcaat gcacagcact   1863

ctacgttgcg tttataattc gccattaatt aacgggtaac ctcgaagtct gagcggtctg   1923
```

-continued ttcccttcct gccacccttc tggctatgtg cactctctta aatccctgaa aactaatctg 1983 cactttttaa cctttgaaaa cctacaagtc aaggtgtggc ccaaggttag ccatttaaat 2043 gtggcaaaaa aaaaaaaaaa aaaaaaaaaa aaaaaaa 2081

<210> SEQ ID NO 12
<211> LENGTH: 468
<212> TYPE: PRT
<213> ORGANISM: Mus musculus

<400> SEQUENCE: 12

Met Val Asp Thr Glu Ser Pro Ile Cys Pro Leu Ser Pro Leu Glu Ala
1 5 10 15

Asp Asp Leu Glu Ser Pro Leu Ser Glu Glu Phe Leu Gln Glu Met Gly
20 25 30

Asn Ile Gln Glu Ile Ser Gln Ser Ile Gly Glu Glu Ser Ser Gly Ser
35 40 45

Phe Gly Phe Ala Asp Tyr Gln Tyr Leu Gly Ser Cys Pro Gly Ser Glu
50 55 60

Gly Ser Val Ile Thr Asp Thr Leu Ser Pro Arg Ser Ser Pro Ser Ser
65 70 75 80

Val Ser Cys Pro Val Ile Pro Ala Ser Thr Asp Glu Ser Pro Gly Ser
85 90 95

Ala Leu Asn Ile Glu Cys Arg Ile Cys Gly Asp Lys Ala Ser Gly Tyr
100 105 110

His Tyr Gly Val His Ala Cys Glu Gly Cys Lys Gly Phe Phe Arg Arg
115 120 125

Thr Ile Arg Leu Lys Leu Val Tyr Asp Lys Cys Asp Arg Ser Cys Lys
130 135 140

Ile Gln Lys Lys Asn Arg Asn Lys Cys Gln Tyr Cys Arg Phe His Lys
145 150 155 160

Cys Leu Ser Val Gly Met Ser His Asn Ala Ile Arg Phe Gly Arg Met
165 170 175

Pro Arg Ser Glu Lys Ala Lys Leu Lys Ala Glu Ile Leu Thr Cys Glu
180 185 190

His Asp Leu Lys Asp Ser Glu Thr Ala Asp Leu Lys Ser Leu Gly Lys
195 200 205

Arg Ile His Glu Ala Tyr Leu Lys Asn Phe Asn Met Asn Lys Val Lys
210 215 220

Ala Arg Val Ile Leu Ala Gly Lys Thr Ser Asn Asn Pro Pro Phe Val
225 230 235 240

Ile His Asp Met Glu Thr Leu Cys Met Ala Glu Lys Thr Leu Val Ala
245 250 255

Lys Met Val Ala Asn Gly Val Glu Asp Lys Glu Ala Glu Val Arg Phe
260 265 270

Phe His Cys Cys Gln Cys Met Ser Val Glu Thr Val Thr Glu Leu Thr
275 280 285

Glu Phe Ala Lys Ala Ile Pro Gly Phe Ala Asn Leu Asp Leu Asn Asp
290 295 300

Gln Val Thr Leu Leu Lys Tyr Gly Val Tyr Glu Ala Ile Phe Thr Met
305 310 315 320

Leu Ser Ser Leu Met Asn Lys Asp Gly Met Leu Ile Ala Tyr Gly Asn
325 330 335

Gly Phe Ile Thr Arg Glu Phe Leu Lys Asn Leu Arg Lys Pro Phe Cys
340 345 350

-continued

```
Asp Ile Met Glu Pro Lys Phe Asp Phe Ala Met Lys Phe Asn Ala Leu
        355                 360                 365

Glu Leu Asp Asp Ser Asp Ile Ser Leu Phe Val Ala Ala Ile Ile Cys
    370                 375                 380

Cys Gly Asp Arg Pro Gly Leu Leu Asn Ile Gly Tyr Ile Glu Lys Leu
385                 390                 395                 400

Gln Glu Gly Ile Val His Val Leu Lys Leu His Leu Gln Ser Asn His
                405                 410                 415

Pro Asp Asp Thr Phe Leu Phe Pro Lys Leu Leu Gln Lys Met Val Asp
            420                 425                 430

Leu Arg Gln Leu Val Thr Glu His Ala Gln Leu Val Gln Val Ile Lys
        435                 440                 445

Lys Thr Glu Ser Asp Ala Ala Leu His Pro Leu Leu Gln Glu Ile Tyr
    450                 455                 460

Arg Asp Met Tyr
465


<210> SEQ ID NO 13
<211> LENGTH: 1323
<212> TYPE: DNA
<213> ORGANISM: Mus musculus
<220> FEATURE:
<221> NAME/KEY: CDS
<222> LOCATION: (1)...(1323)
<300> PUBLICATION INFORMATION:
<308> DATABASE ACCESSION NUMBER: GeneBank U10375
<309> DATABASE ENTRY DATE: 1994-07-22

<400> SEQUENCE: 13

atg gaa cag cca cag gag gag acc cct gag gcc cgg gaa gag gag aaa       48
Met Glu Gln Pro Gln Glu Glu Thr Pro Glu Ala Arg Glu Glu Glu Lys
 1               5                  10                  15

gag gaa gtg gcc atg ggt gac gga gcc ccg gag ctc aat ggg gga cca       96
Glu Glu Val Ala Met Gly Asp Gly Ala Pro Glu Leu Asn Gly Gly Pro
            20                  25                  30

gaa cac acg ctt cct tcc agc agc tgt gca gac ctc tcc cag aat tcc      144
Glu His Thr Leu Pro Ser Ser Ser Cys Ala Asp Leu Ser Gln Asn Ser
        35                  40                  45

tcc cct tcc tcc ctg ctg gac cag ctg cag atg ggc tgt gat ggg gcc      192
Ser Pro Ser Ser Leu Leu Asp Gln Leu Gln Met Gly Cys Asp Gly Ala
     50                  55                  60

tca ggc ggc agc ctc aac atg gaa tgt cgg gtg tgc ggg gac aag gcc      240
Ser Gly Gly Ser Leu Asn Met Glu Cys Arg Val Cys Gly Asp Lys Ala
 65                  70                  75                  80

tcg ggc ttc cac tac ggg gtc cac gcg tgc gag ggg tgc aag ggc ttc      288
Ser Gly Phe His Tyr Gly Val His Ala Cys Glu Gly Cys Lys Gly Phe
                 85                  90                  95

ttc cgc cgg aca atc cgc atg aag ctc gag tat gag aag tgc gat cgg      336
Phe Arg Arg Thr Ile Arg Met Lys Leu Glu Tyr Glu Lys Cys Asp Arg
            100                 105                 110

atc tgc aag atc cag aag aag aac cgc aac aag tgt cag tac tgc cgc      384
Ile Cys Lys Ile Gln Lys Lys Asn Arg Asn Lys Cys Gln Tyr Cys Arg
        115                 120                 125

ttc cag aag tgc ctg gca ctc ggc atg tcg cac aac gct atc cgc ttt      432
Phe Gln Lys Cys Leu Ala Leu Gly Met Ser His Asn Ala Ile Arg Phe
    130                 135                 140

gga cgg atg ccg gac ggc gag aag agg aag ctg gtg gcg ggg ctg act      480
Gly Arg Met Pro Asp Gly Glu Lys Arg Lys Leu Val Ala Gly Leu Thr
145                 150                 155                 160
```

-continued

```
gcc agc gag ggg tgc cag cac aac ccc cag ctg gcc gac ctg aag gcc      528
Ala Ser Glu Gly Cys Gln His Asn Pro Gln Leu Ala Asp Leu Lys Ala
            165                 170                 175

ttc tct aag cac atc tac aac gcc tac ctg aaa aac ttc aac atg acc      576
Phe Ser Lys His Ile Tyr Asn Ala Tyr Leu Lys Asn Phe Asn Met Thr
            180                 185                 190

aaa aag aag gcc cgg agc atc ctc acc ggc aag tcc agc cac aac gca      624
Lys Lys Lys Ala Arg Ser Ile Leu Thr Gly Lys Ser Ser His Asn Ala
        195                 200                 205

ccc ttt gtc atc cac gac atc gag aca ctg tgg cag gca gag aag ggc      672
Pro Phe Val Ile His Asp Ile Glu Thr Leu Trp Gln Ala Glu Lys Gly
    210                 215                 220

ctg gtg tgg aaa cag ctg gtg aac ggg ctg ccg ccc tac aac gag atc      720
Leu Val Trp Lys Gln Leu Val Asn Gly Leu Pro Pro Tyr Asn Glu Ile
225                 230                 235                 240

agt gtg cac gtg ttc tac cgc tgc cag tcc acc aca gtg gag aca gtc      768
Ser Val His Val Phe Tyr Arg Cys Gln Ser Thr Thr Val Glu Thr Val
                245                 250                 255

cga gag ctc acc gag ttc gcc aag aac atc ccc aac ttc agc agc ctc      816
Arg Glu Leu Thr Glu Phe Ala Lys Asn Ile Pro Asn Phe Ser Ser Leu
            260                 265                 270

ttc ctc aat gac cag gtg acc ctc ctc aag tat ggc gtg cac gag gcc      864
Phe Leu Asn Asp Gln Val Thr Leu Leu Lys Tyr Gly Val His Glu Ala
        275                 280                 285

atc ttt gcc atg ctg gcc tcc atc gtc aac aaa gac ggg ctg ctg gtg      912
Ile Phe Ala Met Leu Ala Ser Ile Val Asn Lys Asp Gly Leu Leu Val
    290                 295                 300

gcc aac ggc agt ggc ttc gtc acc cac gag ttc ttg cga agt ctc cgc      960
Ala Asn Gly Ser Gly Phe Val Thr His Glu Phe Leu Arg Ser Leu Arg
305                 310                 315                 320

aag ccc ttc agt gac atc att gag ccc aag ttc gag ttt gct gtc aag     1008
Lys Pro Phe Ser Asp Ile Ile Glu Pro Lys Phe Glu Phe Ala Val Lys
                325                 330                 335

ttc aat gcg ctg gag ctc gat gac agt gac ctg gcg ctc ttc atc gcg     1056
Phe Asn Ala Leu Glu Leu Asp Asp Ser Asp Leu Ala Leu Phe Ile Ala
            340                 345                 350

gcc atc att ctg tgt gga gac cgg cca ggc ctc atg aat gtg ccc cag     1104
Ala Ile Ile Leu Cys Gly Asp Arg Pro Gly Leu Met Asn Val Pro Gln
        355                 360                 365

gta gaa gcc atc cag gac acc att ctg cgg gct cta gaa ttc cat ctg     1152
Val Glu Ala Ile Gln Asp Thr Ile Leu Arg Ala Leu Glu Phe His Leu
    370                 375                 380

cag gtc aac cac cct gac agc cag tac ctc ttc ccc aag ctg ctg cag     1200
Gln Val Asn His Pro Asp Ser Gln Tyr Leu Phe Pro Lys Leu Leu Gln
385                 390                 395                 400

aag atg gca gac ctg cgg cag ctg gtc act gag cat gcc cag atg atg     1248
Lys Met Ala Asp Leu Arg Gln Leu Val Thr Glu His Ala Gln Met Met
                405                 410                 415

cag tgg cta aag aag acg gag agt gag acc ttg ctg cac ccc ctg ctc     1296
Gln Trp Leu Lys Lys Thr Glu Ser Glu Thr Leu Leu His Pro Leu Leu
            420                 425                 430

cag gaa atc tac aag gac atg tac taa                                 1323
Gln Glu Ile Tyr Lys Asp Met Tyr  *
        435                 440
```

<210> SEQ ID NO 14
<211> LENGTH: 440
<212> TYPE: PRT
<213> ORGANISM: Mus musculus

<400> SEQUENCE: 14

-continued

```
Met Glu Gln Pro Gln Glu Glu Thr Pro Glu Ala Arg Glu Glu Glu Lys
 1               5                  10                  15

Glu Glu Val Ala Met Gly Asp Gly Ala Pro Glu Leu Asn Gly Gly Pro
            20                  25                  30

Glu His Thr Leu Pro Ser Ser Ser Cys Ala Asp Leu Ser Gln Asn Ser
        35                  40                  45

Ser Pro Ser Ser Leu Leu Asp Gln Leu Gln Met Gly Cys Asp Gly Ala
    50                  55                  60

Ser Gly Gly Ser Leu Asn Met Glu Cys Arg Val Cys Gly Asp Lys Ala
65                  70                  75                  80

Ser Gly Phe His Tyr Gly Val His Ala Cys Glu Gly Cys Lys Gly Phe
                85                  90                  95

Phe Arg Arg Thr Ile Arg Met Lys Leu Glu Tyr Glu Lys Cys Asp Arg
            100                 105                 110

Ile Cys Lys Ile Gln Lys Lys Asn Arg Asn Lys Cys Gln Tyr Cys Arg
        115                 120                 125

Phe Gln Lys Cys Leu Ala Leu Gly Met Ser His Asn Ala Ile Arg Phe
    130                 135                 140

Gly Arg Met Pro Asp Gly Glu Lys Arg Lys Leu Val Ala Gly Leu Thr
145                 150                 155                 160

Ala Ser Glu Gly Cys Gln His Asn Pro Gln Leu Ala Asp Leu Lys Ala
                165                 170                 175

Phe Ser Lys His Ile Tyr Asn Ala Tyr Leu Lys Asn Phe Asn Met Thr
            180                 185                 190

Lys Lys Lys Ala Arg Ser Ile Leu Thr Gly Lys Ser Ser His Asn Ala
        195                 200                 205

Pro Phe Val Ile His Asp Ile Glu Thr Leu Trp Gln Ala Glu Lys Gly
    210                 215                 220

Leu Val Trp Lys Gln Leu Val Asn Gly Leu Pro Pro Tyr Asn Glu Ile
225                 230                 235                 240

Ser Val His Val Phe Tyr Arg Cys Gln Ser Thr Thr Val Glu Thr Val
                245                 250                 255

Arg Glu Leu Thr Glu Phe Ala Lys Asn Ile Pro Asn Phe Ser Ser Leu
            260                 265                 270

Phe Leu Asn Asp Gln Val Thr Leu Leu Lys Tyr Gly Val His Glu Ala
        275                 280                 285

Ile Phe Ala Met Leu Ala Ser Ile Val Asn Lys Asp Gly Leu Leu Val
    290                 295                 300

Ala Asn Gly Ser Gly Phe Val Thr His Glu Phe Leu Arg Ser Leu Arg
305                 310                 315                 320

Lys Pro Phe Ser Asp Ile Ile Glu Pro Lys Phe Glu Phe Ala Val Lys
                325                 330                 335

Phe Asn Ala Leu Glu Leu Asp Asp Ser Asp Leu Ala Leu Phe Ile Ala
            340                 345                 350

Ala Ile Ile Leu Cys Gly Asp Arg Pro Gly Leu Met Asn Val Pro Gln
        355                 360                 365

Val Glu Ala Ile Gln Asp Thr Ile Leu Arg Ala Leu Glu Phe His Leu
    370                 375                 380

Gln Val Asn His Pro Asp Ser Gln Tyr Leu Phe Pro Lys Leu Leu Gln
385                 390                 395                 400

Lys Met Ala Asp Leu Arg Gln Leu Val Thr Glu His Ala Gln Met Met
                405                 410                 415
```

-continued

```
Gln Trp Leu Lys Lys Thr Glu Ser Glu Thr Leu Leu His Pro Leu Leu
            420                 425                 430

Gln Glu Ile Tyr Lys Asp Met Tyr
        435                 440


<210> SEQ ID NO 15
<211> LENGTH: 1827
<212> TYPE: DNA
<213> ORGANISM: Homo Sapien
<220> FEATURE:
<221> NAME/KEY: CDS
<222> LOCATION: (292)...(1683)
<300> PUBLICATION INFORMATION:
<308> DATABASE ACCESSION NUMBER: GeneBank XM_053680
<309> DATABASE ENTRY DATE: 2002-05-08

<400> SEQUENCE: 15

gtagcggtga cggcggcggc ggcggcggcg gcagcattat gcgtgattac tgacaggcac      60

cagctgctgc cgccacagcc gtctcaaacg cactatgtgg actctccgat ctagaggcag     120

attcctgact aatcccagag ggctggccca gcctgtgctc cccgggctgc taggaagcga     180

tgaccactct tgttagccca agttgaagaa agccgggctg tgcctgggag ccgagagagg     240

cggtaatatt tagaagctgc acaggagagg aacatgaact gacgagtaaa c atg tat      297
                                                         Met Tyr
                                                          1

gga aat tat tct cac ttc atg aag ttt ccc gca ggc tat gga ggc tcc      345
Gly Asn Tyr Ser His Phe Met Lys Phe Pro Ala Gly Tyr Gly Gly Ser
        5                  10                  15

cct ggc cac act ggc tct aca tcc atg agc cca tca gca gcc ttg tcc      393
Pro Gly His Thr Gly Ser Thr Ser Met Ser Pro Ser Ala Ala Leu Ser
     20                  25                  30

aca ggg aag cca atg gac agc cac ccc agc tac aca gat acc cca gtg      441
Thr Gly Lys Pro Met Asp Ser His Pro Ser Tyr Thr Asp Thr Pro Val
 35                  40                  45                  50

agt gcc cca cgg act ctg agt gca gtg ggg acc ccc ctc aat gcc ctg      489
Ser Ala Pro Arg Thr Leu Ser Ala Val Gly Thr Pro Leu Asn Ala Leu
                 55                  60                  65

ggc tct cca tat cga gtc atc acc tct gcc atg ggc cca ccc tca gga      537
Gly Ser Pro Tyr Arg Val Ile Thr Ser Ala Met Gly Pro Pro Ser Gly
             70                  75                  80

gca ctt gca gcg cct cca gga atc aac ttg gtt gcc cca ccc agc tct      585
Ala Leu Ala Ala Pro Pro Gly Ile Asn Leu Val Ala Pro Pro Ser Ser
         85                  90                  95

cag cta aat gtg gtc aac agt gtc agc agt tca gag gac atc aag ccc      633
Gln Leu Asn Val Val Asn Ser Val Ser Ser Ser Glu Asp Ile Lys Pro
    100                 105                 110

tta cca ggg ctt ccc ggg att gga aac atg aac tac cca tcc acc agc      681
Leu Pro Gly Leu Pro Gly Ile Gly Asn Met Asn Tyr Pro Ser Thr Ser
115                 120                 125                 130

ccc gga tct ctg gtt aaa cac atc tgt gcc atc tgt gga gac aga tcc      729
Pro Gly Ser Leu Val Lys His Ile Cys Ala Ile Cys Gly Asp Arg Ser
                135                 140                 145

tca gga aag cac tac ggg gta tac agt tgt gaa ggc tgc aaa ggg ttc      777
Ser Gly Lys His Tyr Gly Val Tyr Ser Cys Glu Gly Cys Lys Gly Phe
            150                 155                 160

ttc aag agg acg ata agg aag gac ctc atc tac acg tgt cgg gat aat      825
Phe Lys Arg Thr Ile Arg Lys Asp Leu Ile Tyr Thr Cys Arg Asp Asn
        165                 170                 175

aaa gac tgc ctc att gac aag cgt cag cgc aac cgc tgc cag tac tgt      873
Lys Asp Cys Leu Ile Asp Lys Arg Gln Arg Asn Arg Cys Gln Tyr Cys
    180                 185                 190
```

-continued

```
cgc tat cag aag tgc ctt gtc atg ggc atg aag agg gaa gct gtg caa      921
Arg Tyr Gln Lys Cys Leu Val Met Gly Met Lys Arg Glu Ala Val Gln
195                 200                 205                 210

gaa gaa aga cag agg agc cga gag cga gct gag agt gag gca gaa tgt      969
Glu Glu Arg Gln Arg Ser Arg Glu Arg Ala Glu Ser Glu Ala Glu Cys
                215                 220                 225

gct acc agt ggt cat gaa gac atg cct gtg gag agg att cta gaa gct     1017
Ala Thr Ser Gly His Glu Asp Met Pro Val Glu Arg Ile Leu Glu Ala
            230                 235                 240

gaa ctt gct gtt gaa cca aag aca gaa tcc tat ggt gac atg aat atg     1065
Glu Leu Ala Val Glu Pro Lys Thr Glu Ser Tyr Gly Asp Met Asn Met
        245                 250                 255

gag aac tcg aca aat gac cct gtt acc aac ata tgt cat gct gct gac     1113
Glu Asn Ser Thr Asn Asp Pro Val Thr Asn Ile Cys His Ala Ala Asp
    260                 265                 270

aag cag ctt ttc acc ctc gtt gaa tgg gcc aag cgt att ccc cac ttc     1161
Lys Gln Leu Phe Thr Leu Val Glu Trp Ala Lys Arg Ile Pro His Phe
275                 280                 285                 290

tct gac ctc acc ttg gag gac cag gtc att ttg ctt cgg gca ggg tgg     1209
Ser Asp Leu Thr Leu Glu Asp Gln Val Ile Leu Leu Arg Ala Gly Trp
                295                 300                 305

aat gaa ttg ctg att gcc tct ttc tcc cac cgc tca gtt tcc gtg cag     1257
Asn Glu Leu Leu Ile Ala Ser Phe Ser His Arg Ser Val Ser Val Gln
            310                 315                 320

gat ggc atc ctt ctg gcc acg ggt tta cat gtc cac cgg agc agt gcc     1305
Asp Gly Ile Leu Leu Ala Thr Gly Leu His Val His Arg Ser Ser Ala
        325                 330                 335

cac agt gct ggg gtc ggc tcc atc ttt gac aga gtc cta act gag ctg     1353
His Ser Ala Gly Val Gly Ser Ile Phe Asp Arg Val Leu Thr Glu Leu
    340                 345                 350

gtt tcc aaa atg aaa gac atg cag atg gac aag tcg gaa ctg gga tgc     1401
Val Ser Lys Met Lys Asp Met Gln Met Asp Lys Ser Glu Leu Gly Cys
355                 360                 365                 370

ctg cga gcc att gta ctc ttt aac cca gat gcc aag ggc ctg tcc aac     1449
Leu Arg Ala Ile Val Leu Phe Asn Pro Asp Ala Lys Gly Leu Ser Asn
                375                 380                 385

ccc tct gag gtg gag act ctg cga gag aag gtt tat gcc acc ctt gag     1497
Pro Ser Glu Val Glu Thr Leu Arg Glu Lys Val Tyr Ala Thr Leu Glu
            390                 395                 400

gcc tac acc aag cag aag tat ccg gaa cag cca ggc agg ttt gcc aag     1545
Ala Tyr Thr Lys Gln Lys Tyr Pro Glu Gln Pro Gly Arg Phe Ala Lys
        405                 410                 415

ctg ctg ctg cgc ctc cca gct ctg cgt tcc att ggc ttg aaa tgc ctg     1593
Leu Leu Leu Arg Leu Pro Ala Leu Arg Ser Ile Gly Leu Lys Cys Leu
    420                 425                 430

gag cac ctc ttc ttc ttc aag ctc atc ggg gac acc ccc att gac acc     1641
Glu His Leu Phe Phe Phe Lys Leu Ile Gly Asp Thr Pro Ile Asp Thr
435                 440                 445                 450

ttc ctc atg gag atg ttg gag acc ccg ctg cag atc acc tga             1683
Phe Leu Met Glu Met Leu Glu Thr Pro Leu Gln Ile Thr  *
                455                 460

gccccaccag ccacagcctc cccacccagg atgacccctg ggcaggtgtg tgtggacccc   1743

caccctgcac tttcctccac ctcccaccct gaccccccttc ctgtccccaa aatgtgatgc   1803

ttataataaa gaaaaccttt ctac                                          1827
```

<210> SEQ ID NO 16
<211> LENGTH: 463
<212> TYPE: PRT

-continued

<213> ORGANISM: Homo Sapien

<400> SEQUENCE: 16

```
Met Tyr Gly Asn Tyr Ser His Phe Met Lys Phe Pro Ala Gly Tyr Gly
 1               5                  10                  15

Gly Ser Pro Gly His Thr Gly Ser Thr Ser Met Ser Pro Ser Ala Ala
            20                  25                  30

Leu Ser Thr Gly Lys Pro Met Asp Ser His Pro Ser Tyr Thr Asp Thr
        35                  40                  45

Pro Val Ser Ala Pro Arg Thr Leu Ser Ala Val Gly Thr Pro Leu Asn
    50                  55                  60

Ala Leu Gly Ser Pro Tyr Arg Val Ile Thr Ser Ala Met Gly Pro Pro
65                  70                  75                  80

Ser Gly Ala Leu Ala Ala Pro Pro Gly Ile Asn Leu Val Ala Pro Pro
                85                  90                  95

Ser Ser Gln Leu Asn Val Val Asn Ser Val Ser Ser Ser Glu Asp Ile
            100                 105                 110

Lys Pro Leu Pro Gly Leu Pro Gly Ile Gly Asn Met Asn Tyr Pro Ser
        115                 120                 125

Thr Ser Pro Gly Ser Leu Val Lys His Ile Cys Ala Ile Cys Gly Asp
    130                 135                 140

Arg Ser Ser Gly Lys His Tyr Gly Val Tyr Ser Cys Glu Gly Cys Lys
145                 150                 155                 160

Gly Phe Phe Lys Arg Thr Ile Arg Lys Asp Leu Ile Tyr Thr Cys Arg
                165                 170                 175

Asp Asn Lys Asp Cys Leu Ile Asp Lys Arg Gln Arg Asn Arg Cys Gln
            180                 185                 190

Tyr Cys Arg Tyr Gln Lys Cys Leu Val Met Gly Met Lys Arg Glu Ala
        195                 200                 205

Val Gln Glu Glu Arg Gln Arg Ser Arg Glu Arg Ala Glu Ser Glu Ala
    210                 215                 220

Glu Cys Ala Thr Ser Gly His Glu Asp Met Pro Val Glu Arg Ile Leu
225                 230                 235                 240

Glu Ala Glu Leu Ala Val Glu Pro Lys Thr Glu Ser Tyr Gly Asp Met
                245                 250                 255

Asn Met Glu Asn Ser Thr Asn Asp Pro Val Thr Asn Ile Cys His Ala
            260                 265                 270

Ala Asp Lys Gln Leu Phe Thr Leu Val Glu Trp Ala Lys Arg Ile Pro
        275                 280                 285

His Phe Ser Asp Leu Thr Leu Glu Asp Gln Val Ile Leu Leu Arg Ala
    290                 295                 300

Gly Trp Asn Glu Leu Leu Ile Ala Ser Phe Ser His Arg Ser Val Ser
305                 310                 315                 320

Val Gln Asp Gly Ile Leu Leu Ala Thr Gly Leu His Val His Arg Ser
                325                 330                 335

Ser Ala His Ser Ala Gly Val Gly Ser Ile Phe Asp Arg Val Leu Thr
            340                 345                 350

Glu Leu Val Ser Lys Met Lys Asp Met Gln Met Asp Lys Ser Glu Leu
        355                 360                 365

Gly Cys Leu Arg Ala Ile Val Leu Phe Asn Pro Asp Ala Lys Gly Leu
    370                 375                 380

Ser Asn Pro Ser Glu Val Glu Thr Leu Arg Glu Lys Val Tyr Ala Thr
385                 390                 395                 400
```

-continued

```
Leu Glu Ala Tyr Thr Lys Gln Lys Tyr Pro Glu Gln Pro Gly Arg Phe
                405                 410                 415

Ala Lys Leu Leu Leu Arg Leu Pro Ala Leu Arg Ser Ile Gly Leu Lys
            420                 425                 430

Cys Leu Glu His Leu Phe Phe Phe Lys Leu Ile Gly Asp Thr Pro Ile
        435                 440                 445

Asp Thr Phe Leu Met Glu Met Leu Glu Thr Pro Leu Gln Ile Thr
    450                 455                 460


<210> SEQ ID NO 17
<211> LENGTH: 1330
<212> TYPE: DNA
<213> ORGANISM: Homo Sapien
<220> FEATURE:
<221> NAME/KEY: CDS
<222> LOCATION: (97)...(837)
<300> PUBLICATION INFORMATION:
<308> DATABASE ACCESSION NUMBER: GeneBank XM_042579
<309> DATABASE ENTRY DATE: 2002-02-06

<400> SEQUENCE: 17

ttggggttgt gctccaggga tggcctttca catagactgc agtgtaaatg acagcctctg      60

gaatgtgcat tgcagggcct tgcttagtgg taggga atg att tcc atc act tct       114
                                        Met Ile Ser Ile Thr Ser
                                        1               5

gtg aca ttc tgc ttc cca ata agt ctt cct gtg act tcc cta ttt ccc       162
Val Thr Phe Cys Phe Pro Ile Ser Leu Pro Val Thr Ser Leu Phe Pro
            10                  15                  20

cca tcc cag att aac tca aca gtg tca ctc cct ggg ggt ggg tct ggc       210
Pro Ser Gln Ile Asn Ser Thr Val Ser Leu Pro Gly Gly Gly Ser Gly
        25                  30                  35

ccc cct gaa gat gtg aag cca cca gtc tta ggg gtc cgg ggc ctg cac       258
Pro Pro Glu Asp Val Lys Pro Pro Val Leu Gly Val Arg Gly Leu His
    40                  45                  50

tgt cca ccc cct cca ggt ggc cct ggg gct ggc aaa cgg cta tgt gca       306
Cys Pro Pro Pro Pro Gly Gly Pro Gly Ala Gly Lys Arg Leu Cys Ala
 55                  60                  65                  70

atc tgc ggg gac aga agc tca ggc aaa cac tac ggg gtt tac agc tgt       354
Ile Cys Gly Asp Arg Ser Ser Gly Lys His Tyr Gly Val Tyr Ser Cys
                75                  80                  85

gag ggt tgc aag ggc ttc ttc aaa cgc acc atc cgc aaa gac ctt aca       402
Glu Gly Cys Lys Gly Phe Phe Lys Arg Thr Ile Arg Lys Asp Leu Thr
            90                  95                  100

tac tct tgc cgg gac aac aaa gac tgc aca gtg gac aag cgc cag cgg       450
Tyr Ser Cys Arg Asp Asn Lys Asp Cys Thr Val Asp Lys Arg Gln Arg
        105                 110                 115

aac cgc tgt cag tac tgc cgc tat cag aag tgc ctg gcc act ggc atg       498
Asn Arg Cys Gln Tyr Cys Arg Tyr Gln Lys Cys Leu Ala Thr Gly Met
    120                 125                 130

aag agg gag gcg gta cag gag gag cgt cag cgg gga aag gac aag gat       546
Lys Arg Glu Ala Val Gln Glu Glu Arg Gln Arg Gly Lys Asp Lys Asp
135                 140                 145                 150

ggg gat ggg gag ggg gct ggg gga gcc ccc gag gag atg cct gtg gac       594
Gly Asp Gly Glu Gly Ala Gly Gly Ala Pro Glu Glu Met Pro Val Asp
                155                 160                 165

agg atc ctg gag gca gag ctt gct gtg gaa cag aag agt gac cag ggc       642
Arg Ile Leu Glu Ala Glu Leu Ala Val Glu Gln Lys Ser Asp Gln Gly
            170                 175                 180

gtt gag ggt cct ggg gga acc ggg ggt agc ggc agc agc gtg agt gtt       690
Val Glu Gly Pro Gly Gly Thr Gly Gly Ser Gly Ser Ser Val Ser Val
        185                 190                 195
```

-continued

```
ggg gtc aat cca ctc tcc ttc gtg atg ggg gtt ggg gga ggc agt cta      738
Gly Val Asn Pro Leu Ser Phe Val Met Gly Val Gly Gly Gly Ser Leu
    200                 205                 210

ggt ctg ttc tac atc ccc tcc ccc tcc ttt ccc ctc ata acc ttc cta      786
Gly Leu Phe Tyr Ile Pro Ser Pro Ser Phe Pro Leu Ile Thr Phe Leu
215                 220                 225                 230

aca cta ctt ggg act gga ggt gct gcc aaa caa ggt ctt tca aac atc      834
Thr Leu Leu Gly Thr Gly Gly Ala Ala Lys Gln Gly Leu Ser Asn Ile
                235                 240                 245

tga ggtggatgtg atagctcctt ctgtctccac tccccaaaca acccactggc           887
 *
agaaccatag gcatgtccca aataaataat tgtttgcact aatgccagaa gagaagactc    947

acttacaggg attggtttgg atggggctca caggaagact atatgtaagg agggggtgtc   1007

aaaagcctct tacaaggggg ctcccagcat atctcaaaat cttccataac tcttaccccc   1067

gtcccctgca gccaaatgac cctgtgacta acatctgtca ggcagctgac aaacagctat   1127

tcacgcttgt tgagtgggcg aagaggatcc cacacttttc ctccttgcct ctggatgatc   1187

aggtcatatt gctgcgggca ggtcagtgac cttggatccc tttgacttct tgacatttga   1247

cccctctttg acttcccgat ctttagtgac cccagtggcc ttaccttgcg tacccaggga   1307

gccaaacttg ctgacctcgc cac                                           1330


<210> SEQ ID NO 18
<211> LENGTH: 246
<212> TYPE: PRT
<213> ORGANISM: Homo Sapien

<400> SEQUENCE: 18

Met Ile Ser Ile Thr Ser Val Thr Phe Cys Phe Pro Ile Ser Leu Pro
 1               5                  10                  15

Val Thr Ser Leu Phe Pro Pro Ser Gln Ile Asn Ser Thr Val Ser Leu
            20                  25                  30

Pro Gly Gly Gly Ser Gly Pro Pro Glu Asp Val Lys Pro Pro Val Leu
        35                  40                  45

Gly Val Arg Gly Leu His Cys Pro Pro Pro Pro Gly Gly Pro Gly Ala
    50                  55                  60

Gly Lys Arg Leu Cys Ala Ile Cys Gly Asp Arg Ser Ser Gly Lys His
65                  70                  75                  80

Tyr Gly Val Tyr Ser Cys Glu Gly Cys Lys Gly Phe Phe Lys Arg Thr
                85                  90                  95

Ile Arg Lys Asp Leu Thr Tyr Ser Cys Arg Asp Asn Lys Asp Cys Thr
            100                 105                 110

Val Asp Lys Arg Gln Arg Asn Arg Cys Gln Tyr Cys Arg Tyr Gln Lys
        115                 120                 125

Cys Leu Ala Thr Gly Met Lys Arg Glu Ala Val Gln Glu Glu Arg Gln
    130                 135                 140

Arg Gly Lys Asp Lys Asp Gly Asp Gly Glu Gly Ala Gly Gly Ala Pro
145                 150                 155                 160

Glu Glu Met Pro Val Asp Arg Ile Leu Glu Ala Glu Leu Ala Val Glu
                165                 170                 175

Gln Lys Ser Asp Gln Gly Val Glu Gly Pro Gly Gly Thr Gly Gly Ser
            180                 185                 190

Gly Ser Ser Val Ser Val Gly Val Asn Pro Leu Ser Phe Val Met Gly
        195                 200                 205

Val Gly Gly Gly Ser Leu Gly Leu Phe Tyr Ile Pro Ser Pro Ser Phe
```

-continued

```
    210                 215                 220

Pro Leu Ile Thr Phe Leu Thr Leu Leu Gly Thr Gly Gly Ala Ala Lys
225                 230                 235                 240

Gln Gly Leu Ser Asn Ile
                245
```